United States Patent
Dota

(10) Patent No.: US 10,091,998 B2
(45) Date of Patent: *Oct. 9, 2018

(54) TETRAZOLINONE COMPOUND AND USE THEREOF

(71) Applicant: SUMITOMO CHEMICAL COMPANY, LIMITED, Tokyo (JP)

(72) Inventor: Koichiro Dota, Takarazuka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/029,112

(22) PCT Filed: Oct. 27, 2014

(86) PCT No.: PCT/JP2014/079007
§ 371 (c)(1),
(2) Date: Apr. 13, 2016

(87) PCT Pub. No.: WO2015/064727
PCT Pub. Date: May 7, 2015

(65) Prior Publication Data
US 2016/0249617 A1    Sep. 1, 2016

(30) Foreign Application Priority Data
Oct. 28, 2013    (JP) ................ 2013-222984

(51) Int. Cl.
| | | |
|---|---|---|
| A01N 43/713 | (2006.01) | |
| C07D 401/12 | (2006.01) | |
| C07D 417/12 | (2006.01) | |
| A01N 43/78 | (2006.01) | |
| C07D 403/12 | (2006.01) | |
| C07D 403/10 | (2006.01) | |
| C07D 413/12 | (2006.01) | |
| A01N 43/76 | (2006.01) | |
| C07D 405/12 | (2006.01) | |
| C07D 409/12 | (2006.01) | |
| C07D 417/10 | (2006.01) | |
| C07D 413/10 | (2006.01) | |

(Continued)

(52) U.S. Cl.
CPC .......... *A01N 43/713* (2013.01); *A01N 43/76* (2013.01); *A01N 43/78* (2013.01); *C07D 257/04* (2013.01); *C07D 401/10* (2013.01); *C07D 401/12* (2013.01); *C07D 403/10* (2013.01); *C07D 403/12* (2013.01); *C07D 405/10* (2013.01); *C07D 405/12* (2013.01); *C07D 409/10* (2013.01); *C07D 409/12* (2013.01); *C07D 413/10* (2013.01); *C07D 413/12* (2013.01); *C07D 417/10* (2013.01); *C07D 417/12* (2013.01)

(58) Field of Classification Search
CPC ................................. A01N 43/713

USPC ........................................... 514/34
See application file for complete search history.

(56) References Cited

U.S. PATENT DOCUMENTS

| | | |
|---|---|---|
| 6,583,090 B1 | 6/2003 | Gewehr et al. |
| 9,271,501 B2 | 3/2016 | Rheinheimer et al. |

(Continued)

FOREIGN PATENT DOCUMENTS

| | | |
|---|---|---|
| JP | 9-208565 A | 8/1997 |
| JP | 2001-521027 A | 11/2001 |

(Continued)

OTHER PUBLICATIONS

European Patent Office Communication and extended search report issued in the corresponding European Patent Application No. 14857896.6 dated May 19, 2017.

(Continued)

*Primary Examiner* — Kortney L. Klinkel
*Assistant Examiner* — William Y Lee
(74) *Attorney, Agent, or Firm* — Birch, Stewart, Kolasch & Birch, LLP

(57) ABSTRACT

A tetrazolinone compound represented by formula (1):

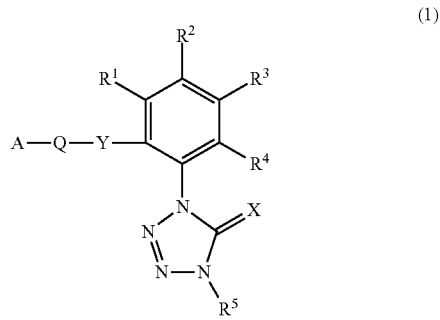

(1)

wherein $R^1$ represents a C1-C6 alkyl group; $R^2$, $R^3$, and $R^4$ are the same or different and represent a hydrogen atom; $R^5$ represents a C1-C3 alkyl group optionally having one or more halogen atoms; Y represents #—C($R^{4\,1}$ $R^{4\,2}$)—Z— in which left end and Q are bound to each other, and $R^{4\,1}$ and $R^{4\,2}$ each represents a hydrogen atom; Q represents a divalent C3-C10 carbocyclic group; X represents an oxygen atom; and A represents a C6-C10 aryl group, has excellent control activity against pests.

5 Claims, No Drawings

(51) Int. Cl.
*C07D 405/10* (2006.01)
*C07D 409/10* (2006.01)
*C07D 401/10* (2006.01)
*C07D 257/04* (2006.01)

(56) References Cited

U.S. PATENT DOCUMENTS

| | | | | |
|---|---|---|---|---|
| 9,314,023 | B2* | 4/2016 | Arimori | A01N 43/713 |
| 9,380,782 | B2* | 7/2016 | Yoshimoto | A01N 43/76 |
| 9,512,090 | B2* | 12/2016 | Shioda | C07D 403/12 |
| 9,521,848 | B2* | 12/2016 | Shioda | C07D 401/14 |
| 9,554,576 | B2* | 1/2017 | Arimori | C07D 403/12 |
| 9,565,856 | B2* | 2/2017 | Yoshimoto | C07D 403/12 |
| 9,635,857 | B2* | 5/2017 | Shioda | A01N 43/713 |
| 9,655,364 | B2* | 5/2017 | Matsuzaki | A01N 43/713 |
| 9,675,072 | B2* | 6/2017 | Arimori | C07D 403/12 |
| 9,730,448 | B2* | 8/2017 | Akioka | A01N 43/713 |
| 9,781,931 | B2* | 10/2017 | Matsuzaki | A01N 43/713 |
| 9,781,932 | B2* | 10/2017 | Matsuzaki | A01N 43/713 |
| 9,781,933 | B2* | 10/2017 | Hou | C07D 401/14 |
| 9,822,095 | B2* | 11/2017 | Dota | A01N 43/713 |
| 9,826,741 | B2* | 11/2017 | Dota | C07D 403/12 |
| 9,828,389 | B2* | 11/2017 | Arimori | C07D 403/12 |
| 2002/0133007 | A1 | 9/2002 | Gupta et al. | |
| 2011/0130415 | A1 | 6/2011 | Singh et al. | |
| 2015/0336908 | A1 | 11/2015 | Shioda et al. | |
| 2016/0081339 | A1 | 3/2016 | Yoshimoto et al. | |
| 2016/0081340 | A1 | 3/2016 | Arimori et al. | |
| 2016/0150787 | A1 | 6/2016 | Azuma et al. | |
| 2016/0157489 | A1 | 6/2016 | Shioda et al. | |
| 2016/0159755 | A1 | 6/2016 | Shioda et al. | |
| 2016/0174558 | A1 | 6/2016 | Hou et al. | |
| 2016/0205935 | A1* | 7/2016 | Akioka | A01N 43/713 |

FOREIGN PATENT DOCUMENTS

| | | |
|---|---|---|
| JP | 2013-512281 A | 4/2013 |
| JP | 2014-141451 A | 8/2014 |
| WO | WO 96/36229 A1 | 11/1996 |
| WO | WO 2013/092224 A1 | 6/2013 |
| WO | WO 2013/162072 A1 | 10/2013 |
| WO | WO 2013/162077 A1 | 10/2013 |
| WO | WO 2014/051161 A1 | 4/2014 |
| WO | WO 2014/051165 A1 | 4/2014 |
| WO | WO 2014/104268 A1 | 7/2014 |
| WO | WO 2014/104382 A1 | 7/2014 |
| WO | WO 2014/104384 A1 | 7/2014 |
| WO | WO 2014/175465 A1 | 10/2014 |
| WO | WO 2014/192953 A1 | 12/2014 |
| WO | WO 2015/005499 A1 | 1/2015 |
| WO | WO 2015/016335 A1 | 2/2015 |
| WO | WO 2015/016372 A1 | 2/2015 |
| WO | WO 2015/016373 A1 | 2/2015 |
| WO | WO 2015/030217 A1 | 3/2015 |
| WO | WO 2015/046480 A1 | 4/2015 |
| WO | WO 2015/056806 A1 | 4/2015 |
| WO | WO 2015/056811 A1 | 4/2015 |
| WO | WO 2015/060461 A1 | 4/2015 |

OTHER PUBLICATIONS

International Search Report for PCT/JP2014/079007 dated Jan. 6, 2015.
Written Opinion of the International Searching Authority for PCT/JP2014/079007 (PCT/ISA/237) dated Jan. 6, 2015.
Office Action (including an English translation thereof) issued in the corresponding Chinese Patent Application No. 201480058489.6 dated Apr. 5, 2017.

* cited by examiner

TETRAZOLINONE COMPOUND AND USE THEREOF

TECHNICAL FIELD

The present invention relates to a tetrazolinone compound and application for same.

BACKGROUND ART

Heretofore, various chemicals have been developed so as to control pests and provided in practice use, but in some cases, these chemicals may not exert enough activity.

Meanwhile, there have been known, as compounds having a tetrazolinone ring, compounds represented by the following formula (A):

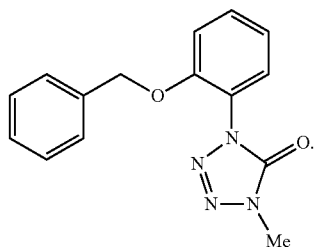

(see JPH09-208565 A)

DISCLOSURE OF THE INVENTION

The present invention provides compounds having excellent control activity against pests.

The present inventors have intensively studied so as to find compounds having excellent control activity against pests, and found that a tetrazolinone compound represented by the following formula (1) has excellent control activity against pests, thus completing the present invention.

The present invention includes the followings [1] to [6].

[1] A tetrazolinone compound represented by formula (1):

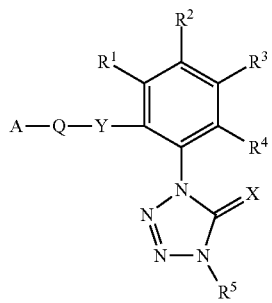

wherein $R^1$ represents a C1-C6 alkyl group, a C3-C6 cycloalkyl group, a halogen atom, a C1-C6 haloalkyl group, a C2-C6 alkenyl group, a C1-C6 alkoxy group, a C1-C6 alkylthio group, a C2-C6 alkynyl group, a nitro group, a cyano group, an aminocarbonyl group optionally having a C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a C2-C6 alkoxycarbonyl group, a hydroxy group, a sulfanyl group, an amino group optionally having a C1-C6 alkyl group, a pentafluorosulfanyl group, a C3-C9 trialkylsilyl group, a C5-C14 trialkylsilylethynyl group, a C1-C6 alkylsulfonyl group, a C1-C6 haloalkylsulfonyl group, a C1-C6 alkylsulfinyl group, a C1-C6 haloalkylsulfinyl group, a C2-C6 alkoxyalkyl group, or a C2-C6 alkylthioalkyl group;

$R^2$, $R^3$, and $R^4$ each independently represents a hydrogen atom, a halogen atom, a C1-C3 alkyl group, a C1-C3 haloalkyl group, a C2-C3 alkenyl group, a C2-C3 haloalkenyl group, or a C1-C3 alkoxy group;

$R^5$ represents a C1-C3 alkyl group optionally having one or more halogen atoms;

Y represents #—C($R^{A\,1}$ $R^{A\,2}$)—Z—, #—C($R^{A\,1}$ $R^{A\,2}$)C($R^{A\,3}$ $R^{A\,4}$)—Z—, #—C($R^{A\,1}$ $R^{A\,2}$)—Z—C($R^{A\,3}$ $R^{A\,4}$)—, #—Z—C($R^{A\,1}$ $R^{A\,2}$)C($R^{A\,3}$ $R^{A\,4}$)—, #—C($R^{A\,1}$ $R^{A\,2}$)C($R^{A\,3}$ $R^{A\,4}$)C($R^{A\,5}$ $R^{A\,6}$)—Z—, #—C($R^{A\,1}$ $R^{A\,2}$)C($R^{A\,3}$ $R^{A\,4}$)—Z—C($R^{A\,5}$ $R^{A\,6}$)—, #—C($R^{A\,1}$ $R^{A\,2}$)—Z—C($R^{A\,3}$ $R^{A\,4}$)C($R^{A\,5}$ $R^{A\,6}$)—, #—Z—C($R^{A\,1}$ $R^{A\,2}$)C($R^{A\,3}$ $R^{A\,4}$)C($R^{A\,5}$ $R^{A\,6}$)—, #—C($R^{A\,1}$)=C($R^{A\,2}$)C($R^{A\,3}$ $R^{A\,4}$)—Z—, #—Z—C($R^{A\,1}$ $R^{A\,2}$)C($R^{A\,3}$)=C($R^{A\,4}$)—, #—C≡C—C($R^{A\,1}$ $R^{A\,2}$)—Z—, #—Z—C($R^{A\,1}$ $R^{A\,2}$)—C≡C—, #—Z—C($R^{A\,1}$ $R^{A\,2}$)C($R^{A\,3}$ $R^{A\,4}$)—Z—, #—C($R^{A\,1}$)=C($R^{A\,2}$)—, #—C($R^{A\,1}$)=C($R^{A\,2}$)C($R^{A\,3}$ $R^{A\,4}$)—, #—C($R^{A\,1}$)=C($R^{A\,2}$)C($R^{A\,3}$ $R^{A\,4}$)C($R^{A\,5}$ $R^{A\,6}$)—, #—C($R^{A\,1}$ $R^{A\,2}$)C($R^{A\,3}$)=C($R^{A\,4}$) C($R^{A\,5}$ $R^{A\,6}$)—, #—C($R^{A\,1}$ $R^{A\,2}$)C($R^{A\,3}$ $R^{A\,4}$)C($R^{A\,5}$)= C($R^{A\,6}$)—, #—C($R^{A\,1}$)=C($R^{A\,2}$)C($R^{A\,3}$)=C($R^{A\,4}$)—, —C≡C—, #—C≡C—C($R^{A\,1}$ $R^{A\,2}$)—, #—C≡C—C($R^{A\,1}$ $R^{A\,2}$)C($R^{A\,3}$ $R^{A\,4}$)—, #—C($R^{A\,1}$ $R^{A\,2}$)C($R^{A\,3}$ $R^{A\,4}$)—C≡C—, or #—C($R^{A\,1}$ $R^{A\,2}$)—C≡C—C($R^{A\,3}$ $R^{A\,4}$)—, wherein the symbol # represents a binding site for Q, $R^{A\,1}$, $R^{A\,2}$, $R^{A\,3}$, $R^{A\,4}$, $R^{A\,5}$, and $R^{A\,6}$ each independently represents a hydrogen atom, a halogen atom, or a C1-C3 alkyl group, Z represents an oxygen atom, a sulfur atom, or $NR^C$, and $R^C$ represents a C1-C6 alkyl group, a C1-C6 haloalkyl group, a C3-C6 cycloalkyl group, or a C3-C6 halocycloalkyl group;

Q represents a divalent C3-C10 carbocyclic group or a divalent heterocyclic group, wherein the divalent heterocyclic group is a single or fused ring having, as a ring-constituent atom, one or more atoms selected from the group consisting of a nitrogen atom, an oxygen atom, and a sulfur atom, and when two or more of the atoms are present, those atoms may be the same or different to each other, and the heterocyclic group represents a ring in which a 5-membered ring is fused with a 5-membered ring, a 5-membered ring is fused with a 6-membered ring, and a 6-membered ring is fused with a 6-membered ring when the heterocyclic group is a fused ring;

X represents an oxygen atom or a sulfur atom;

A represents a C6-C10 aryl group, a C6-C10 aryloxy group, a C6-C10 arylthio group, a C6-C10 arylsulfonyl group, a C6-C10 arylamino group, a hydrogen atom, a heterocyclic group, or $R^B$—O—N=C($R^B$)—, wherein the heterocyclic group has, as a ring-constituent atom, one or more atoms selected from the group consisting of a nitrogen atom, an oxygen atom, and a sulfur atom, and when two or more of the atoms are present, those atoms may be the same or different to each other, and $R^B$ represents a C1-C6 alkyl group, a C1-C6 haloalkyl group, a C3-C6 cycloalkyl group, or a C3-C6 halocycloalkyl group, wherein the divalent C3-C10 carbocyclic group and the divalent heterocyclic group of Q, and the C6-C10 aryl group, the C6-C10 aryloxy group, the C6-C10 arylthio group, the C6-C10 arylamino group, and the heterocyclic group of A optionally have one or more atoms or groups selected from Group $P^1$:

Group $P^1$: Group consisting of a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a carboxy group, a formyl group, a C2-C6 alkoxycarbonyl group, a nitro group, a cyano group, a hydroxy group, a C1-C6 alkylsulfonyl group, a C1-C6 haloalkylsulfonyl group, a C1-C6 alkylsulfinyl group, a C1-C6 haloalkylsulfinyl group, an amino group optionally having a C1-C6 alkyl group, an aminosulfonyl group optionally having a C1-C6 alkyl group, and an aminocarbonyl group optionally having a C1-C6 alkyl group.

[2] The tetrazolinone compound according to [1], wherein, in formula (1),
$R^1$ is a methyl group;
$R^2$, $R^3$, and $R^4$ are hydrogen atoms;
$R^5$ is a methyl group;
Y is #—CH($R^{4\ 7}$)—O—, #—CH($R^{4\ 7}$)—O—CH$_2$—, #—CH($R^{4\ 7}$)CH$_2$—O—CH$_2$—, or —CH═CH—, wherein is the same as defined above, and $R^{4\ 7}$ represents a hydrogen atom or a methyl group);
Q is a divalent benzene ring, a thiazole ring, or a pyrazole ring group (in which the divalent benzene ring, the thiazole ring, or the pyrazole ring group of Q optionally has one or more atoms or groups selected from Group $P^2$);
X is an oxygen atom; and
A is a phenyl group, a phenoxy group, a hydrogen atom, a 2-pyridyl group, or a 2-pyrimidinyl group, wherein the phenyl group, the phenoxy group, the hydrogen atom, the 2-pyridyl group, or the 2-pyrimidinyl group optionally has one or more atoms or groups selected from Group $P^2$:
Group $P^2$: Group consisting of a halogen atom, a methyl group, a trifluoromethyl group, a methoxy group, a methylsulfonyl group, and a diethylaminosulfonyl group.
[3] The tetrazolinone compound according to [1], wherein, in formula (1),
$R^1$ is a methyl group;
$R^2$, $R^3$, and $R^4$ are hydrogen atoms;
$R^5$ is a methyl group;
Y is #—CH($R^{4\ 7}$)—O— (in which # and $R^{4\ 7}$ are the same as defined above);
Q is a divalent benzene ring, a thiazole ring, or a pyrazole ring group, wherein the divalent benzene ring, the thiazole ring, or the pyrazole ring group of Q optionally has one or more atoms or groups selected from Group $P^2$;
X is an oxygen atom; and
A is a phenyl group, a hydrogen atom, or a 2-pyridyl group, wherein the phenyl group or the 2-pyridyl group optionally has one or more atoms or groups selected from Group $P^2$:

Group $P^2$: Group consisting of a halogen atom, a methyl group, a trifluoromethyl group, and a methoxy group.
[4] A pest control agent comprising the tetrazolinone compound according to any one of [1], [2], and [3].
[5] A method for controlling pests, which comprises treating plants or soil with an effective amount of the tetrazolinone compound according to any one of [1], [2], and [3].
[6] Use of the tetrazolinone compound according to any one of [1], [2], and [3] for controlling pests.

According to the present invention, pests can be controlled.

MODE FOR CARRYING OUT THE INVENTION

A tetrazolinone compound represented by formula (1):

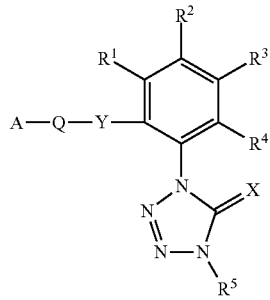

wherein $R^1$ to $R^5$, Y, Q, X, and A are the same as defined above, sometimes referred to as the present compound, and a pest control agent including the present compound sometimes referred to as the present control agent.

Substituents as used herein will be mentioned below.
Examples of the halogen atom include a fluorine atom, a chlorine atom, a bromine atom, and an iodine atom.
Examples of the C1-C6 alkyl group include a methyl group, an ethyl group, a propyl group, an isopropyl group, a butyl group, an isobutyl group, a sec-butyl group, a tert-butyl group, a pentyl group, and a hexyl group.
The C1-C6 haloalkyl group represents a group in which at least one hydrogen atom of a C1-C6 alkyl group is substituted with a halogen atom, and examples thereof include a fluoromethyl group, a chloromethyl group, a trifluoromethyl group, a trichloromethyl group, a pentafluoroethyl group, a 3,3,3-trifluoropropyl group, and a perfluorohexyl group.
Examples of the C2-C6 alkenyl group include a vinyl group, a 1-propenyl group, an isopropenyl group, a 2-propenyl group, a 1-butenyl group, a 2-butenyl group, a 1-methyl-2-propenyl group, a 1,3-butadienyl group, a 1-pentenyl group, a 1-methyl-1-butenyl group, a 1,1-dimethyl-2-propenyl group, a 3-methyl-2-butenyl group, a 1,3-pentadienyl group, a 1-vinyl-2-propenyl group, and a 5-hexenyl group.
The C2-C6 haloalkenyl group represents a group in which at least one hydrogen atom of a C2-C6 alkenyl group is substituted with a halogen atom, and examples thereof include a 2,2-dichlorovinyl group, a 2,2-difluorovinyl group, a 3-chloro-2-propenyl group, a 3,3,3-trifluoro-1-propenyl group, a 3,3,3-trichloro-1-propenyl group, a 4,4,4-trifluoro-2-butenyl group, a perfluorobutenyl group, a 5,5-difluoro-4-pentenyl group, a perfluoropentenyl group, and a perfluorohexenyl group.
Examples of the C2-C6 alkynyl group include an ethynyl group, a propargyl group, a 2-butynyl group, a 3-butynyl group, a 4-pentynyl group, and a 5-hexynyl group.

The C2-C6 haloalkynyl group represents a group in which at least one hydrogen atom of a C2-C6 alkynyl group is substituted with a halogen atom, and examples thereof include a perfluoroethynyl group, a 3-chloro-2-propynyl group, a 3,3,3-trifluoro-1-propynyl group, a perfluoro-2-butynyl group, a perfluoro-2-pentynyl group, a 5-trifluoro-1-pentynyl group, a 6-trifluoro-1-hexynyl group, and a perfluoro-1-hexynyl group.

Examples of the C3-C6 cycloalkyl group include a cyclopropyl group, a cyclobutyl group, a cyclopentyl group, and a cyclohexyl group.

The C3-C6 halocycloalkyl group represents a group in which at least one hydrogen atom of a C3-C6 cycloalkyl group is substituted with a halogen atom, and examples thereof include a 2-fluorocyclopropyl group, a 2,2-difluorocyclopropyl group, a 2,2-dichlorocyclopropyl group, a 2,2,3,3-tetrafluorocyclopropyl group, a 4,4-difluorocyclohexyl group, and a perfluorocyclohexyl group.

Examples of the C1-C6 alkoxy group include a methoxy group, an ethoxy group, a propoxy group, an isopropoxy group, a butoxy group, a tert-butoxy group, a pentyloxy group, and a hexyloxy group.

The C1-C6 haloalkoxy group represents a group in which at least one hydrogen atom of a C1-C6 alkoxy group is substituted with a halogen atom, and examples thereof include a trifluoromethoxy group, a trichloromethoxy group, a perfluoroethoxy group, a perchloroethoxy group, a 2,2,2-trichloroethoxy group, a 2,2,2-trifluoroethoxy group, a 3,3,3-trifluoropropoxy group, a 3,3,3-trichloropropoxy group, a perfluorobutoxy group, a perchlorobutoxy group, a perfluoropentyloxy group, and a perfluorohexyloxy group.

Examples of the C1-C6 alkylthio group include a methylthio group, an ethylthio group, a propylthio group, an isopropylthio group, a butylthio group, a sec-butylthio group, a tert-butylthio group, a pentylthio group, and a hexylthio group.

The C1-C6 haloalkylthio group represents a group in which at least one hydrogen atom of a C1-C6 alkylthio group is substituted with a halogen atom, and examples thereof include a fluoromethylthio group, a difluoromethylthio group, a trifluoromethylthio group, a trichloromethylthio group, a pentafluoroethylthio group, a 2,2,2-trichloroethylthio group, a 2,2,2-trifluoroethylthio group, a perfluoropropylthio group, a 3,3,3-trifluoropropylthio group, a 3,3,3-trichloropropylthio group, a perfluorobutylthio group, a perfluoropentylthio group, and a perfluorohexylthio group.

Examples of the C3-C6 cycloalkyloxy group include a cyclopropyloxy group, a cyclobutyloxy group, a cyclopentyloxy group, and a cyclohexyloxy group.

The C3-C6 halocycloalkyloxy group represents a group in which at least one hydrogen atom of a C3-C6 cycloalkyloxy group is substituted with a halogen atom, and examples thereof include a 2-fluorocyclopropyloxy group, a 2,2-difluorocyclopropyloxy group, a 2,2,3,3-tetrafluorocyclopropyloxy group, a 2-chlorocyclohexyloxy group, a 4,4-difluorocyclohexyloxy group, and a 4-chlorocyclohexyloxy group.

Examples of the C3-C6 cycloalkylthio group include a cyclopropylthio group, a cyclobutylthio group, a cyclopentylthio group, and a cyclohexylthio group.

Examples of the C3-C6 alkenyloxy group include a 2-propenyloxy group, a 2-butenyloxy group, a 3-butenyloxy group, 2-pentenyloxy group, a 4-pentenyloxy group, and a 5-hexenyloxy group.

Examples of the C3-C6 alkynyloxy group include a propargyloxy group, a 3-butyn-2-yloxy group, a 2-methyl-3-butyn-2-yloxy group, a 2-butynyloxy group, a 3-butynyloxy group, a 2-pentynyloxy group, a 3-pentynyloxy group, a 4-pentynyloxy group, and a 5-hexynyloxy group.

The C3-C6 haloalkenyloxy group represents a group in which at least one hydrogen atom of a C3-C6 alkenyloxy group is substituted with a halogen atom, and examples thereof include a 3-chloro-2-propenyloxy group, a 2,3,3,3-tetrachloro-1-propenyloxy group, a 3,3-difluoro-2-propenyloxy group, a 3,3-dichloro-2-propenyloxy group, a 3,3,3-trifluoropropenyloxy group, a 4,4,4-trifluoro-2-butenyloxy group, and a 5,5,5-trifluoro-2-pentenyloxy group.

The C3-C6 haloalkynyloxy group represents a group in which at least one hydrogen atom of a C3-C6 alkynyloxy group is substituted with a halogen atom, and examples thereof include a 3-chloro-2-propynyloxy group, a 3-bromo-2-propynyloxy group, a 3-iodo-2-propynyloxy group, a 5-chloro-4-pentynyloxy group, a 3-fluoro-2-propynyloxy group, a perfluoro-2-butynyloxy group, a perfluoro-3-butynyloxy group, a perfluoro-2-pentynyloxy group, a perfluoro-3-pentynyloxy group, a perfluoro-4-pentynyloxy group, and a perfluoro-5-hexynyloxy group.

Examples of the C3-C6 alkenylthio group include a 2-propenylthio group, a 2-butenylthio group, a 1-methyl-2-propenylthio group, a 3-butenylthio group, a 2-methyl-2-propenylthio group, a 2-pentenylthio group, a 3-pentenylthio group, a 4-pentenylthio group, a 1-methyl-3-butenylthio group, a 1,2-dimethyl-2-propenylthio group, a 1,1-dimethyl-2-propenylthio group, a 2-methyl-2-butenylthio group, a 3-methyl-2-butenylthio group, a 2-methyl-3-butenylthio group, a 3-methyl-3-butenylthio group, a 1-vinyl-2-propenylthio group, and a 5-hexenylthio group.

Examples of the C3-C6 alkynylthio group include a propargylthio group, a 3-butyn-2-ylthio group, a 2-methyl-3-butyn-2-ylthio group, a 2-butynylthio group, a 3-butynylthio group, a 2-pentynylthio group, a 3-pentynylthio group, a 4-pentynylthio group, and a 5-hexynylthio group.

The C3-C6 haloalkenylthio group represents a group in which at least one hydrogen atom of a C3-C6 alkenylthio group is substituted with a halogen atom, and examples thereof include a 3,3-difluoro-2-propenylthio group, a 3,3-dichloro-2-propenylthio group, a 4,4,4-trifluoro-2-butenylthio group, a 3,3-difluoro-2-methyl-2-propenylthio group, a 4,4,4-trifluoro-3-methyl-2-butenylthio group, a 3,5,5-trifluoro-2,4-pentadienylthio group, a 4,4,5,5,6,6,6-heptafluoro-2-hexenylthio group, a 4,5,5,5-tetrafluoro-4-trifluoromethyl-2-pentenylthio group, and a 5-bromo-4,5,5-trifluoro-4-trifluoromethyl-2-pentenylthio group.

The C3-C6 haloalkynylthio group represents a group in which at least one hydrogen atom of a C3-C6 alkynylthio group is substituted with a halogen atom, and examples thereof include a 3-chloro-2-propynylthio group, a 3-bromo-2-propynylthio group, a 3-iodo-2-propynylthio group, a 5-chloro-4-pentynylthio group, a 3-fluoro-2-propynylthio group, a perfluoro-2-butynylthio group, a perfluoro-3-butynylthio group, a perfluoro-2-pentynylthio group, a perfluoro-3-pentynylthio group, a perfluoro-4-pentynylthio group, and a perfluoro-5-hexynylthio group.

The C2-C6 alkylcarbonyl group represents a carbonyl group having an alkyl group having 1-5 carbon atoms, and examples thereof include an acetyl group, a propionyl group, a butyryl group, an isobutyryl group, a pivaloyl group, a pentanoyl group, and a hexanoyl group.

The C2-C6 haloalkylcarbonyl group represents a group in which at least one hydrogen atom of a C2-C6 alkylcarbonyl group is substituted with a halogen atom, and examples thereof include a trichloroacetyl group, a trifluoroacetyl group, a pentafluoropropionyl group, a 2,2,2-trichloropropionyl group, a 2,2,2-trifluoropropionyl group, a heptafluorobutyryl group, a heptachlorobutyryl group, a 3,3,3-trifluorobutyryl group, a 3,3,3-trichlorobutyryl group, a nonafluoropentanoyl group, a nonachloropentanoyl group, and a perfluorohexanoyl group.

The C2-C6 alkylcarbonyloxy group represents a carbonyloxy group having an alkyl group having 1-5 carbon atoms, and examples thereof include an acetyloxy group, a propionyloxy group, a butyryloxy group, a pentanoyloxy group, and a hexanoyloxy group.

The C2-C6 alkylcarbonylthio group represents a carbonylthio group having an alkyl group having 1-5 carbon atoms, and examples thereof include an acetylthio group, a propionylthio group, a butyrylthio group, a pentanoylthio group, and a hexanoylthio group.

The C2-C6 alkoxycarbonyl group represents a carbonylthio group which has an alkoxy group having 1-5 carbon atoms, and examples thereof include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isoamyloxycarbonyl group, a neopentyloxycarbonyl group, a 2-pentyloxycarbonyl group, a 3-pentyloxycarbonyl group, and a 2-methylbutoxycarbonyl group.

The aminocarbonyl group optionally having a C1-C6 alkyl group represents an aminocarbonyl group in which one or two hydrogen atoms on nitrogen are optionally substituted with the same or different C1-C6 alkyl group(s), and examples thereof include an aminocarbonyl group, a methylaminocarbonyl group, an ethylaminocarbonyl group, a propylaminocarbonyl group, an isopropylaminocarbonyl group, a butylaminocarbonyl group, a dimethylaminocarbonyl group, a diethylaminocarbonyl group, a dipropylaminocarbonyl group, a diisopropylaminocarbonyl group, a pentylaminocarbonyl group, and a hexylaminocarbonyl group.

The aminosulfonyl group optionally having a C1-C6 alkyl group represents an aminosulfonyl group in which one or two hydrogen atoms on nitrogen are optionally substituted with the same or different C1-C6 alkyl group(s), and examples thereof include an aminosulfonyl group, a methylaminosulfonyl group, an ethylaminosulfonyl group, a propylaminosulfonyl group, an isopropylaminosulfonyl group, a butylaminosulfonyl group, a dimethylaminosulfonyl group, a diethylaminosulfonyl group, a dipropylaminosulfonyl group, a diisopropylaminosulfonyl group, a pentylaminosulfonyl group, and a hexylaminosulfonyl group.

"Optionally having one or more atoms or groups selected from Group $P^1$" represents that a hydrogen atom is optionally substituted with one or more atoms or groups selected from Group $P^1$ and, when substituted with two or more atoms or groups, those atoms and groups may be the same or different to each other.

Examples of the C6-C10 aryl group include a phenyl group, a 1-naphthyl group, and a 2-naphthyl group.

The C3-C10 carbocyclic ring represents a monocyclic or bicyclic saturated carbocyclic ring such as cyclopropane, cyclobutane, cyclohexane, or bicyclo[4.4.0]decane (in which bicyclic saturated carbocyclic ring represents a ring in which a 5-membered ring is fused with a 5-membered ring, a 5-membered ring is fused with a 6-membered ring, or a 6-membered ring is fused with a 6-membered ring); and a monocyclic or bicyclic aromatic carbocyclic ring such as benzene or naphthalene (in which the dicyclic aromatic carbocyclic ring represents a ring in which a 5-membered ring is fused with a 5-membered ring, a 5-membered ring is fused with a 6-membered ring, or a 6-membered ring is fused with a 6-membered ring).

Examples of the divalent C3-C10 carbocyclic group include a divalent C6-C10 aryl group such as a phenylene group or a napthylene group, and a monocyclic or bicyclic divalent saturated carbocyclic group such as a cyclopropane-diyl group, a cyclobutane-diyl group, a cyclopentane-diyl group, a cyclohexane-diyl group, a cycloheptane-diyl group, a cyclooctane-diyl group, or a decahydronaphthalene-diyl group, and the divalent C3-C10 carbocyclic group is preferably a divalent C6-C10 aryl group, and more preferably a phenylene group.

Examples of the C6-C10 aryloxy group include a phenoxy group, a 1-naphthyloxy group, and a 2-naphthyloxy group.

Examples of the C6-C10 arylthio group include a phenylthio group, a 1-naphthylthio group, and a 2-naphthylthio group.

The C6-C10 arylamino group represents a group in which one hydrogen atom on nitrogen of an amino group is substituted with a C6-C10 aryl group, and examples thereof include a phenylamino group, a 1-naphthylamino group, and a 2-naphthylamino group.

Examples of the C3-C9 trialkylsilyl group include a trimethylsilyl group, a tert-butyl(dimethyl)silyl group, a triethylsilyl group, an isopropyl(dimethyl)silyl group, and a triisopropylsilyl group.

The C5-C14 trialkylsilylethynyl group represents an ethynyl group to which a trialkylsilyl group is bound, and represents a group in which the total number of carbon atoms including the number of carbon atoms of an ethynyl group is within a range of 5 to 14, and examples thereof include a (trimethylsilyl)ethynyl group, a (trimethylsilyl)ethynyl group, a (triethylsilyl)ethynyl group, a [isopropyl(dimethyl)silyl]ethynyl group, a (triisopropylsilyl)ethynyl group, a [tri(tert-butyl)silyl]ethynyl group, and a (tributylsilyl)ethynyl group.

Examples of the C1-C6 alkylsulfonyl group include a methylsulfonyl group, an ethylsulfonyl group, a propylsulfonyl group, an isopropylsulfonyl group, a butylsulfonyl group, an isobutylsulfonyl group, a pentylsulfonyl group, an isoamylsulfonyl group, a neopentylsulfonyl group, a 2-pentylsulfonyl group, a 3-pentylsulfonyl group, a 2-methylbutylsulfonyl group, and a hexylsulfonyl group.

The C1-C6 haloalkylsulfonyl group represents a group in which at least one hydrogen atom of a C1-C6 alkylsulfonyl group is substituted with a halogen atom, and examples thereof include a trifluoromethylsulfonyl group, a trichloromethylsulfonyl group, a pentafluoroethylsulfonyl group, a pentachloroethylsulfonyl group, a 2,2,2-trichloroethylsulfonyl group, a 2,2,2-trifluoroethylsulfonyl group, a heptafluoropropylsulfonyl group, a heptachloropropylsulfonyl group, a 3,3,3-trifluoropropylsulfonyl group, a 3,3,3-trichloropropylsulfonyl group, a nonafluorobutylsulfonyl group, a nonachlorobutylsulfonyl group, a perfluoropentylsulfonyl group, a perchloropentylsulfonyl group, a perfluorohexylsulfonyl group, and a perchlorohexylsulfonyl group.

Examples of the C6-C10 arylsulfonyl group include a phenylsulfonyl group, a 1-naphthylsulfonyl group, and a 2-naphthylsulfonyl group.

Examples of the C1-C6 alkylsulfinyl group include a methylsulfinyl group, an ethylsulfinyl group, a propylsulfinyl group, an isopropylsulfinyl group, a butylsulfinyl group, an isobutylsulfinyl group, a pentylsulfinyl group, an isoamylsulfinyl group, a neopentylsulfinyl group, a 2-pentylsulfinyl group, a 3-pentylsulfinyl group, a 2-methylbutylsulfinyl group, a hexylsulfinyl group, an isohexylsulfinyl group, a 3-methylpentylsulfinyl group, and a 4-methylpentylsulfinyl group.

The C1-C6 haloalkylsulfinyl group represents a group in which at least one hydrogen atom of a C1-C6 alkylsulfinyl group is substituted with a halogen atom, and examples thereof include a trifluoromethylsulfinyl group, a trichloromethylsulfinyl group, a tribromomethylsulfinyl group, a triiodomethylsulfinyl group, a pentafluoroethylsulfinyl group, a pentachloroethylsulfinyl group, a 2,2,2-trichloroethylsulfinyl group, a 2,2,2-trifluoroethylsulfinyl group, a heptafluoropropylsulfinyl group, a heptachloropropylsulfinyl group, a 3,3,3-trifluoropropylsulfinyl group, a 3,3,3-trichloropropylsulfinyl group, a nonafluorobutylsulfinyl group, a nonachlorobutylsulfinyl group, a perfluoropentylsulfinyl group, a perchloropentylsulfinyl group, a perfluorohexylsulfinyl group, and a perchlorohexylsulfinyl group.

Examples of the C1-C3 alkyl group include a methyl group, an ethyl group, a propyl group, and an isopropyl group.

The C1-C3 alkyl group optionally having one or more halogen atoms represents a group in which at least one hydrogen atom of a C1-C3 alkyl group is substituted with a halogen atom, and examples thereof include a methyl group, an ethyl group, a propyl group, an isopropyl group, a chloromethyl group, a dichloromethyl group, a fluoromethyl group, a difluoromethyl group, a trifluoromethyl group, a trichloromethyl group, a 2,2,2-trifluoroethyl group, a 2,2,2-trichloroethyl group, a pentafluoroethyl group, a pentachloroethyl group, a 3,3,3-trifluoropropyl group, a heptafluoropropyl group, and a 1-(fluoromethyl)-2-fluoroethyl group.

The C1-C3 haloalkyl group represents a group in which at least one hydrogen atom of a C1-C3 alkyl group is substituted with a halogen atom, and examples thereof include a chloromethyl group, a dichloromethyl group, a fluoromethyl group, a difluoromethyl group, a trifluoromethyl group, a trichloromethyl group, a 2-fluoroethyl group, a 2,2-difluoroethyl group, a 2,2,2-trifluoroethyl group, a 2-chloroethyl group, a 2,2-dichloroethyl group, a 2,2,2-trichloroethyl group, a pentafluoroethyl group, a pentachloroethyl group, a 2-fluoropropyl group, a 3-fluoropropyl group, a 2,2-difluoropropyl group, a 2,3-difluoropropyl group, a 3,3,3-trifluoropropyl group, and a heptafluoropropyl group.

Examples of the C2-C3 alkenyl group include an ethenyl group and a propenyl group.

The C2-C3 haloalkenyl group represents a group in which at least one hydrogen atom of a C2-C3 alkenyl group is substituted with a halogen atom, and examples thereof include a 1-bromoethenyl group, a 2-bromoethenyl group, a 2-dibromoethenyl group, a 1-fluoroethenyl group, a 2-fluoroethenyl group, a 2-difluoroethenyl group, a 1-chloroethenyl group, a 2-chloroethenyl group, a 2-dichloroethenyl group, a 1,2-dichloroethenyl group, a 2-iodoethenyl group, a 3-fluoro-1-propenyl group, a 3,3,3-trifluoro-1-propenyl group, a 3-chloro-1-propenyl group, a 3,3,3-trichloro-1-propenyl group, a 3-fluoro-2-propenyl group, a 3-difluoro-2-propenyl group, a 3,3,3-trifluoro-2-propenyl group, a 3-chloro-2-propenyl group, a 3-dichloro-2-propenyl group, and a 3,3,3-trichloro-2-propenyl group.

The amino group optionally having a C1-C6 alkyl group represents an amino group in which one or two hydrogen atoms on nitrogen are optionally substituted with the same or different C1-C6 alkyl group(s), and examples thereof include an amino group, a methylamino group, an ethylamino group, a propylamino group, an isopropylamino group, a butylamino group, a dimethylamino group, a diethylamino group, a dipropylamino group, an ethyl(methyl)amino group, and a methyl(propyl)amino group.

The C2-C6 alkoxyalkyl group represents a group in which the total number of carbon atoms of the alkoxy moiety and the alkyl moiety is within a range of 2 to 6, and examples thereof include a methoxymethyl group, an ethoxymethyl group, a propoxymethyl group, an isopropoxymethyl group, a butoxymethyl group, an isobutoxymethyl group, a sec-butoxymethyl group, a pentyloxymethyl group, a 1-methoxyethyl group, a 2-methoxyethyl group, a 2-propoxyethyl group, a 2-isopropoxyethyl group, a 2-butoxyethyl group, and a 2-isobutoxyethyl group.

The C2-C6 alkylthioalkyl group represents a group in which the total number of carbon atoms of the entire alkylthioalkyl group is within a range of 2 to 6, and examples thereof include a methylthiomethyl group, an ethylthiomethyl group, a propylthiomethyl group, an isopropylthiomethyl group, a butylthiomethyl group, an isobutylthiomethyl group, a sec-butylthiomethyl group, a pentylthiomethyl group, a 1-methylthioethyl group, a 2-methylthioethyl group, a 2-propylthioethyl group, a 2-isopropylthioethyl group, a 2-butylthioethyl group, and a 2-isobutylthioethyl group.

Examples of the C1-C3 alkoxy group include a methoxy group, an ethoxy group, a propoxy group, and an isopropoxy group.

The hetero ring represents a 5-membered ring, a 6-membered ring, a ring in which a 5-membered ring is fused with a 6-membered ring, and a ring in which a 6-membered ring is fused with a 6-membered ring, and the hetero ring may be either saturated or unsaturated, and has, as a ring-constituent atom, one or more atoms selected from the group consisting of a nitrogen atom, an oxygen atom, and a sulfur atom, and when having two or more atoms, those atoms may be the same or different to each other. Examples of the hetero ring include thiazole, oxazole, pyridine, benzimidazole, and quinolone.

Examples of the heterocyclic group include a pyridyl group, a pyrimidinyl group, a pyrazinyl group, a pyridazinyl group, a triazinyl group, a furyl group, a thienyl group, a thiazolyl group, an oxazolyl group, an isoxazolyl group, an isothiazolyl group, a pyrazolyl group, an imidazolyl group, a triazolyl group, a thiadiazolyl group, an oxadiazolyl group, a 1,2,3,4-tetrahydronaphthalenyl group, a pyrazolopyridyl group, a pyrazolopyrimidinyl group, a benzotriazinyl group, a quinolyl group, an isoquinolyl group, a quinoxalinyl group, a benzotriazinyl group, a cinnolinyl group, a naphthylidinyl group, an oxacyclopentyl group, an oxacyclohexyl group, a pyrrolidinyl group, a piperazyl group, a morpholinyl group, and an oxazine group; and a pyridyl group, a pyrazolyl group, and a thiazolyl group are preferably exemplified.

Examples of the divalent heterocyclic group include a pyridine-di-yl group, a pyrimidine-di-yl group, a pyrazine-di-yl group, a pyridazine-di-yl group, a 1,3,5-triazine-di-yl group, a 1,2,4-triazine-di-yl group, a furan-di-yl group, a thiophene-di-yl group, a thiazoline-di-yl group, an oxazoline-di-yl group, an isoxazoline-di-yl group, an isothiazoline-di-yl group, a pyrazoline-di-yl group, an imidazoline-di-yl group, a 1,2,4-triazoline-di-yl group, a 1,2,3-triazoline-di-yl group, a 1,2,4-thiadiazoline-di-yl group, a 1,2,4-oxadiazoline-di-yl group, a 1,3,4-thiadiazoline-di-yl group, a 1,3,4-oxadiazoline-di-yl group, a 1,2,3-thiadiazoline-di-yl group, a 1,2,3-oxadiazoline-di-yl group, a tetrazoline-di-yl group, a 1,2,3,4-tetrahydronaphthalene-di-yl group, a pyrazolopyridine-di-yl group, a pyrazolopyrimidine-di-yl group, a 1,2,4-benzotriazine-di-yl group, a quinoline-di-yl group, an isoquinoline-di-yl group, a quinoxaline-di-yl group, an oxacyclopropane-di-yl group, an oxacyclobutane-di-yl group, an oxacyclopentane-di-yl group, an oxacyclohexane-di-yl group, an azacyclopropane-di-yl group, an azacyclobutane-di-yl group, a pyrrolidine-di-yl group, a piperazine-di-yl group, a morpholine-di-yl group, a thiocyclopropane-di-yl group, a thiocyclobutane-di-yl group, a thiocyclopentane-di-yl group, an oxazoline-di-yl group, an isoxazoline-di-yl group, a thiazoline-di-yl group, and an oxazine-di-yl group.

As used herein, in structural formulas represented by general formulas, individual isomers and isomer mixtures, such as all active geometrical isomers and optical isomers are included in the present invention.

Examples of the aspect of the compound represented by formula (1) include following compounds.

A tetrazolinone compound in which Y is #—$CH_2Z$—.
A tetrazolinone compound in which Y is #—$CH_2O$—.
A tetrazolinone compound in which Y is #—$CH_2S$—.
A tetrazolinone compound in which Y is —CH=CH—.
[Aspect 1]
A tetrazolinone compound in which $R^2$, $R^3$, and $R^4$ are hydrogen atoms; $R^4$ is a C1-C3 alkyl group, a C1-C3 haloalkyl group, a C3-C4 cycloalkyl group, a halogen atom, a C1-C3 alkoxy group, a C1-C3 haloalkoxy group, or a C1-C3 alkylthio group; $R^5$ is a methyl group; and X is an oxygen atom.
[Aspect 2]
A tetrazolinone compound in which Q is a phenylene group optionally having one or more groups or atoms selected from Group $P^1$ in [Aspect 1].
[Aspect 3]
A tetrazolinone compound in which Q is a pyridylene group optionally having one or more groups or atoms selected from Group $P^1$ in [Aspect 1].
[Aspect 4]
A tetrazolinone compound in which Q is a pyrimidylene group optionally having one or more groups or atoms selected from Group $P^1$ in [Aspect 1].
[Aspect 5]
A tetrazolinone compound in which Q is a thiazolylene group optionally having one or more groups or atoms selected from Group $P^1$ in [Aspect 1].
[Aspect 6]
A tetrazolinone compound in which Q is a pyrazolylene group optionally having one or more groups or atoms selected from Group $P^1$ in [Aspect 1].

A tetrazolinone compound in which A is a phenyl group optionally having one or more groups or atoms selected from Group $P^1$; and Y is #—$CH_2O$— in [Aspect 2].

A tetrazolinone compound in which A is a pyridyl group optionally having one or more groups or atoms selected from Group $P^1$; and Y is #—$CH_2O$— in [Aspect 2].

A tetrazolinone compound in which A is a pyrimidinyl group optionally having one or more groups or atoms selected from Group $P^1$; and Y is #—$CH_2O$— in [Aspect 2]

A tetrazolinone compound in which A is a pyrazolyl group optionally having one or more groups or atoms selected from Group $P^1$; and Y is #—$CH_2O$— in [Aspect 2]

A tetrazolinone compound in which A is a phenyl group optionally having one or more groups or atoms selected from Group $P^1$; and Y is #—$CH_2O$— in [Aspect 3].

A tetrazolinone compound in which A is a pyridyl group optionally having one or more groups or atoms selected from Group $P^1$; and Y is #—$CH_2O$— in [Aspect 3].

A tetrazolinone compound in which A is a pyrimidinyl group optionally having one or more groups or atoms selected from Group $P^1$; and Y is #—$CH_2O$— in [Aspect 3].

A tetrazolinone compound in which A is a thiazolyl group optionally having one or more groups or atoms selected from Group $P^1$; and Y is #—$CH_2O$— in [Aspect 3].

A tetrazolinone compound in which A is a pyrazolyl group optionally having one or more groups or atoms selected from Group $P^1$; and Y is #—$CH_2O$— in [Aspect 3].

A tetrazolinone compound in which A is a phenyl group optionally having one or more groups or atoms selected from Group $P^1$; and Y is #—$CH_2O$— in [Aspect 5].

A tetrazolinone compound in which A is a pyridyl group optionally having one or more groups or atoms selected from Group $P^1$; and Y is #—$CH_2O$— in [Aspect 5].

A tetrazolinone compound in which A is a phenyl group optionally having one or more groups or atoms selected from Group $P^1$; and Y is #—$CH_2O$— in [Aspect 6].

A tetrazolinone compound in which A is a pyridyl group optionally having one or more groups or atoms selected from Group $P^1$; and Y is #—$CH_2O$— in [Aspect 6].

A tetrazolinone compound in which A is a phenyl group optionally having one or more groups or atoms selected from Group $P^1$; and Y is —CH=CH— in [Aspect 2].

A tetrazolinone compound in which A is a pyridyl group optionally having one or more groups or atoms selected from Group $P^1$; and Y is —CH=CH— in [Aspect 2].

A tetrazolinone compound in which A is a pyrimidinyl group optionally having one or more groups or atoms selected from Group $P^1$; and Y is —CH=CH— in [Aspect 2].

A tetrazolinone compound in which A is a pyrazolyl group optionally having one or more groups or atoms selected from Group $P^1$; and Y is —CH=CH— in [Aspect 2].

A tetrazolinone compound in which A is a phenyl group optionally having one or more groups or atoms selected from Group $P^1$; and Y is —CH=CH— in [Aspect 3].

A tetrazolinone compound in which A is a pyridyl group optionally having one or more groups or atoms selected from Group $P^1$; and Y is —CH=CH— in [Aspect 3].

A tetrazolinone compound in which A is a pyrimidinyl group optionally having one or more groups or atoms selected from Group $P^1$; and Y is —CH=CH— in [Aspect 3].

A tetrazolinone compound in which A is a thiazolyl group optionally having one or more groups or atoms selected from Group $P^1$; and Y is —CH=CH— in [Aspect 3].

A tetrazolinone compound in which A is a pyrazolyl group optionally having one or more groups or atoms selected from Group $P^1$; and Y is —CH=CH— in [Aspect 3].

A tetrazolinone compound in which A is a phenyl group optionally having one or more groups or atoms selected from Group $P^1$; and Y is —CH=CH— in [Aspect 5].

A tetrazolinone compound in which A is a pyridyl group optionally having one or more groups or atoms selected from Group $P^1$; and Y is —CH=CH— in [Aspect 5].

A tetrazolinone compound in which A is a phenyl group optionally having one or more groups or atoms selected from Group $P^1$; and Y is —CH=CH— in [Aspect 6].

A tetrazolinone compound in which A is a pyridyl group optionally having one or more groups or atoms selected from Group $P^1$; and Y is —CH=CH— in [Aspect 6].

A tetrazolinone compound in which $R^1$ is a C1-C6 alkyl group or a C3-C6 cycloalkyl group, $R^2$, $R^3$, and $R^4$ are hydrogen atoms, $R^5$ is a C1-C3 alkyl group, X is an oxygen atom, Y is #—$CR^4{}_2O$— or —CH=CH—, $R^4$ each is a hydrogen atom or a C1-C3 alkyl group, Q is a phenylene group, and A is a hydrogen atom, a phenyl group (which optionally has one or more groups selected from the group consisting of a C1-C6 alkyl group and a C1-C6 alkoxy group), a phenoxy group, or a pyridyl group which optionally has one or more groups or atoms selected from the group consisting of a halogen atom, a C1-C6 alkyl group, and a C1-C6 alkoxy group).

A tetrazolinone compound in which $R^1$ is a C1-C6 alkyl group, $R^2$, $R^3$, and $R^4$ are hydrogen atoms, $R^5$ is a C1-C3 alkyl group, X is an oxygen atom, Y is #—$CR^4{}_2O$— or —CH═CH—, $R^A$ each is a hydrogen atom or a C1-C3 alkyl group, Q is a phenylene group, and A is a hydrogen atom, a phenyl group which optionally has one or more groups selected from the group consisting of a C1-C6 alkyl group and a C1-C6 alkoxy group, a phenoxy group, or a pyridyl group which optionally has one or more groups or atoms selected from the group consisting of a halogen atom, a C1-C6 alkyl group, and a C1-C6 alkoxy group.

A tetrazolinone compound in which $R^1$ is a C3-C6 cycloalkyl group, $R^2$, $R^3$, and $R^4$ are hydrogen atoms, $R^5$ is a C1-C3 alkyl group, X is an oxygen atom, Y is —CH═CH—, Q is a phenylene group, and A is a phenyl group which optionally has one or more groups selected from the group consisting of a C1-C6 alkyl group and a C1-C6 alkoxy group.

A tetrazolinone compound in which $R^1$ is a C1-C6 alkyl group, $R^2$, $R^3$, and $R^4$ are hydrogen atoms, $R^5$ is a C1-C3 alkyl group, X is an oxygen atom, Y is #—$CR^4{}_2O$—, $R^A$ each is a hydrogen atom or a C1-C3 alkyl group, Q is a phenylene group, and A is a hydrogen atom, a phenyl group which optionally has one or more groups selected from the group consisting of a C1-C6 alkyl group and a C1-C6 alkoxy group), a phenoxy group, or a pyridyl group (which optionally has one or more groups or atoms selected from the group consisting of a halogen atom, a C1-C6 alkyl group, and a C1-C6 alkoxy group.

A tetrazolinone compound in which $R^1$ is a C1-C6 alkyl group or a C3-C6 cycloalkyl group, $R^2$, $R^3$, and $R^4$ are hydrogen atoms, $R^5$ is a C1-C3 alkyl group, X is an oxygen atom, Y is —CH═CH—, Q is a phenylene group, and A is a phenyl group which optionally has a C1-C6 alkyl group.

A tetrazolinone compound in which $R^1$ is a C1-C6 alkyl group, $R^2$, $R^3$, and $R^4$ are hydrogen atoms, $R^5$ is a C1-C3 alkyl group, X is an oxygen atom, Y is #—$CH_2O$—, Q is a phenylene group, and A is a hydrogen atom.

A tetrazolinone compound in which $R^1$ is a C1-C6 alkyl group, $R^2$, $R^3$, and $R^4$ are hydrogen atoms, $R^5$ is a C1-C3 alkyl group, X is an oxygen atom, Y is #—$CR^4{}_2O$—, $R^A$ each is a hydrogen atom or a C1-C3 alkyl group, Q is a phenylene group, and A is a phenyl group which optionally has one or more groups selected from the group consisting of a C1-C6 alkyl group and a C1-C6 alkoxy group.

A tetrazolinone compound in which $R^1$ is a C1-C6 alkyl group, $R^2$, $R^3$, and $R^4$ are hydrogen atoms, $R^5$ is a C1-C3 alkyl group, X is an oxygen atom, Y is #—$CH_2O$—, Q is a phenylene group, and A is a phenoxy group.

A tetrazolinone compound in which $R^1$ is a C1-C6 alkyl group, $R^2$, $R^3$, and $R^4$ are hydrogen atoms, $R^5$ is a C1-C3 alkyl group, X is an oxygen atom, Y is #—$CH_2O$—, Q is a phenylene group, and A is a pyridyl group which optionally has one or more groups or atoms selected from the group consisting of a halogen atom, a C1-C6 alkyl group, and a C1-C6 alkoxy group.

A tetrazolinone compound in which $R^1$ is a methyl group, $R^2$, $R^3$, and $R^4$ are hydrogen atoms, $R^5$ is a methyl group, X is an oxygen atom, Y is #—$CH_2O$—, Q is a phenylene group, and A is a pyridyl group which optionally has one or more groups or atoms selected from the group consisting of a halogen atom, a C1-C6 alkyl group, and a C1-C6 alkoxy group.

A tetrazolinone compound in which $R^1$ is a C1-C6 alkyl group, $R^2$, $R^3$, and $R^4$ are hydrogen atoms, $R^5$ is a C1-C3 alkyl group, X is an oxygen atom, Y is —CH═CH—, Q is a phenylene group, and A is a hydrogen atom.

A tetrazolinone compound in which $R^1$ is a C1-C6 alkyl group, $R^2$, $R^3$, and $R^4$ are hydrogen atoms, $R^5$ is a C1-C3 alkyl group, X is an oxygen atom, Y is —CH═CH—, and A is a phenyl group which optionally has one or more groups selected from the group consisting of a C1-C6 alkyl group and a C1-C6 alkoxy group.

A tetrazolinone compound in which $R^1$ is a C1-C6 alkyl group, $R^2$, $R^3$, and $R^4$ are hydrogen atoms, $R^5$ is a C1-C3 alkyl group, X is an oxygen atom, Y is —CH═CH—, Q is a phenylene group, and A is a phenoxy group.

A tetrazolinone compound in which $R^1$ is a C1-C6 alkyl group, $R^2$, $R^3$, and $R^4$ are hydrogen atoms, $R^5$ is a C1-C3 alkyl group, X is an oxygen atom, Y is —CH═CH—, Q is a phenylene group, and A is a pyridyl group which optionally has one or more groups or atoms selected from the group consisting of a halogen atom, a C1-C6 alkyl group, and a C1-C6 alkoxy group.

A tetrazolinone compound in which $R^1$ is a C1-C6 alkyl group or a C3-C6 cycloalkyl group, $R^2$, $R^3$, and $R^4$ are hydrogen atoms, $R^5$ is a C1-C3 alkyl group, X is an oxygen atom, Y is —CH═CH—, Q is a phenylene group, and A is a phenyl group (which optionally has a C1-C6 alkyl group).

$R^1$ is a C1-C6 alkyl group, $R^2$, $R^3$, and $R^4$ are hydrogen atoms, $R^5$ is a C1-C3 alkyl group, X is an oxygen atom, Y is —CH═CH—, Q is a phenylene group, and A is a phenyl group which optionally has a C1-C6 alkyl group.

A tetrazolinone compound in which $R^1$ is a methyl group, $R^2$, $R^3$, and $R^4$ are hydrogen atoms, $R^5$ is a methyl group, X is an oxygen atom, Y is —CH═CH—, Q is a phenylene group, and A is a phenyl group which optionally has a methyl group.

As used herein, in structural formulas represented by general formulas, individual isomers and isomer mixtures, such as all active geometrical isomers and optical isomers are included in the present invention.

Next, a process for producing the present compound will be described.

The present compound can be produced, for example, by the following Production Processes.

(Production Process A)

A compound represented by formula (A3) (hereinafter referred to as the compound (A3)) can be produced by reacting a compound represented by formula (A1) (hereinafter referred to as the compound (A1)) with a compound represented by formula (A2) (hereinafter referred to as the compound (A2)) in the presence of a base:

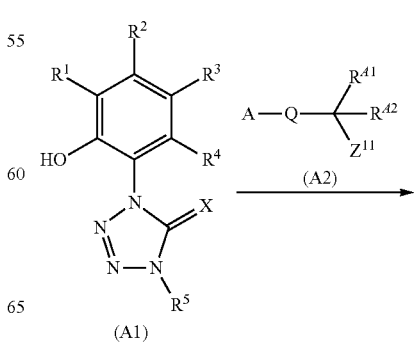

-continued

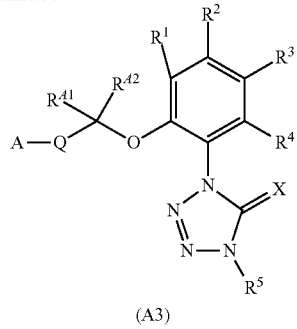

(A3)

wherein $R^1$, $R^2$, $R^3$, $R^4$, $R^5$, $R^{A\,1}$, $R^{A\,2}$, A, Q, and X are the same as defined above, and $Z^{11}$ represents a leaving group such as a chlorine atom, a bromine atom, an iodine atom, a methanesulfonyloxy group, a trifluoromethanesulfonyloxy group, or a p-toluenesulfonyloxy group.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the base to be used in the reaction include organic bases such as 4-dimethylaminopyridine and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (A2) is usually used in the proportion within a range of 1 to 10 mols, and the base is usually used in the proportion within a range of 0.5 to 5 mols, based on 1 mol of the compound (A1).

The reaction temperature of the reaction is usually within a range of −20 to 150° C. The reaction time is usually within a range of 0.1 to 24 hours.

In the reaction, if necessary, sodium iodide, tetrabutylammonium iodide, and the like may be added, and these compounds are usually used in the proportion of 0.001 to 1.2 mols based on 1 mol of the compound (A1).

After completion of the reaction, the compound (A3) can be isolated by performing post-treatment operations such as extraction of the reaction mixture with an organic solvent, and drying and concentration of the organic layer. The isolated compound (A3) can be further purified by chromatography, recrystallization, and the like.

(Production Process B)

A compound represented by formula (AA3) (hereinafter referred to as the compound (AA3)) can be produced by reacting a compound represented by formula (XH2) (hereinafter referred to as the compound (XH2)) with a compound represented by formula (AA2) (hereinafter referred to as the compound (AA2)) in the presence of a base:

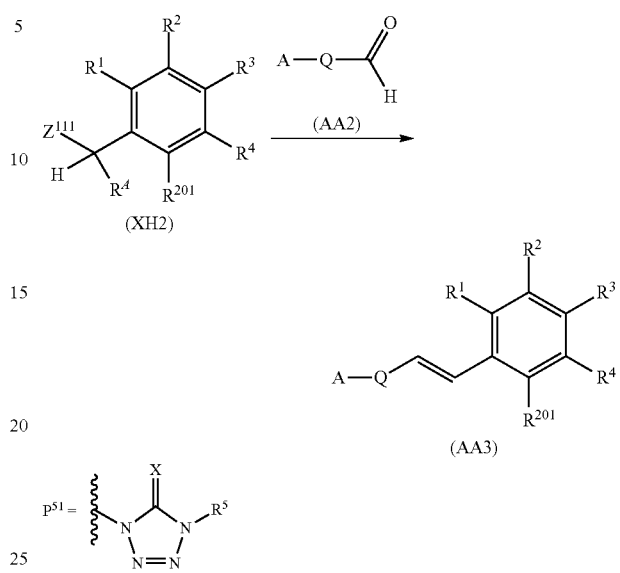

wherein $R^1$, $R^2$, $R^3$, $R^4$, $R^5$, A, Q, and X are the same as defined above, $Z^{111}$ represents a dimethyl phosphate group, a diethoxyphosphate group, or a dipropyl phosphate group, a phosphonic acid ester such as triphenylphosphine or tributylphosphine, alkylphosphine oxide, and trialkylphosphine, $R^{201}$ represents $P^{51}$ or a nitro group, and the wavy line represents a binding site.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; nitriles such as acetonitrile; water; and mixtures thereof.

Examples of the base to be used in the reaction include alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal hydrides such a lithium hydride, sodium hydride, and potassium hydride; and alkali metal alkoxides such as sodium tert-butoxide and potassium tert-butoxide.

In the reaction, the compound (AA2) is usually used in the proportion within a range of 1 to 10 mols, and the base is usually 0.5 to 5 mols, based on 1 mol of the compound (XH1).

The reaction temperature of the reaction is usually within a range of −20 to 150° C. The reaction time is usually within a range of 0.1 to 24 hours.

After completion of the reaction, the compound (AA3) can be isolated by performing post-treatment operations such as extraction of the reaction mixture with an organic solvent, and drying and concentration of the organic layer. The isolated compound (AA3) can be further purified by chromatography, recrystallization, and the like.

(Production Process C)

A compound represented by formula (1) (hereinafter referred to as the compound (1)) can be produced by subjecting a compound represented by formula (B1) (hereinafter referred to as the compound (B1)) and a compound represented by formula (B2) (hereinafter referred to as the compound (B2)) to a coupling reaction in the presence of a base and a catalyst:

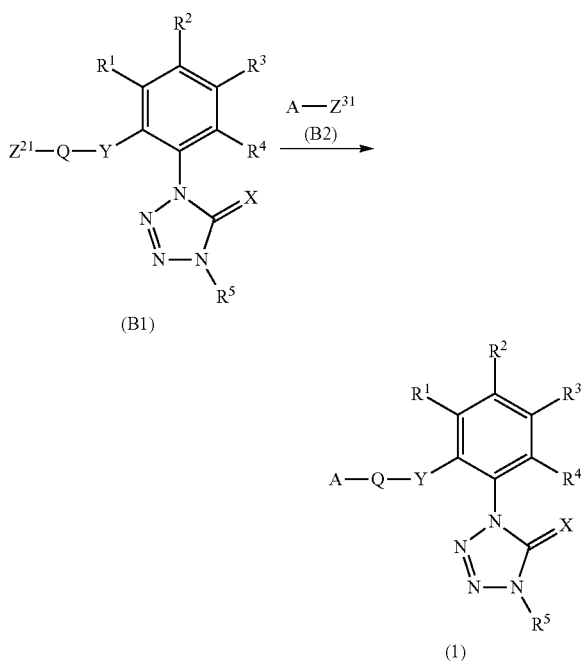

wherein $R^1$, $R^2$, $R^3$, $R^4$, $R^5$, A, Q, Y, and X are the same as defined above, $Z^{21}$ represents a chlorine atom, a bromine atom, or an iodine atom, and $Z^{31}$ represents $B(OH)_2$, an alkoxyboranyl group, or a trifluoroborate ($BF_3^-K^+$).

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; alcohols such as methanol, ethanol, propanol, and butanol; water; and mixtures thereof.

It is possible to usually use, as the compound (B2) to be used in the reaction, commercially available compounds, or compounds produced by a known method mentioned in N. Miyaura and A. Suzuki, Chem. Rev., 1995, 95, 2457. It is also possible to produce a trifluoroborate ($BF_3^-K^+$) by fluorinating the boronic acid ester with potassium hydrogen fluoride in accordance with a known method mentioned in Molander et al. Acc. Chem. Res., 2007, 40, 275.

Examples of the catalyst to be used in the reaction include palladium(II) acetate, dichlorobis(triphenylphosphine)palladium, tetrakis(triphenylphosphine)palladium(0), palladium(II) acetate/triscyclohexylphosphine, bis(diphenylphosphinoferrocenyl)palladium(II) dichloride, 1,3-bis(2,6-diisopropylphenyl)imidazol-2-ylidene(1,4-naphthoquinone)palladium dimer, allyl(chloro) (1,3-dimesityl-1,3-dihydro-2H-imidazol-2-ylidene)palladium or palladium(II) acetate/dicyclohexyl(2',4',6'-triisopropylbiphenyl-2-yl)phosphine, tris(dibenzylidineacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (B2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B1).

The reaction temperature of the reaction is usually within a range of 0 to 150° C. The reaction time is usually within a range of 0.1 to 24 hours.

After completion of the reaction, the compound (1) can be isolated by performing post-treatment operations such as extraction of the reaction mixture with an organic solvent, and drying and concentration of the organic layer. The isolated compound (1) can be further purified by chromatography, recrystallization, and the like.

(Production Process D)

The compound (1) can be produced by subjecting a compound represented by formula (C1) (hereinafter referred to as the compound (C1)) and a compound represented by formula (C2) (hereinafter referred to as the compound (C2)) to a coupling reaction in the presence of a base and a catalyst:

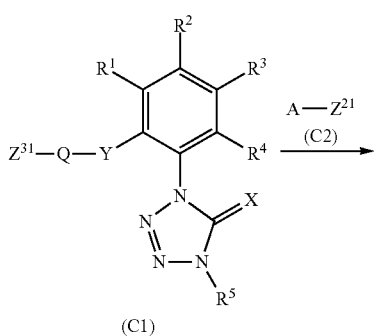

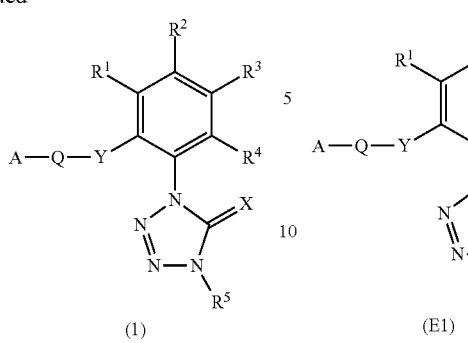

wherein symbols are the same as defined above.

The reaction can be carried out in accordance with Production Process C.

(Production Process E)

The compound (1) can be produced by reacting a compound represented by formula (D1) (hereinafter referred to as the compound (D1)) with a compound represented by formula (D2) (hereinafter referred to as the compound (D2)) in the presence of a base:

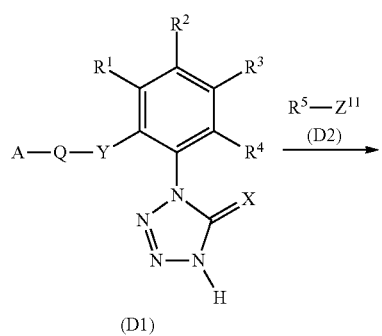

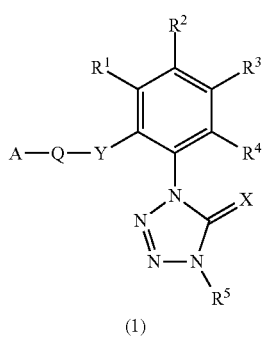

wherein symbols are the same as defined above.

The reaction can be carried out in accordance with the reaction of Production Process A.

(Production Process F)

Among the compounds (1), a compound in which X is a sulfur atom (hereinafter referred to as the compound (E2)) can be produced from a compound in which X is an oxygen atom (hereinafter referred to as the compound (E1)) among the compounds (1) by a known sulfidation reaction using a sulfurizing agent:

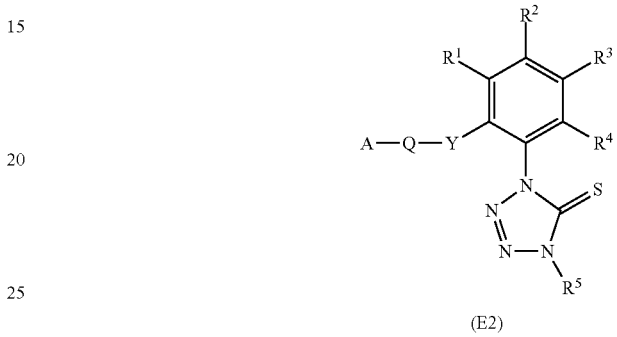

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; nitriles such as acetonitrile; and mixtures thereof.

Examples of the sulfurizing agent to be used in the reaction include phosphorous pentasulfide and Lawesson's reagent (2,4-Bis(4-methoxyphenyl)-1,3,2,4-dithiadiphosphetane 2,4-disulfide).

In the reaction, the sulfurizing agent is preferably used in the proportion within a range of 0.5 to 1.5 mols based on 1 mol of the compound (E1).

The reaction temperature of the reaction is usually within a range of $-20$ to $150°$ C. The reaction time is usually within a range of 0.1 to 24 hours.

In the reaction, if necessary, organic bases such as pyridine and triethylamine; and inorganic bases such as alkali metal hydroxide and alkali metal carbonate may be added, and the amount of the base to be added is within a range of 0.5 to 1.5 mols based on the compound (E1).

After completion of the reaction, the compound (E2) can be isolated by performing post-treatment operations such as extraction of the reaction mixture with an organic solvent, and drying and concentration of the organic layer. The isolated compound (E2) can be further purified by chromatography, recrystallization, and the like.

(Production Process G)

Among the compounds (1), a compound represented by formula (F3) in which $R^1$ is $R^{71}$ (hereinafter referred to as the compound (F3)) can be produced by subjecting a compound represented by formula (F1) (hereinafter referred to as the compound (F1)) and a compound represented by formula (F2) (hereinafter referred to as the compound (F2)) to a coupling reaction in the presence of a base and a catalyst:

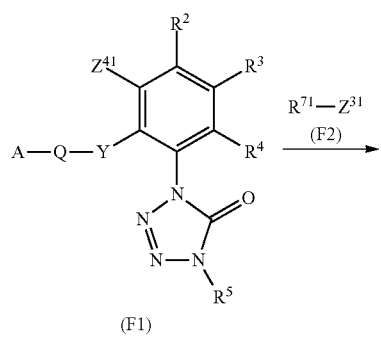

(F1)

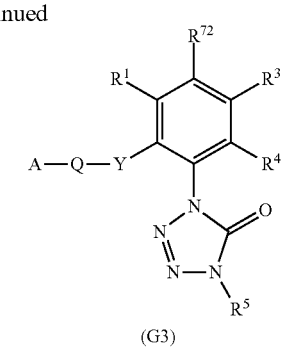

(G3)

wherein $R^1$, $R^3$, $R^4$, $R^5$, A, Q, Y, $R^{72}$, $Z^{31}$, and $Z^{41}$ are the same as defined above, and $R^{72}$ represents a C1-C3 alkyl group, a C1-C3 haloalkyl group, a C2-C3 alkenyl group, or a C2-C3 haloalkenyl group.

The reaction can be carried out in accordance with Production Process C.

(Production Process I)

Among the compounds (1), a compound represented by formula (H3) in which $R^3$ is $R^{72}$ (hereinafter referred to as the compound (H3)) can be produced by subjecting a compound represented by formula (H1) (hereinafter referred to as the compound (H1)) and the compound (G2) to a coupling reaction in the presence of a base and a catalyst:

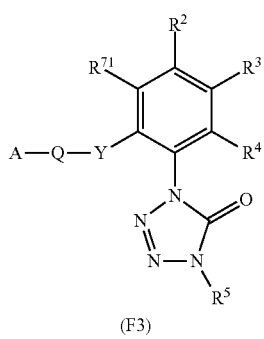

(F3)

wherein $R^2$, $R^3$, $R^4$, $R^5$, A, Q, Y, and $Z^{31}$ are the same as defined above, $Z^{41}$ represents a chlorine atom, a bromine atom, an iodine atom, or a trifluoromethanesulfonyloxy group, and $R^{71}$ represents a C1-C6 alkyl group, a C3-C6 cycloalkyl group, a C1-C6 haloalkyl group, a C2-C6 alkenyl group, a C2-C6 haloalkenyl group, a C2-C6 alkynyl group, or a C2-C6 haloalkynyl group.

The reaction can be carried out in accordance with Production Process C.

(Production Process H)

Among the compounds (1), a compound represented by formula (G3) in which $R^2$ is $R^{72}$ (hereinafter referred to as the compound (G3)) can be produced by subjecting a compound represented by formula (G1) (hereinafter referred to as the compound (G1)) and a compound represented by formula (G2) (hereinafter referred to as the compound (G2)) to a coupling reaction in the presence of a base and a catalyst:

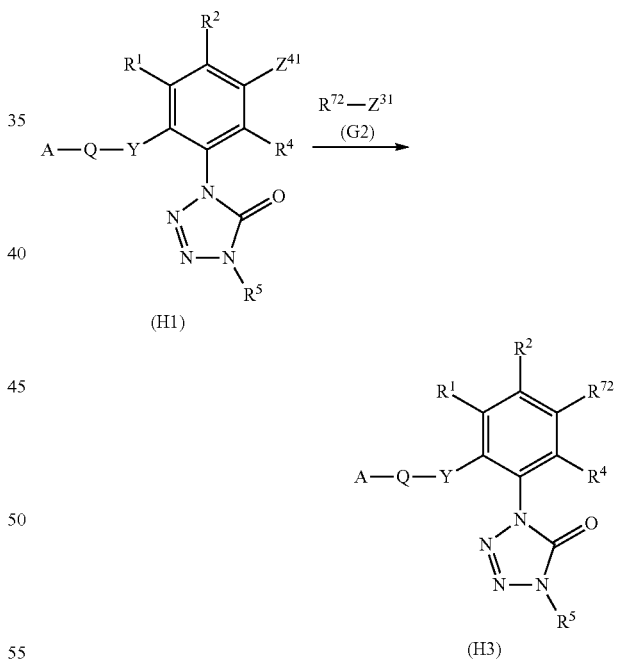

wherein symbols are the same as defined above.

The reaction can be carried out in accordance with Production Process C.

(Production Process J)

Among the compounds (1), a compound represented by formula (I3) in which $R^4$ is $R^{72}$ (hereinafter referred to as the compound (I3)) can be produced by subjecting a compound represented by formula (I1) (hereinafter referred to as the compound (I1)) and the compound (G2) to a coupling reaction in the presence of a base and a catalyst:

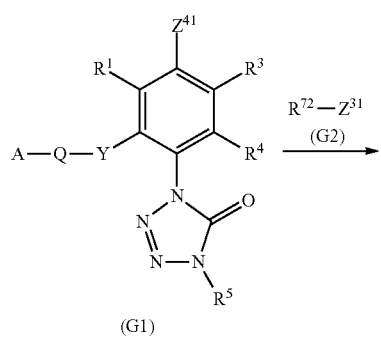

(G1)

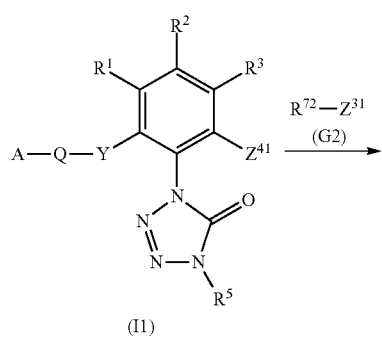

(I1)

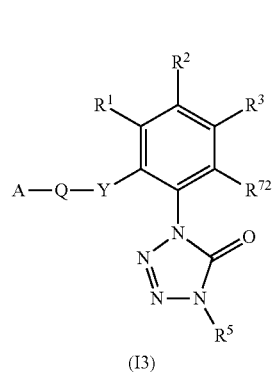

(I3)

wherein $R^1$, $R^2$, $R^3$, $R^5$, A, Q, $R^{72}$, $Z^{31}$, and $Z^{41}$ are the same as defined above.

The reaction can be carried out in accordance with Production Process C.

In accordance with the reaction of Production Process C, it is possible to produce a compound in which two or more substituents selected from $R^1$, $R^2$, $R^3$, and $R^4$ are $R^{71}$ and/or $R^{72}$, among the compounds (1).

It is also possible to produce the present compound represented by formula (1) by using other known coupling reactions in place of the coupling reaction of Production Process C.

The process for synthesizing an intermediate compound will be mentioned in detail below.

(Reference Production Process A)

A compound represented by formula (XA3) (hereinafter referred to as the compound (XA3)) can be produced by reacting a compound represented by formula (XA1) (hereinafter referred to as the compound (XA1)) or a compound represented by formula (XA2) (hereinafter referred to as the compound (XA2)) with an azidation agent:

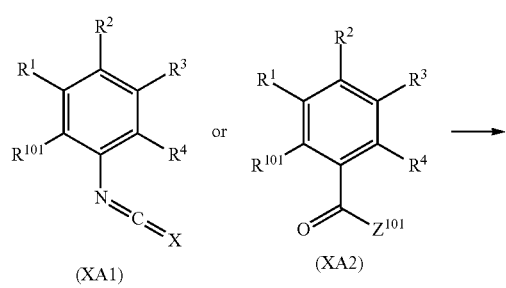

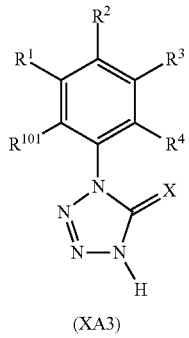

(XA3)

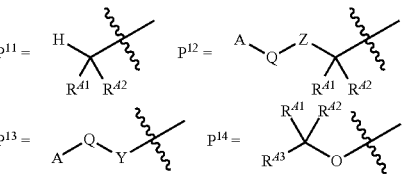

wherein $R^1$, $R^2$, $R^3$, $R^4$, $R^{4\,1}$, $R^{4\,2}$, $R^{4\,3}$, Z, A, Q, and X are the same as defined above, $R^{101}$ represents $P^{11}$, $P^{12}$, $P^{13}$, or $P^{14}$, $Z^{101}$ represents a chlorine atom or a bromine atom, and the wavy line represents a binding site.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is usually used in the proportion within a range of 1 to 10 mols based on 1 mol of the compound (XA1) or the compound (XA2).

The reaction temperature of the reaction is usually within a range of −20 to 150° C. The reaction time is usually within a range of 0.1 to 24 hours.

In the reaction, if necessary, Lewis acid such as aluminum chloride or zinc chloride may be added, and these compounds are usually used in the proportion within a range of 0.05 to 5 mols based on 1 mol of the compound (XA1) or the compound (XA2).

After completion of the reaction, the compound (XA3) can be isolated by performing post-treatment operations such as extraction of the reaction mixture with an organic solvent, and drying and concentration of the organic layer. The isolated compound (XA3) can be further purified by chromatography, recrystallization, and the like.

(Reference Production Process B)

The compound (XA1) can be produced by reacting a compound represented by formula (XB1) (hereinafter referred to as the compound (XB1)) with an isocyanating agent:

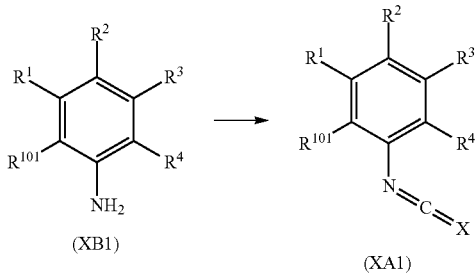

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the isocyanating agent to be used in the reaction include phosgene, diphosgene, triphosgene, thiophosgene, N,N-carbodiimidazole, and N,N-thiocarbodiimidazole.

In the reaction, the isocyanating agent is usually used in the proportion within a range of 0.34 to 10 mols based on 1 mol of the compound (XB1).

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate may be added, and these compounds are usually used in the proportion within a range of 0.05 to 5 mols based on 1 mol of the compound (XB1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process C)

The compound (XA2) can be produced by reacting a compound represented by formula (XC1) (hereinafter referred to as the compound (XC1)) with a halogenating agent:

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent to be used in the reaction include phosphorus oxychloride, phosphorus trichloride, phosphorus pentachloride, thionyl chloride, phosphorus oxybromide, phosphorus tribromide, phosphorus pentabromide, phosphorus triiodide, oxalyl dichloride, oxalyl dibromide, triphosgene, diphosgene, phosgene, and sulfuryl chloride.

In the reaction, the halogenating agent is usually used in the proportion within a range of 1 to 10 mols based on 1 mol of the compound (XC1).

The reaction temperature of the reaction is usually within a range of −20 to 150° C. The reaction time is usually within a range of 0.1 to 24 hours.

In the reaction, a catalyst may be added, and dimethylformamide is used. The catalyst is usually used in the proportion within a range of 0.001 to 1 mols based on 1 mol of the compound (XC1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate may be added, and these compounds are usually used in the proportion within a range of 0.05 to 5 mols based on 1 mol of the compound (XC1).

After completion of the reaction, the compound (XA2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process D)

The compound (XA1) can be produced by reacting the compound (XB1) with a carbamating agent to obtain a compound represented by formula (XD1) (hereinafter referred to as the compound (XD1)), and then reacting the compound (XD1) with an isocyanating agent:

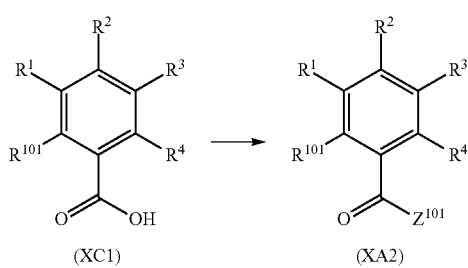

wherein symbols are the same as defined above.

-continued

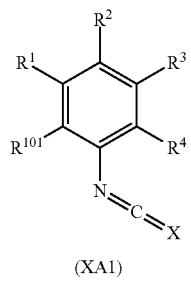

(XA1)

wherein $R^1$, $R^2$, $R^3$, $R^4$, $R^{101}$, and X are the same as defined above, and $R^{111}$ represents a C1-C12 alkyl group or a phenyl group.

The process for producing the compound (XD1) from the compound (XB1) will be described below.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the carbamating agent to be used in the reaction include phenyl chlorocarbonate, methyl chlorocarbonate, ethyl chlorocarbonate, propyl chlorocarbonate, isopropyl chlorocarbonate, n-butyl chlorocarbonate, tert-butyl chlorocarbonate, di-tert-butyl dicarbonate, dimethyl dicarbonate, diethyl dicarbonate, O-phenyl chlorothioformate, O-methyl chlorothioformate, O-ethyl chlorothioformate, and the like.

In the reaction, the carbamating agent is usually used in the proportion within a range of 1 to 10 mols based on 1 mol of the compound (XB1).

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate may be added, and these compounds are usually used in the proportion within a range of 0.05 to 5 mols based on 1 mol of the compound (XB1).

After completion of the reaction, the compound (XD1) can be isolated by performing post-treatment operations such as extraction of the reaction mixture with an organic solvent, and drying and concentration of the organic layer. The isolated compound may be further purified by operations such as distillation, chromatography, and recrystallization.

The process for producing the compound (XA1) from the compound (XD1) will be described below.

The reaction is usually performed in a solvent.

Examples of the solvent to be used in the reaction include ethers such as tetrahydrofuran, 1,4-dioxane, ethylene glycol dimethyl ether, and methyl tert-butyl ether; aromatic hydrocarbons such as toluene and xylene; halogenated hydrocarbons such as carbon tetrachloride, chloroform or 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

It is possible to use, as the isocyanating agent to be used in the reaction, for example, phosphorus pentachloride, phosphorus oxychloride, diphosphorus pentaoxide, trichlorosilane, dichlorosilane, monochlorosilane, boron trichloride, 2-chloro-1,3,2-benzodioxaborole, diiodosilane, methyltrichlorosilane, dimethyldichlorosilane, chlorotrimethylsilane, and the like.

In the reaction, the isocyanating agent is usually used in the proportion within a range of 1 to 10 mols based on 1 mol of the compound (XD1).

The reaction temperature of the reaction is usually within a range of −20 to 250° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate may be added, and these compounds are usually used in the proportion within a range of 0.05 to 5 mols based on 1 mol of the compound (XD1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process E)

The compound (XB1) can be produced by reacting a compound represented by the following formula (XE1) (hereinafter referred to as the compound (XE1)) with hydrogen in the presence of a catalyst:

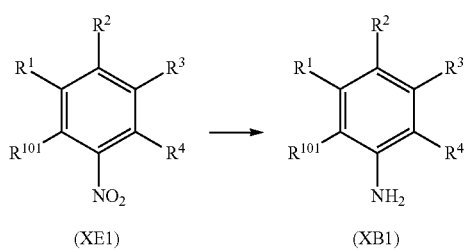

(XE1)    (XB1)

wherein symbols are the same as defined above.

The reaction is usually performed in a solvent.

Examples of the solvent to be used in the reaction include alcohols such as methanol, ethanol, propanol, and butanol; esters such as ethyl acetate and butyl acetate; halogenated hydrocarbons such as chloroform, 1,2-dichloroethane, and chlorobenzene; ethers such as tetrahydrofuran, 1,4-dioxane, ethylene glycol dimethyl ether, methyl tert-butyl ether, and diisopropyl ether; hydrocarbons such as n-heptane, n-hexane, cyclohexane, n-pentane, toluene, and xylene; water; and mixtures thereof.

The reaction is carried out in the presence of a hydrogen gas. Examples of the catalyst to be used in the reaction include palladium-supported carbon (Pd/C), platinum-supported carbon (Pt/C), osmium-supported carbon (Os/C), ruthenium-supported carbon (Ru/C), rhodium-supported carbon (Rh/C), Raney nickel, and the like.

In the reaction, the catalyst is usually used in the proportion within a range of 0.0001 to 1 mols based on 1 mol of the compound (XE1), hydrogen pressure is within a range of 0.1 to 20 atm, and hydrogen is used in the proportion within a range of 1 mol to large excess.

The reaction temperature of the reaction is usually within a range of −20 to 150° C. The reaction time is usually within a range of 0.1 to 24 hours.

After completion of the reaction, the compound (XB1) can be isolated by performing post-treatment operations such as concentration of the organic layer after filtration of the catalyst. The isolated compound may be further purified by operations such as distillation, chromatography, and recrystallization.

(Reference Production Process F)

The compound (XB1) can be produced by reacting the compound (XE1) with a reducing agent in the presence of an acid:

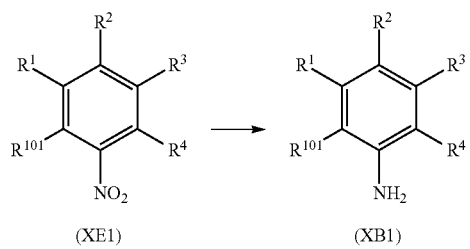

wherein symbols are the same as defined above.

The reaction is usually performed in a solvent.

Examples of the solvent to be used in the reaction include aliphatic carboxylic acids such as acetic acid; alcohols such as methanol and ethanol; water; and mixtures thereof.

Examples of the reducing agent to be used in the reaction include iron, tin, and zinc.

Examples of the acid to be used in the reaction include hydrochloric acid, sulfuric acid, acetic acid, an aqueous ammonium chloride solution, and the like.

In the reaction, the reducing agent is usually used in the proportion within a range of 1 to 30 mols based on 1 mol of the compound (XE1).

The reaction temperature of the reaction is usually within a range of −20 to 150° C. The reaction time is usually within a range of 0.1 to 24 hours.

After completion of the reaction, the compound (XB1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process G)

A compound represented by formula (XA3) (hereinafter referred to as the compound (XG2)) can be produced by reacting a compound represented by formula (XG1) (hereinafter referred to as the compound (XG1)) with the compound (D2) in the presence of a base:

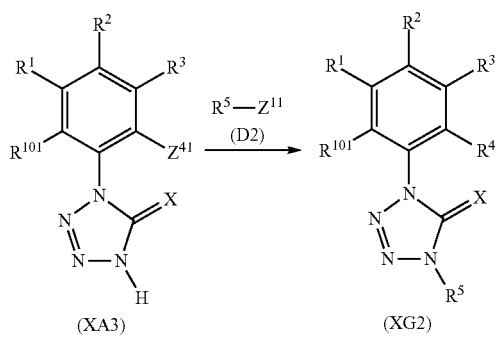

wherein symbols are the same as defined above.

The reaction can be carried out in accordance with Production Process D.

(Reference Production Process H)

A compound represented by formula (XH2) (hereinafter referred to as the compound (XH2)) can be produced by reacting a compound represented by formula (XH1) (hereinafter referred to as the compound (XH1)) with a halogenating agent:

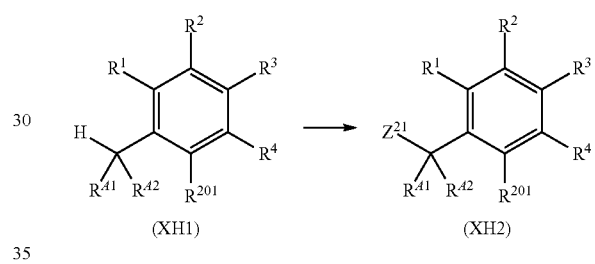

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent usable in the reaction include a chlorinating agent, a brominating agent, or an iodinating agent, for example, chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonimide, N-bromophthalimide, and the like.

In the reaction, a radical initiator can also be used.

Examples of the radical initiator to be used in the reaction include benzoyl peroxide, azobisisobutyronitrile (AIBN), diacyl peroxide, dialkyl peroxydicarbonate, tert-alkylperoxyester, monoperoxycarbonate, di(tert-alkylperoxy)ketal, and ketone peroxide.

In the reaction, the halogenating agent is usually used in the proportion within a range of 1 to 10 mols, and the radical initiator is usually used in the proportion within a range of 0.01 to 5 mols, based on 1 mol of the compound (XH1).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process I)

A compound represented by formula (XM4) (hereinafter referred to as the compound (XM4)) can be produced by reacting the compound (XH2) with a phosphonic acid ester, triarylphosphine, or trialkylphosphine:

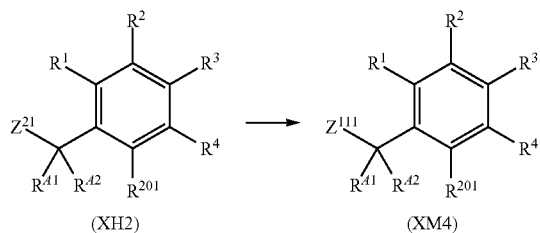

wherein symbols are the same as defined above.

The reaction is usually performed in a solvent.

Examples of the solvent to be used in the reaction include ethers such as tetrahydrofuran, 1,4-dioxane, ethylene glycol dimethyl ether, methyl tert-butyl ether, and diisopropyl ether; hydrocarbons such as n-heptane, n-hexane, cyclohexane, n-pentane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the phosphonic acid ester, triarylphosphine, or trialkylphosphine usable in the reaction include trimethyl phosphite, triethyl phosphite, tripropyl phosphite, triphenylphosphine, tributylphosphine, and the like.

In the reaction, the phosphonic acid ester or trialkylphosphine is usually used in the proportion within a range of 1 to 10 mols based on 1 mol of the compound (XH2).

The reaction temperature of the reaction is usually within a range of −20 to 150° C. The reaction time is usually within a range of 0.1 to 24 hours.

After completion of the reaction, the compound (XM4) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process J)

A compound represented by formula (XK1) (hereinafter referred to as the compound (XK1)) can be produced by reacting the compound (XH2) with water in the presence of a base:

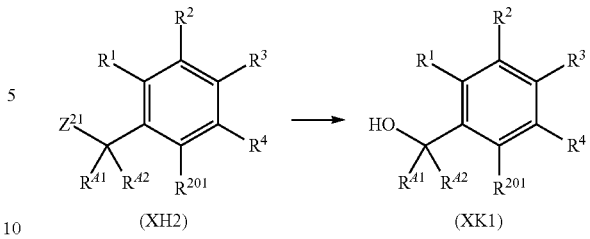

wherein symbols are the same as defined above.

The reaction is usually performed in water, or a solvent containing water.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as n-heptane, n-hexane, cyclohexane, n-pentane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the base to be used in the reaction include organic bases such as triethylamine, pyridine, N-methylmorpholine, 4-dimethylaminopyridine, diisopropylethylamine, and diazabicycloundecene; metal organic acid salts such as lithium formate, lithium acetate, sodium formate, sodium acetate, potassium formate, and potassium acetate; metal nitrates such as silver nitrate and sodium nitrate; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; and alkali metal alkoxides such as sodium methoxide, sodium ethoxide, sodium tert-butoxide, and potassium tert-butoxide.

In the reaction, the base is usually used in the proportion within a range of 1 to 100 mols based on 1 mol of the compound (XH2).

In the reaction, water is usually used in the proportion within a range of 1 mol to large excess based on 1 mol of the compound (XH2).

The reaction temperature of the reaction is usually within a range of −20 to 150° C. The reaction time is usually within a range of 0.1 to 24 hours.

After completion of the reaction, the compound (XK1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process K)

The compound (XH2) can be produced by reacting a compound represented by formula (XJ2) (hereinafter referred to as the compound (XJ2)) with a halogenating agent:

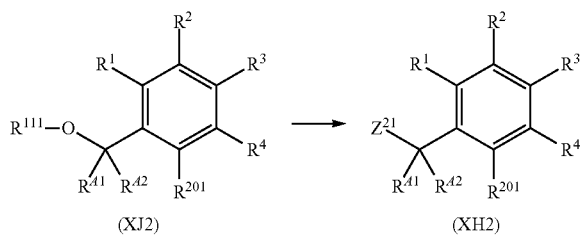

(XJ2)  (XH2)

wherein symbols are the same as defined above.

The reaction is usually performed in a solvent.

Examples of the solvent to be used in the reaction include hydrocarbons such as n-hexane, cyclohexane, toluene, and xylene; halogenated hydrocarbons such as chloroform, 1,2-dichloroethane, and chlorobenzene; ketones such as acetone, methyl ethyl ketone, and methyl isobutyl ketone; nitriles such as acetonitrile; organic acids such as formic acid, acetic acid, and trifluoroacetic acid; water; and mixtures thereof.

Examples of the halogenating agent to be used in the reaction include hydrochloric acid, hydrogen bromide, hydrobromic acid, and hydroiodic acid.

In the reaction, the halogenating agent is usually used in the proportion of 1 mol or more based on 1 mol of the compound (XJ2).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process L)

The compound (XH2) can be produced by reacting the compound (XK1) with a halogenating agent:

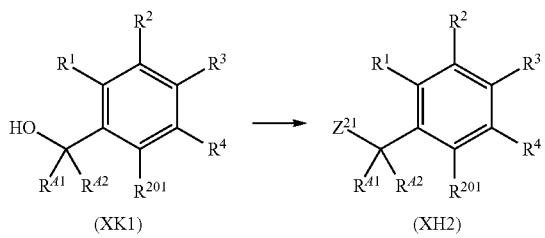

(XK1)  (XH2)

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; organic acids such as formic acid, acetic acid, and trifluoroacetic acid; water; and mixtures thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorus oxychloride, phosphorus trichloride, phosphorus pentachloride, thionyl chloride, phosphorus oxybromide, phosphorus pentabromide, phosphorus triiodide, oxalyl dichloride, oxalyl dibromide, combination of acetyl chloride and zinc chloride, combination of N-bromosuccinimide and dimethyl sulfide, combination of lithium chloride, triethylamine, and methanesulfonyl chloride, combination of sodium iodide and a boron trifluoride diethyl ether complex, aluminum chloride or trimethylsilyl chloride, and combination of acetyl bromide and a boron trifluoride diethyl ether complex.

In the reaction, the halogenating agent is usually used in the proportion within a range of 1 to 10 mols based on 1 mol of the compound (XK1).

Zinc chloride, dimethyl sulfide, a boron trifluoride diethyl ether complex, a boron trifluoride diethyl ether complex, lithium chloride, aluminum chloride, and trimethylsilyl chloride are used as additives for acceleration of the reaction, and any additive is usually used in the proportion within a range of 0.01 to 5 mols based on 1 mol of the compound (XK1).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process M)

A compound represented by formula (XM3) (hereinafter referred to as the compound (XM3)) can be produced by reacting the compound (XK1) with a compound represented by formula (XM2) (hereinafter referred to as the compound (XM2)) in the presence of a base:

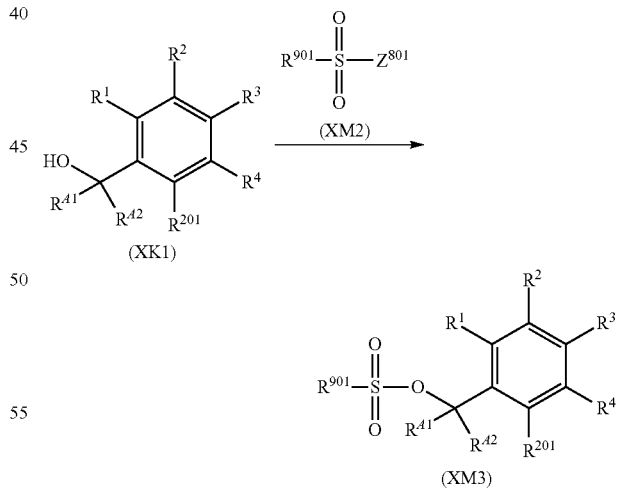

(XK1)

(XM3)

wherein $R^1$, $R^2$, $R^3$, $R^4$, $R^{A1}$, $R^{A2}$, and $R^{201}$ are the same as defined above, $R^{901}$ represents a C1-C6 alkyl group, a C1-C6 haloalkyl group, a C6-C16 aryl group, or a C6-C16 haloaryl group, and $Z^{801}$ represents a fluorine atom, a chlorine atom, a bromine atom, or an iodine atom.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium methoxide, sodium ethoxide, sodium tert-butoxide, and potassium tert-butoxide.

It is possible to use, as the compound (XM2), commercially available compounds.

In the reaction, the compound (XM2) is usually used in the proportion within a range of 1 to 10 mols, and the base is usually in the proportion within a range of 1 to 5 mols, based on 1 mol of the compound (XK1).

The reaction temperature of the reaction is usually within a range of −20 to 150° C. The reaction time is usually within a range of 0.1 to 24 hours.

In the reaction, if necessary, sodium iodide, tetrabutylammonium iodide, and the like may be added, and these compounds are usually used in the proportion within a range of 0.001 to 1.2 mols based on 1 mol of the compound (XK1).

After completion of the reaction, the compound (XM3) can be isolated by performing post-treatment operations such as extraction of the reaction mixture with an organic solvent, and drying and concentration of the organic layer. The isolated compound may be further purified by operations such as distillation, chromatography, and recrystallization.

A pest control agent of the present invention includes the present compound and an inert carrier. The pest control agent of the present invention is obtained by mixing the present compound with inert carriers such as solid carriers, liquid carriers, and gaseous carriers, and optionally adding surfactants and auxiliary agents for formulation to thereby formulate into emulsifiable concentrates, oil solutions, dusts, granules, wettable powders, flowables, microcapsules, and the like. The pest present control agent of the present invention usually includes the present compound in the proportion within a range of 0.01 to 95% by weight.

Examples of the solid carriers used in the formulation include clays (kaolin clay, diatomaceous earth, bentonite, Fubasami clay, and acid clay), synthetic hydrated silicon dioxide, talc, ceramic, other inorganic minerals (sericite, quartz powder, sulfur powder, activated charcoal, calcium carbonate, and hydrated silica), chemical fertilizers (ammonium sulfate, ammonium phosphate, ammonium nitrate, urea, and ammonium chloride) in the form of fine powders or particulates, and synthetic resins (polyester resins such as polypropylene, polyacrylonitrile, methyl polymethacrylate, and polyethylene terephthalate, nylon resins such as nylon-6, nylon-11, and nylon-66, polyamide resin, polyvinyl chloride, polyvinylidene chloride, vinyl chloride-propylene copolymer).

Examples of the liquid carriers include water, alcohols (methanol, ethanol, isopropyl alcohol, butanol, hexanol, benzyl alcohol, ethylene glycol, propylene glycol, and phenoxyethanol), ketones (acetone, methyl ethyl ketone, and cyclohexanone), aromatic hydrocarbons (toluene, xylene, ethylbenzene, dodecylbenzene, phenylxylylethane, methylnaphthalene), aliphatic hydrocarbons (hexane, cyclohexane, kerosene, and light oil), esters (ethyl acetate, butyl acetate, isopropyl myristate, ethyl oleate, diisopropyl adipate, diisobutyl adipate, and propylene glycol monomethyl ether acetate), nitriles (acetonitrile and isobutyronitrile), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, and 3-methoxy-3-methyl-1-butanol), acid amides (N,N-dimethylformamide and N,N-dimethylacetamide), halogenated hydrocarbons (dichloromethane, trichloroethane, and carbon tetrachloride), sulfoxides (dimethyl sulfoxide), propylene carbonate, and vegetable oil (soybean oil and cottonseed oil).

Examples of the gaseous carriers include fluorocarbon, butane gas, liquefied petroleum gas (LPG), dimethyl ether, and carbonic acid gas.

Examples of the surfactants include nonionic surfactants such as polyoxyethylene alkyl ether, polyoxyethylene alkyl aryl ether, and polyethylene glycol fatty acid ester; and anionic surfactants such as alkyl sulfonate, alkylbenzene sulfonate, and alkyl sulfate.

Examples of other auxiliary agents for formulation include stickers, dispersers, colorants and stabilizers, specifically casein, gelatin, saccharides (starch, gum arabic, cellulose derivatives, and alginic acid), lignin derivatives, bentonite, water-soluble synthetic polymers (polyvinyl alcohol, polyvinylpyrrolidone, and polyacrylic acids), PAP (acidic isopropyl phosphate), BHT (2,6-di-tert-butyl-4-methylphenol), and BHA (a mixture of 2-tert-butyl-4-methoxyphenol and 3-tert-butyl-4-methoxyphenol).

Examples of plants, for which the present compound can be used, include the followings.

Crops: corn, rice, wheat, barley, rye, triticale, oat, sorghum, cotton, soybean, peanut, kidney bean, lime bean, adzuki bean, cowpea, mung bean, urd bean, scarlet runner bean, ricebean, moth bean, tepary bean, broad bean, garden pea, chickpea, lentil, lupine, pigeon pea, alfalfa, buckwheat, sugar beet, rapeseed, sunflower, sugar cane, tobacco, and the like;

Vegetables: solanaceous vegetables (for example, eggplant, tomato, pimento, pepper, bell pepper, and potato), cucurbitaceous vegetables (for example, cucumber, pumpkin, zucchini, water melon, melon, and squash), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), umbelliferous vegetables (for example, carrot, parsley, celery, and parsnip), chenopodiaceous vegetables (for example, spinach and Swiss chard), lamiaceous vegetables (for example, *Perilla frutescens*, mint, basil, and lavender), strawberry, sweet potato, *Dioscorea japonica, colocasia*, and the like;

Fruits: pomaceous fruits (for example, apple, pear, Japanese pear, Chinese quince, and quince), stone fruits (for example, peach, plum, nectarine, *Prunus mume*, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, persimmon, olive, loquat, banana, coffee, date palm, coconuts, and the like;

tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus*, spruce, and yew); flowering plants, foliage plants, *zoysia*, grasses, and the like.

The above-mentioned plants are not limited as long as cultivars thereof are generally cultivated.

The above-mentioned plants may also be plants bled by hybrid technology.

Namely, plants bled by hybrid technology mean an F1 hybrid obtained by crossbleeding of cultivars of two different lines, and are generally plants having properties of a hybrid vigor (which generally brings an increase in yield potential, improvement in resistance to biotic and abiotic stress factors, and the like) with nature better than those of parents.

Examples of pests, which can be controlled by the present compound, include plant pathogenic fungi/bacteria such as filamentous fungi and bacteria, and specific examples include, but are not limited to the followings.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (Sclerophthora *macrospora*); Wheat diseases: powdery mildew (*Erysiphe graminis*), *fusarium* blight (*Fusarium* gaminearum, *F. avenaceum, F. culmorum*, Microdochium *nivale*), rust (*Puccinia striiformis, P. graminis, P. recondita*), pink snow mould (*Micronectriella nivale, M. majus*), *typhula* snow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), seeding dieback caused by *Rhizoctonia* (*Rhizoctonia solani*), and take-all disease (*Gaeumannomyces graminis*); Barley diseases: powdery mildew (*Erysiphe graminis*), *fusarium* blight (*Fusarium* gaminearum, *F. avenaceum, F. culmorum*, Microdochium *nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), *Ramularia* disease (*Ramularia collo-cygni*), and seeding dieback caused by *Rhizoctonia* (*Rhizoctonia solani*); Corn diseases: rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum graminicola*), gray leaf spot (*Cercospora zeae-maydis*), eyespot (*Kabatiella zeae*), and *phaeosphaeria* leaf spot (*Phaeosphaeria maydis*); Cotton diseases: anthracnose (*Colletotrichum gossypii*), grey mildew (*Ramularia areola*), and *alternaria* leaf spot (*Alternaria macrospora, A. gossypii*); Coffee diseases: rust (*Hemileia vastatrix*); Rape seed diseases: *sclerotinia* rot (*Sclerotinia sclerotiorum*), black spot (*Alternaria brassicae*), and black leg (*Phoma lingam*); Citrus diseases: melanose (*Diaporthe citri*), scab (*Elsinoe fawcetti*), and fruit rot (*Penicillium digitatum, P. italicum*); Apple diseases: blossom blight (*Monilinia mali*), canker (*Valsa ceratosperma*), powdery mildew (*Podosphaera leucotricha*), *alternaria* leaf spot (*Alternaria alternata* apple pathotype), scab (*Venturia inaequalis*), bitter rot (*Glomerella cingulata*), brown spot (*Diplocarpon mali*), and ring spot (*Botryosphaeria berengeriana*); Pear diseases: scab (*Venturia nashicola, V. pirina*), black spot (*Alternaria alternata* Japanese pear pathotype), and rust (*Gymnosporangium haraeanum*);

Peach diseases: brown rot (*Monilinia fructicola*), scab (*Cladosporium carpophilum*), and *Phomopsis* rot (*Phomopsis* sp.); Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), *fusarium* wilt (*Fusarium oxysporum*), downy mildew (*Pseudoperonospora cubensis*), *phytophthora* rot (*Phytophthora* sp.), and damping-off (*Pythium* sp.); Tomato diseases: early blight (*Alternaria solani*), leaf mold (*Cladosporium fulvum*), leaf mold (*Pseudocercospora fuligena*), and late blight (*Phytophthora infestans*), powdery mildew (*Leveillula taurica*); Eggplant diseases: brown spot (*Phomopsis vexans*) and powdery mildew (*Erysiphe cichoracearum*); Cruciferous vegetables diseases: *alternaria* leaf spot (*Alternaria japonica*), white spot (*Cercosporella brassicae*), clubroot (*Plasmodiophora brassicae*), and downy mildew (*Peronospora parasitica*); Welsh onion diseases: rust (*Puccinia allii*); Soybean diseases: purple stain (*Cercospora kikuchii*), *sphaceloma* scad (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum* glycines, *C. truncatum*), *Rhizoctonia* aerial blight (*Rhizoctonia solani*), *septoria* brown spot (*Septoria glycines*), and frog eye leaf spot (*Cercospora sojina*); Kidney bean diseases: anthracnose (*Colletotrichum lindemuthianum*); Peanut diseases: early leaf spot (*Cercospora personata*), late leaf spot (*Cercospora arachidicola*), and southern blight (*Sclerotium rolfsii*); Garden pea diseases: powdery mildew (*Erysiphe pisi*); Potato diseases: early blight (*Alternaria solani*), late blight (*Phytophthora infestans*), and *verticillium* wilt (*Verticillium alboatrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theaesinensis*); Tobacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*); Sugar beet diseases: *cercospora* leaf spot (*Cercospora beticola*), leaf blight (*Thanatephorus cucumeris*), root rot (*Thanatephorus cucumeris*), and *aphanomyces* root rot (*Aphanomyces cochlioides*); Rose diseases: black spot (*Diplocarpon rosae*) and powdery mildew (*Sphaerotheca pannosa*); Chrysanthemum diseases: leaf blight (*Septoria chrysanthemi-indici*) and white rust (*Puccinia horiana*); Onion diseases: *botrytis* leaf blight (*Botrytis cinerea, B. byssoidea, B. squamosa*), gray-mold neck rot (*Botrytis alli*), and small sclerotial rot (*Botrytis squamosa*); various crops diseases: gray mold (*Botrytis cinerea*) and *sclerotinia* rot (*Sclerotinia sclerotiorum*); Japanese radish diseases: *alternaria* leaf spot (*Alternaria brassicicola*); Turfgrass diseases: dollar spot (*Sclerotinia homoeocarpa*) and brown patch and large patch (*Rhizocto-* nia solani); and Banana diseases: Sigatoka disease (Mycosphaerella fijiensis, Mycosphaerella musicola).

Seed diseases or diseases in the early growth phase in various crops caused by fungi from genera of Aspergillus, Penicillium, Fusarium, Gibberella, Tricoderma, Thielaviopsis, Rhizopus, Mucor, Corticium, Phoma, Rhizoctonia, Diplodia, and the like.

Viral diseases intermediated by genera of Polymyxa, Olpidium, or the like in various crops.

Rice damping-off (Burkholderia plantarii); cucumber bacterial blight (Pseudomonas syringae pv. Lachrymans); eggplant bacterial wilt disease (Ralstonia solanacearum), citrus canker (Xanthomonas citri); Chinese cabbage soft rod (Erwinia carotovora) and the like.

Examples of pests, against which the present compound has control activity, include pests such as pest insects and pest mites. Specific examples of these pests include, but are not limited, to the followings.

Hemiptera: planthoppers such as small brown planthopper (Laodelphax striatellus), brown rice planthopper (Nilaparvata lugens), white-backed rice planthopper (Sogatella furcifera), and corn planthopper (Peregrinus maidis); leafhoppers such as green rice leafhopper (Nephotettix cincticeps), Taiwan green rice leafhopper (Nephotettix virescens), rice green leafhopper (Nephotettix nigropictus), zig-zag rice leafhopper (Recilia dorsalis), tea green leafhopper (Empoasca onukii), potato leafhopper (Empoasca fabae), corn leafhopper (Dalbulus maidis), Sugarcane froghopper (Mahanarva posticata), Sugarcane root spittlebug (Mahanarva fimbriolata), white giant leafhopper (Cofana spectra), cross-di-green rice leafhopper (Nephotettix nigropictus), and zig-zag rice leafhopper (Recilia dorsalis); aphids such as cotton aphid (Aphis gossypii), green peach aphid (Myzus persicae), cabbage aphid (Brevicoryne brassicae), spiraea aphid (Aphis spiraecola), tulip aphid (Macrosiphum euphorbiae), potato aphid (Aulacorthum solani), oat bird-cherry aphid (Rhopalosiphum padi), tropical citrus aphid (Toxoptera citricidus), mealy plum aphid (Hyalopterus pruni), soybean aphid (Aphis glycines Matsumura), corn aphid (Rhopalosiphum maidis), rice root aphid (Tetraneura nigriabdominalis), grape root aphid (Viteus vitifoliae), grape phylloxera (Daktulosphaira vitifoliae), pecan phylloxera (Phylloxera devastatrix Pergande), pecan leaf phylloxera (Phylloxera notabilis pergande), and southern pecan leaf phylloxera (Phylloxera russellae Stoetzel); stink bugs such as Japanese black rice bug (Scotinophara lurida), Malayan rice black bug (Scotinophara coarctata), green stink bug (Nezara antennata), white spotted spined bug (Eysarcoris parvus), stink bug (Halyomorpha mista), southern green stink bug (Nezara viridula), Brown stink bug (Euschistus heros), Southern green stink bug (Nezara viridula), Red banded stink bug (Piezodorus guildinii), Burrower brown bug (Scaptocoris castanea), Oebalus pugnax, and Dichelops melacanthus; broad-headed bugs such as bean bug (Riptortus clavetus), rice bug (Leptocorisa chinensis), rice seed bug (Leptocorisa acuta), and Leptocorisa genus; plant bugs such as rice leaf bug (Trigonotylus caelestialium), sorghum plant bug (Stenotus rubrovittatus), tarnished plant bug (Lygus lineolaris), and chinchi bug (Blissus leucopterus leucopterus); whiteflies such as greenhouse whitefly (Trialeurodes vaporariorum), tobacco whitefly (Bemisia tabaci), citrus whitefly (Dialeurodes citri), and orange spiny whitefly (Aleurocanthus spiniferus); scales such as California red scale (Aonidiella aurantii), san Jose scale (Comstockaspis perniciosa), citrus north scale (Unaspis citri), red wax scale (Ceroplastes rubens), cottony cushion scale (Icerya purchasi), Japanese mealybug (Planococcus kraunhiae), comstock mealybug (Pseudococcus longispinus), white peach scale (Pseudaulacaspis pentagona), and tuttle mealybug (Brevennia rehi); psylla such as Asian citrus psyllid (Diaphorina citri), pear sucker (Psylla pyrisuga), and potato psyllid (Bactericerca cockerelli); lace bugs such as pear lace bug (Stephanitis nashi); bed bugs such as bed bug (Cimex lectularius); and Giant Cicada (Quesada gigas).

Lepidoptera: pyralid moths such as rice stem borer (Chilo suppressalis), Darkheaded stm borer (Chilo polychrysus), yellow rice borer (Tryporyza incertulas), tropical borer (Chilo suppressalis), white rice borer (Scirpophaga innotata), Yellow stem borer (Scirpophaga incertulas), Pink borer (Sesamia inferens), Rupela albinellam, rice leafroller (Cnaphalocrocis medinalis), Marasmia patnalis, Marasmia exigna, cotton leafroller (Notarcha derogata), Indian meal moth (Plodia interpunctella), oriental corn borer (Ostrinia furnacalis), cabbage webworm (Hellula undalis), bluegrass webworm (Pediasia teterrellus), Rice Caseworm (Nymphula depunctalis), Marasmia genus, Hop vine borer (Hydraecia immanis), European corn borer (Ostrinia nubilalis), Lesser cornstalk borer (Elasmopalpus lignosellus), Bean Shoot Borer (Epinotia aporema), Sugarcane borer (Diatraea saccharalis), and Giant Sugarcane borer (Telchin licus); owlet moths such as common cutworm (Spodoptera litura), beet armyworm (Spodoptera exigua), armyworm (Pseudaletia separata), cabbage armyworm (Mamestra brassicae), pink borer (Sesamia inferens), lawn armyworm (Spodoptera mauritia), fall armyworm (Spodoptera frugiperda), Spodoptera exempta, black cutworm (Agrotis ipsilon), beet semilooper (Plusia nigrisigna), Soybean looper (Pseudoplusia includens), Thoricoplusia genus, Heliothis genus such as oriental tobacco budworm (Heliothis virescens), Helicoverpa genus such as corn earworm (Helicoverpa armigera), velvetbean caterpillar (Anticarsia gemmatalis), and Cotton leafworm (Alabama argillacea); white butterflies such as common white (Pieris rapae); tortricid moths such as Adoxophyes genus, oriental fruit moth (Grapholita molesta), soybean pod borer (Leguminivora glycinivorella), azuki bean podworm (Matsumuraeses azukivora), summer fruit tortrix (Adoxophyes orana fasciata), smaller tea tortrix (Adoxophyes honmai.), oriental tea tortrix (Homona magnanima), apple tortrix (Archips fuscocupreanus), and codling moth (Cydia pomonella); leafblotch miners such as tea leafroller (Caloptilia theivora) and apple leafminer (Phyllonorycter ringoneella); fruitworm moths such as peach fruit moth (Carposina niponensis) and Citrus fruit borer (Ecdytolopha aurantiana); lyonetiid moths such as coffee Leaf miner (Leucoptera coffeela) and Lyonetia genus; tussock moths such as Lymantria genus and Euproctis genus; yponomeutid moths such as diamondback (Plutella xylostella); gelechiid moths such as pink bollworm (Pectinophora gossypiella) and potato tubeworm (Phthorimaea operculella); tiger moths such as fall webworm (Hyphantria cunea).

Thysanoptera: thrips such as yellow citrus thrips (Frankliniella occidentalis), melon thrips (Thrips palmi), yellow tea thrips (Scirtothrips dorsalis), onion thrips (Thrips tabaci), flower thrips (Frankliniella intonsa), western flower thrips (Frankliniella occidentalis), rice aculeated thrips (Haplothrips aculeatus), and rice thrips (Stenchaetothrips biformis).

Diptera: anthomyiid flies such as seedcorn maggot (Delia platura), onion maggot (Delia antiqua), and sugar beet root maggot (Tetanops myopaeformis); leafminers such as rice leafminer (Agromyza oryzae), rice leafminer (Hydrellia griseola), tomato leafminer (Liriomyza sativae), bean leafminer (Liriomyza trifolii), and garden pea leafminer (Chromatomyia horticola); grass flies such as rice stem maggot (Chlorops oryzae); fruit flies such as melon fly (Dacus cucurbitae) and Mediterranean fruit fly (Ceratitis capitata); shore flies such as oriental rice whorl maggot (Hydrellia philippina), and rice whorl maggot (Hydrellia sasakii); drosophila; phorid flies such as humpbacked fly (Megaselia spiracularis); moth flies such as bath room fly (Clogmia albipunctata); Sciarid flies. Gall midges such as Hessian fly (Mayetiola destructor) and rice gall midge (Orseolia oryzae); Stalk-eyed flies such as Diopsis macrophthalma; craneflies such as Common cranefly (Tipula oleracea) and European cranefly (Tipula paludosa).

Coleoptera: leaf beetles such as western corn rootworm (Diabrotica virgifera virgifera), southern corn rootworm (Diabrotica undecimpunctata howardi), northern corn rootworm (Diabrotica barberi), Mexican corn rootworm (Diabrotica virgifera zeae), banded cucumber beetle (Diabrotica balteata LeConte), San Antonio beetle (Diabrotica speciosa), Cucurbit Beetle (Diabrotica speciosa), bean leaf beetle (Cerotoma trifurcata), cereal leaf beetle (Oulema melanopus), cucurbit leaf beetle (Aulacophora femoralis), yellow striped flea beetle (Phyllotreta striolata), colorado potato beetle (Leptinotarsa decemlineata), rice leaf beetle (Oulema oryzae), grape colaspis (Colaspis brunnea), corn flea beetle (Chaetocnema pulicaria), potato flea beetle (Epitrix cucumeris), rice hispa (Dicladispa armigera), Seedcorn beetle (Stenolophus lecontei), and Slender seedcorn beetle (Clivinia impressifrons); chafers such as cupreous chafer (Anomala cuprea), soybean beetle (Anomala rufocuprea), Japanese beetle (Popillia japonica), European chafer (Rhizotrogus majalis), carrot beetle (Bothynus gibbosus), Grape Colaspis (Colaspis brunnea), southern corn leaf beetle (Myochrous denticollis), Holotrichia genus, Phyllophaga genus, for example June beetle (Phyllophaga crinita); rice plant weevils such as maize weevil (Sitophilus zeamais), rice plant weevil (Echinocnemus squameus), rice water weevil (Lissorhoptrus oryzophilus), and hunting billbug (Sphenophorus venatus); weevils such as boll weevil (Anthonomus grandis), southern corn billbug (Sphenophorus callosus), Soybean stalk weevil (Sternechus subsignatus) and Sphenophorus genus, for example Sphenophorus levis; Epilachna such as twenty-eight-spotted ladybirds (Epilachna vigintioctopunctata); bark beetles such as powder post beetle (Lyctus brunneus) and pine shoot beetle (Tomicus piniperda); larger grain borers; museum beetles; longicorn beetles such as white-spotted longicorn beetle (Anoplophora malasiaca) and Migdolus fryanus; click beetles (Agriotes sp., Aelous sp., Anchastus sp., Melanotus sp., Limonius sp., Conoderus sp., Ctenicera sp.) such as sugarcane wireworm (Melanotus okinawensis), barley wireworm (Agriotes ogurae fuscicollis), and click beetle (Melanotus legatus); staphylinids such as rove beetles (Paederus fuscipes); and Coffee Barry Borer (Hypothenemus hampei).

Orthoptera: crickets such as asiatic locusts (Locusta migratoria), African mole cricket (Gryllotalpa africana), Moroccan locust (Dociostaurus maroccanus), Australian plague locust (Chortoicetes terminifera), red locust (Nomadacris septemfasciata), brown locust (Locustana pardalina), tree locust (Anacridium melanorhodon), Italian locust (Calliptamus italicus), differential grasshopper (Melanoplus differentialis), twostriped grasshopper (Melanoplus bivittatus), migratory grasshopper (Melanoplus sanguinipes), redlegged grasshopper (Melanoplus femurrubrum), clearwinged grasshopper (Camnula pellucida), desert locust (Schistocerca gregaria), yellow-winged locust (Gastrimargus musicus), spur-throated locust (Austracris guttulosa), rice grasshopper (Oxya yezoensis), Japanese grasshopper (Oxya japonica), Bombay locust (Patanga succincta), house cricket (Acheta domesticus), emma field cricket (Teleogryllus emma), and Mormon cricket (Anabrus simplex).

Hymenoptera: sawflies such as cabbage sawflies (Athalia rosae) and Japanese cabbage sawfly (Athalia japonica). Fire ants. Leaf cutting ants such as Brown leaf-cutting ant (Atta capiguara).

Nematodes: white-tip nematode (Aphelenchoides besseyi), strawberry bud nematode (Nothotylenchus acris), southern root-knot nematode (Meloidogyne incognita), northern root-knot nematode (Meloidogyne hapla), javanese root-knot nematode (Meloidogyne javanica), soybean cyst nematode (Heterodera glycines), golden nematode (Globodera rostochiensis), coffee root-lesion nematode (Pratylenchus coffeae), california root-lesion nematode (Pratylenchus neglectus), Meloidogyne javanica, Meloidogyne incognita, Rotylenchulus reniformis, and Pratylenchus brachyurus.

Blattariae: German cockroach (Blattella germanica), smoky-brown cockroach (Periplaneta fuliginosa), American cockroach (Periplaneta americana), brown cockroach (Periplaneta brunnea), and oriental cockroach (Blatta orientalis).

Isoptera: Japanese subterranean termite (Reticulitermes speratus), formosan subterranean termite (Coptotermes formosanus), western drywood termite (Incisitermes minor), drywood termite (Cryptotermes domesticus), Taiwan termite (Odontotermes formosanus), Kosyun termite (Neotermes koshunensis), Satsuma termite (Glyptotermes satsumensis), Nakajima termite (Glyptotermes nakajimai), Katan termite (Glyptotermes fuscus), Kodama termite (Glyptotermes kodamai), Kushimoto termite (Glyptotermes kushimensis), Japanese damp-wood termite (Hodotermopsis japonica), Koshu formosan termite (Coptotermes guangzhoensis), Amami termite (Reticulitermes miyatakei), Kiashi termite (Reticulitermes flaviceps amamianus), Kanmon termite (Reticulitermes sp.), Takasago termite (Nasutitermes takasagoensis), Nitobe termite (Pericapritermes nitobei), Musya termite (Sinocapritermes mushae), Cornitermes cumulans, and the like.

Acarina: Tetranychidae such as two-spotted spider mite (Tetranychus urticae), kanzawa spider mite (Tetranychus kanzawai), citrus red mite (Panonychus citri), European red mite (Panonychus ulmi), Oligonychus genus and southern turkey spider mites (Brevipalpus phoenicis); Eriophyidae such as pink citrus rust mite (Aculops pelekassi), Ryukyu tangerine rust mite (Phyllocoptruta citri), tomato russet mite (Aculops lycopersici), tea rust mite (Calacarus carinatus), tea Roh Naga rust mite (Acaphylla theavagrans), fake pear rust mite (Eriophyes chibaensis), and apple rust mite (Aculus schlechtendali); Tarsonemidae such as tea dust mite (Polyphagotarsonemus latus); Tenuipalpidae such as Southern Hime spider mite (Brevipalpus phoenicis); Tuckerellidae; Ixodidae such as cattle tick (Haemaphysalis longicornis), Yamatochi tick (Haemaphysalis flava), Taiwan Kaku tick (Dermacentor taiwanicus), American dog Kaku tick (Dermacentor variabilis), tick (Ixodes ovatus), Schultz tick (Ixodes persulcatus), black-legged tick (Ixodes scapularis), lone star tick (Amblyomma americanum), Oshima tick (Boophilus microplus), and brown dog tick (Rhipicephalus sanguineus); Acaridae such as common grain mite (Tyrophagus putrescentiae) and spinach common grain mite (Tyrophagus similis); Pyroglyphidae such as American house dust mite (Dermatophagoides farinae) and house dust mite (Dermatophagoides pteronyssinus).

Cheyletidae such as cheyletid mite (Cheyletus eruditus), Stag Tsumedani (Cheyletus malaccensis), Minami Tsumedani (Cheyletus moorei), and Inutsumedani (Cheyletiella yasguri); Cheyletidae such as ear mite (*Octodectes cynotis*) and itch mite (*Sarcoptes scabiei*); Demodicidae such as dog follicle mite (*Demodex canis*); Listrophoridae; Oribatulidae; Dermanyssidae such as tropical rat mite (*Ornithonyssus bacoti*), northern fowl mite (*Ornithonyssus sylvairum*), and red mite (*Dermanyssus gallinae*); Trombiculidae such as blue chigger (*Leptotrombidium akamushi*); and Araneida such as Japanese foliage spider (*Chiracanthium japonicum*) and red back spider (*Latrodectus hasseltii*).

Chilopoda: house centipede (*Thereuonema hilgendorfi*), Chinese red headed centipede (*Scolopendra subspinipes*) and the like.

Diplopoda: garden millipede (*Oxidus gracilis*), garden millipede (*Nedyopus tambanus*) and the like.

Isopoda: pill bug (*Armadillidium vulgare*) and the like.

Gastropoda: tree slug (*Limax marginatus*), yellow slug (*Limax flavus*) and the like.

Target pest insects and pest mites may also be insects and mites each having reduced chemical sensitivity or enhanced chemical resistance to insecticides and acaricides. When chemical sensitivity is significantly reduced or chemical resistance is significantly enhanced, use of the present composition containing insecticides and acaricides other than target insecticides and acaricides is desirable.

The present compound can also be used to protect plants from plant diseases due to insect-borne virus.

Examples of plant diseases caused by insect-borne viruses, against which the present compound has control activity, include the followings.

Rice waika (Rice waika virus), rice tungro (Rice tungro spherical virus, Rice tungro bacilliform virus), rice grassy stunt (Rice grassy stunt virus), rice ragged stunt (Rice ragged stunt virus), rice stripe (Rice stripe virus), rice black streaked dwarf (Rice black streaked dwarf virus), southern rice black-streaked dwarf (Southern rice black-streaked dwarf virus), rice gall dwarf (Rice gall dwarf virus), rice hoja blanca (Rice hoja blanca virus), rice white leaf (White leaf disease of rice), yellow dwarf (Yellow dwarf virus), red disease (Rice penyakit merah virus), rice yellow stunt (Rice yellow stunt virus), rice transitory yellowing (Rice transitory yellowing virus), rice yellow mottle (Rice Yellow Mottle Virus), rice necrosis mosaic (Rice necrosis mosaic virus), rice dwarf stunt (Rice dwarf stunt virus), northern cereal mosaic (Northern Cereal Mosaic Virus), barley yellow dwarf (Barley Yellow Dwarf Virus), wheat yellow dwarf (Wheat yellow dwarf virus), Oat sterile dwarf (Oat sterile dwarf virus), wheat streak mosaic (Wheat streak mosaic virus), maize dwarf mosaic (Maize dwarf mosaic virus), maize stripe disease (maize stripe tenuivirus), maize chlorotic dwarf (Maize chlorotic dwarf virus), maize chlorotic mottle (maize chlorotic mottle virus), maize rayado fino (maize rayado fino marafivirus), corn stunt (Corn stunt spiroplasma), maize bushy stunt (Maize bushy stunt phytoplasma), sugarcane mosaic (Sugarcane mosaic virus), soybean mild mosaic (Soybean mild mosaic virus), alfalfa mosaic (Alfalfa Mosaic Virus, Bean yellow-spot mosaic virus, Soybean mosaic virus, Bean yellow mosaic virus, Cowpea severe mosaic virus), broad bean wilt (Broad bean wilt virus, Bean common mosaic virus, Peanut stunt virus, Southern bean mosaic virus), soybean dwarf (Soybean dwarf luteovirus, Milk-vetch dwarf luteovirus), bean-pod mottle (Bean-pod mottle virus), brazilian bud blight (Tobacco streak virus), cowpea chlorotic mottle (Cowpea chlorotic mottle), mung bean yellow mosaic (Mung bean yellow mosaic virus), peanut stripe (Peanut stripe mottle), soybean crinkle leaf (Soybean crinkle leaf virus), soybean severe stunt (Soybean severe stunt virus), tomato chlorosis (Tomato chlorosis virus), tomato spotted wilt (Tomato spotted wilt virus), tomato yellow leaf curl (Tomato yellow leaf curl virus), melon yellow spot (Melon yellow spot virus), watermelon mosaic (Watermelon mosaic virus), cucumber mosaic (Cucumber mosaic virus), zucchini yellow mosaic (Zucchini yellow mosaic virus), turnip mosaic (Turnip mosaic virus), cucurbit chlorotic yellows (Cucurbit chlorotic yellows virus), *capsicum* chlorosis (*Capsicum* chlorosis virus), beet pseudo yellows (Beet pseudo yellows virus), *chrysanthemum* stem necrosis (*chrysanthemum* stem necrosis virus), *impatiens* necrotic spot (*Impatiens* necrotic spot virus), iris yellow spot (Iris yellow spot virus), sweet potato internal cork (Sweet potato internal cork virus), sweet potato shukuyo mosaic (Sweet potato shukuyo mosaic virus), and mosaic virus diseases of various plants transmitted by the genus *Polymyxa* or Olpidium.

The formulation comprising the present compound or salts thereof can be used in the field relating to a treatment of livestock diseases or livestock industry, and can exterminate the living things or parasites which are parasitic on the inside and/or the outside of vertebrates such as human being, cow, sheep, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), *Dermacentor* spp., *Ornithodoros* spp. (for example, *Ornithodoros moubata*), red mite (*Dermanyssus gallinae*), ghost ant (*Ornithonyssus sylviarum*), *Sarcoptes* spp. (for example, *Sarcoptes scabiei*), *Psoroptes* spp., *Chorioptes* spp., *Demodex* spp., *Eutrombicula* spp., *Aedes* spp. (for example, Asian tiger mosquito (*Aedes albopictus*)), *Anopheles* spp., *Culex* spp., *Culicoides* spp., *Musca* spp., *Hypoderma* spp., *Gasterophilus* spp., *Haematobia* spp., *Tabanus* spp., *Simulium* spp., *Triatoma* spp., lice (*Phthiraptera*) (for example, *Damalinia* spp., *Linognathus* spp., *Haematopinus* spp.), *Ctenocephalides* spp. (for example, cat flea (*Ctenocephalides felis*)) *Xenopsylla* spp., Pharaoh's ant (*Monomorium pharaonic*) and nematodes [for example, hairworm (for example, *Nippostrongylus brasiliensis, Trichostrongylus axei, Trichostrongylus colubriformis*), *Trichinella* spp. (for example, *Trichinella spiralis*), barber pole worm (*Haemonchus contortus*), *Nematodirus* spp. (for example, *Nematodirus battus*), *Ostertagia circumcincta, Cooperia* spp., *Hymenolepis nana*, and the like.

EXAMPLES

The present invention will be described in more detail below by way of Production Examples, Formulation Examples, and Test Examples, but the present invention is not limited to these Examples.

Names of intermediates used in Production Examples are names to be given to intermediates produced in Reference Production Examples mentioned below, for example, 4A. When the numerical portion of the name of this intermediate is the number of Reference Production Example and the name of the intermediate is 4A, the intermediate means an intermediate produced in Reference Production Example 4.

First, Production Examples are shown.

Production Example 1

A mixture of 37 g of 2-phenylmethoxy-3-methylbenzoic acid, 22 g of oxalyl dichloride, 30 mg of N,N-dimethylformamide, and 300 mL of tetrahydrofuran was stirred at room temperature for 1 hour. The reaction mixture was concentrated under reduced pressure to obtain 2-phenylmethoxy-3-methylbenzoic acid chloride.

A mixture of 41 g of aluminum chloride, 60 g of sodium azide, and 300 mL of tetrahydrofuran was stirred with heating under reflux for 2 hours. After ice cooling of the reaction mixture, a mixture of the entire amount of 2-phenylmethoxy-3-methylbenzoic acid chloride and 100 mL of tetrahydrofuran was added, followed by stirring with heating under reflux for 10 hours. After cooling, the reaction mixture was added in a mixture of 92 g of sodium nitrite and about 500 mL of water while stirring. The mixture was acidified with concentrated hydrochloric acid and then extracted with ethyl acetate. The organic layer was dried over anhydrous sodium sulfate and then concentrated under reduced pressure to obtain 45 g of a crude product of 1-(2-phenylmethoxy-3-methylphenyl)-1,4-dihydrotetrazol-5-one.

To a mixture of 45 g of the thus obtained crude product of 1-(2-phenylmethoxy-3-methylphenyl)-1,4-dihydrotetrazol-5-one, 50 mL of N,N-dimethylformamide, and 70 g of potassium carbonate, 23 g of dimethylsulfuric acid was added dropwise at room temperature. The mixture was stirred at room temperature for 1 hour. The reaction mixture was poured into water, and the mixture was extracted three times with ethyl acetate. The organic layer was washed with 5% hydrochloric acid, water, a saturated sodium bicarbonate solution, and a saturated saline solution, dried over anhydrous magnesium sulfate, and then concentrated under reduced pressure. The residue thus obtained was subjected to silica gel column chromatography to obtain 28 g of 1-(2-phenylmethoxy-3-methylphenyl)-4-methyl-1,4-dihydrotetrazol-5-one (hereinafter referred to as the present compound 1).

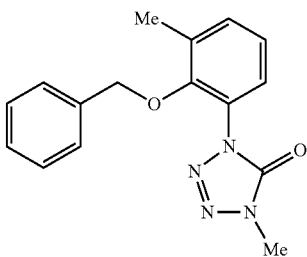 [SMILES: Cc1cccc(-n2nnn(C)c2=O)c1OCc1ccccc1]

$^1$H-NMR (CDCl$_3$) δ (ppm): 7.37-7.15 (8H, m), 4.85 (2H, s), 3.57 (3H, s), 2.39 (3H, s).

Production Example 2

A mixture of 0.30 g (0.68 mmol) of 2A mentioned in Reference Production Example 2, 0.21 g (1.49 mmol) of 3-methylbenzyl chloride, 0.26 g (1.88 mmol) of potassium carbonate, and 10 mL of acetonitrile was stirred with heating under reflux for 5 hours. The reaction mixture was cooled and then concentrated under reduced pressure. The residue thus obtained was subjected to silica gel column chromatography to obtain 0.34 g of 1-[2-(3-methylphenyl)methoxy-3-methylphenyl]-4-methyl-1,4-dihydrotetrazol-5-one (hereinafter referred to as the present compound 2).

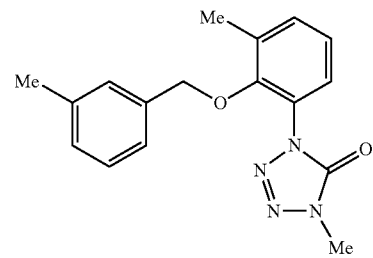 [SMILES: Cc1cccc(COc2c(C)cccc2-n2nnn(C)c2=O)c1]

$^1$H-NMR (CDCl$_3$) δ (ppm): 7.37-7.34 (1H, m), 7.26-7.15 (4H, m), 7.13-7.05 (2H, m), 4.81 (2H, s), 3.58 (3H, s), 2.40 (3H, s), 2.35 (3H, s).

Using commercially available compounds, the present compounds 3 to 12 and 50 were synthesized by the same reaction as in Production Example 2. Structures of the present compounds 3 to 12 and analytical values of $^1$H-NMR thereof are shown below.

Present Compound 3

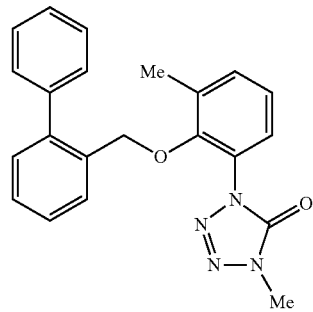

Present Compound 4

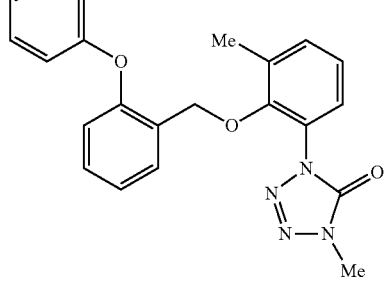

Present Compound 5

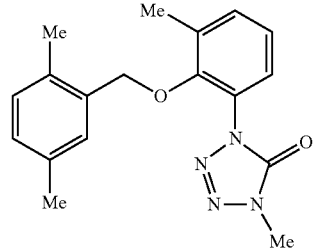

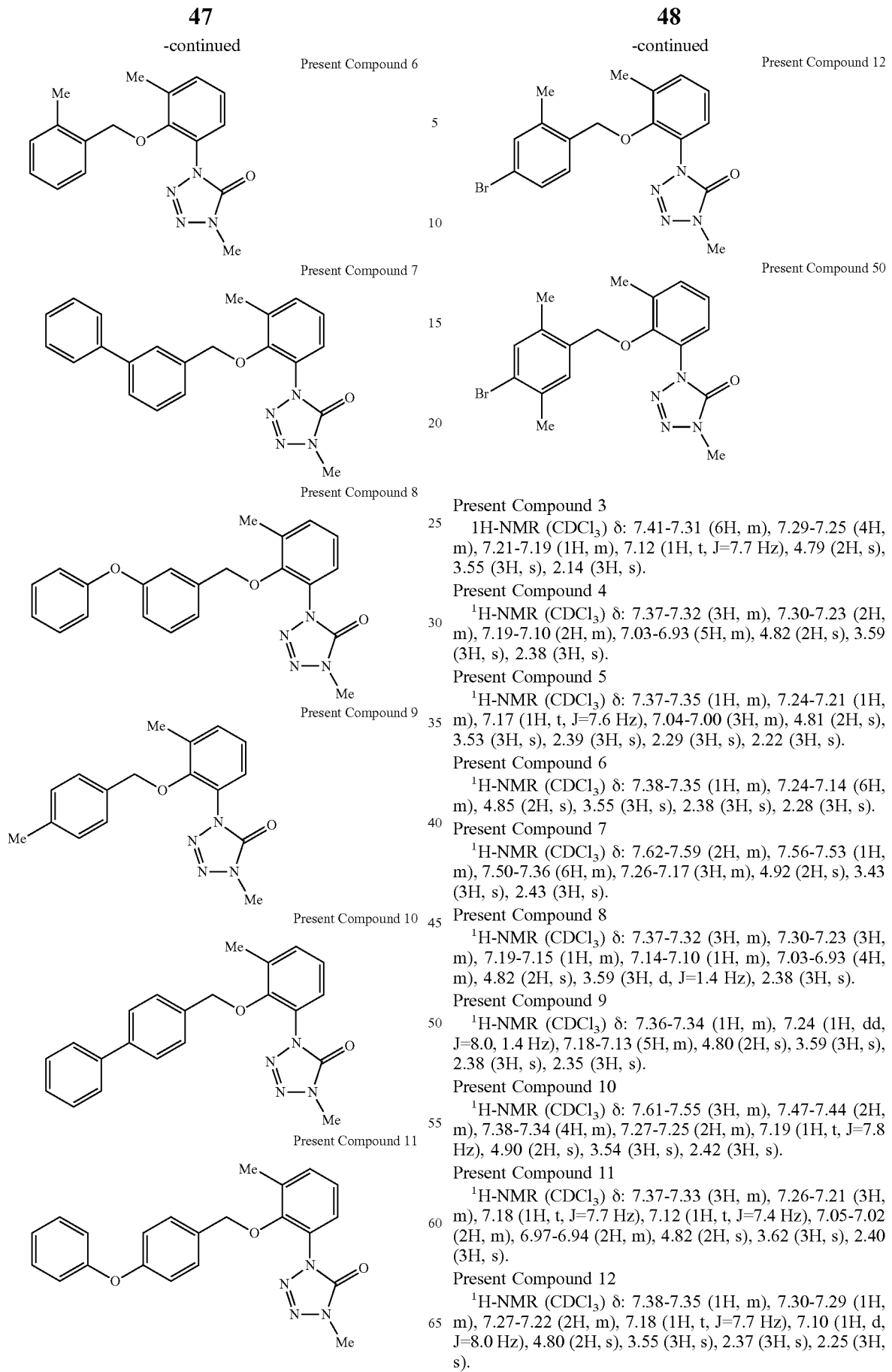

Present Compound 3
 ¹H-NMR (CDCl₃) δ: 7.41-7.31 (6H, m), 7.29-7.25 (4H, m), 7.21-7.19 (1H, m), 7.12 (1H, t, J=7.7 Hz), 4.79 (2H, s), 3.55 (3H, s), 2.14 (3H, s).
Present Compound 4
 ¹H-NMR (CDCl₃) δ: 7.37-7.32 (3H, m), 7.30-7.23 (2H, m), 7.19-7.10 (2H, m), 7.03-6.93 (5H, m), 4.82 (2H, s), 3.59 (3H, s), 2.38 (3H, s).
Present Compound 5
 ¹H-NMR (CDCl₃) δ: 7.37-7.35 (1H, m), 7.24-7.21 (1H, m), 7.17 (1H, t, J=7.6 Hz), 7.04-7.00 (3H, m), 4.81 (2H, s), 3.53 (3H, s), 2.39 (3H, s), 2.29 (3H, s), 2.22 (3H, s).
Present Compound 6
 ¹H-NMR (CDCl₃) δ: 7.38-7.35 (1H, m), 7.24-7.14 (6H, m), 4.85 (2H, s), 3.55 (3H, s), 2.38 (3H, s), 2.28 (3H, s).
Present Compound 7
 ¹H-NMR (CDCl₃) δ: 7.62-7.59 (2H, m), 7.56-7.53 (1H, m), 7.50-7.36 (6H, m), 7.26-7.17 (3H, m), 4.92 (2H, s), 3.43 (3H, s), 2.43 (3H, s).
Present Compound 8
 ¹H-NMR (CDCl₃) δ: 7.37-7.32 (3H, m), 7.30-7.23 (3H, m), 7.19-7.15 (1H, m), 7.14-7.10 (1H, m), 7.03-6.93 (4H, m), 4.82 (2H, s), 3.59 (3H, d, J=1.4 Hz), 2.38 (3H, s).
Present Compound 9
 ¹H-NMR (CDCl₃) δ: 7.36-7.34 (1H, m), 7.24 (1H, dd, J=8.0, 1.4 Hz), 7.18-7.13 (5H, m), 4.80 (2H, s), 3.59 (3H, s), 2.38 (3H, s), 2.35 (3H, s).
Present Compound 10
 ¹H-NMR (CDCl₃) δ: 7.61-7.55 (3H, m), 7.47-7.44 (2H, m), 7.38-7.34 (4H, m), 7.27-7.25 (2H, m), 7.19 (1H, t, J=7.8 Hz), 4.90 (2H, s), 3.54 (3H, s), 2.42 (3H, s).
Present Compound 11
 ¹H-NMR (CDCl₃) δ: 7.37-7.33 (3H, m), 7.26-7.21 (3H, m), 7.18 (1H, t, J=7.7 Hz), 7.12 (1H, t, J=7.4 Hz), 7.05-7.02 (2H, m), 6.97-6.94 (2H, m), 4.82 (2H, s), 3.62 (3H, s), 2.40 (3H, s).
Present Compound 12
 ¹H-NMR (CDCl₃) δ: 7.38-7.35 (1H, m), 7.30-7.29 (1H, m), 7.27-7.22 (2H, m), 7.18 (1H, t, J=7.7 Hz), 7.10 (1H, d, J=8.0 Hz), 4.80 (2H, s), 3.55 (3H, s), 2.37 (3H, s), 2.25 (3H, s).

Present Compound 50

¹H-NMR (CDCl₃) δ: 7.37 (1H, dd, J=7.4, 1.2 Hz), 7.32 (1H, s), 7.23 (1H, dd, J=7.9, 1.8 Hz), 7.18 (1H, t, J=7.7 Hz), 7.06 (1H, s), 4.77 (2H, s), 3.53 (3H, s), 2.38 (3H, s), 2.33 (3H, s), 2.21 (3H, s).

Production Example 3

A mixture of 0.39 g of the present compound 12, 0.12 g of phenylboronic acid, 0.43 g of tripotassium phosphate, 1 ml of water, 0.033 of [1,1'-bis(diphenylphosphino)ferrocene]palladium(II) dichloride dichloromethane adduct, and 10 mL of 1,4-dioxane was stirred with heating under reflux for 5 hours. The reaction mixture was cooled and then concentrated under reduced pressure. The residue thus obtained was subjected to silica gel column chromatography to obtain 0.31 g of 1-{2-[(4-phenyl-2-methylphenyl)methoxy]-3-methylphenyl}-4-methyl-1,4-dihydrotetrazol-5-one (hereinafter referred to as the present compound 13).

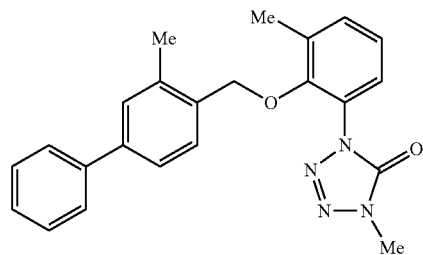 [SMILES: Cc1cc(-c2ccccc2)ccc1COc1c(C)cccc1-n1nnn(C)c1=O]

¹H-NMR (CDCl₃) δ: 7.61-7.59 (2H, m), 7.45 (2H, t, J=7.6 Hz), 7.39-7.34 (4H, m), 7.30-7.24 (2H, m), 7.19 (1H, t, J=7.7 Hz), 4.90 (2H, s), 3.51 (3H, s), 2.42 (3H, s), 2.35 (3H, s).

Using commercially available compounds, the present compounds 14 to 17 were synthesized by the same reaction as in Production Example 3. Structures of the present compounds 14 to 17 and analytical values of ¹H-NMR thereof are shown below.

Present Compound 14

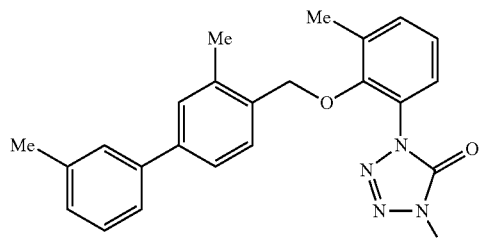

Present Compound 15

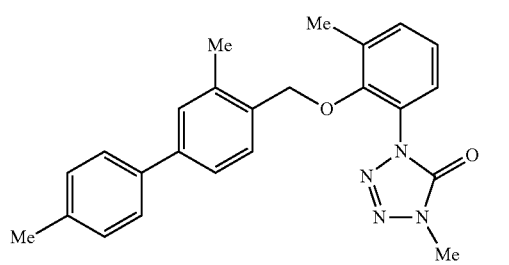

Present Compound 16

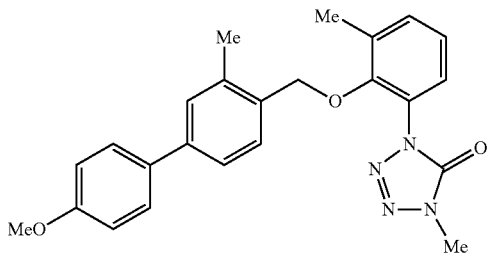

Present Compound 17

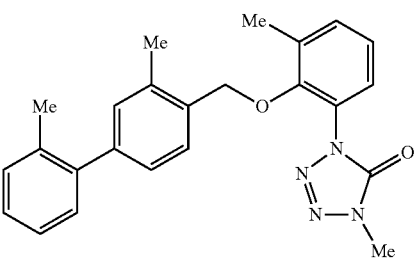

Present Compound 14

¹H-NMR (CDCl₃) δ: 7.40-7.36 (5H, m), 7.35-7.31 (1H, m), 7.29-7.23 (2H, m), 7.20-7.16 (2H, m), 4.89 (2H, s), 3.50 (3H, s), 2.42 (3H, s), 2.41 (3H, s), 2.34 (3H, s).

Present Compound 15

¹H-NMR (CDCl₃) δ: 7.51-7.49 (2H, m), 7.39-7.36 (3H, m), 7.28-7.23 (4H, m), 7.18 (1H, t, J=7.7 Hz), 4.89 (2H, s), 3.50 (3H, s), 2.41 (3H, s), 2.40 (3H, s), 2.34 (3H, s).

Present Compound 16

¹H-NMR (CDCl₃) δ: 7.55-7.51 (2H, m), 7.39-7.36 (1H, m), 7.34-7.32 (2H, m), 7.26-7.23 (2H, m), 7.18 (1H, t, J=7.7 Hz), 7.00-6.96 (2H, m), 4.88 (2H, s), 3.86 (3H, s), 3.50 (3H, s), 2.41 (3H, s), 2.34 (3H, s).

Present Compound 17

¹H-NMR (CDCl₃) δ: 7.39-7.37 (2H, m), 7.30-7.18 (5H, m), 7.12-7.09 (3H, m), 4.90 (2H, s), 3.58 (3H, s), 2.42 (3H, s), 2.29 (3H, s), 2.25 (3H, s).

Production Example 4

A mixture of 0.20 g of 5A mentioned in Reference Production Example 5, 0.075 g of [1,1'-bis(diphenylphosphino)ferrocene]palladium(II) dichloride dichloromethane adduct, 0.29 g of tripotassium phosphate, 0.052 g of 2-chloro-pyridine, 50 μL of water, and 2 mL of 1,2-dimethoxyethane was stirred at 80° C. for 4 hours. After cooling to room temperature, the reaction mixture was filtered and the filtrate was concentrated. The residue thus obtained was subjected to silica gel column chromatography to obtain 0.20 g of 1-(2-{[4-(pyridin-2-yl)-2-methylphenyl]methoxy}-3-methylphenyl)-4-methyl-1,4-dihydrotetrazol-5-one (hereinafter referred to as the present compound 18).

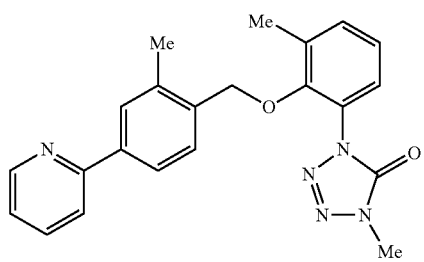 [SMILES: Cc1cc(-c2ccccn2)ccc1COc1c(C)cccc1-n1nnn(C)c1=O]

¹H-NMR (CDCl3) δ: 8.70-8.69 (1H, m), 7.83 (1H, br s), 7.78-7.73 (3H, m), 7.37 (1H, d, J=7.5 Hz), 7.34 (1H, d, J=7.9 Hz), 7.27-7.16 (3H, m), 4.91 (2H, s), 3.52 (3H, s), 2.39 (3H, s), 2.36 (3H, s).

Using commercially available compounds, the present compounds 19 to 22 and 32 to 40 were synthesized by the same reaction as in Production Example 4. Structures of the present compounds 19 to 22 and 32 to 40 and analytical values of ¹H-NMR thereof are shown below.

Present Compound 19

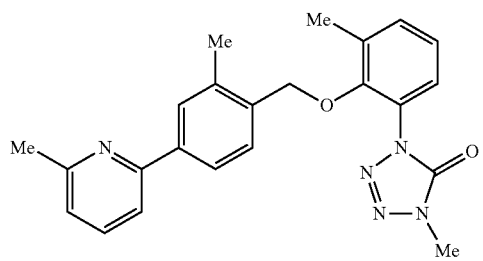

Present Compound 20

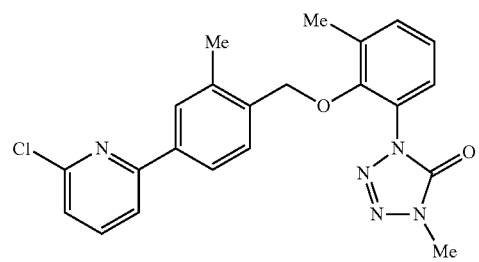

Present Compound 21

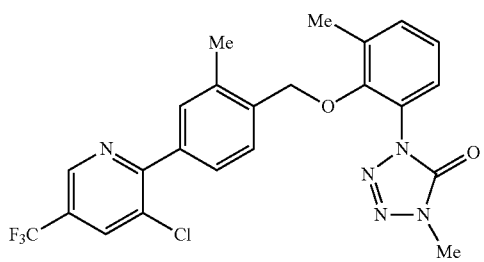

Present Compound 22

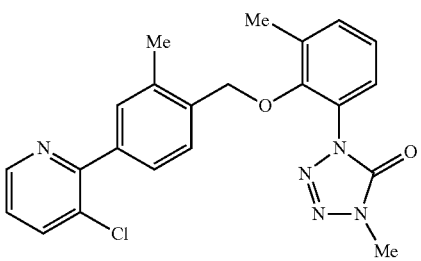

Present Compound 32

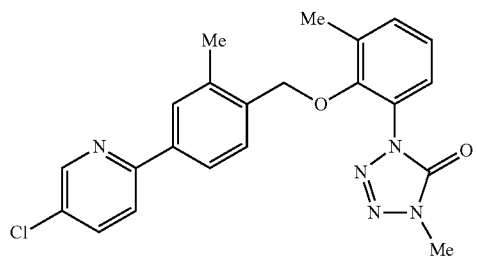

Present Compound 33

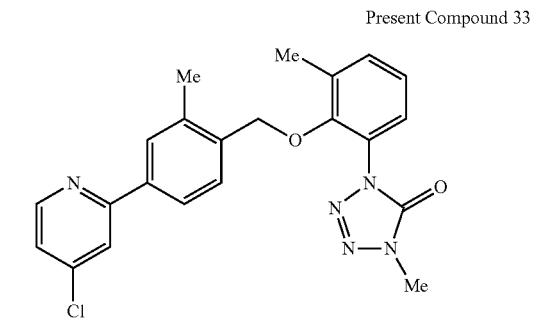

Present Compound 34

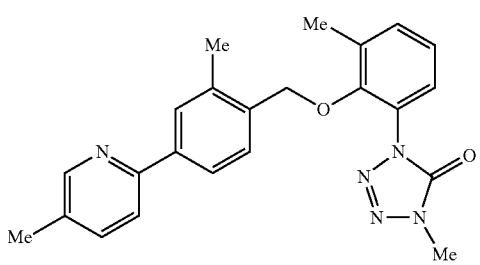

Present Compound 35

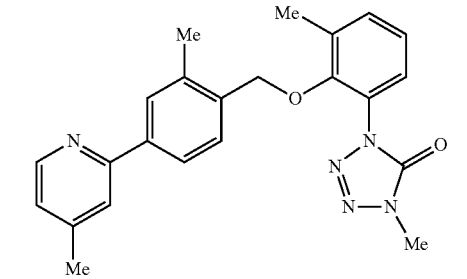

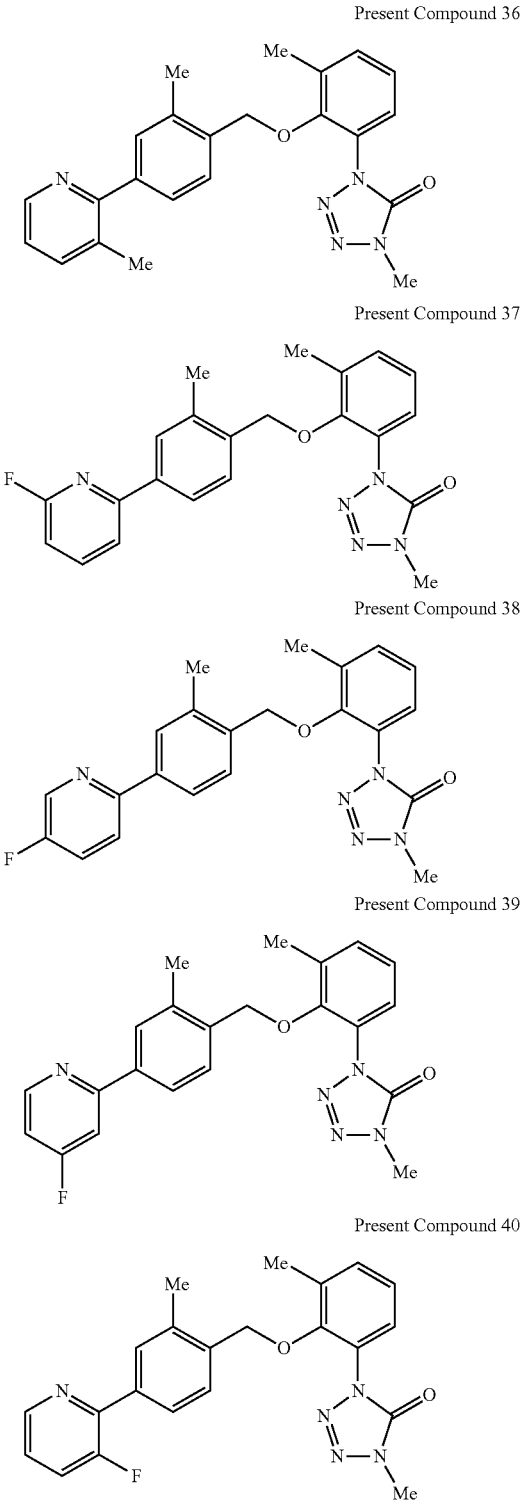

Present Compound 36

Present Compound 37

Present Compound 38

Present Compound 39

Present Compound 40

Present Compound 19

¹H-NMR (CDCl₃) 1H-NMR (CDCl3) δ: 7.81 (1H, s), 7.73 (1H, d, J=8.0 Hz), 7.63 (1H, t, J=7.8 Hz), 7.51 (1H, d, J=7.8 Hz), 7.36 (1H, d, J=7.6 Hz), 7.32 (1H, d, J=7.8 Hz), 7.25 (1H, d, J=8.0 Hz), 7.18 (1H, t, J=7.7 Hz), 7.10 (1H, d, J=7.6 Hz), 4.90 (2H, s), 3.53 (3H, s), 2.63 (3H, s), 2.38 (3H, s), 2.36 (3H, s).

Present Compound 20
¹H-NMR (CDCl₃) δ: 7.83 (1H, s), 7.74 (1H, d, J=10.8 Hz), 7.70 (1H, d, J=7.8 Hz), 7.65 (1H, d, J=7.8 Hz), 7.37 (1H, d, J=7.3 Hz), 7.34 (1H, d, J=7.8 Hz), 7.26-7.24 (2H, m), 7.18 (1H, t, J=7.7 Hz), 4.90 (2H, s), 3.53 (3H, s), 2.38 (3H, s), 2.35 (3H, s).

Present Compound 21
¹H-NMR (CDCl₃) δ: 8.84 (1H, s), 8.05-8.04 (1H, m), 7.59 (1H, d, J=7.9 Hz), 7.55 (1H, br s), 7.44 (1H, d, J=7.9 Hz), 7.39 (1H, d, J=7.7 Hz), 7.26-7.25 (1H, m), 7.20 (1H, t, J=7.7 Hz), 4.93 (2H, s), 3.56 (3H, s), 2.40 (3H, s), 2.34 (3H, s).

Present Compound 22
¹H-NMR (CDCl₃) δ: 8.59 (1H, dd, J=4.7, 1.5 Hz), 7.80 (1H, dd, J=8.1, 1.5 Hz), 7.55 (1H, d, J=7.8 Hz), 7.52 (1H, br s), 7.40-7.37 (2H, m), 7.23-7.20 (3H, m), 4.91 (2H, s), 3.57 (3H, s), 2.39 (3H, s), 2.34 (3H, s).

Present Compound 32
¹H-NMR (CDCl₃) δ: 8.63 (1H, d, J=2.1 Hz), 7.79 (1H, s), 7.74-7.67 (3H, m), 7.38-7.33 (2H, m), 7.25 (1H, dd, J=9.4, 3.0 Hz), 7.19 (1H, t, J=7.1 Hz), 4.91 (2H, s), 3.51 (3H, s), 2.39 (3H, s), 2.36 (3H, s).

Present Compound 33
¹H-NMR (CDCl₃) δ: 8.58 (1H, dd, J=5.3, 0.5 Hz), 7.81 (1H, d, J=1.4 Hz), 7.74-7.72 (2H, m), 7.41-7.34 (2H, m), 7.26-7.23 (2H, m), 7.19 (1H, t, J=7.7 Hz), 4.91 (2H, s), 3.52 (3H, s), 2.39 (3H, s), 2.36 (3H, s).

Present Compound 34
¹H-NMR (CDCl₃) δ: 8.52 (1H, s), 7.80 (1H, s), 7.71 (1H, dd, J=7.9, 1.7 Hz), 7.63 (1H, d, J=8.0 Hz), 7.56 (1H, dd, J=7.9, 1.7 Hz), 7.37 (1H, dq, J=7.7, 0.8 Hz), 7.31 (1H, d, J=8.0 Hz), 7.24 (1H, dd, J=8.0, 1.9 Hz), 7.18 (1H, t, J=7.7 Hz), 4.90 (2H, s), 3.51 (3H, s), 2.39 (3H, s), 2.38 (3H, s), 2.36 (3H, s).

Present Compound 35
¹H-NMR (CDCl₃) δ: 8.54 (1H, d, J=5.0 Hz), 7.82 (1H, s), 7.73 (1H, dd, J=8.0, 1.7 Hz), 7.55 (1H, s), 7.38-7.35 (1H, m), 7.32 (1H, d, J=8.0 Hz), 7.24 (1H, dd, J=7.6, 1.5 Hz), 7.18 (1H, td, J=7.6, 3.0 Hz), 7.06 (1H, dd, J=5.0, 0.7 Hz), 4.90 (2H, s), 3.51 (3H, s), 2.42 (3H, s), 2.38 (3H, s), 2.36 (3H, s).

Present Compound 36
¹H-NMR (CDCl₃) δ: 8.52 (1H, ddd, J=4.8, 1.6, 0.7 Hz), 7.58 (1H, dq, J=7.8, 0.8 Hz), 7.39-7.34 (2H, m), 7.32-7.29 (2H, m), 7.26-7.24 (1H, m), 7.20-7.16 (2H, m), 4.90 (2H, s), 3.59 (3H, s), 2.39 (3H, s), 2.38 (3H, s), 2.33 (3H, s).

Present Compound 37
¹H-NMR (CDCl₃) δ: 7.85-7.83 (2H, m), 7.75 (1H, dd, J=8.0, 1.8 Hz), 7.63 (1H, dd, J=7.3, 2.9 Hz), 7.37 (1H, dq, J=7.9, 0.9 Hz), 7.34 (1H, d, J=8.0 Hz), 7.24 (1H, dd, J=8.0, 1.8 Hz), 7.19 (1H, t, J=7.9 Hz), 6.87 (1H, dd, J=7.9, 2.9 Hz), 4.91 (2H, s), 3.52 (3H, s), 2.39 (3H, s), 2.35 (3H, s).

Present Compound 38
¹H-NMR (CDCl₃) δ: 8.65 (1H, ddd, J=8.8, 5.6, 1.0 Hz), 7.81 (1H, s), 7.73 (1H, d, J=7.7 Hz), 7.44 (1H, d, J=10.5 Hz), 7.36 (2H, t, J=6.6 Hz), 7.24 (1H, d, J=8.8 Hz), 7.19 (1H, td, J=7.7, 1.1 Hz), 7.01-6.96 (1H, m), 4.91 (2H, s), 3.52 (3H, d, J=1.6 Hz), 2.39 (3H, s), 2.36 (3H, s).

Present Compound 39
¹H-NMR (CDCl₃) δ: 8.54 (1H, d, J=3.0 Hz), 7.77 (1H, s), 7.73 (1H, dd, J=8.7, 4.4 Hz), 7.69 (1H, dd, J=8.0, 1.8 Hz), 7.47 (1H, td, J=8.7, 3.0 Hz), 7.39-7.36 (1H, m), 7.33 (1H, d, J=8.0 Hz), 7.24 (1H, dd, J=8.0, 2.1 Hz), 7.18 (1H, t, J=8.0 Hz), 4.90 (2H, s), 3.52 (3H, s), 2.39 (3H, s), 2.36 (3H, s).

Present Compound 40
¹H-NMR (CDCl₃) δ: 8.52 (1H, dt, J=4.6, 1.5 Hz), 7.79-7.74 (2H, m), 7.49 (1H, ddd, J=11.0, 8.2, 1.4 Hz), 7.37 (2H, d, J=7.8 Hz), 7.30-7.23 (2H, m), 7.19 (1H, t, J=7.7 Hz), 4.92 (2H, s), 3.54 (3H, s), 2.40 (3H, s), 2.35 (3H, s).

Using 23A mentioned in Reference Production Example 23 in place of 5A and using commercially available compounds, the present compounds 41 to 49 were synthesized by the same reaction as in Production Example 4. Structural formulas of the thus obtained present compounds 41 to 49 and analytical values of $^1$H-NMR thereof are shown below.

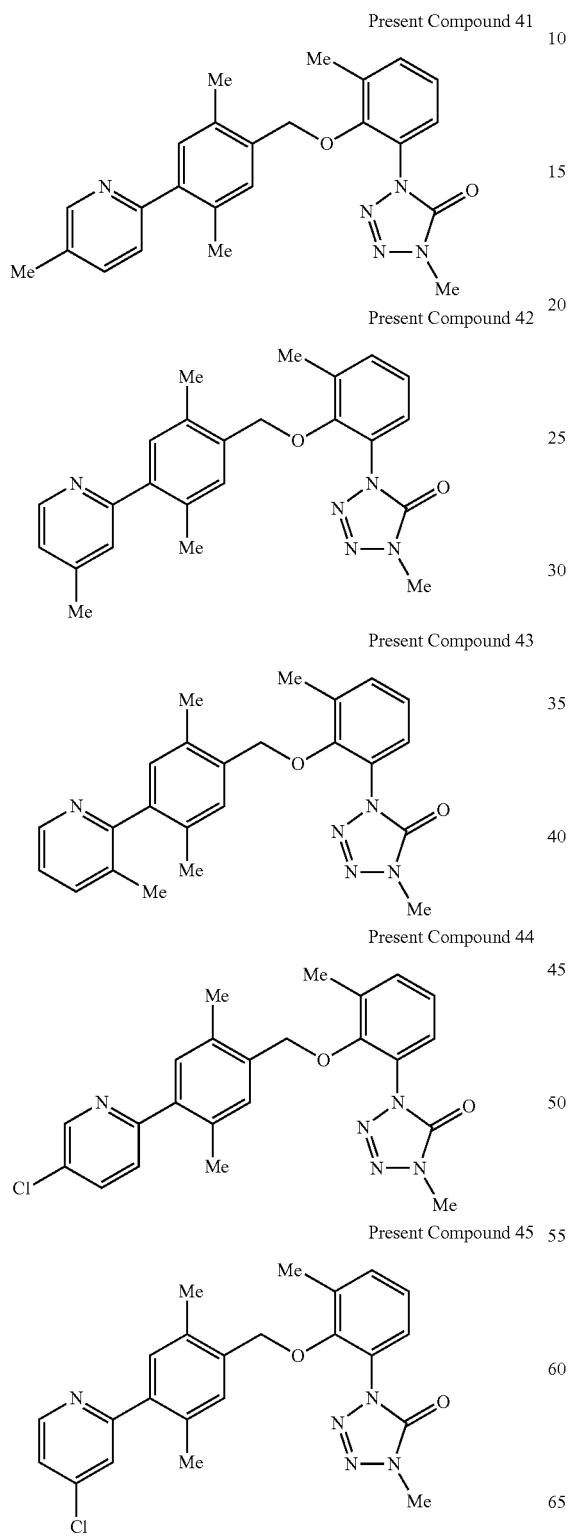

Present Compound 41

Present Compound 42

Present Compound 43

Present Compound 44

Present Compound 45

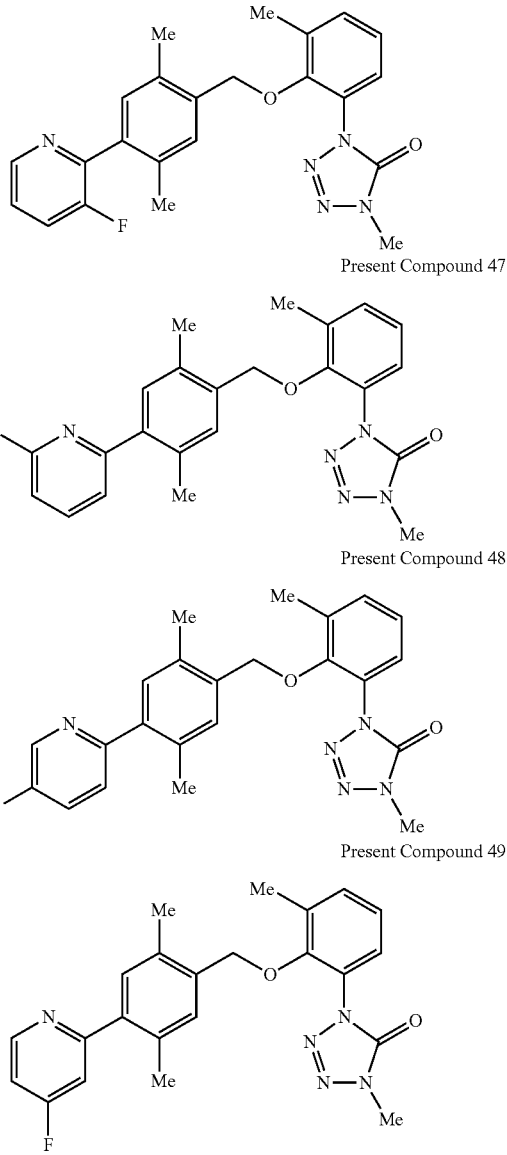

Present Compound 46

Present Compound 47

Present Compound 48

Present Compound 49

Present Compound 41
$^1$H-NMR (CDCl$_3$) 1H-NMR (CDCl3) δ: 8.52 (1H, dd, J=1.5, 0.8 Hz), 7.55 (1H, dd, J=7.9, 1.8 Hz), 7.38-7.36 (1H, m), 7.30 (1H, d, J=7.9 Hz), 7.24 (1H, dd, J=8.2, 2.0 Hz), 7.20-7.13 (3H, m), 4.86 (2H, s), 3.56 (3H, s), 2.41 (3H, s), 2.39 (3H, s), 2.31 (3H, s), 2.26 (3H, s).
The Present Compound 42
$^1$H-NMR (CDCl$_3$) δ: 8.54 (1H, d, J=5.0 Hz), 7.38-7.37 (1H, m), 7.26-7.11 (5H, m), 7.07 (1H, t, J=2.5 Hz), 4.86 (2H, s), 3.57 (3H, s), 2.41 (3H, s), 2.40 (3H, s), 2.31 (3H, s), 2.26 (3H, s).
Present Compound 43
$^1$H-NMR (CDCl$_3$) δ: 8.50 (1H, dq, J=4.8, 0.7 Hz), 7.58 (1H, dq, J=7.7, 0.8 Hz), 7.38 (1H, dq, J=7.5, 0.8 Hz), 7.26 (1H, dd, J=7.7, 2.0 Hz), 7.18 (3H, td, J=7.5, 3.5 Hz), 6.97 (1H, s), 4.86 (2H, s), 3.64 (3H, s), 2.39 (3H, s), 2.24 (3H, s), 2.12 (3H, s), 2.03 (3H, s).
Present Compound 44
$^1$H-NMR (CDCl$_3$) δ: 8.65 (1H, dd, J=2.5, 0.7 Hz), 7.72 (1H, dd, J=8.4, 2.7 Hz), 7.38-7.36 (2H, m), 7.24 (1H, dd, J=7.9, 1.6 Hz), 7.20-7.15 (3H, m), 4.87 (2H, s), 3.55 (3H, s), 2.41 (3H, s), 2.31 (3H, s), 2.26 (3H, s).

Present Compound 45

¹H-NMR (CDCl₃) δ: 8.59 (1H, dd, J=5.4, 0.5 Hz), 7.42 (1H, dd, J=2.0, 0.7 Hz), 7.38 (1H, dq, J=7.5, 0.8 Hz), 7.28-7.23 (2H, m), 7.19-7.18 (3H, m), 4.87 (2H, s), 3.57 (3H, s), 2.41 (3H, s), 2.32 (3H, s), 2.26 (3H, s).

Present Compound 46

¹H-NMR (CDCl₃) δ: 8.52 (1H, dt, J=4.5, 1.6 Hz), 7.51-7.47 (1H, m), 7.40-7.37 (1H, m), 7.34-7.30 (1H, m), 7.27-7.17 (4H, m), 4.88 (2H, s), 3.55 (3H, s), 2.41 (3H, s), 2.26 (3H, s), 2.21 (3H, s).

Present Compound 47

¹H-NMR (CDCl₃) δ: 7.84 (1H, q, J=8.0 Hz), 7.38 (1H, dd, J=7.6, 1.1 Hz), 7.30 (1H, dd, J=7.3, 2.3 Hz), 7.25-7.23 (2H, m), 7.19 (1H, d, J=6.4 Hz), 7.15 (1H, d, J=6.4 Hz), 6.89 (1H, dd, J=8.1, 2.9 Hz), 4.87 (2H, s), 3.55 (3H, s), 2.41 (3H, s), 2.35 (3H, s), 2.26 (3H, s).

Present Compound 48

¹H-NMR (CDCl₃) δ: 8.55 (1H, d, J=2.7 Hz), 7.46 (1H, td, J=8.4, 2.8 Hz), 7.42-7.36 (2H, m), 7.24 (1H, ddd, J=8.0, 1.8, 0.5 Hz), 7.20-7.14 (3H, m), 4.87 (2H, s), 3.56 (3H, s), 2.41 (3H, s), 2.30 (3H, s), 2.26 (3H, s).

Present Compound 49

¹H-NMR (CDCl₃) δ: 8.66 (1H, dd, J=8.8, 5.7 Hz), 7.38 (1H, dq, J=7.5, 0.9 Hz), 7.25 (1H, ddd, J=7.9, 2.0, 0.5 Hz), 7.21-7.13 (4H, m), 7.03-6.98 (1H, m), 4.87 (2H, s), 3.57 (3H, s), 2.41 (3H, s), 2.32 (3H, s), 2.26 (3H, s).

Production Example 5

A mixture of 0.30 g of 6A mentioned in Reference Production Example 6, 0.11 g of [1,1'-bis(diphenylphosphino)ferrocene]palladium(II) dichloride dichloromethane adduct, 0.45 g of tripotassium phosphate, 0.091 g of 2-chloro-6-methylpyridine, 50 µL of water, and 3 mL of 1,2-dimethoxyethane was stirred at 80° C. for 4 hours. After cooling to room temperature, the reaction mixture was filtered and the filtrate was concentrated. The residue thus obtained was subjected to silica gel column chromatography to obtain 0.22 g of 1-(2-{[4-(6-methylpyridin-2-yl)phenyl]methoxy}-3-methylphenyl)-4-methyl-1,4-dihydrotetrazol-5-one (hereinafter referred to as the present compound 23).

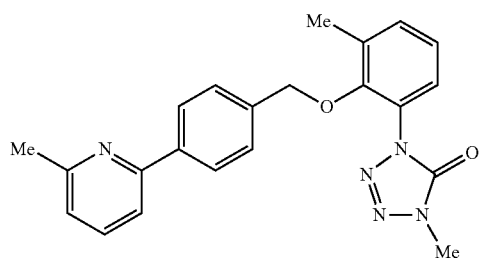 [SMILES: Cc1cccc(-c2ccc(COc3c(C)cccc3-n3nnn(C)c3=O)cc2)n1]

¹H-NMR (CDCl₃) δ: 7.96-7.94 (2H, m), 7.64 (1H, t, J=7.8 Hz), 7.52 (1H, d, J=7.8 Hz), 7.36 (3H, d, J=8.5 Hz), 7.25 (1H, d, J=7.3 Hz), 7.18 (1H, t, J=7.7 Hz), 7.10 (1H, d, J=7.8 Hz), 4.90 (2H, s), 3.56 (3H, s), 2.63 (3H, s), 2.39 (3H, s).

Using 2,6-dichloropyridine in place of 2-chloro-6-methylpyridine, the present compound 24 was synthesized by the same reaction as in Production Example 5. Structural formulas of the present compound 24 and analytical values of ¹H-NMR thereof are shown below.

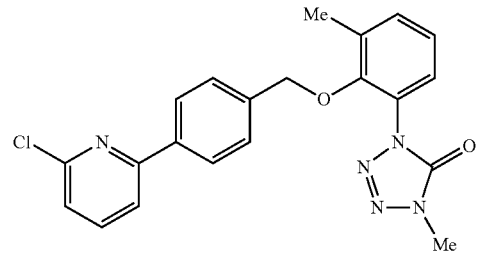 [SMILES: Cc1cccc(-n2nnn(C)c2=O)c1OCc1ccc(-c2cccc(Cl)n2)cc1]

¹H-NMR (CDCl₃) δ: 7.97 (2H, d, J=8.4 Hz), 7.72 (1H, t, J=7.7 Hz), 7.66 (1H, d, J=7.7 Hz), 7.38-7.36 (3H, m), 7.28-7.26 (2H, m), 7.19 (1H, t, J=7.7 Hz), 4.91 (2H, s), 3.57 (3H, s), 2.40 (3H, s).

Production Example 6

A mixture of 0.30 g of 2A mentioned in Reference Production Example 2, 0.67 g of 1-(biphenyl-4-yl)ethyl p-toluenesulfonate, 0.22 g of potassium carbonate, and 5 mL of dimethylformamide was stirred with heating under reflux for 6 hours. After cooling the reaction mixture, water was added and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.34 g of 1-{2-[1-(biphenyl-4-yl)ethoxy]-3-methylphenyl}-4-methyl-1,4-dihydrotetrazol-5-onedimethylformamide (hereinafter referred to as the present compound 25).

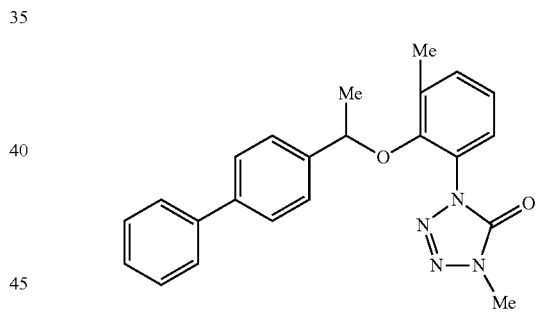

¹H-NMR (CDCl₃) δ: 7.59 (2H, d, J=8.2 Hz), 7.51 (2H, d, J=8.2 Hz), 7.44 (2H, t, J=7.2 Hz), 7.34 (2H, dd, J=14.4, 8.2 Hz), 7.27 (2H, d, J=8.2 Hz), 7.17-7.10 (2H, m), 4.75 (1H, q, J=6.5 Hz), 3.37 (3H, s), 2.34 (3H, s), 1.58 (3H, d, J=6.5 Hz).

Production Example 7

A mixture of 1.5 g of 17A mentioned in Reference Production Example 17, 0.25 g of sodium hydride (purity of 55%), and 10 mL of tetrahydrofuran was stirred at room temperature for 30 minutes and then 0.88 g of 4-biphenylcarboaldehyde was added, followed by stirring at room temperature for 3 hours. Water was added to the reaction mixture and the mixture was extracted with ethyl acetate. The organic layer was dried over anhydrous sodium sulfate and then concentrated under reduced pressure. The residue thus obtained was subjected to silica gel column chromatography to obtain 1.3 g of 1-{2-[2-(biphenyl-4-yl)ethenyl]-3-methylphenyl}-4-methyl-1,4-dihydrotetrazol-5-one (hereinafter referred to as the present compound 26).

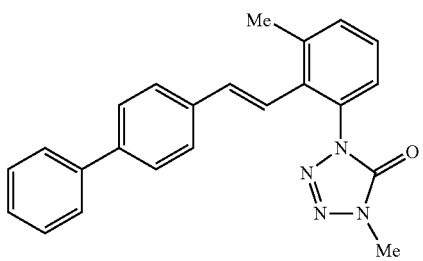 [SMILES: Cc1cccc(-n2nnn(C)c2=O)c1/C=C/c1ccc(-c2ccccc2)cc1]

¹H-NMR (CDCl₃) δ (ppm): 7.61-7.56 (4H, m), 7.46-7.44 (4H, m), 7.40-7.32 (3H, m), 7.27 (1H, d, J=9.1 Hz), 7.06 (1H, d, J=16.5 Hz), 6.45 (1H, d, J=16.5 Hz), 3.62 (3H, s), 2.44 (3H, s).

Production Example 8

A mixture of 0.12 g of 18A mentioned in Reference Production Example 18, 0.051 g of [1,1'-bis(diphenylphosphino)ferrocene]palladium(II) dichloride dichloromethane adduct, 0.197 g of tripotassium phosphate, 0.045 g of phenylboronic acid, and 5 mL of dimethoxyethane was stirred at 80° C. for 6 hours. After cooling to room temperature, the reaction mixture was filtered and the filtrate was concentrated. The residue thus obtained was subjected to silica gel column chromatography to obtain 0.1 g of 1-{2-[2-(3-methylbiphenyl-4-yl)ethenyl]-3-methylphenyl}-4-methyl-1,4-dihydrotetrazol-5-one (hereinafter referred to as the present compound 27).

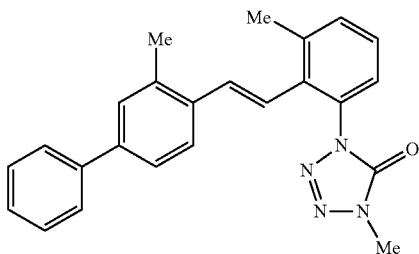 [SMILES: Cc1cc(-c2ccccc2)ccc1/C=C/c1c(C)cccc1-n1nnn(C)c1=O]

¹H-NMR (CDCl₃) δ (ppm): 7.59 (2H, d, J=7.9 Hz), 7.46-7.26 (9H, m), 6.95 (1H, d, J=16.5 Hz), 6.65 (1H, d, J=16.5 Hz), 3.63 (3H, s), 2.45 (3H, s), 2.31 (3H, s).

Using commercially available compounds, the present compounds 28 to 30 were synthesized by the same reaction as in Production Example 8. Structures of the thus obtained present compounds 28 to 30 and analytical values of ¹H-NMR thereof are shown below.

Present Compound 28

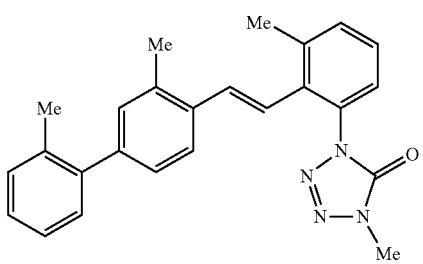

Present Compound 29

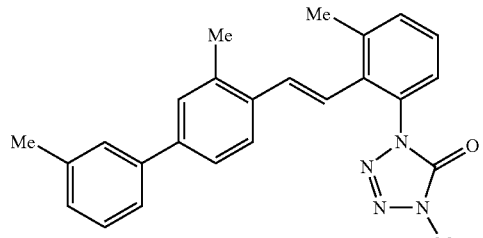

Present Compound 30

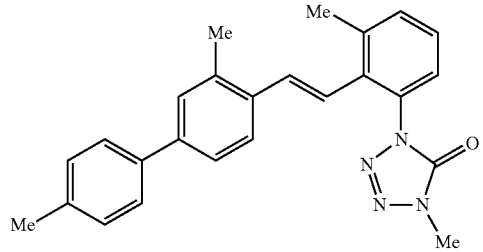

Present Compound 28
1H-NMR (CDCl₃) δ: 7.55 (1H, d, J=7.9 Hz), 7.41-7.12 (9H, m), 6.95 (1H, d, J=16.5 Hz), 6.67 (1H, d, J=16.3 Hz), 3.65 (3H, s), 2.46 (3H, s), 2.30 (3H, s), 2.28 (3H, s).
Present Compound 29
¹H-NMR (CDCl₃) δ (ppm): 7.57 (1H, d, J=8.0 Hz), 7.37-7.32 (8H, m), 7.16 (1H, d, J=7.1 Hz), 6.94 (1H, d, J=16.5 Hz), 6.65 (1H, d, J=16.5 Hz), 3.63 (3H, s), 2.45 (3H, s), 2.42 (3H, s), 2.30 (3H, s).
Present Compound 30
¹H-NMR (CDCl₃) δ: 7.57 (1H, d, J=8.2 Hz), 7.49 (2H, d, J=8.2 Hz), 7.43-7.26 (7H, m), 6.93 (1H, d, J=16.5 Hz), 6.65 (1H, d, J=16.5 Hz), 3.63 (3H, s), 2.45 (3H, s), 2.40 (3H, s), 2.30 (3H, s).

Production Example 9

A mixture of 2 g of 21A mentioned in Reference Production Example 21, 0.31 g of sodium hydride (purity of 55%), and 10 mL of tetrahydrofuran was stirred at room temperature for 30 minutes and then 1.1 g of 4-biphenylcarboxyaldehyde was added, followed by stirring at room temperature for 3 hours. Water was added to the reaction mixture and then the mixture was extracted with ethyl acetate. The organic layer was dried over anhydrous sodium sulfate and then concentrated under reduced pressure. The residue thus obtained was subjected to silica gel column chromatography to obtain 1.5 g of 1-{2-[2-(biphenyl-4-yl)ethenyl]-3-cyclopropylphenyl}-4-methyl-1,4-dihydrotetrazol-5-one (hereinafter referred to as the present compound 31).

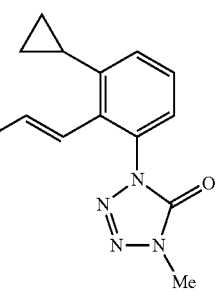

¹H-NMR (CDCl₃) δ (ppm): 7.60-7.58 (4H, m), 7.48-7.44 (4H, m), 7.38-7.32 (2H, m), 7.27-7.26 (1H, m), 7.24-7.23 (1H, m), 7.14 (1H, d, J=7.7 Hz), 6.54 (1H, d, J=16.8 Hz), 3.62 (3H, s), 2.13-2.05 (1H, m), 1.02 (2H, ddd, J=8.8, 6.3, 5.0 Hz), 0.78 (2H, ddd, J=6.3, 5.0, 4.5 Hz).

Production Example 10

A mixture of 0.13 g of 2-methylbenzyl alcohol, 0.62 g of sodium hydride (purity of 55%), and 5 mL of dimethylformamide was stirred at room temperature for 30 minutes and then 0.30 g of 16A mentioned in Reference Production Example 16 was added, followed by stirring at room temperature for 6 hours. After cooling the reaction mixture, water was added and the mixture was extracted with ethyl acetate. The organic layer was washed with water and a saturated saline solution, dried over anhydrous magnesium sulfate and then concentrated under reduced pressure. The residue thus obtained was subjected to silica gel column chromatography to obtain 0.20 g of 1-(2-{[(2-methylphenyl)methoxy]methyl}-3-methylphenyl)-4-methyl-1,4-dihydrotetrazol-5-one (hereinafter referred to as the present compound 51).

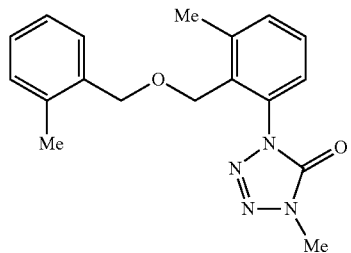 [SMILES: Cc1ccccc1COCc1c(C)cccc1-n1nnn(C)c1=O]

¹H-NMR (CDCl₃) δ (ppm): 7.44-7.07 (7H, m), 4.52 (2H, s), 4.42 (2H, s), 3.59 (3H, s), 2.47 (3H, s), 2.26 (3H, s).

Using commercially available compounds, the present compounds 52 and 53 were synthesized by the same reaction as in Production Example 10. Structures of the thus obtained present compounds 28 to 30 and analytical values of ¹H-NMR thereof are shown below.

Present Compound 52

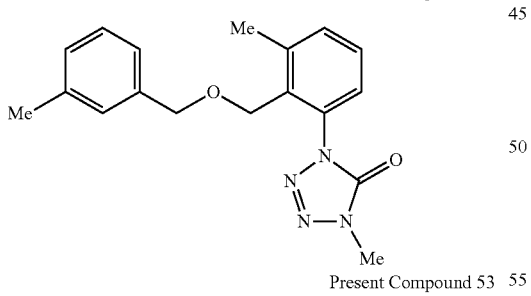

Present Compound 53

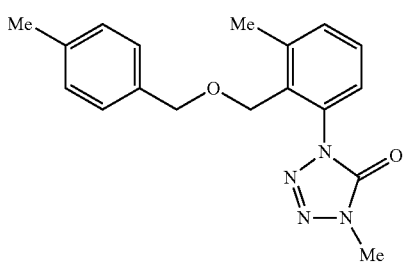

Present Compound 52

¹H-NMR (CDCl₃) δ (ppm): 7.36-7.35 (2H, m), 7.21-7.19 (2H, m), 7.07-7.03 (3H, m), 4.50 (2H, s), 4.37 (2H, s), 3.59 (3H, s), 2.47 (3H, s), 2.34 (3H, s).

Present Compound 53

¹H-NMR (CDCl₃) δ: 7.34-7.33 (2H, m), 7.25-7.09 (5H, m), 4.48 (2H, s), 4.35 (2H, s), 3.58 (3H, s), 2.45 (3H, s), 2.33 (3H, s).

Production Example 11

A mixture of 0.22 g of 24A mentioned in Reference Production Example 24, 0.088 g of phenylboronic acid, 0.35 g of tripotassium phosphate, 0.090 g of [1,1'-bis(diphenylphosphino)ferrocene]palladium(II) dichloride dichloromethane adduct, and 5 mL of dimethoxyethane was stirred with heating under reflux for 10 hours. The reaction mixture was cooled and then concentrated under reduced pressure. The residue thus obtained was subjected to silica gel column chromatography to obtain 0.15 g of 1-(2-{[1-(biphenyl-4-yl)ethoxy]methyl}-3-methylphenyl)-4-methyl-1,4-dihydrotetrazol-5-one (hereinafter referred to as the present compound 54).

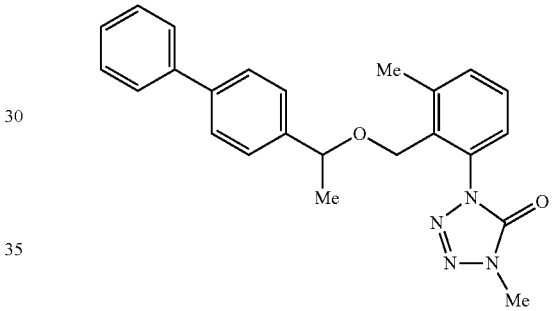

¹H-NMR (CDCl₃) δ: 7.62-7.09 (12H, m), 4.41-4.25 (3H, m), 3.48 (3H, s), 2.44 (3H, s), 1.38 (3H, d, J=6.4 Hz).

Production Example 12

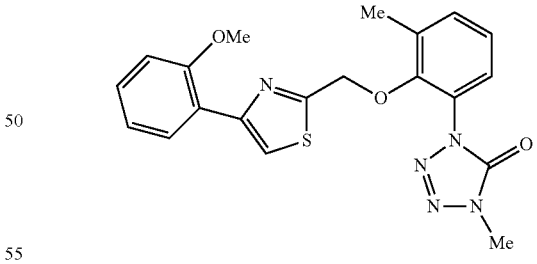

A mixture of 0.25 g of 2A mentioned in Reference Production Example 2, 0.28 g of 26A mentioned in Reference Production Example 26, 0.25 g of potassium carbonate, and 10 mL of acetonitrile was stirred with heating under reflux for 2 hours. After the reaction mixture was cooled to room temperature, water was poured into the reaction mixture and then the mixture was extracted with ethyl acetate. The organic layer was washed with water and a saturated saline solution. The organic layer was dried over anhydrous sodium sulfate and concentrated under reduced pressure. The residue thus obtained was subjected to silica gel column chromatography to obtain 0.30 g of 2-({[1-(4,5-dihydro-4-methyl-5-oxo-1H-tetrazol-1-yl)-3-methylphenyl-2-yl]oxy}methyl)-4-(2-methoxyphenyl)thiazole (hereinafter referred to as the present compound 55).

¹H-NMR (CDCl₃) δ: 8.18 (1H, dd, J=7.8, 1.4 Hz), 7.93 (1H, s), 7.37 (1H, dt, J=7.5, 0.9 Hz), 7.33-7.27 (2H, m), 7.21 (1H, t, J=7.8 Hz), 7.05 (1H, td, J=7.5, 0.9 Hz), 6.99 (1H, d, J=8.2 Hz), 5.23 (2H, s), 3.94 (3H, s), 3.61 (3H, s), 2.44 (3H, s).

Production Example 13

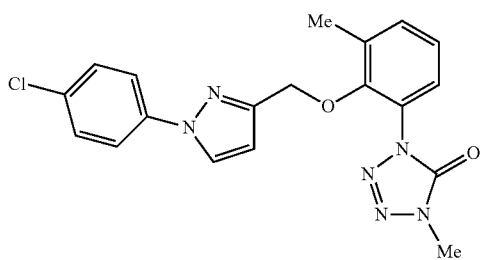 [SMILES: Cc1cccc(-n2nnn(C)c2=O)c1OCc1ccn(-c2ccc(Cl)cc2)n1]

A mixture of 0.28 g of 2A mentioned in Reference Production Example 2, 0.39 g of 28A mentioned in Reference Production Example 28, 0.28 g of potassium carbonate, and 5 mL of acetonitrile was stirred with heating under reflux for 2 hours. After the reaction mixture was cooled to room temperature, water was poured into the reaction mixture and then the mixture was extracted with ethyl acetate. The organic layer was washed with water and a saturated saline solution. The organic layer was dried over anhydrous sodium sulfate and concentrated under reduced pressure. The residue thus obtained was subjected to silica gel column chromatography to obtain 0.39 g of 1-(2-{[1-(4-chlorophenyl)-1H-pyrazol-3-yl]methoxy}-3-methylphenyl)-4-methyl-1,4-dihydrotetrazol-5-one (hereinafter referred to as the present compound 56).

¹H-NMR (CDCl₃) δ: 7.79 (1H, d, J=2.5 Hz), 7.61-7.57 (2H, m), 7.38-7.42 (2H, m), 7.33-7.37 (1H, m), 7.23-7.27 (1H, m), 7.17 (1H, t, J=8.9 Hz), 6.38 (1H, d, J=2.5 Hz), 4.95 (2H, s), 3.58 (3H, s), 2.43 (3H, s).

Production Example 14

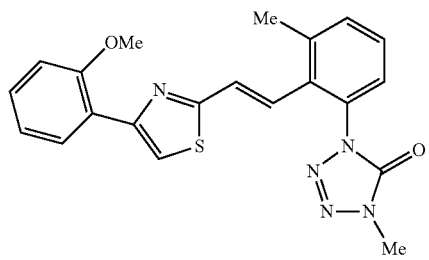 [SMILES: COc1ccccc1-c1csc(/C=C/c2c(C)cccc2-n2nnn(C)c2=O)n1]

To a mixture of 0.23 g of 17A mentioned in Reference Production Example 17 and 5 mL of tetrahydrofuran, 0.10 g of sodium hydride was added under ice cooling. The reaction mixture was stirred at room temperature for 30 minutes and then a mixture of 0.16 g of 4-(2-methoxyphenyl)thiazole-2-carbaldehyde and 5 mL of tetrahydrofuran was added, followed by stirring at room temperature for 4 hours. Water was poured into the reaction mixture and the mixture was extracted with ethyl acetate. The organic layer was washed with water and a saturated saline solution. The organic layer was dried over anhydrous sodium sulfate and then concentrated under reduced pressure. The residue thus obtained was subjected to silica gel column chromatography to obtain 0.08 g of (E)-2-{2-[1-(4,5-dihydro-4-methyl-5-oxo-1H-tetrazol-1-yl)-3-methylphenyl-2-yl]ethenyl}-4-(2-methoxyphenyl)thiazole (hereinafter referred to as the present compound 57).

¹H-NMR (CDCl₃) δ: 8.22 (1H, dd, J=7.8, 1.8 Hz), 7.86 (1H, s), 7.28-7.41 (5H, m), 7.05-7.09 (1H, m), 7.00 (1H, d, J=8.2 Hz), 6.73 (1H, d, J=16.7 Hz), 3.96 (3H, s), 3.66 (3H, s), 2.49 (3H, s)

Production Example 15

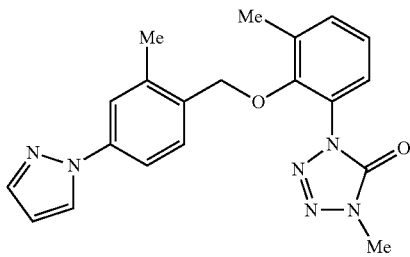 [SMILES: Cc1cc(-n2cccn2)ccc1COc1c(C)cccc1-n1nnn(C)c1=O]

A mixture of 0.50 g of 5A mentioned in Reference Production Example 5, 0.16 g of pyrazole, 0.64 g of copper (II) acetate, 0.37 g of pyridine, 0.62 g of molecular sieves 4A, and 12 mL of acetonitrile was stirred at 80° C. for 24 hours. The reaction mixture was concentrated under reduced pressure and the residue thus obtained was subjected to silica gel column chromatography to obtain 0.20 g of the present compound 58. ¹H-NMR (CDCl₃) δ: 7.93 (1H, d, J=2.1 Hz), 7.73 (1H, d, J=1.6 Hz), 7.63 (1H, d, J=1.6 Hz), 7.56 (1H, d, J=2.1 Hz), 7.43 (1H, dd, J=8.2, 2.1 Hz), 7.38-7.36 (1H, m), 7.29-7.23 (1H, m), 7.19 (1H, t, J=7.7 Hz), 6.47 (1H, t, J=1.9 Hz), 4.88 (2H, s), 3.53 (3H, s), 2.38 (3H, s), 2.35 (3H, s).

Using commercially available compounds, the present compound 59 was synthesized by the same reaction as in Production Example 15. Structures of the thus obtained present compound 59 and analytical values of ¹H-NMR thereof are shown below.

Present Compound 59

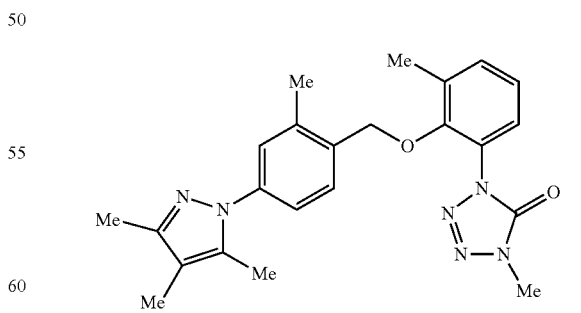

Present Compound 59

¹H-NMR (CDCl₃) δ: 7.38-7.36 (1H, m), 7.29 (1H, d, J=8.0 Hz), 7.24 (4H, dd, J=8.0, 2.2 Hz), 7.19 (1H, d, J=7.6 Hz), 7.15 (1H, dd, J=7.6, 1.9 Hz), 4.87 (2H, s), 3.58 (3H, s), 2.37 (3H, s), 2.31 (3H, s), 2.24 (6H, s), 1.98 (3H, s).

Reference Production Example 1

A mixture of 50 g of salicylic acid, 136 g of benzyl bromide, 124 g of potassium carbonate, and 600 mL of acetonitrile was stirred with heating under reflux. The reaction mixture was filtered and the filtrate was concentrated under reduced pressure. To the residue thus obtained, 21.6 g of lithium hydroxide monohydrate, 200 mL of water, and 500 mL of methanol were added, followed by stirring at 100° C. The reaction mixture was concentrated under reduced pressure and the residue was acidified with 5% dilute hydrochloric acid, and then the mixture was extracted with ethyl acetate. The organic layer was washed with water and a saturated saline solution, dried over anhydrous magnesium sulfate, and then concentrated under reduced pressure to obtain 32 g of 2-benzyloxybenzoic acid.

Subsequently, 12.6 mL of oxalyl dichloride was added dropwise to a mixed solution of 32 g of 2-benzyloxybenzoic acid, 0.2 mL of dimethylformamide, and 300 mL of tetrahydrofuran (also referred to as THF) at room temperature. This solution was stirred for 2 hours and then concentrated under reduced pressure to obtain 2-benzyloxybenzoic acid chloride as a crude product.

To 300 mL of THF, 35 g of aluminum chloride was slowly added in a nitrogen atmosphere at 0° C., followed by addition of 50.9 g of sodium azide and further stirring with heating under reflux for 2 hours. A solution prepared by dissolving the entire amount of the crude product of 2-benzyloxybenzoyl chloride in 50 mL of THF was added to the reaction solution cooled to 50° C. The reaction solution was stirred with heating under reflux for 2 hours and cooled to 0° C., and then the reaction solution was added to an aqueous 10% sodium nitrite solution. After adding concentrated hydrochloric acid until the pH becomes 1, the mixture was extracted with ethyl acetate. The organic layer was washed with water and a saturated saline solution, dried over anhydrous magnesium sulfate, and then concentrated under reduced pressure to obtain 38 g of 1-([2-(phenylmethoxy)phenyl]-1,4-dihydrotetrazol-5-one as a crude product.

A mixture of 38 g of the thus obtained crude product of 1-[2-(phenylmethoxy)phenyl]-1,4-dihydrotetrazol-5-one, 59.3 g of potassium carbonate, 19.7 g of dimethylsulfuric acid, and 260 mL of dimethylformamide was stirred at room temperature. To the reaction mixture, water was added and the mixture was extracted with ethyl acetate. The organic layer was washed with water and a saturated saline solution, dried over anhydrous magnesium sulfate, and then concentrated under reduced pressure. The residue thus obtained was recrystallized in ethyl acetate and then washed with hexane. This crystal was dried under reduced pressure to obtain 21 g of 1-[2-(phenylmethoxy)phenyl]-4-methyl-1,4-dihydrotetrazol-5-one.

A mixture of 17 g of the thus obtained 1-[2-(phenylmethoxy)phenyl]-4-methyl-1,4-dihydrotetrazol-5-one, 8 g of 5% palladium-carbon, 50 mL of ethanol, and 150 ml of ethyl acetate was stirred in a hydrogen atmosphere under a normal pressure at room temperature. The reaction mixture was filtered and the filtrate was concentrated under reduced pressure. The residue thus obtained was washed with hexane to obtain 10 g of 1-(2-hydroxyphenyl)-4-methyl-1,4-dihydrotetrazol-5-one (referred to as 1A).

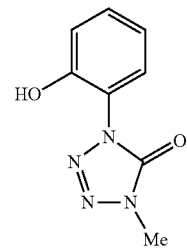 [SMILES: Cn1nnn(-c2ccccc2O)c1=O]

$^1$H-NMR (CDCl$_3$) δ: 7.63 (1H, dd, J=8.2, 1.4 Hz), 7.35 (1H, ddd, J=8.0, 7.3, 1.4 Hz), 7.14 (1H, dd, J=8.2, 1.4 Hz), 7.05 (1H, ddd, J=8.0, 7.3, 1.4 Hz), 3.78 (3H, s).

Reference Production Example 2

Using 3-methylsalicylic acid in place of salicylic acid, 1-(2-hydroxy-3-methylphenyl)-4-methyl-1,4-dihydrotetrazol-5-one (referred to as 2A) was synthesized by the same reaction as in Reference Production Example 1. Structural formula of the thus obtained compound and analytical values of $^1$H-NMR thereof are shown below.

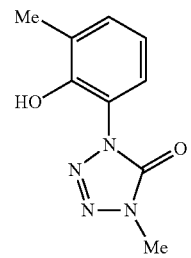

$^1$H-NMR (CDCl$_3$) δ (ppm): 8.57 (1H, s), 7.44 (1H, d, J=8.0 Hz), 7.23 (1H, d, J=6.9 Hz), 6.95 (1H, t, J=7.9 Hz), 3.78 (3H, t, J=0.8 Hz), 2.34 (3H, s).

Reference Production Example 3

A mixture of 4 g of 2A mentioned in Reference Production Example 2, 4.8 g of 4-bromobenzyl bromide, 8 g of potassium carbonate, and 40 mL of dimethylformamide was stirred at 80° C. for 10 hours and cooled to room temperature, followed by addition of water and further extraction with ethyl acetate. The organic layer was washed with water and a saturated saline solution, dried over anhydrous magnesium sulfate, and then concentrated under reduced pressure. The residue thus obtained was subjected to silica gel column chromatography to obtain 3.5 g of 1-[2-(4-bromophenyl)methoxy-3-methylphenyl]-4-methyl-1,4-dihydrotetrazol-5-one (referred to as 3A).

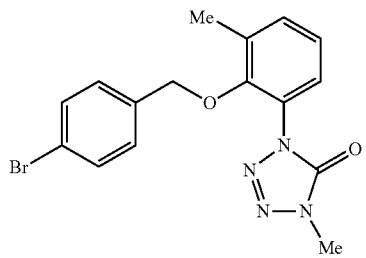 [SMILES: Cc1cccc(-n2nnn(C)c2=O)c1OCc1ccc(Br)cc1]

$^1$H-NMR (CDCl$_3$) δ: 7.46 (2H, d, J=8.2 Hz), 7.36 (1H, d, J=7.5 Hz), 7.25 (1H, d, J=8.2 Hz), 7.19 (1H, d, J=7.5 Hz), 7.15 (2H, d, J=8.2 Hz), 4.81 (2H, s), 3.58 (3H, s), 2.38 (3H, s).

Reference Production Example 4

Using 1A in place of 2A, the following compounds were synthesized by the same reaction as in Reference Production Example 3. Structural formula of the thus obtained compound (4A) and analytical values of $^1$H-NMR thereof are shown below.

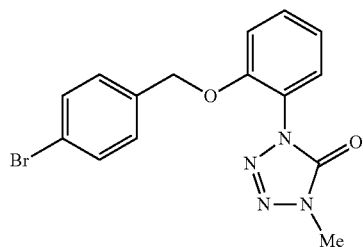 [SMILES: Cn1nnn(-c2ccccc2OCc2ccc(Br)cc2)c1=O]

$^1$H-NMR (CDCl$_3$) δ: 7.79 (2H, d, J=8.2 Hz), 7.38 (4H, dd, J=14.0, 7.8 Hz), 7.07 (2H, dd, J=14.0, 7.8 Hz), 5.16 (2H, s), 3.70 (3H, s).

Reference Production Example 5

A mixture of 3.5 g of the present compound 13, 0.77 g of [1,1'-bis(diphenylphosphino)ferrocene]palladium(II) dichloride dichloromethane adduct, 2.8 g of potassium acetate, 2.6 g of bis(pinacolato)diboron, and 19 mL of dimethyl sulfoxide was stirred at 90° C. for 12 hours. After cooling to room temperature, the reaction mixture was filtered and the filtrate was concentrated. The residue thus obtained was subjected to silica gel column chromatography to obtain 2.7 g of 1-(2-{[4-(4,4,5,5-tetramethyl-1,3,2-dioxaborolan-2-yl)-2-methylphenyl]methoxy}-3-methylphenyl)-4-methyl-1,4-dihydrotetrazol-5-one (referred to as 5A).

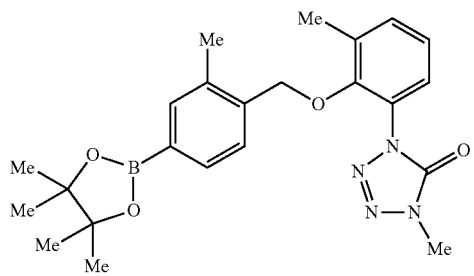 [SMILES: Cc1cc(B2OC(C)(C)C(C)(C)O2)ccc1COc1c(C)cccc1-n1nnn(C)c1=O]

$^1$H-NMR (CDCl$_3$) δ: 7.60 (2H, d, J=6.8 Hz), 7.35 (1H, d, J=7.5 Hz), 7.28-7.22 (2H, m), 7.17 (1H, t, J=7.7 Hz), 4.86 (2H, s), 3.54 (3H, s), 2.35 (3H, s), 2.27 (3H, s), 1.35 (12H, s).

Reference Production Example 6

A mixture of 3.5 g of 3A mentioned in Reference Production Example 3, 0.77 g of [1,1'-bis(diphenylphosphino)ferrocene]palladium(II) dichloride dichloromethane adduct, 2.8 g of potassium acetate, 2.6 g of bis(pinacolato)diboron, and 19 mL of dimethyl sulfoxide was stirred at 90° C. for 12 hours. After cooling to room temperature, the reaction mixture was filtered and the filtrate was concentrated. The residue thus obtained was subjected to silica gel column chromatography to obtain 2.7 g of 1-(2-{[4-(4,4,5,5-tetramethyl-1,3,2-dioxaborolan-2-yl)phenyl]methoxy}-3-methylphenyl)-4-methyl-1,4-dihydrotetrazol-5-one (referred to as 6A).

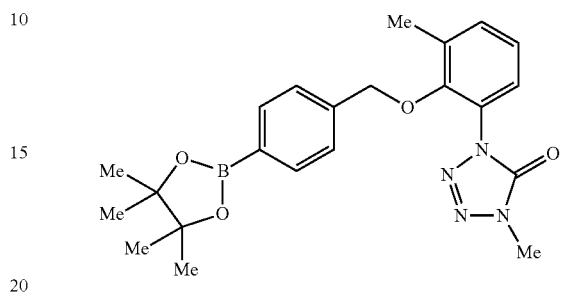

$^1$H-NMR (CDCl$_3$) δ: 7.77 (2H, d, J=8.2 Hz), 7.35 (1H, d, J=7.7 Hz), 7.29-7.23 (3H, m), 7.17 (1H, t, J=7.7 Hz), 4.86 (2H, s), 3.57 (3H, s), 2.37 (3H, s), 1.35 (12H, s).

Reference Production Example 7

A mixture of 5.4 g of 4A mentioned in Reference Production Example 4, 1.3 g of [1,1'-bis(diphenylphosphino)ferrocene]palladium(II) dichloride dichloromethane adduct, 4.7 g of potassium acetate, 4.5 g of bis(pinacolato)diboron, and 20 mL of dimethyl sulfoxide was stirred at 90° C. for 12 hours. After cooling to room temperature, the reaction mixture was filtered and the filtrate was concentrated. The residue thus obtained was subjected to silica gel column chromatography to obtain 2 g of 1-(2-{[4-(4,4,5,5-tetramethyl-1,3,2-dioxaborolan-2-yl)phenyl]methoxy}phenyl)-4-methyl-1,4-dihydrotetrazol-5-one (referred to as 7A).

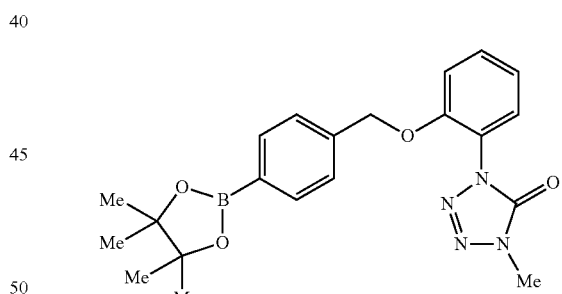

$^1$H-NMR (CDCl$_3$) δ: 7.79 (2H, d, J=8.2 Hz), 7.43-7.36 (4H, m), 7.10-7.04 (2H, m), 5.16 (2H, s), 3.70 (3H, s), 1.34 (12H, s).

Reference Production Example 9

A mixture of 0.30 g of 7A mentioned in Reference Production Example 7, 0.11 g of [1,1'-bis(diphenylphosphino)ferrocene]palladium(II) dichloride dichloromethane adduct, 0.45 g of tripotassium phosphate, 0.091 g of 2-methyl-pyridine, 50 μL of water, and 3 mL of 1,2-dimethoxyethane was stirred at 80° C. for 4 hours. After cooling to room temperature, the reaction mixture was filtered and the filtrate was concentrated. The residue thus obtained was subjected to silica gel column chromatography to obtain 0.22 g of 1-(2-{[4-(pyridin-2-yl)phenyl]methoxy}phenyl)-4-methyl-1,4-dihydrotetrazol-5-one.

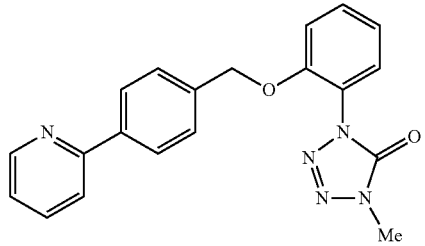 [SMILES: Cn1nnn(-c2ccccc2OCc2ccc(-c3ccccn3)cc2)c1=O]

¹H-NMR (CDCl3) δ: 8.69 (1H, d, J=4.8 Hz), 7.98 (2H, d, J=8.2 Hz), 7.76-7.72 (2H, m), 7.49 (2H, d, J=8.5 Hz), 7.43-7.41 (2H, m), 7.25-7.23 (1H, m), 7.10-7.07 (2H, m), 5.21 (2H, s), 3.70 (3H, s).

The following compounds were synthesized by the same reaction as in Reference Production Example 9. Structural formulas of the thus obtained compounds and analytical values of ¹H-NMR thereof are shown below.

1-(2-{[4-(6-Chloropyridin-2-yl)phenyl]methoxy}phenyl)-4-methyl-1,4-dihydrotetrazol-5-one

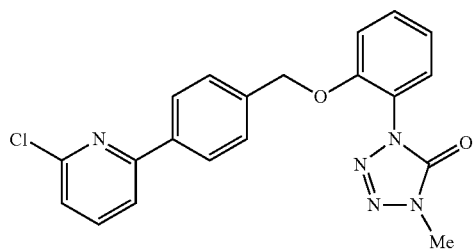 [SMILES: Cn1nnn(-c2ccccc2OCc2ccc(-c3cccc(Cl)n3)cc2)c1=O]

¹H-NMR (CDCl₃) δ: 8.58 (1H, d, J=5.3 Hz), 7.96 (2H, d, J=8.5 Hz), 7.72 (1H, d, J=1.4 Hz), 7.49 (2H, d, J=8.5 Hz), 7.44-7.41 (2H, m), 7.25 (1H, dd, J=5.3, 1.8 Hz), 7.10-7.08 (2H, m), 5.21 (2H, s), 3.70 (3H, s).

1-(2-{[4-(6-Methylpyridin-2-yl)phenyl]methoxy}phenyl)-4-methyl-1,4-dihydrotetrazol-5-one

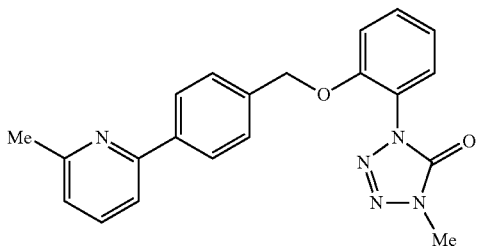 [SMILES: Cc1cccc(-c2ccc(COc3ccccc3-n3nnn(C)c3=O)cc2)n1]

¹H-NMR (CDCl₃) δ: 7.97-7.95 (2H, m), 7.63 (1H, t, J=7.7 Hz), 7.50-7.47 (3H, m), 7.43-7.40 (2H, m), 7.11-7.06 (3H, m), 5.21 (2H, s), 3.71 (3H, s), 2.62 (3H, s).

Reference Production Example 10

A mixture of 25.0 g of 3-bromo-2-methylaniline, 60.0 g of triphosgene, and 400 ml of toluene was stirred with heating under reflux for 3 hours. The reaction mixture allowed to cool was concentrated under reduced pressure to obtain 30.3 g of 1-bromo-3-isocyanate-2-methylbenzene (referred to as 10A).

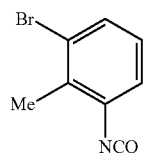

¹H-NMR (CDCl₃) δ (ppm): 2.42 (3H, s), 7.00 (1H, dt, J=0.5, 8.0 Hz), 7.05 (1H, dd, J=1.7, 8.0 Hz), 7.39 (1H, dd, 1.5, 7.7 Hz).

Reference Production Example 11

Under ice cooling, 19.7 g of anhydrous aluminum chloride was added to 220 mL of N,N-dimethylformamide, followed by stirring for 15 minutes. To this was added 9.6 g of sodium azide and, after stirring for 15 minutes, 30.3 g of 11A was added, followed by heating at 80° C. for 5 hours. After cooling, the reaction solution was added in a mixture of 33 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 31.4 g of 1-(2-methyl-3-bromophenyl)-1,4-dihydrotetrazol-5-one (referred to as 11A).

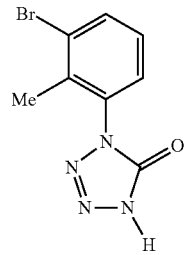

¹H-NMR (DMSO-D₆) δ (ppm): 2.22 (3H, s), 7.34 (1H, t, J=7.2 Hz), 7.49 (1H, dd, J=8.2, 1.1 Hz), 7.82 (1H, dd, J=8.0, 1.0 Hz), 14.72 (1H, s).

Reference Production Example 12

To a mixture of 31.4 g of 11A and 250 mL of N,N-dimethylformamide, 5.90 g of sodium hydride (purity of 55%) was added under ice cooling. The temperature of the mixture was raised to room temperature, followed by stirring for 1 hour. To the reaction mixture, 8.4 mL of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 8.47 g of 1-(2-methyl-3-bromophenyl)-4-methyl-1,4-dihydrotetrazol-5-one (referred to as 12A).

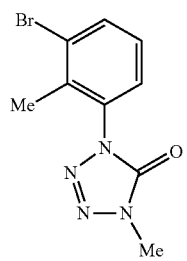

$^1$H-NMR (CDCl$_3$) δ (ppm): 2.33 (3H, s), 3.73 (3H, s), 7.21 (1H, dt, J=0.5, 7.8 Hz), 7.30 (1H, dd, J=1.0, 8.0 Hz), 7.71 (1H, dd, J=1.2, 8.3 Hz).

Reference Production Example 13

A mixture of 8.47 g of 12A, 1.54 g of 1,1'-azobis(cyclohexane-1-carbonitrile), 6.44 g of N-bromosuccinimide, and 125 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 7.52 g of 1-[2-(bromomethyl)-3-bromophenyl]-4-methyl-1,4-dihydrotetrazol-5-one (referred to as 13A).

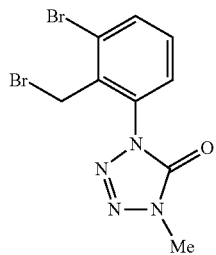 [SMILES: Cn1nnn(-c2cccc(Br)c2CBr)c1=O]

$^1$H-NMR (CDCl$_3$) δ (ppm): 3.76 (3H, s), 4.71 (2H, s), 7.34 (1H, t, J=7.8 Hz), 7.38 (1H, dd, J=8.0, 1.7 Hz), 7.77 (1H, dd, J=7.8, 1.7 Hz).

Reference Production Example 14

A mixture of 45.0 g of 13A, 37.4 g of sodium methoxide, and 600 mL of tetrahydrofuran was stirred at room temperature for 3 hours. A saturated sodium bicarbonate solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 36.2 g of 1-[2-(methoxymethyl)-3-bromophenyl]-4-methyl-1,4-dihydrotetrazol-5-one (referred to as 14A).

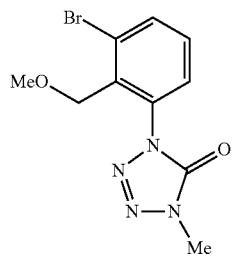 [SMILES: COCc1c(Br)cccc1-n1nnn(C)c1=O]

$^1$H-NMR (CDCl$_3$) δ (ppm): 3.23 (3H, s), 3.72 (3H, s), 4.67 (2H, s), 7.33 (1H, t, J=7.8 Hz), 7.38 (1H, dd, J=1.2, 8.1 Hz), 7.76 (1H, dd, J=1.5, 7.8 Hz).

Reference Production Example 15

A mixture of 36.2 g of 14A, 23.2 g of methylboronic acid, 66.7 g of cesium fluoride, 10.6 g of [1,1'-bis(diphenylphosphino)ferrocene]palladium(II) dichloride dichloromethane adduct, and 500 ml of 1,4-dioxane was stirred at 90° C. for 5.5 hours. After cooling, the reaction mixture was filtered and the filtrate was concentrated under reduced pressure. The residue thus obtained was subjected to silica gel column chromatography to obtain 25.6 g of 1-[2-(methoxymethyl)-3-methylphenyl]-4-methyl-1,4-dihydrotetrazol-5-one 1 (referred to as 15A).

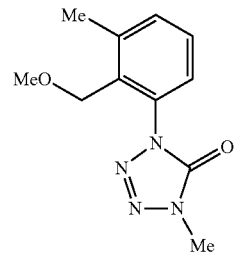 [SMILES: COCc1c(C)cccc1-n1nnn(C)c1=O]

$^1$H-NMR (CDCl$_3$) δ (ppm): 2.48 (3H, s), 3.23 (3H, s), 3.72 (3H, s), 4.42 (2H, s), 7.21 (1H, t, J=5.1 Hz), 7.35 (2H, d, J=4.8 Hz).

Reference Production Example 16

A mixture of 25.6 g of 15A, 50 mL of acetic acid, and 50 mL of a 25% hydrogen bromide-acetic acid solution was stirred at 65° C. for 1 hour. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 27.9 g of 1-[2-(bromomethyl)-3-methyl1-[2-(bromomethyl)-3-(referred to as 16A).

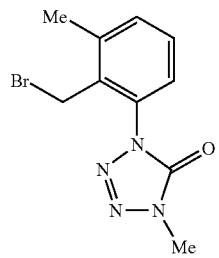

¹H-NMR (CDCl₃) δ (ppm): 2.51 (3H, s), 3.75 (3H, s), 4.51 (2H, s), 7.22-7.24 (1H, m), 7.36-7.39 (2H, m).

Reference Production Example 17

A mixture of 20 g of 16A and 16.5 mL of trimethyl phosphite was stirred with heating under reflux. The reaction mixture was concentrated under reduced pressure and then subjected to silica gel column chromatography to obtain 10.7 g of 17A.

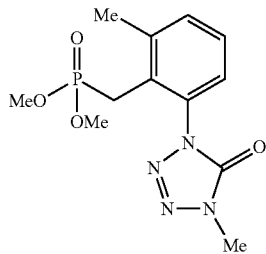

¹H-NMR (CDCl₃) δ (ppm): 7.35 (1H, d, J=7.2 Hz), 7.31 (1H, td, J=7.5, 2.2 Hz), 7.22 (1H, d, J=7.0 Hz), 3.73 (3H, s), 3.58 (3H, s), 3.56 (3H, s), 3.44 (2H, d, J=22.4 Hz), 2.50 (3H, d, J=1.8 Hz).

Reference Production Example 18

To a solution of 2 g of 17A and 10 mL of tetrahydrofuran, 0.28 g of sodium hydride (purity of 55%) was added at room temperature, followed by stirring for 30 minutes. To the solution, 1.5 g of 2-methyl-4-bromobenzaldehyde was added, followed by stirring at room temperature for 1 hour. Water was poured into this reaction mixture and the mixture was extracted with ethyl acetate. The organic layer was washed with a saturated sodium bicarbonate solution, dried over anhydrous sodium sulfate, and then concentrated under reduced pressure, and the residue thus obtained was subjected to silica gel column chromatography to obtain 1.5 g of 18A.

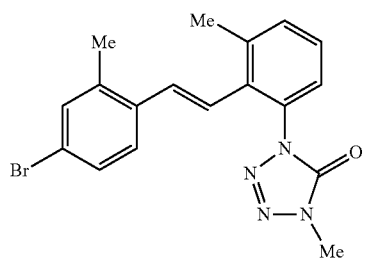 [SMILES: Cc1cc(Br)ccc1/C=C/c1c(C)cccc1-n1nnn(C)c1=O]

¹H-NMR (CDCl₃) δ (ppm): 7.39-7.23 (6H, m), 6.87 (1H, d, J=16.5 Hz), 6.52 (1H, d, J=16.5 Hz), 3.61 (3H, s), 2.42 (3H, s), 2.20 (3H, s).

Reference Production Example 19

A mixture of 30.1 g of 14A, 12.9 g of cyclopropylboronic acid, 46.2 g of cesium fluoride, 8.2 g of [1,1'-bis(diphenylphosphino)ferrocene]palladium(II) dichloride dichloromethane adduct, and 680 mL of 1,4-dioxane was stirred at 90° C. for 4 hours. After cooling, the reaction mixture was filtered and the filtrate was concentrated under reduced pressure. The residue thus obtained was subjected to silica gel column chromatography to obtain 26.0 g of 1-[2-(methoxymethyl)-3-cyclopropylphenyl]-4-methyl-1,4-dihydrotetrazol-5-one (referred to as 19A).

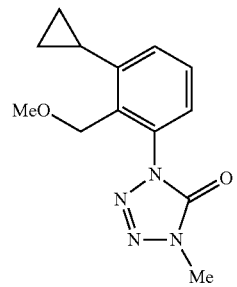 [SMILES: COCc1c(C2CC2)cccc1-n1nnn(C)c1=O]

¹H-NMR (CDCl₃) δ (ppm): 7.36 (1H, t, J=8.0 Hz), 7.20 (2H, d, J=8.0 Hz), 4.64 (2H, s), 3.72 (3H, s), 3.24 (3H, s), 2.20-2.13 (1H, m), 1.04-1.00 (2H, m), 0.76-0.72 (2H, m).

Reference Production Example 20

A mixture of 26.0 g of 19A, 40 mL of acetic acid, and 40 mL of a 25% hydrogen bromide-acetic acid solution was stirred at 65° C. for 2 hours. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 30.8 g of 1-[2-(bromomethyl)-3-cyclopropylphenyl]-4-methyl-1,4-dihydrotetrazol-5-one (referred to as 20A).

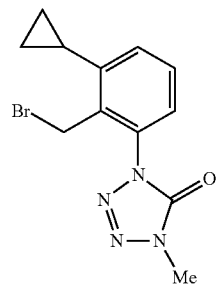

¹H-NMR (CDCl₃) δ (ppm): 7.38 (1H, t, J=7.8 Hz), 7.26-7.22 (2H, m), 4.77 (2H, s), 3.75 (3H, s), 2.16-2.09 (1H, m), 1.10-1.06 (2H, m), 0.82-0.78 (2H, m).

Reference Production Example 21

A mixture of 8 g of 20A and 12.8 g of trimethyl phosphite was stirred with heating under reflux. The reaction mixture was concentrated under reduced pressure and then subjected to silica gel column chromatography to obtain 6 g of 21A.

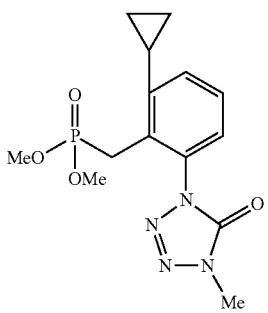

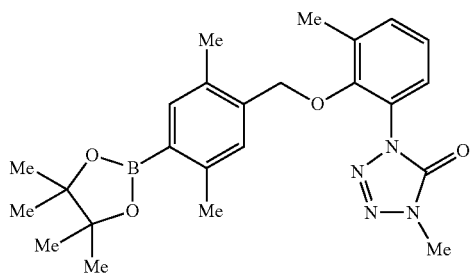

¹H-NMR (CDCl₃) δ (ppm): 7.33 (1H, td, J=7.8, 2.4 Hz), 7.27 (1H, d, J=7.8 Hz), 7.23 (1H, d, J=7.8 Hz), 3.76 (3H, s), 3.73 (3H, s), 3.58 (3H, s), 3.56 (2H, s), 2.24-2.16 (1H, m), 1.06-1.04 (2H, m), 0.74-0.72 (2H, m).

¹H-NMR (CDCl₃) δ: 7.52 (1H, s), 7.35 (1H, dd, J=7.7, 1.0 Hz), 7.23 (1H, dd, J=7.7, 1.7 Hz), 7.16 (1H, t, J=7.7 Hz), 7.05 (1H, s), 4.81 (2H, s), 3.53 (3H, s), 2.48 (3H, s), 2.36 (3H, s), 2.21 (3H, s), 1.34 (12H, s).

Reference Production Example 22

A mixture of 0.3 g of 18A mentioned in Reference Production Example 18, 0.05 g of sodium hydride (purity of 55%), and 3 mL of tetrahydrofuran was stirred at room temperature for 30 minutes and then 0.23 g of 4-benzyloxy-benzaldehyde was added, followed by stirring at room temperature for 3 hours. Water was added to the reaction mixture and the mixture was extracted with ethyl acetate. The organic layer was dried over anhydrous sodium sulfate and then concentrated under reduced pressure. The residue thus obtained was subjected to silica gel column chromatography to obtain 0.3 g of 1-{2-[2-(4-benzyloxyphenyl)ethenyl]-3-methylphenyl}-4-methyl-1,4-dihydrotetrazol-5-one (hereinafter referred to as the compound 22A).

Reference Production Example 24

A mixture of 0.4 g of 25A mentioned in Reference Production Example 25, 0.40 g of sodium hydride (purity of 55%), and 5 mL of dimethylformamide was stirred at room temperature for 30 minutes, and then 0.4 g (0.30 g) of 16A mentioned in Reference Production Example 16 was added, followed by stirring at 80° C. for 6 hours. After cooling the reaction mixture, water was added and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.20 g of 1-(2-{[1-(4-bromophenyl)ethoxy]methyl}-3-methylphenyl)-4-methyl-1,4-dihydrotetrazol-5-one (referred to as 24A).

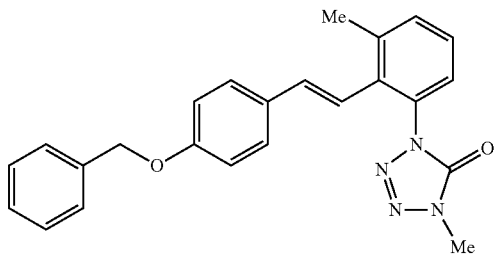 [SMILES: Cc1cccc(-n2nnn(C)c2=O)c1/C=C/c1ccc(OCc2ccccc2)cc1]

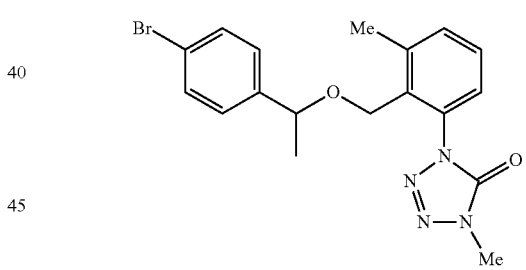

¹H-NMR (CDCl₃) δ (ppm): 7.61-7.56 (4H, m), 7.46-7.44 (4H, m), 7.40-7.32 (3H, m), 7.27 (1H, d, J=9.1 Hz), 7.06 (1H, d, J=16.5 Hz), 6.45 (1H, d, J=16.5 Hz), 3.62 (3H, s), 2.44 (3H, s).

¹H-NMR (CDCl₃) δ: 7.44 (1H, t, J=2.2 Hz), 7.42 (1H, t, J=2.2 Hz), 7.36-7.33 (2H, m), 7.20-7.17 (1H, m), 7.11 (1H, t, J=2.1 Hz), 7.09 (1H, t, J=2.1 Hz), 4.33-4.24 (3H, m), 3.60 (3H, s), 2.43 (3H, s), 1.31 (3H, d, J=6.4 Hz).

Reference Production Example 23

A mixture of 4 g of the present compound 50, 2.03 g of [1,1'-bis(diphenylphosphino)ferrocene]palladium(II) dichloride dichloromethane adduct, 2.91 g of potassium acetate, 2.76 g of bis(pinacolato)diboron, and 25 mL of dimethyl sulfoxide was stirred at 90° C. for 12 hours. After cooling to room temperature, the reaction mixture was filtered and the filtrate was concentrated. The residue thus obtained was subjected to silica gel column chromatography to obtain 3.7 g of 1-(2-{[4-(4,4,5,5-tetramethyl-1,3,2-dioxaborolan-2-yl)-2,5-dimethylphenyl]methoxy}phenyl)-4-methyl-1,4-dihydrotetrazol-5-one (referred to as 23A).

Reference Production Example 25

A mixture of 30 g of 4-bromoacetophenone, 8.6 g of sodium borohydride, and 200 mL of ethanol was mixed at 0° C., and stirred at room temperature for 3 hours. After adding acetone, the solution was concentrated and the residue thus obtained was dissolved in ethyl acetate, and then the mixture was washed with water and a saturated saline solution. Subsequently, the mixture was dried over anhydrous magnesium sulfate, and then concentrated under reduced pressure. The residue thus obtained was subjected to silica gel column chromatography to obtain 20 g of 1-(4-bromophenyl)ethanol (referred to as 25A).

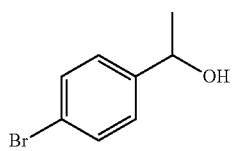

$^1$H-NMR (CDCl$_3$) δ: 7.49 (1H, t, J=2.3 Hz), 7.46 (1H, t, J=2.2 Hz), 7.27 (1H, t, J=2.3 Hz), 7.25 (1H, t, J=2.1 Hz), 4.88 (1H, dq, J=2.5, 6.9 Hz), 1.48 (3H, d, J=6.9 Hz).

Reference Production Example 26

To a mixture of 0.51 g of [4-(2-methoxyphenyl)-thiazol-2-yl]methanol and 20 mL of chloroform, 0.24 g of phosphorus tribromide was added, followed by stirring at room temperature and further stirring with heating under reflux for 30 minutes. After cooling the reaction mixture to room temperature, water was poured into the reaction mixture and the mixture was extracted with chloroform. The organic layer was washed with water and a saturated saline solution. The organic layer was dried over anhydrous sodium sulfate and concentrated under reduced pressure. The residue thus obtained was subjected to silica gel column chromatography to obtain 0.71 g of 2-bromomethyl-4-(2-methoxyphenyl)-thiazole (referred to as 26A).

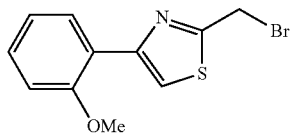 [SMILES: COc1ccccc1-c1csc(CBr)n1]

$^1$H-NMR (CDCl$_3$) δ: 8.20 (1H, d, J=7.5 Hz), 7.96 (1H, s), 7.31 (1H, t, J=7.5 Hz), 7.06 (1H, t, J=7.5 Hz), 6.99 (1H, d, J=7.5 Hz), 4.79 (2H, s), 3.93 (3H, s)

Reference Production Example 27

To a mixture of 1.97 g of methyl 1-(4-chlorophenyl)-pyrazole-3-carboxylate and 83 mL of tetrahydrofuran, a mixture of 0.68 g of lithium aluminum hydride and 8.3 mL of tetrahydrofuran was added little by little under cooling with ice water. The mixture was stirred at room temperature for 3 hours. After cooling the reaction solution to 0° C., 0.5 mL of water was added, followed by stirring for 30 minutes. To the reaction mixture, 10 mL of an aqueous 10% sodium hydroxide solution was added, followed by stirring at room temperature for 30 minutes, addition of 0.5 mL of water, and further stirring for 30 minutes. To the reaction mixture, an appropriate amount of magnesium sulfate was added and the mixture was filtered through Cerite. The residue thus obtained was concentrated to obtain 1.47 g of [1-(4-chlorophenyl)-pyrazol-3-yl]methanol (referred to as 27A).

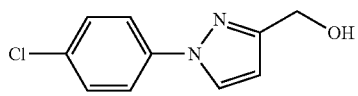

$^1$H-NMR (CDCl$_3$) δ: 7.84 (1H, d, J=2.4 Hz), 7.60 (2H, dt, J=9.3, 2.4 Hz), 7.41 (2H, dt, J=9.3, 2.4 Hz), 6.47 (1H, d, J=2.4 Hz), 4.77 (2H, d, J=6.0 Hz), 2.27 (1H, t, J=6.0 Hz).

Reference Production Example 28

To a mixture of 0.25 g of 27A mentioned in Reference Production Example 27 and 5 mL of chloroform, 0.19 g of phosphorus tribromide was added at room temperature, followed by stirring under reflux for 2.5 hours. After cooling the reaction mixture to room temperature, water was poured into the reaction mixture and the mixture was extracted with ethyl acetate. The organic layer was washed with water and a saturated saline solution. The organic layer was dried over anhydrous sodium sulfate and concentrated under reduced pressure. The residue thus obtained was subjected to silica gel column chromatography to obtain 0.39 g of 3-(bromomethyl)-1-(4-chlorophenyl)-1H-pyrazole (referred to as 28A).

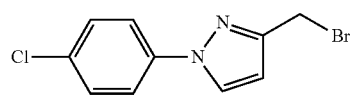

$^1$H-NMR (CDCl$_3$) δ: 7.83 (1H, d, J=2.7 Hz), 7.61 (2H, dt, J=8.9, 2.2 Hz), 7.41 (2H, dt, J=8.9, 2.2 Hz), 6.53 (1H, d, J=2.7 Hz), 4.56 (2H, s).

In accordance with the process mentioned above, it is possible to obtain the following compounds [in which A is a substituent corresponding to each of substituent numbers 1 to 5122 shown below].

Compounds PA1-1 to PH19-5122, HB1001-001 to HB7069-5122, RA1-001 to RG19-5122, C0001-001 to C0714-5122, and D0001-001 to D0714-5122 are tetrazolinone compounds [in which A is a substituent corresponding to each of substituent numbers 1 to 5122 shown below].

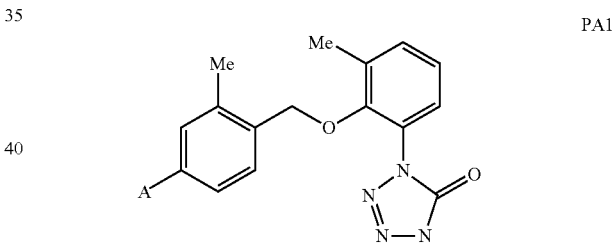

PA1

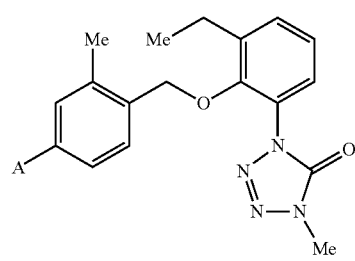

PB1

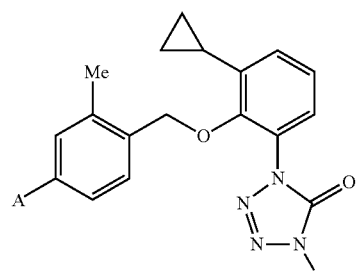

PC1

PD1
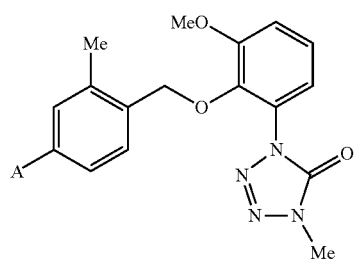
PE1
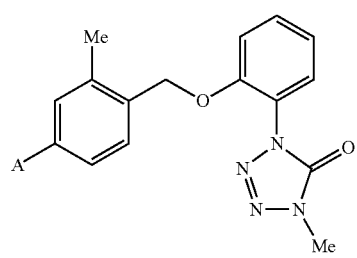
PF1
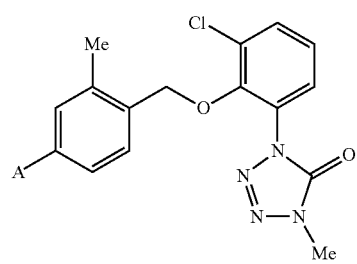
PG1
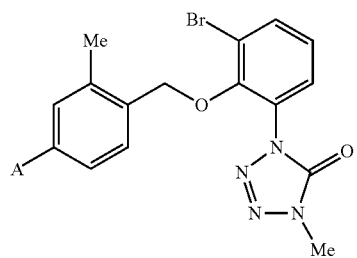
PH1
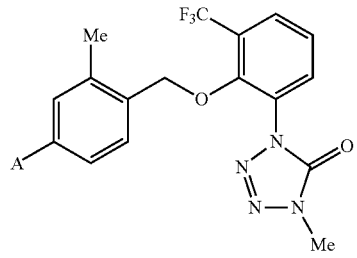
PA2
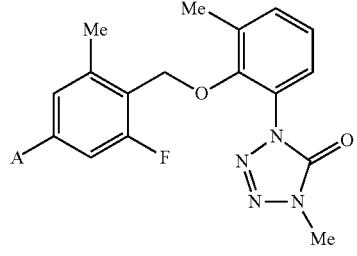
PB2
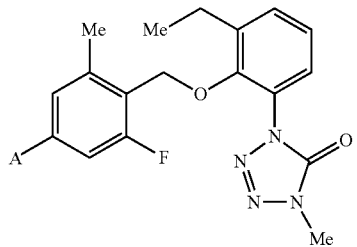
PC2
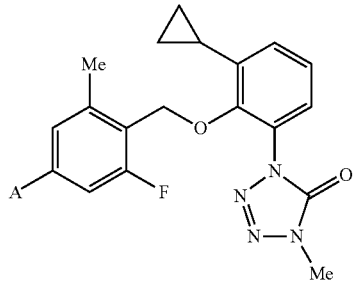
PD2
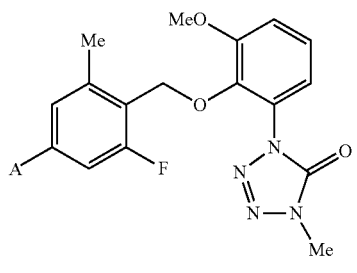
PE2
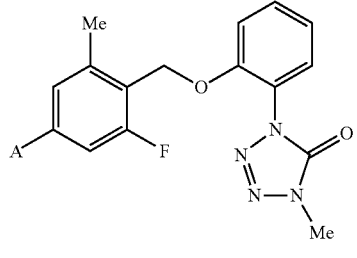
PF2
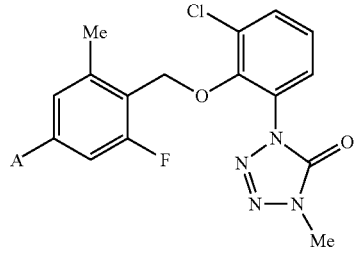
PG2
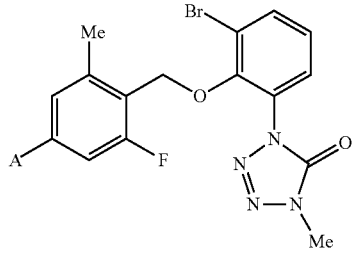

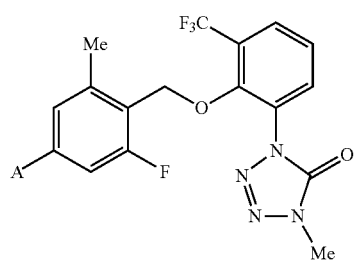
PH2
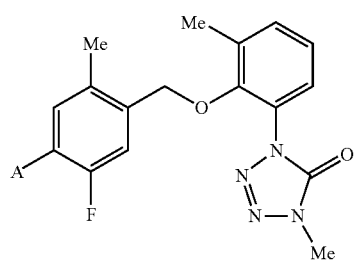
PA3
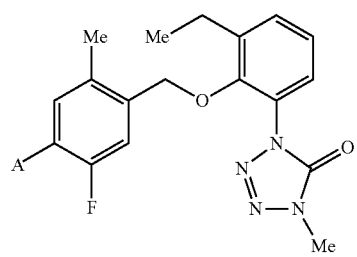
PB3
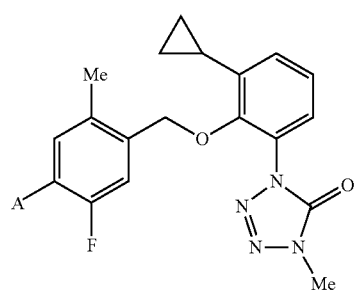
PC3
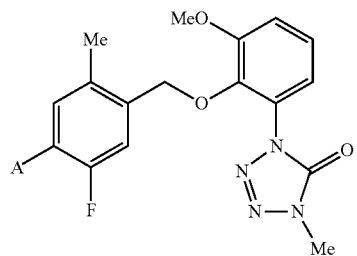
PD3
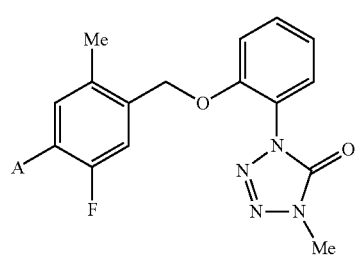
PE3
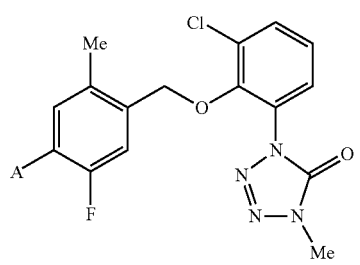
PF3
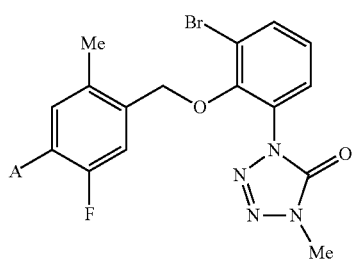
PG3
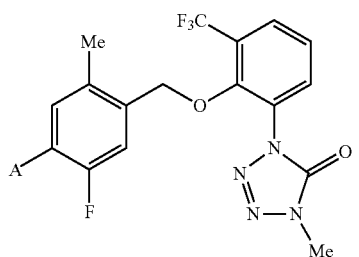
PH3
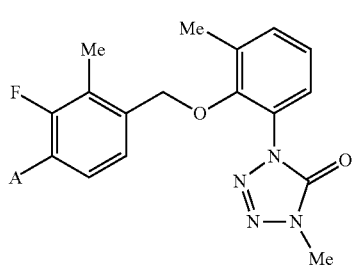
PA4
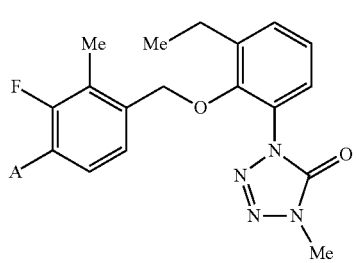
PB4
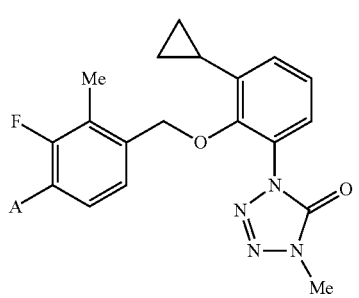
PC4

-continued
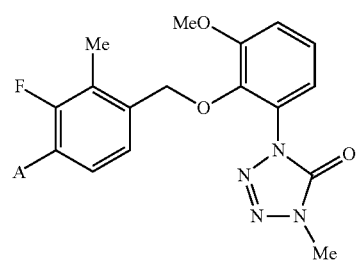 PD4
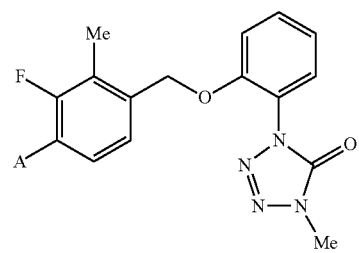 PE4
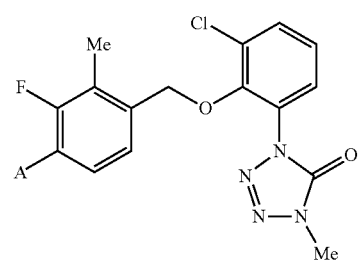 PF4
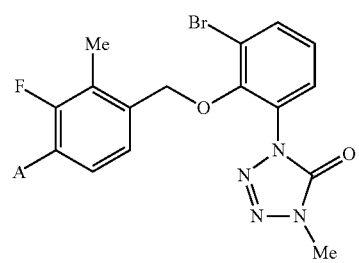 PG4
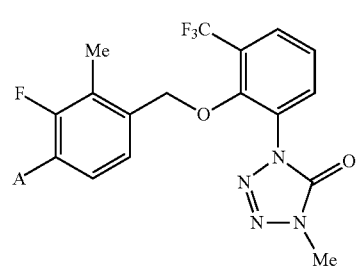 PH4
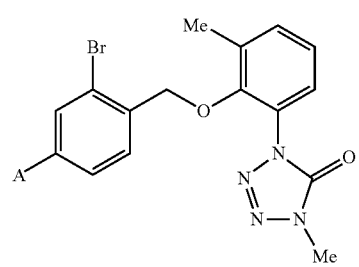 PA5
-continued
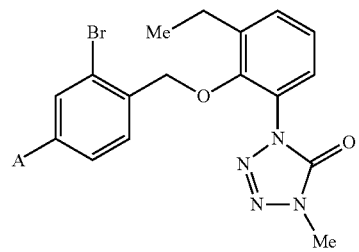 PB5
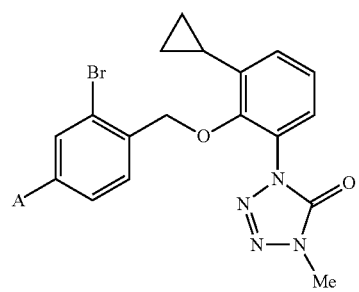 PC5
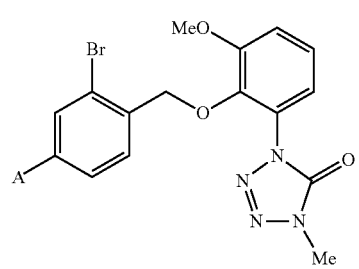 PD5
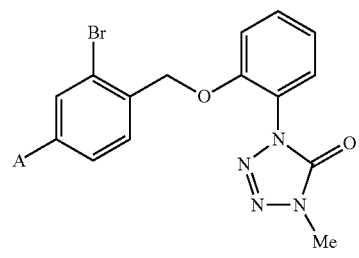 PE5
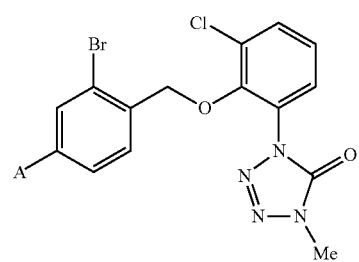 PF5
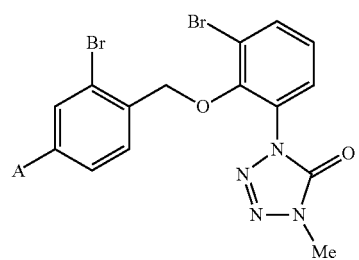 PG5

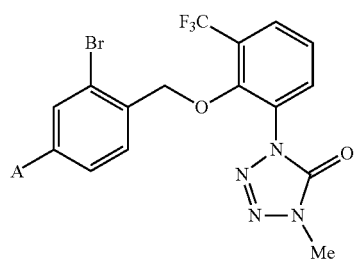
PH5

PA6
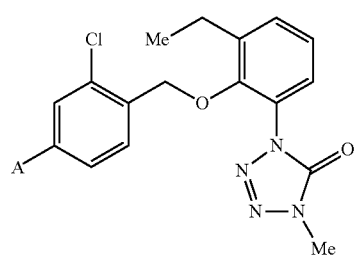
PB6
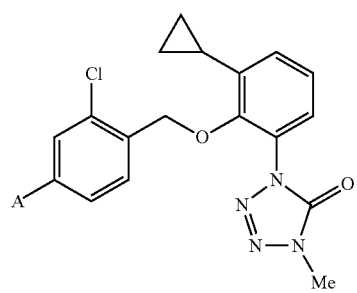
PC6
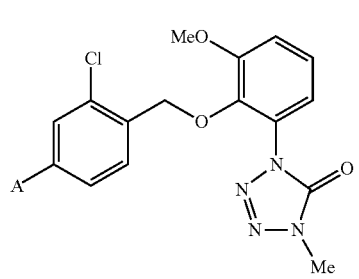
PD6
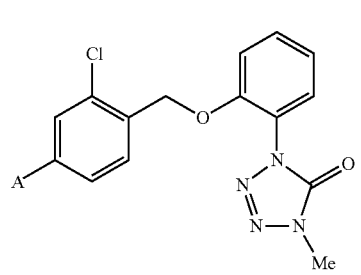
PE6
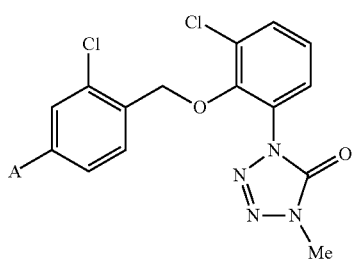
PF6
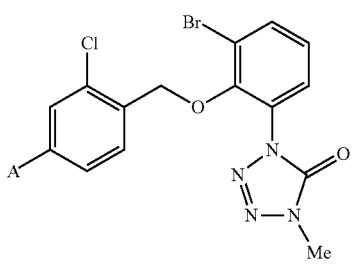
PG6
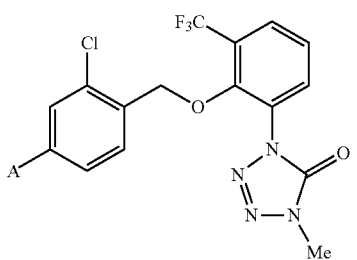
PH6
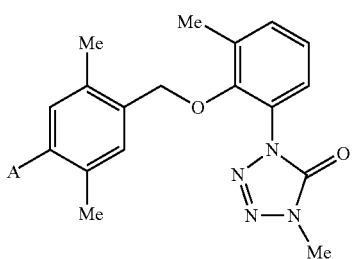
PA7
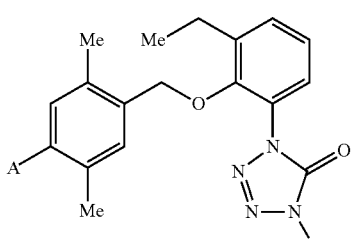
PB7
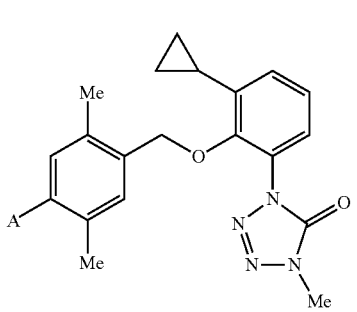
PC7

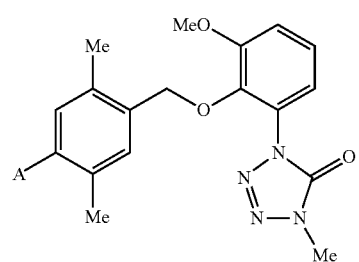
PD7
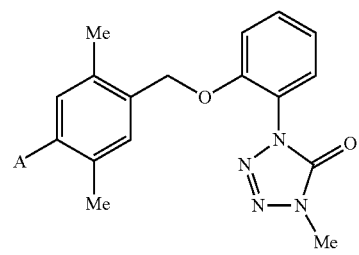
PE7
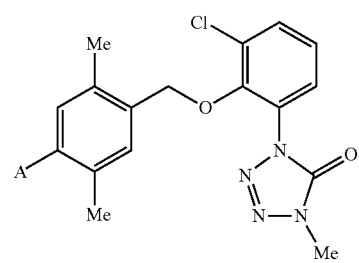
PF7
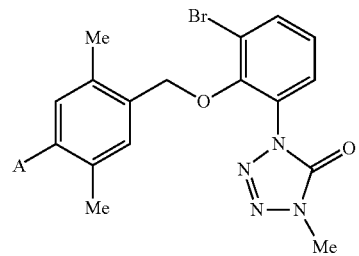
PG7
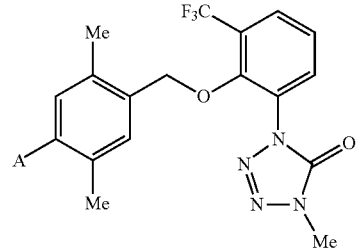
PH7
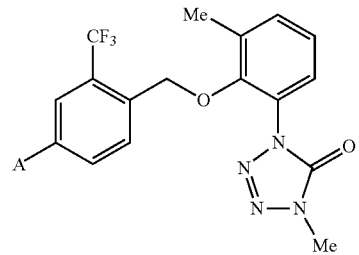
PA8
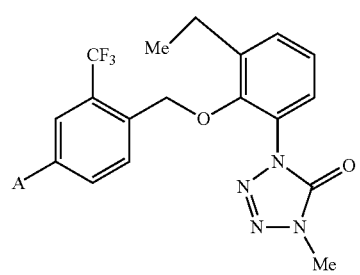
PB8
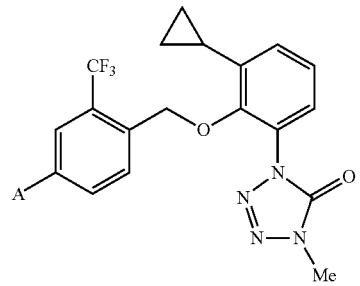
PC8
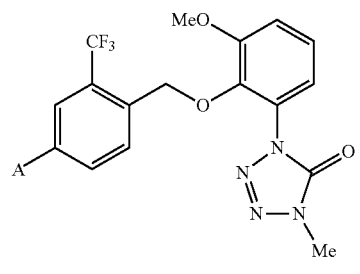
PD8
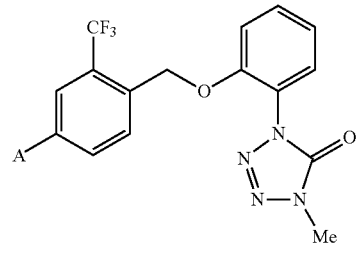
PE8
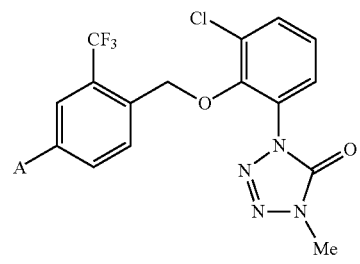
PF8
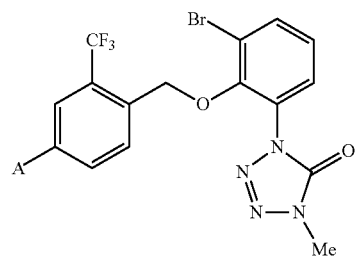
PG8

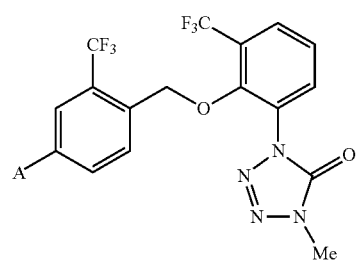
PH8
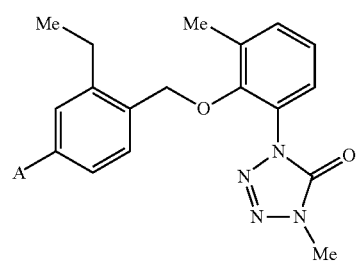
PA9
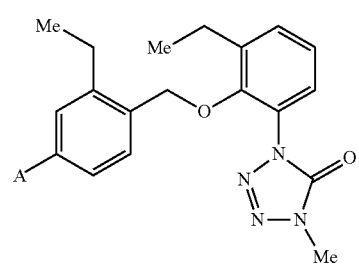
PB9
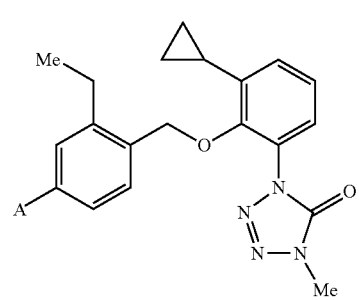
PC9
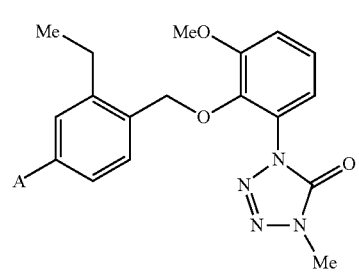
PD9
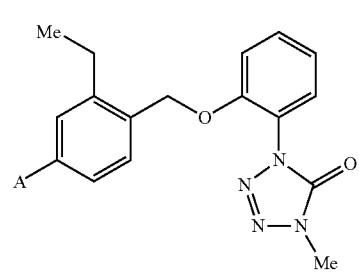
PE9
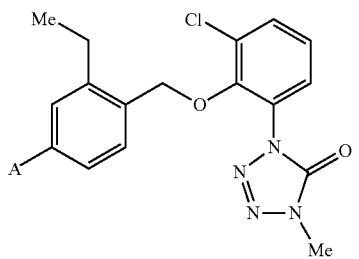
PF9
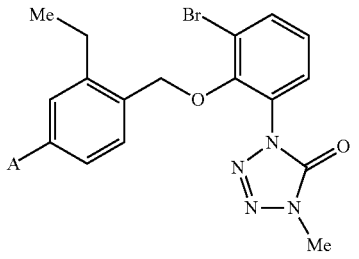
PG9
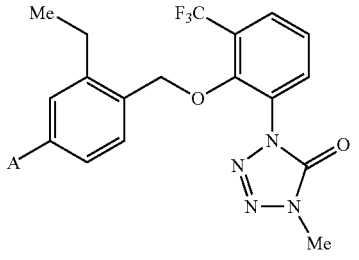
PH9
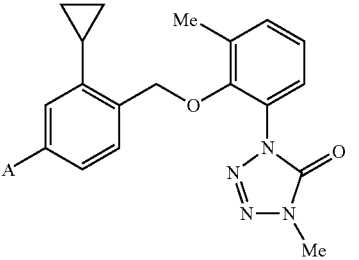
PA10
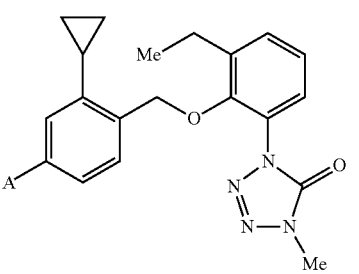
PB10
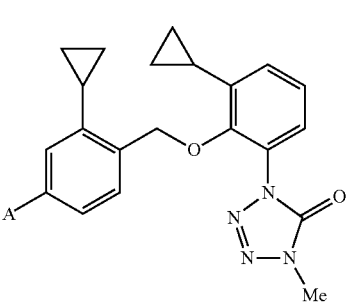
PC10

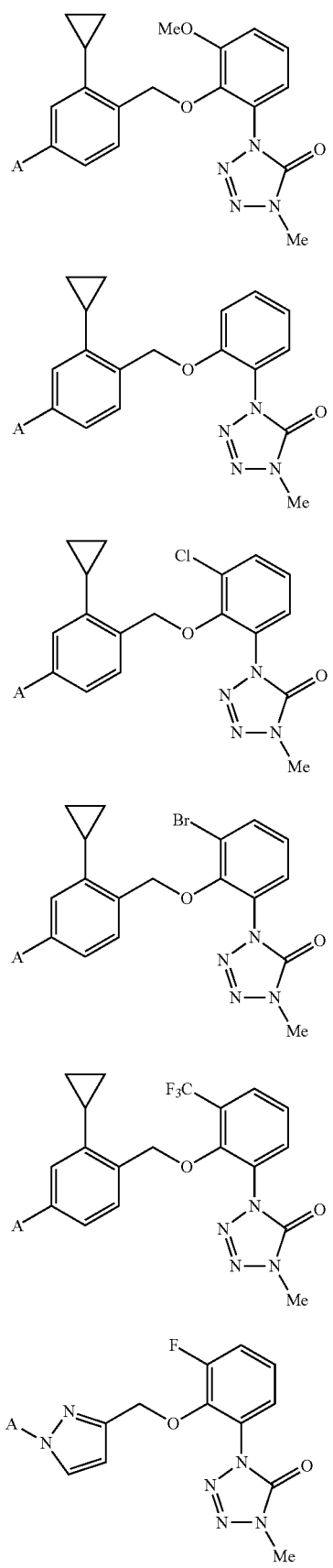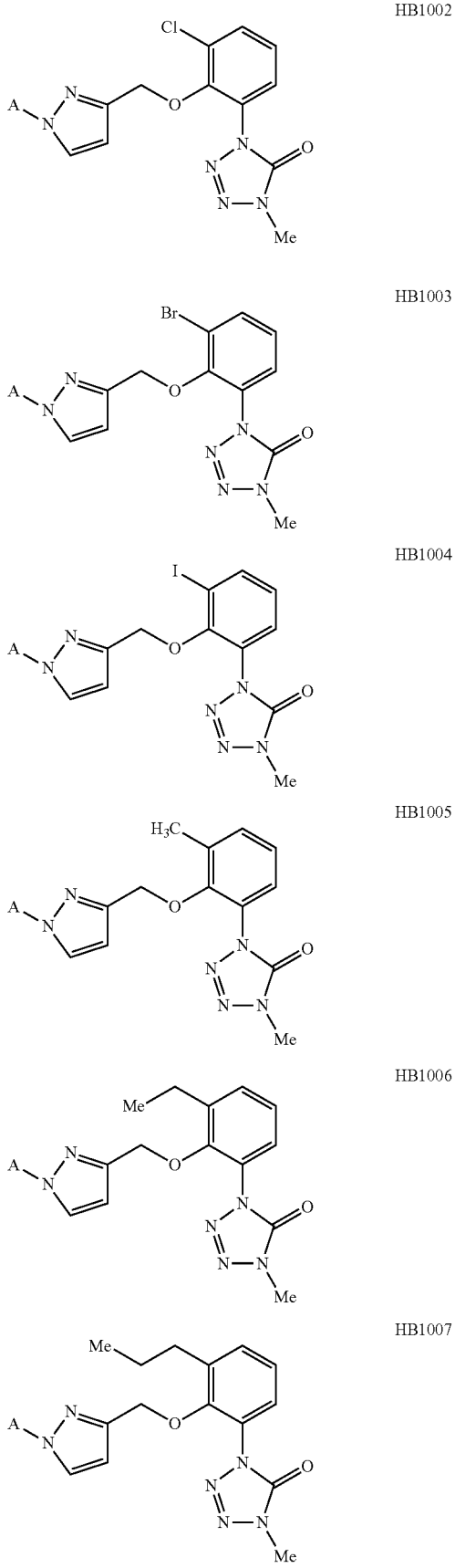

HB1008
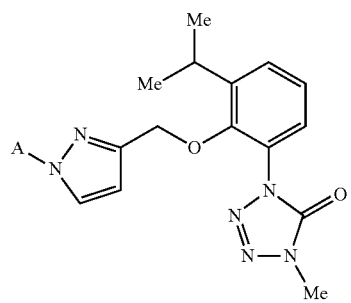
HB1009
HB1010
HB1011
HB1012
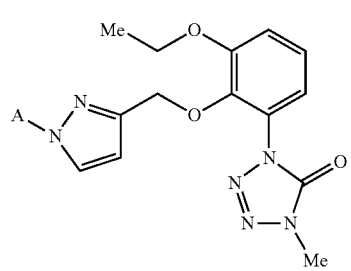
HB1013
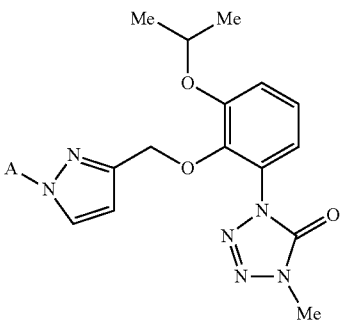
HB1014
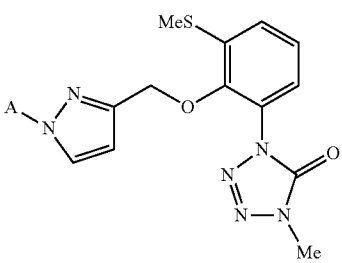
HB1015
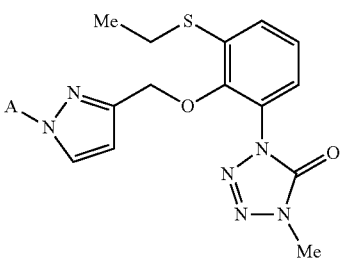
HB1016
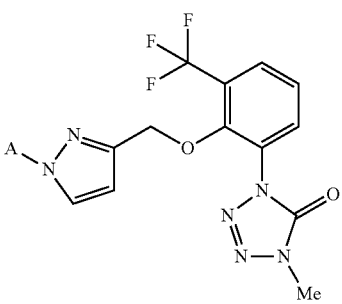
HB1017
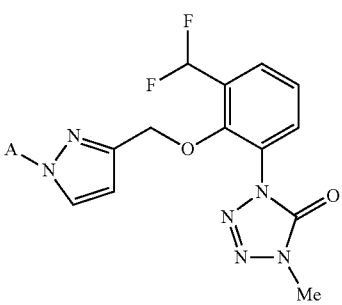

-continued
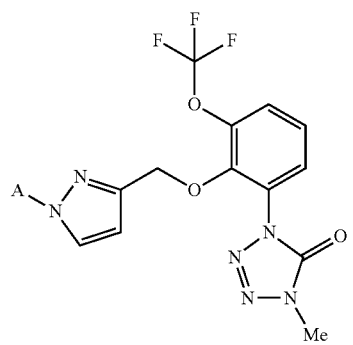
HB1018
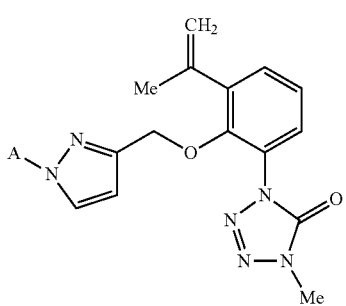
HB1023
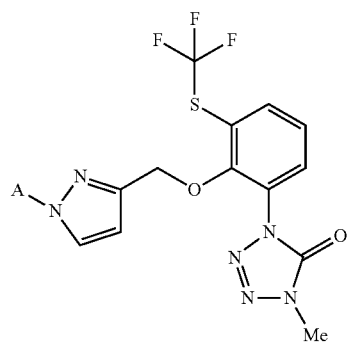
HB1019
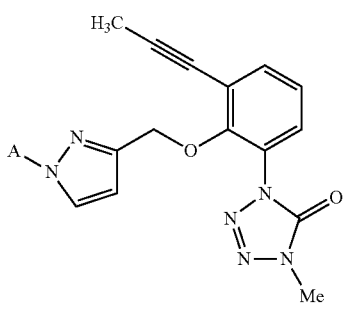
HB1024
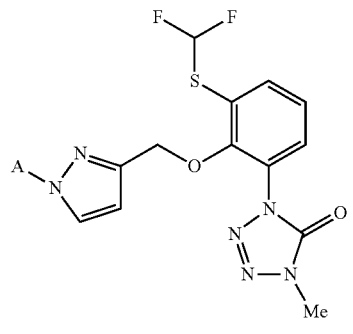
HB1020
HB1025
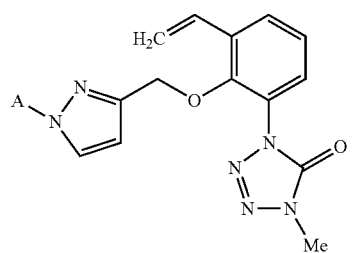
HB1021
HB1026
HB1022
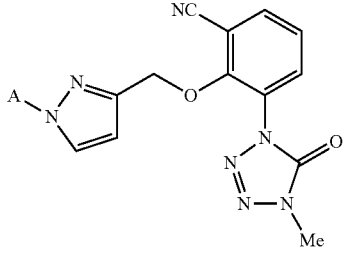
HB1027

| | |
|---|---|
| 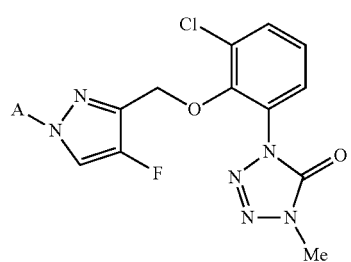 HB1028 | 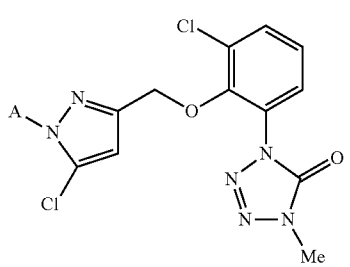 HB1034 |
| 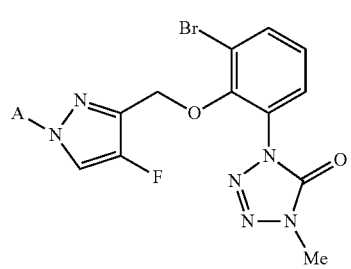 HB1029 | 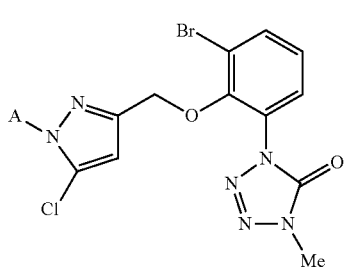 HB1035 |
| 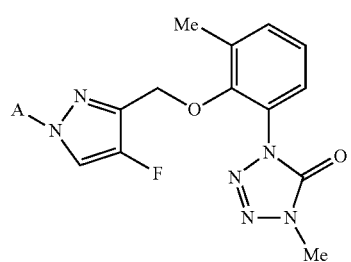 HB1030 | 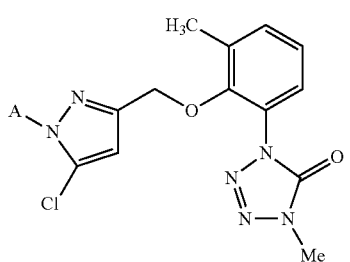 HB1036 |
| 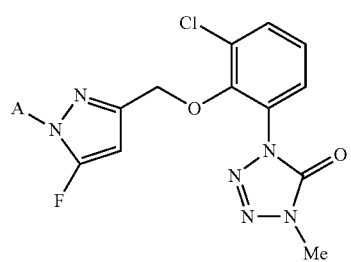 HB1031 | 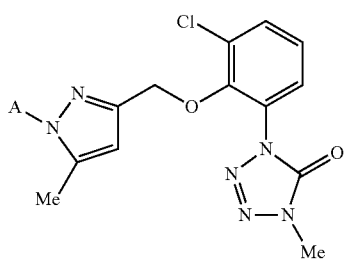 HB1037 |
| 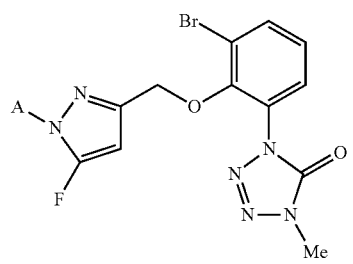 HB1032 | 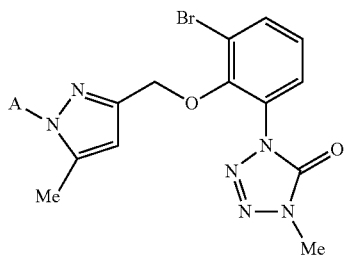 HB1038 |
| 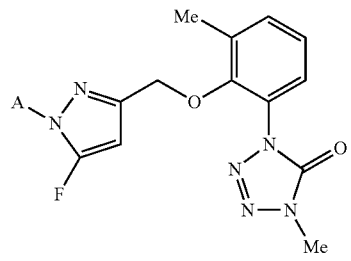 HB1033 | 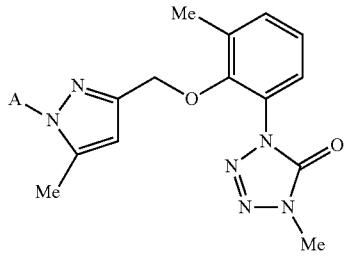 HB1039 |

-continued
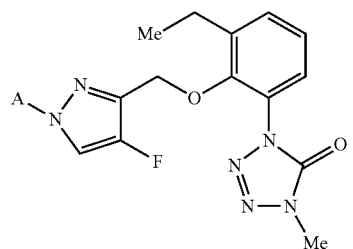
HB1040
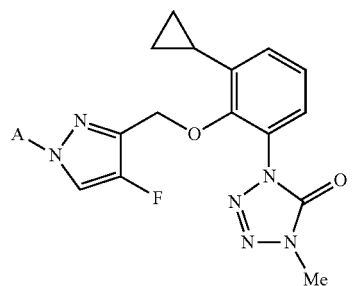
HB1041
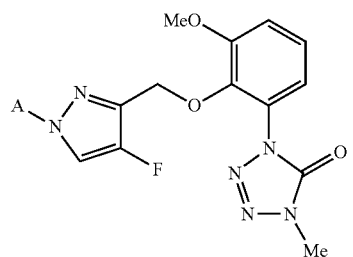
HB1042
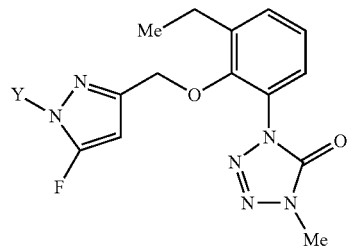
HB1043
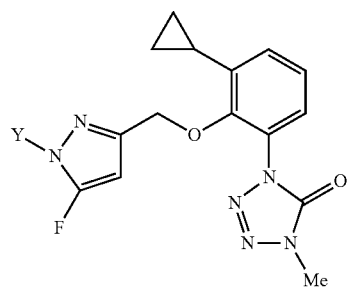
HB1044
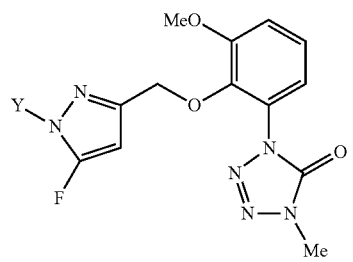
HB1045
-continued
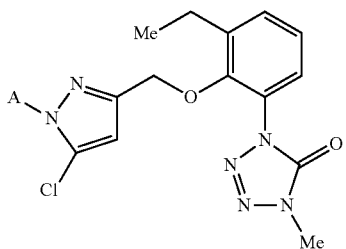
HB1046
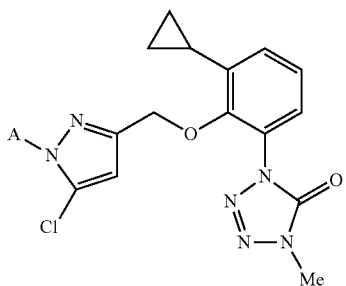
HB1047
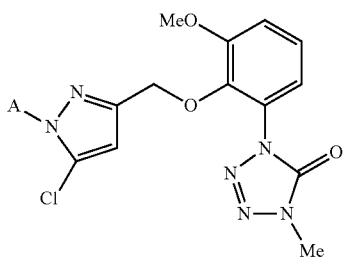
HB1048
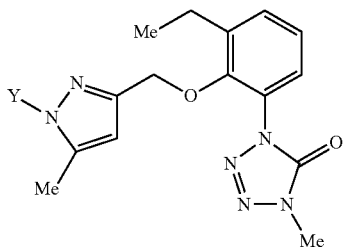
HB1049
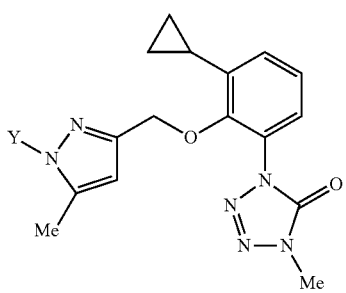
HB1050
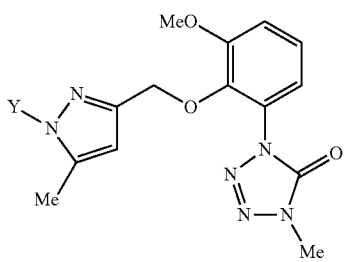
HB1051

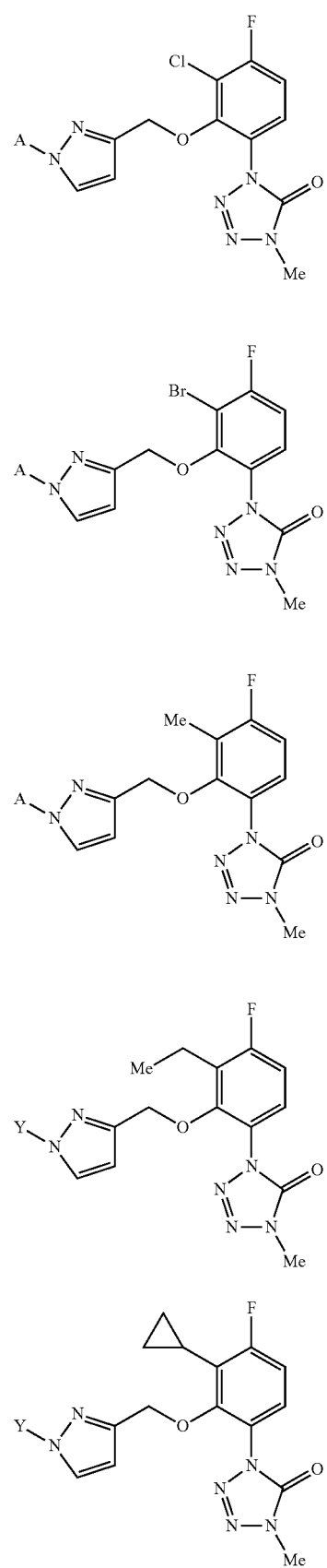
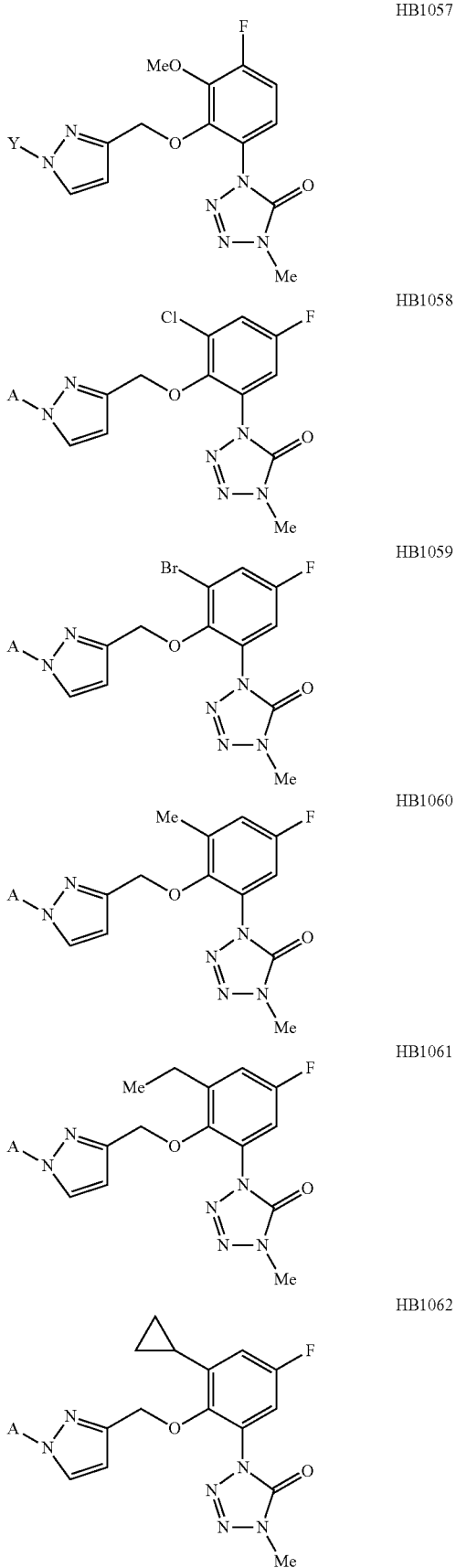

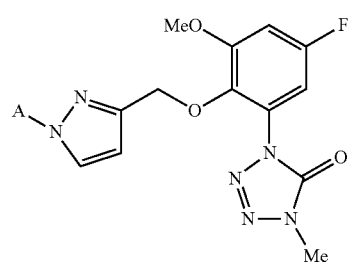
HB1063
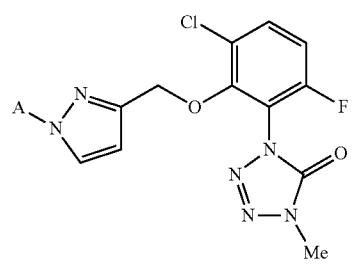
HB1064
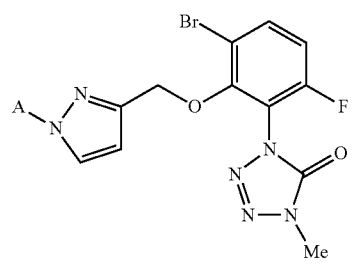
HB1065
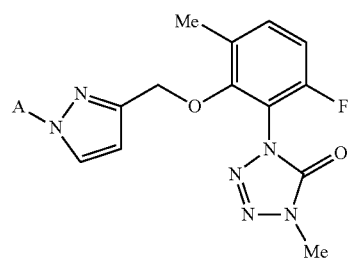
HB1066
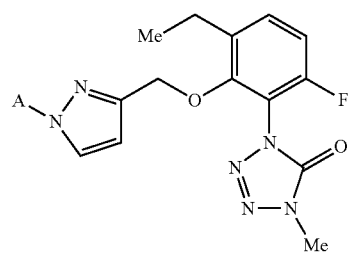
HB1067
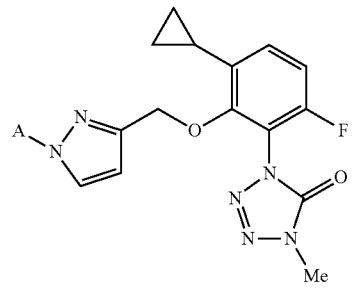
HB1068
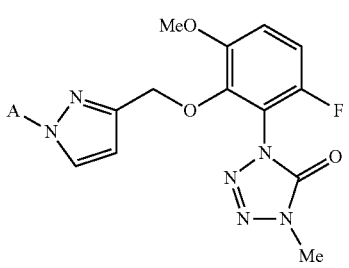
HB1069
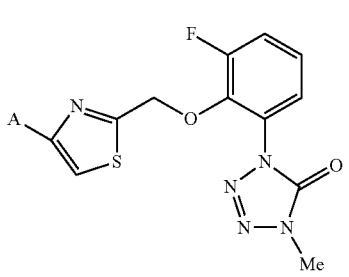
HB2001
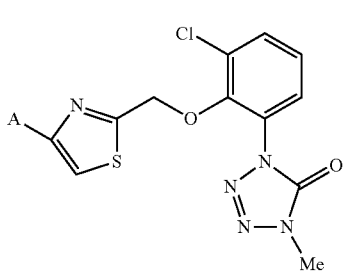
HB2002
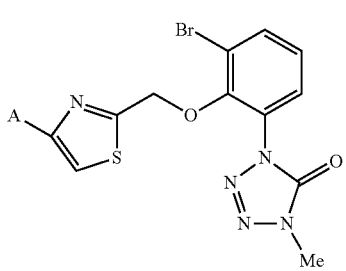
HB2003
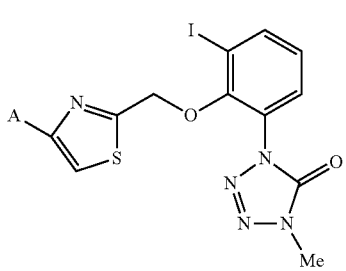
HB2004
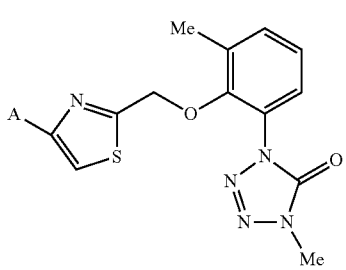
HB2005

-continued
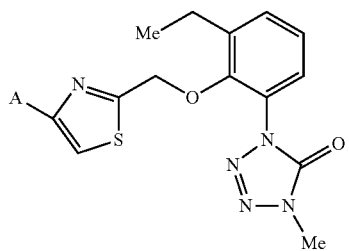 HB2006
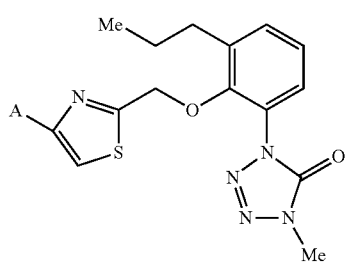 HB2007
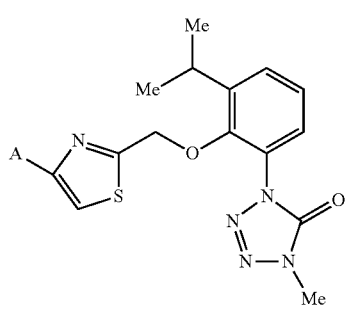 HB2008
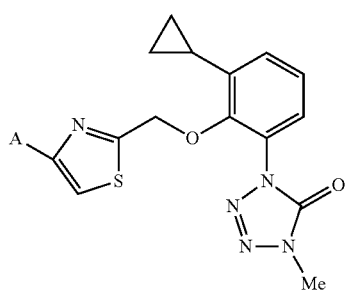 HB2009
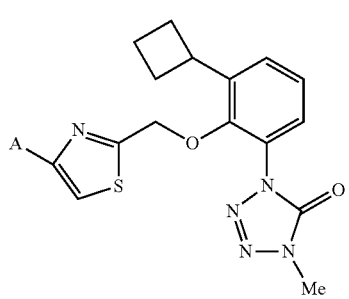 HB2010
-continued
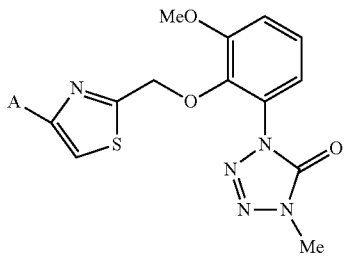 HB2011
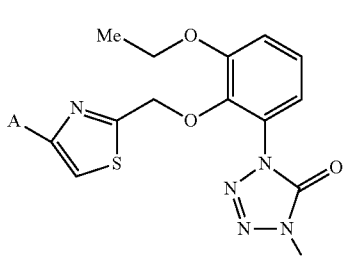 HB2012
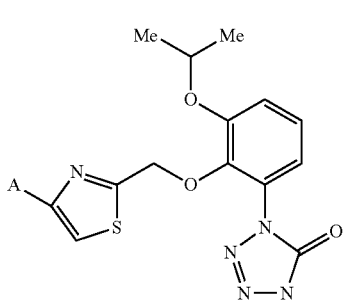 HB2013
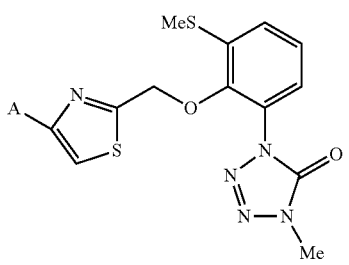 HB2014
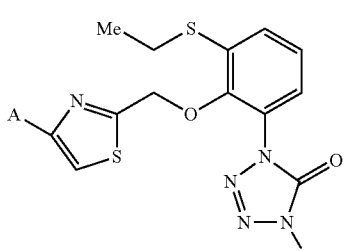 HB2015

| | |
|---|---|
| HB2016 | HB2021 |
| HB2017 | HB2022 |
| HB2018 | HB2023 |
| HB2019 | HB2024 |
| HB2020 | HB2025 |

HB2026 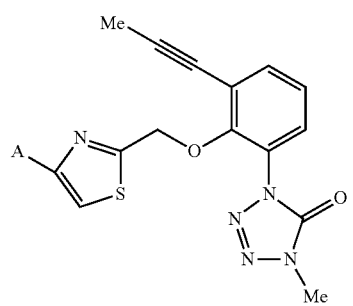
HB2027 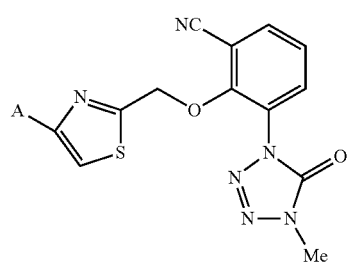
HB2028 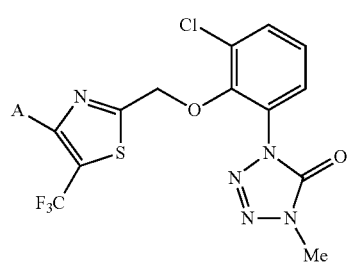
HB2029 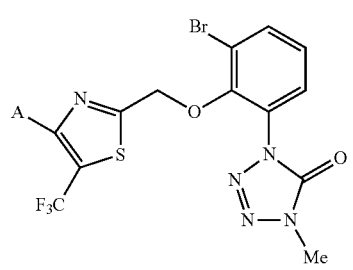
HB2030 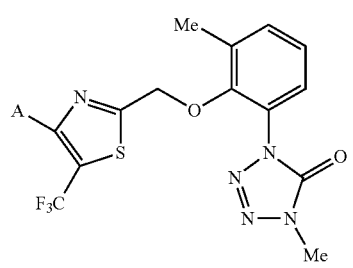
HB2031 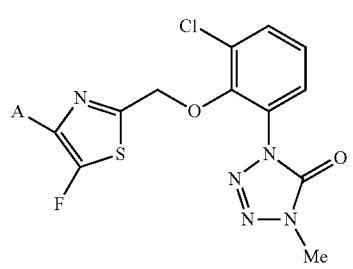
HB2032 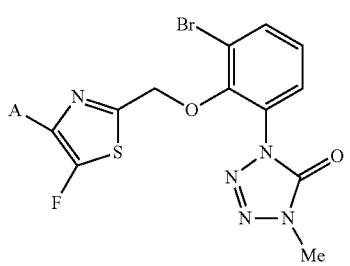
HB2033 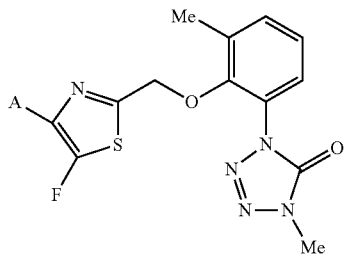
HB2034 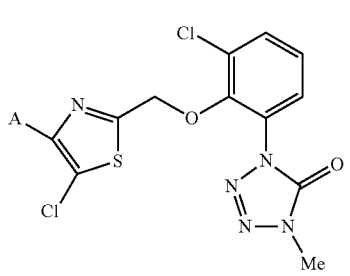
HB2035 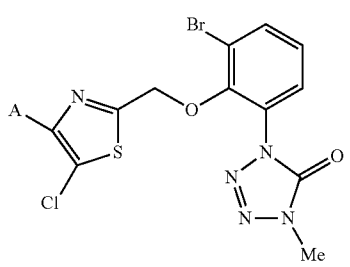
HB2036 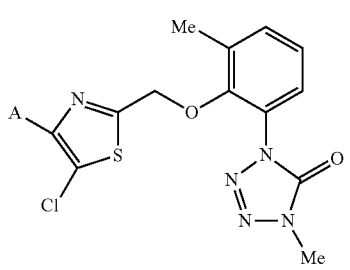
HB2037 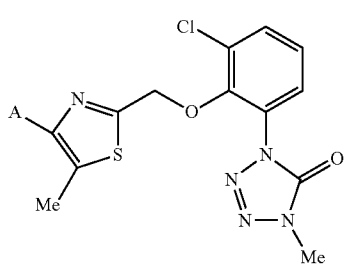

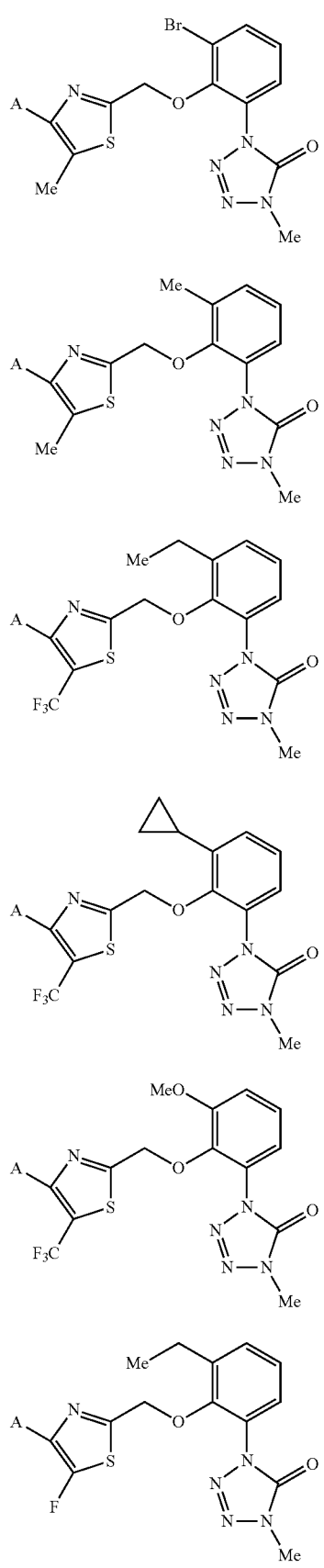
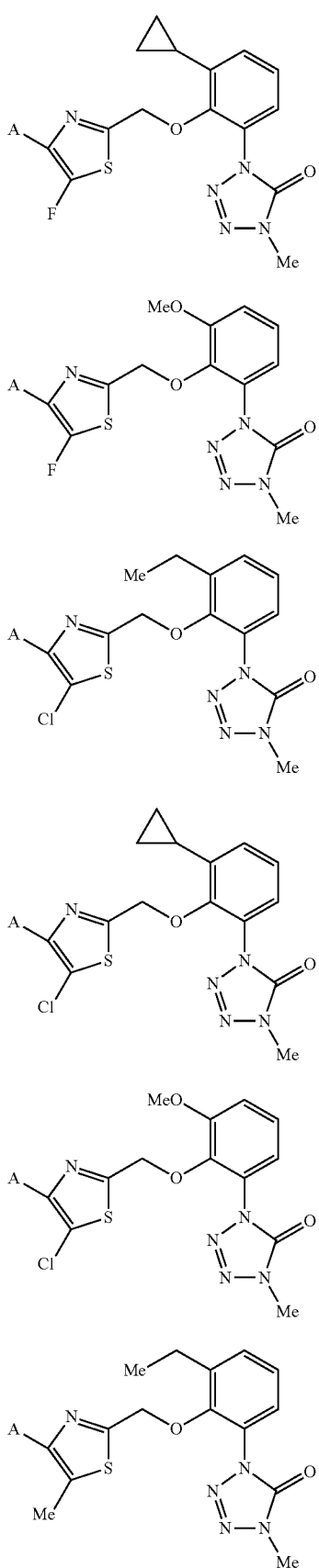

HB2050 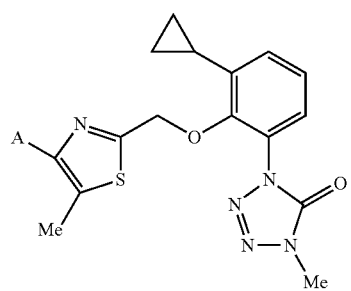
HB2051 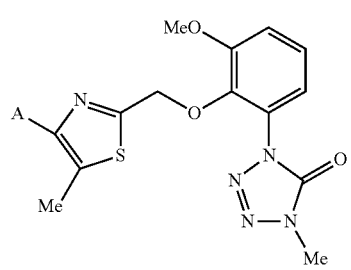
HB2052 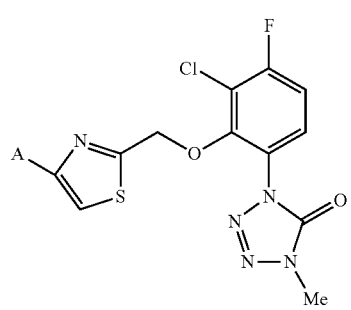
HB2053 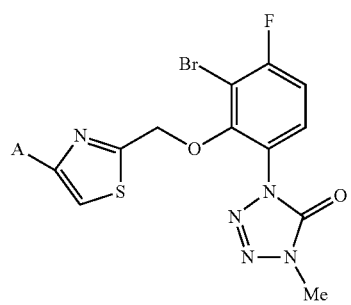
HB2054 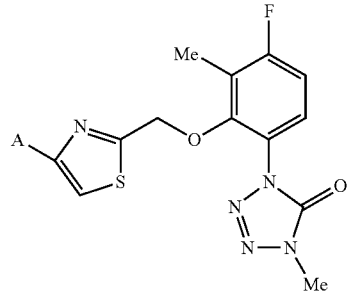
HB2055 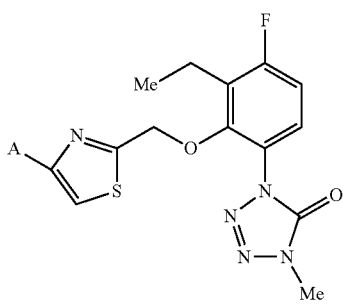
HB2056 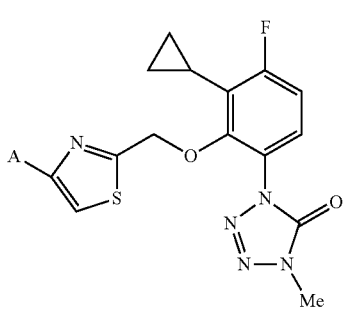
HB2057 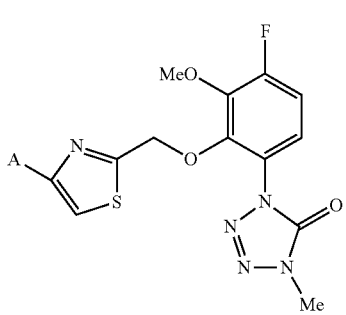
HB2058 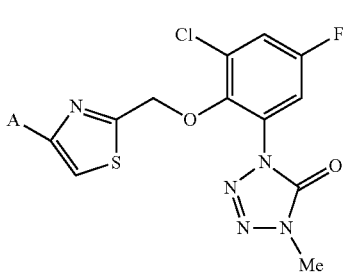
HB2059 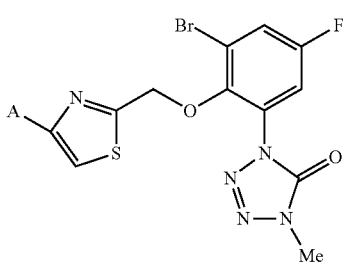

-continued
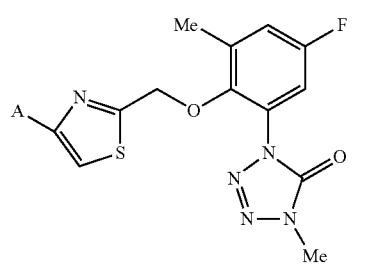
HB2060
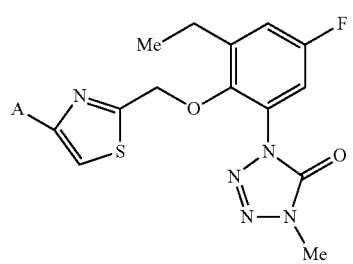
HB2061
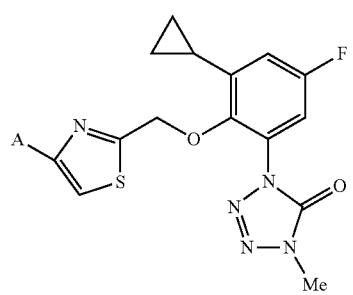
HB2062
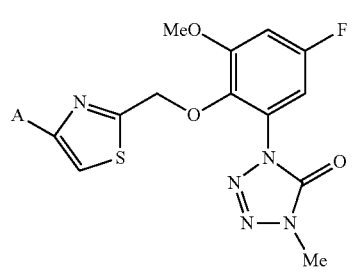
HB2063
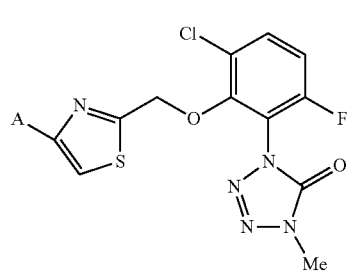
HB2064
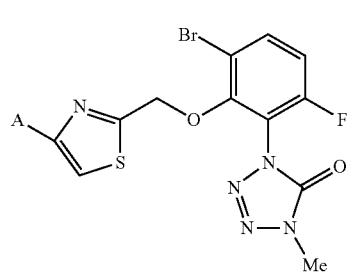
HB2065
-continued
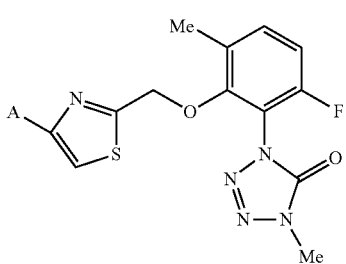
HB2066
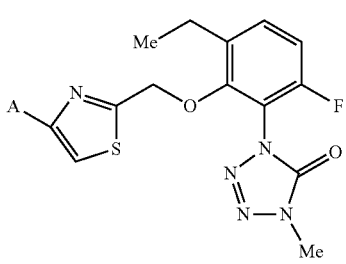
HB2067
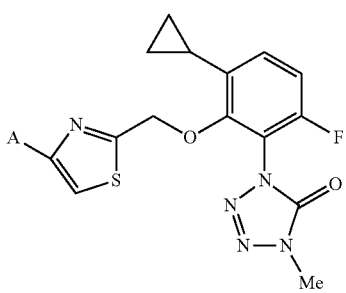
HB2068
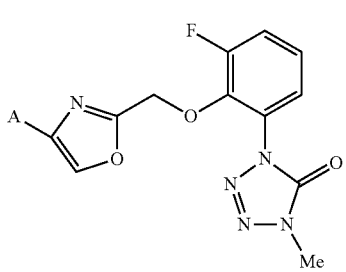
HB3001
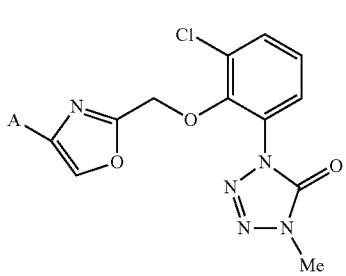
HB3002
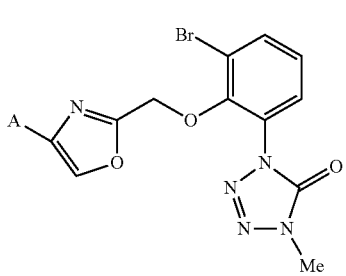
HB3003

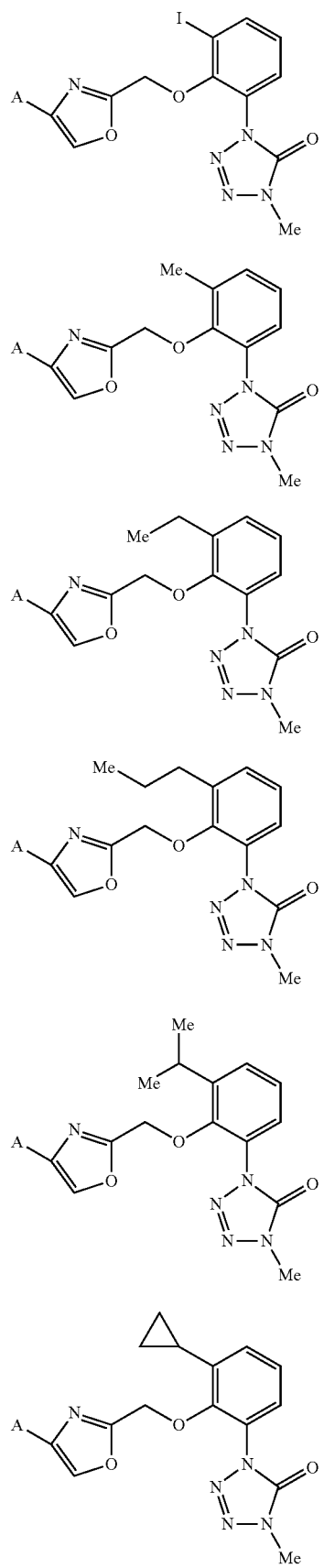
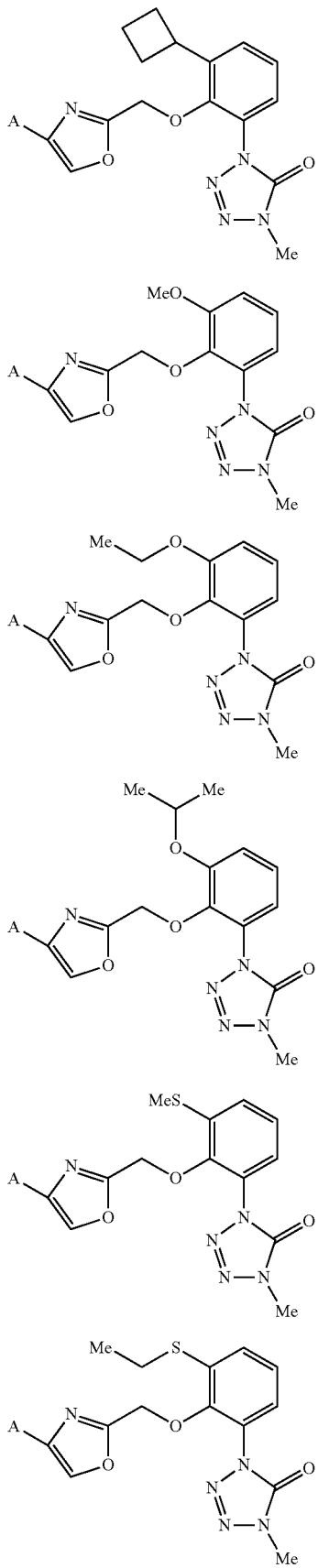

-continued
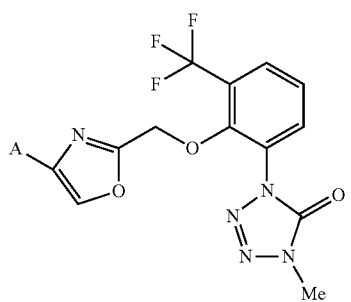
HB3016
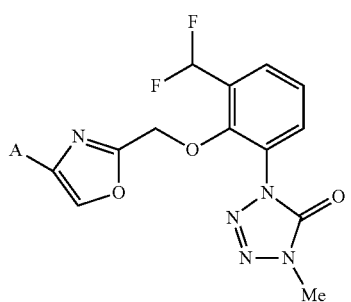
HB3017
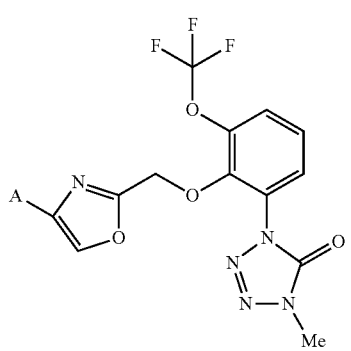
HB3018
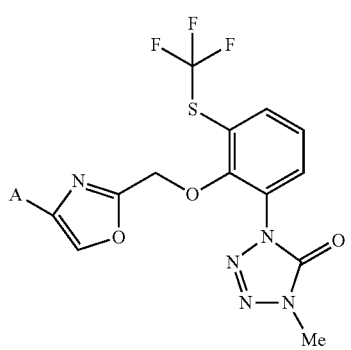
HB3019
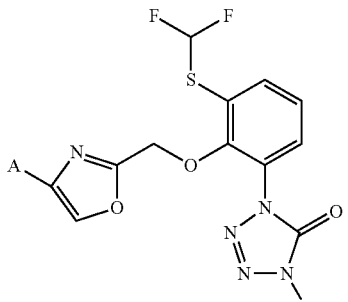
HB3020
-continued
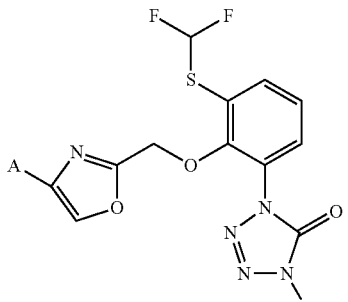
HB3021
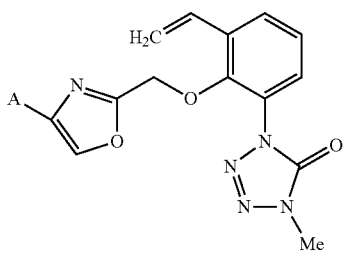
HB3022
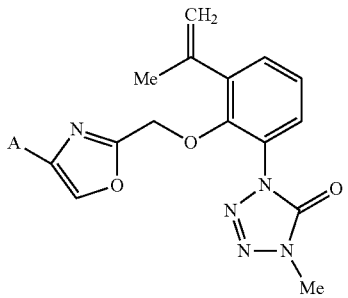
HB3023
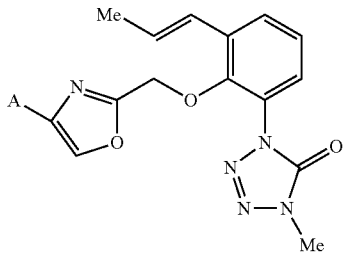
HB3024
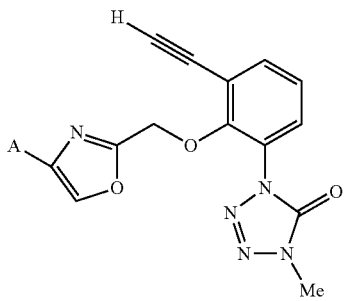
HB3025

| | |
|---|---|
| 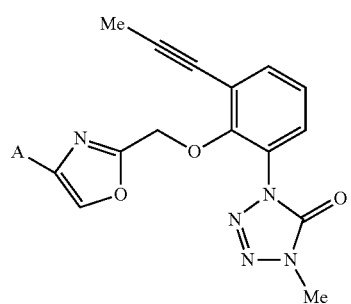 HB3026 | 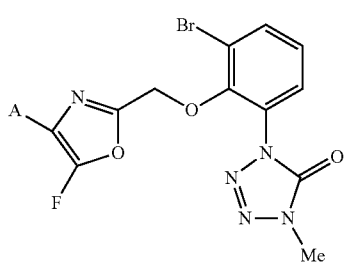 HB3032 |
| 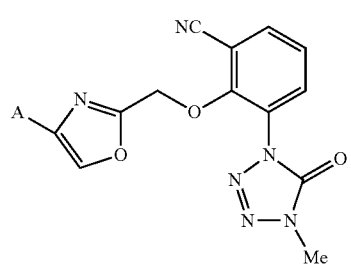 HB3027 | 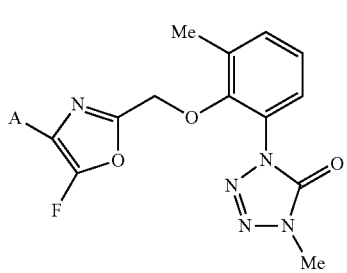 HB3033 |
| 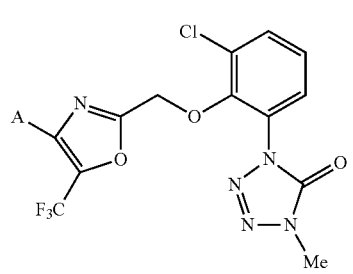 HB3028 | 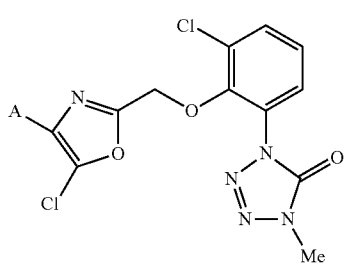 HB3034 |
| 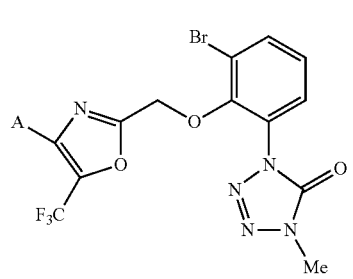 HB3029 | 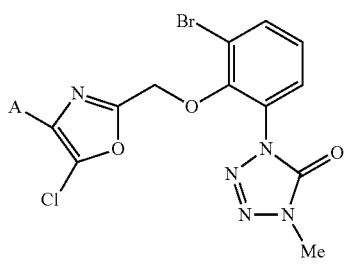 HB3035 |
| 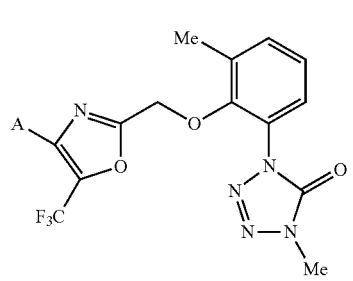 HB3030 | 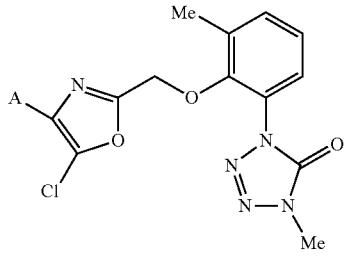 HB3036 |
| 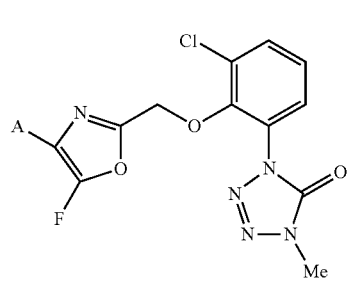 HB3031 | 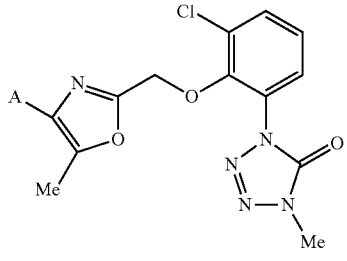 HB3037 |

| | |
|---|---|
| 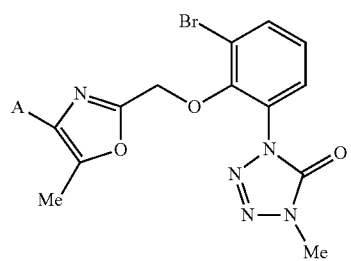 HB3038 | 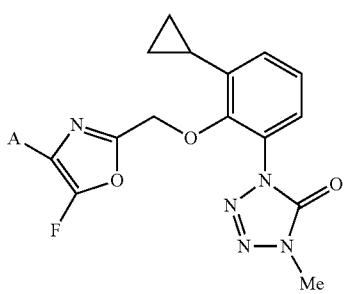 HB3044 |
| 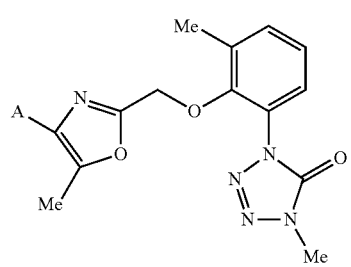 HB3039 | 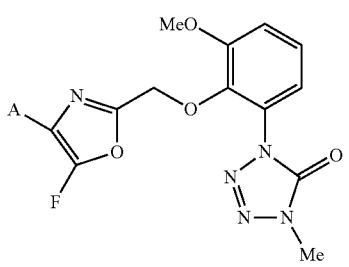 HB3045 |
| 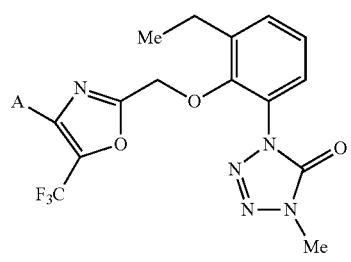 HB3040 | 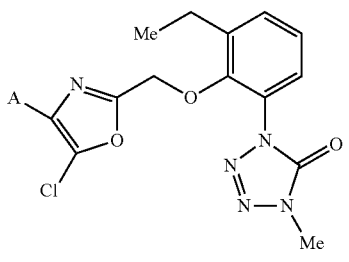 HB3046 |
| 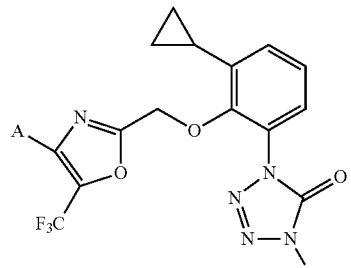 HB3041 | 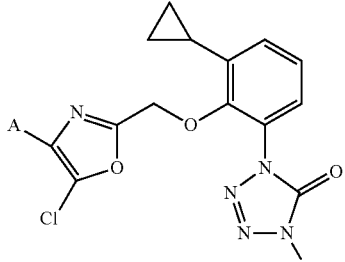 HB3047 |
| 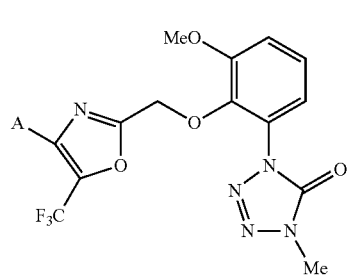 HB3042 | 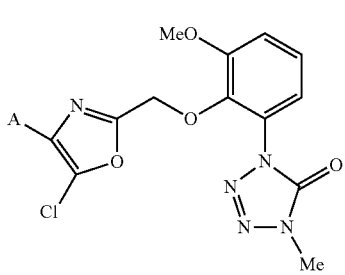 HB3048 |
| 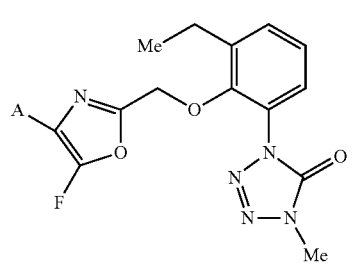 HB3043 | 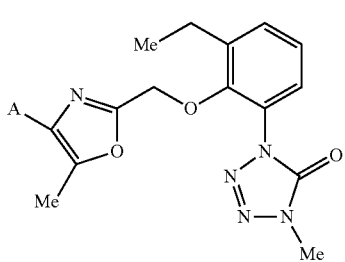 HB3049 |

HB3050
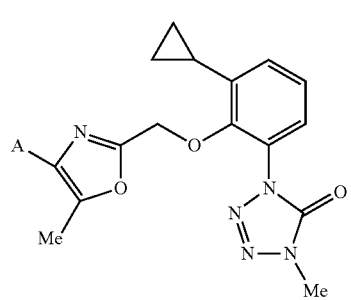
HB3051
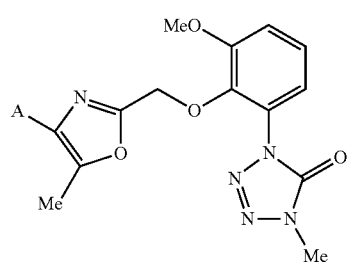
HB3052
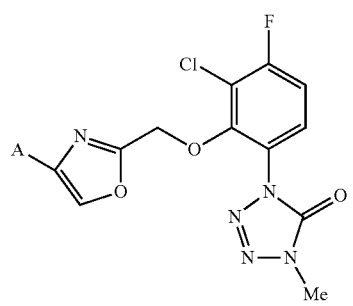
HB3053
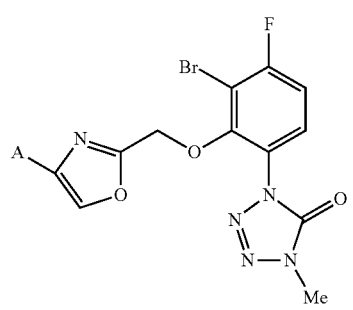
HB3054
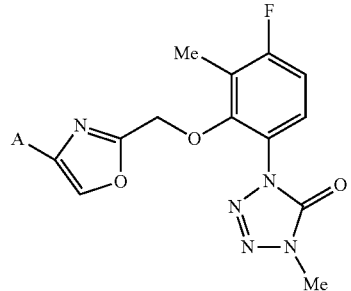
HB3055
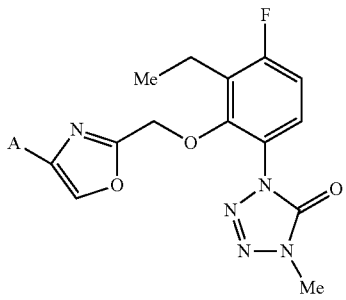
HB3056
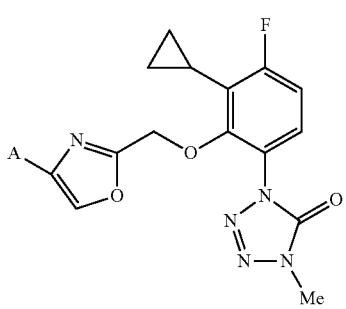
HB3057
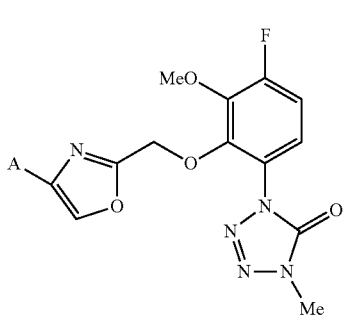
HB3058
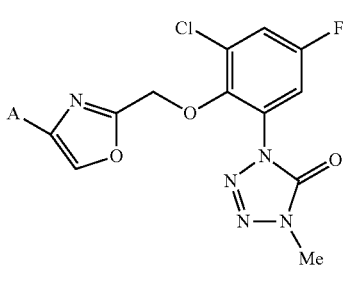
HB3059
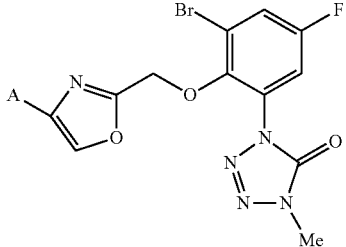

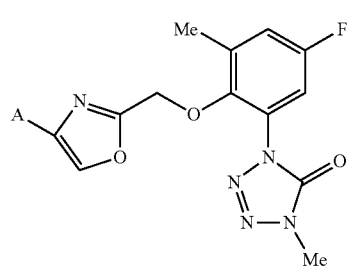 HB3060
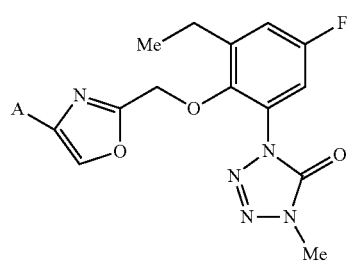 HB3061
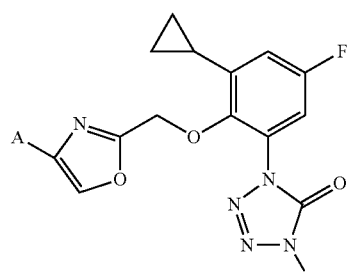 HB3062
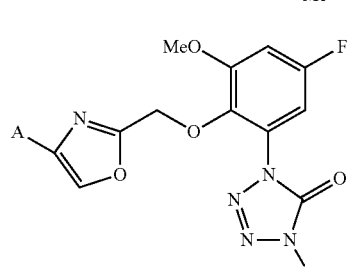 HB3063
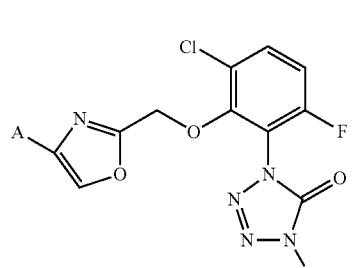 HB3064
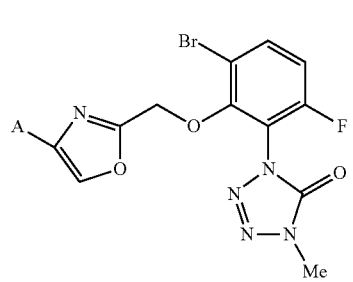 HB3065
HB3066
HB3067
HB3068
HB3069
HB4001
HB4002

-continued
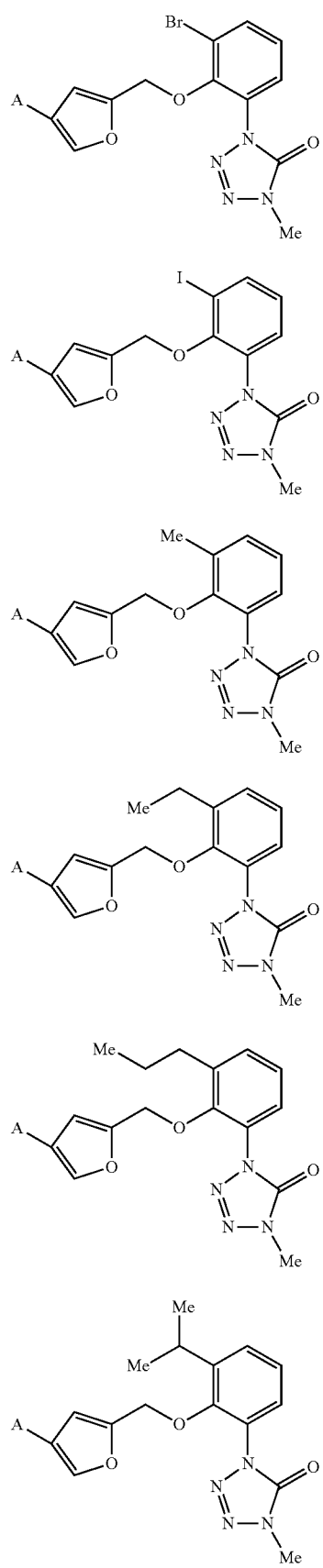
HB4003
HB4004
HB4005
HB4006
HB4007
HB4008
-continued
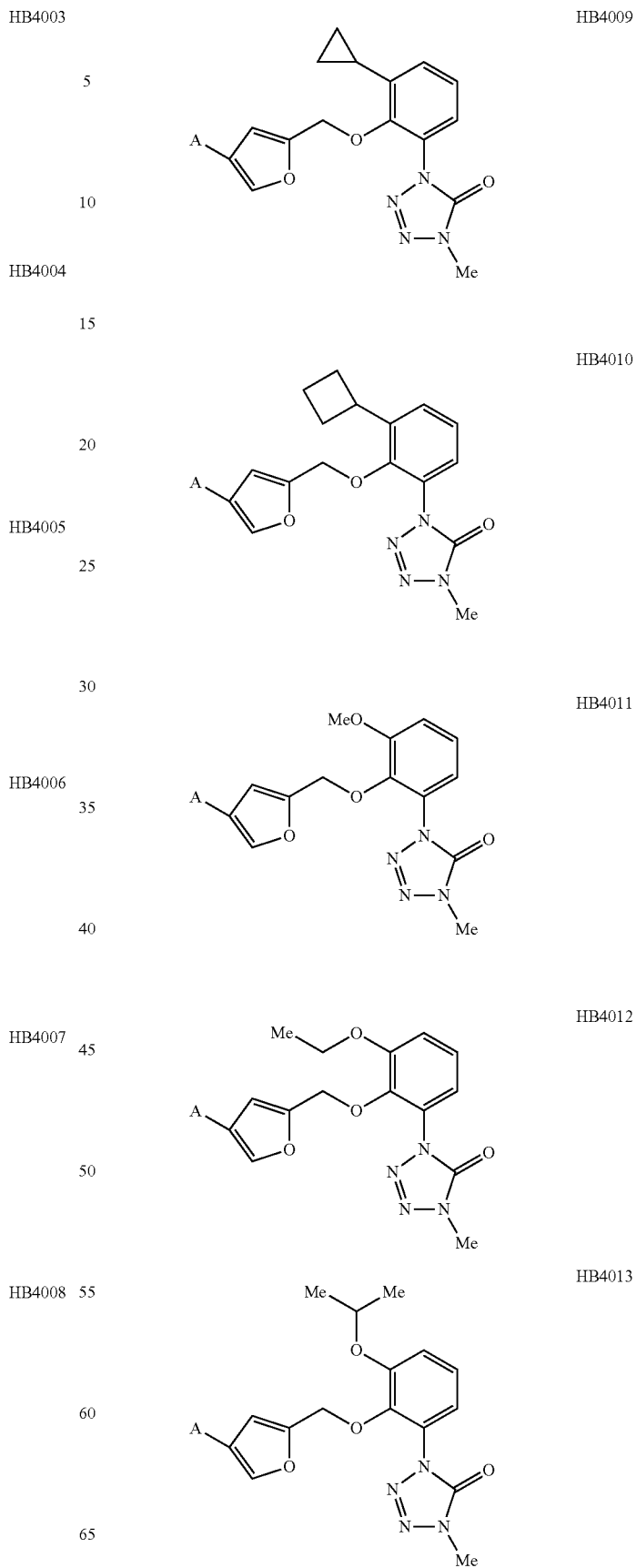
HB4009
HB4010
HB4011
HB4012
HB4013

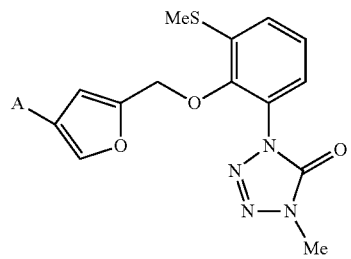
HB4014
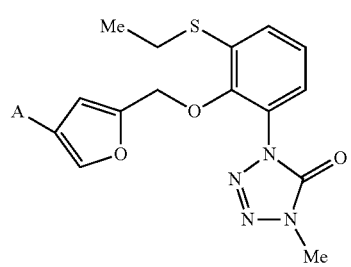
HB4015
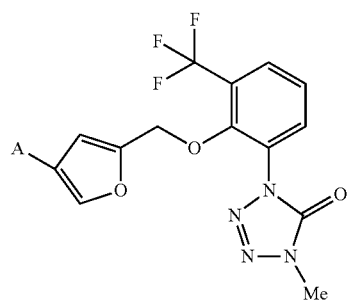
HB4016
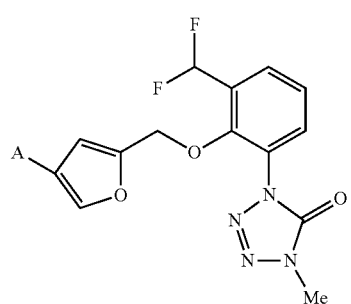
HB4017
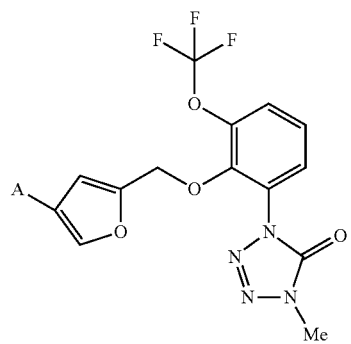
HB4018
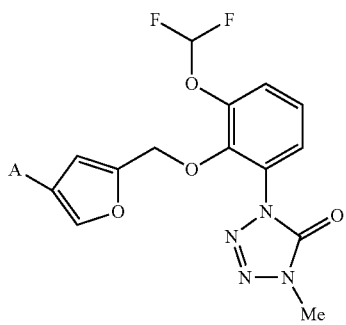
HB4019
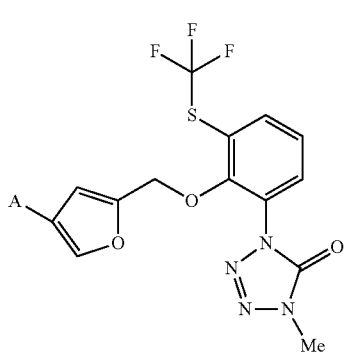
HB4020
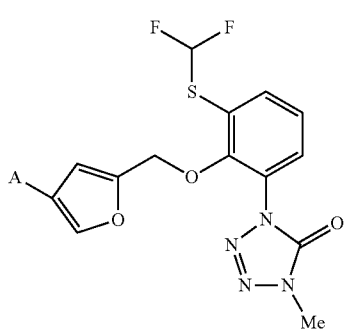
HB4021
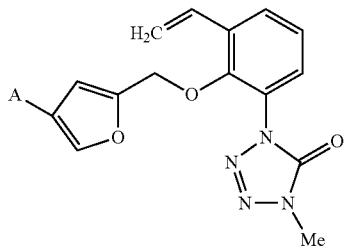
HB4022
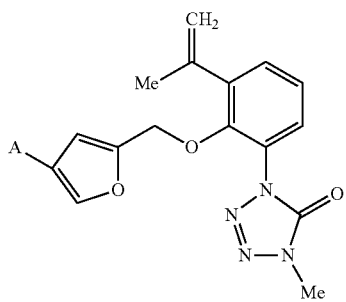
HB4023

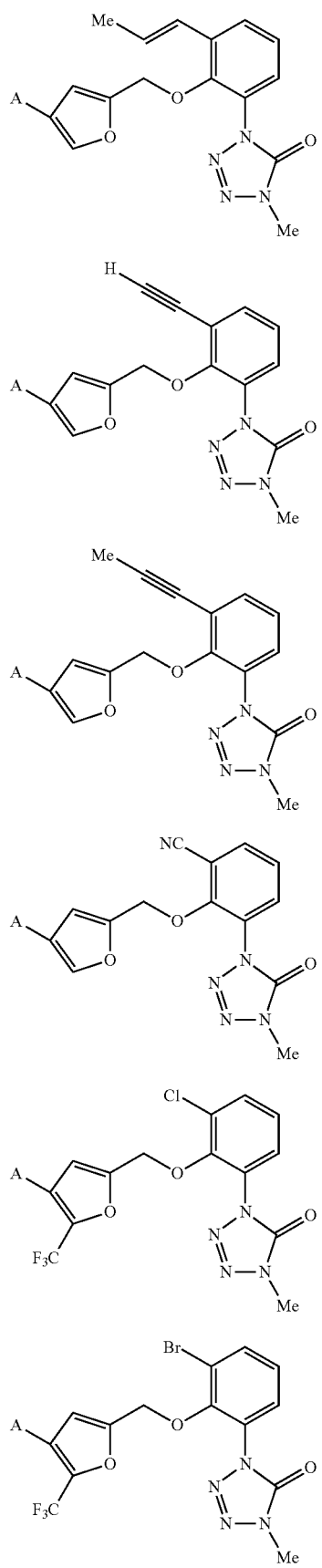
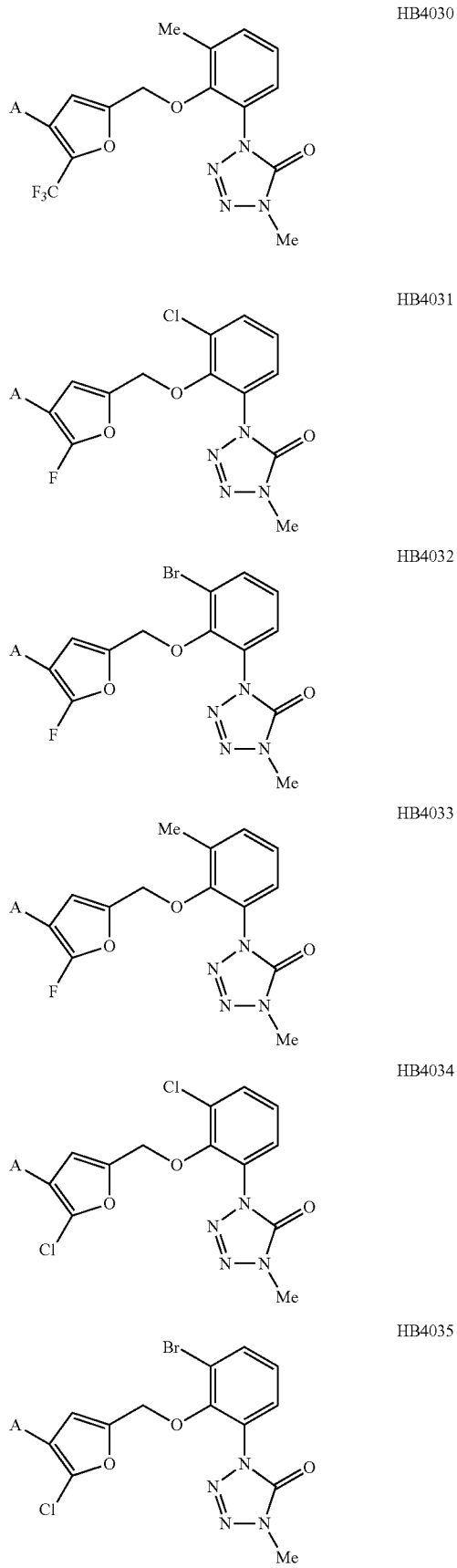

HB4036 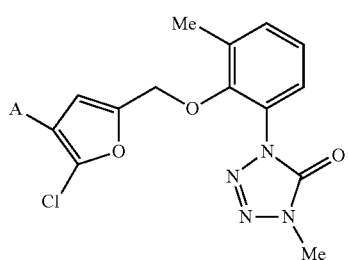
HB4037 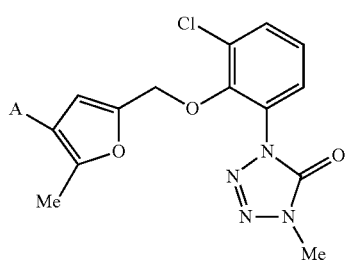
HB4038 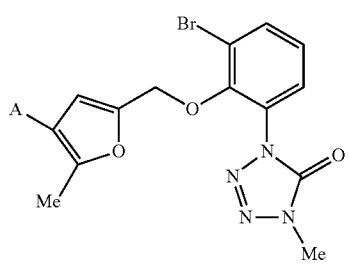
HB4039 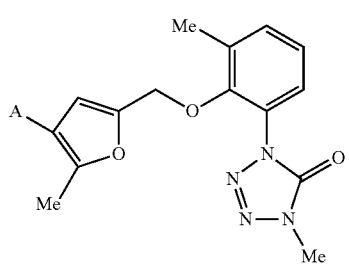
HB4040 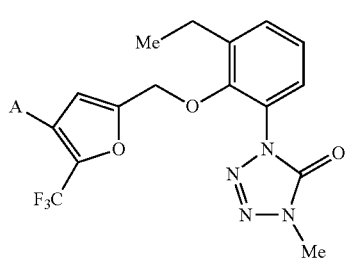
HB4041 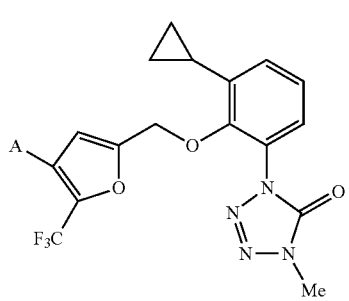
HB4042 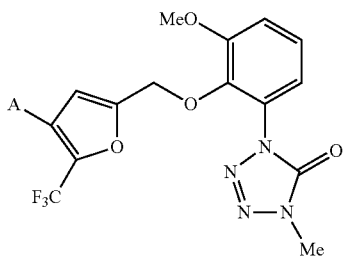
HB4043 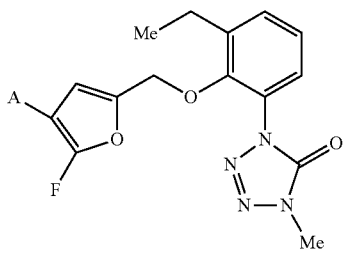
HB4044 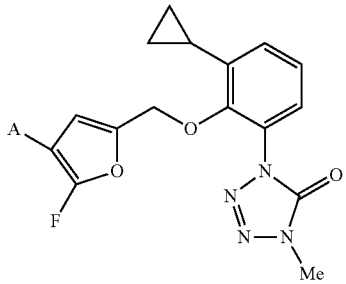
HB4045 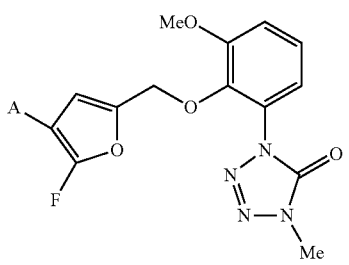
HB4046 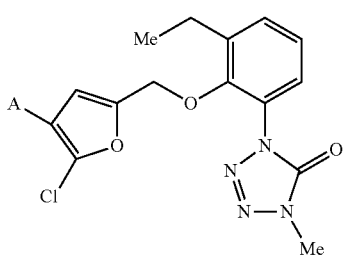
HB4047 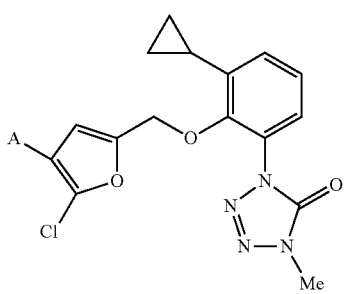

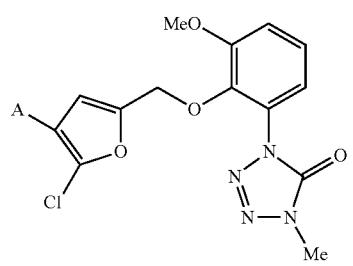 HB4048
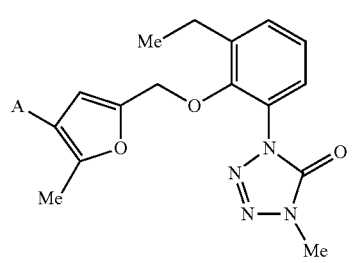 HB4049
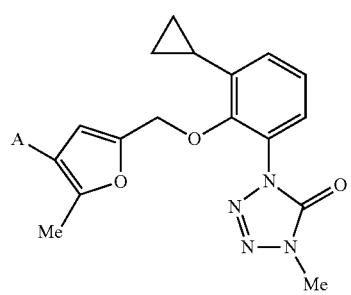 HB4050
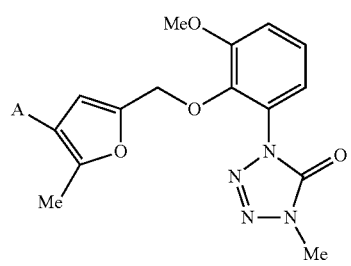 HB4051
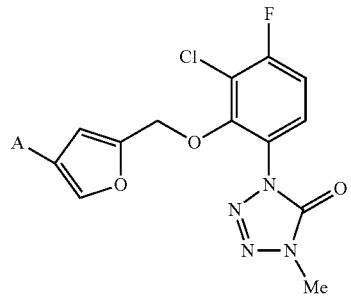 HB4052
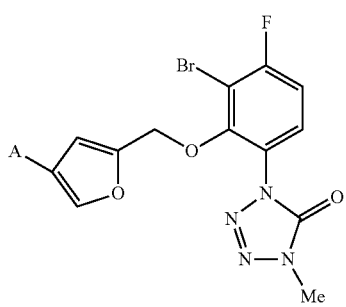 HB4053
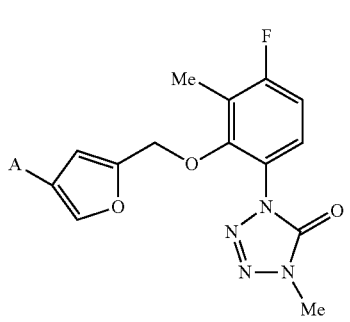 HB4054
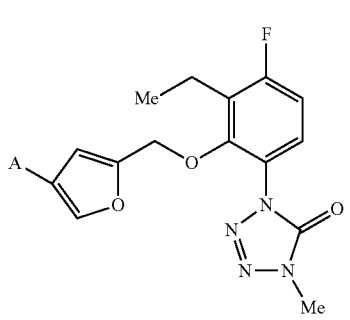 HB4055
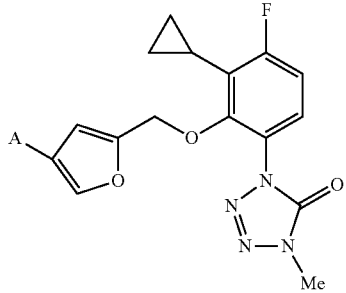 HB4056
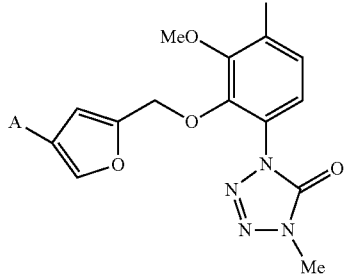 HB4057

-continued
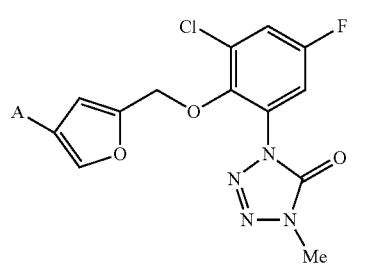 HB4058
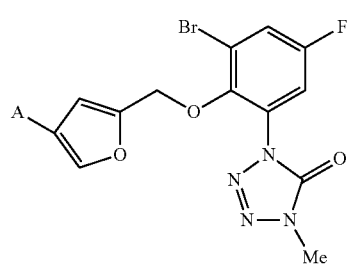 HB4059
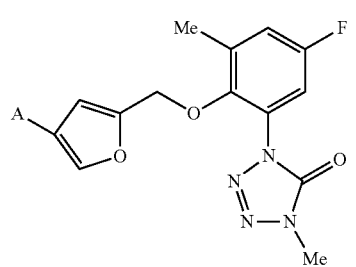 HB4060
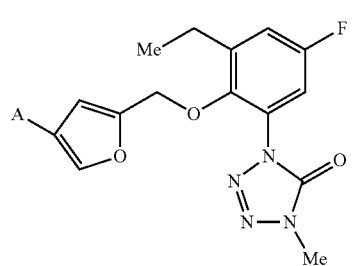 HB4061
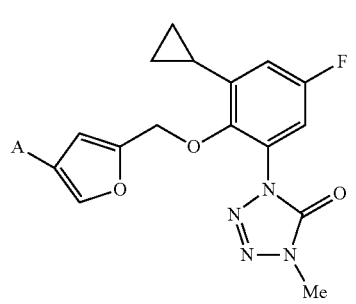 HB4062
 HB4063
-continued
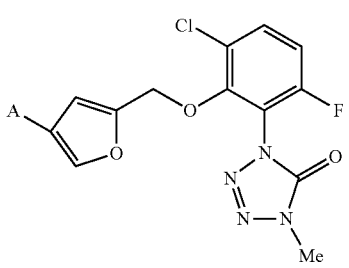 HB4064
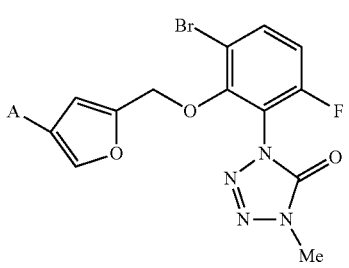 HB4065
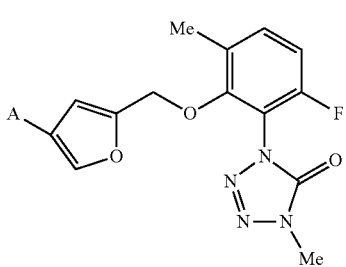 HB4066
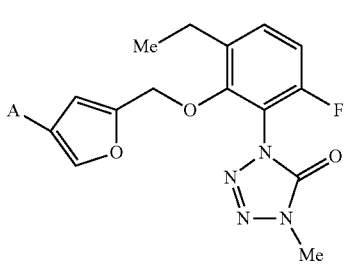 HB4067
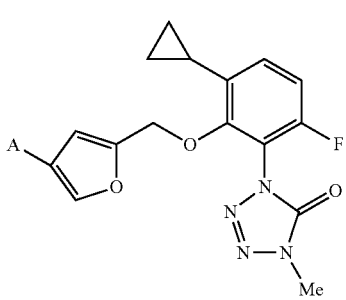 HB4068
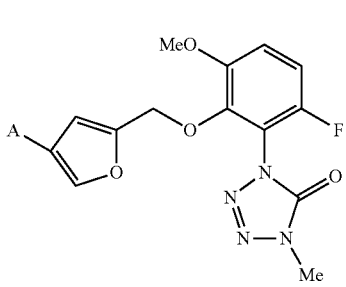 HB4069

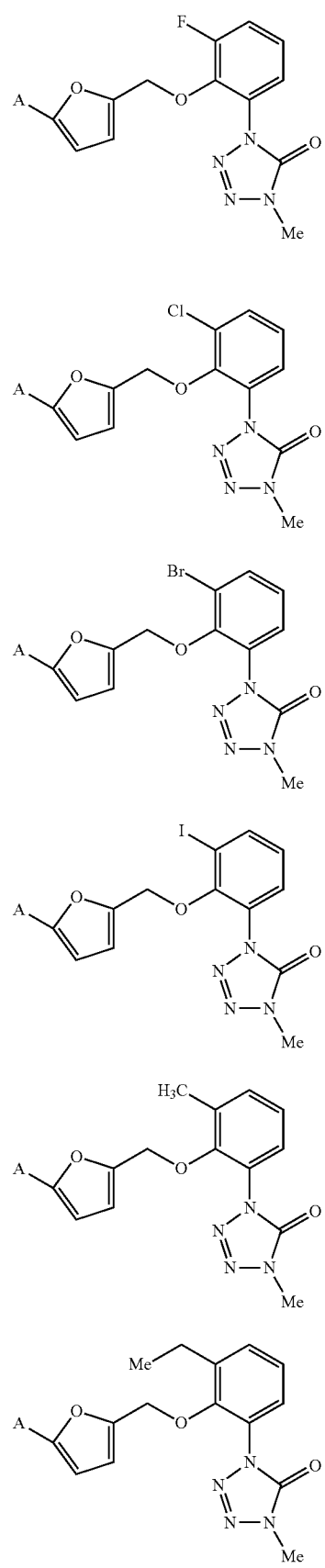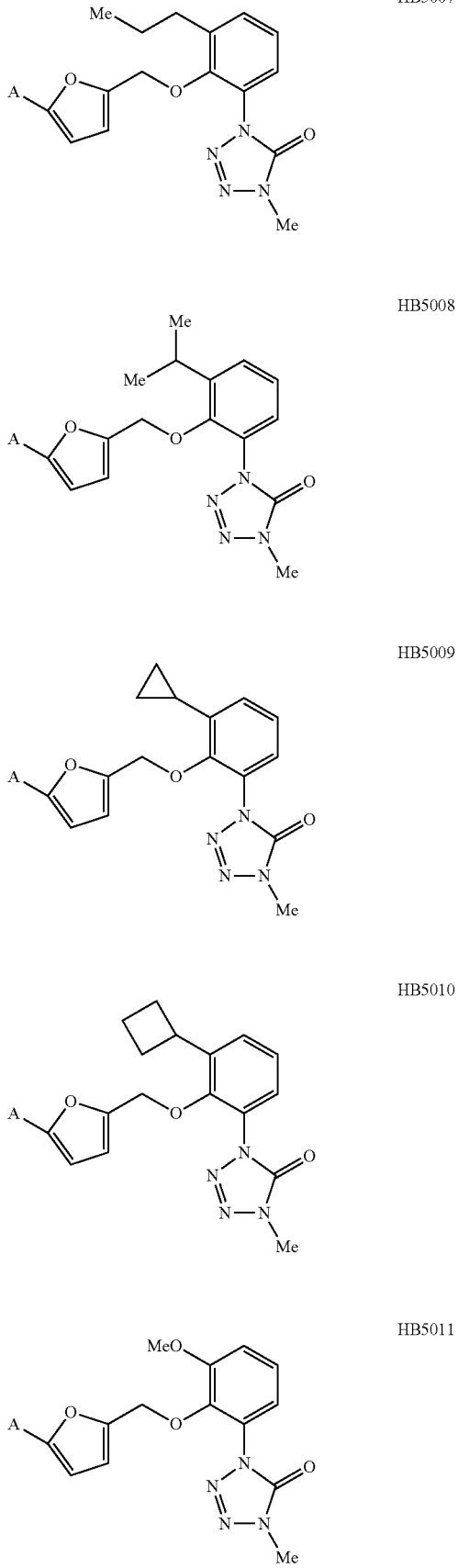

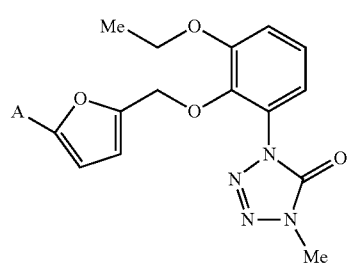 HB5012
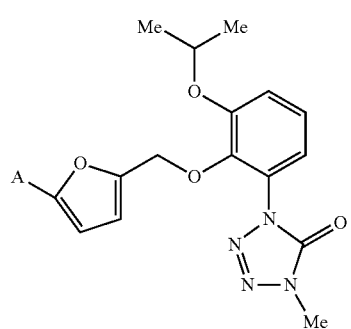 HB5013
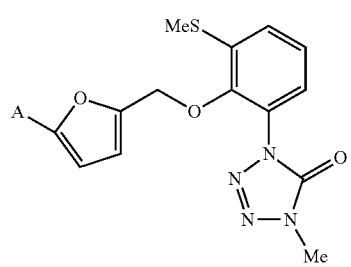 HB5014
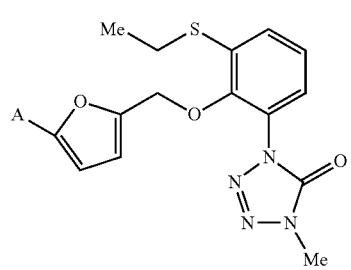 HB5015
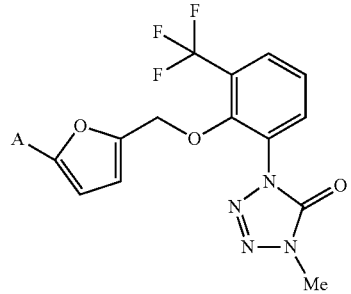 HB5016
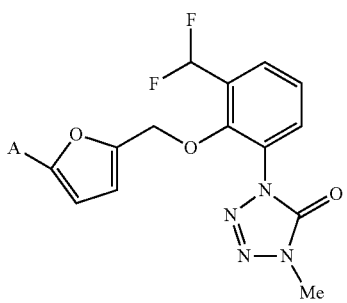 HB5017
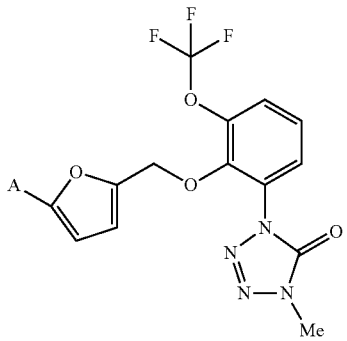 HB5018
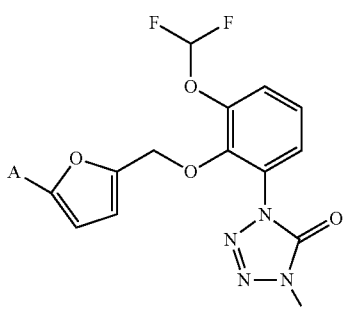 HB5019
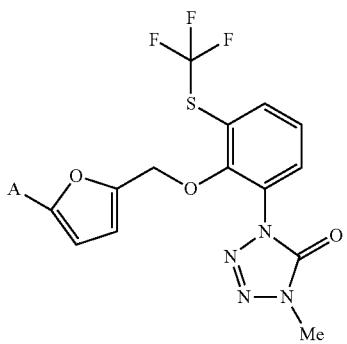 HB5020
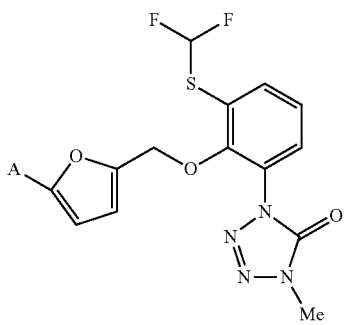 HB5021

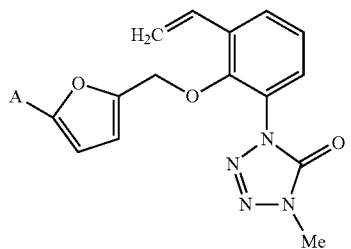 HB5022
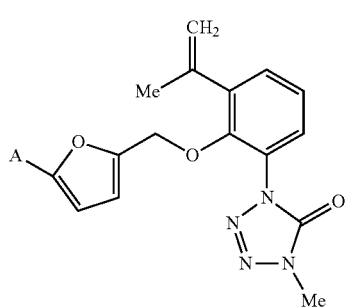 HB5023
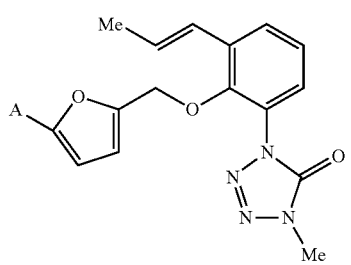 HB5024
 HB5025
 HB5026
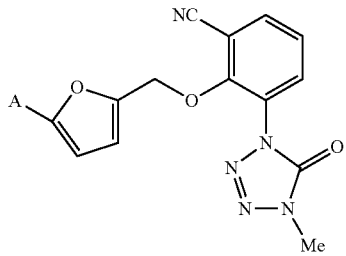 HB5027
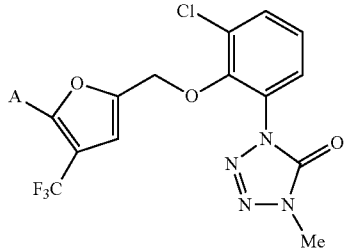 HB5028
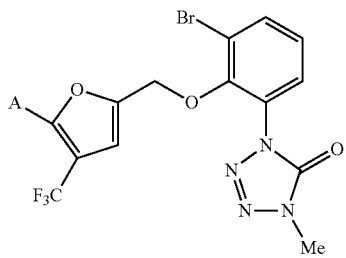 HB5029
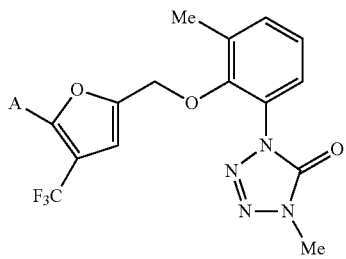 HB5030
 HB5031
 HB5032

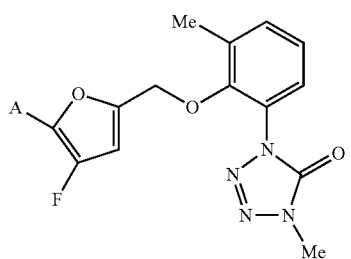
HB5033
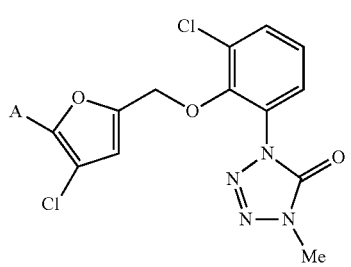
HB5034
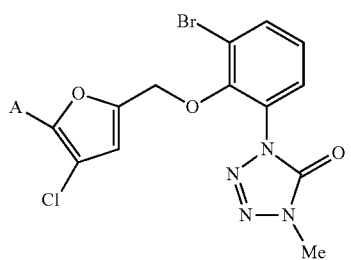
HB5035
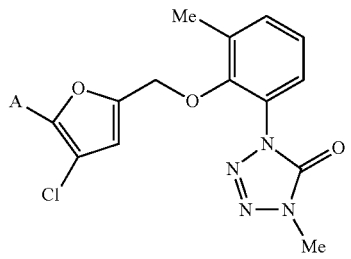
HB5036
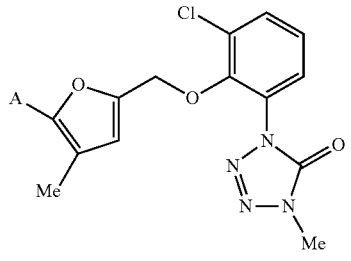
HB5037
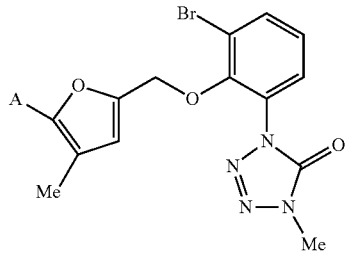
HB5038
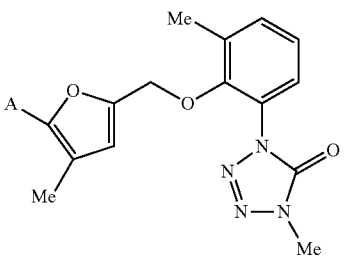
HB5039
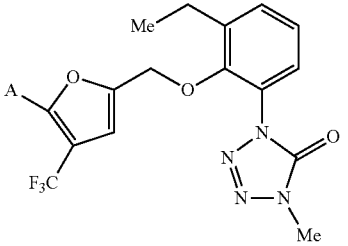
HB5040
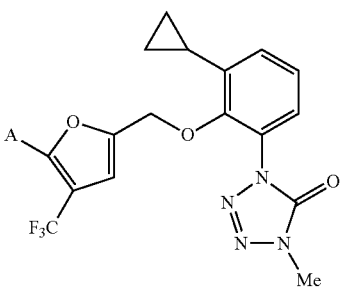
HB5041
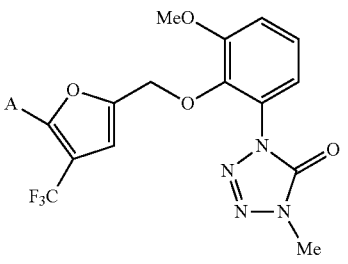
HB5042
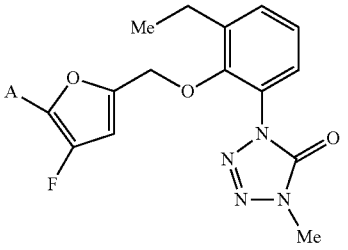
HB5043
HB5044

HB5045 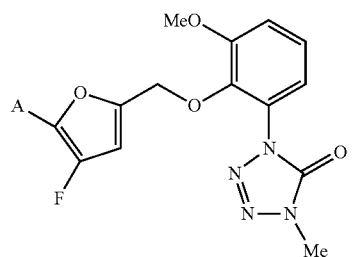
HB5046 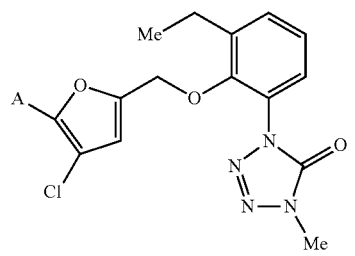
HB5047 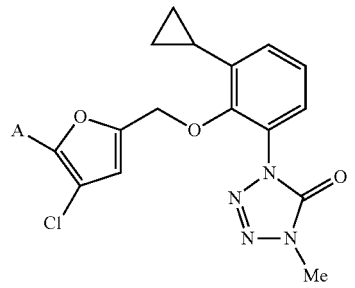
HB5048 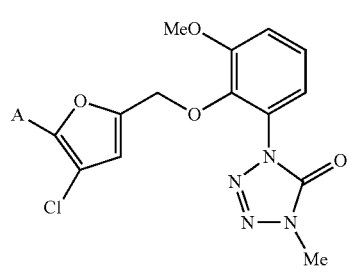
HB5049 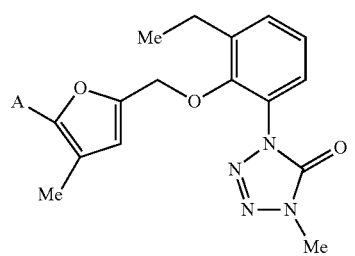
HB5050 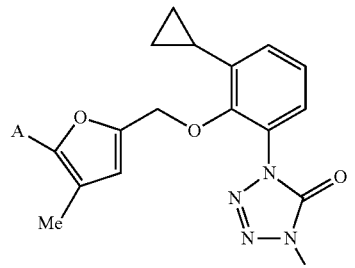
HB5051 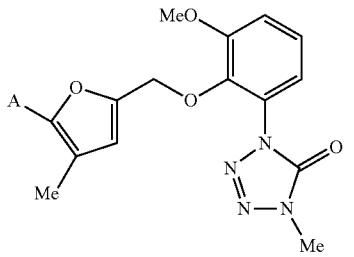
HB5052 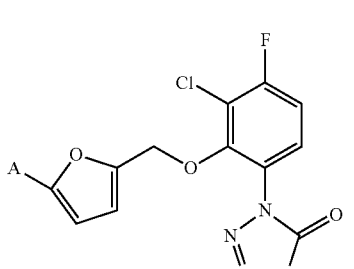
HB5053 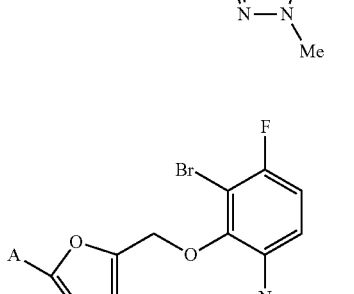
HB5054 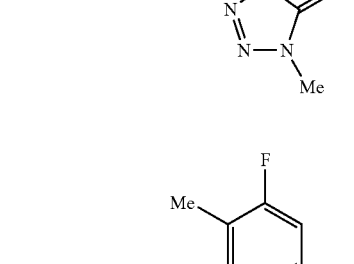
HB5055 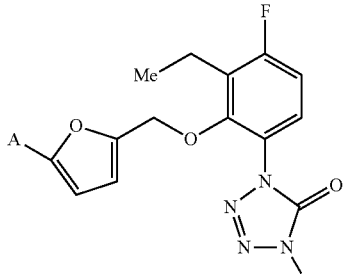

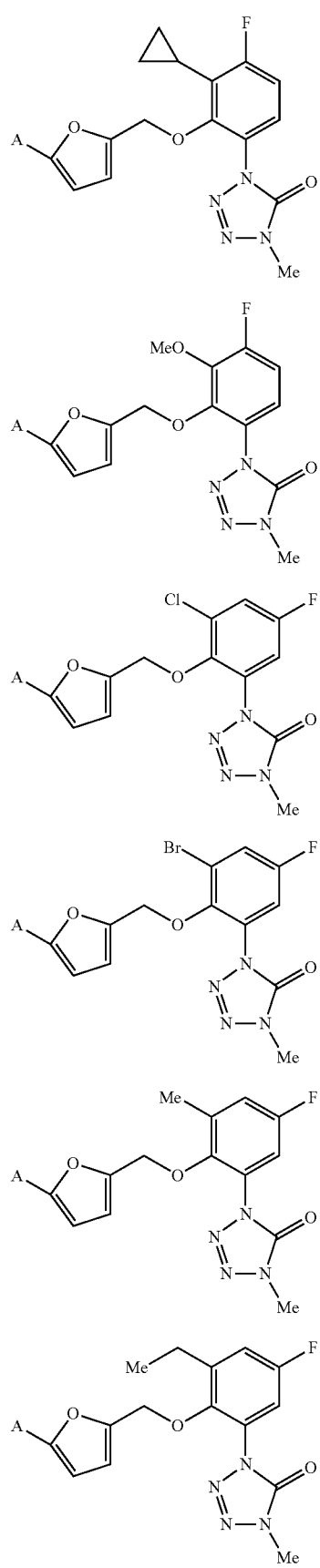
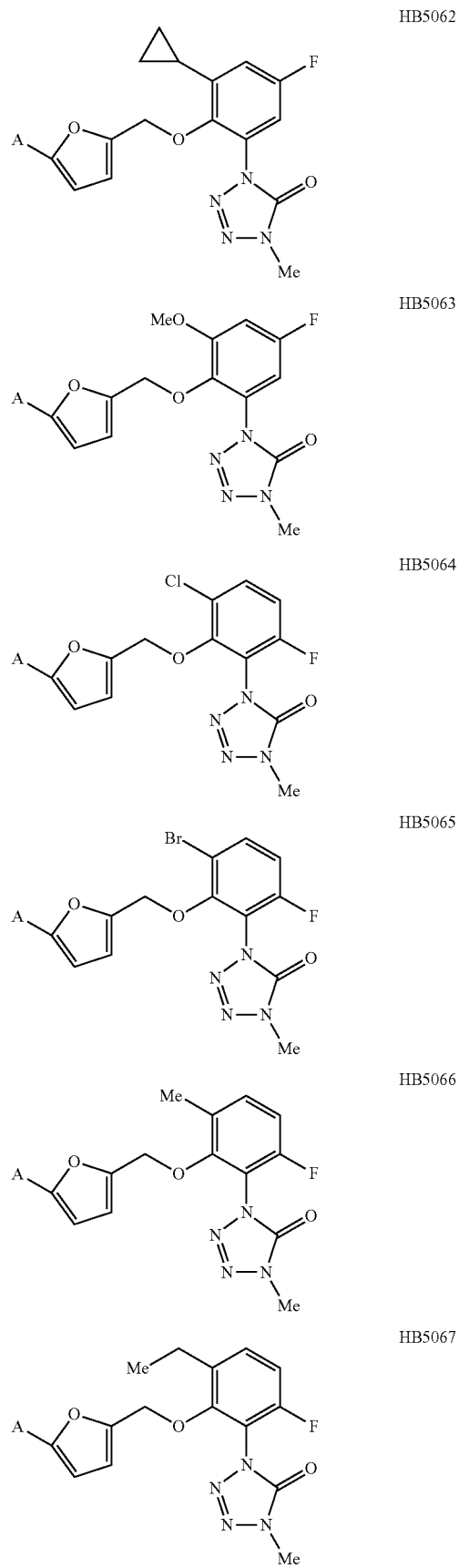

| | |
|---|---|
| 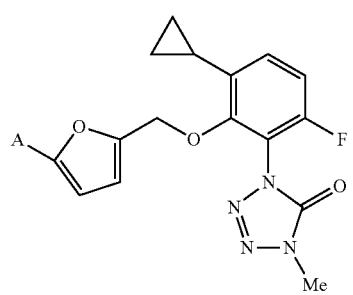 HB5068 | 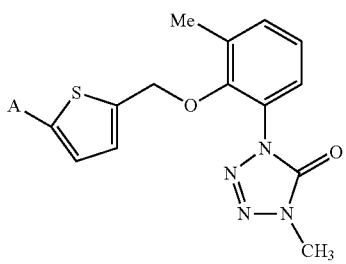 HB6005 |
| 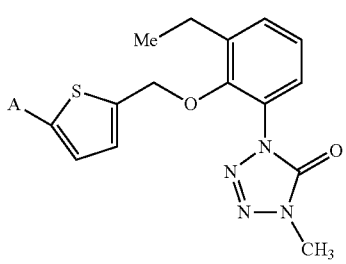 HB5069 | 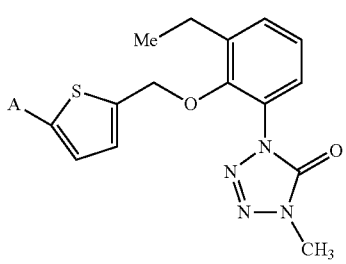 HB6006 |
| HB6001 | |
| | 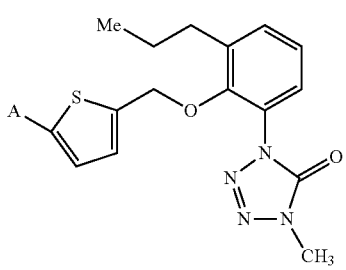 HB6007 |
| HB6002 | |
| | 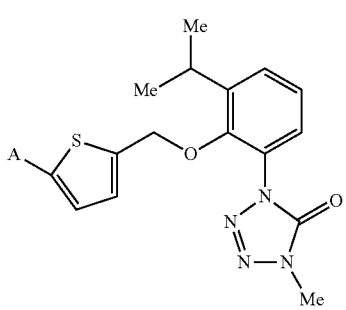 HB6008 |
| HB6003 | |
| HB6004 | 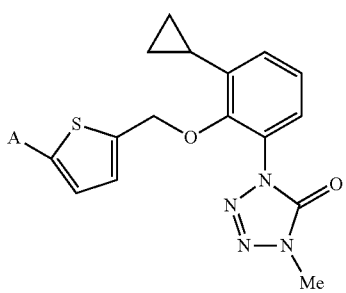 HB6009 |

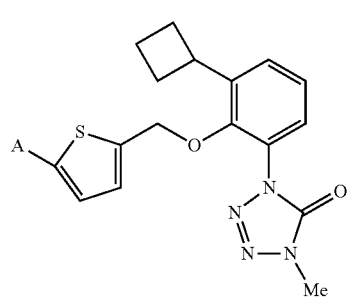
HB6010
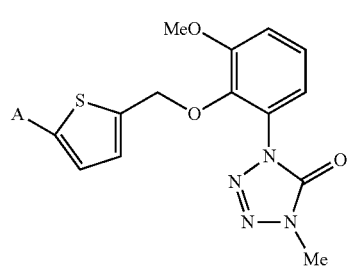
HB6011
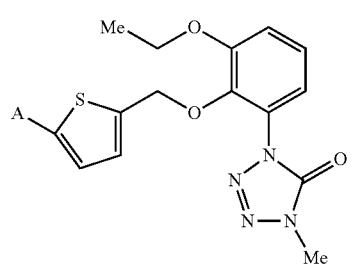
HB6012
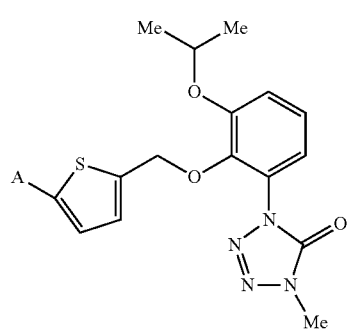
HB6013
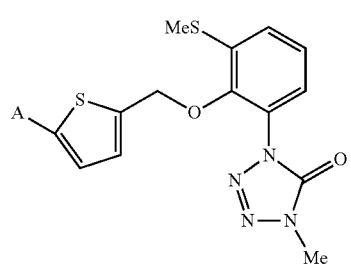
HB6014
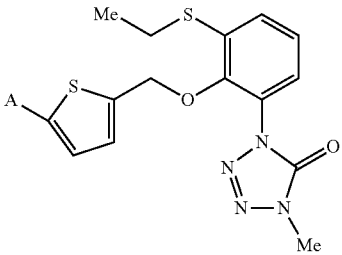
HB6015
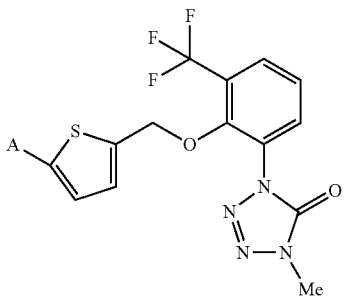
HB6016
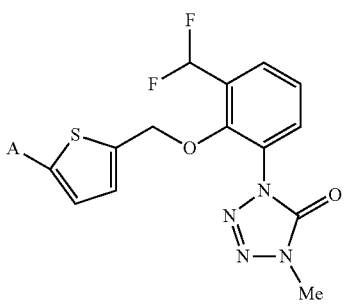
HB6017
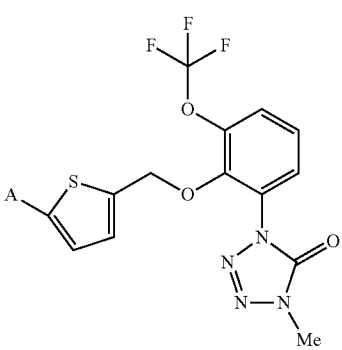
HB6018
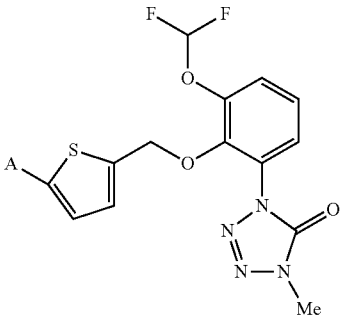
HB6019

-continued
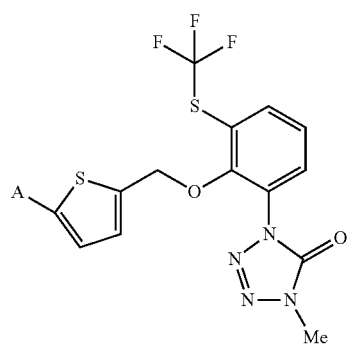
HB6020
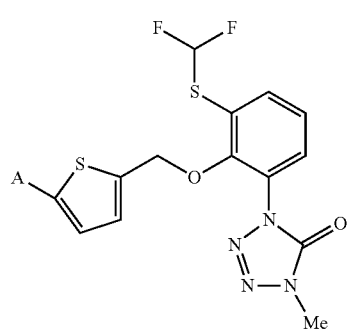
HB6021
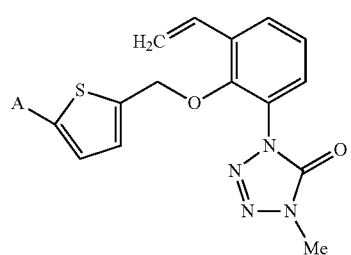
HB6022
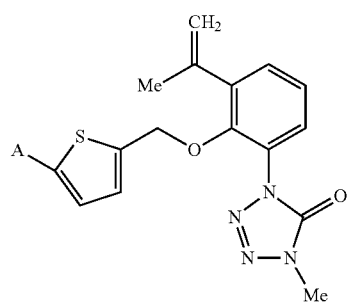
HB6023
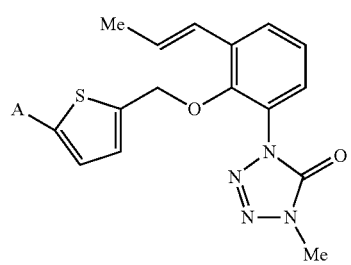
HB6024
-continued
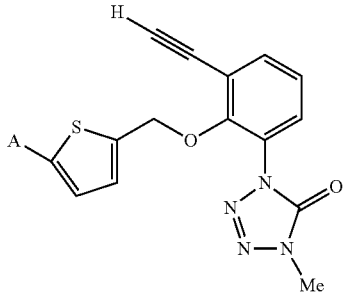
HB6025
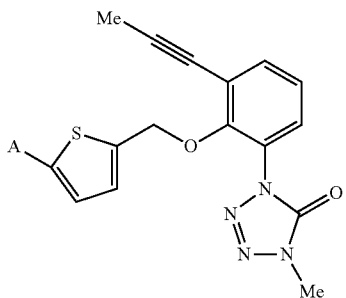
HB6026
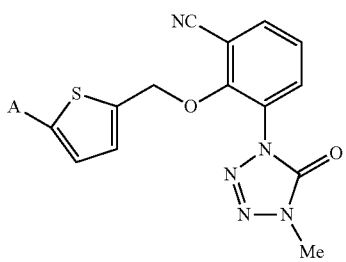
HB6027
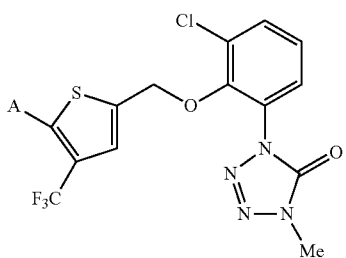
HB6028
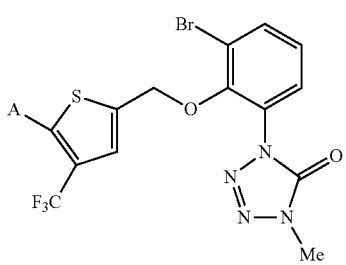
HB6029
HB6030

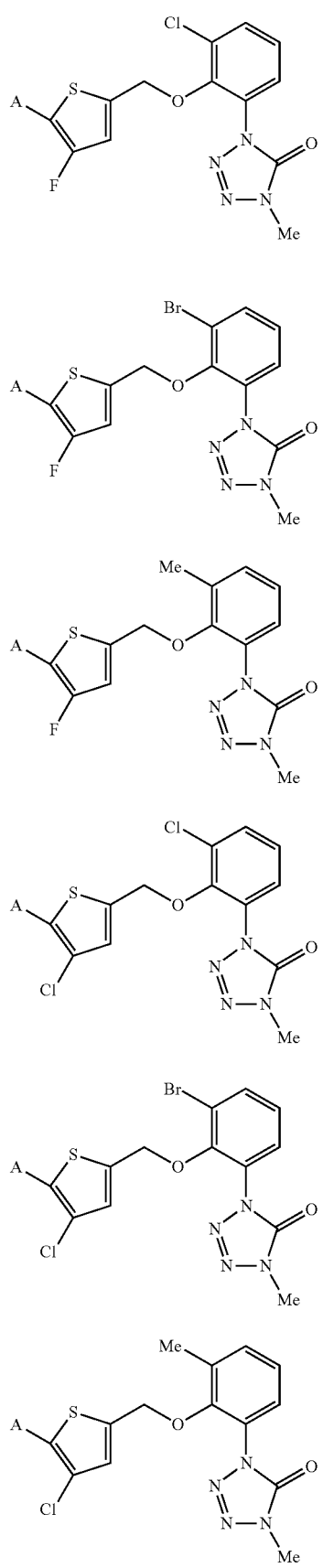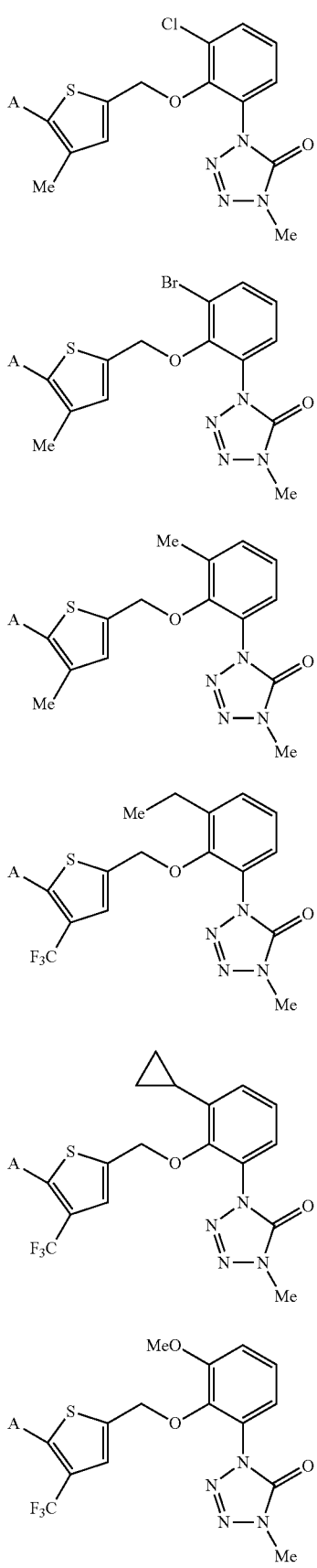

-continued
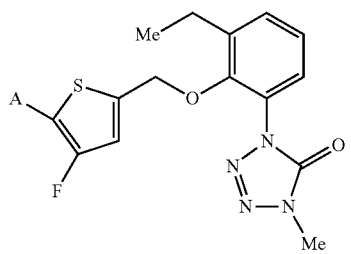 HB6043
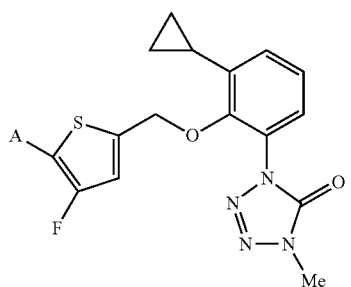 HB6044
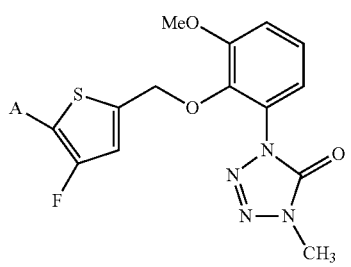 HB6045
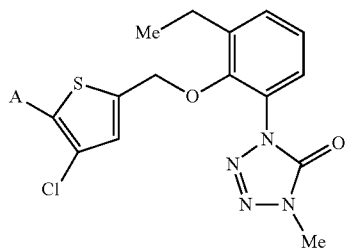 HB6046
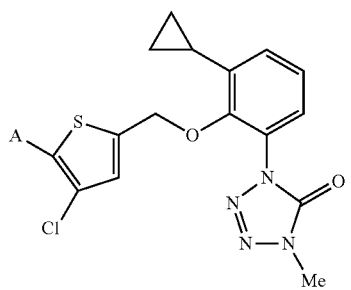 HB6047
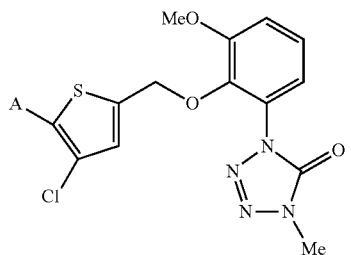 HB6048
-continued
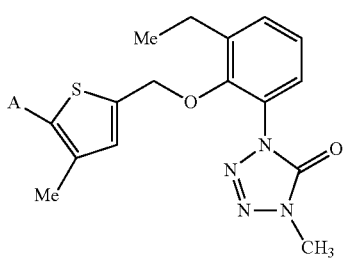 HB6049
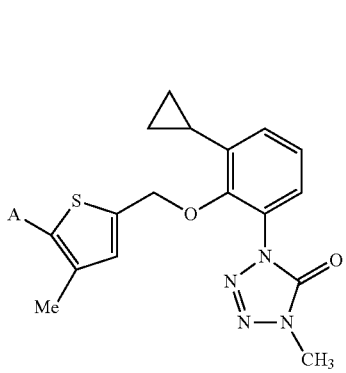 HB6050
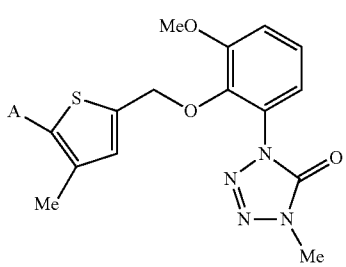 HB6051
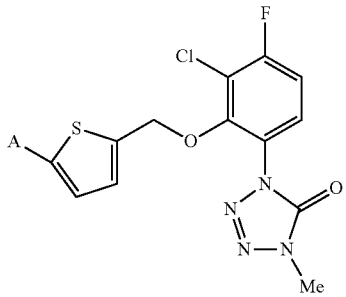 HB6052
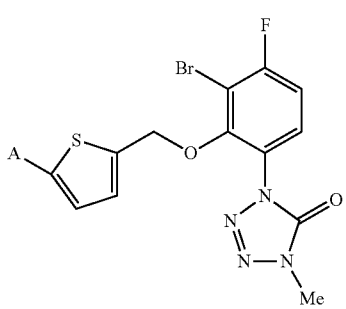 HB6053

-continued
HB6054
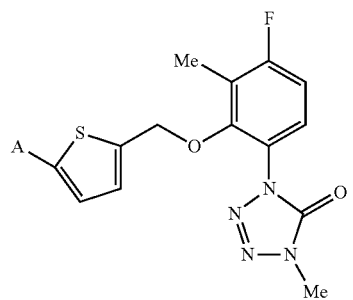
HB6055
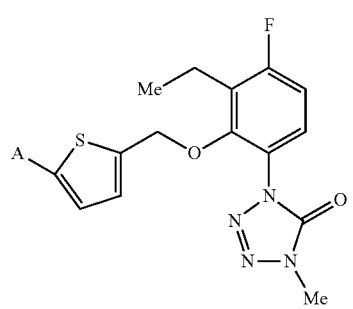
HB6056
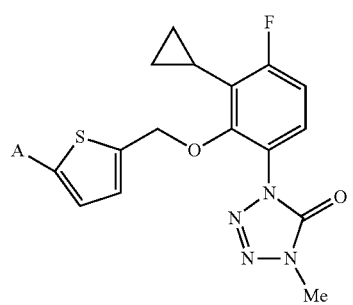
HB6057
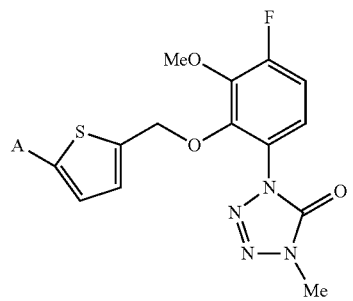
HB6058
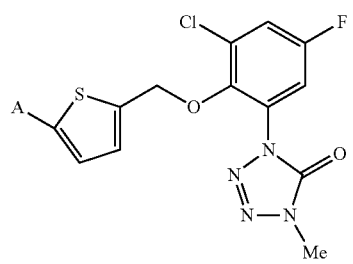
-continued
HB6059
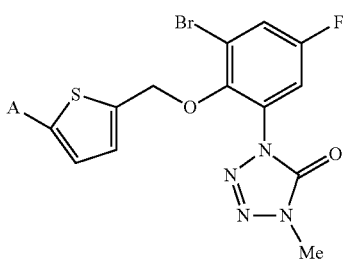
HB6060
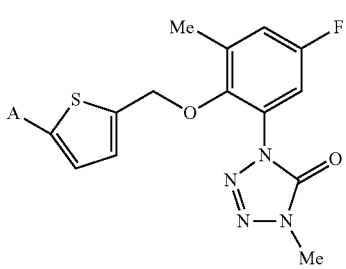
HB6061
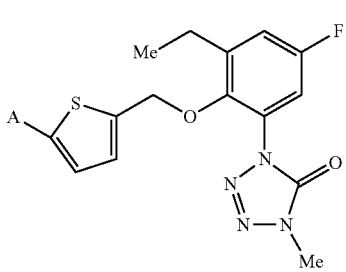
HB6062
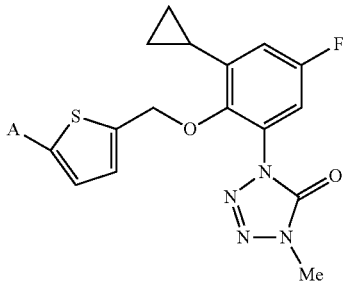
HB6063
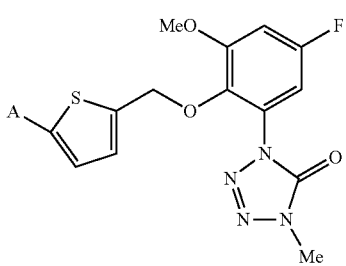
HB6064

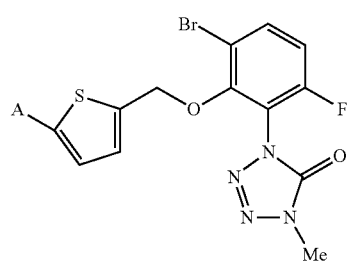
HB6065

HB6066
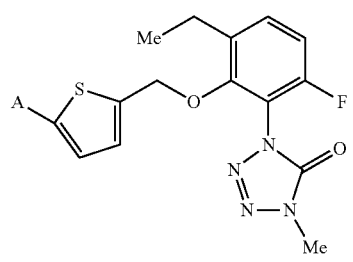
HB6067
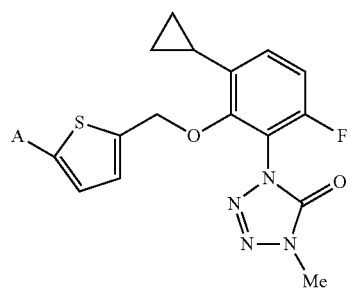
HB6068
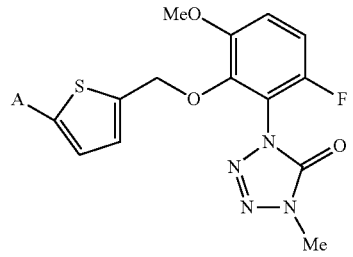
HB6069
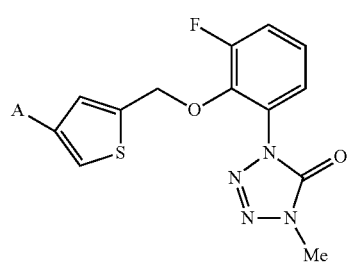
HB7001
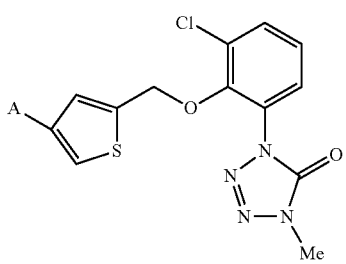
HB7002
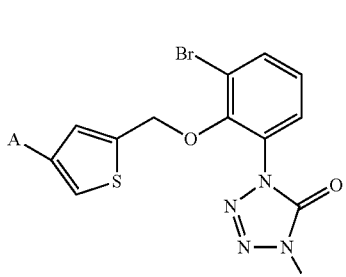
HB7003
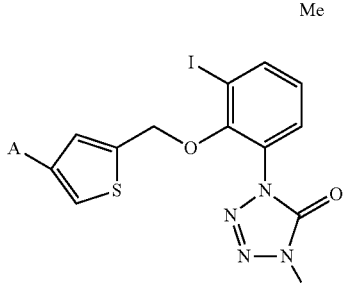
HB7004
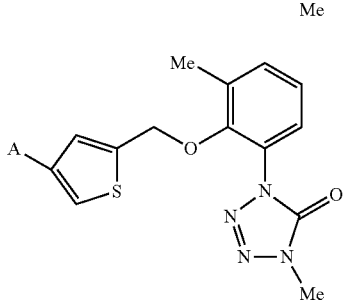
HB7005
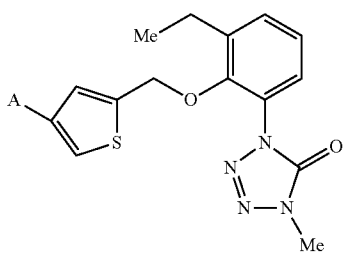
HB7006
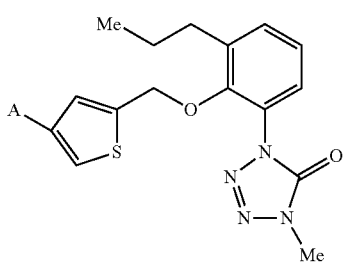
HB7007

HB7008 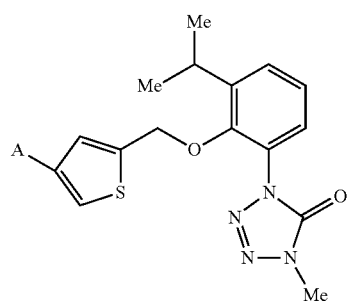
HB7009 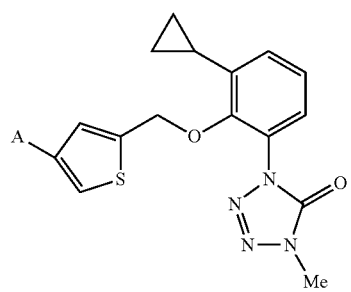
HB7010 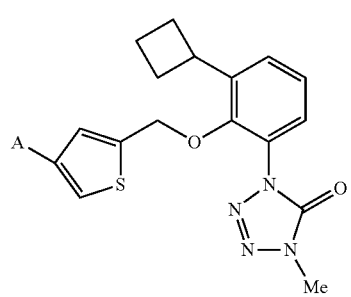
HB7011 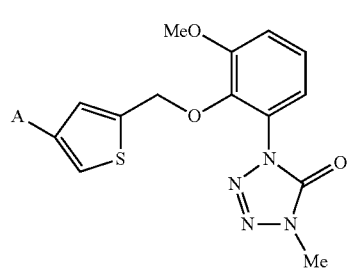
HB7012 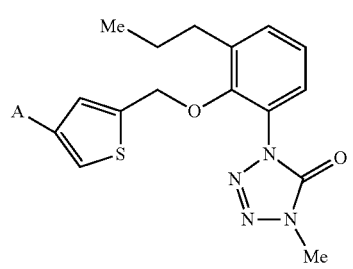
HB7013 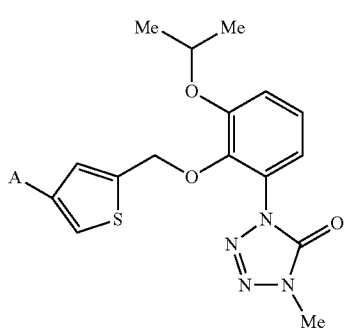
HB7014 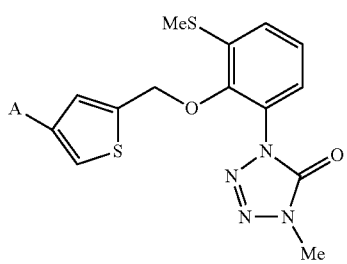
HB7015 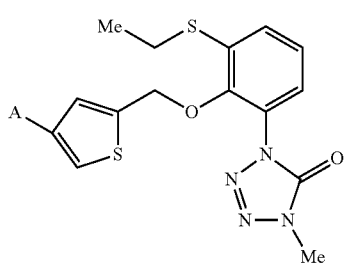
HB7016 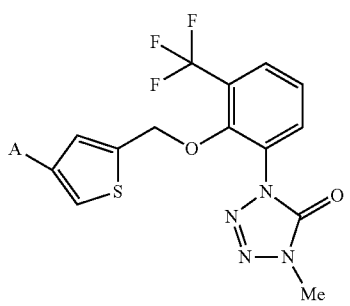
HB7017 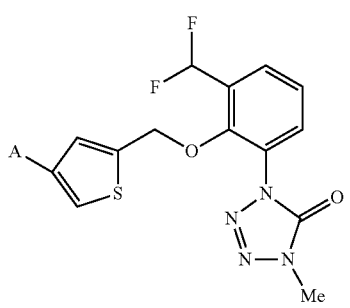

HB7018 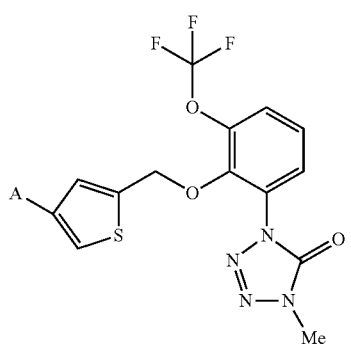
HB7019 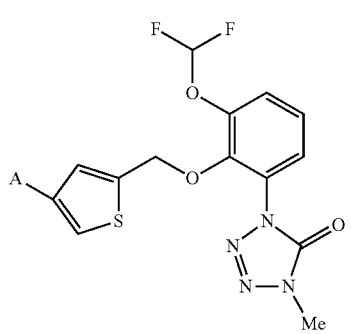
HB7020 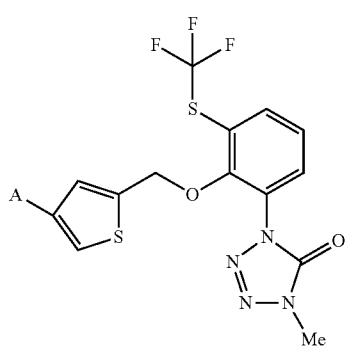
HB7021 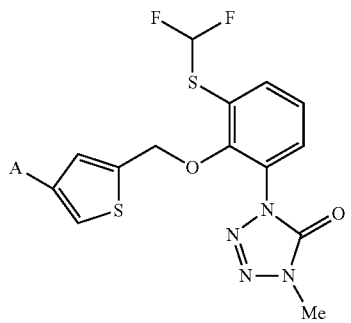
HB7022 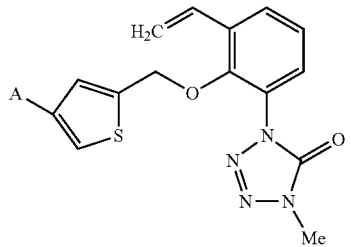
HB7023 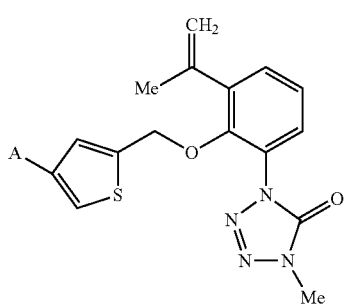
HB7024 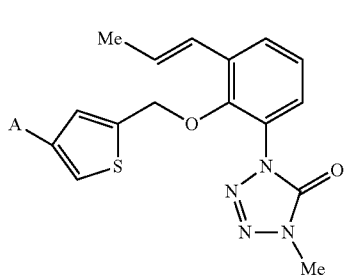
HB7025 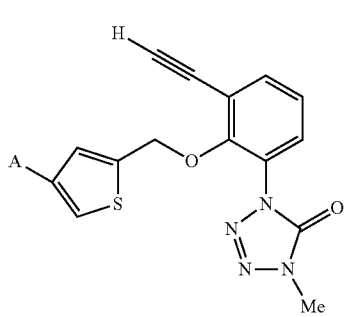
HB7026 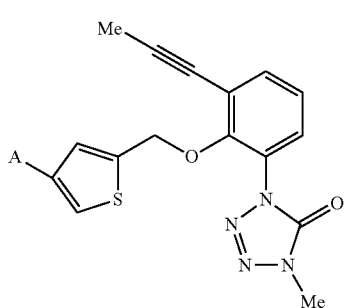
HB7027

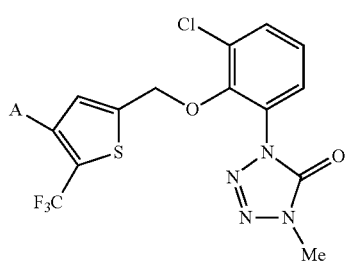 HB7028
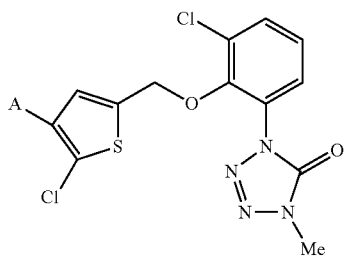 HB7034
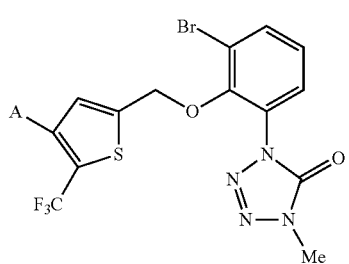 HB7029
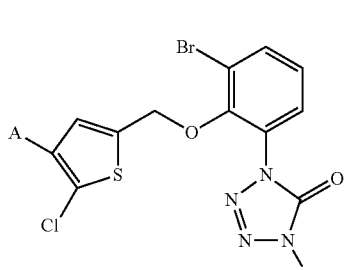 HB7035
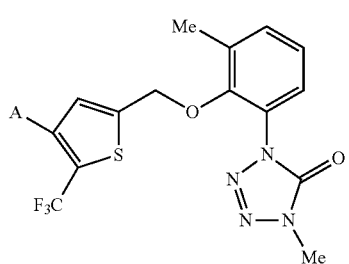 HB7030
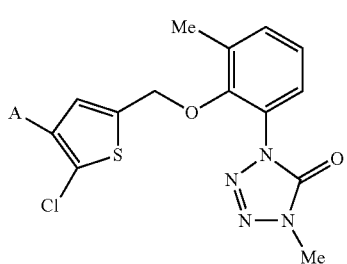 HB7036
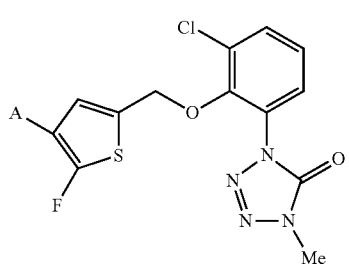 HB7031
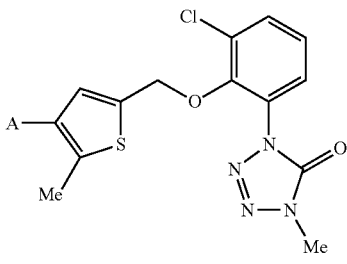 HB7037
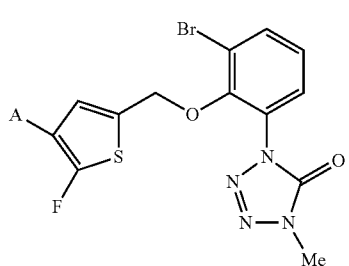 HB7032
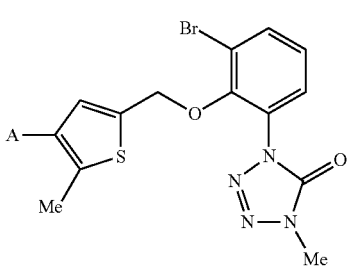 HB7038
HB7033

173
-continued
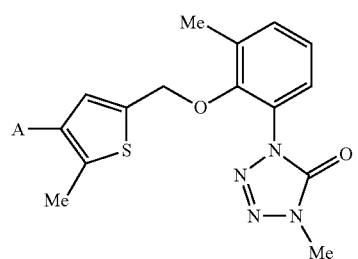
HB7039
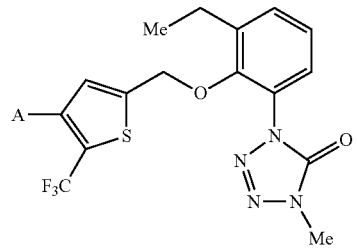
HB7040
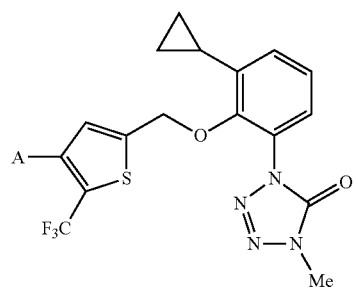
HB7041
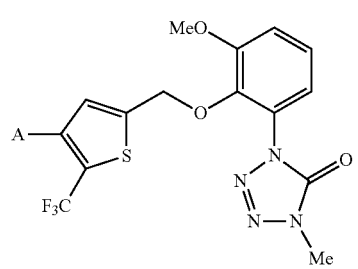
HB7042
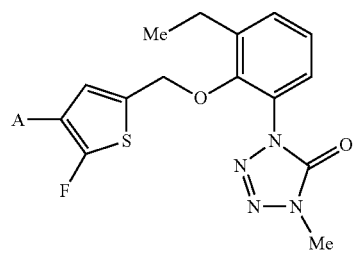
HB7043
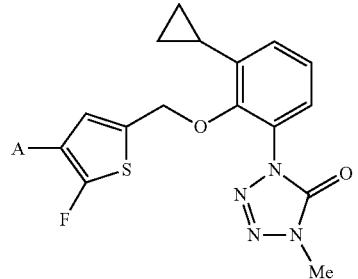
HB7044
174
-continued
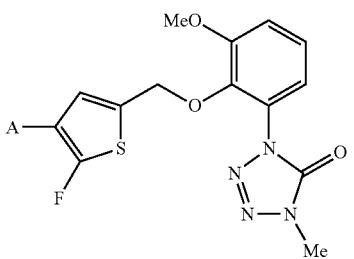
HB7045
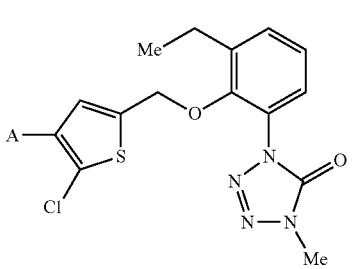
HB7046
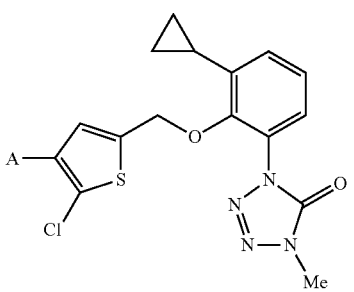
HB7047
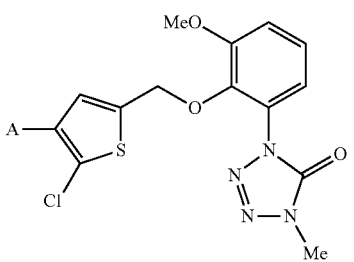
HB7048
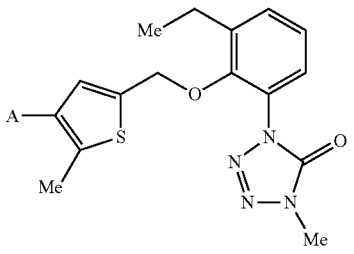
HB7049
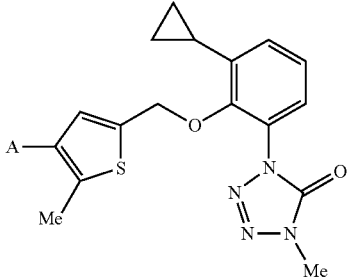
HB7050

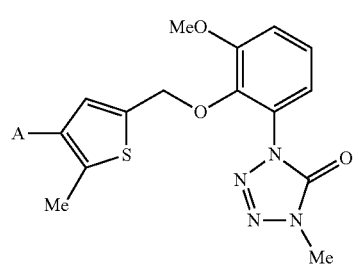
HB7051
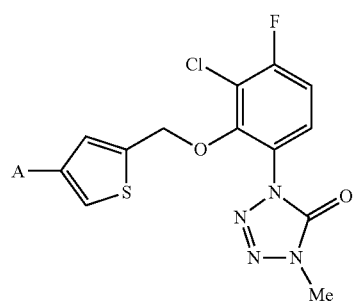
HB7052
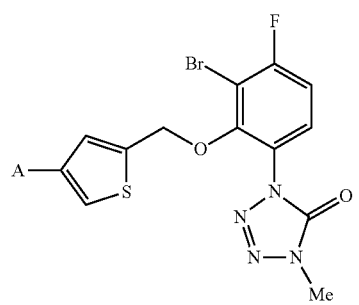
HB7053
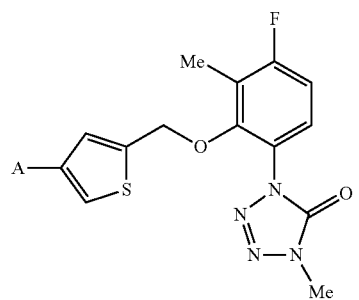
HB7054
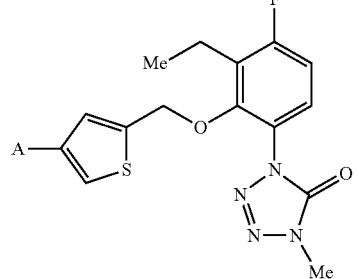
HB7055
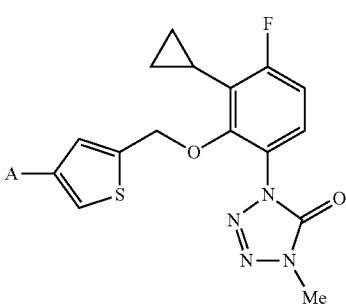
HB7056
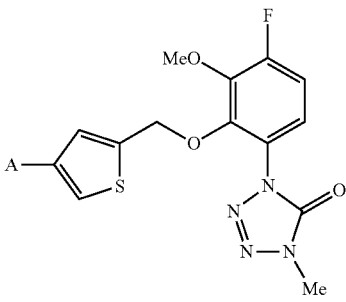
HB7057
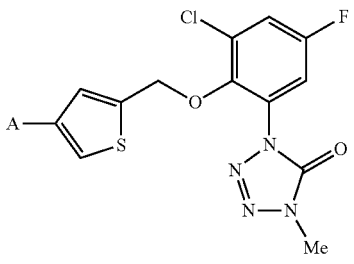
HB7058
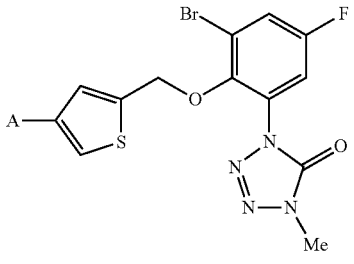
HB7059
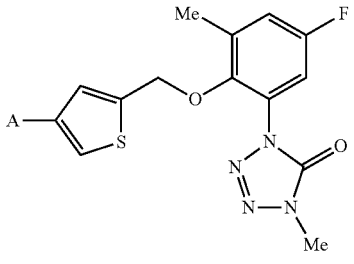
HB7060
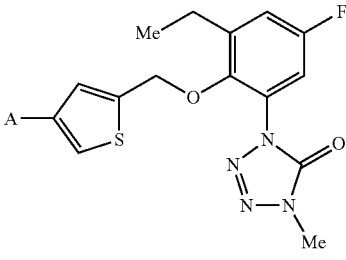
HB7061

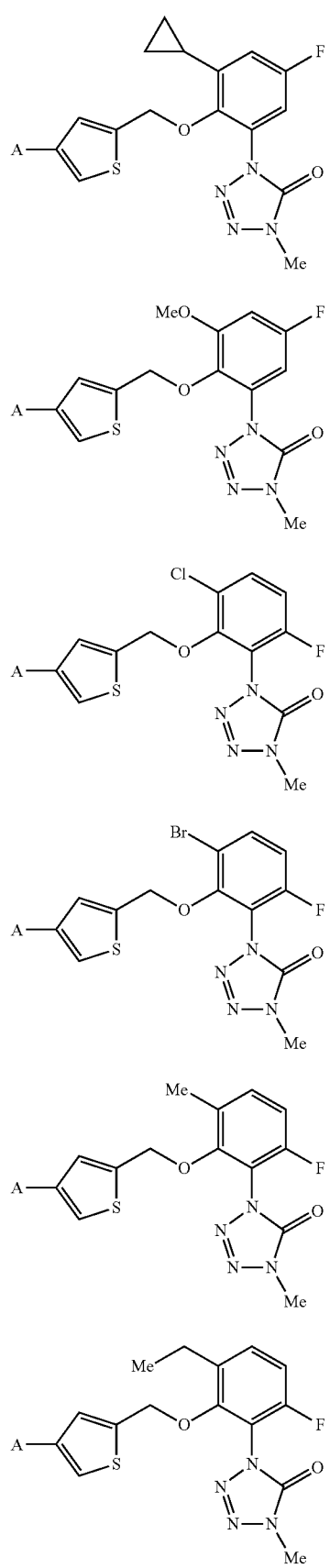
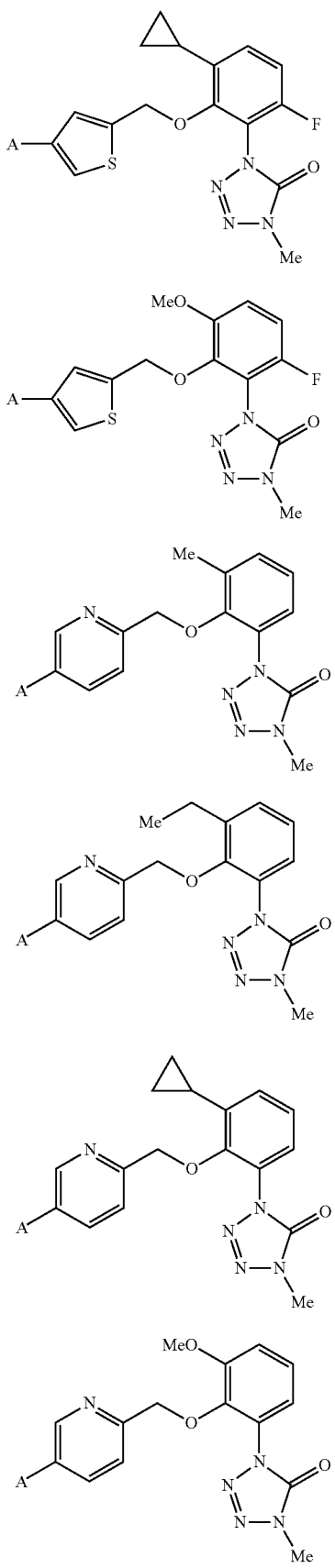

PE11
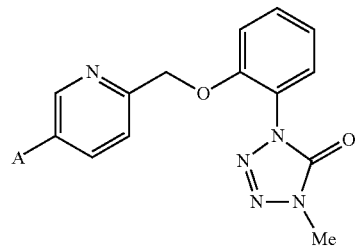
PF11
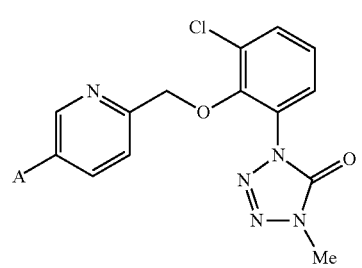
PG11
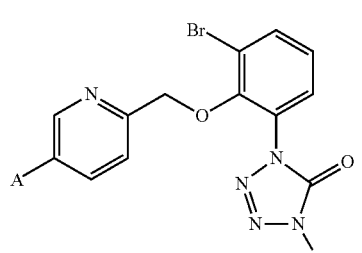
PH11
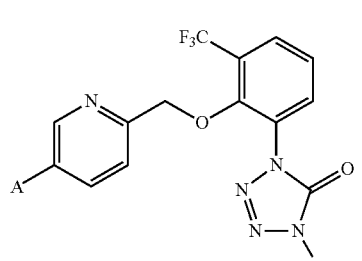
PA12
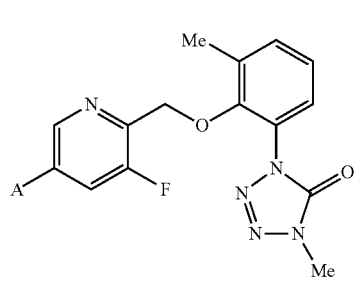
PB12

PC12
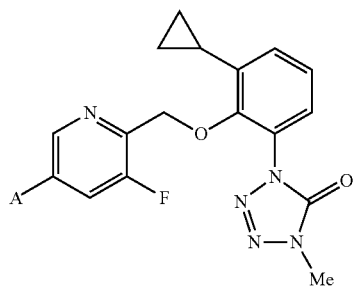
PD12
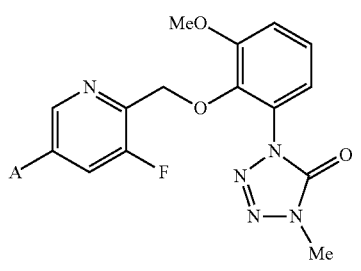
PE12
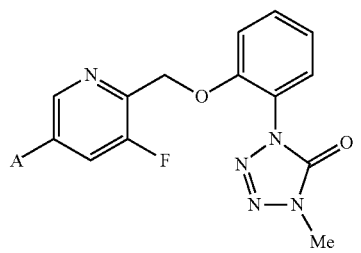
PF12
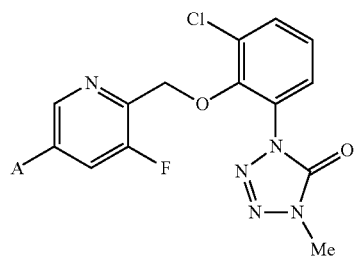
PG12
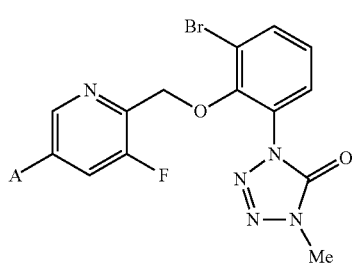
PH12
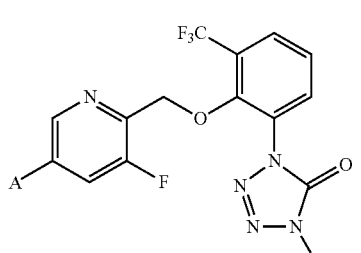

PA13

PB13

PC13

PD13

PE13

PF13

PG13

PH13

PA14

PB14

PC14

PD14

PE14
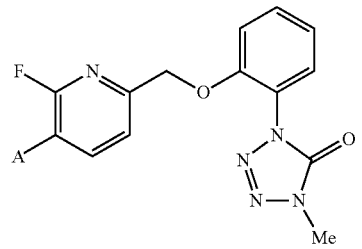
PF14
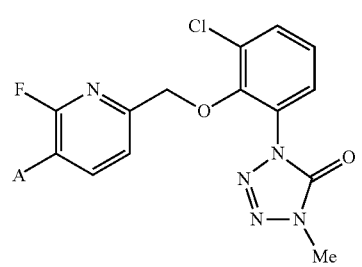
PG14
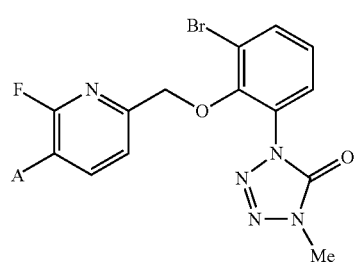
PH14
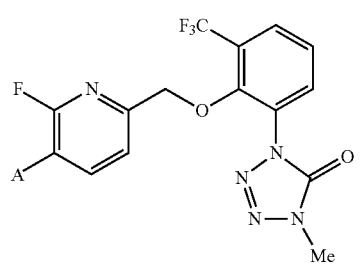
PA15
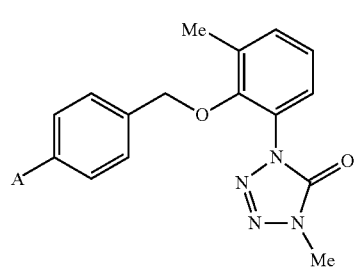
PB15
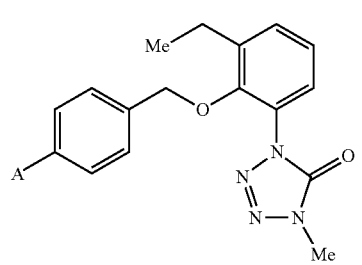
PC15
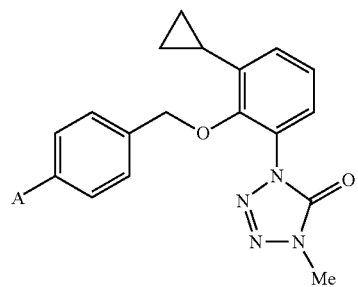
PD15
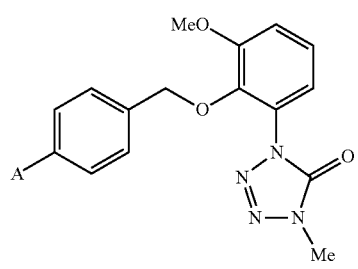
PE15
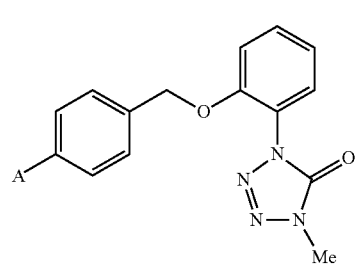
PF15
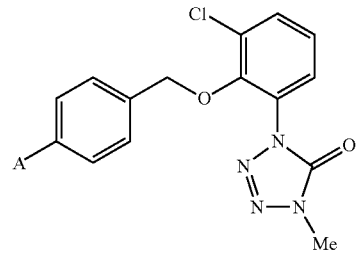
PG15
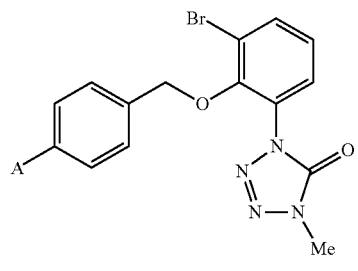
PH15
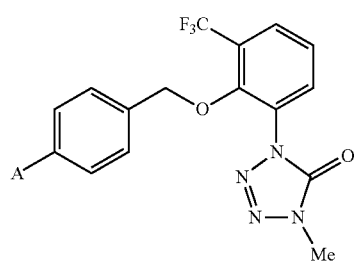

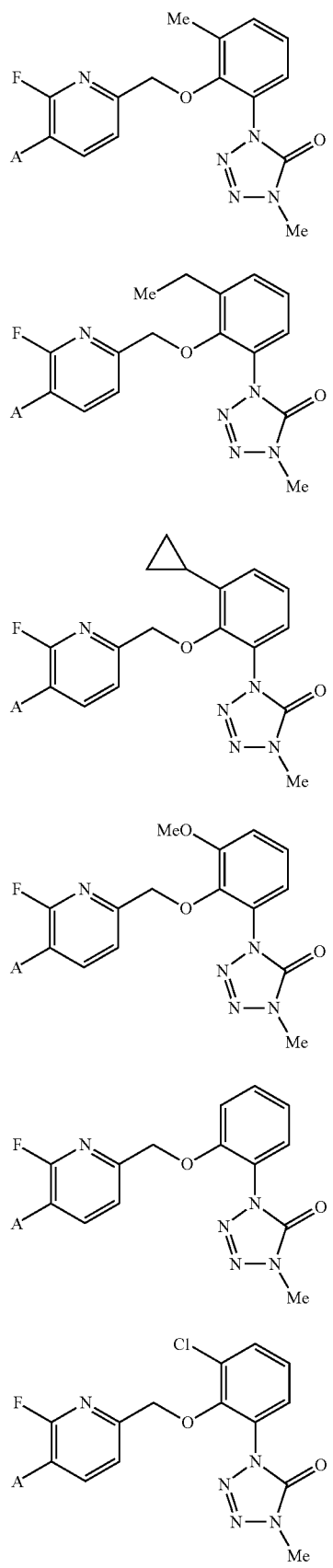
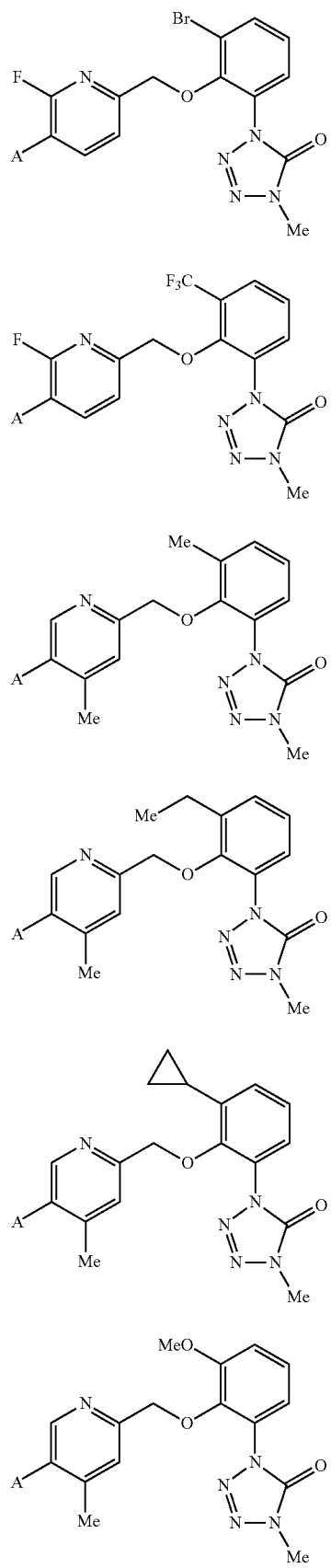

-continued
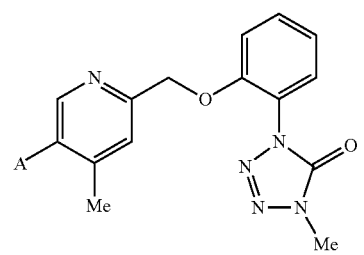 PE17
 PF17
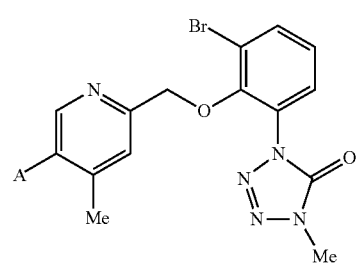 PG17
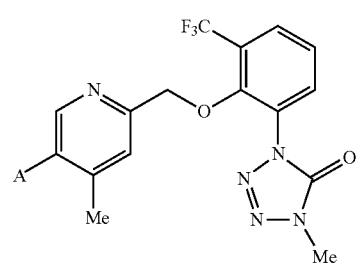 PH17
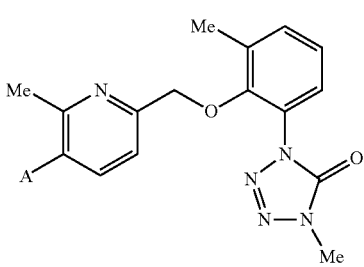 PA18
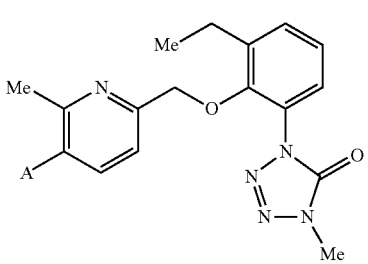 PB18
-continued
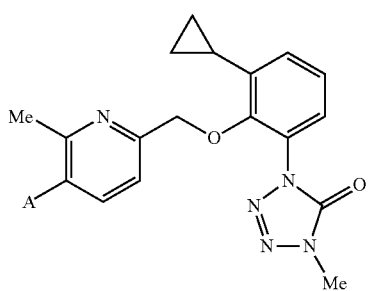 PC18
 PD18
 PE18
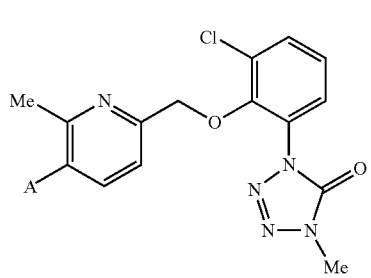 PF18
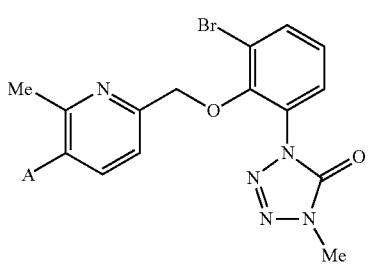 PG18
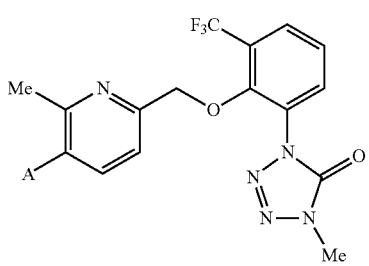 PH18

PA19 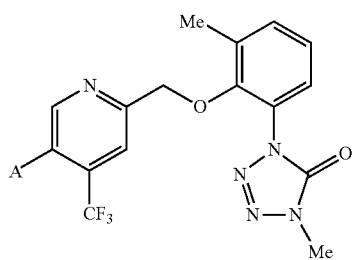
PB19 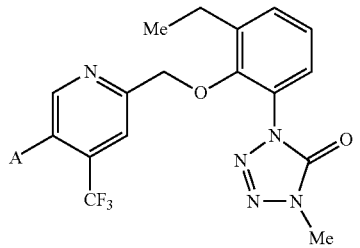
PC19 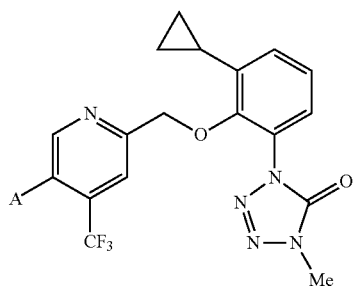
PD19 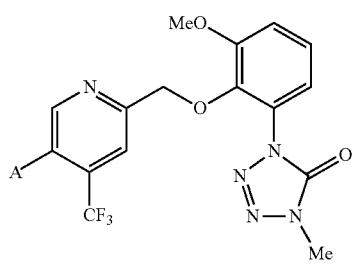
PE19 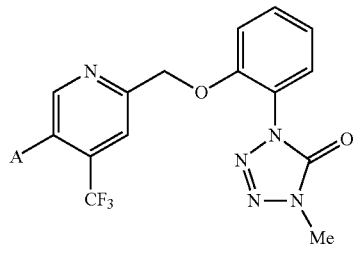
PF19 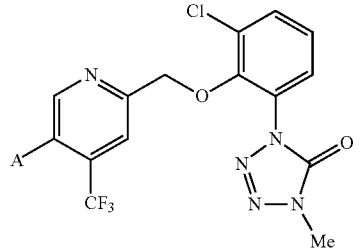
PG19 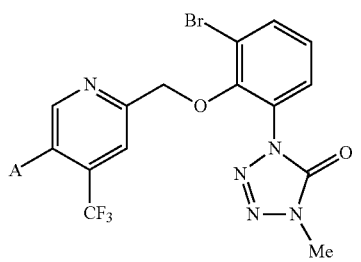
PH19 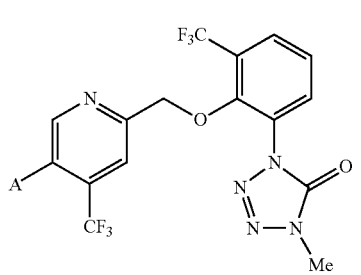
PA20 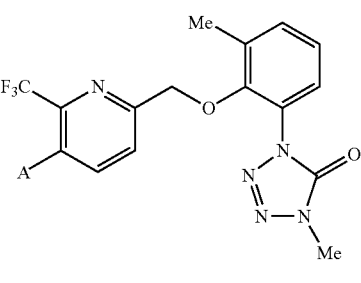
PB20 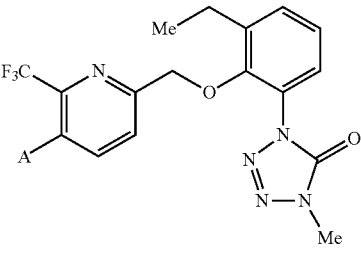
PC20 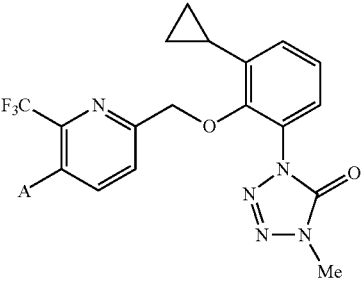
PD20 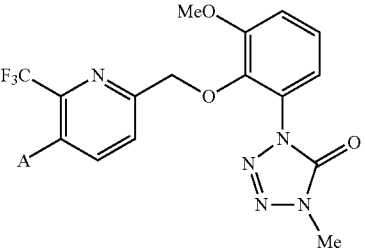

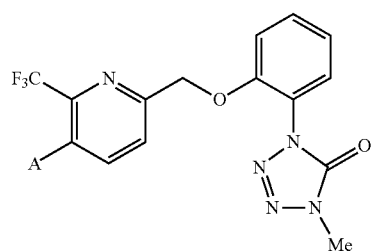 PE20
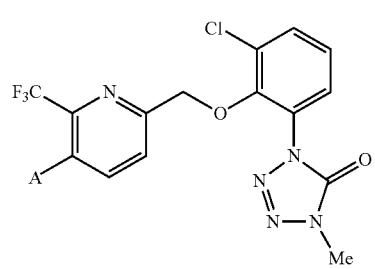 PF20
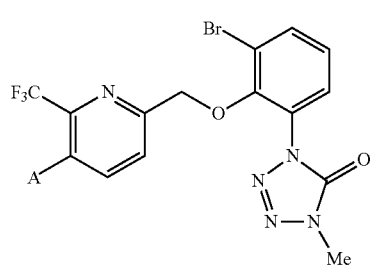 PG20
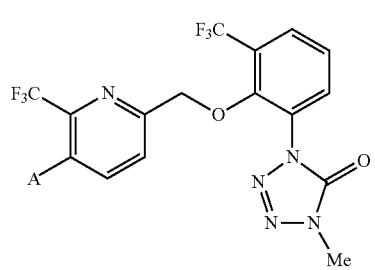 PH20
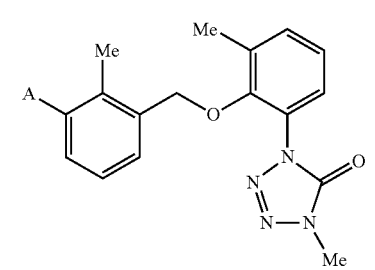 RA1
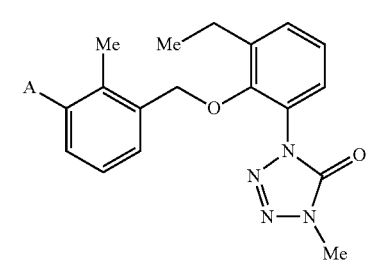 RB1
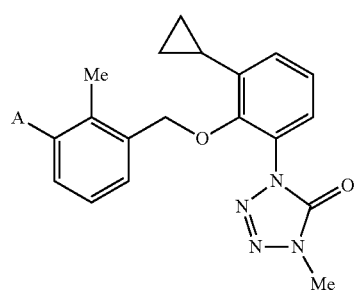 RC1
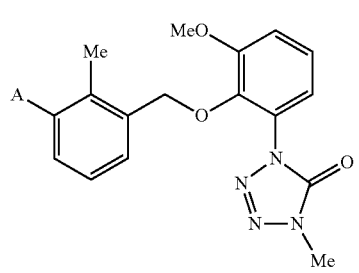 RD1
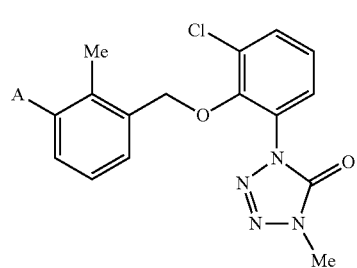 RE1
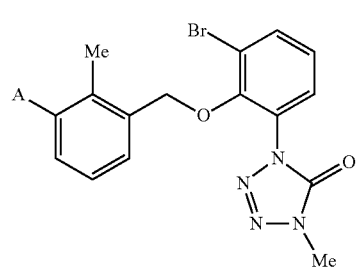 RF1
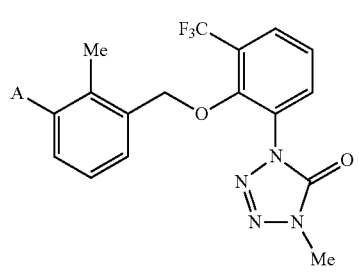 RG1
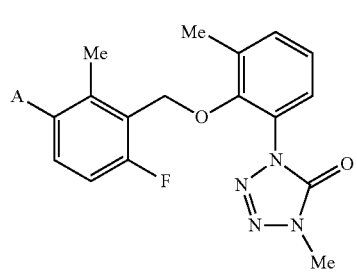 RA2

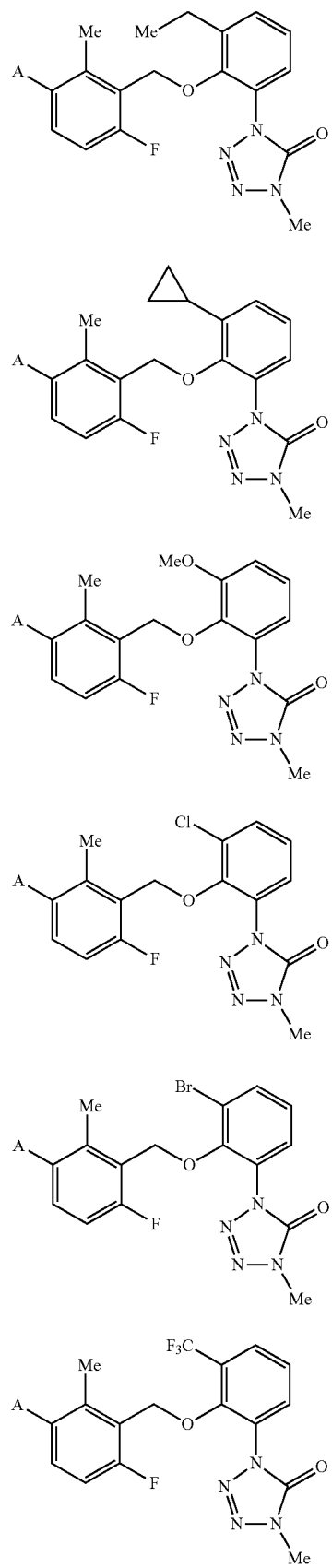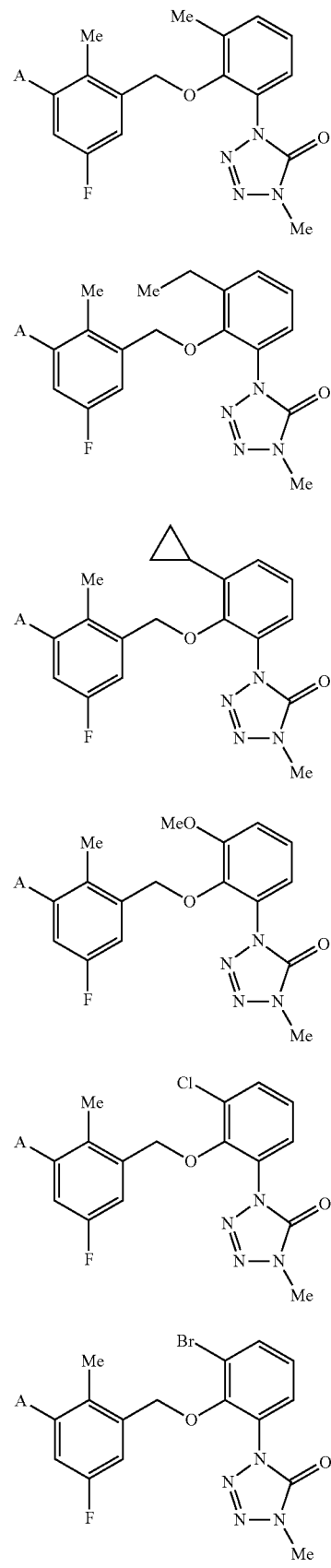

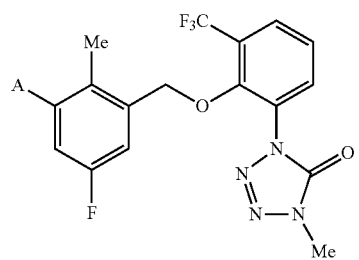 RG3
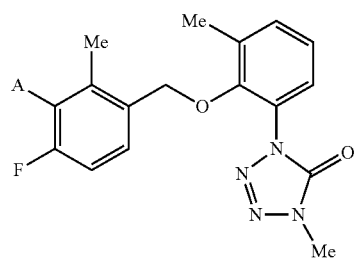 RA4
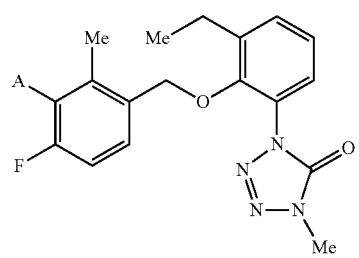 RB4
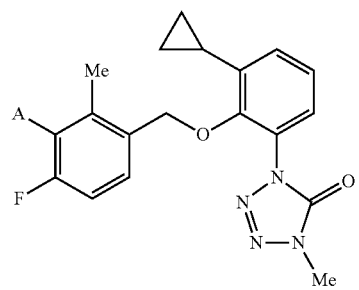 RC4
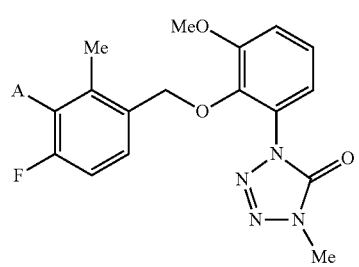 RD4
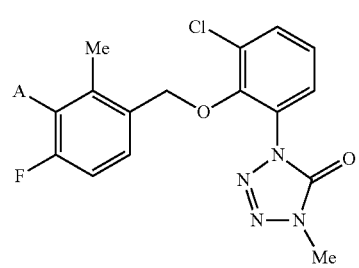 RE4
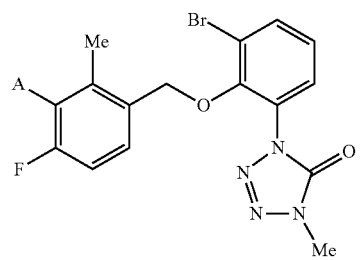 RF4
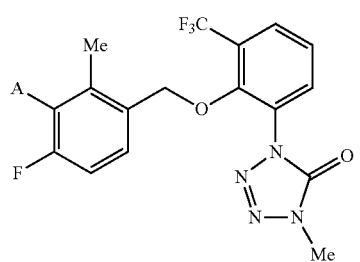 RG4
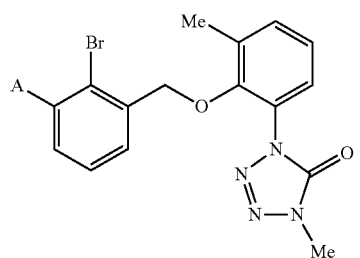 RA5
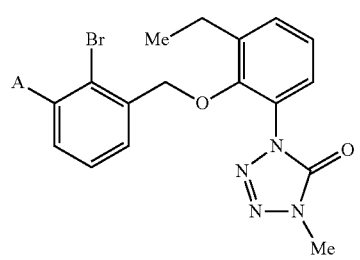 RB5
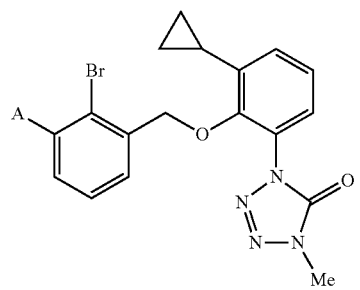 RC5
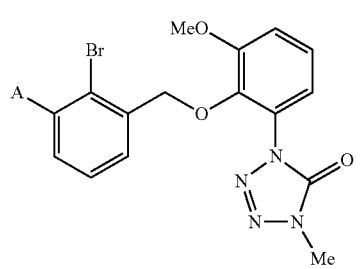 RD5

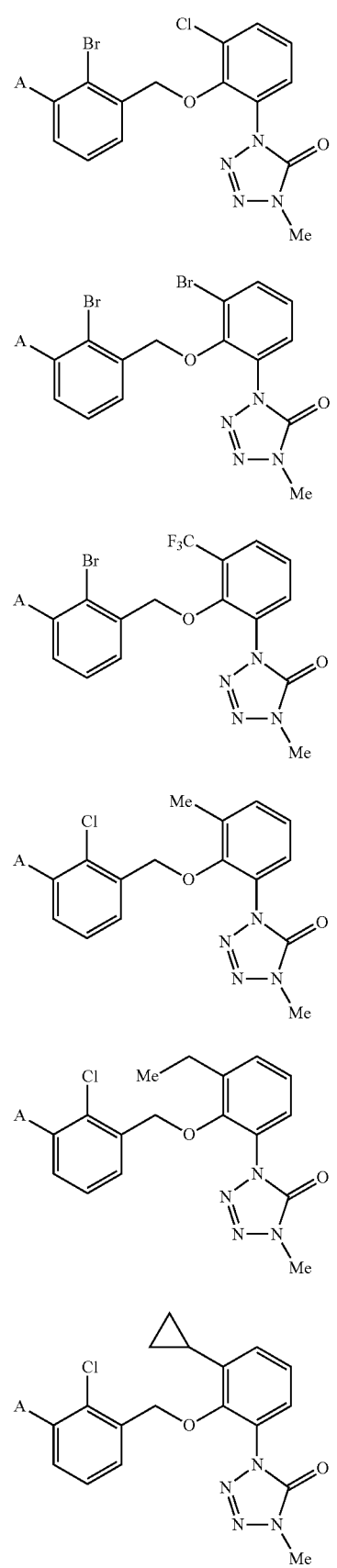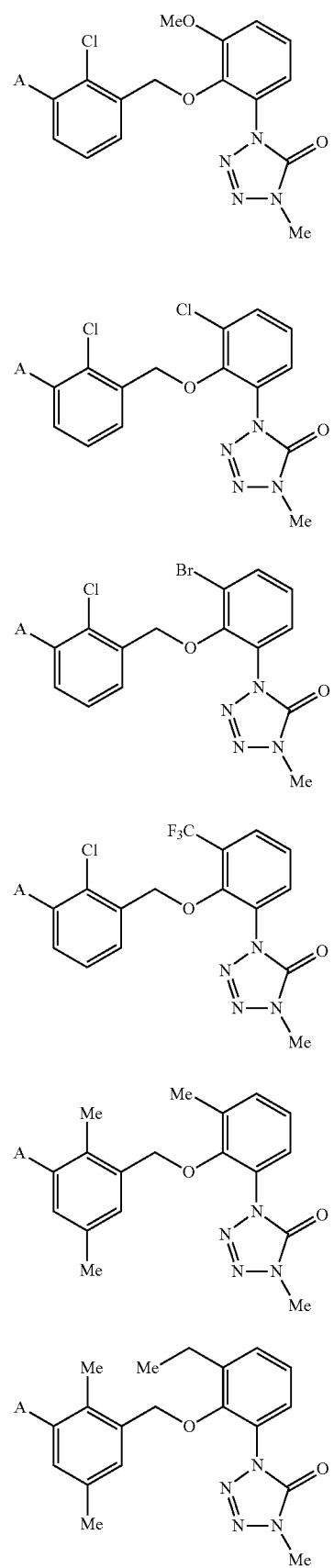

| | |
|---|---|
| 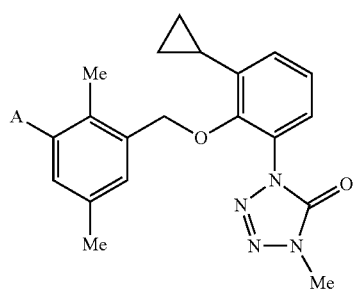 RC7 | 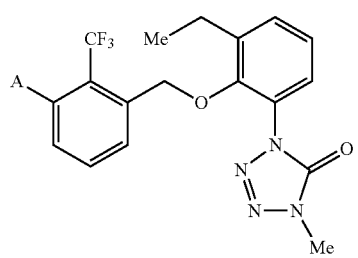 RB8 |
| 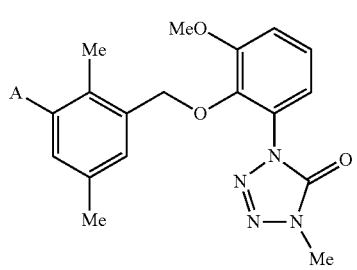 RD7 | 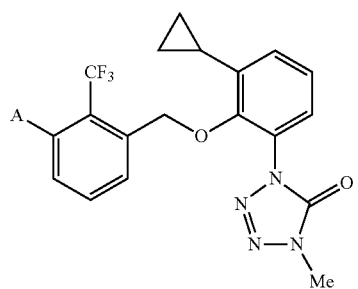 RC8 |
| 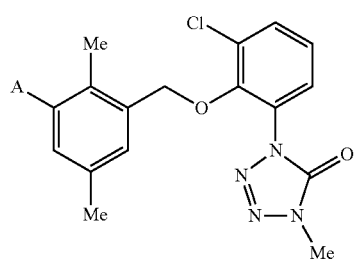 RE7 | 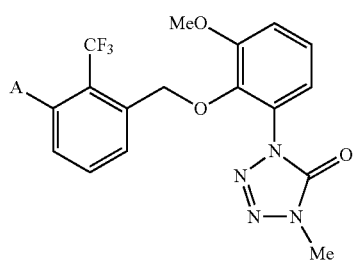 RD8 |
| 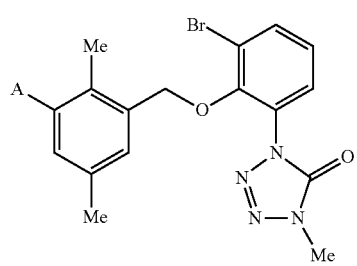 RF7 | 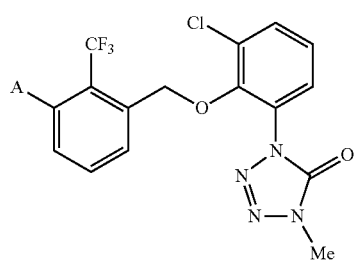 RE8 |
| 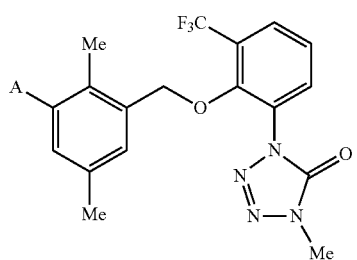 RG7 | 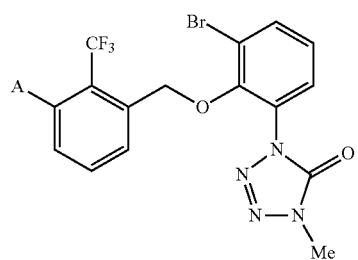 RF8 |
| 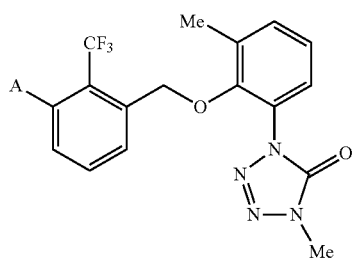 RA8 | 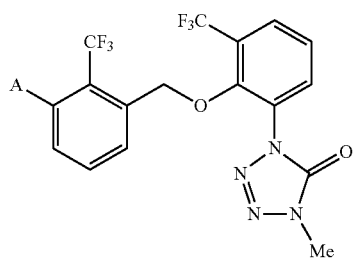 RG8 |

201
-continued
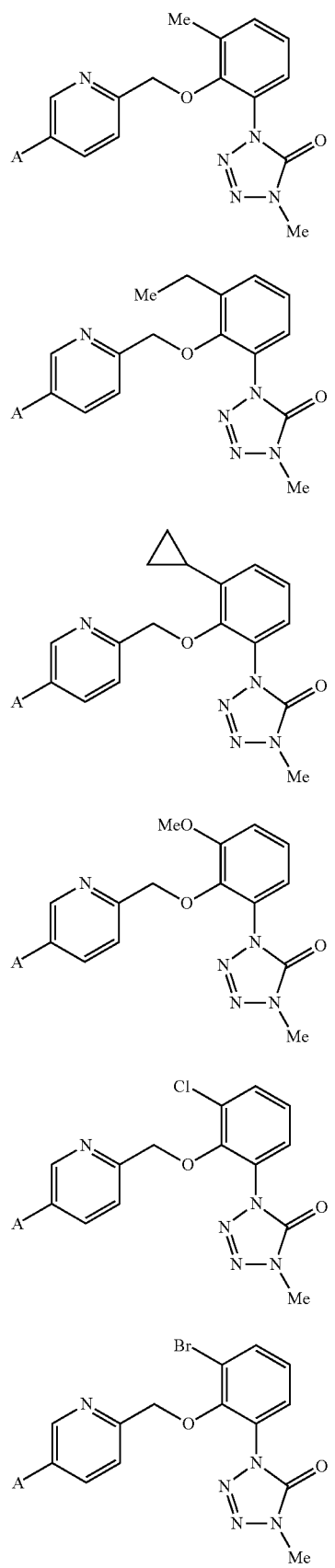
RA11
RB11
RC11
RD11
RE11
RF11
202
-continued
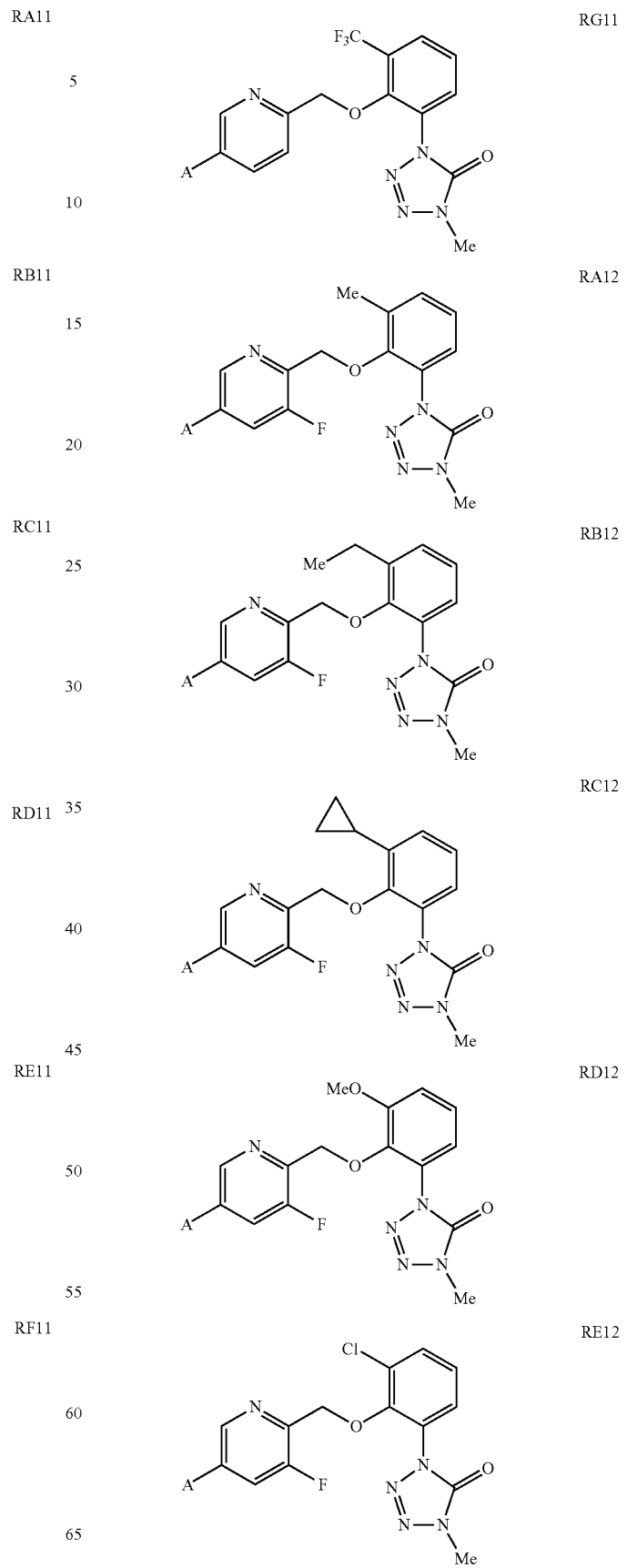
RG11
RA12
RB12
RC12
RD12
RE12

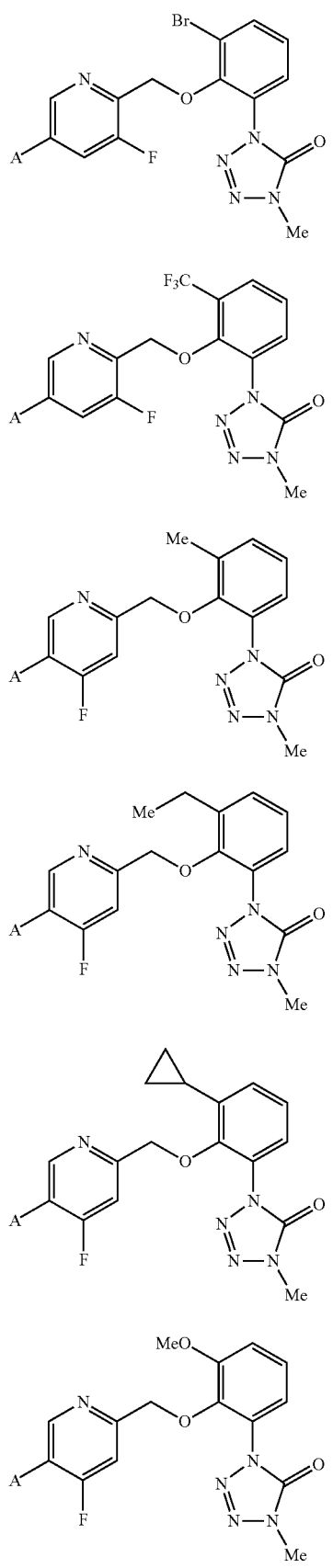
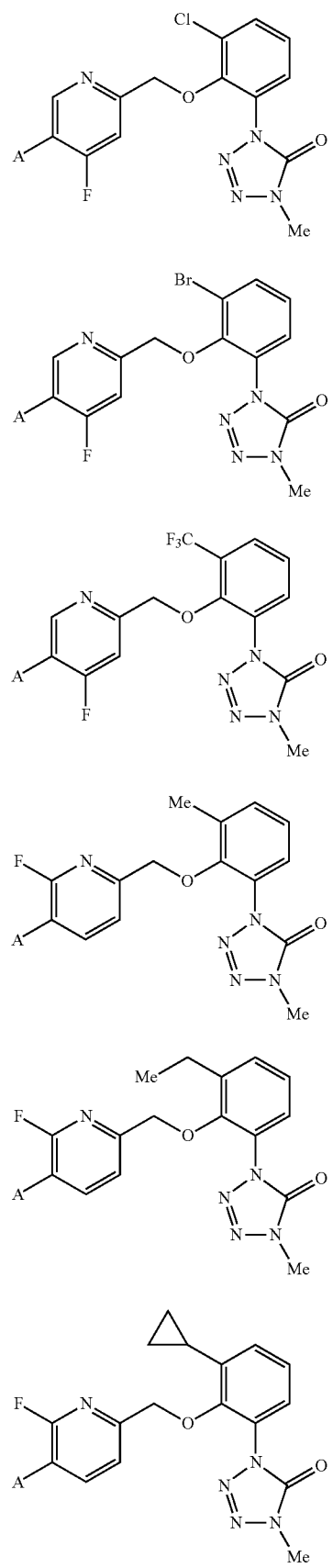

-continued
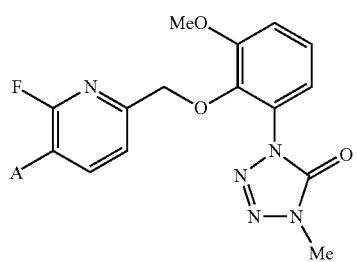 RD14
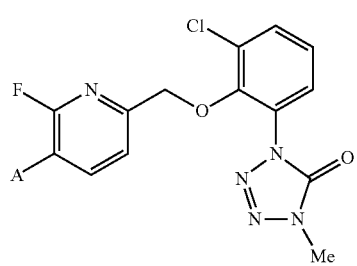 RE14
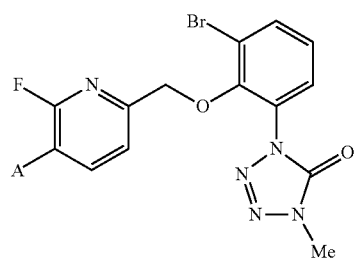 RF14
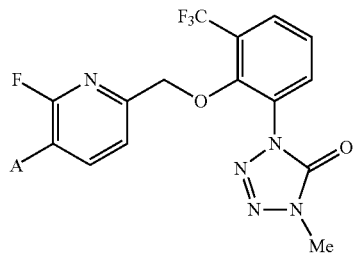 RG14
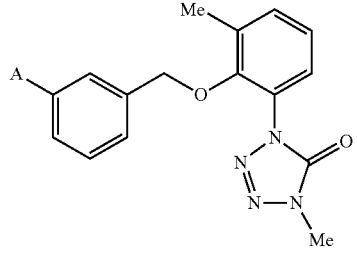 RA15
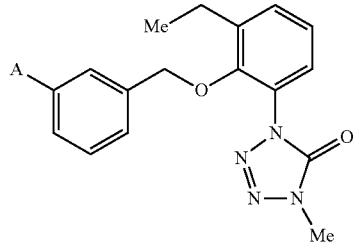 RB15
-continued
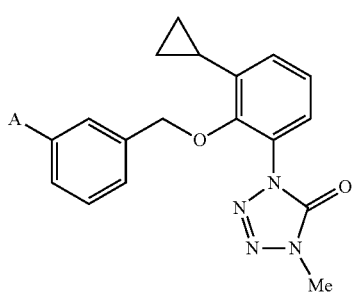 RC15
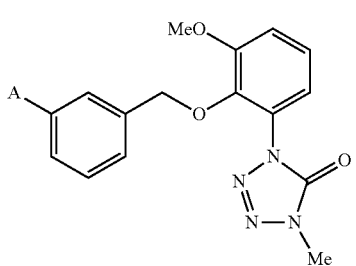 RD15
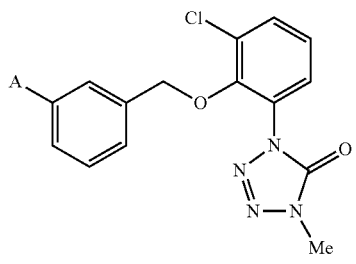 RE15
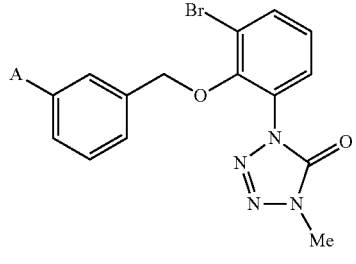 RF15
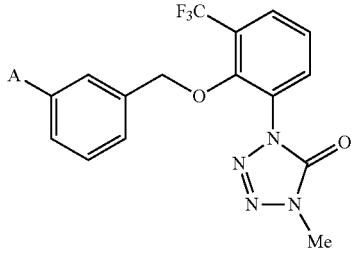 RG15
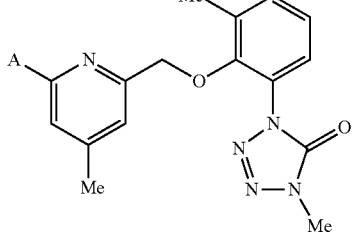 RA16

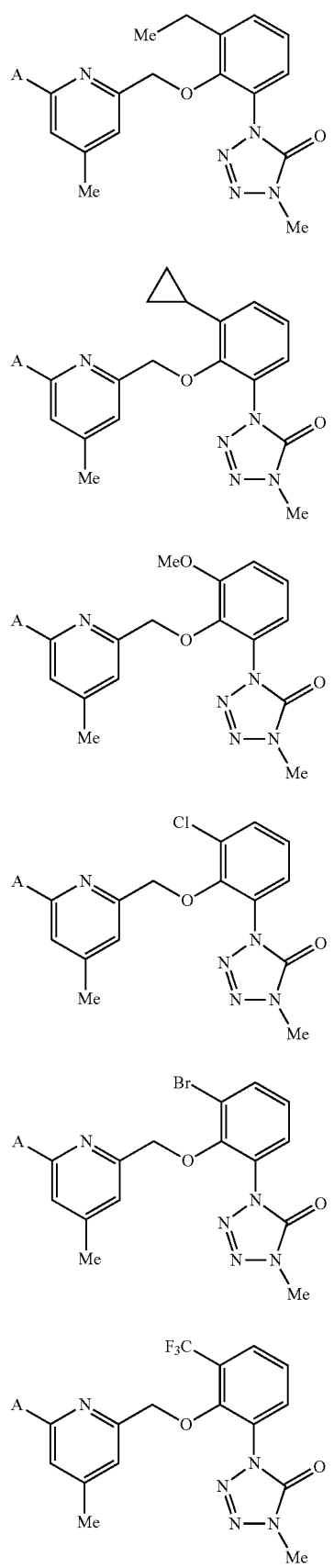
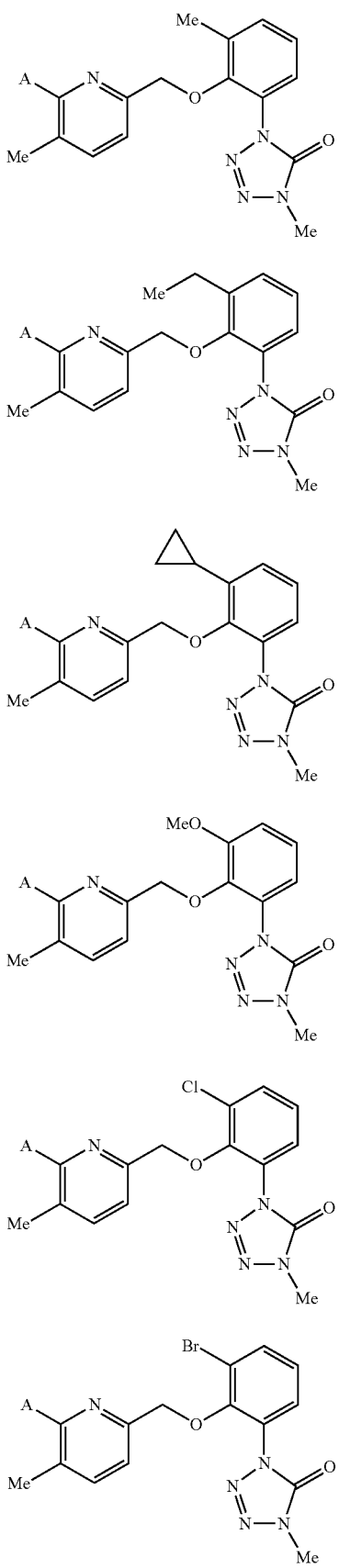

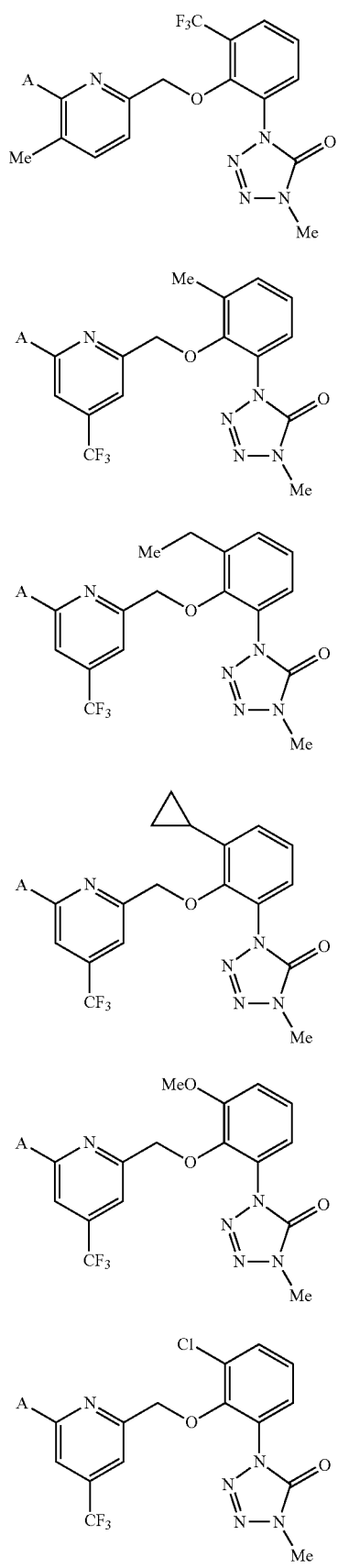
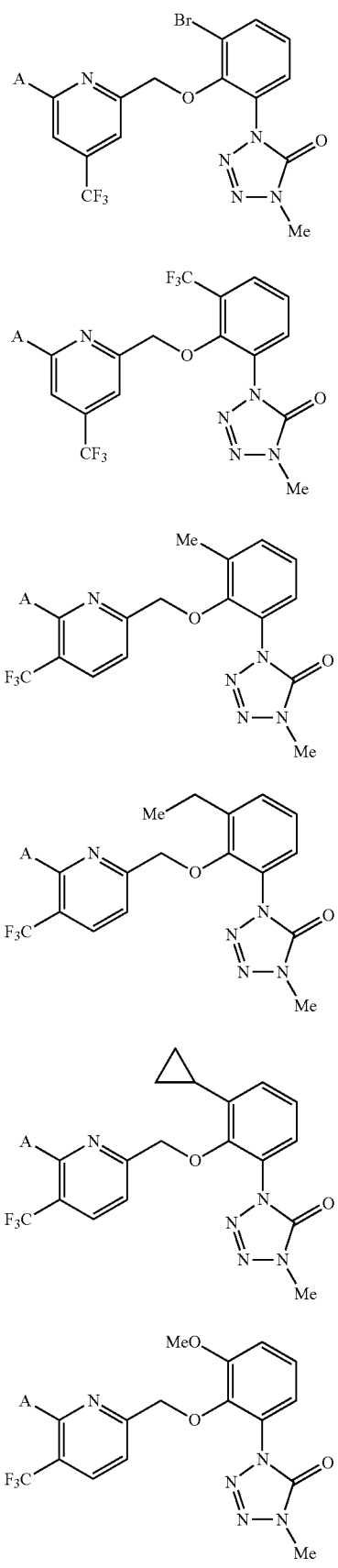

211
-continued
RE19
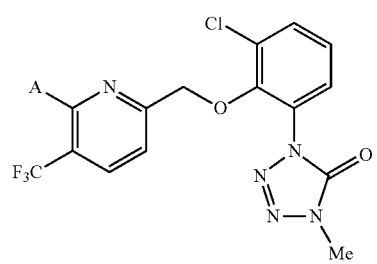
RF19
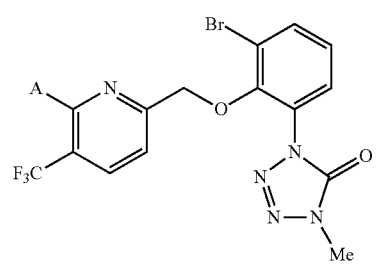
RG19
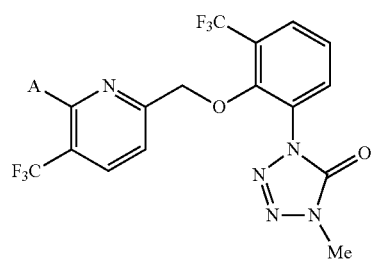
C0001
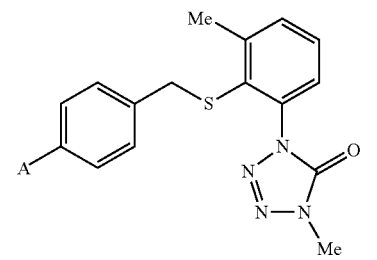
C0002
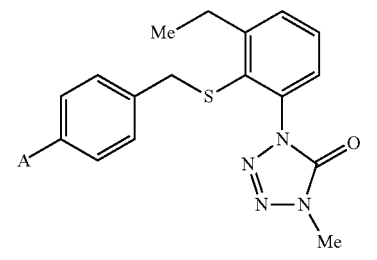
C0003
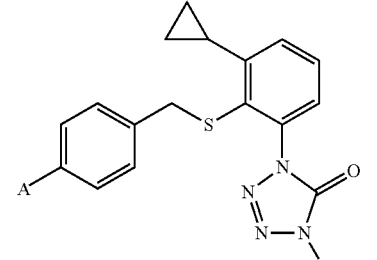
212
-continued
C0004
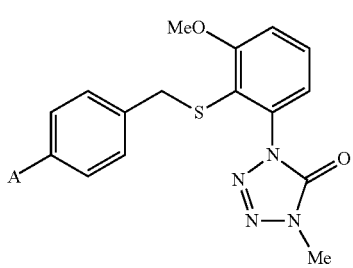
C0005
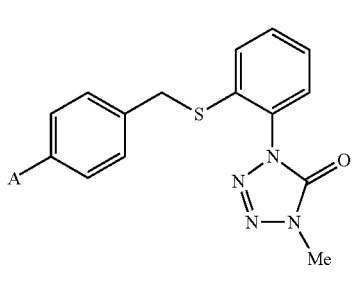
C0006
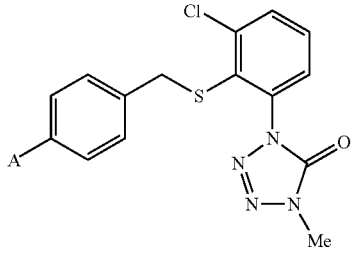
C0007
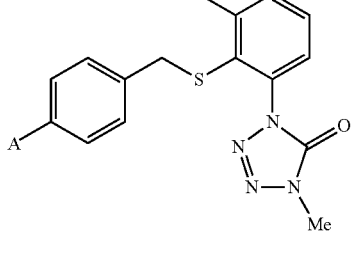
C0008
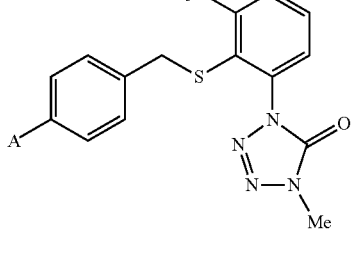
C0009
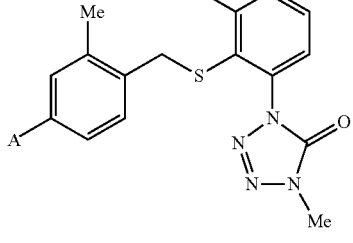

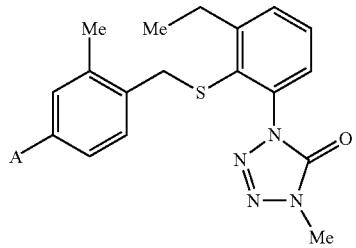
C0010
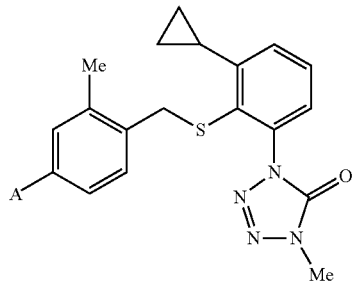
C0011
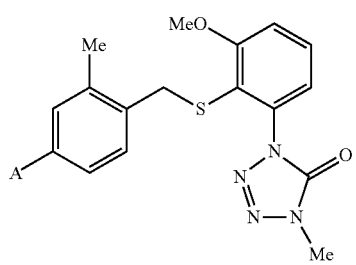
C0012
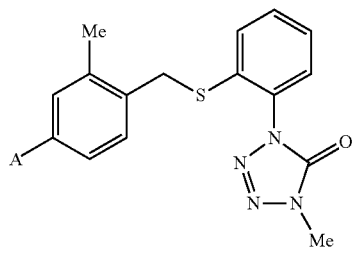
C0013
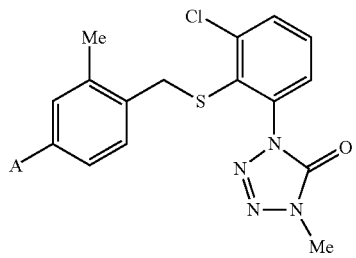
C0014
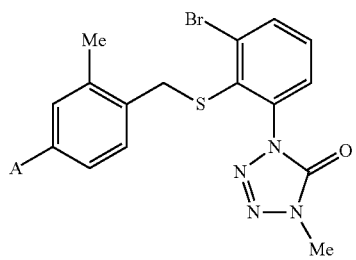
C0015
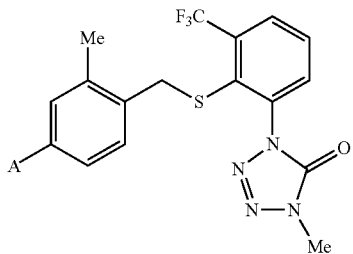
C0016
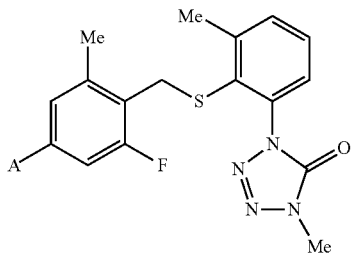
C0017
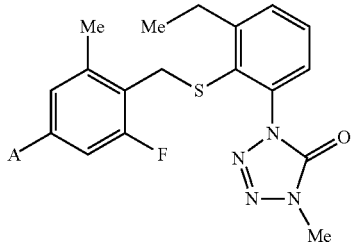
C0018
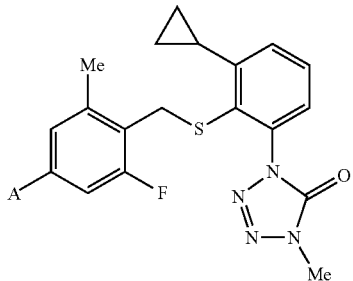
C0019
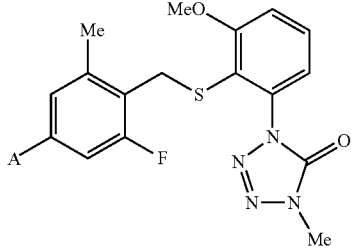
C0020
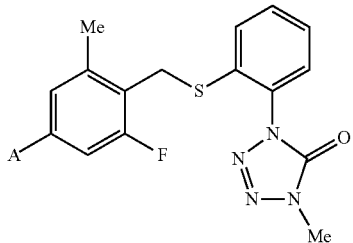
C1017

-continued
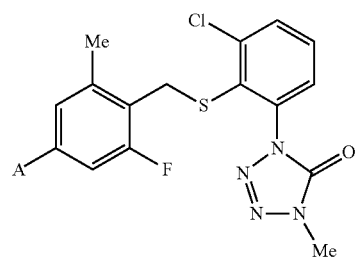
C1018
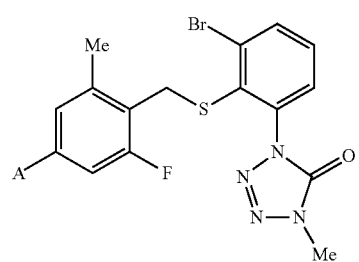
C1019
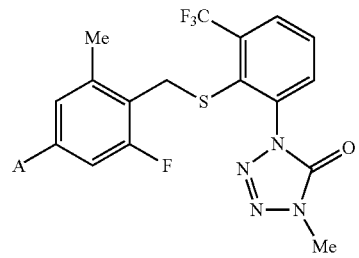
C1020
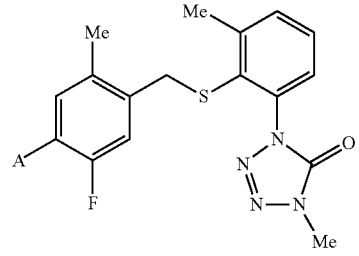
C0021
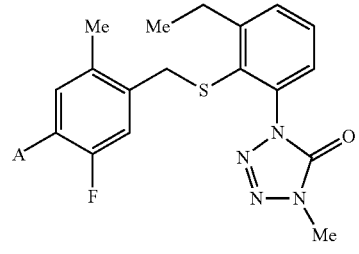
C0022
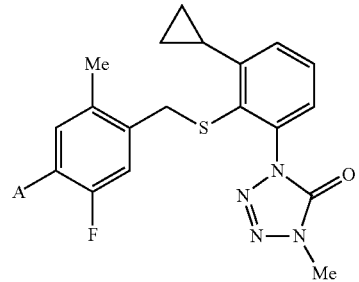
C0023
-continued
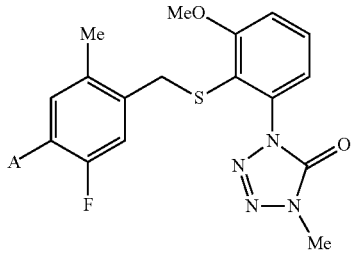
C0024
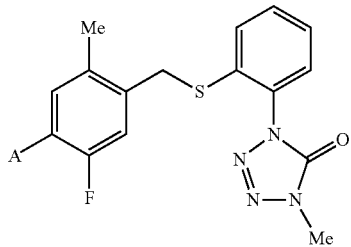
C0025
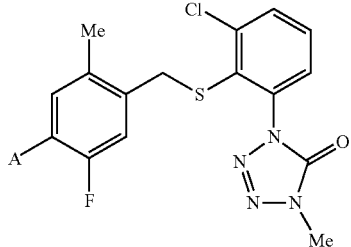
C0026
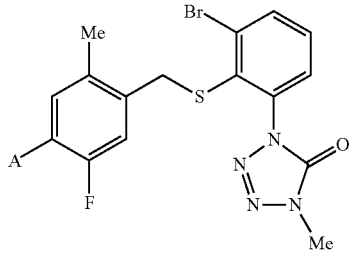
C0027
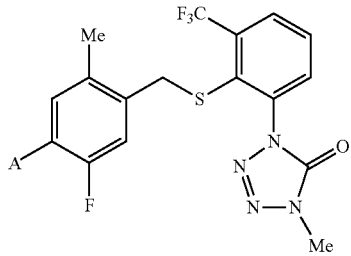
C0028
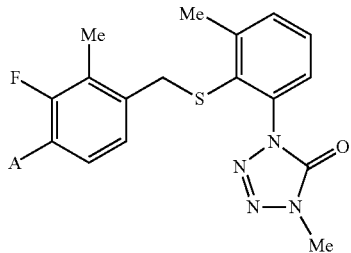
C0029

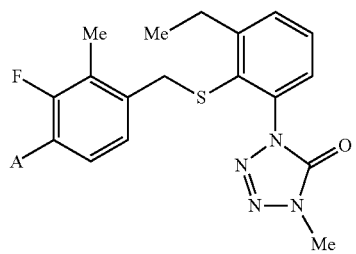
C0030
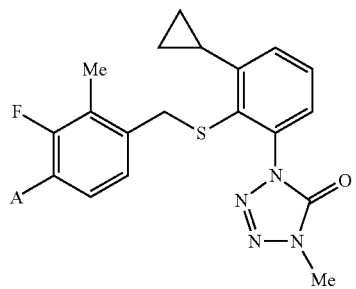
C0031
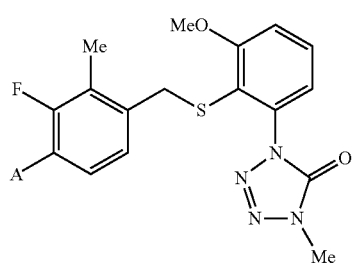
C0032
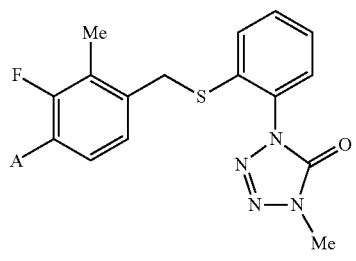
C0033
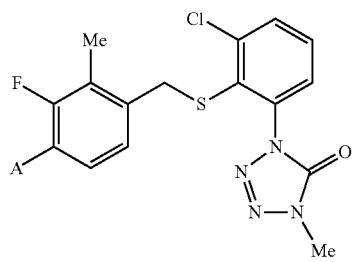
C0034
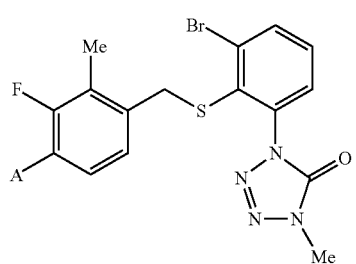
C0035
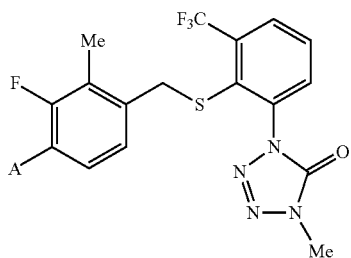
C0036
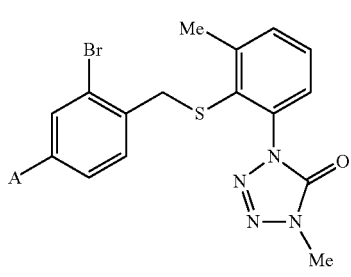
C0037
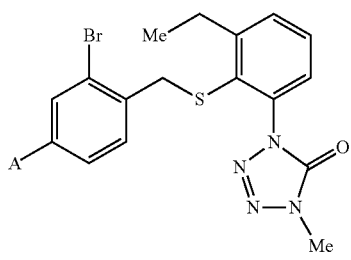
C0038
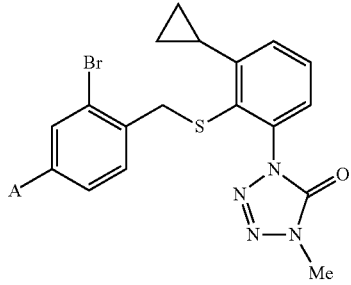
C0039
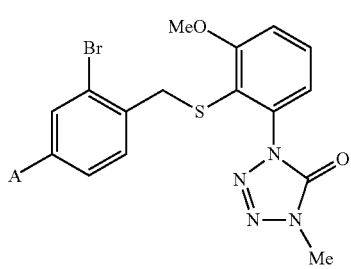
C0040
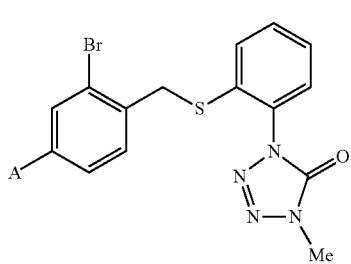
C0041

C0042 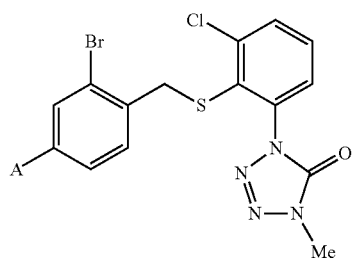
C0043 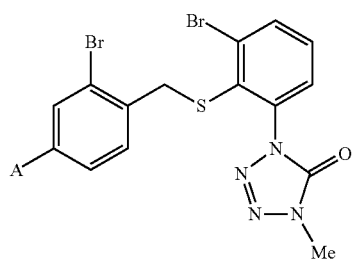
C0044 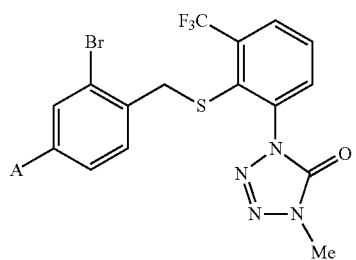
C0045 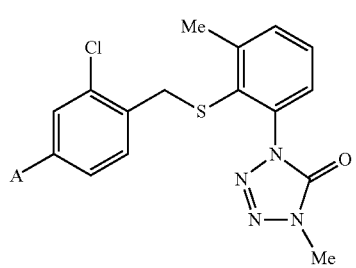
C0046 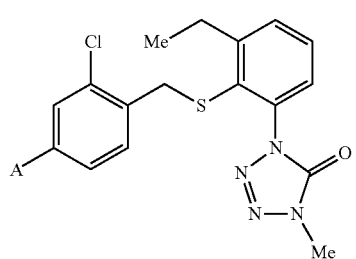
C0047 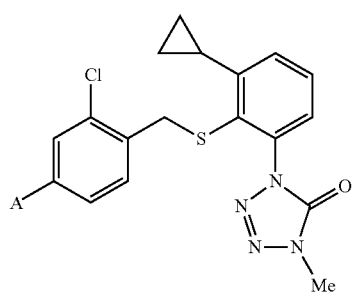
C0048 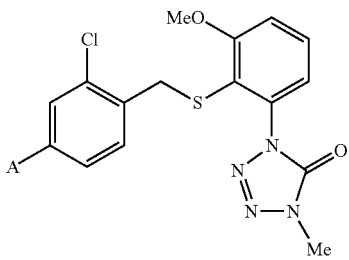
C0049 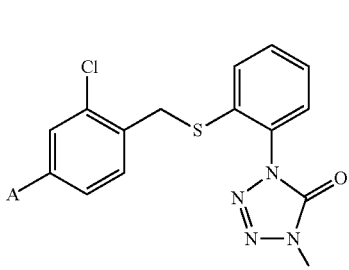
C0050 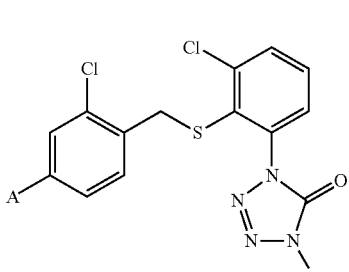
C0051 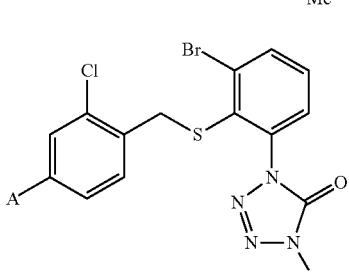
C0052 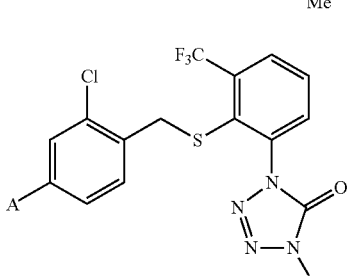
C0053 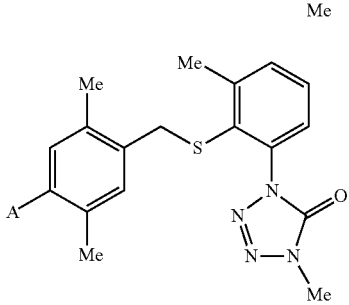

-continued
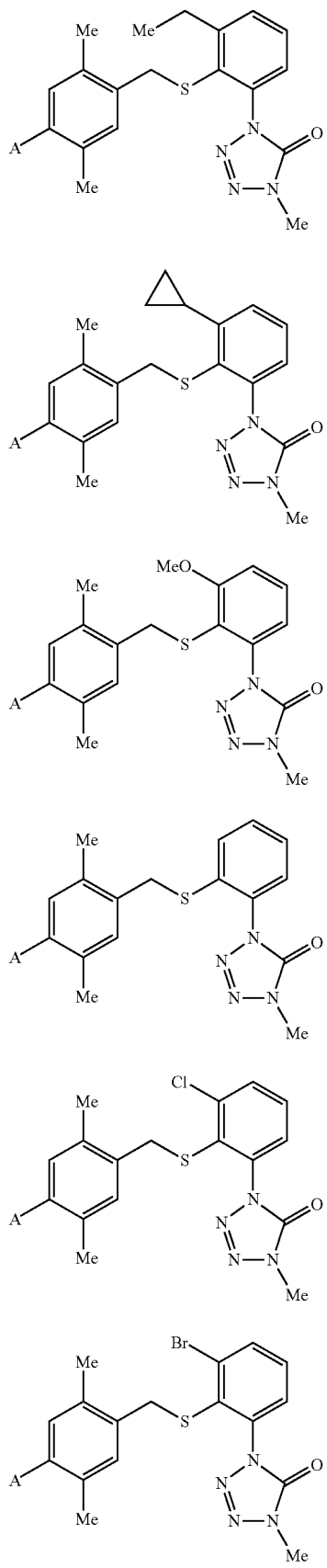
C0054
C0055
C0056
C0057
C0058
C0059
-continued
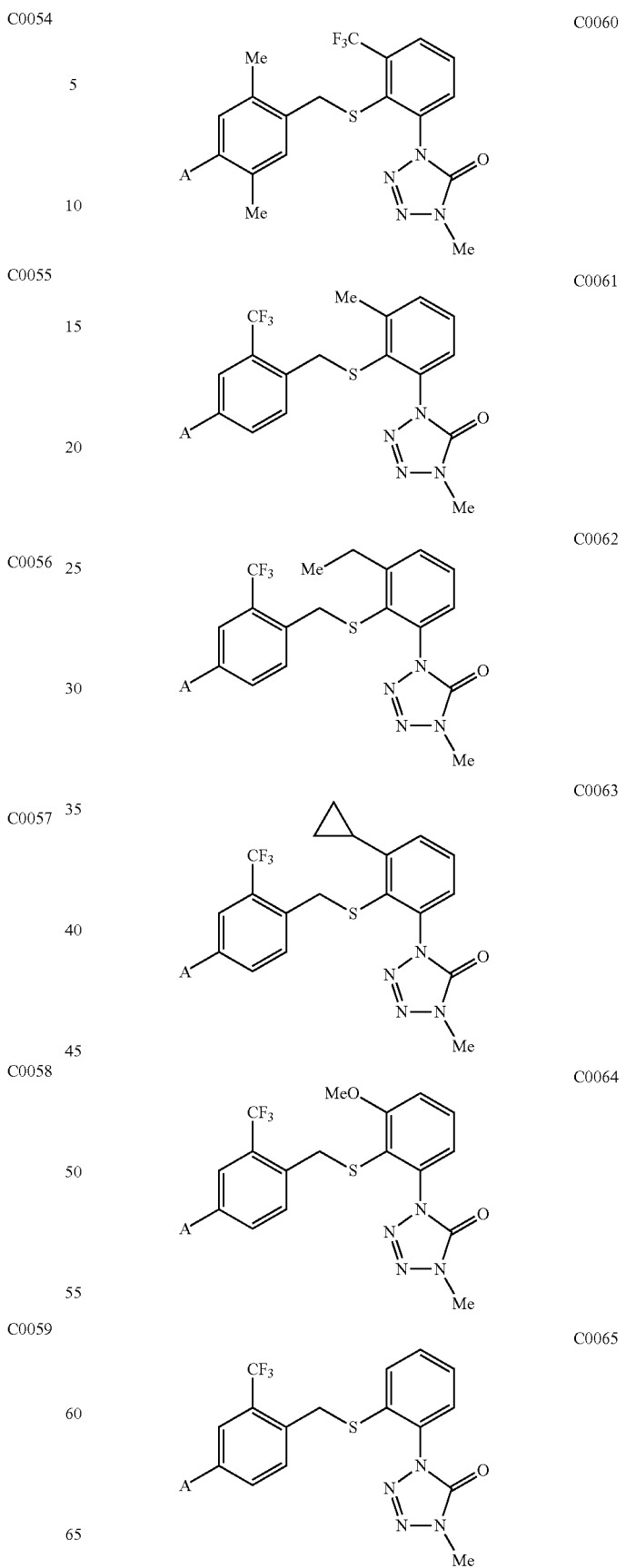
C0060
C0061
C0062
C0063
C0064
C0065

-continued
C0066 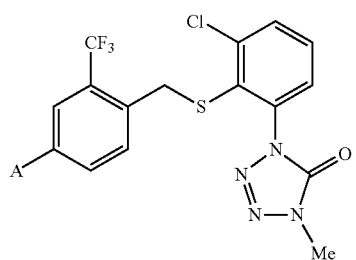
C0067 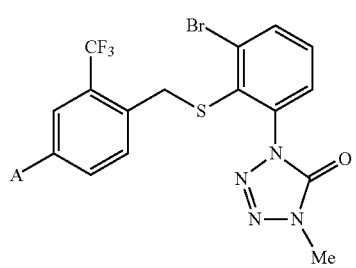
C0068 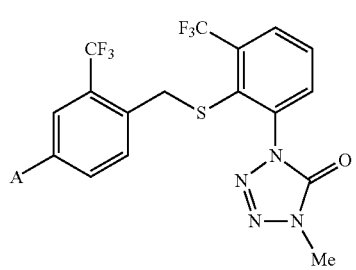
C0069 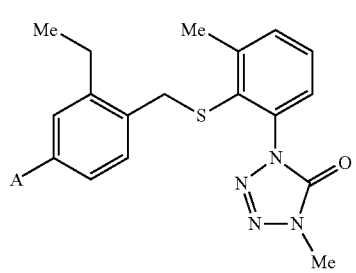
C0070 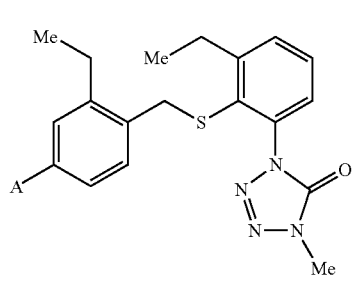
C0071 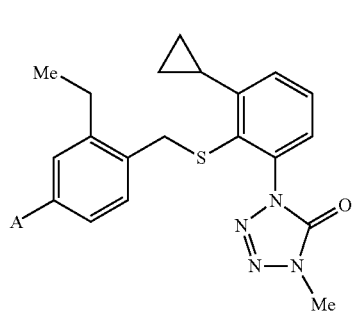
-continued
C0072 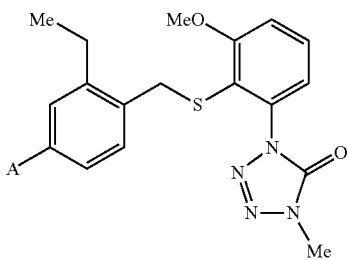
C0073 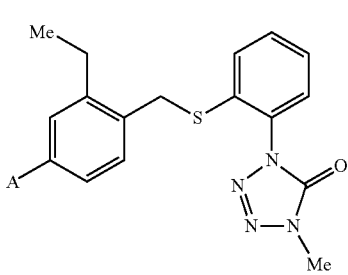
C0074 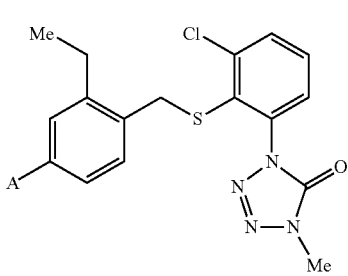
C0075 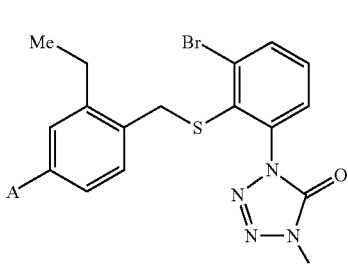
C0076 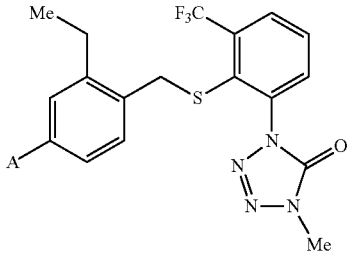
C0077 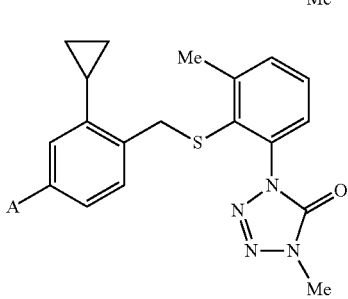

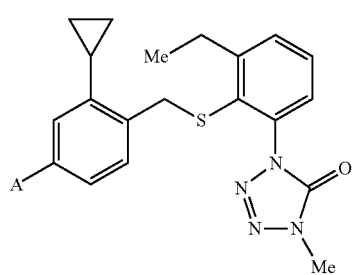
C0078
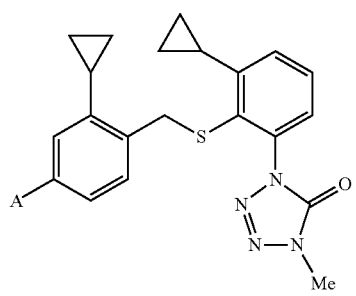
C0079
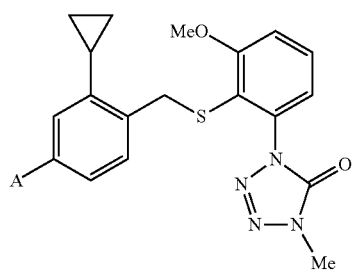
C0080
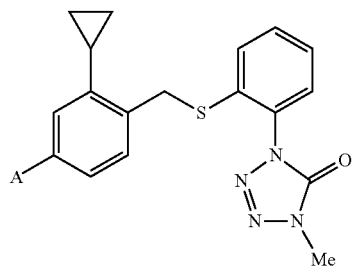
C0081
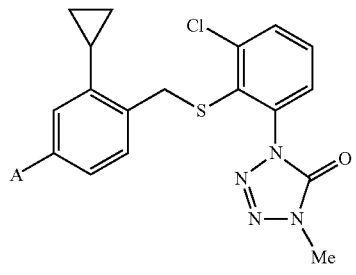
C0082
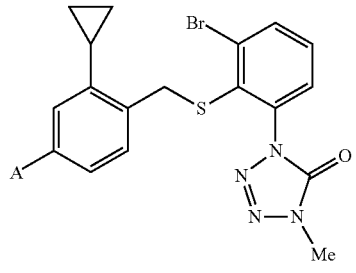
C0083
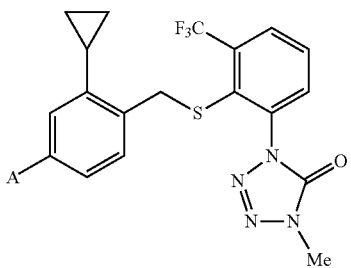
C0084
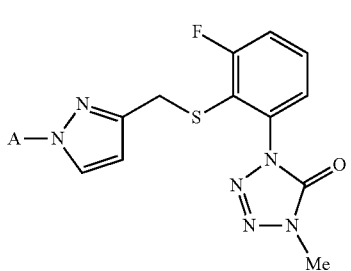
C0085
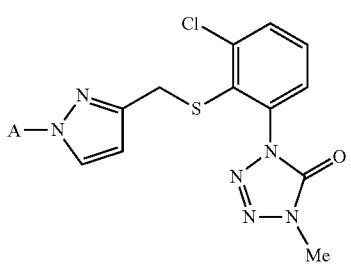
C0086
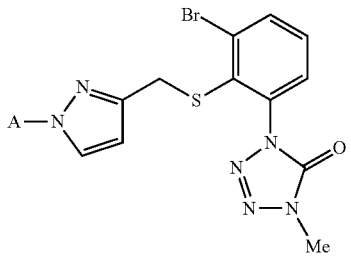
C0087
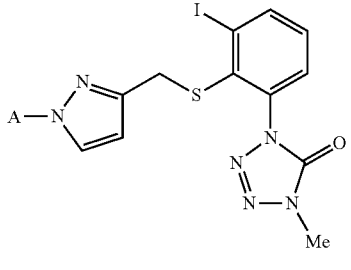
C0088
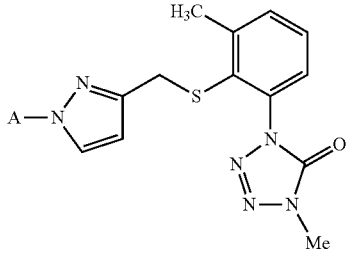
C0089

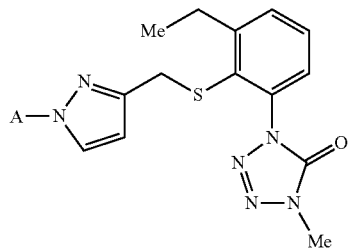
C0090
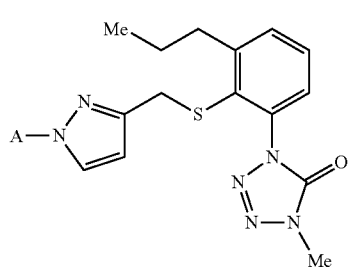
C0091
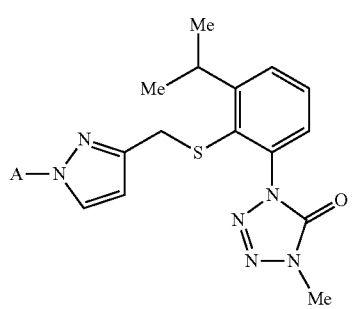
C0092
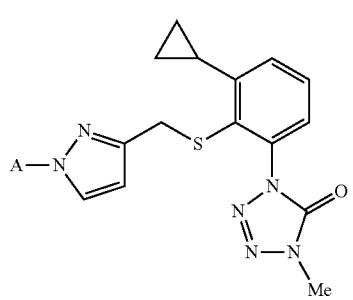
C0093
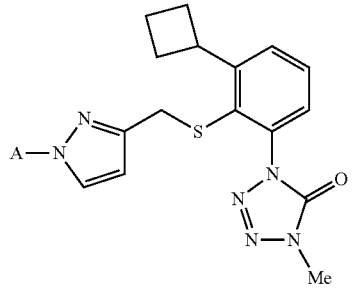
C0094
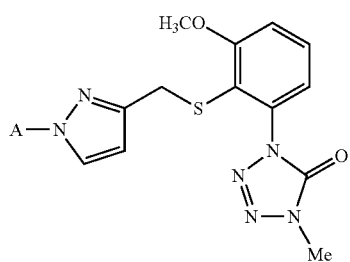
C0095
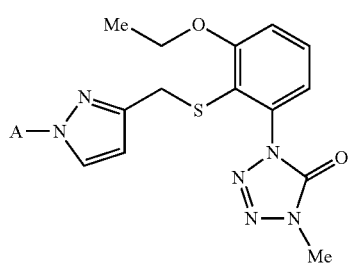
C0096
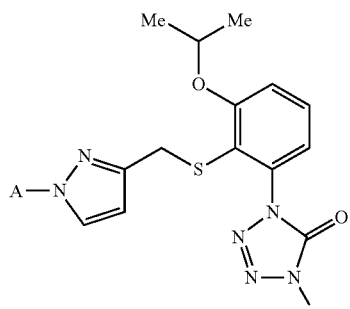
C0097
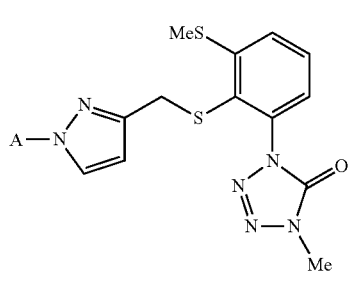
C0098
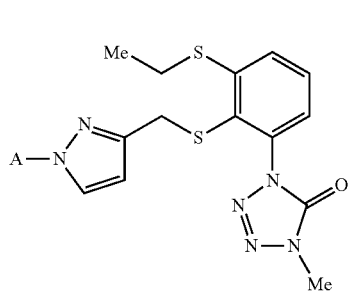
C0099

C0100
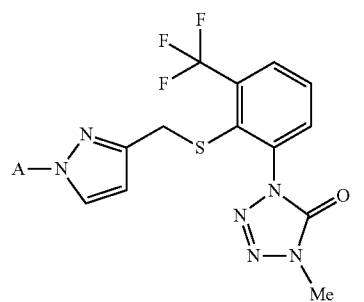
C0101
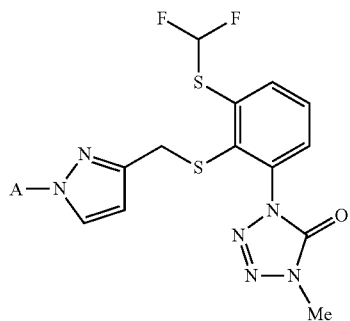
C0102
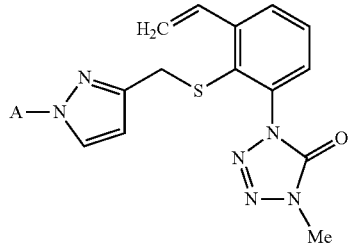
C0103
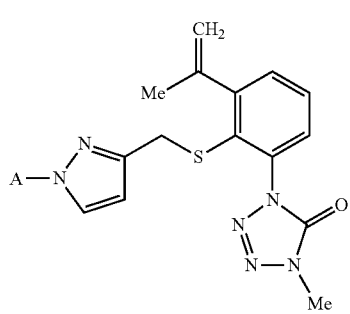
C0104
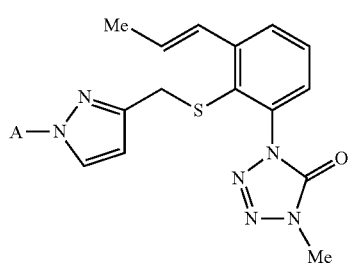
C0105
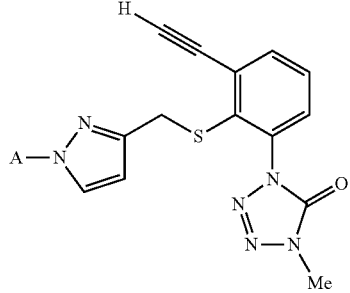
C0106
C0107
C0108
C0109

233
-continued

C0122

C0123

C0124

C0125

C0126

C0127

234
-continued

C0128

C0129

C0130

C0131

C0132

C0133

-continued
C0134
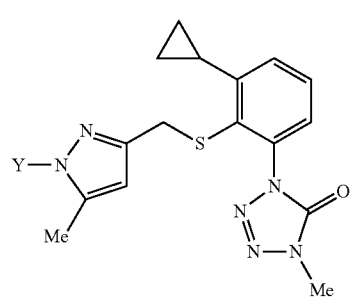
C0135
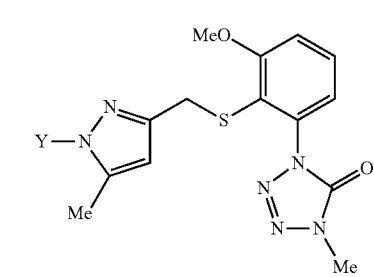
C0136
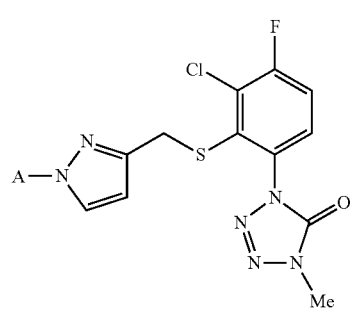
C0137
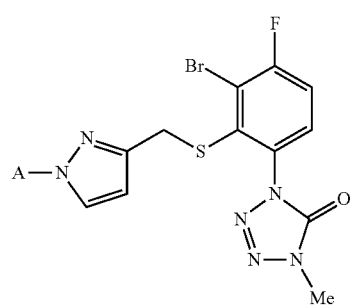
C0138
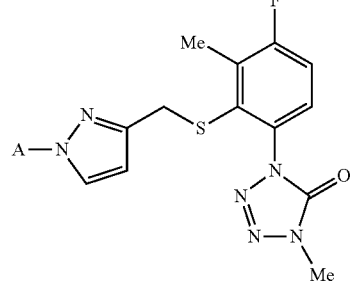
-continued
C0139
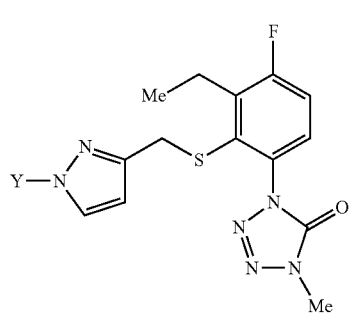
C0140
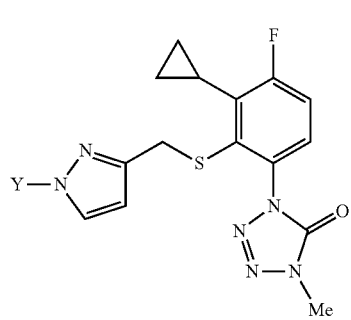
C0141
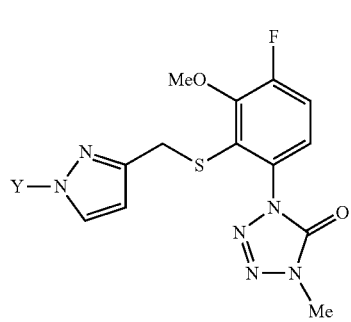
C0142
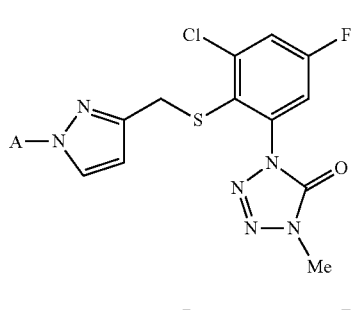
C0143
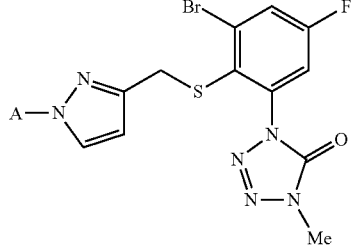

-continued

C0144

C0145

C0146

C0147

C0148

C0149

-continued

C0150

C0151

C0152

C0153

C0154

C0155

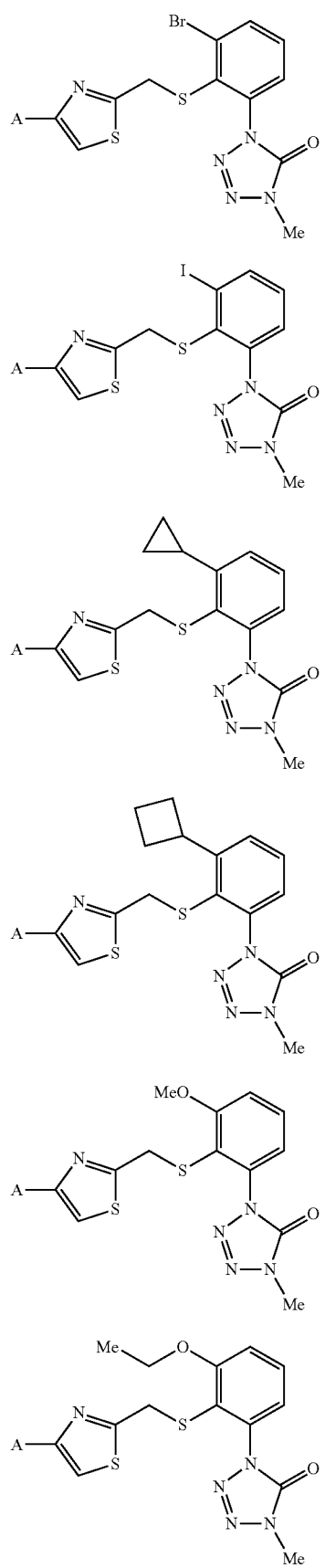
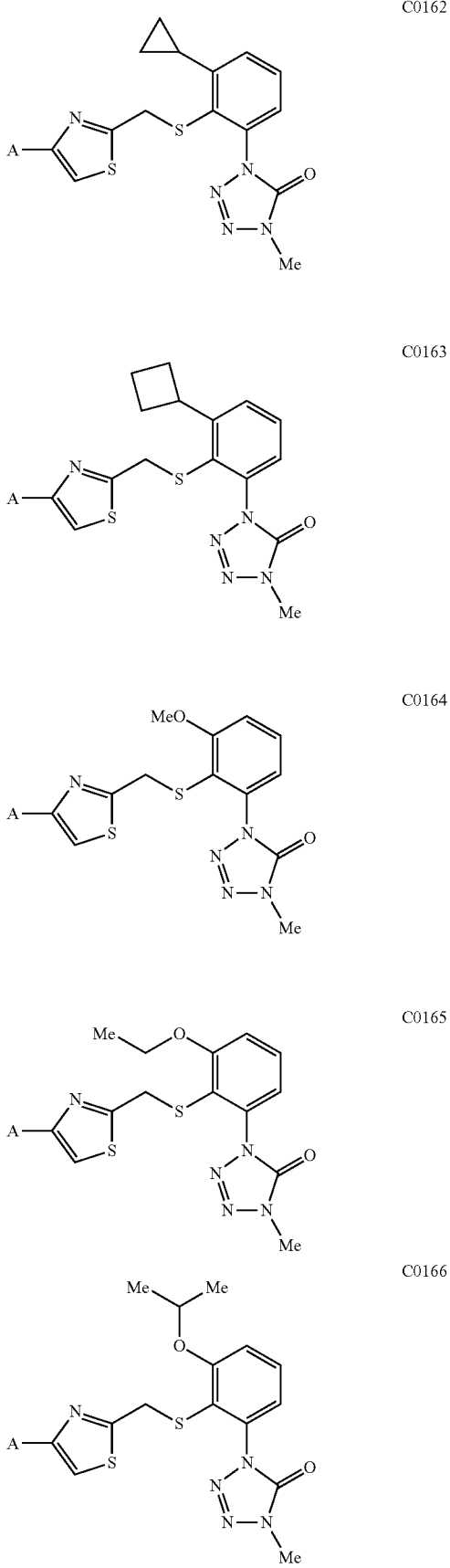

-continued
C0167
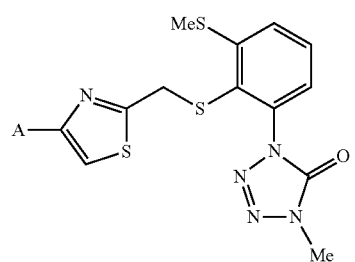
C0168
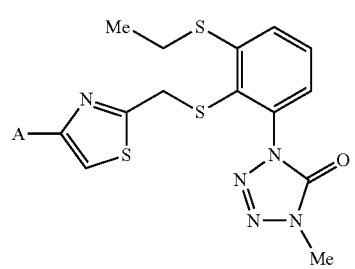
C0169
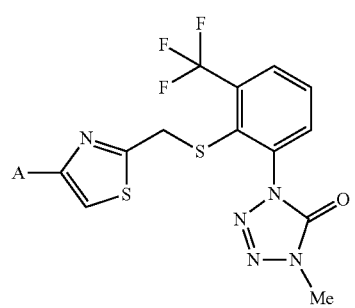
C0170
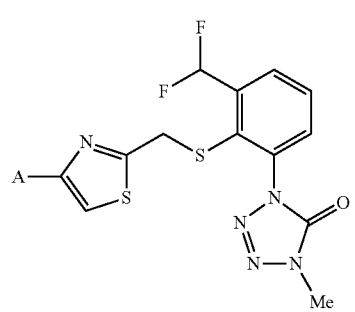
C0171
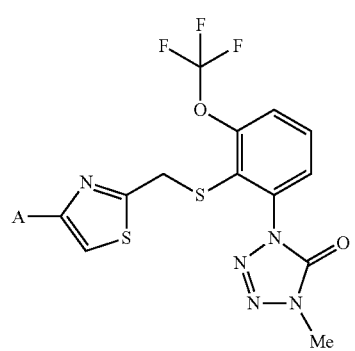
-continued
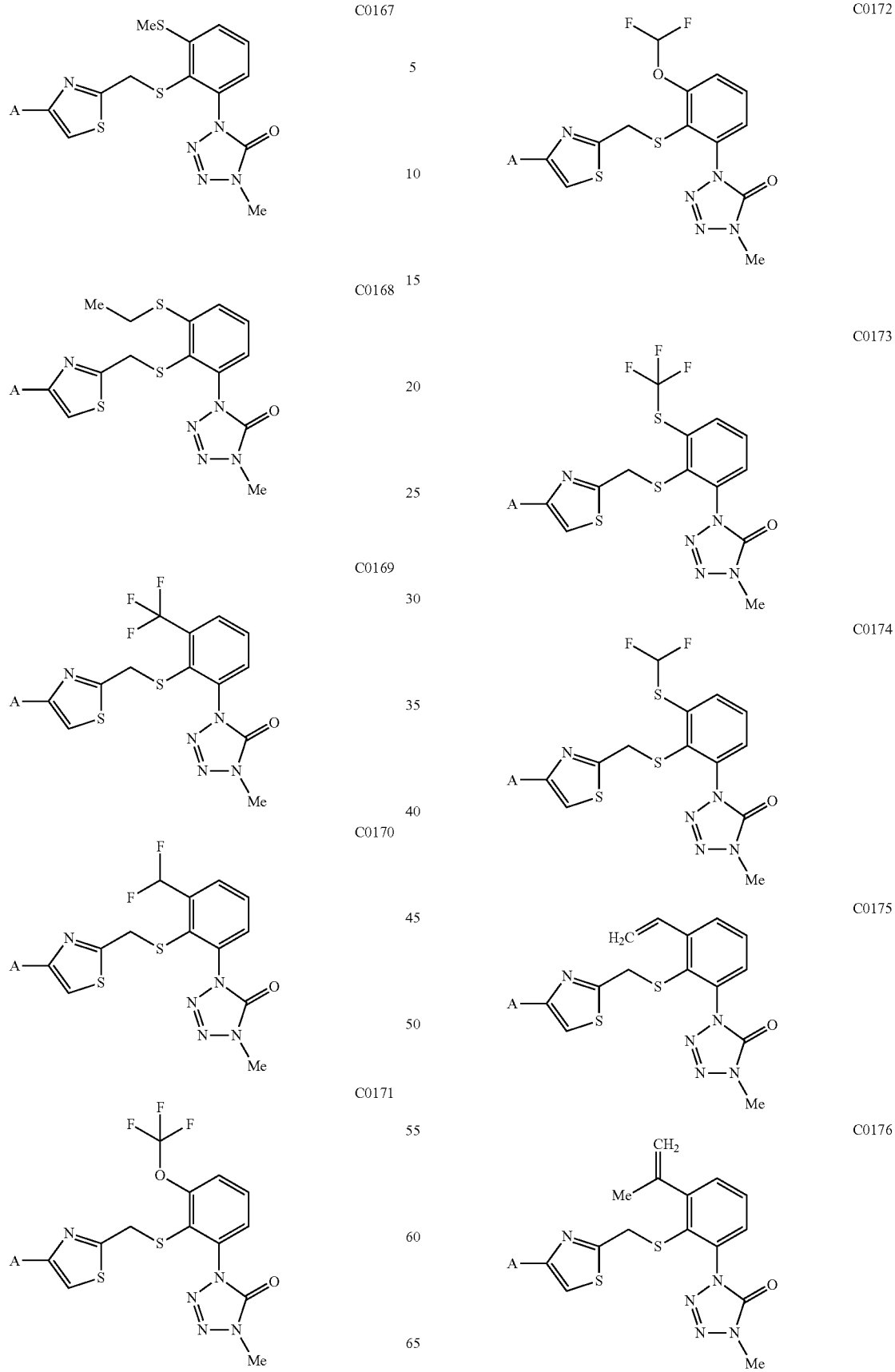

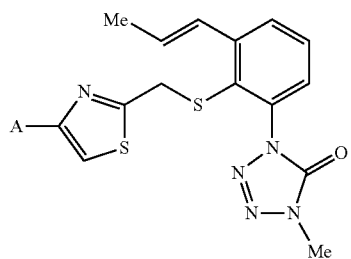
C0177
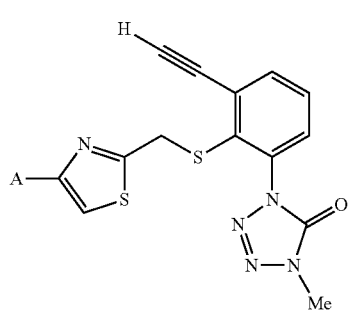
C0178
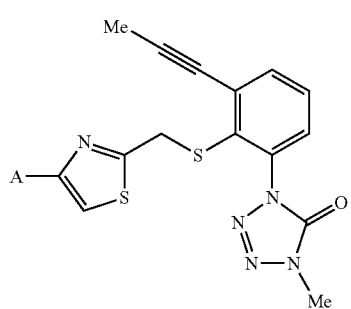
C0179
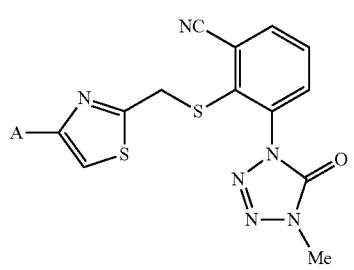
C0180
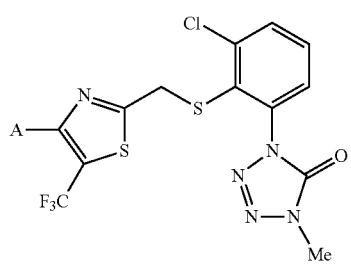
C0181
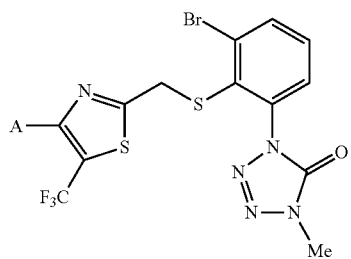
C0182
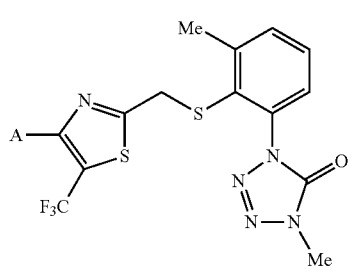
C0183
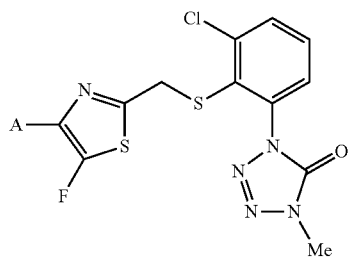
C0184
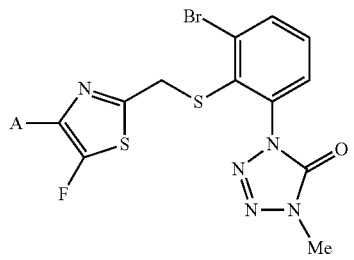
C0185
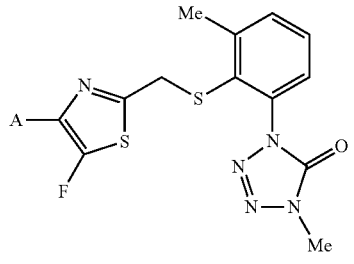
C0186
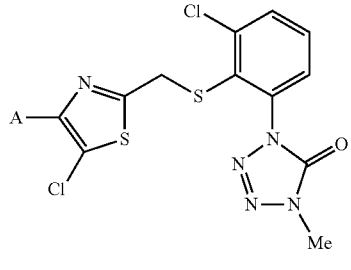
C0187

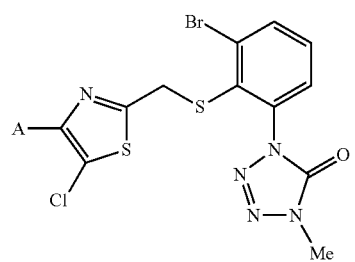
C0188
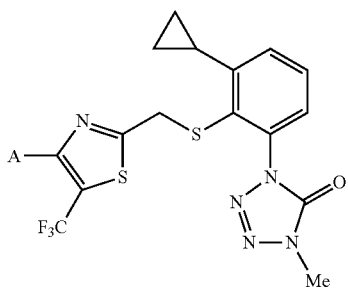
C0194
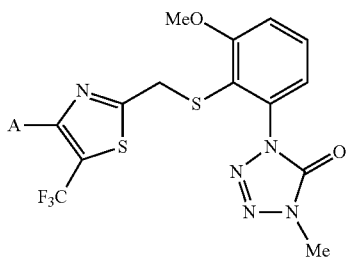
C0189
C0195
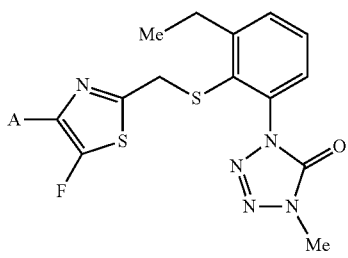
C0190
C0196
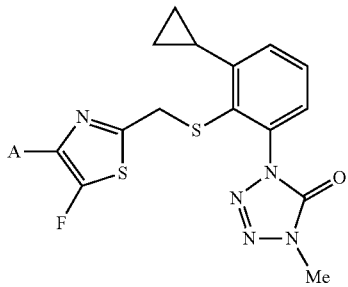
C0191
C0197
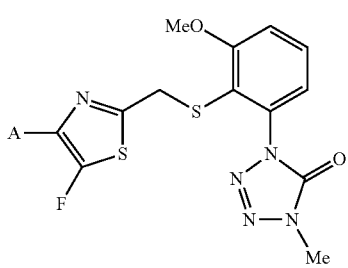
C0192
C0198
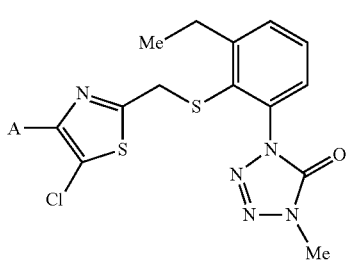
C0193
C0199

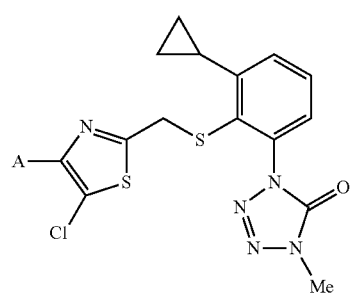
C0200
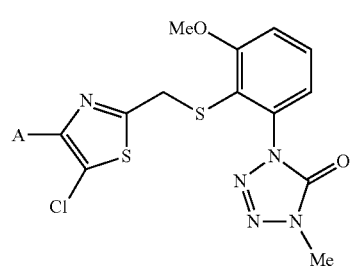
C0201
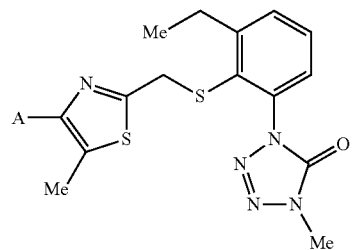
C0202
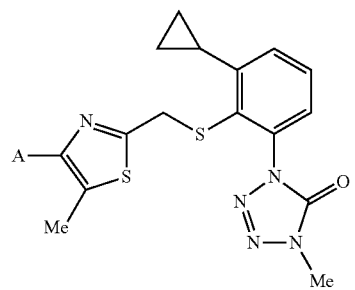
C0203
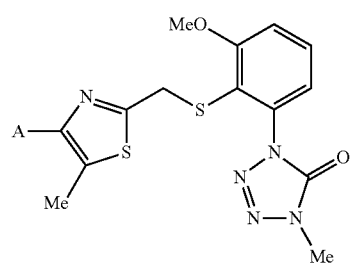
C0204
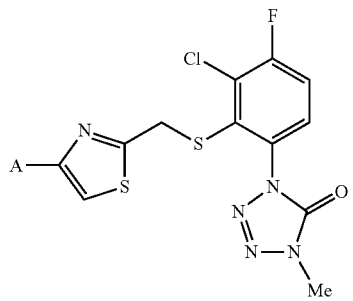
C0205
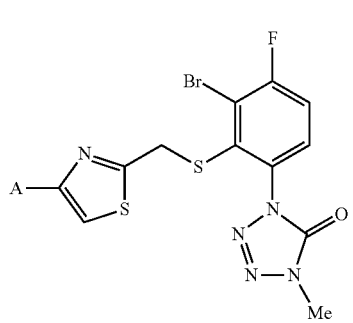
C0206
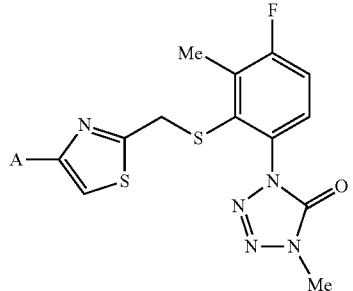
C0207
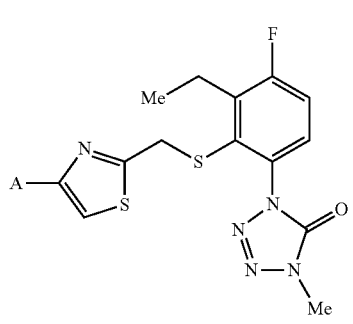
C0208
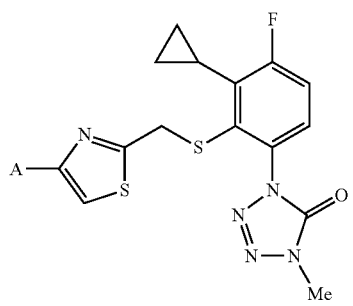
C0209

-continued
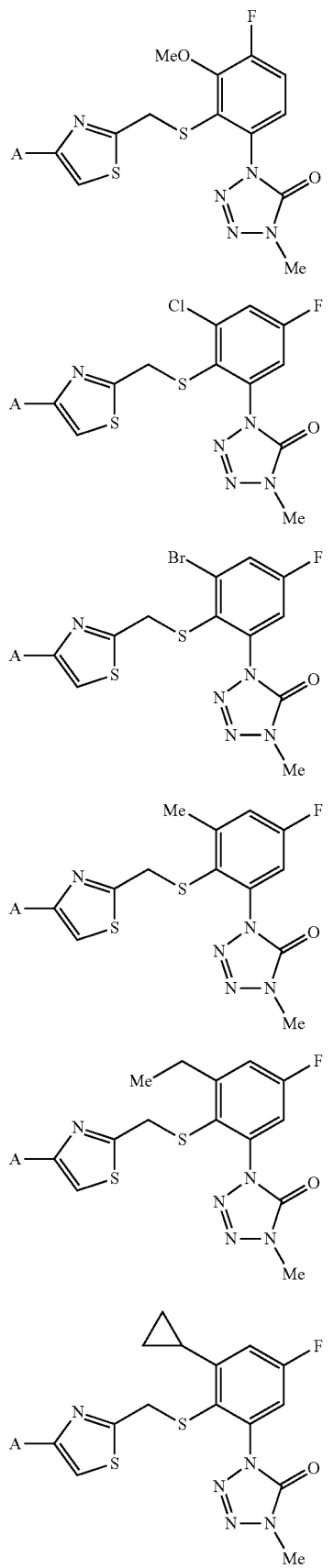
C0210
C0211
C0212
C0213
C0214
C0215
-continued
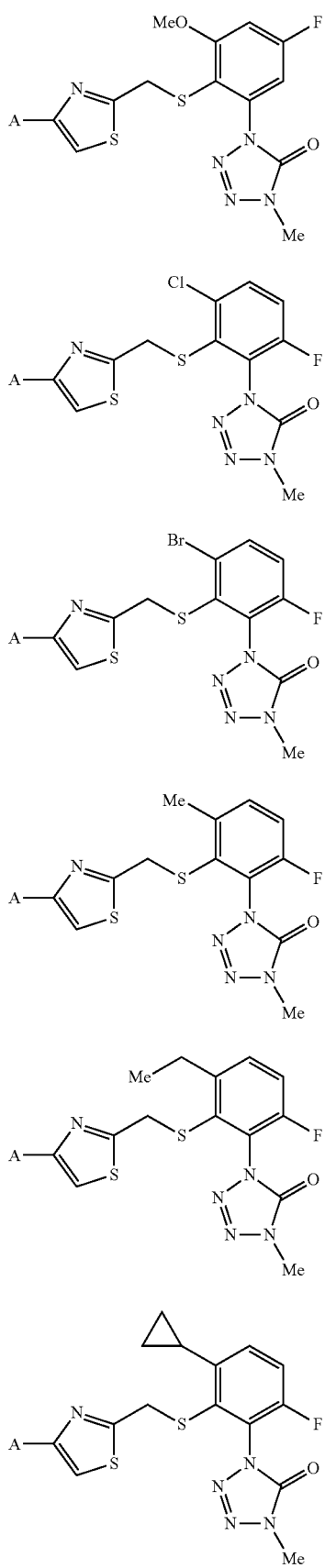
C0216
C0217
C0218
C0219
C0220
C0221

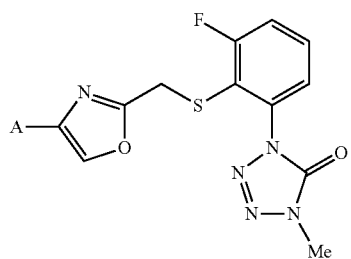
C0222
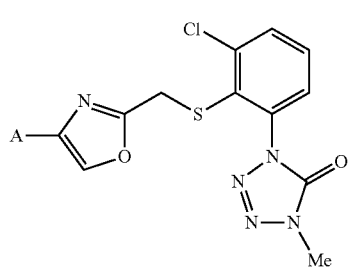
C0223
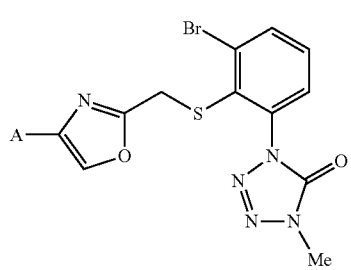
C0224
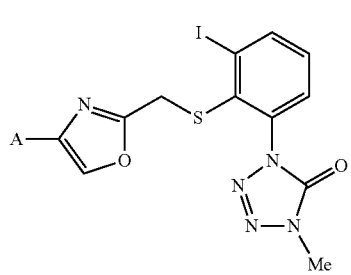
C0225
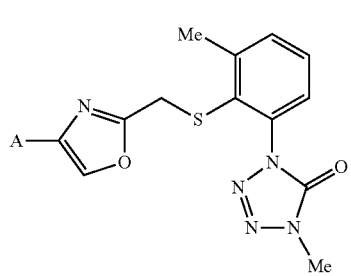
C0226
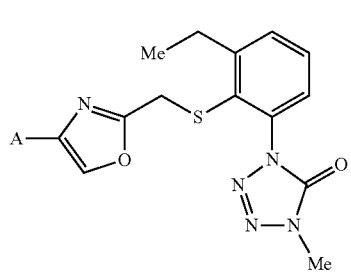
C0227
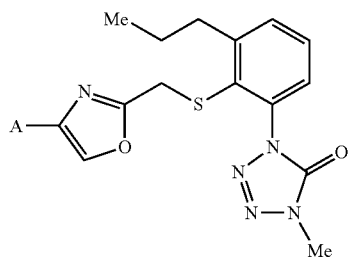
C0228
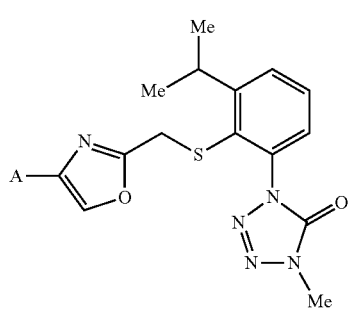
C0229
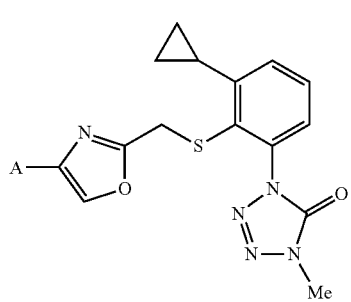
C0230
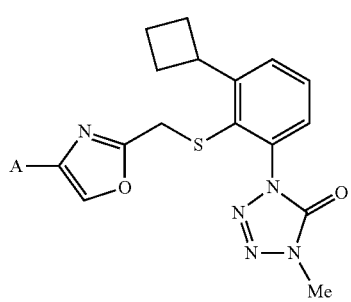
C0231
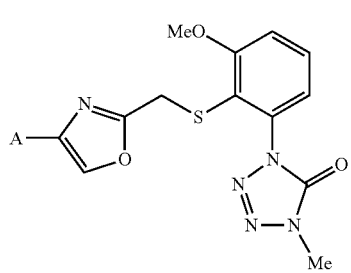
C0232

-continued
C0233
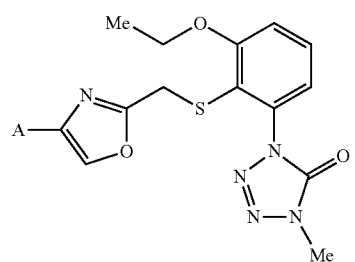
C0234
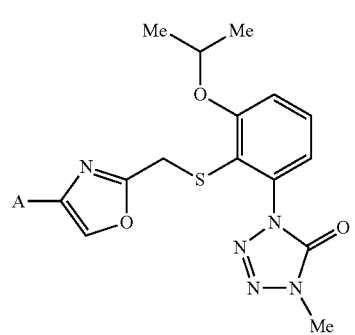
C0235
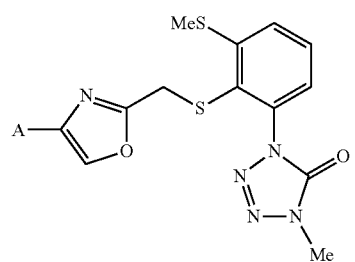
C0236
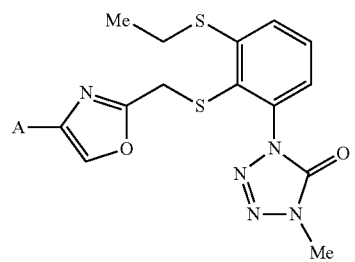
C0237
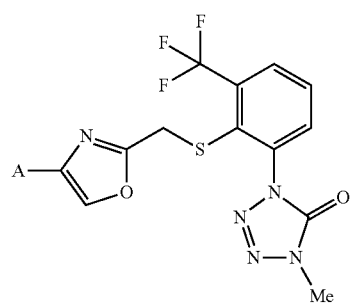
-continued
C0238
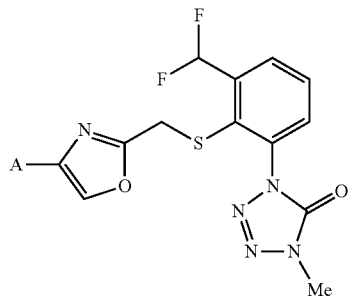
C0239
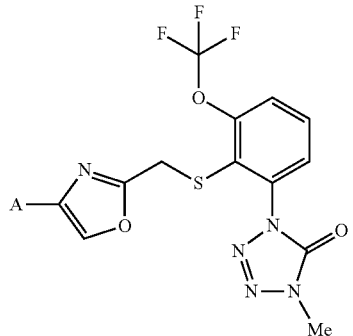
C0240
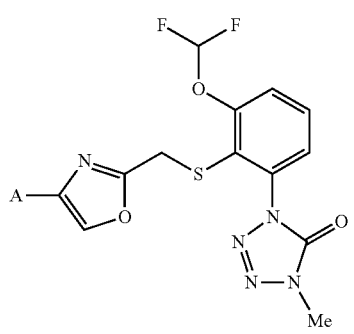
C0241
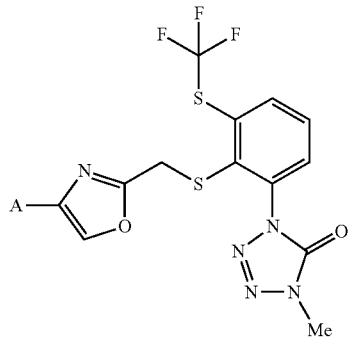
C0242

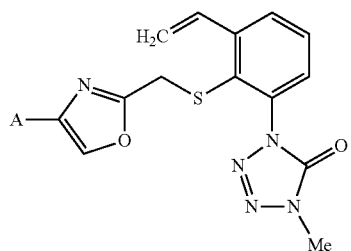
C0243
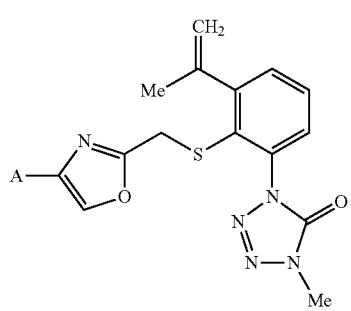
C0244
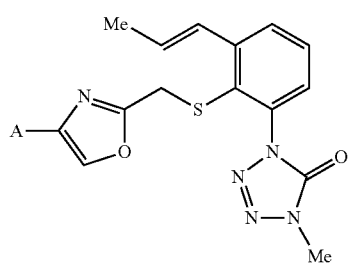
C0245
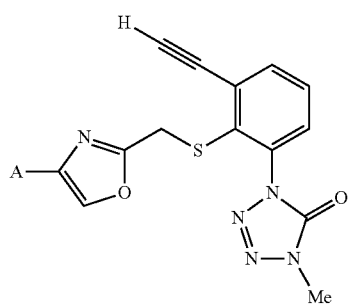
C0246
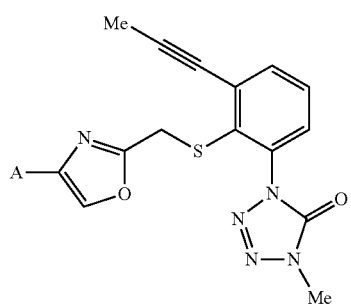
C0247
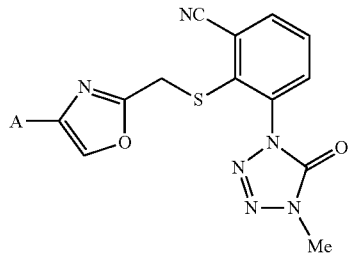
C0248
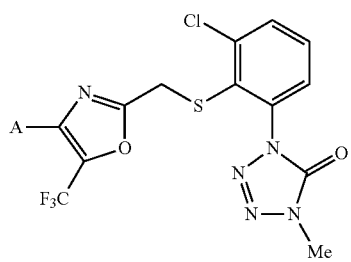
C0249
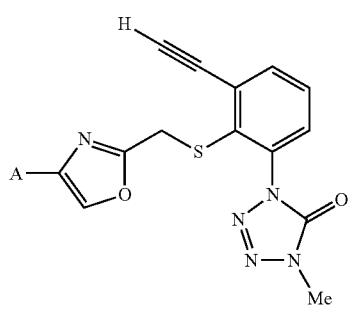
C0250
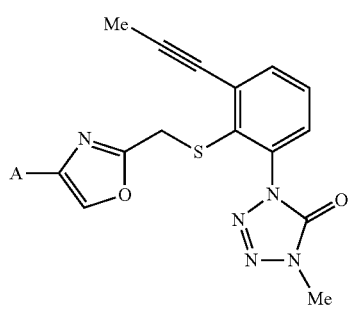
C0251
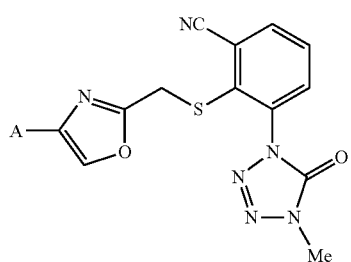
C0252

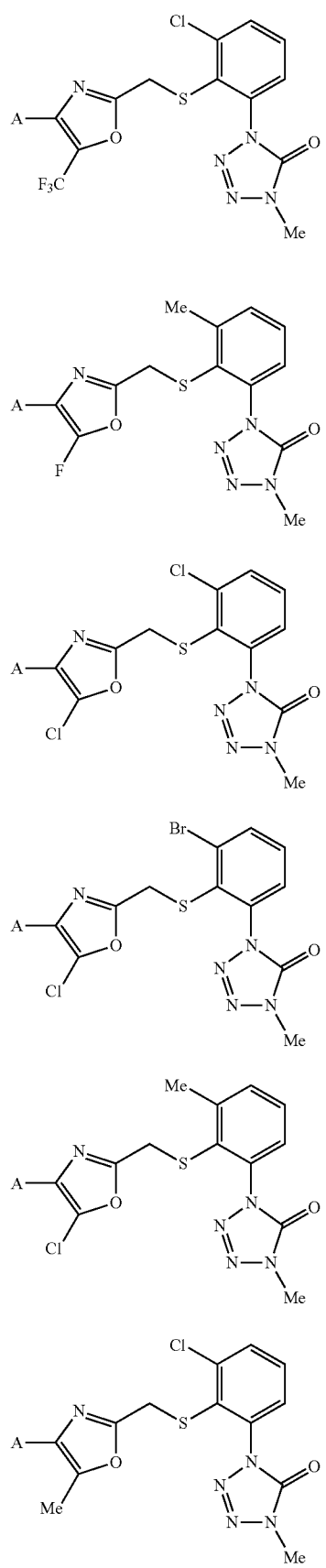
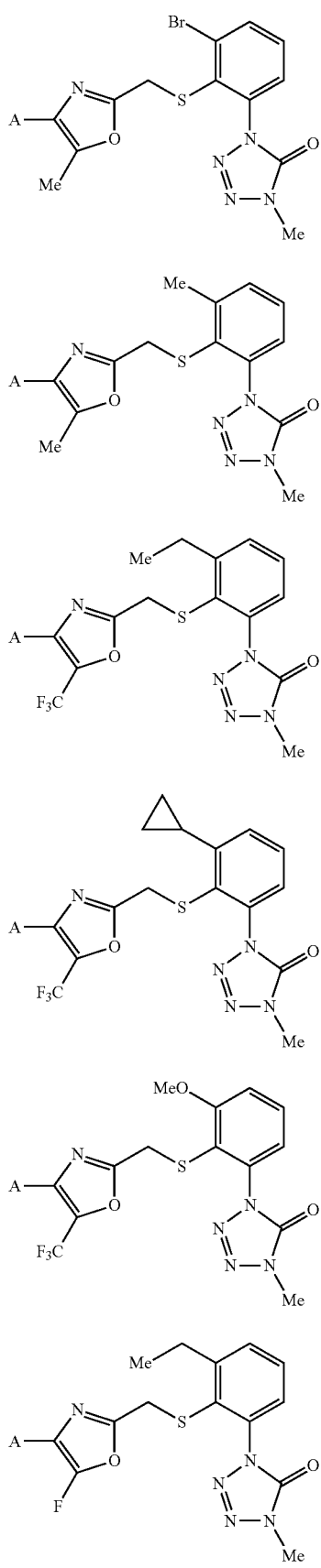

C0265 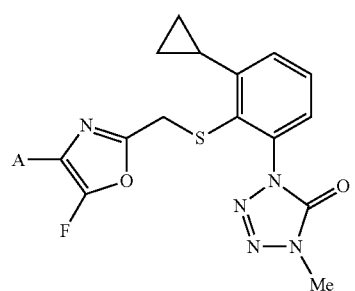
C0266 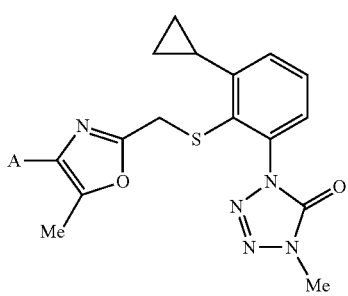

-continued
C0276
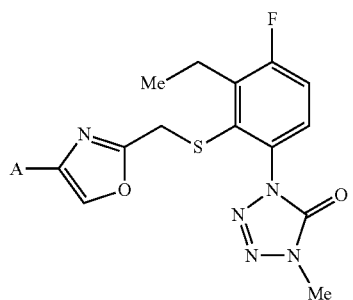
C0277
C0278
C0279
C0280
-continued
C0281
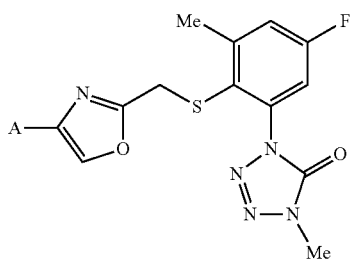
C0282
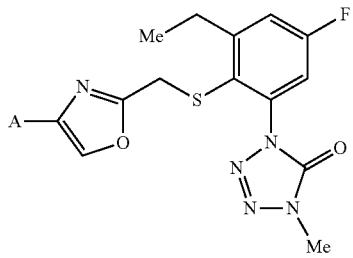
C0283
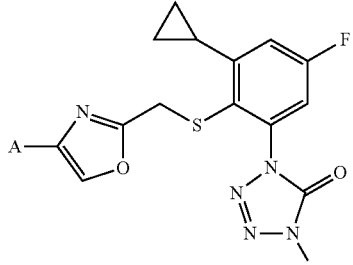
C0284
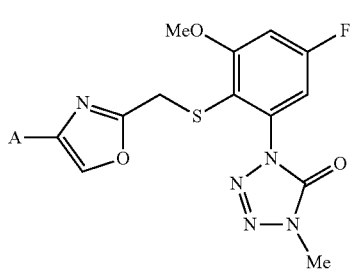
C0285
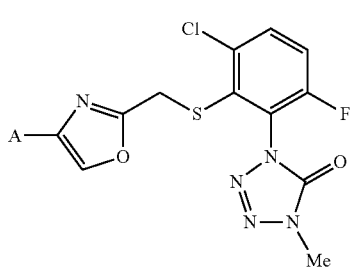
C0286
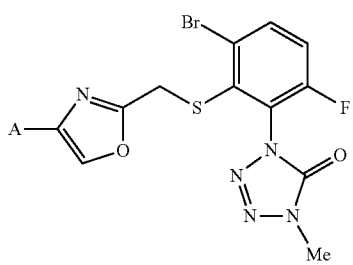

-continued
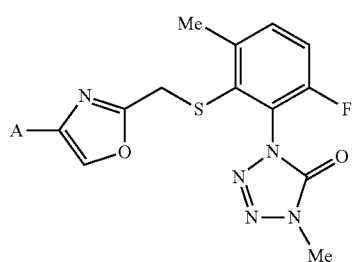
C0287
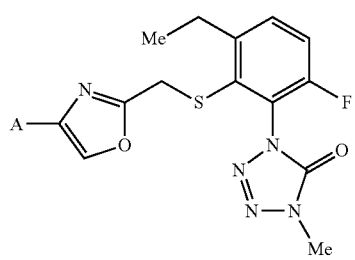
C0288
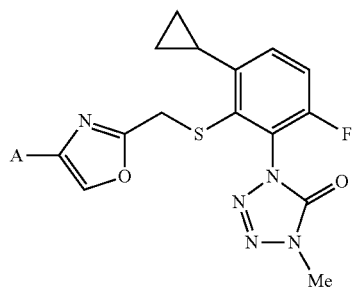
C0289
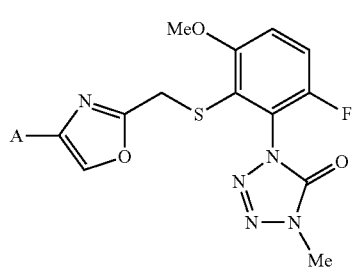
C0290
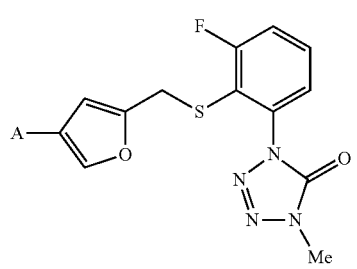
C0291
-continued
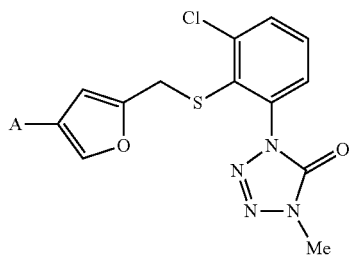
C0292
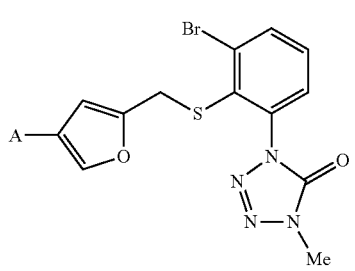
C0293
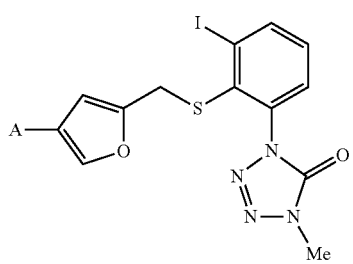
C0294
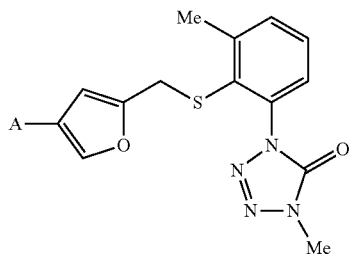
C0295
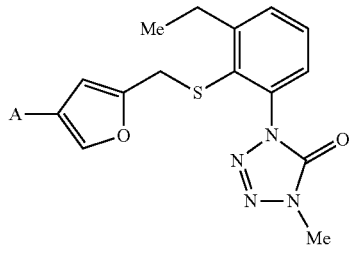
C0296
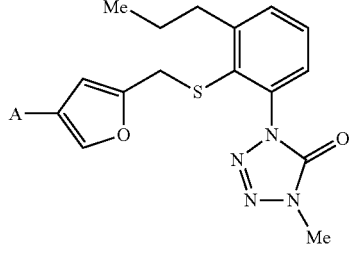
C0297

C0298 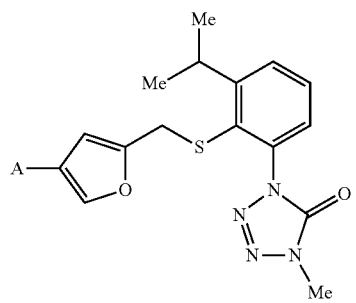
C0299 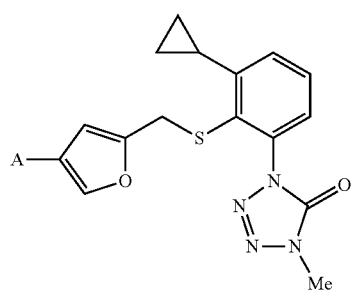
C0300 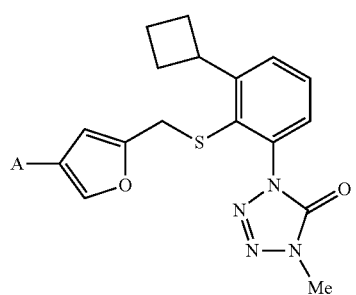
C0301 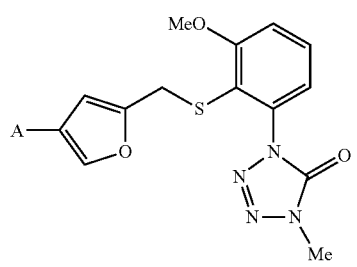
C0302 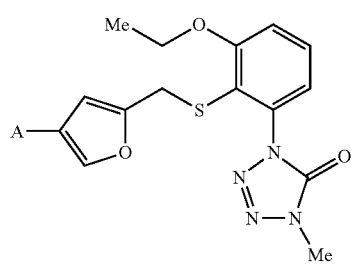
C0303 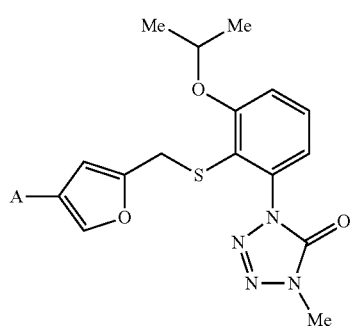
C0304 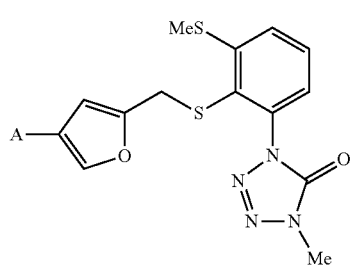
C0305 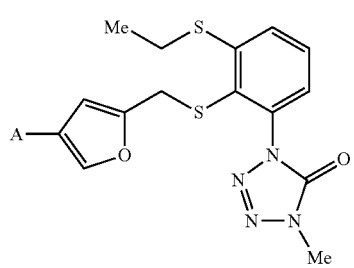
C0306 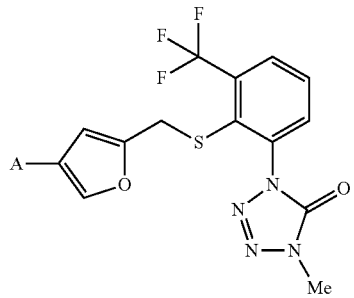
C0307 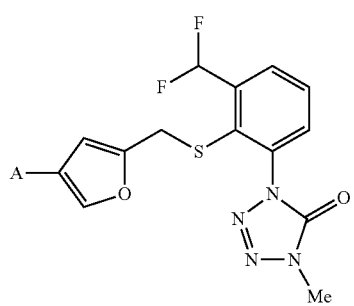

-continued
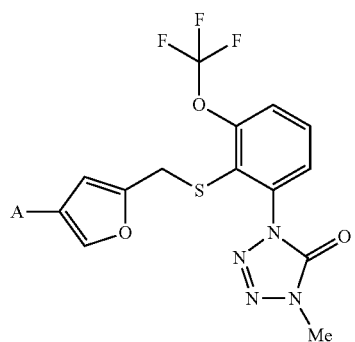 C0308
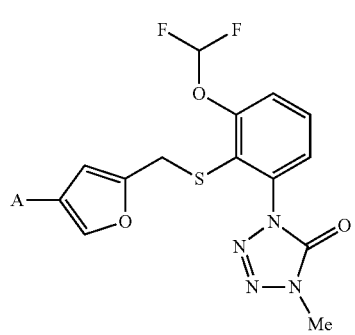 C0309
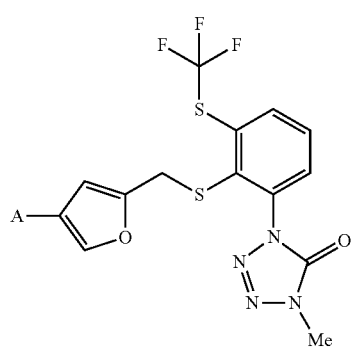 C0310
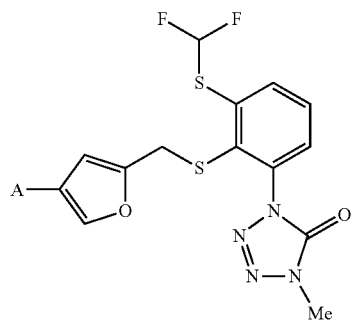 C0311
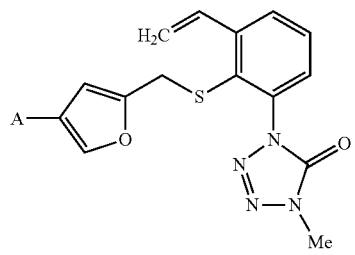 C0312
-continued
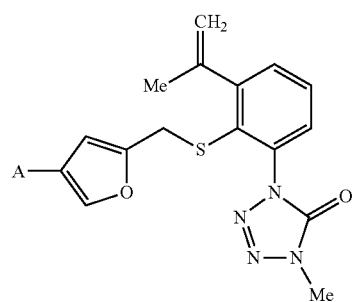 C0313
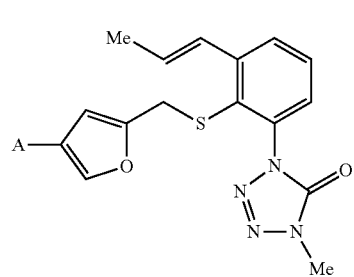 C0314
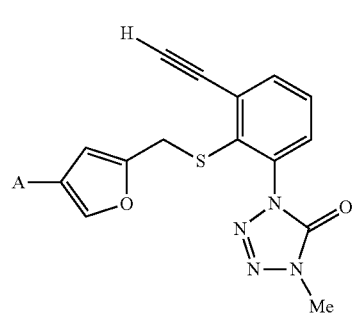 C0315
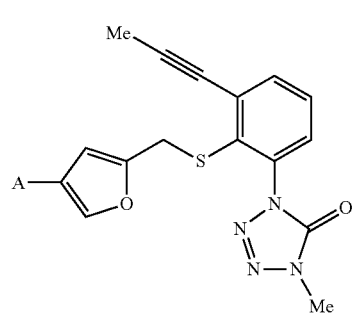 C0316
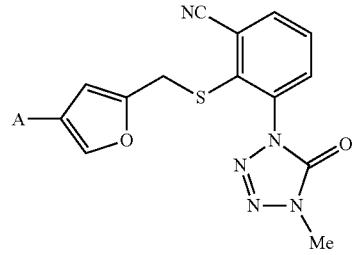 C0317

-continued
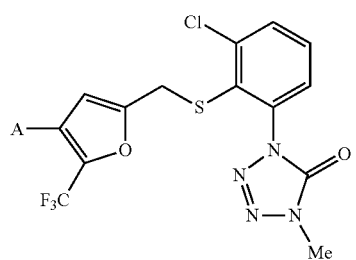
C0318
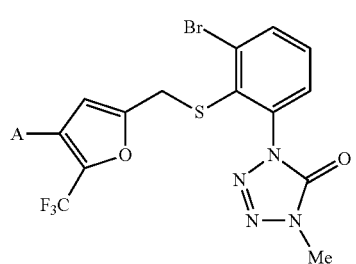
C0319
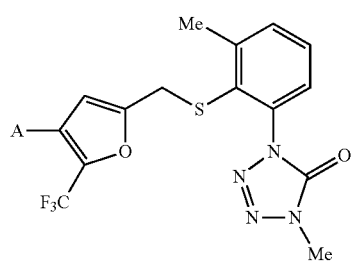
C0320
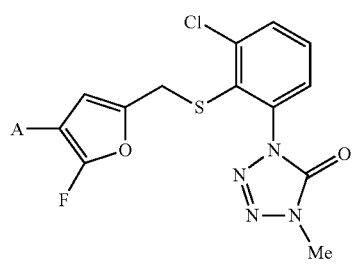
C0321
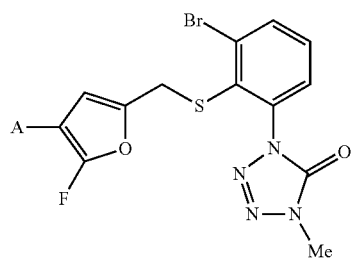
C0322
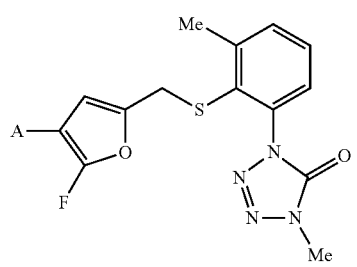
C0323
-continued
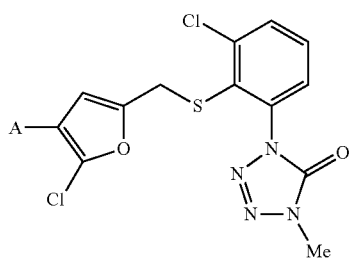
C0324
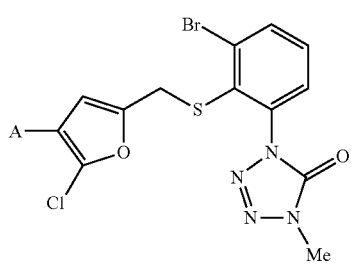
C0325
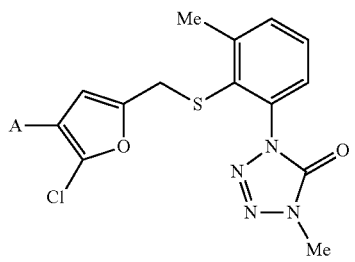
C0326
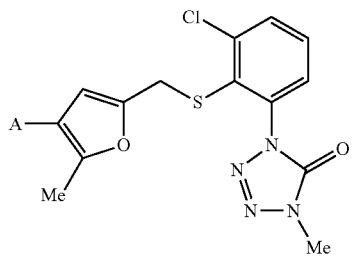
C0327
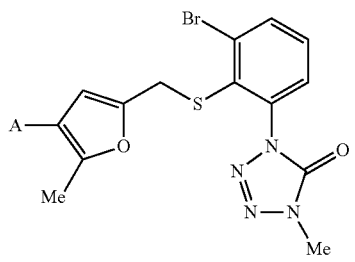
C0328
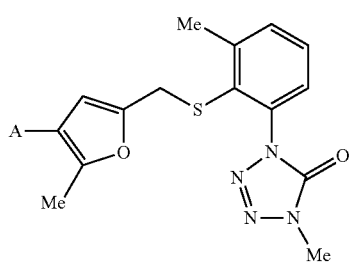
C0329

| | |
|---|---|
| C0330 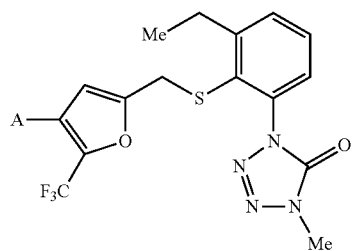 | C0336 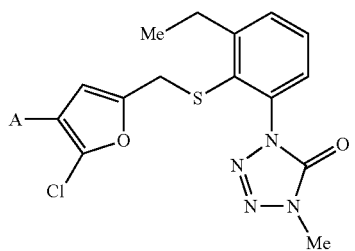 |
| C0331 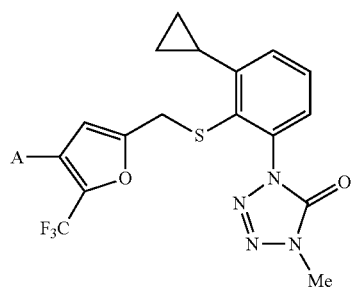 | C0337 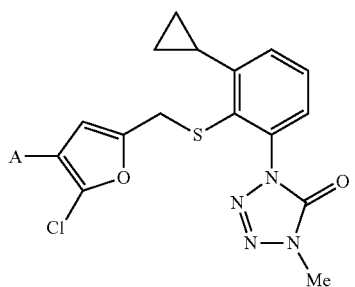 |
| C0332 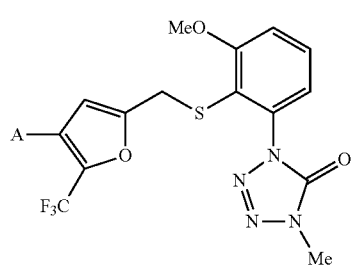 | C0338 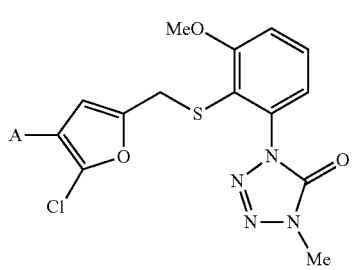 |
| C0333 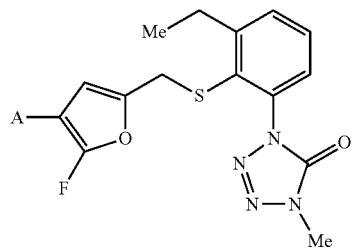 | C0339 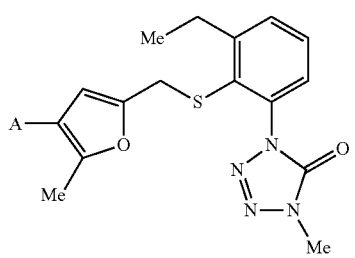 |
| C0334 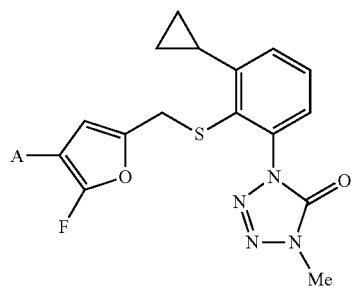 | C0340 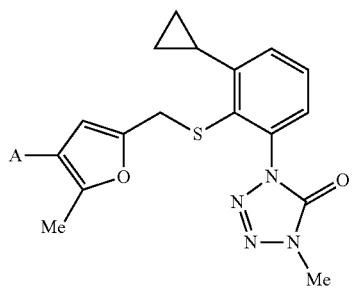 |
| C0335 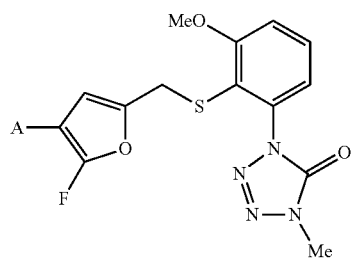 | C0341 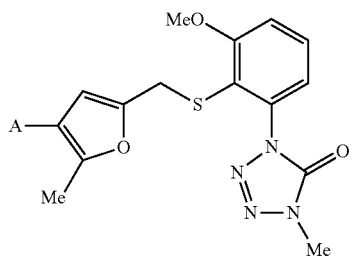 |

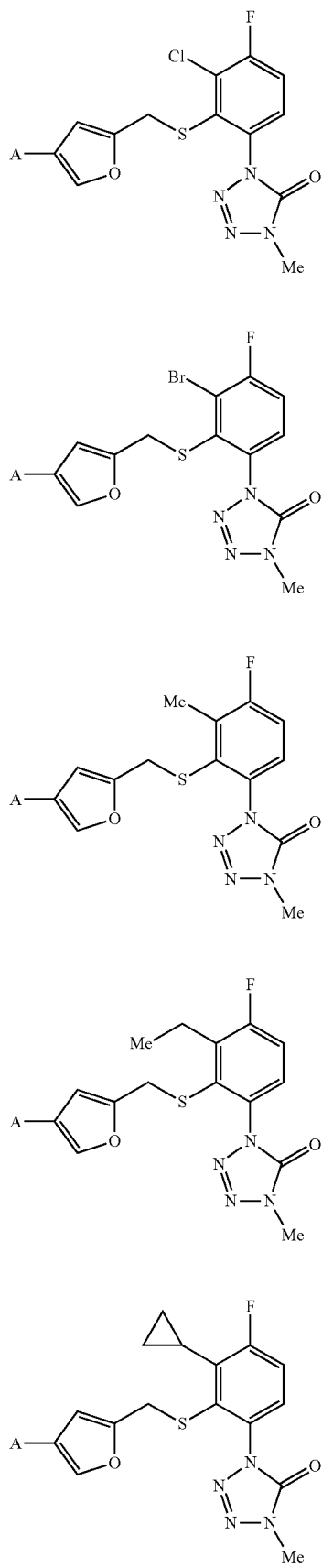
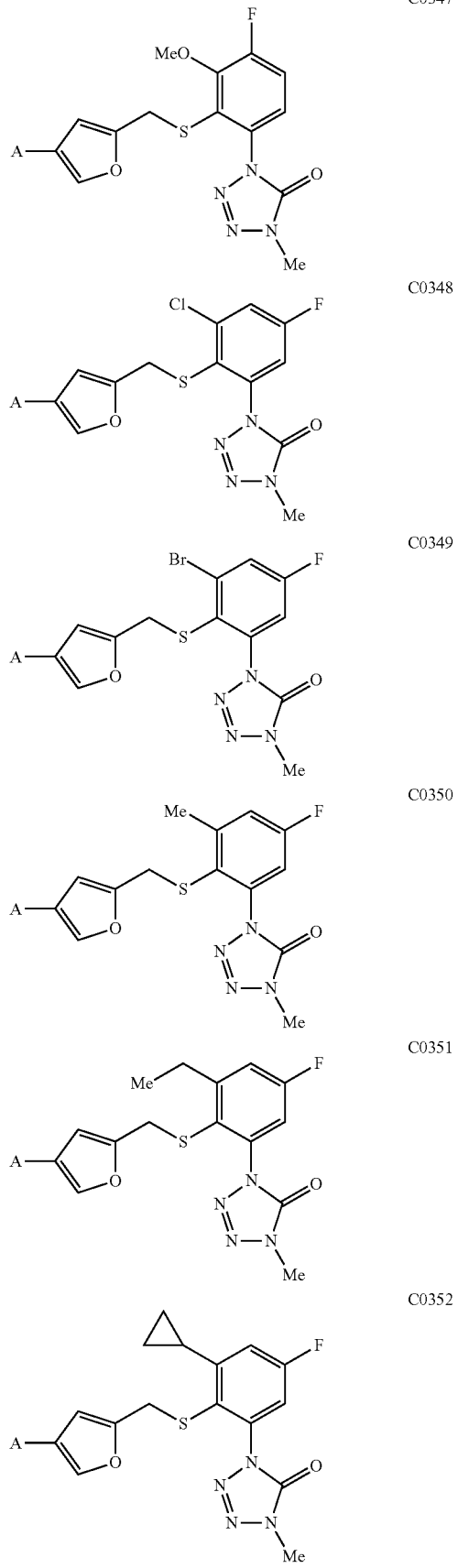

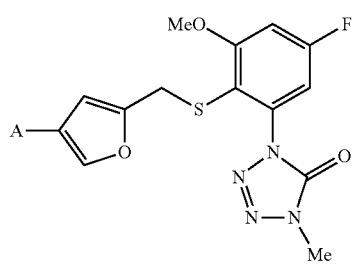
C0353
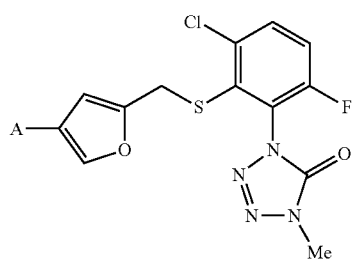
C0354
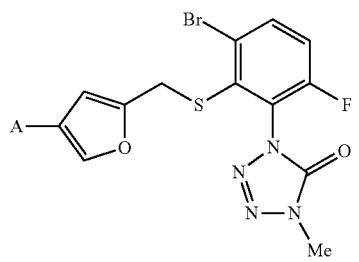
C0355
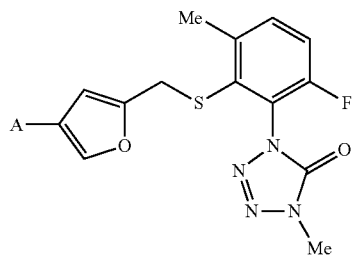
C0356
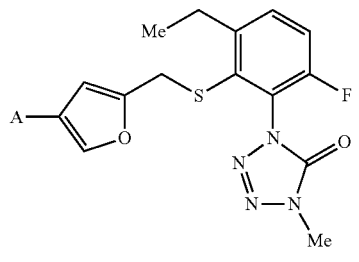
C0357
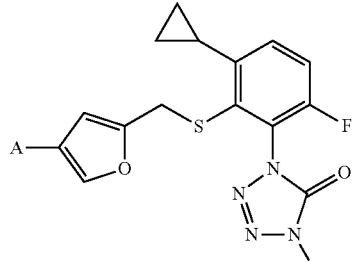
C0358
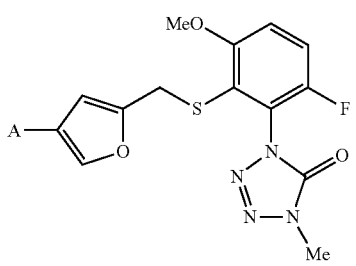
C0359
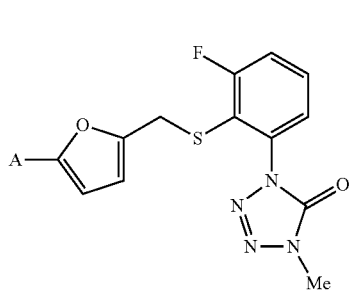
C0360
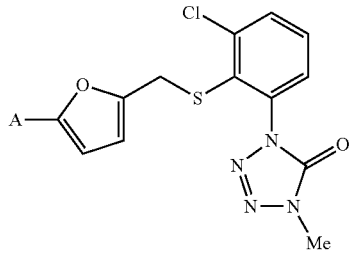
C0361
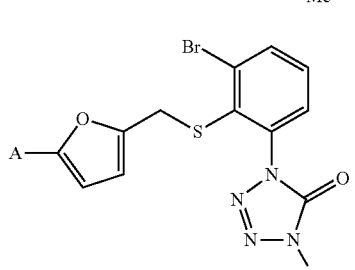
C0362
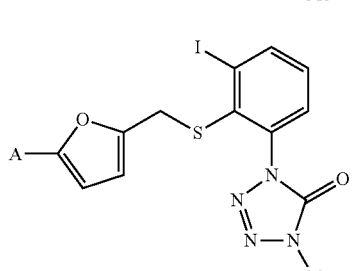
C0363
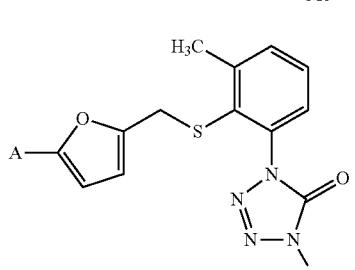
C0364

| | |
|---|---|
| C0365 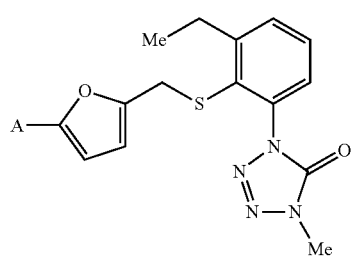 | C0370 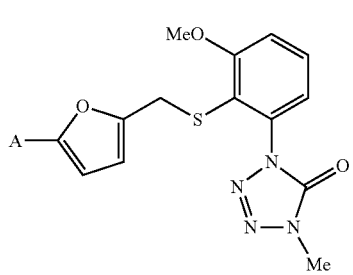 |
| C0366 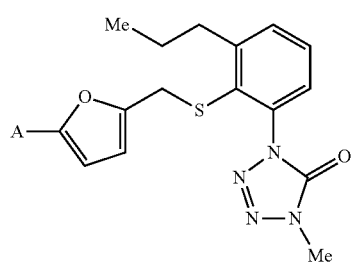 | C0371 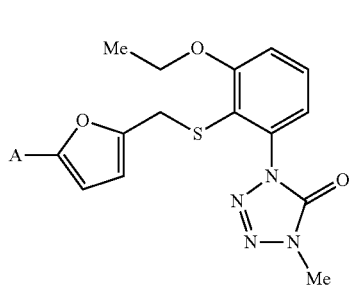 |
| C0367 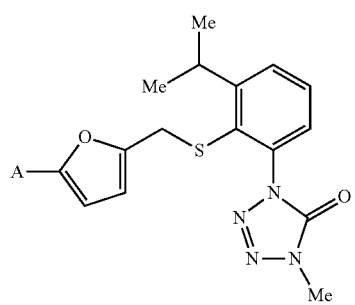 | C0372 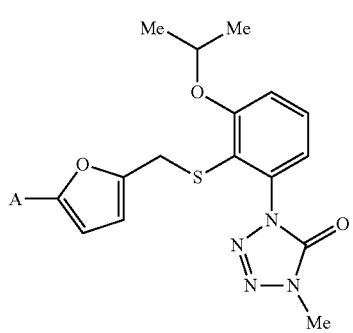 |
| C0368 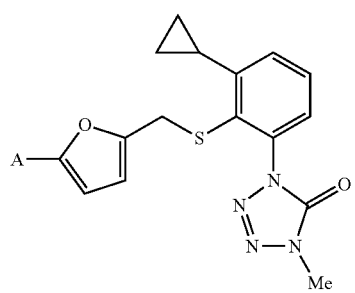 | C0373 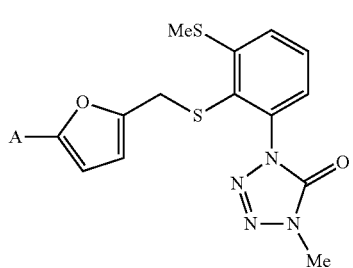 |
| C0369 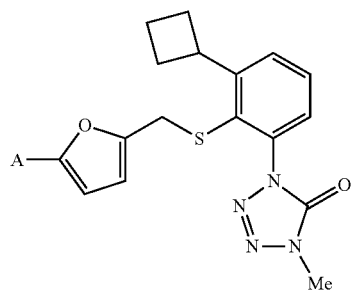 | C0374 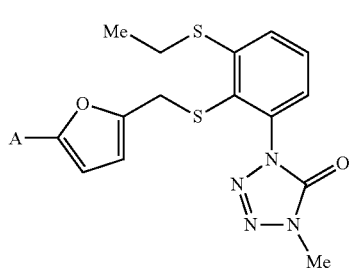 |

C0375
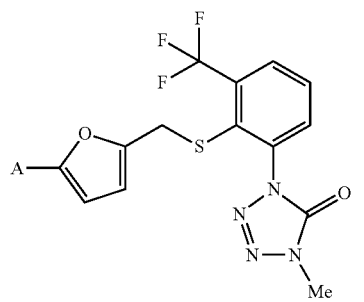
C0376
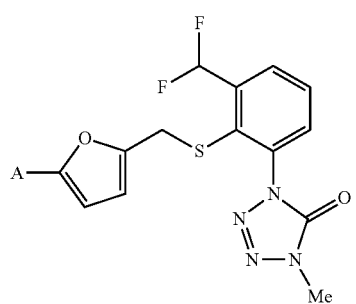
C0377
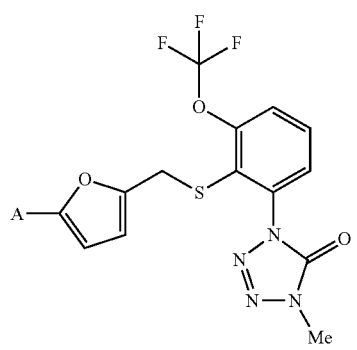
C0378
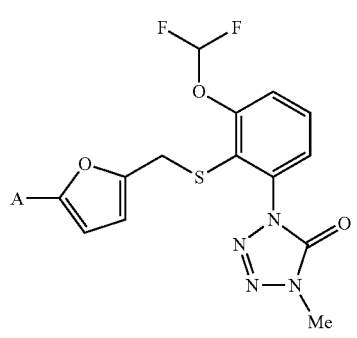
C0379

C0380
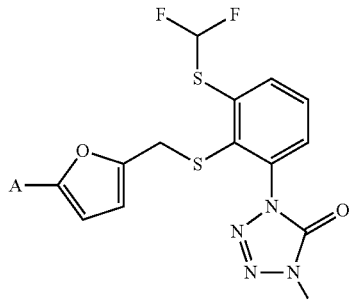
C0381
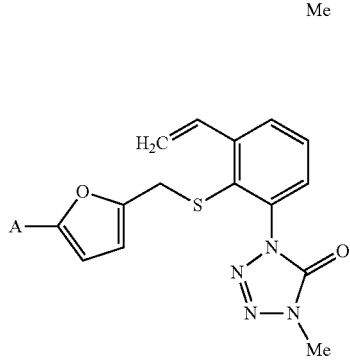
C0382
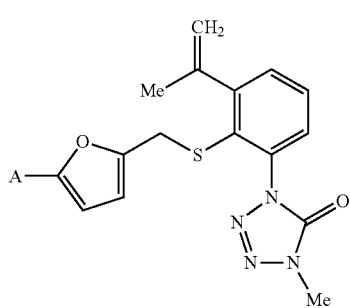
C0383
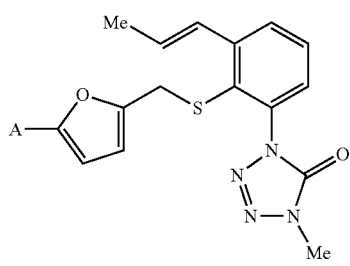
C0384
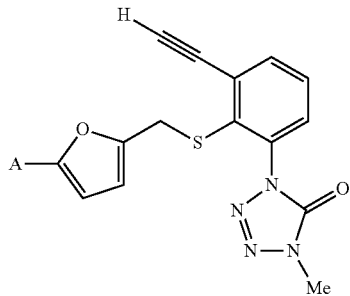

C0385 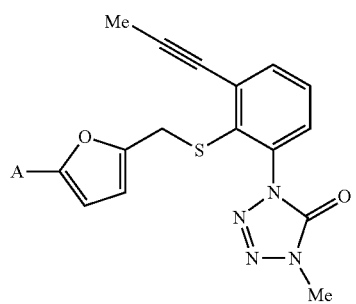
C0386 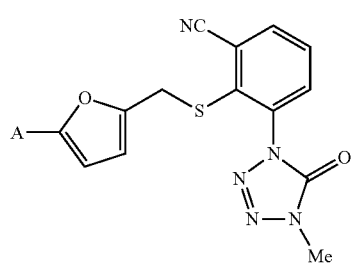
C0387 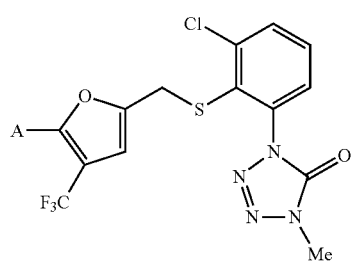
C0388 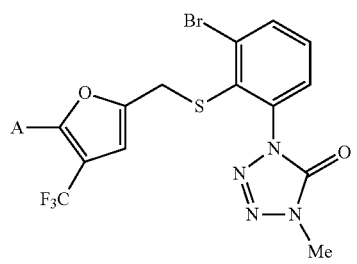
C0389 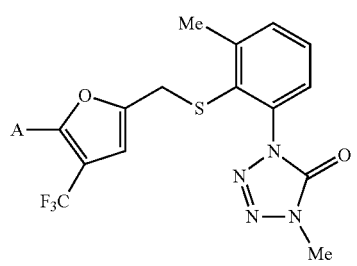
C0390 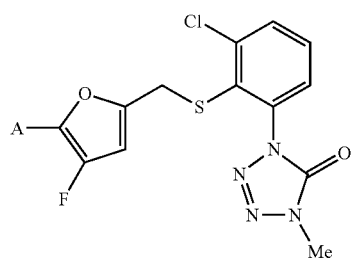
C0391 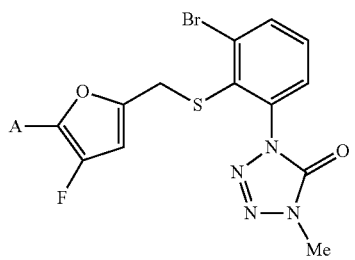
C0392 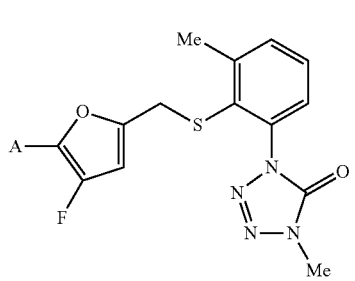
C0393 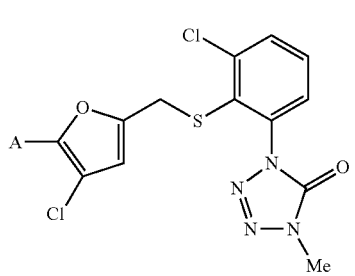
C0394 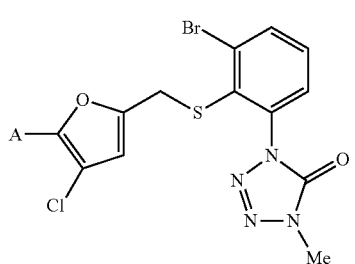
C0395 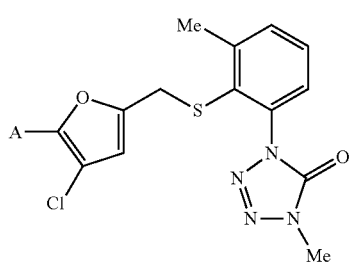
C0396 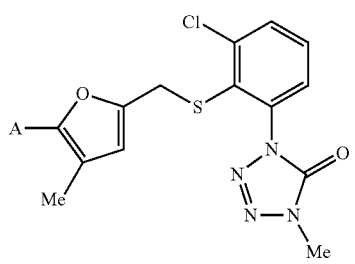

-continued
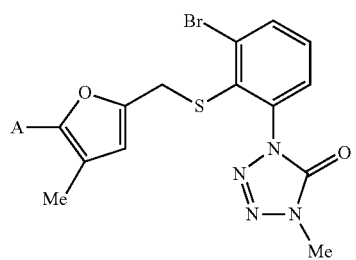
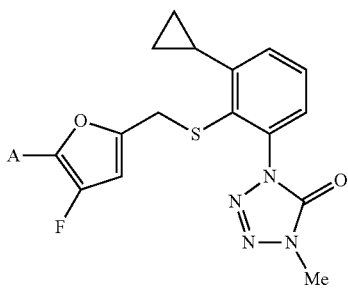

C0409
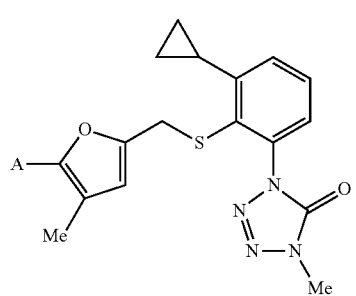
C0410
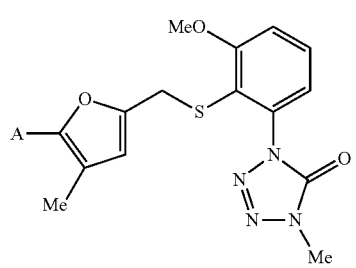
C0411
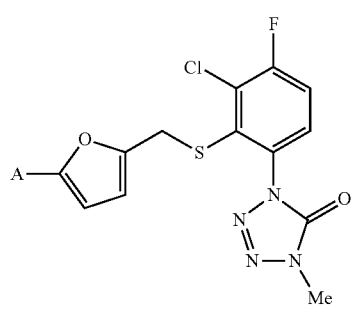
C0412
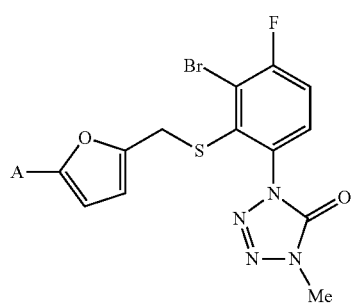
C0413
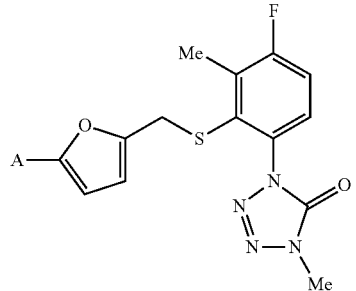
C0414
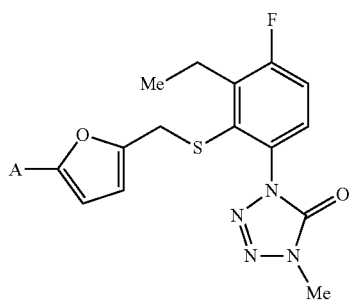
C0415
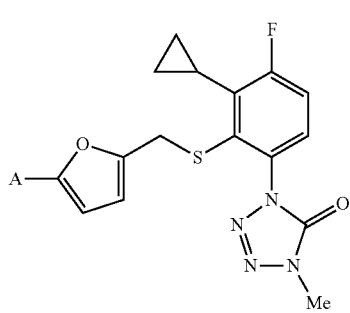
C0416
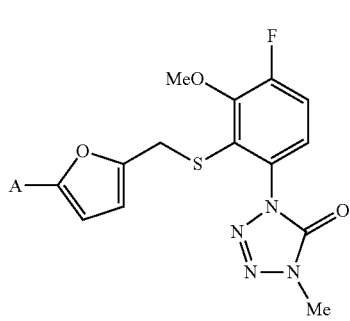
C0417
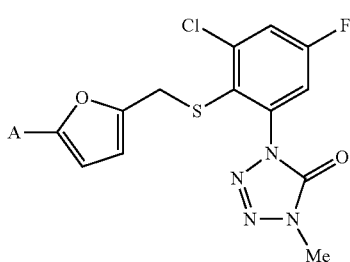
C0418
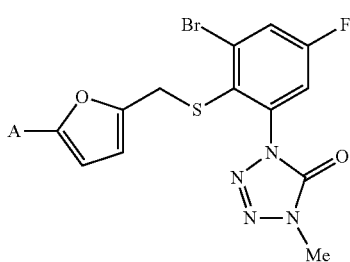

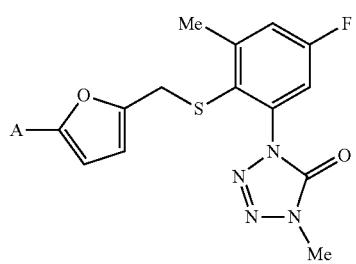
C0419
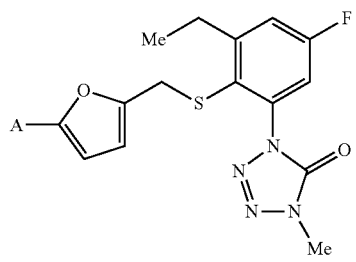
C0420
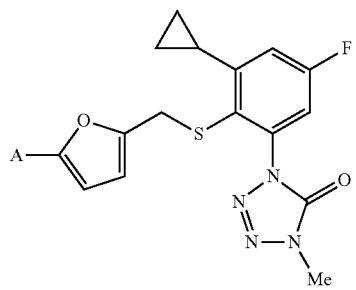
C0421
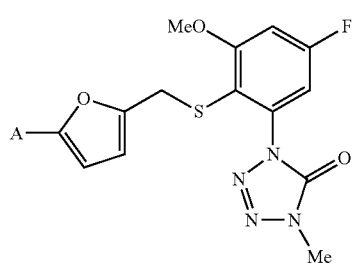
C0422
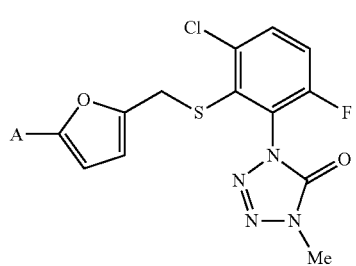
C0423
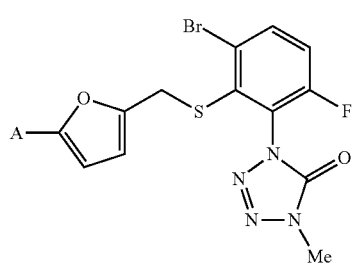
C0424
C0425
C0426
C0427
C0428
C0429
C0430

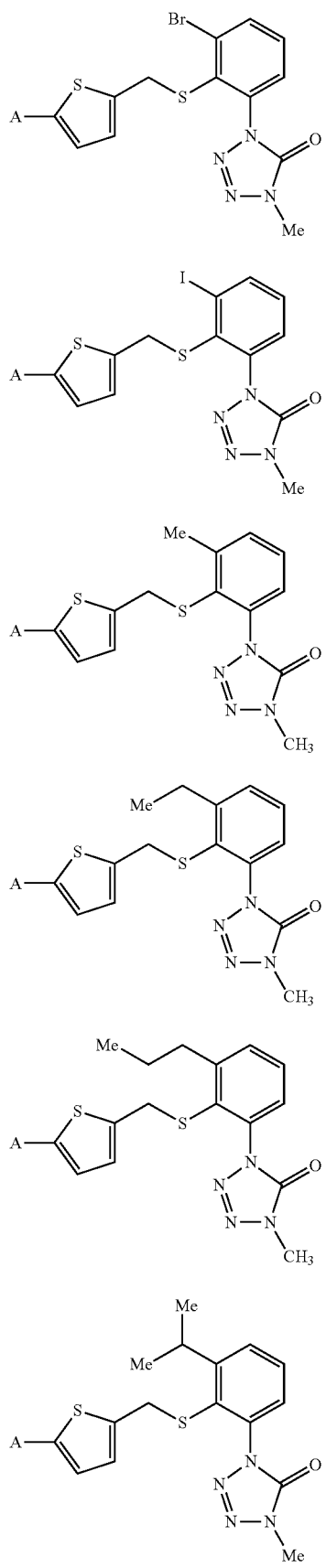
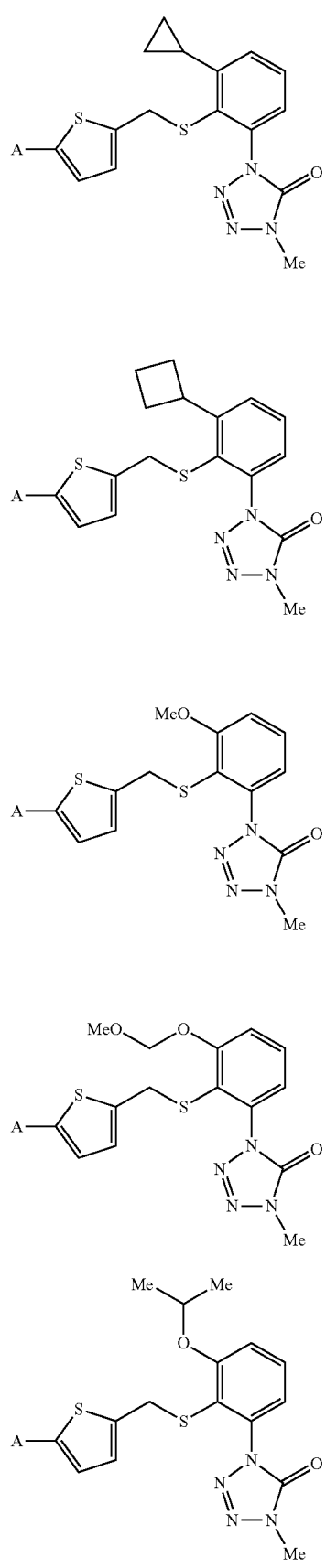

| | |
|---|---|
| C0442 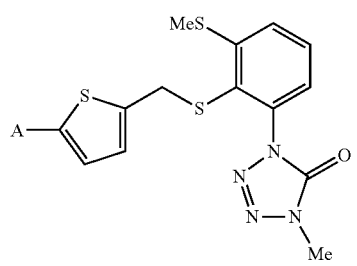 | C0447 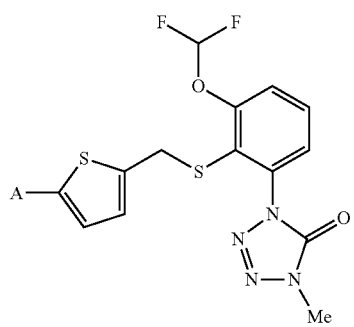 |
| C0443 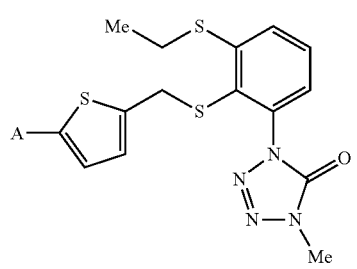 | C0448 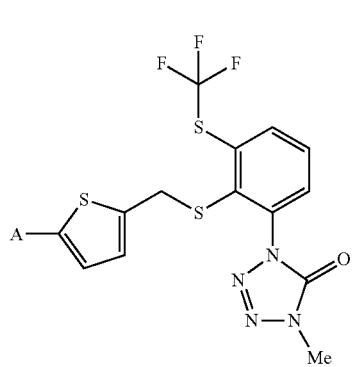 |
| C0444 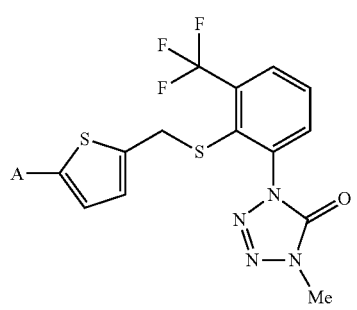 | C0449 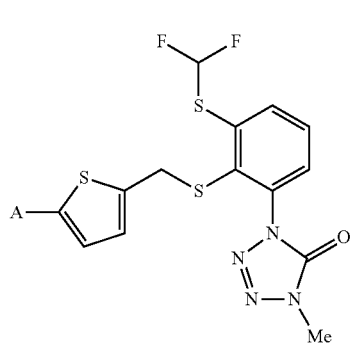 |
| C0445 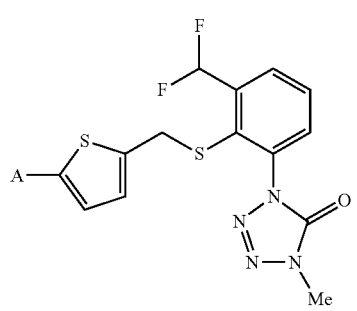 | C0450 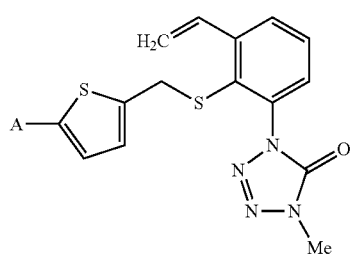 |
| C0446 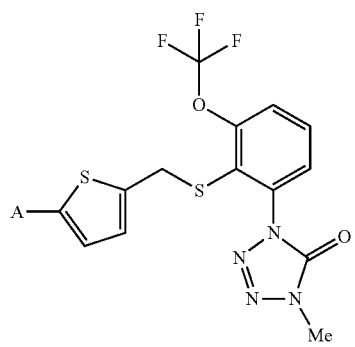 | C0451 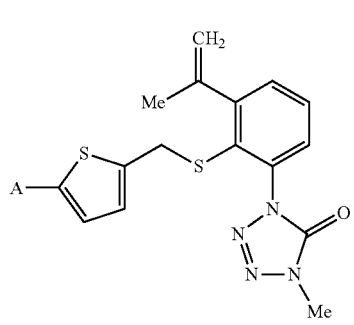 |

| | |
|---|---|
| C0452 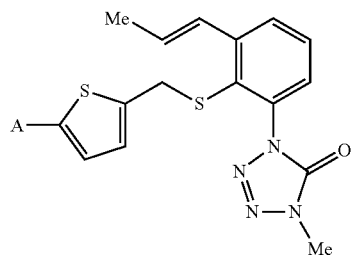 | C0458 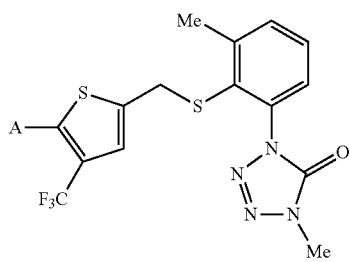 |
| C0453 | C0459 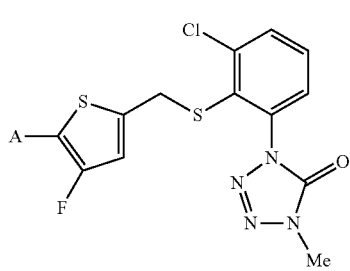 |
| C0454 | C0460 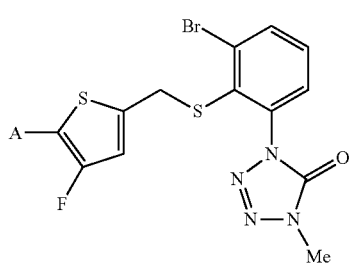 |
| C0455 | C0461 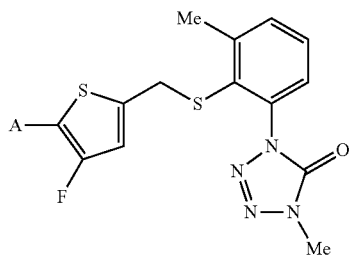 |
| C0456 | C0462 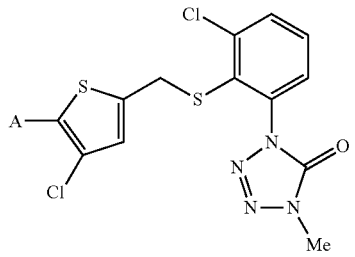 |
| C0457 | C0463 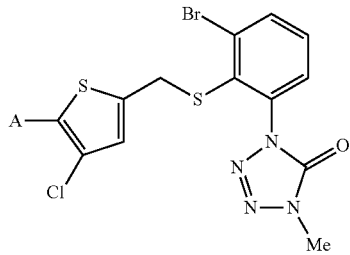 |

-continued
C0464
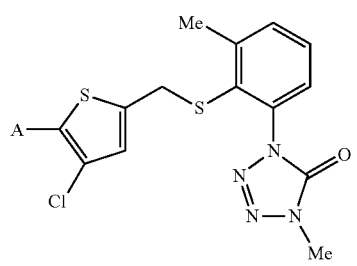
C0465
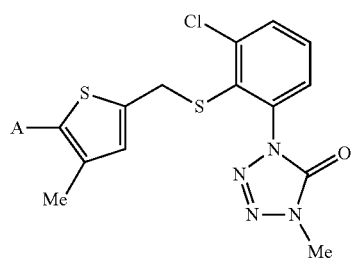
C0466
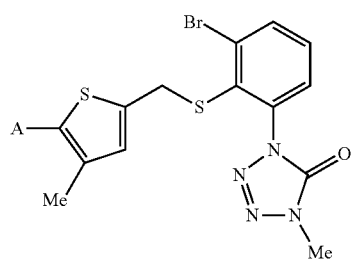
C0467
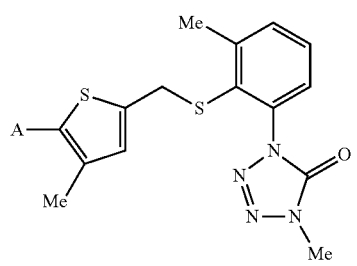
C0468
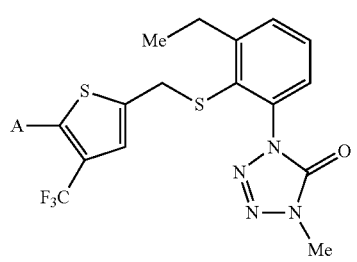
C0469
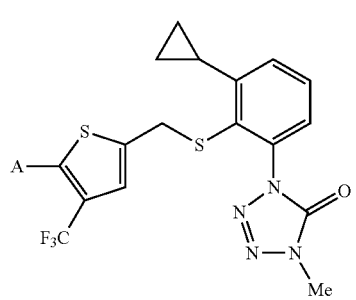
-continued
C0470
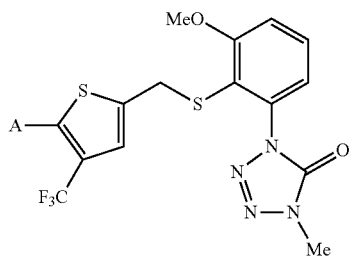
C0471
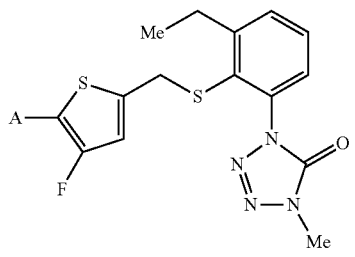
C0472
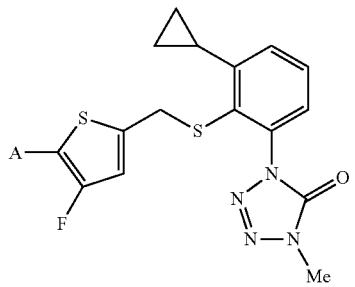
C0473
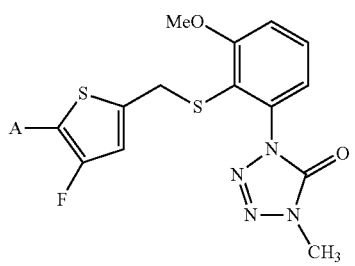
C0474
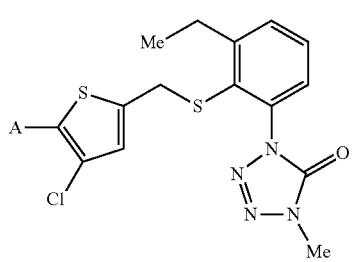
C0475
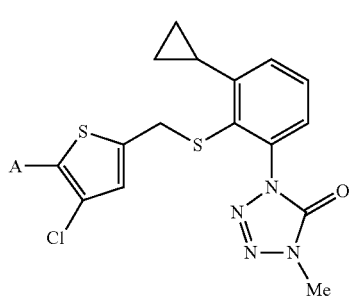

C0476
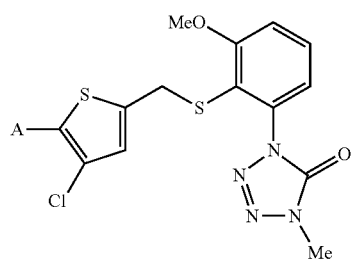
C0477
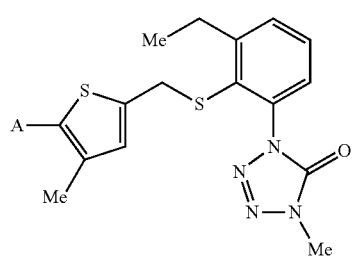
C0478
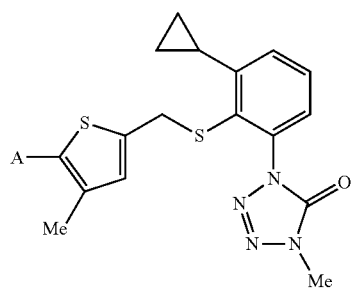
C0479
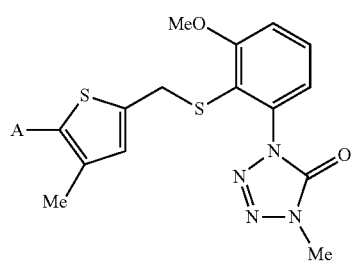
C0480
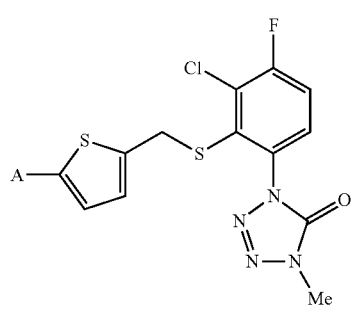
C0481
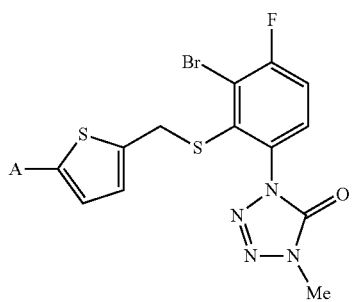
C0482
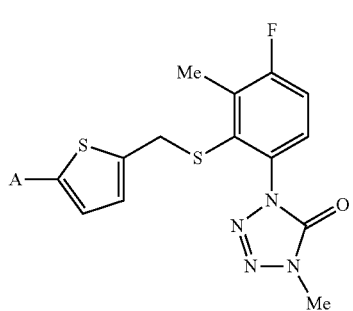
C0483
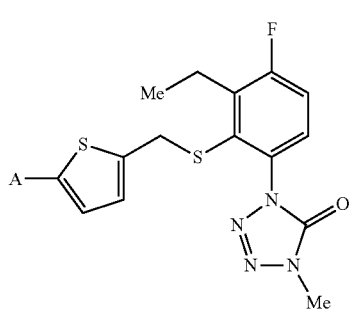
C0484
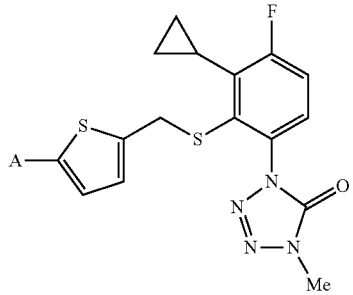
C0485
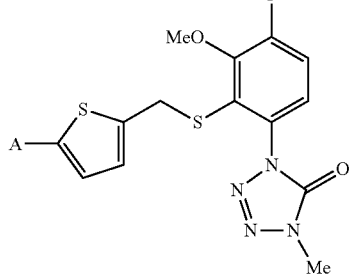

299
-continued
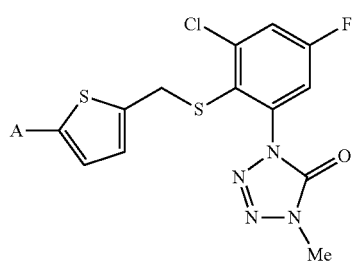
C0486
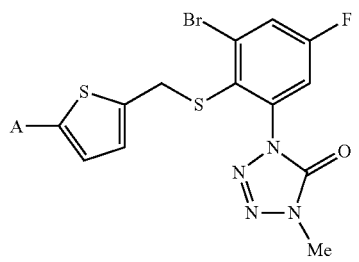
C0487
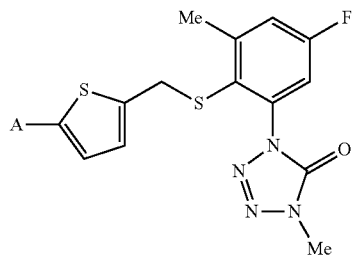
C0488
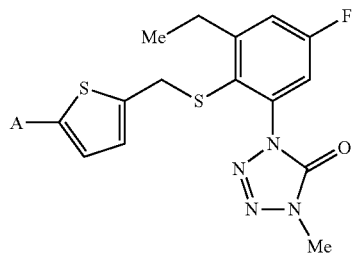
C0489
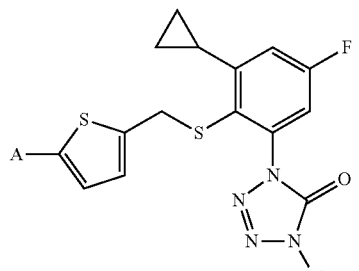
C0490
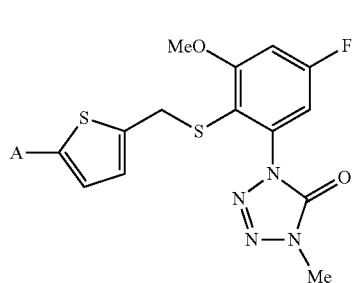
C0491
300
-continued
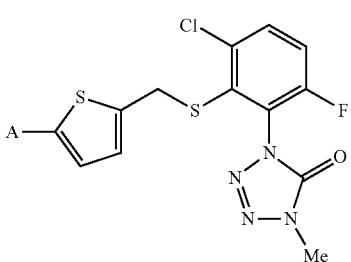
C0492
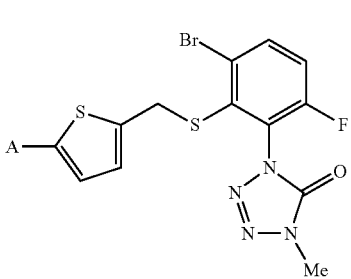
C0493
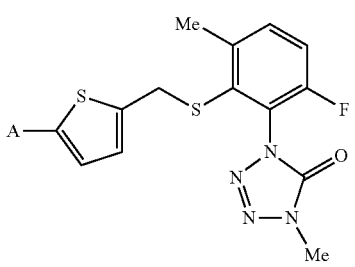
C0494
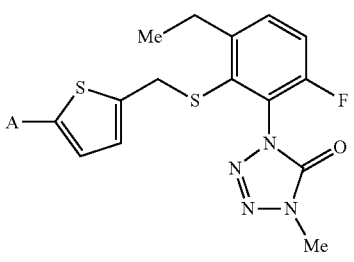
C0495
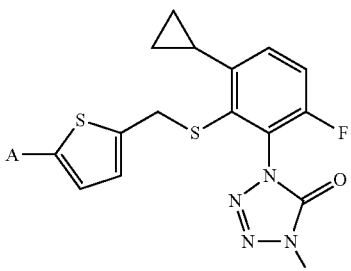
C0496
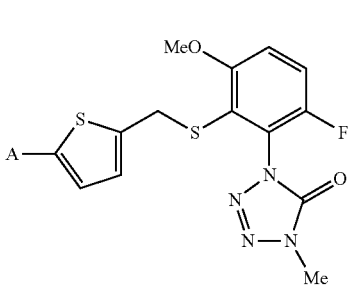
C0497

C0498 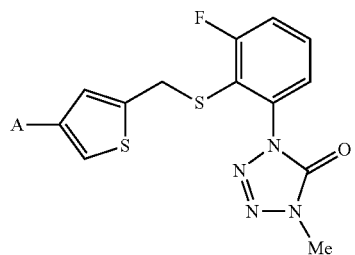
C0499 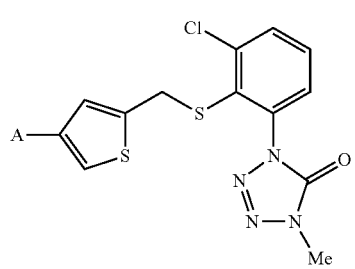
C0500 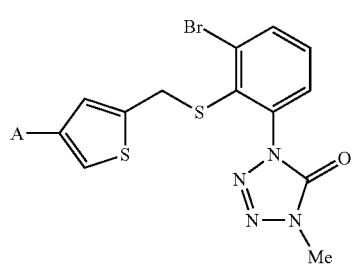
C0501 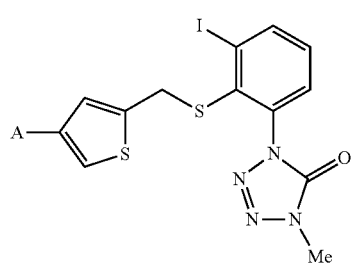
C0502 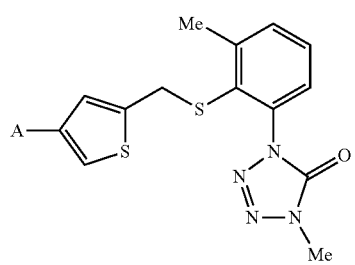
C0503 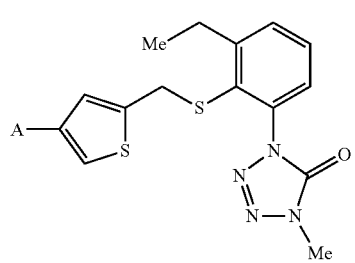
C0504 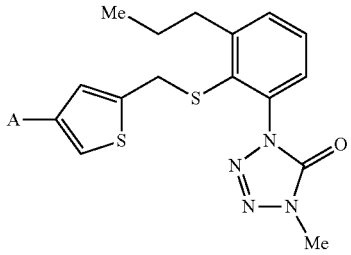
C0505 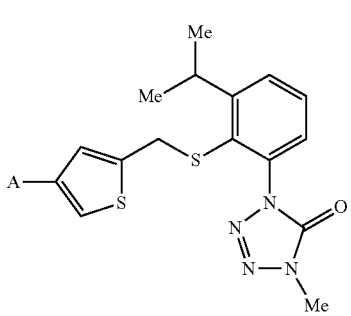
C0506 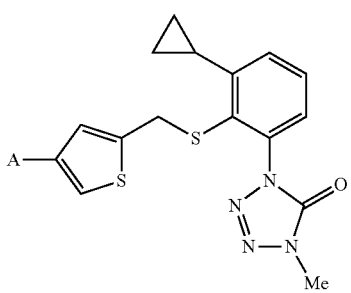
C0507 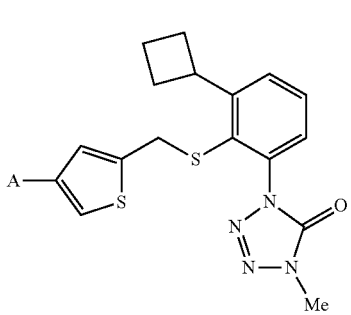
C0508 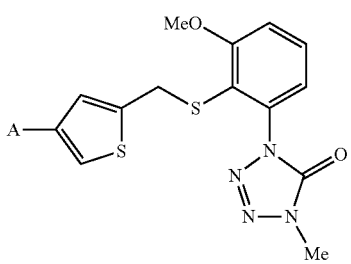

| | |
|---|---|
| C0509 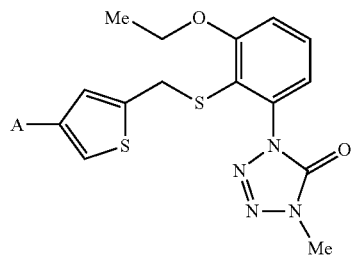 | C0514 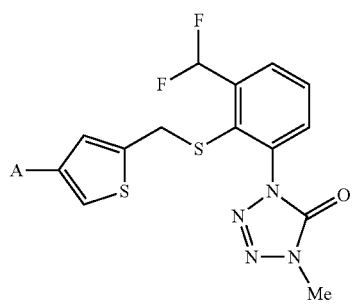 |
| C0510 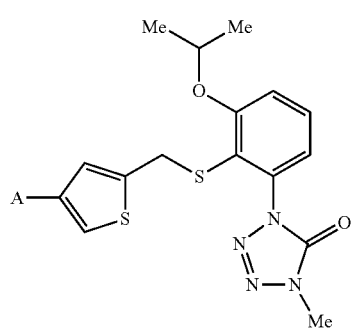 | C0515 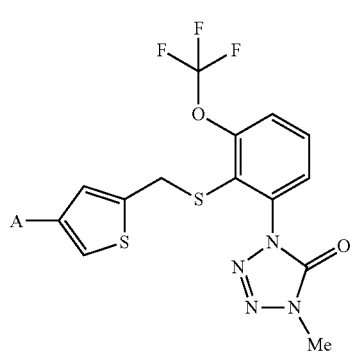 |
| C0511 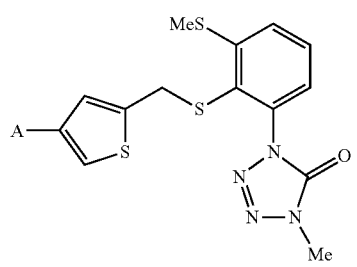 | C0516 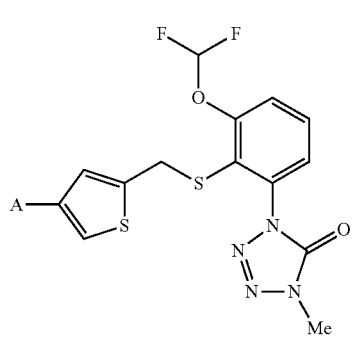 |
| C0512 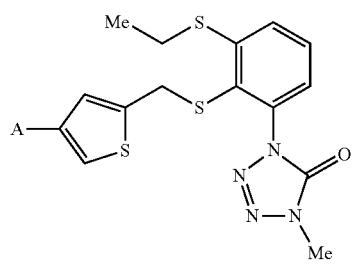 | C0517 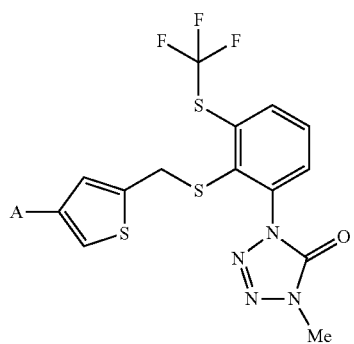 |
| C0513 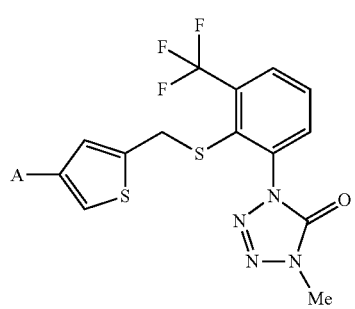 | C0518 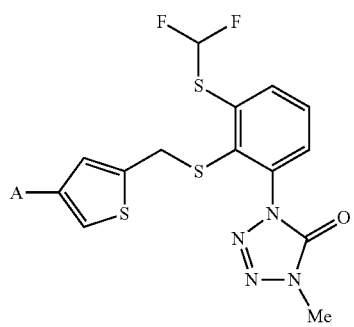 |

-continued
| | |
|---|---|
| 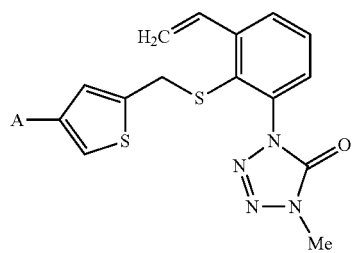 C0519 | 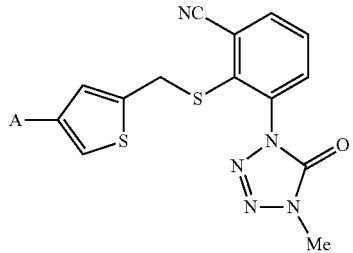 C0524 |
| 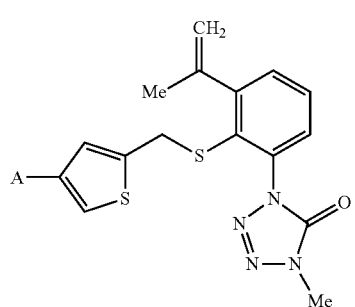 C0520 | 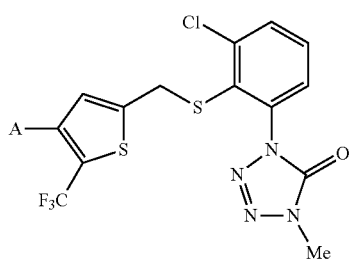 C0525 |
| 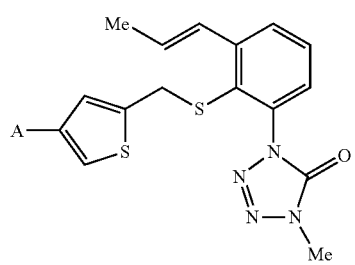 C0521 | 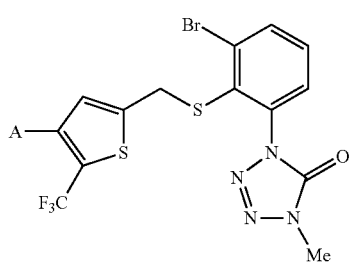 C0526 |
| 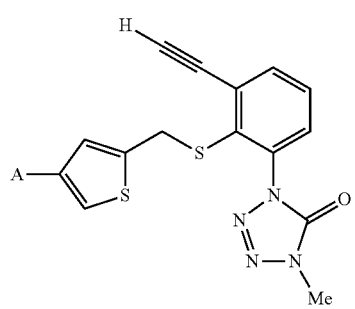 C0522 | 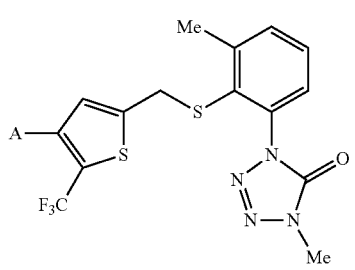 C0527 |
| 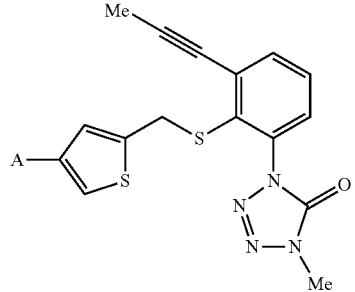 C0523 | 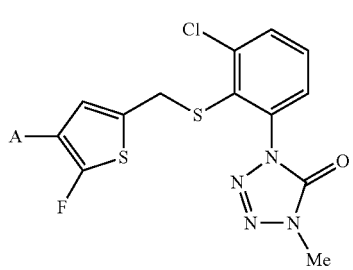 C0528 |
| | 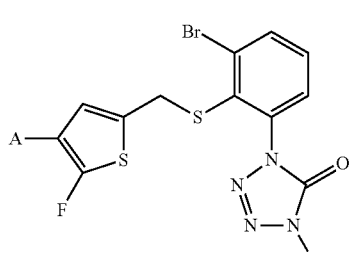 C0529 |

-continued
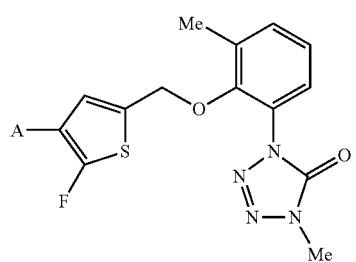
C0530
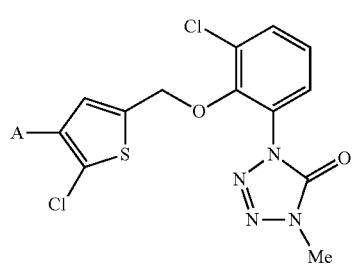
C0531
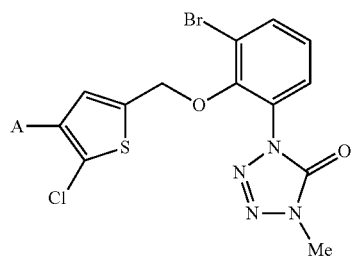
C0532
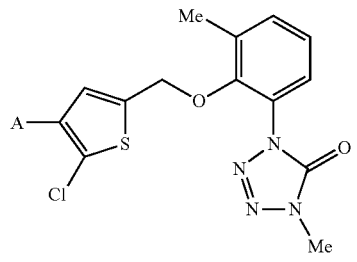
C0533
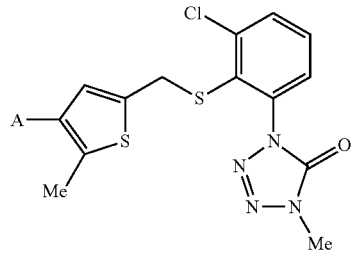
C0534
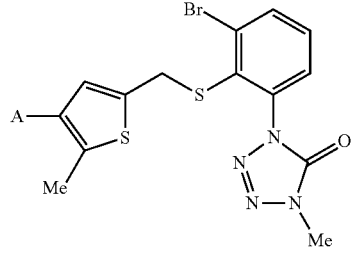
C0535
-continued
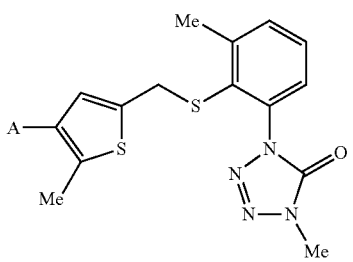
C0536
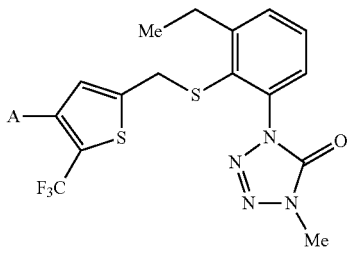
C0537
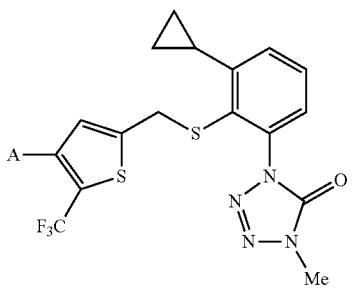
C0538
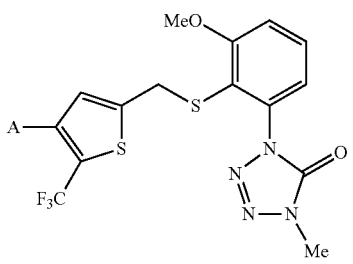
C0539
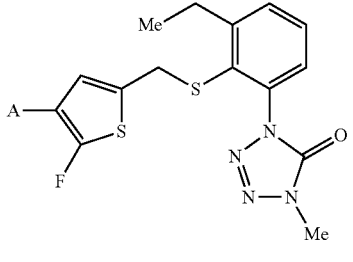
C0540
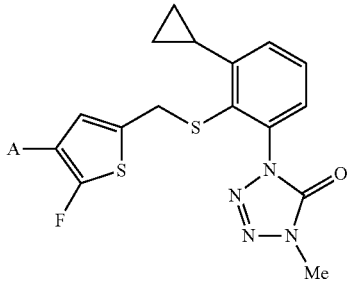
C0541

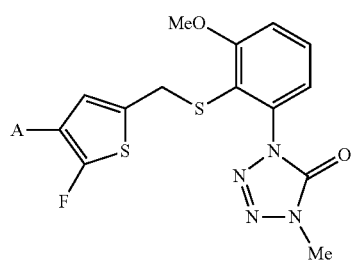
C0542

C0543
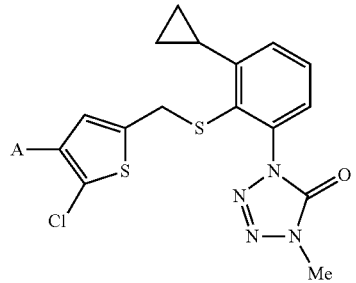
C0544
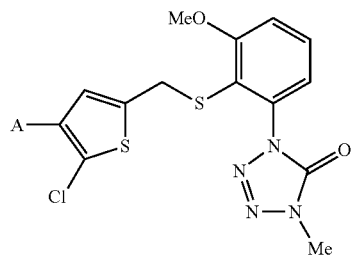
C0545
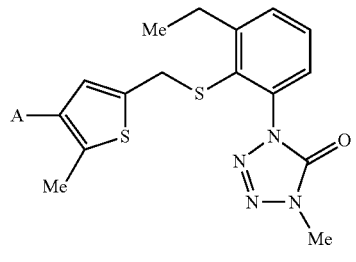
C0546
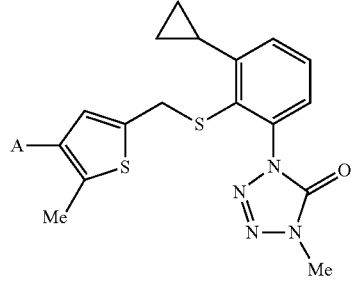
C0547
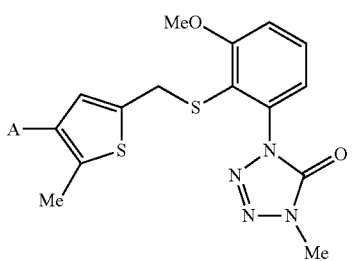
C0548
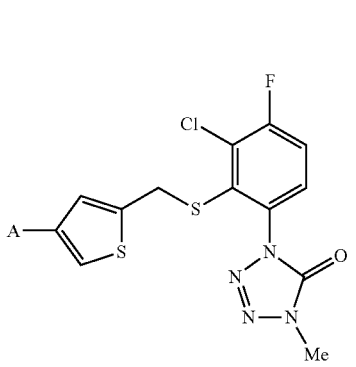
C0549
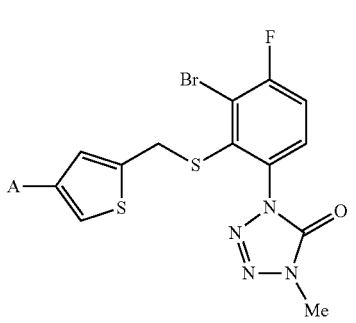
C0550
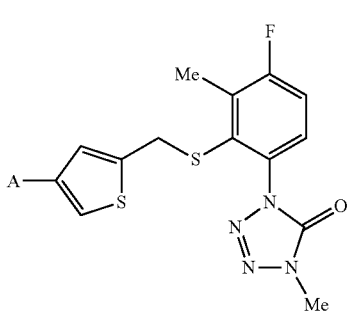
C0551
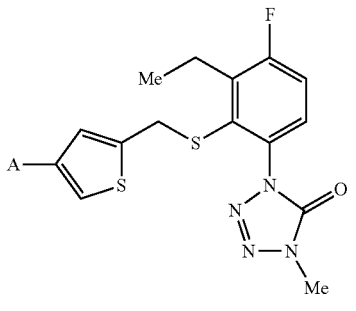
C0552

311
-continued
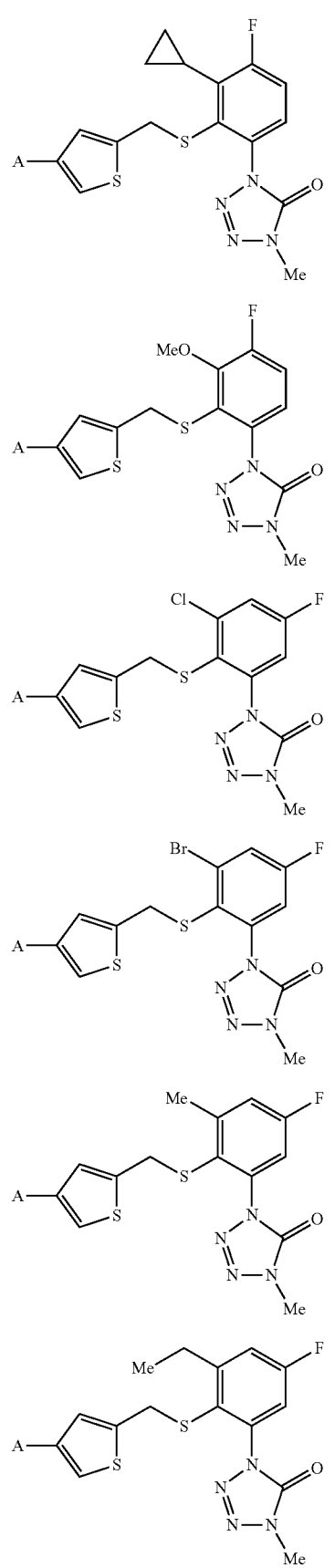
312
-continued
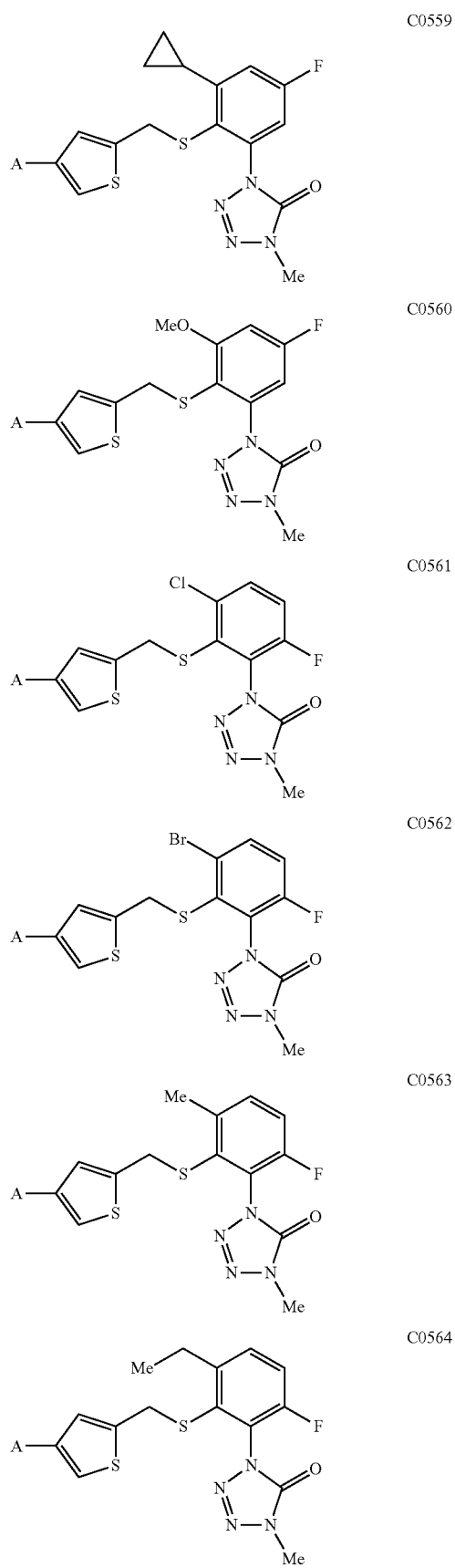

C0565 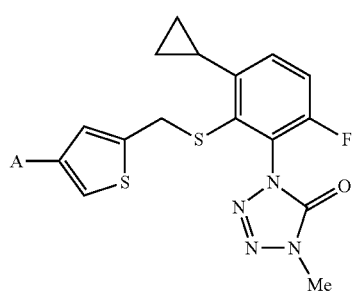
C0566 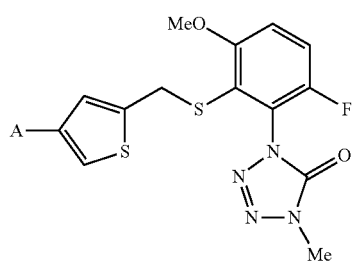
C0568 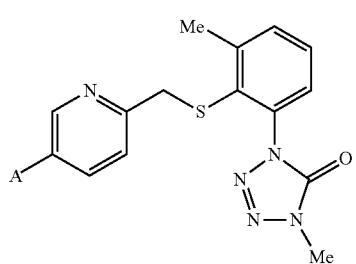
C0569 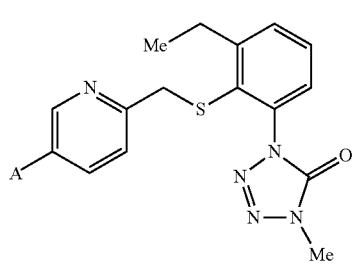
C0570 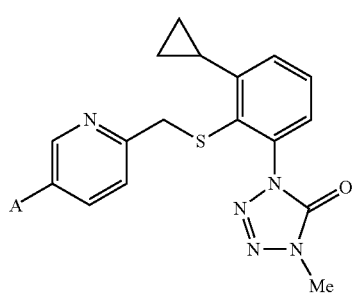
C0571 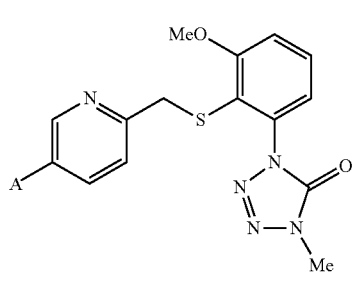
C0572 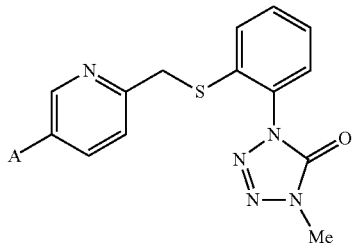
C0573 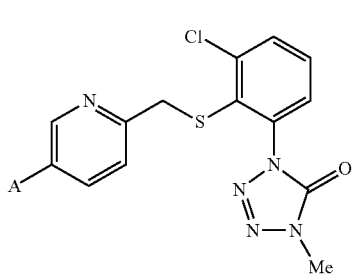
C0574 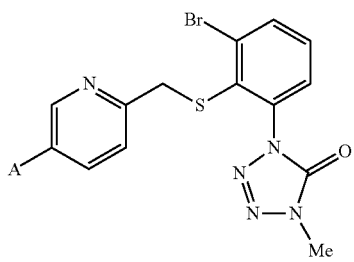
C0575 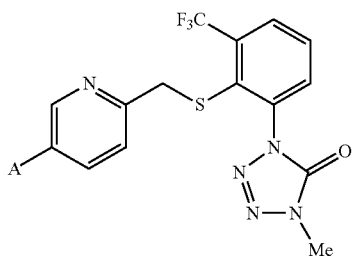
C0566 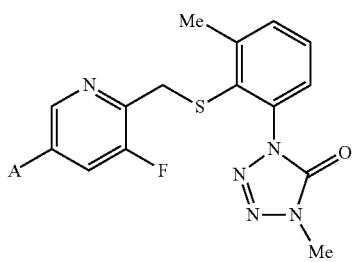
C0577 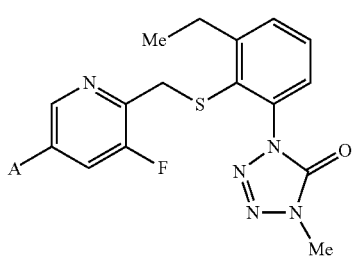

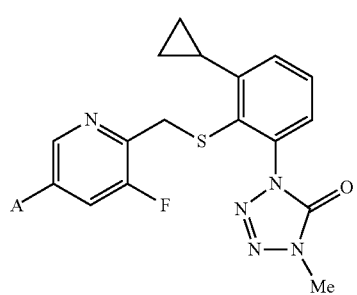
C0578
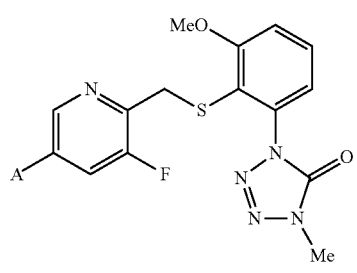
C0579
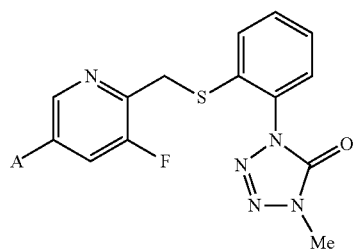
C0580
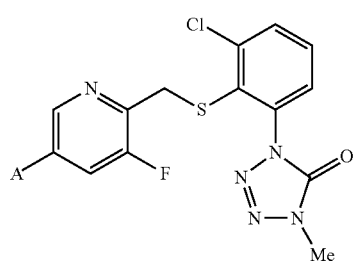
C0581
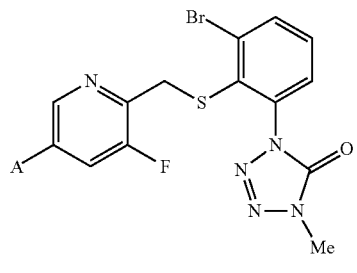
C0582
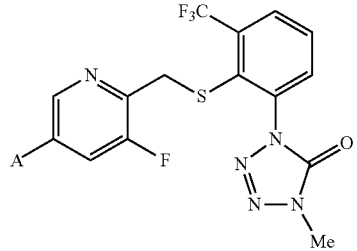
C0583
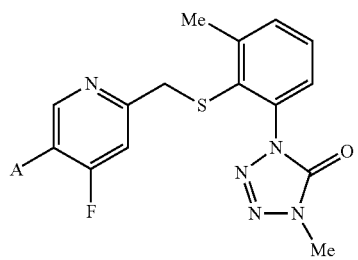
C0584
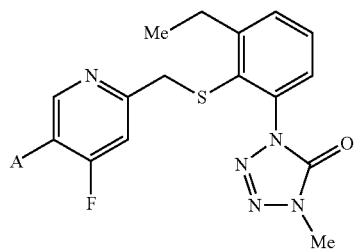
C0585
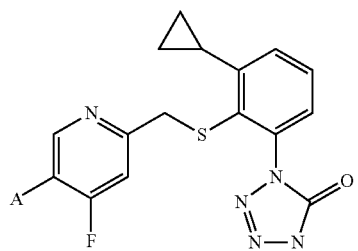
C0586
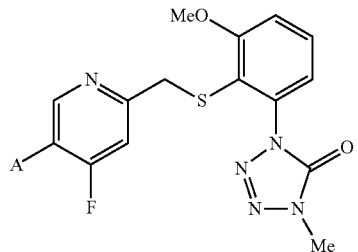
C0587
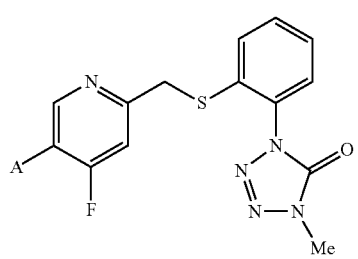
C0588
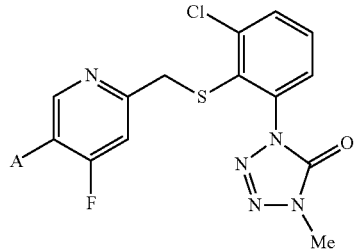
C0589

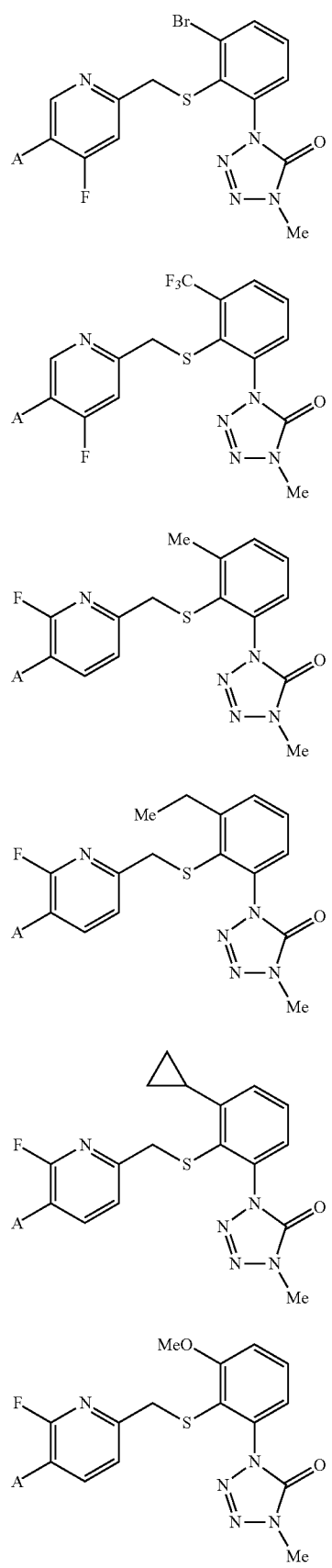

C0602 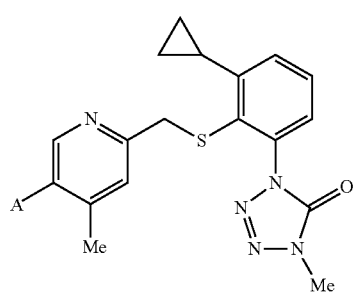
C0603 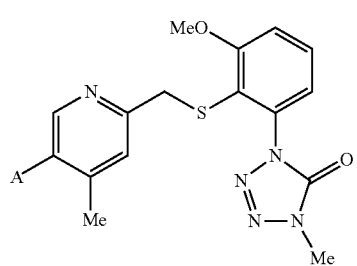
C0604 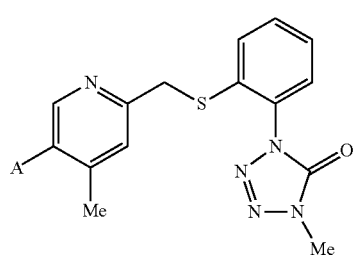
C0605 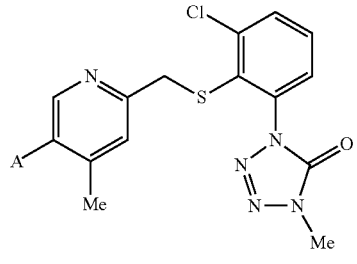
C0606 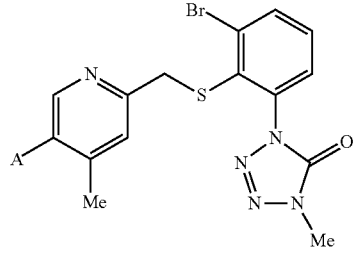
C0607 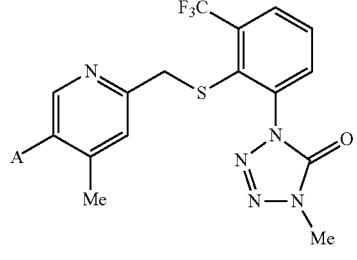
C0608 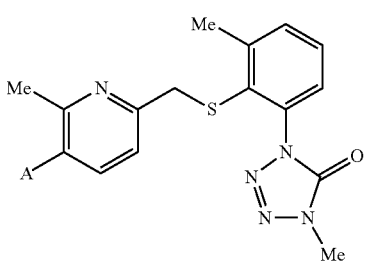
C0609 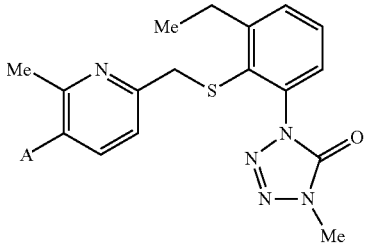
C0610 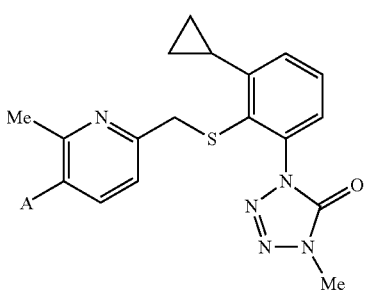
C0611 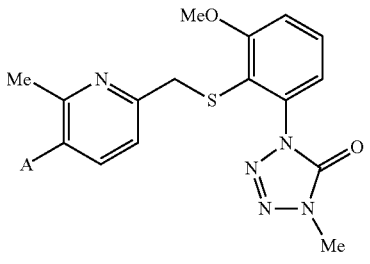
C0612 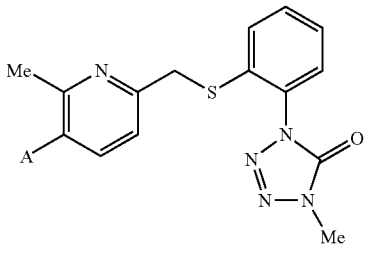
C0613 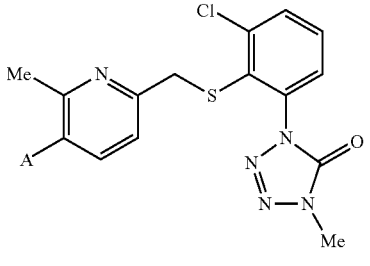

| | |
|---|---|
| C0614 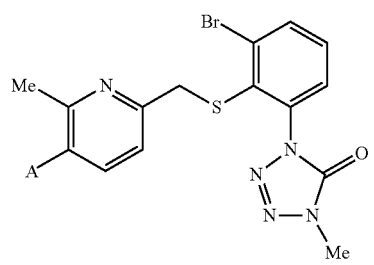 | C0620 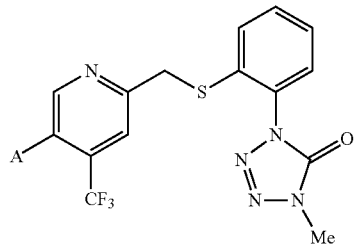 |
| C0615 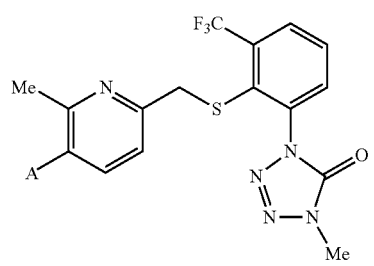 | C0621 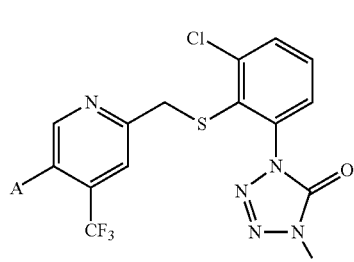 |
| C0616 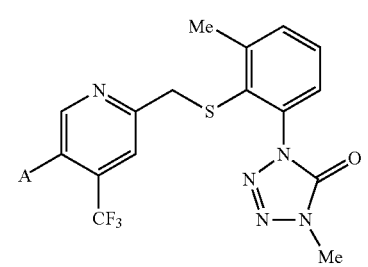 | C0622 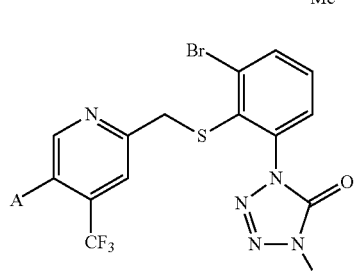 |
| C0617 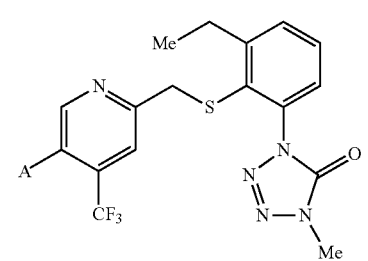 | C0623 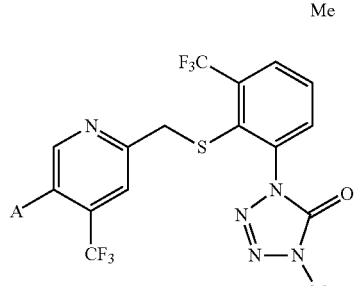 |
| C0618 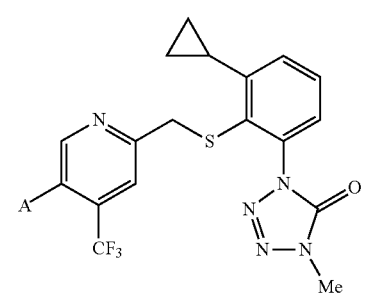 | C0624 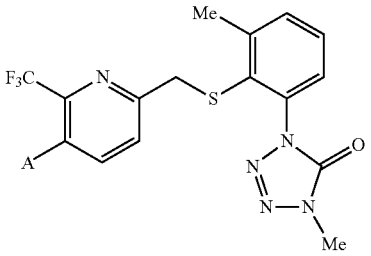 |
| C0619 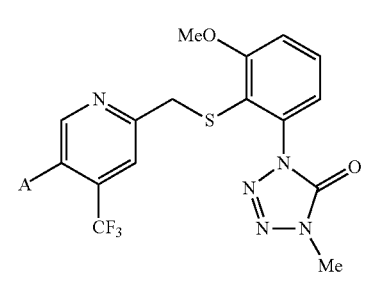 | C0625 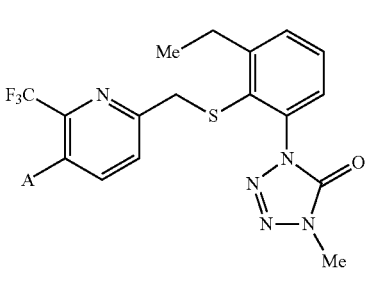 |

323
-continued
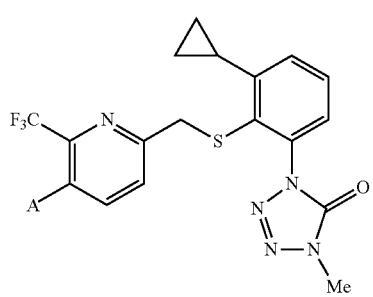
C0626
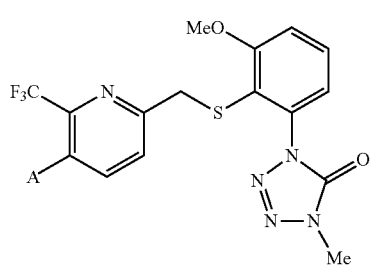
C0627
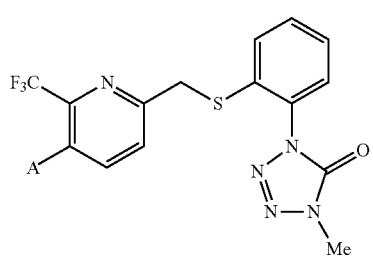
C0628
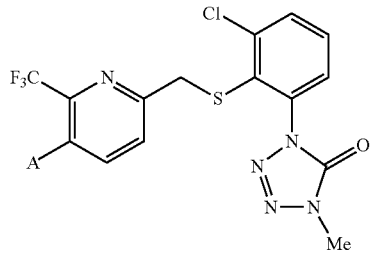
C0629
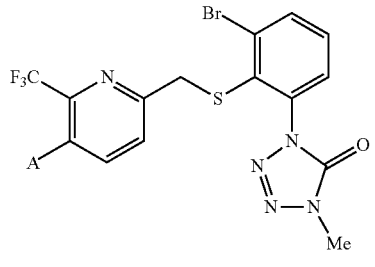
C0630
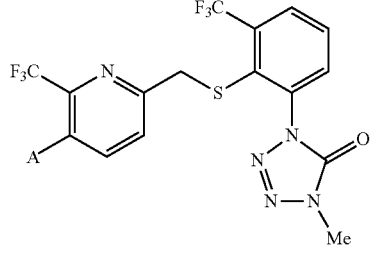
C0631
324
-continued
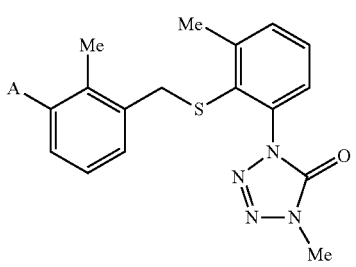
C0632
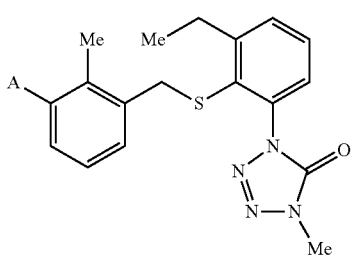
C0633
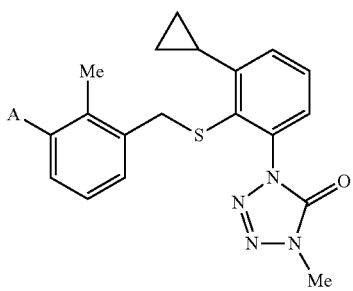
C0634
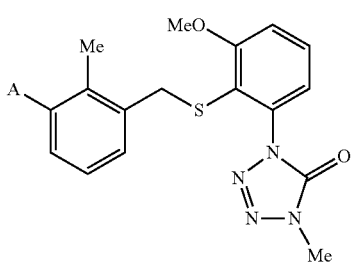
C0635
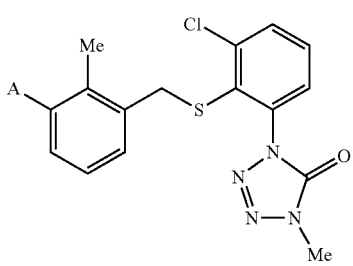
C0636
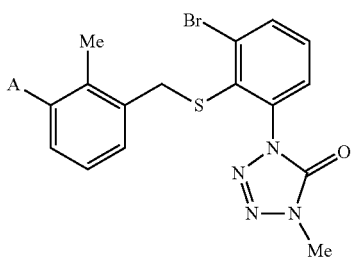
C0637

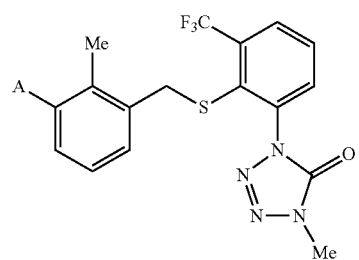
C0638
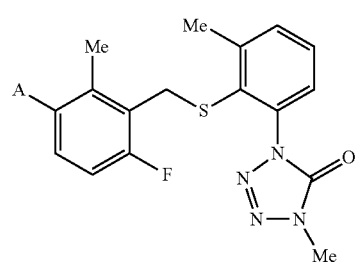
C0639
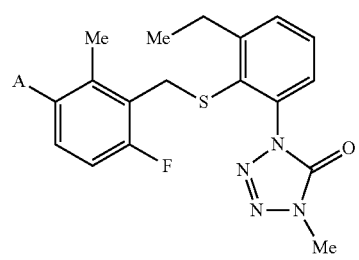
C0640
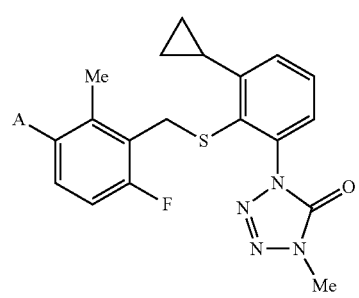
C0641
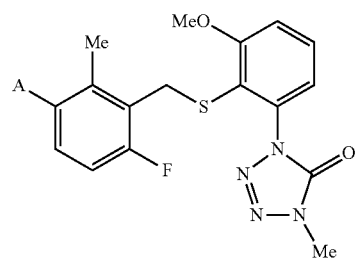
C0642
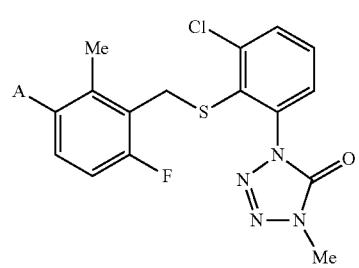
C0643
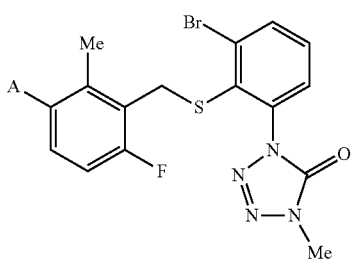
C0644
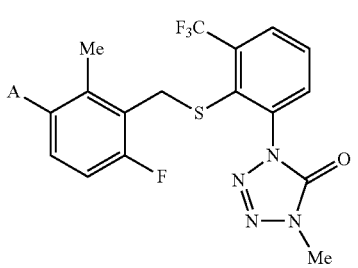
C0645
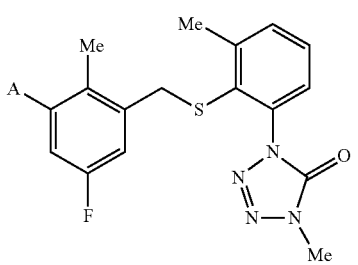
C0646
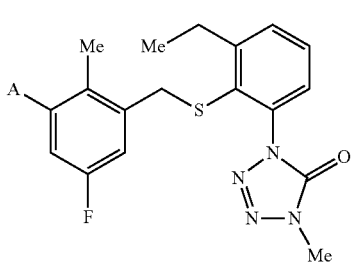
C0647
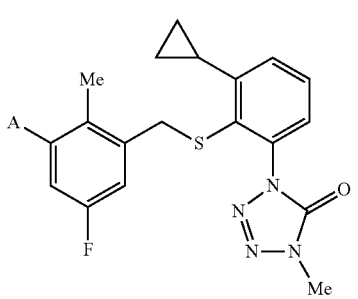
C0648
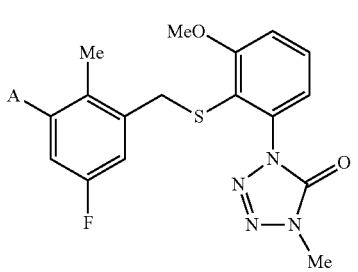
C0649

-continued
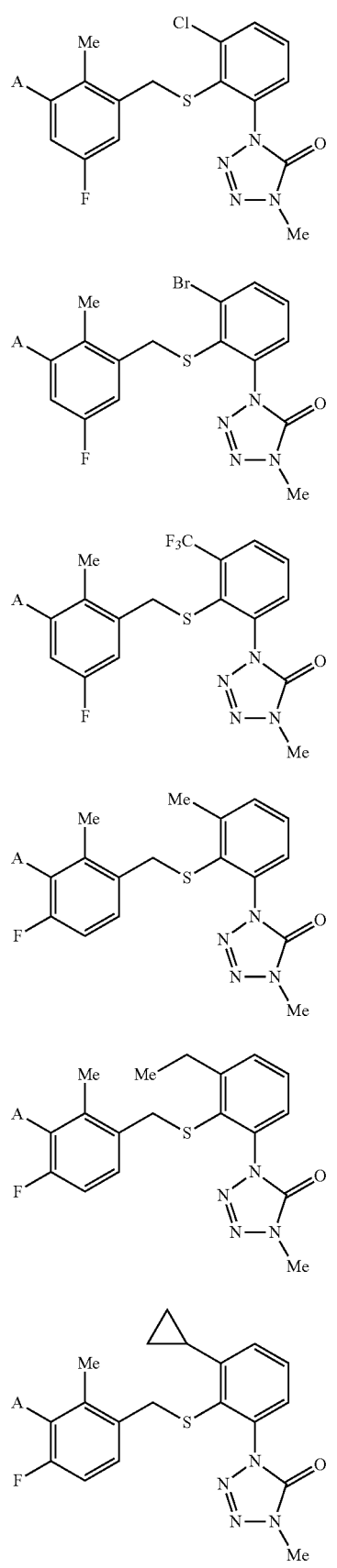
C0650
C0651
C0652
C0653
C0654
C0655
-continued
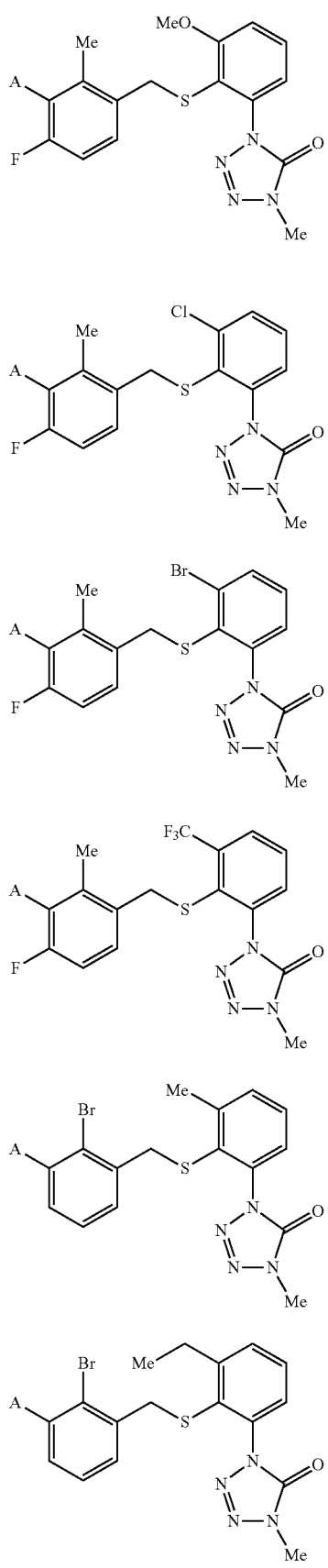
C0656
C0657
C0658
C0659
C0660
C0661

| | |
|---|---|
| 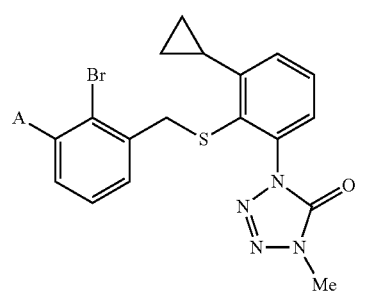 C0662 | 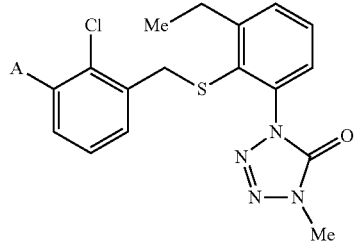 C0668 |
| 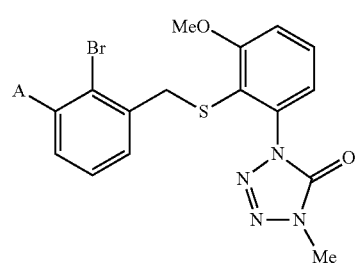 C0663 | 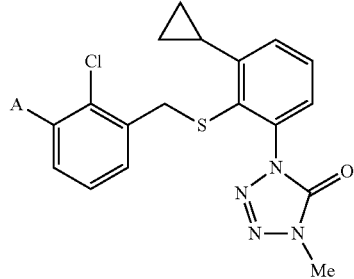 C0669 |
| 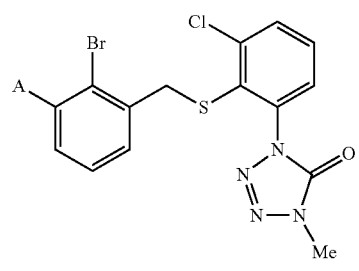 C0664 | 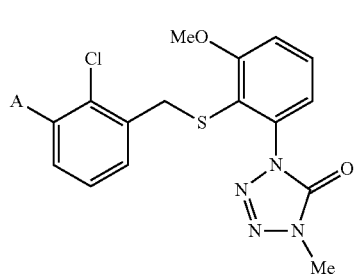 C0670 |
| 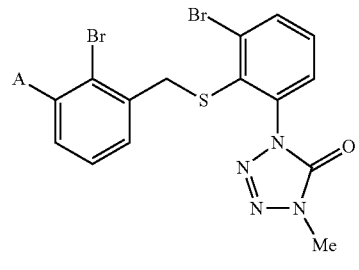 C0665 | 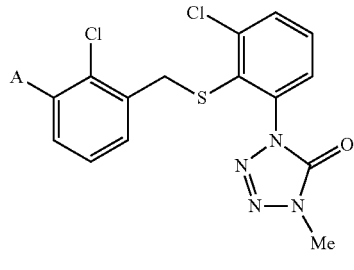 C0671 |
| 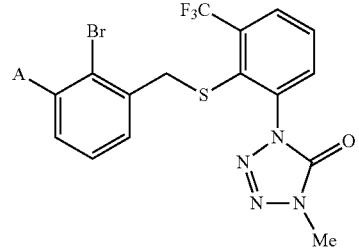 C0666 | 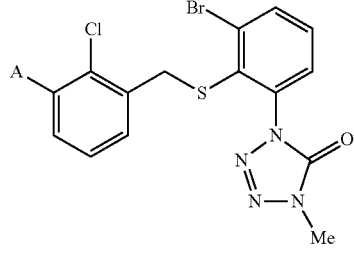 C0672 |
| 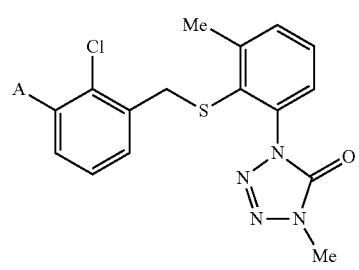 C0667 | C0673 |

-continued
C0674
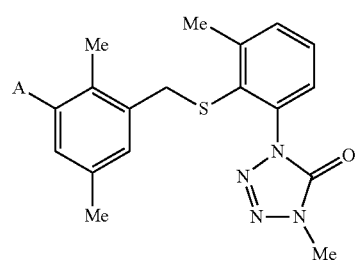
C0675
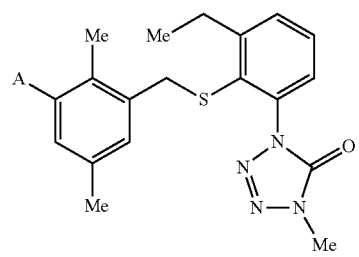
C0664
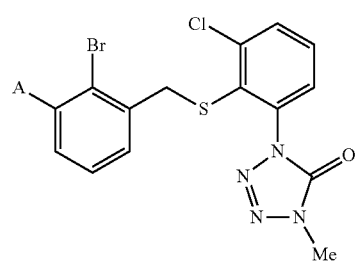
C0665
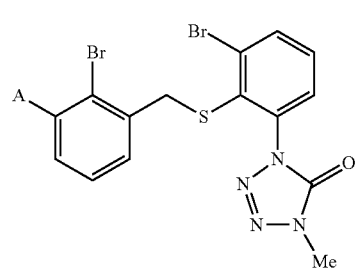
C0666
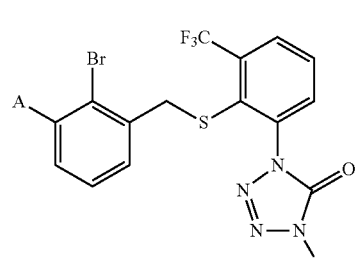
C0667
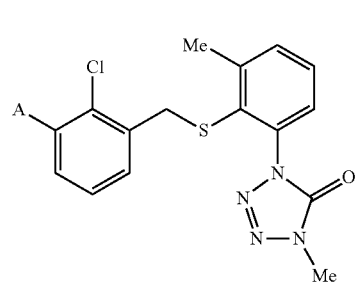
-continued
C0668
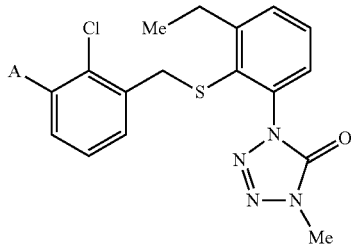
C0669
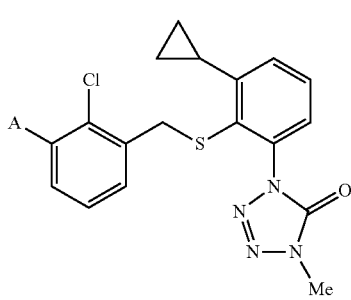
C0670
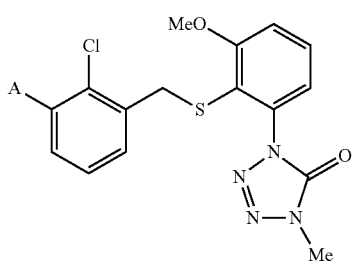
C0671
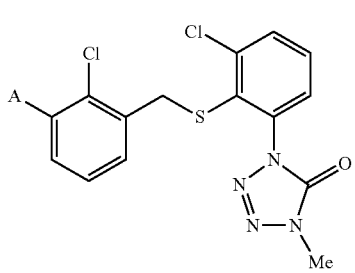
C0672
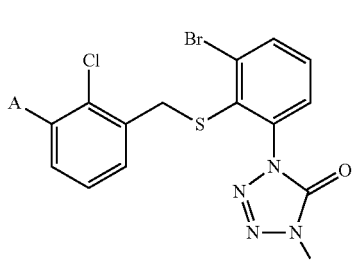
C0673
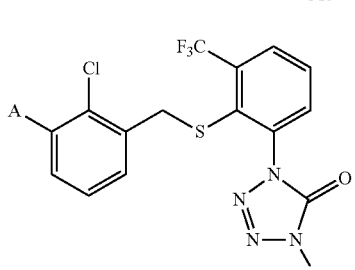

| | |
|---|---|
| C0674 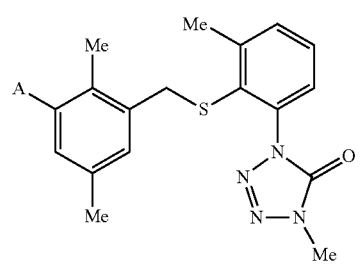 | C0680 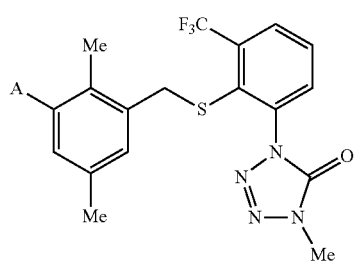 |
| C0675 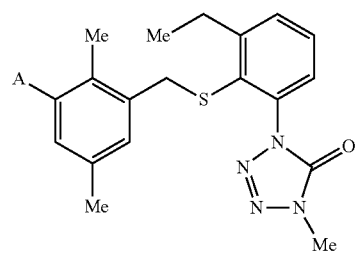 | C0681 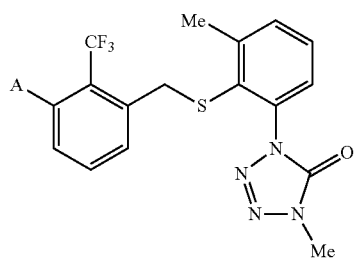 |
| C0676 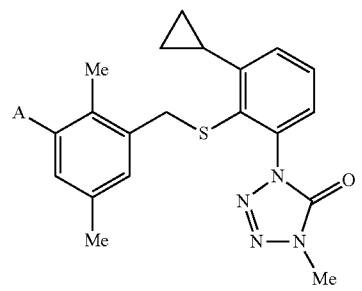 | C0682 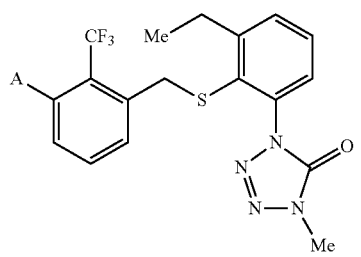 |
| C0677 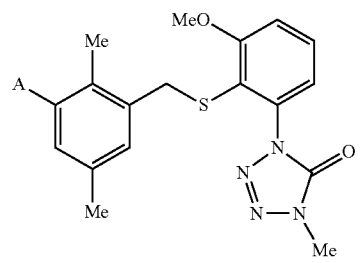 | C0683 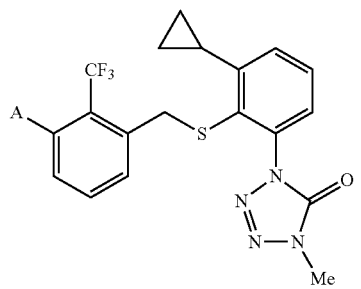 |
| C0678 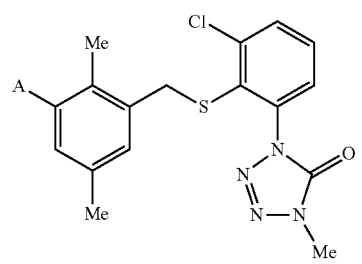 | C0684 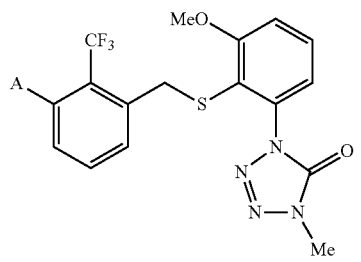 |
| C0679 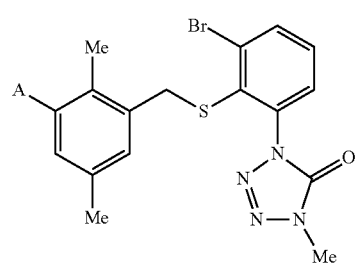 | C0685 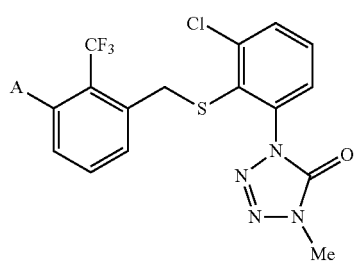 |

| | |
|---|---|
| C0686 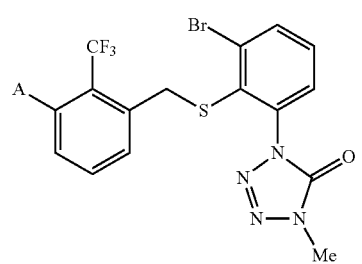 | C0692 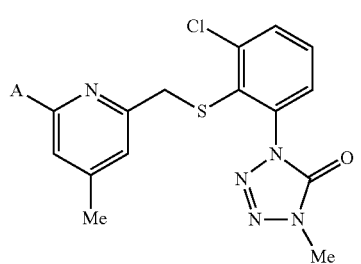 |
| C0687 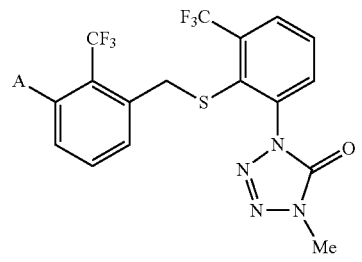 | C0693 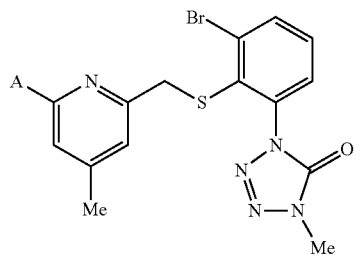 |
| C0688 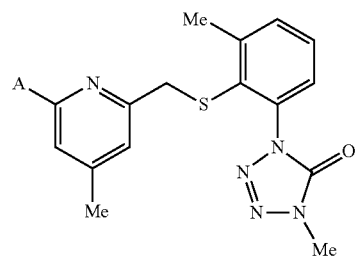 | C0694 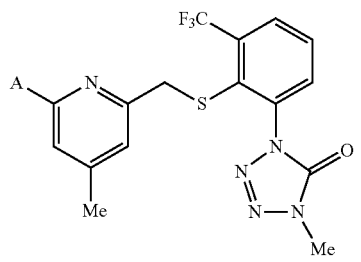 |
| C0689 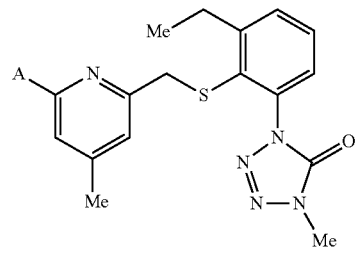 | C0695 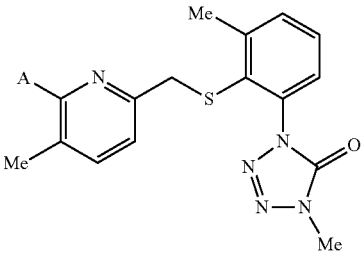 |
| C0690 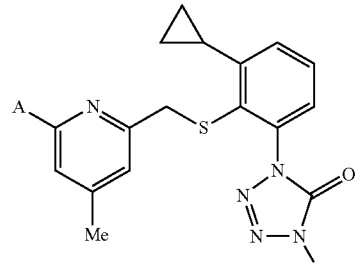 | C0696 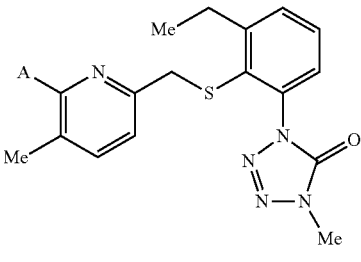 |
| C0691 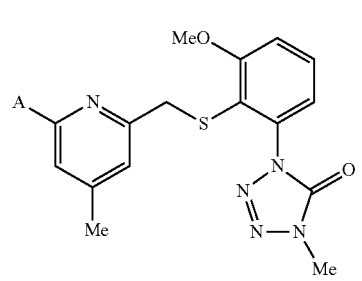 | C0697 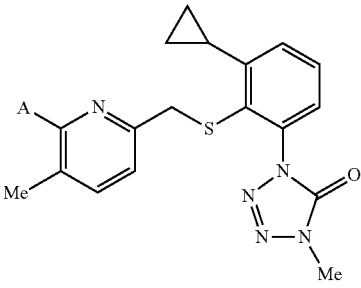 |

C0698 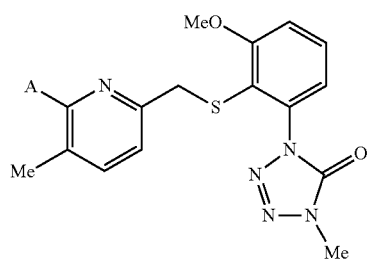
C0699 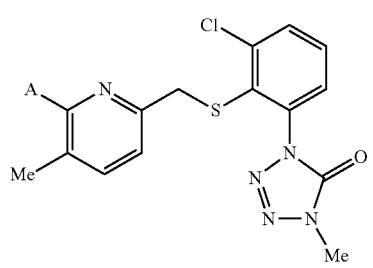
C0700 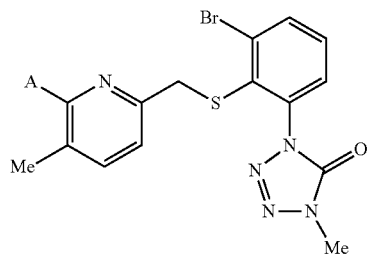
C0701 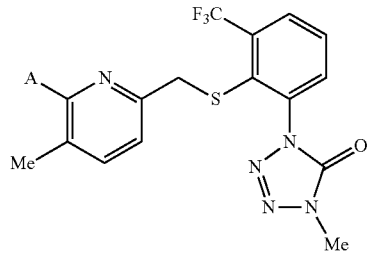
C0702 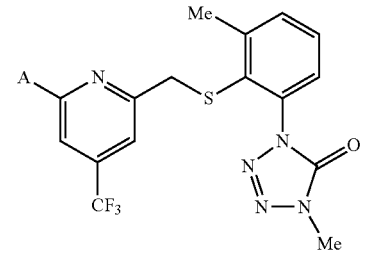
C0703 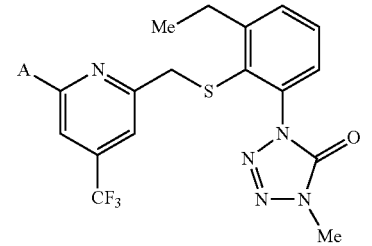
C0704 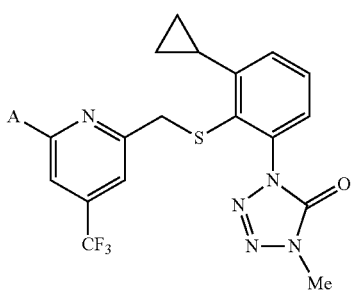
C0705 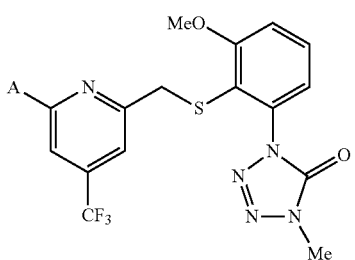
C0706 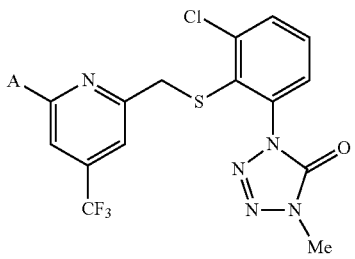
C0707 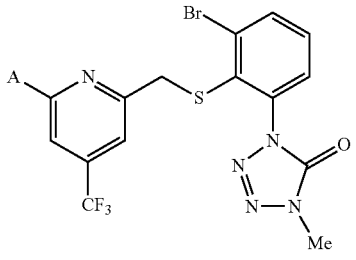
C0708 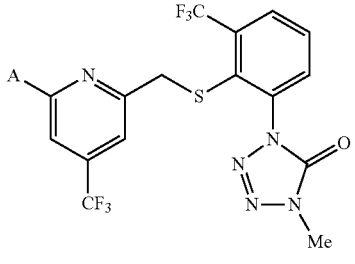
C0709 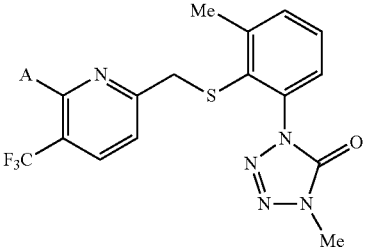

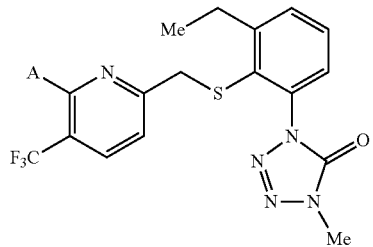
C0710
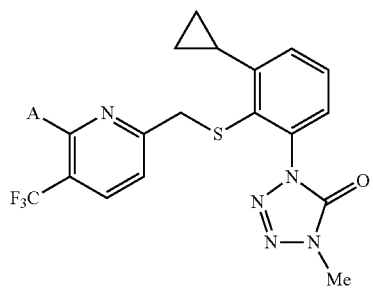
C0711
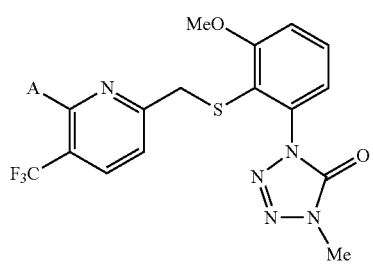
C0712
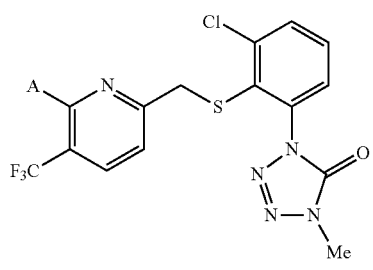
C0713
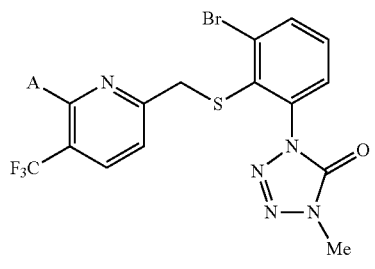
C0714
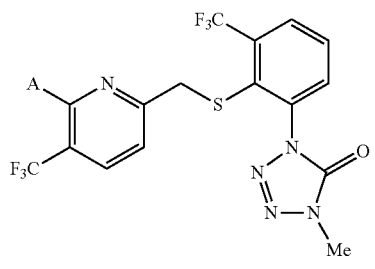
C0715
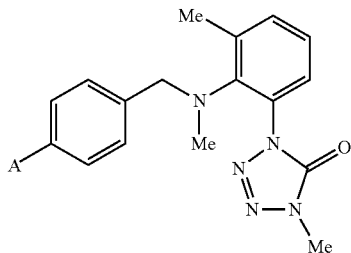
D0001
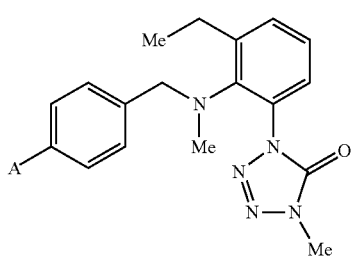
D0002
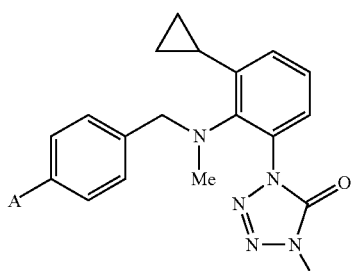
D0003
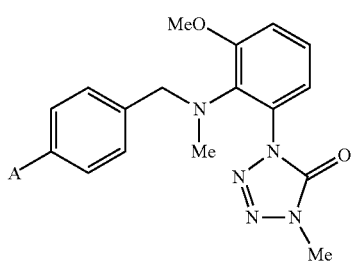
D0004
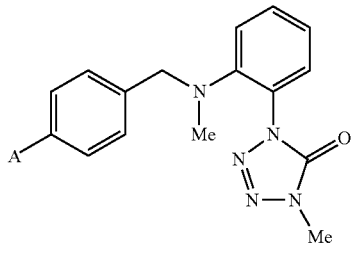
D0005
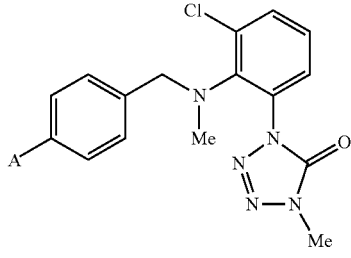
D0006

D0007 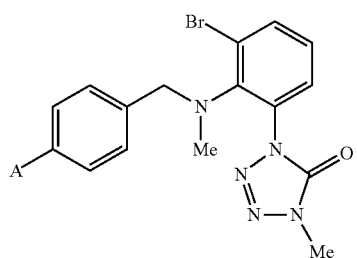
D0008 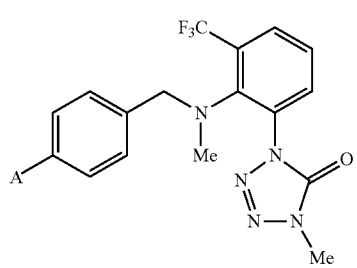
D0009 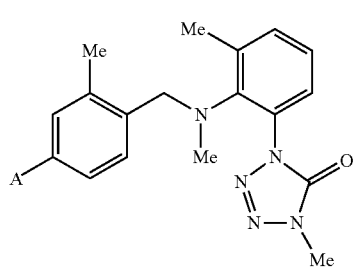
D0010 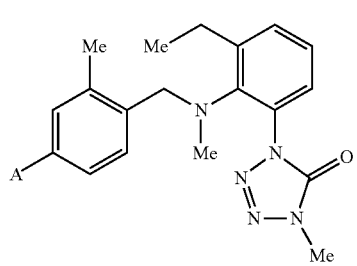
D0011 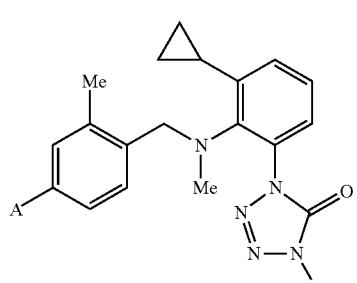
D0012 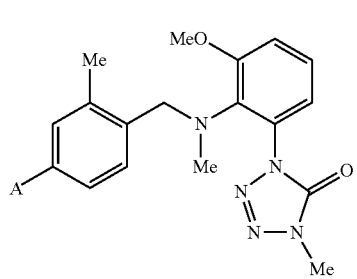
D0013 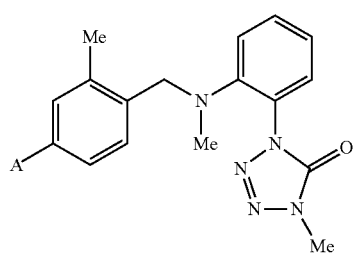
D0014 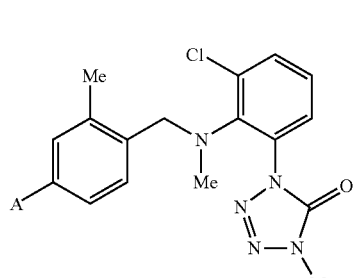
D0015 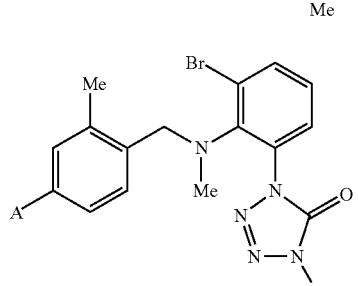
D0016 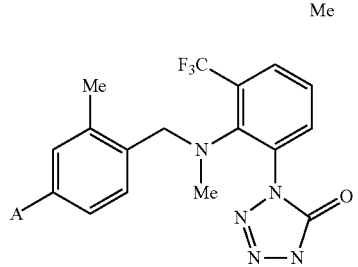
D0017 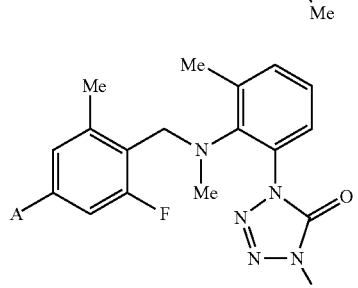
D0018 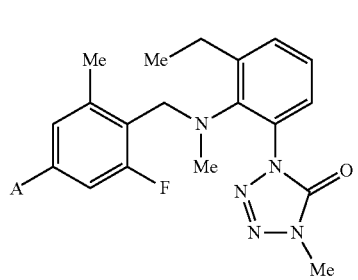

D0019
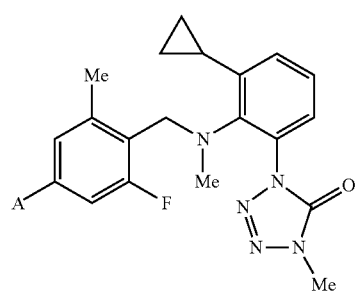
D0020
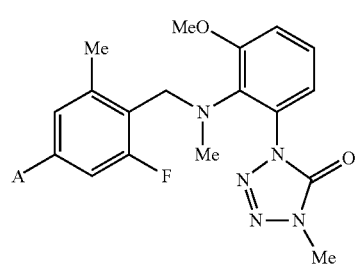
D0021
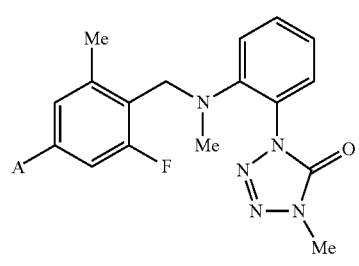
D0022
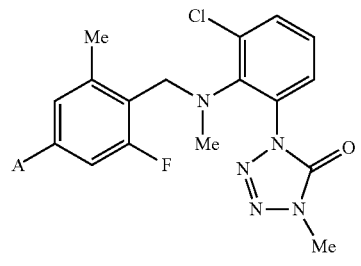
D0023
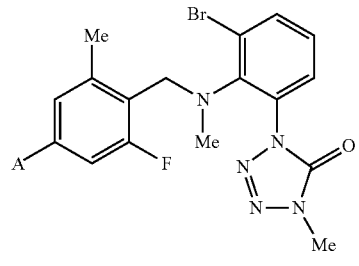
D0024
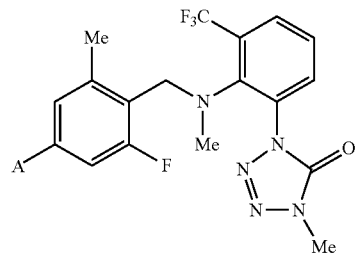
D0025
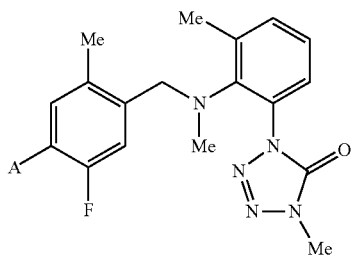
D0026
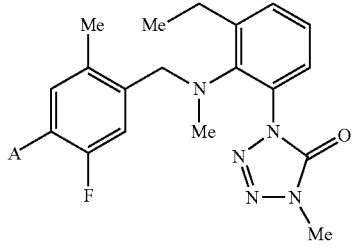
D0027
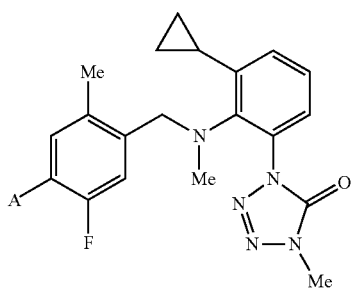
D0028
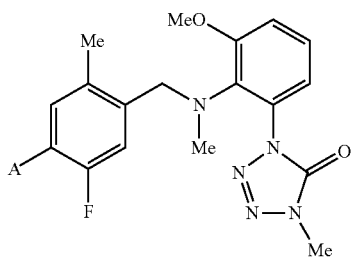
D0029
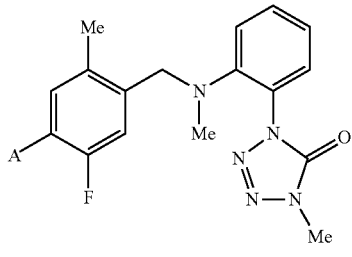
D0030
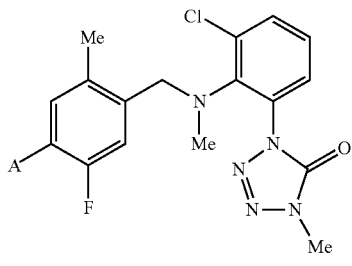

| | |
|---|---|
| D0031 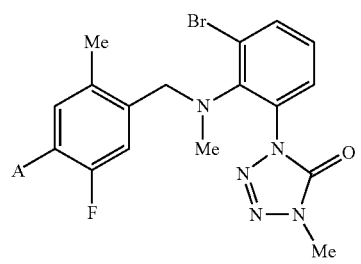 | D0037 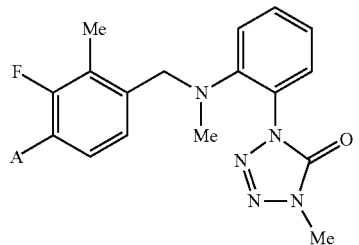 |
| D0032 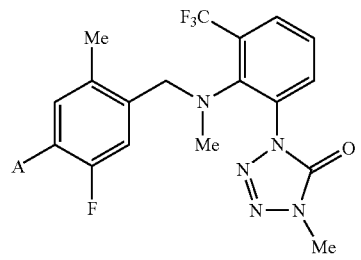 | D0038 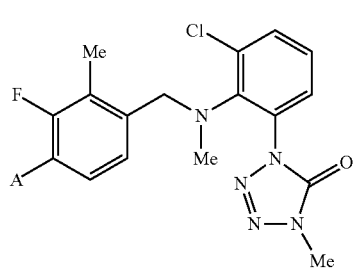 |
| D0033 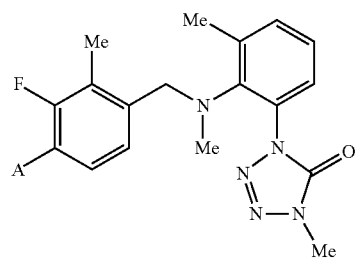 | D0039 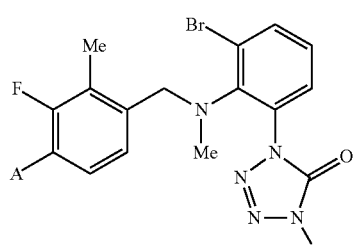 |
| D0034 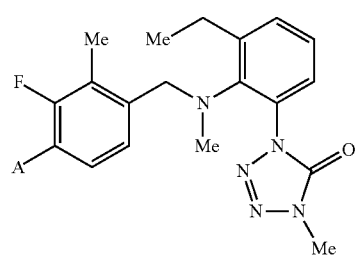 | D0040 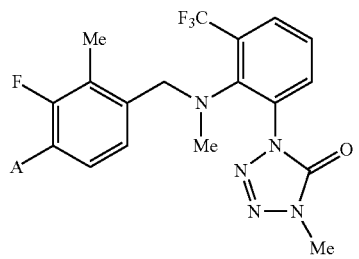 |
| D0035 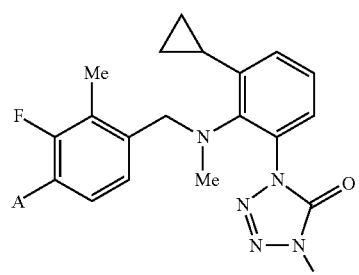 | D0041 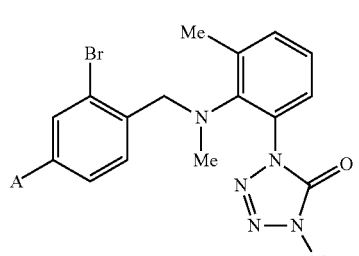 |
| D0036 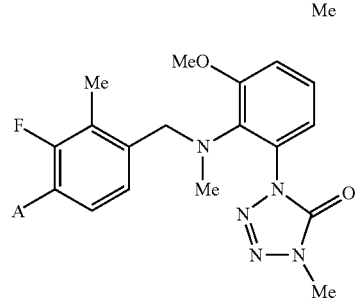 | D0042 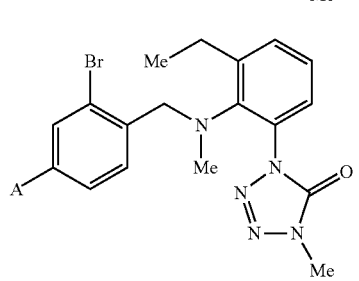 |

D0043
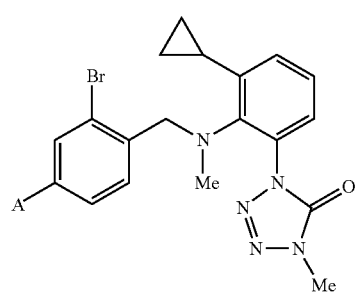
D0044
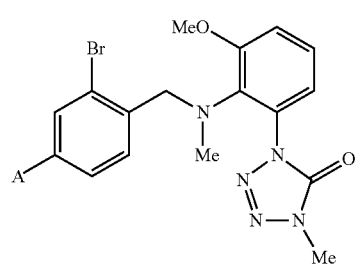
D0045
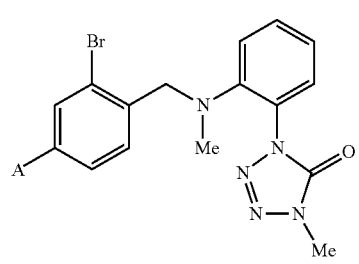
D0046
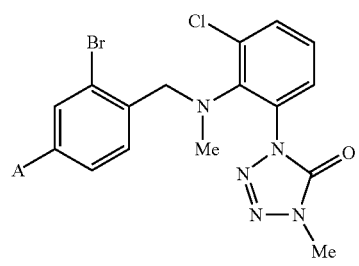
D0047
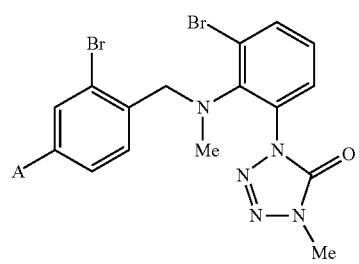
D0048
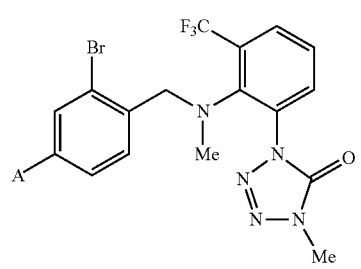
D0049
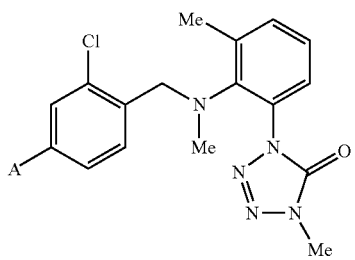
D0050
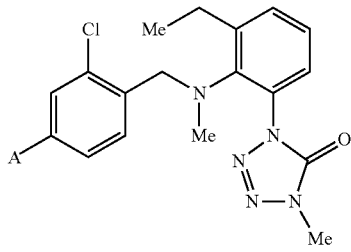
D0051
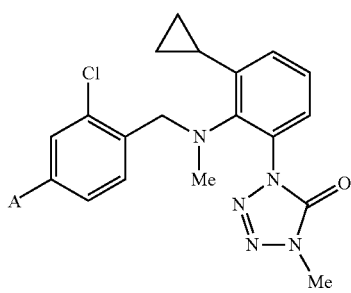
D0052
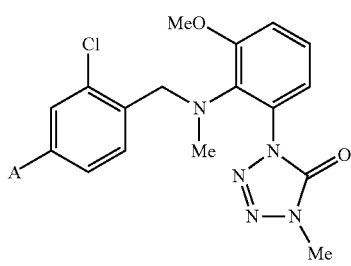
D0053
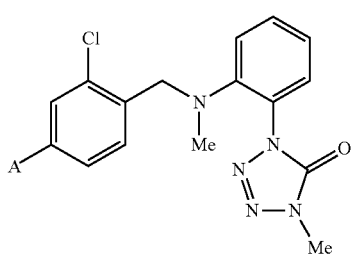
D0054
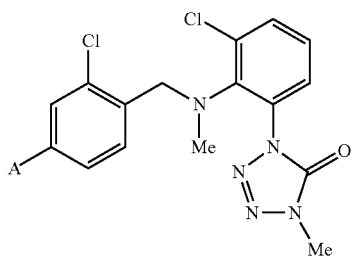

| D0055 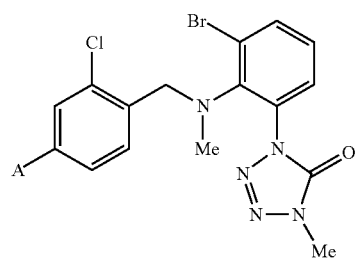 | D0061 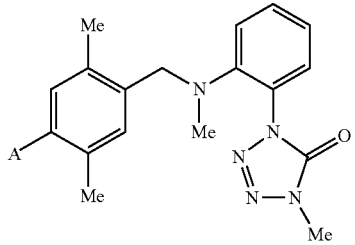 |
| --- | --- |
| D0056 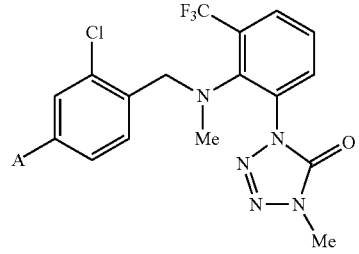 | D0062 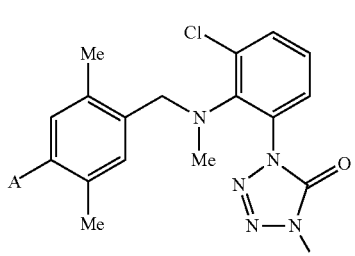 |
| D0057 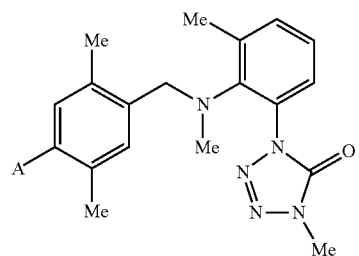 | D0063 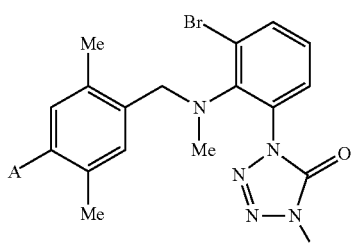 |
| D0058 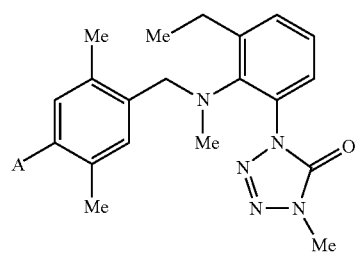 | D0064 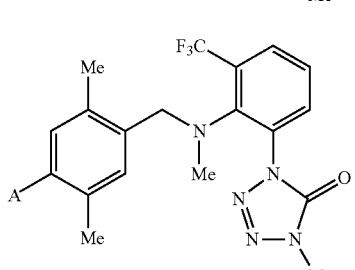 |
| D0059 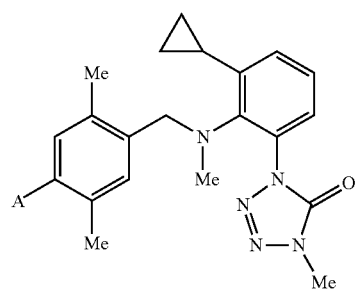 | D0065 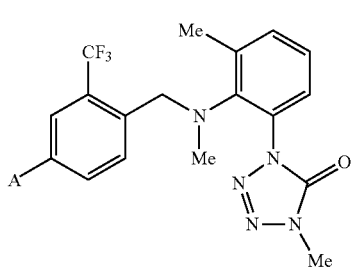 |
| D0060 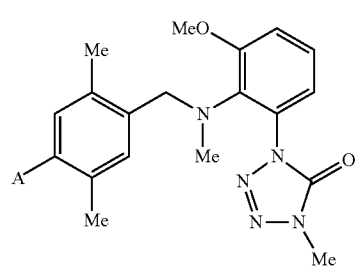 | D0066 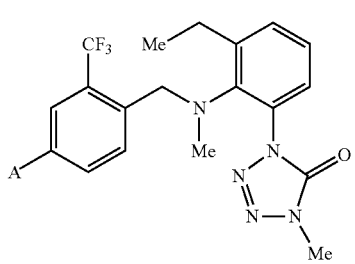 |

-continued
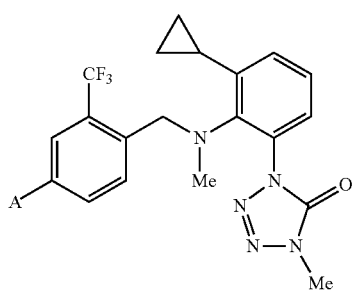
D0067
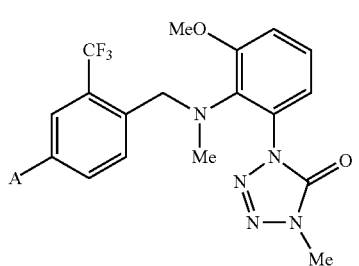
D0068
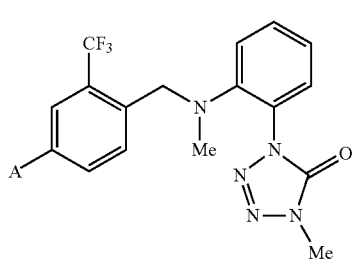
D0069
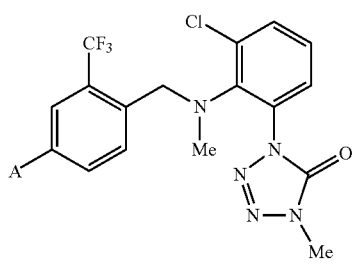
D0070
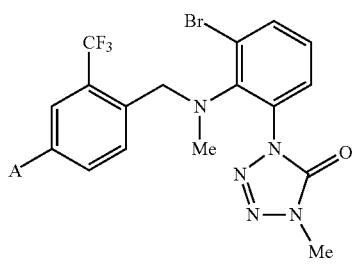
D0071
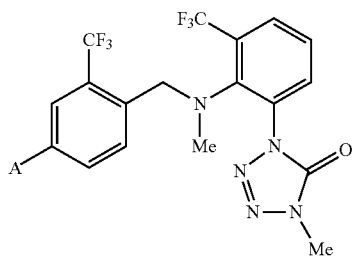
D0072
-continued
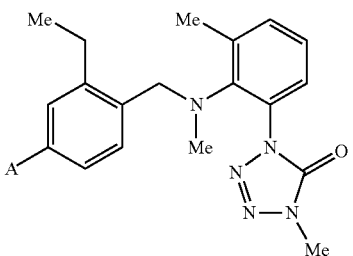
D0073
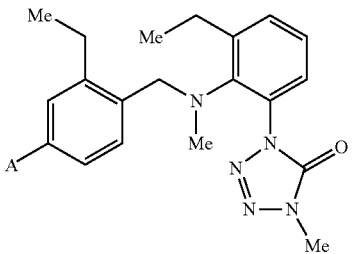
D0074
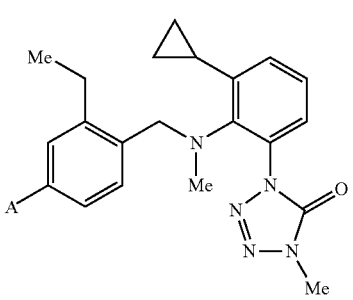
D0075
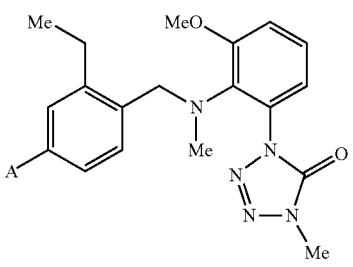
D0076
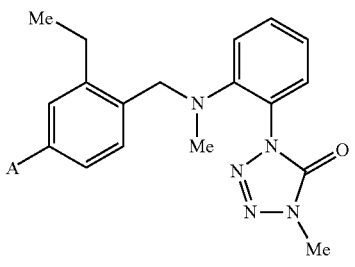
D0077
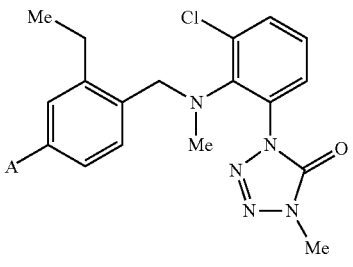
D0078

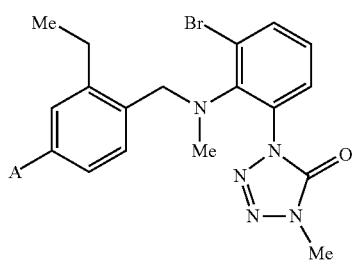
D0079
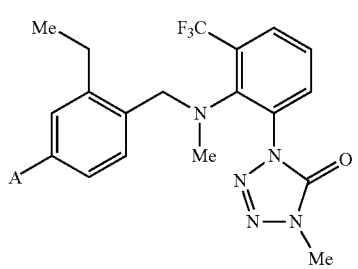
D0080
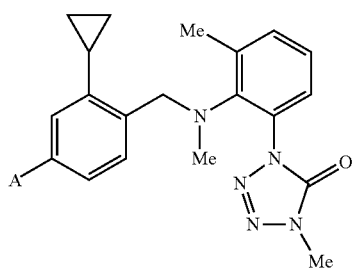
D0081
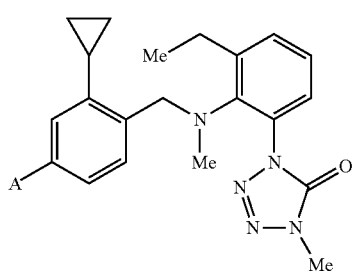
D0082
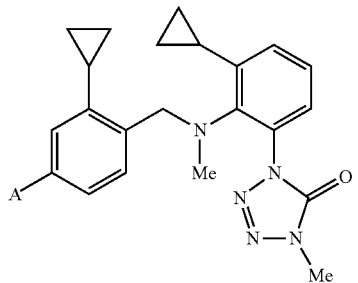
D0083
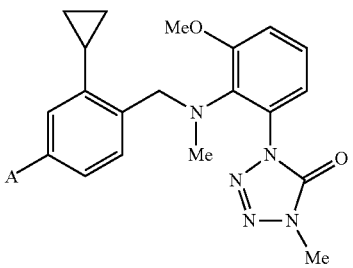
D0084
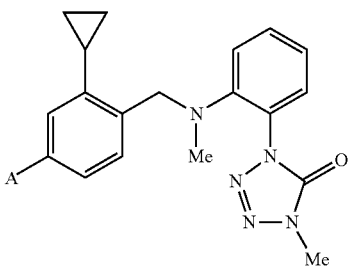
D0085
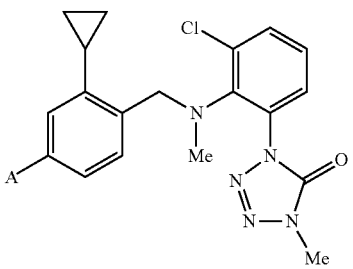
D0086
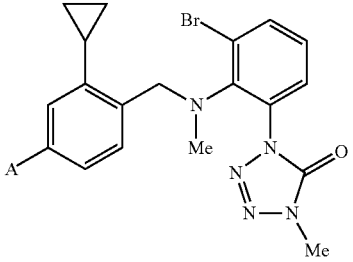
D0087
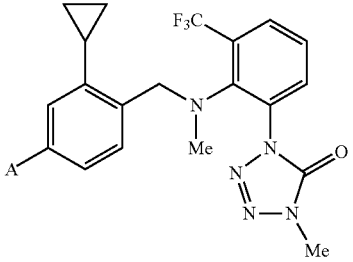
D0088
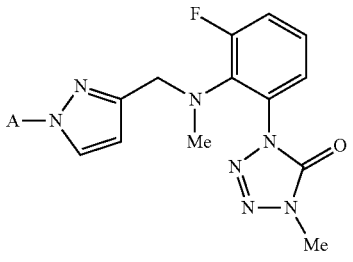
D0089

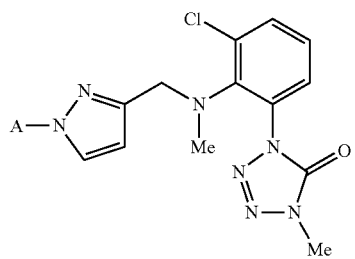 D0090
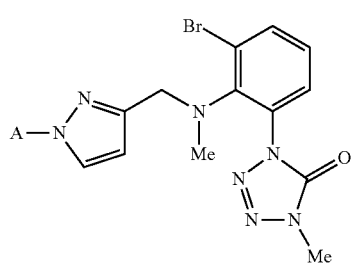 D0091
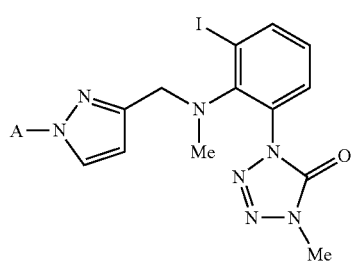 D0092
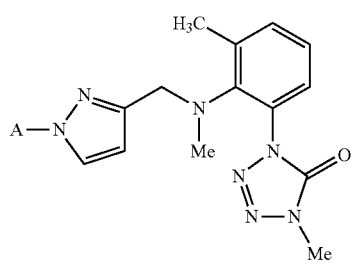 D0093
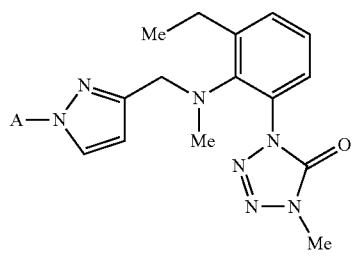 D0094
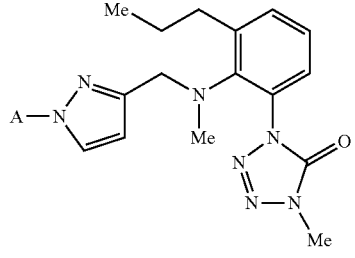 D0095
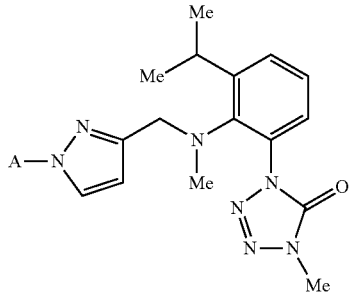 D0096
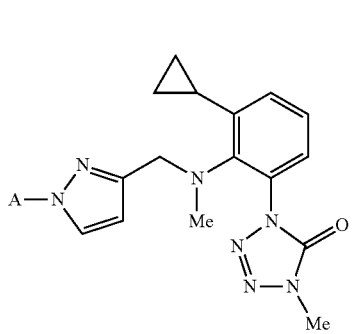 D0097
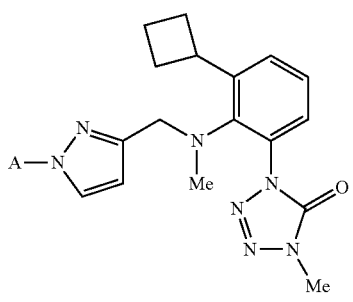 D0098
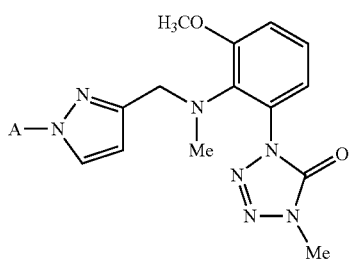 D0099
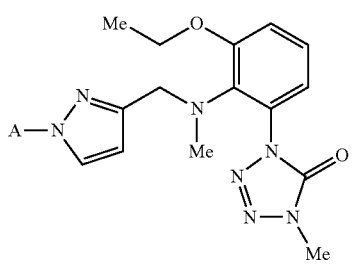 D0100

-continued
D0101
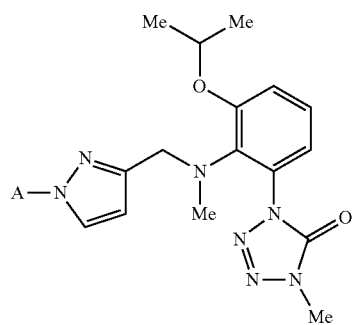
D0102
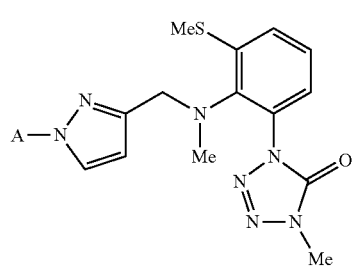
D0103
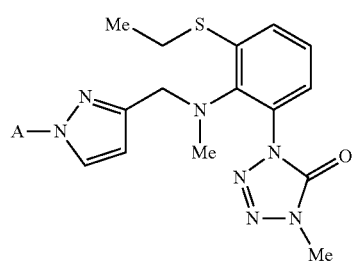
D0104
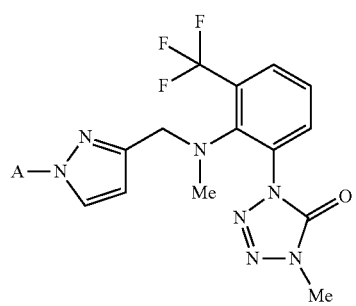
D0106
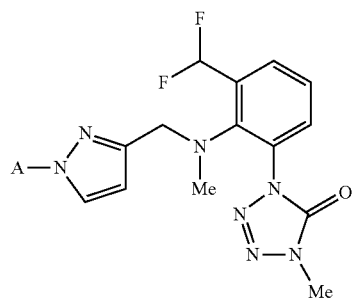
-continued
D0106
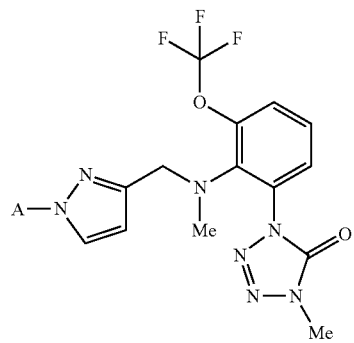
D0107
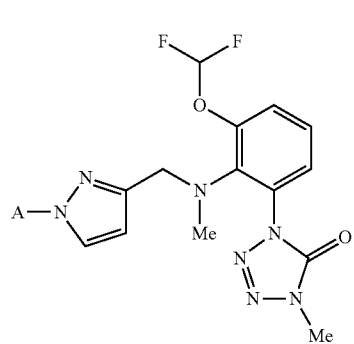
D0108
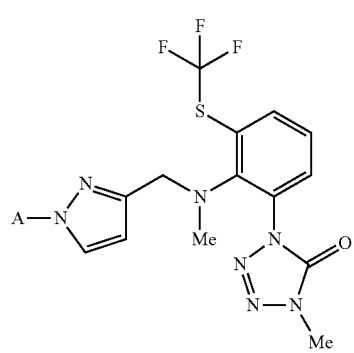
D0109
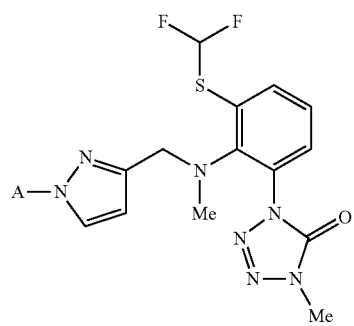
D0110
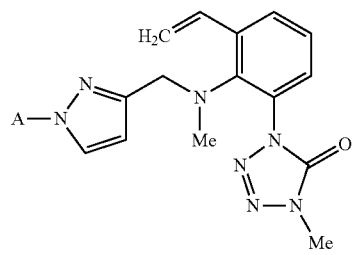

D0111 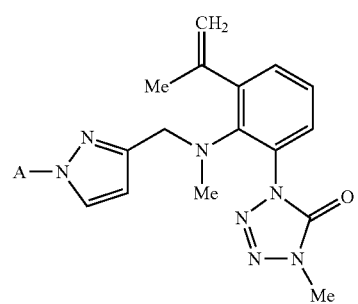
D0112 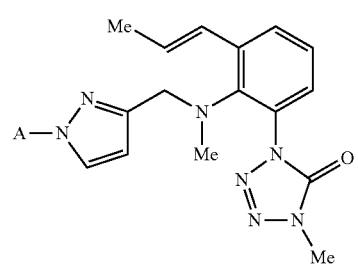
D0113 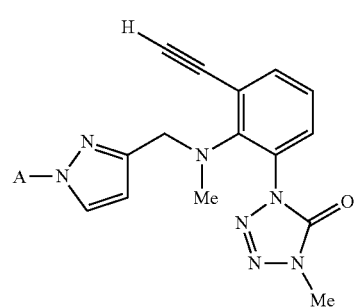
D0114 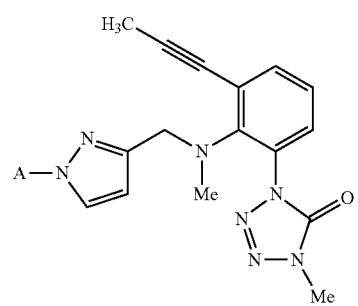
D0115 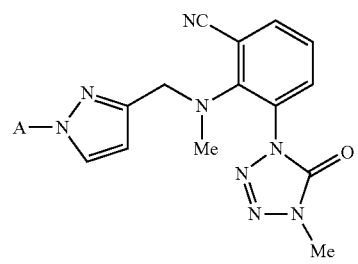
D0116 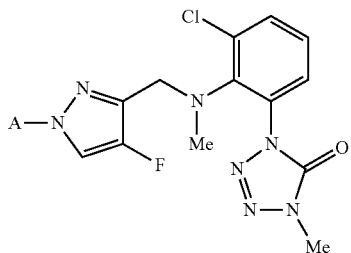
D0117 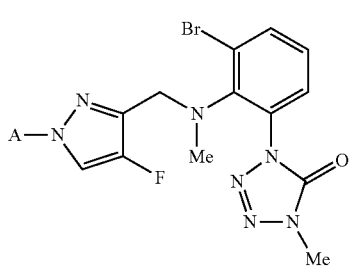
D0118 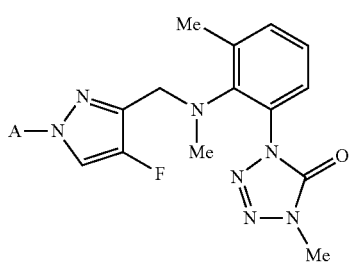
D0119 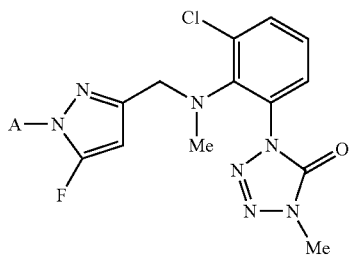
D0120 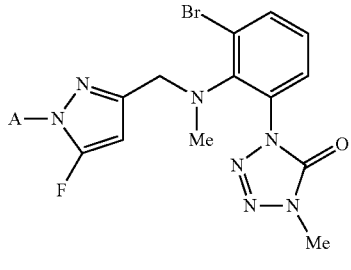
D0121 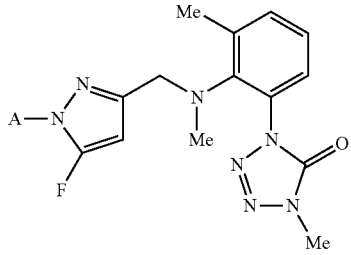

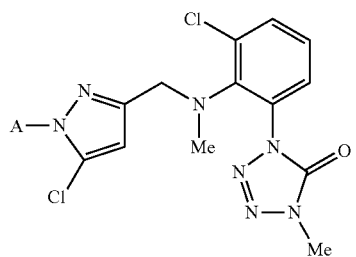
D0122
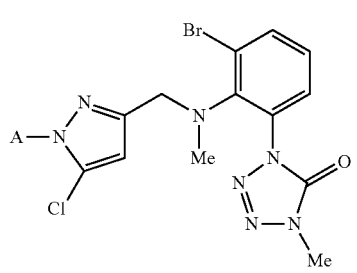
D0123
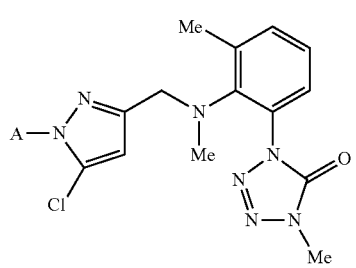
D0124
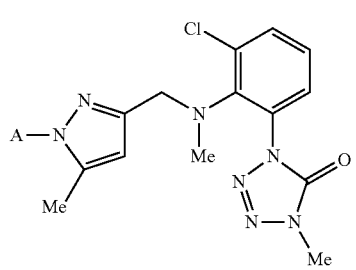
D0125
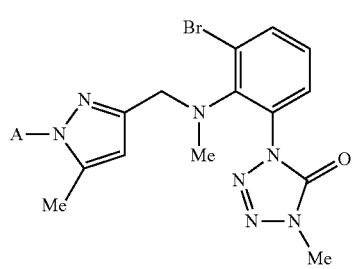
D0126
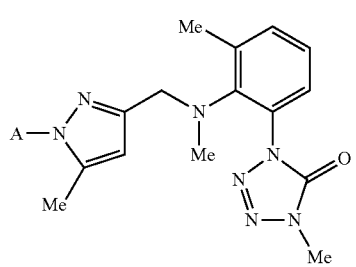
D0127
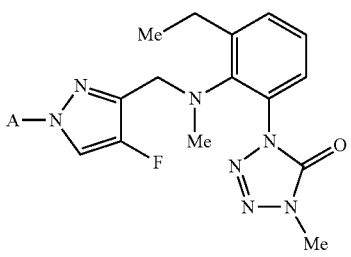
D0128
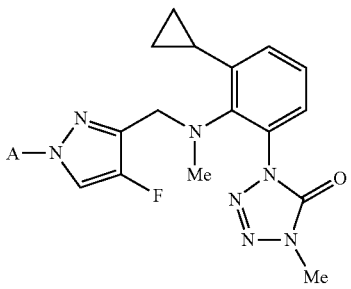
D0129
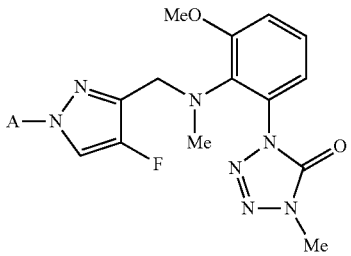
D0130
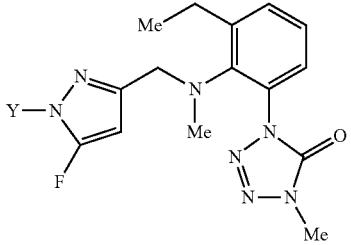
D0131
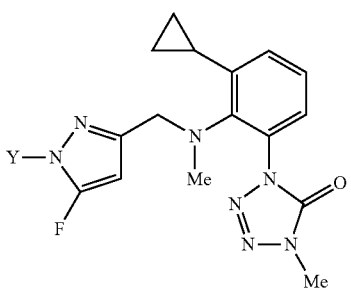
D0132
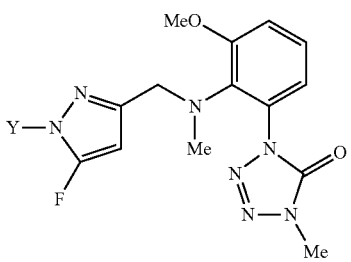
D0133

D0134 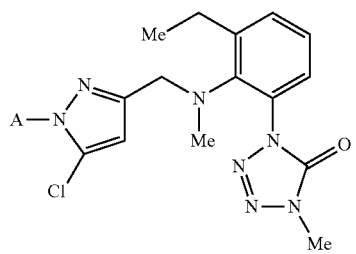
D0135 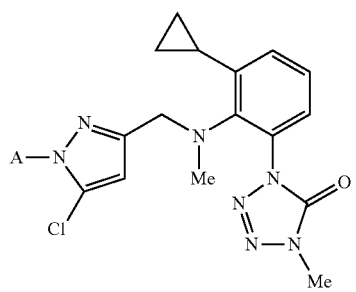
D0136 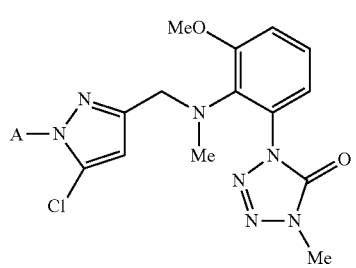
D0137 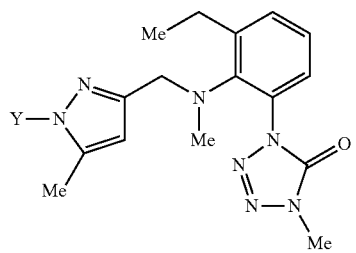
D0138 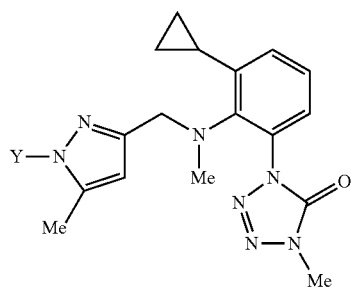
D0139 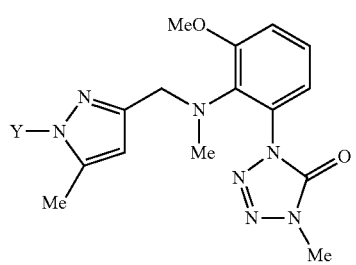
D0140 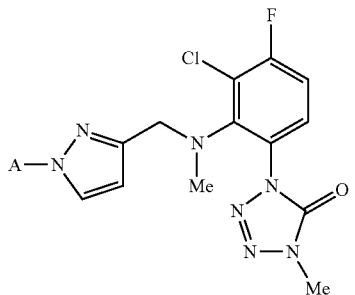
D0141 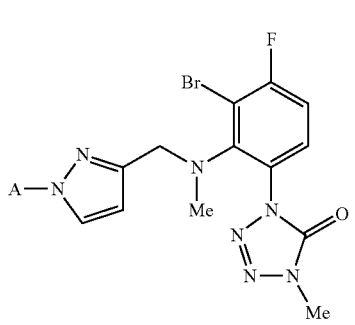
D0142 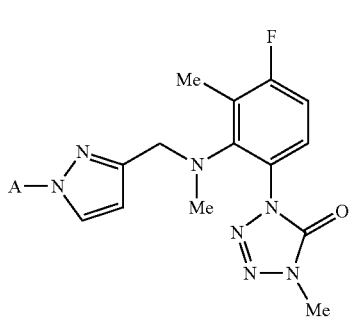
D0143 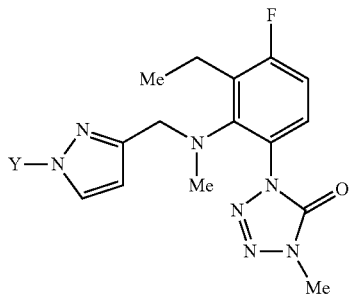
D0144 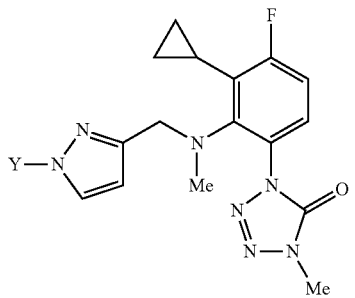

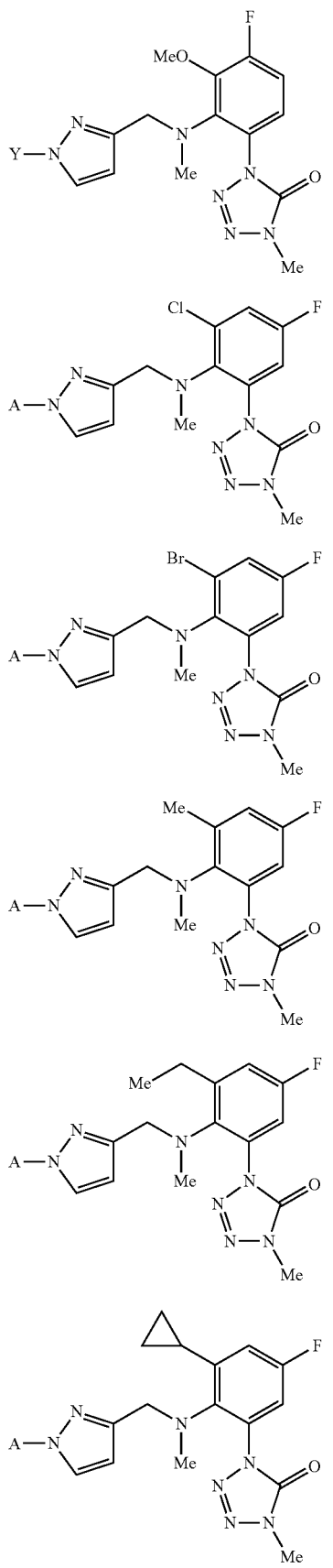
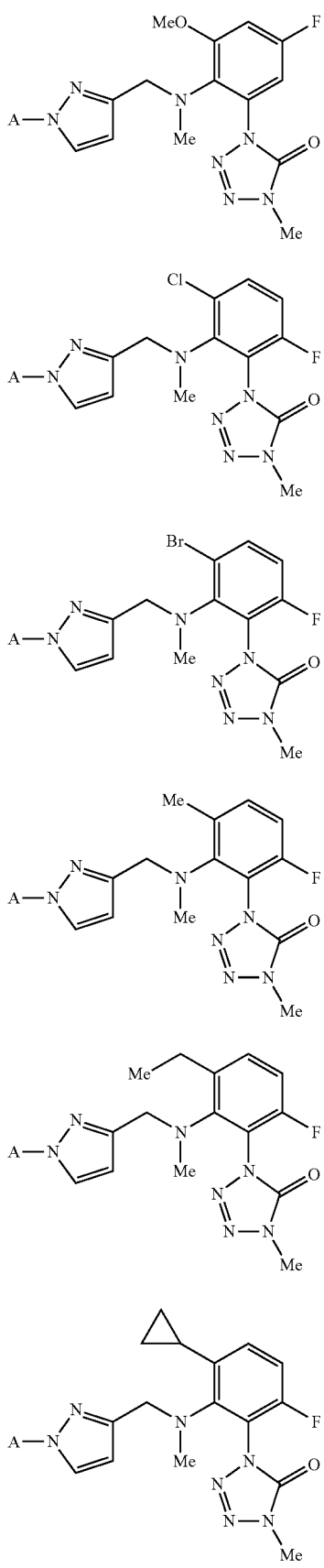

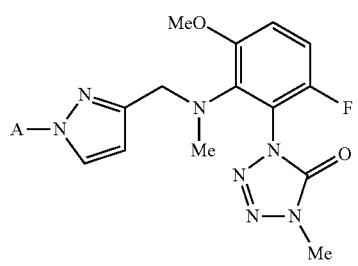
D0157
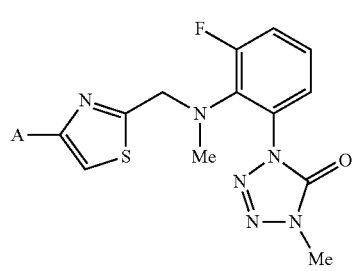
D0158
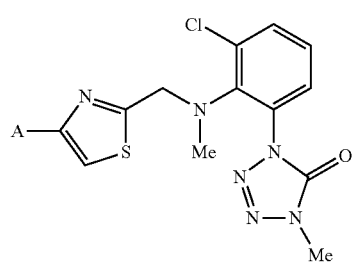
D0159
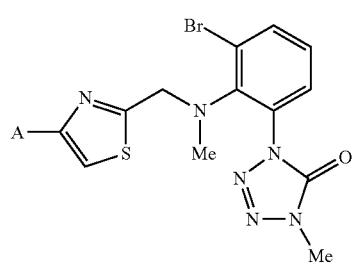
D0160
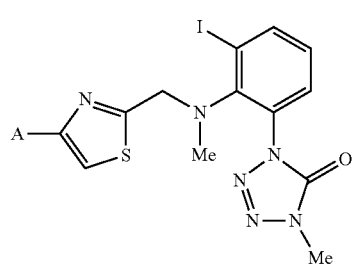
D0161
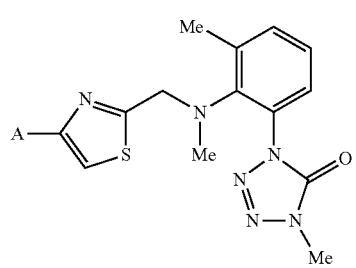
D0162
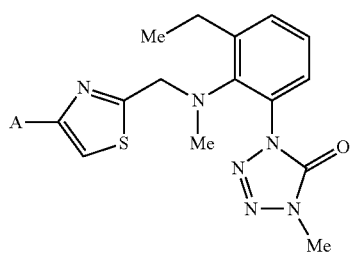
D0163
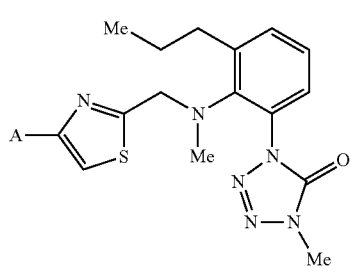
D0164
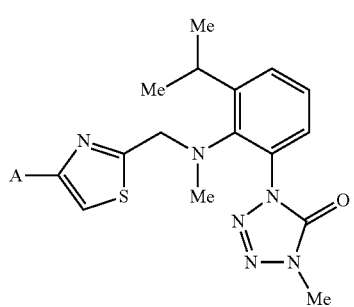
D0165
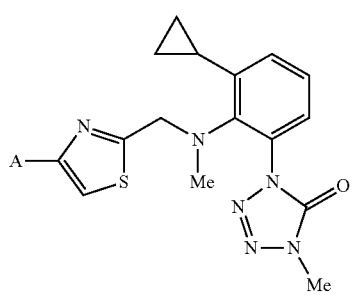
D0166
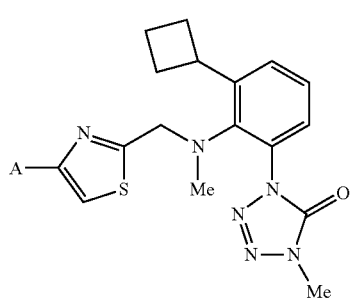
D0167

-continued
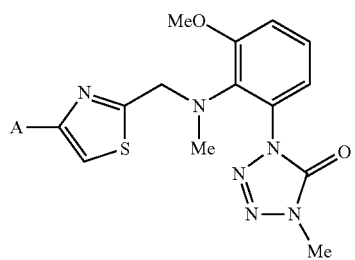
D0168
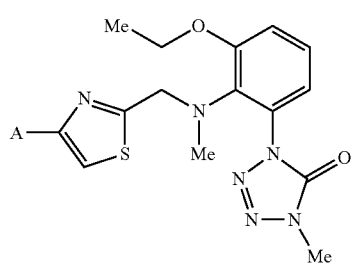
D0169
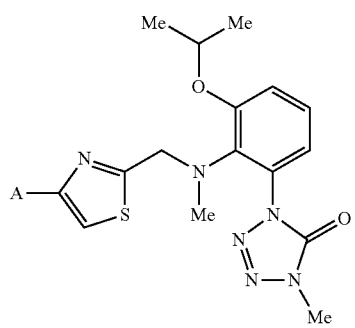
D0170
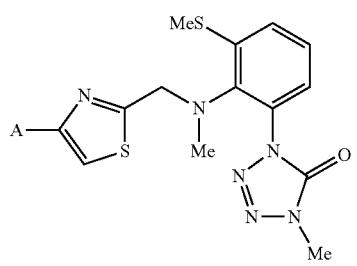
D0171
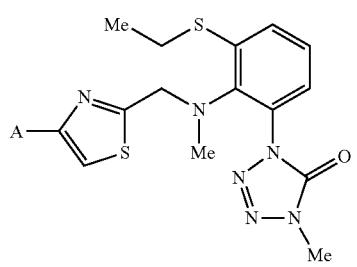
D0172
-continued
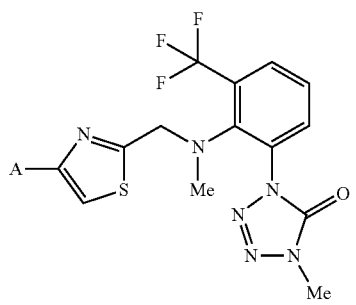
D0173
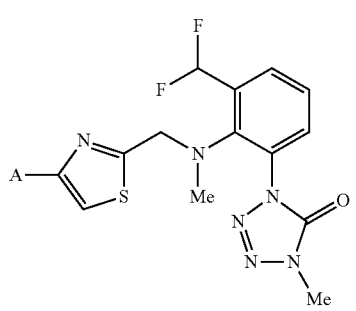
D0174
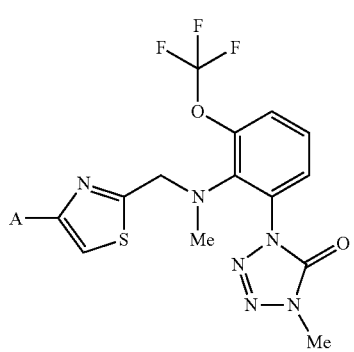
D0175
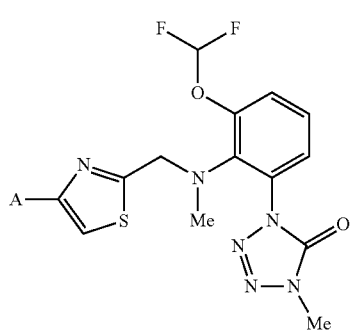
D0176
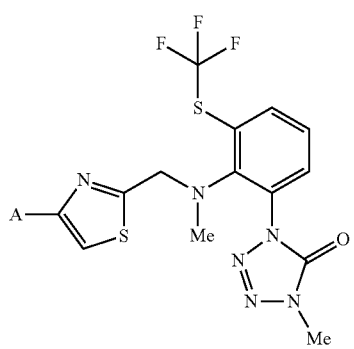
D0177

-continued
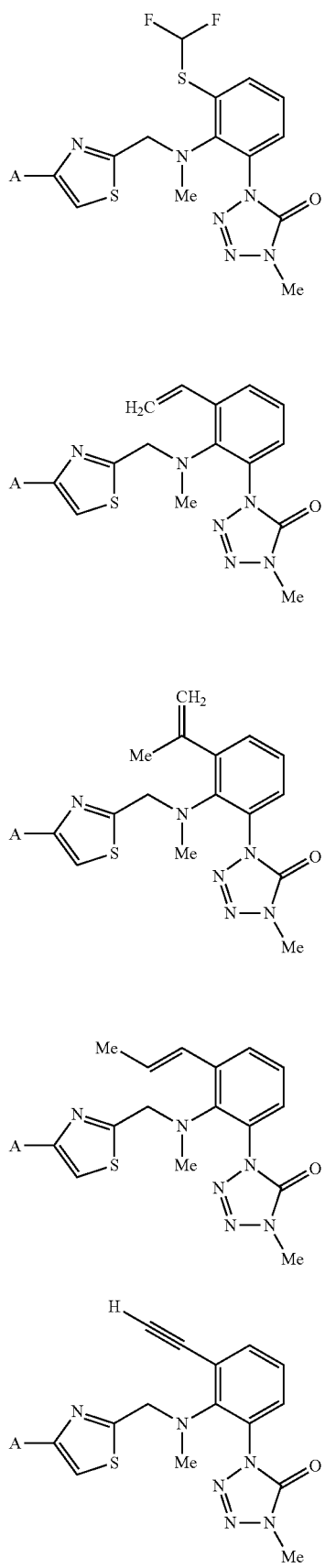
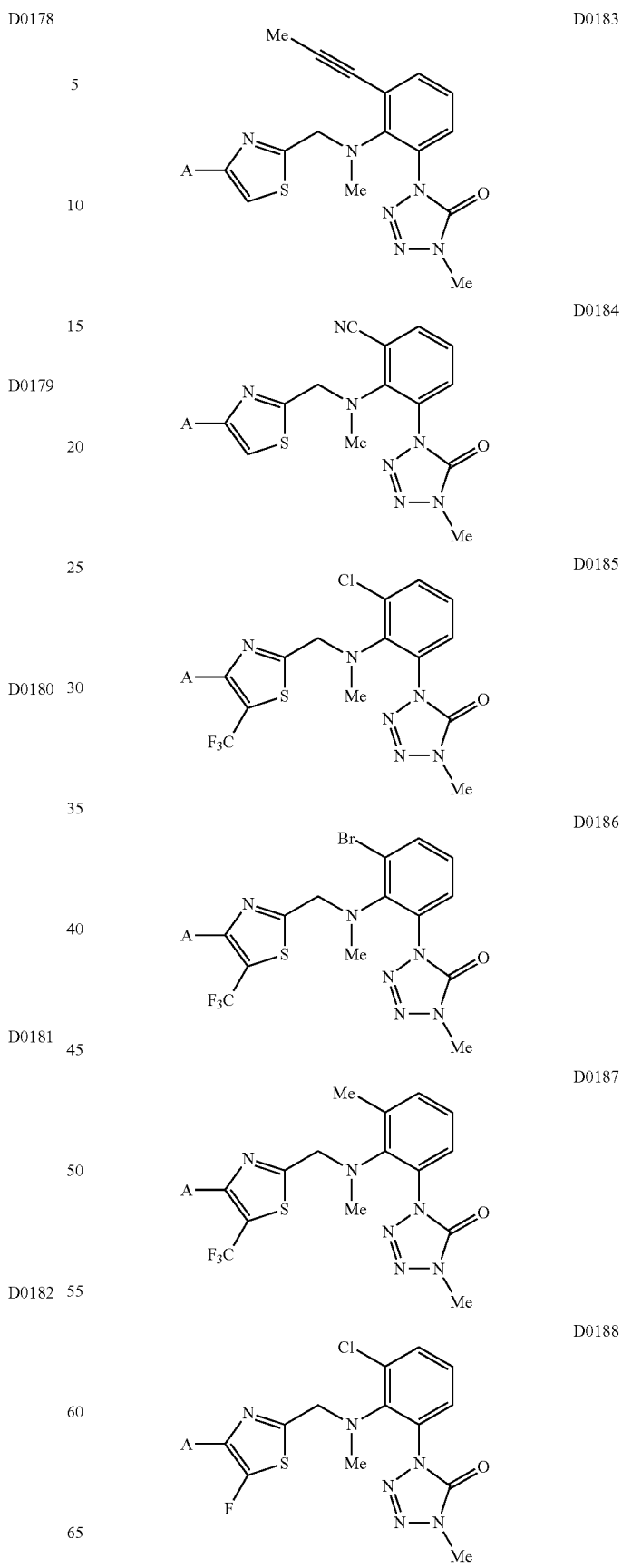

-continued
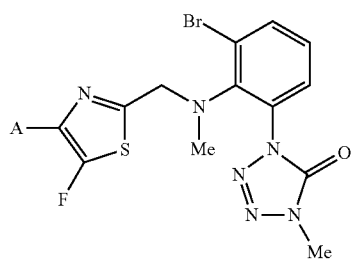
D0189
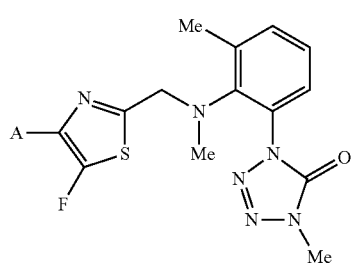
D0190
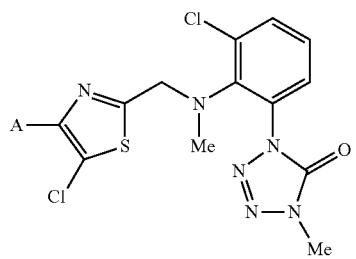
D0191
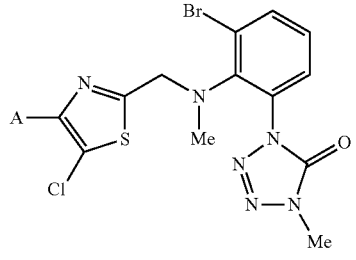
D0192
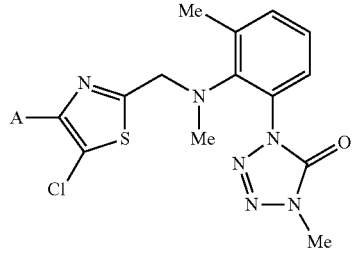
D0193
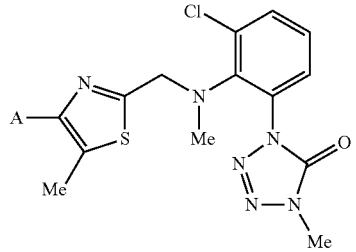
D0194
-continued
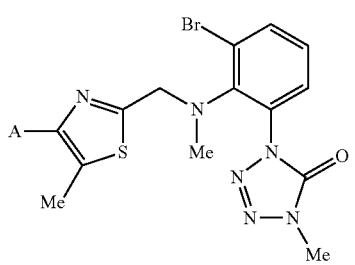
D0195
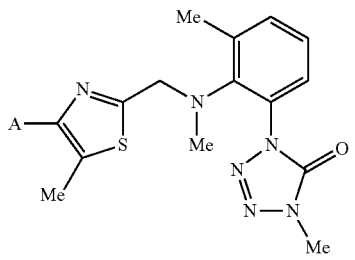
D0196
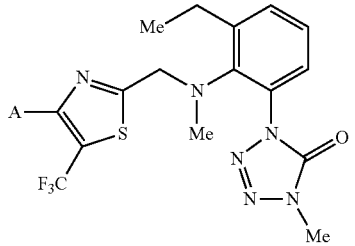
D0197
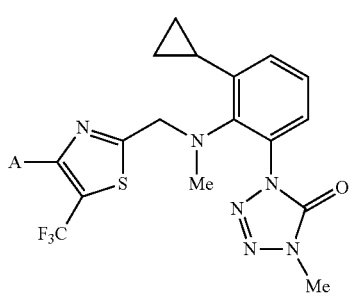
D0198
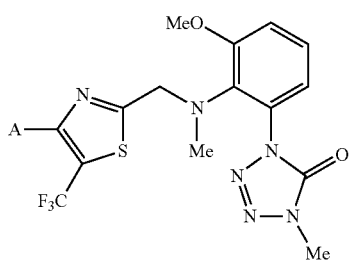
D0199
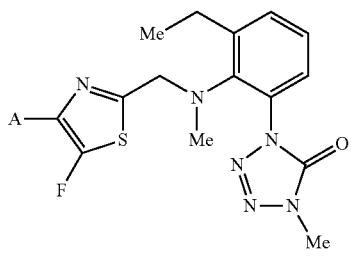
D0200

D0201 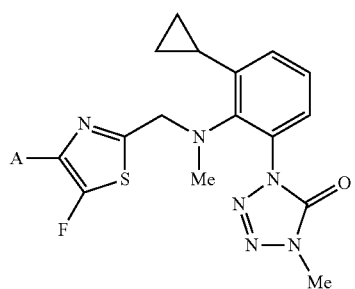
D0202 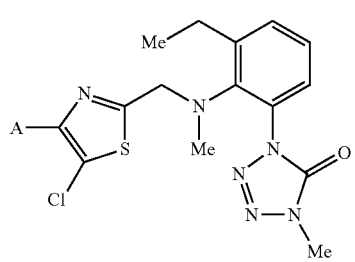
D0203 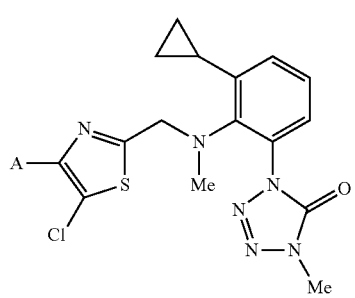
D0204 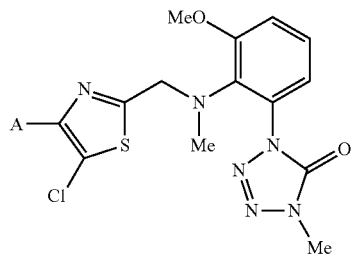
D0205 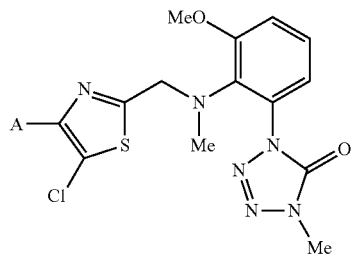
D0206 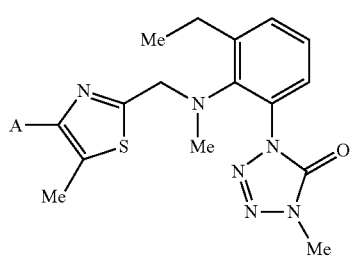
D0207 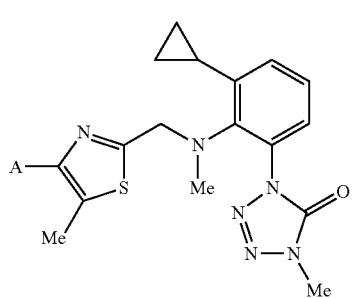
D0208 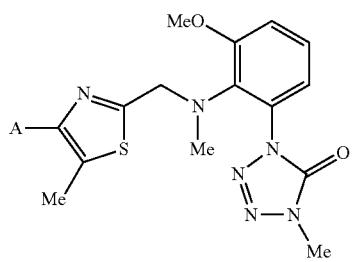
D0209 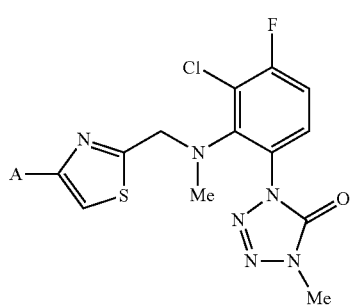
D0210 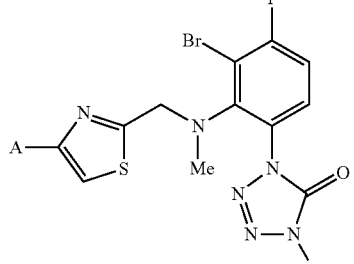

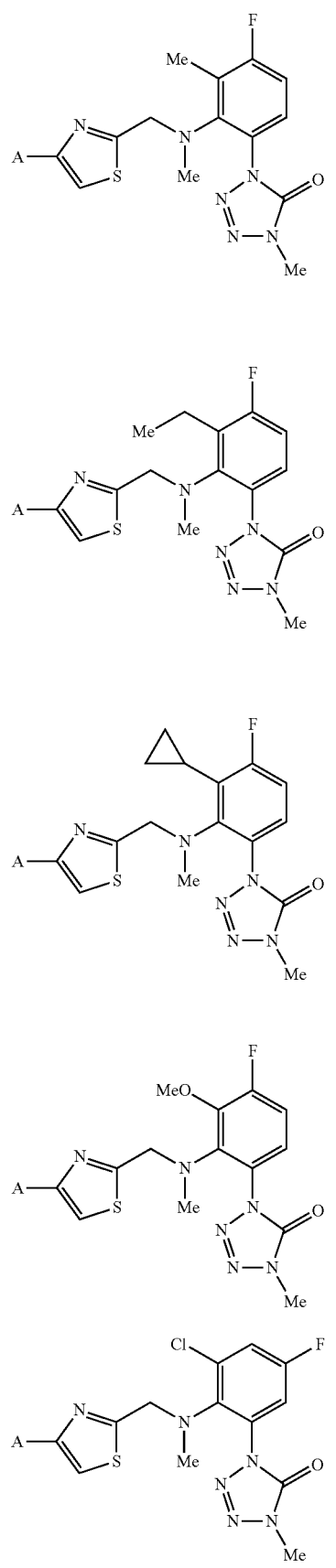
D0211
D0212
D0213
D0214
D0215
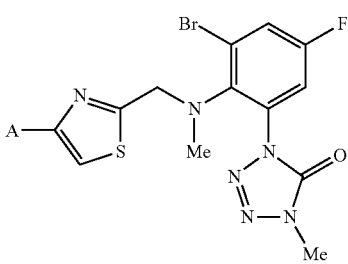
D0216
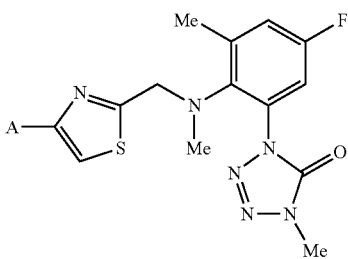
D0217
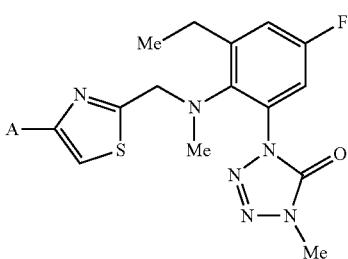
D0218
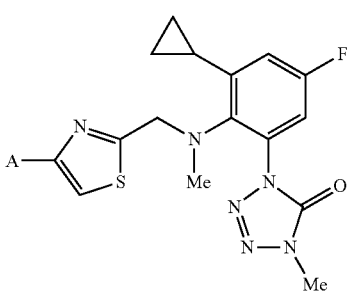
D0219
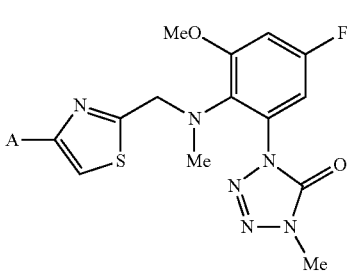
D0220
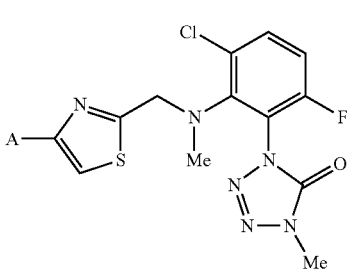
D0221

-continued
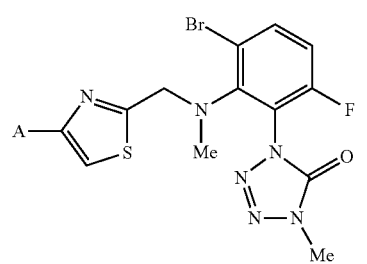 D0222
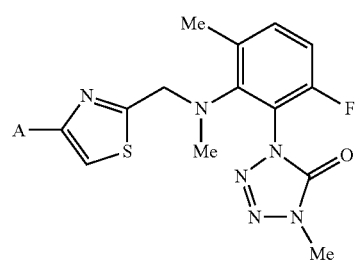 D0223
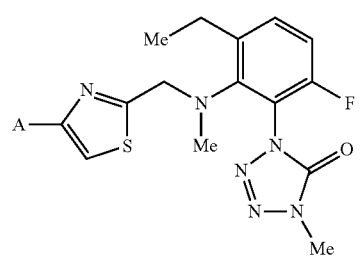 D0224
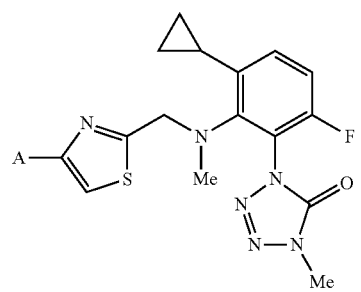 D0225
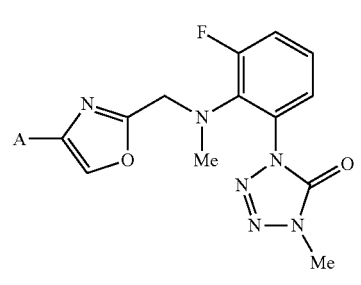 D0226
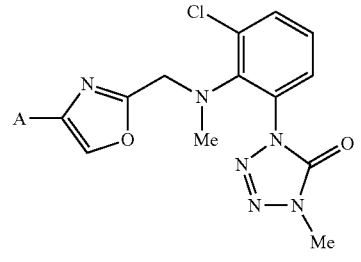 D0227
-continued
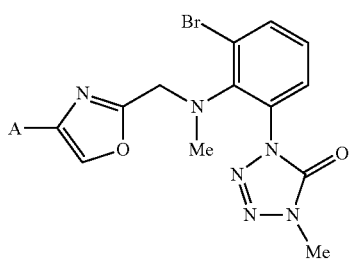 D0228
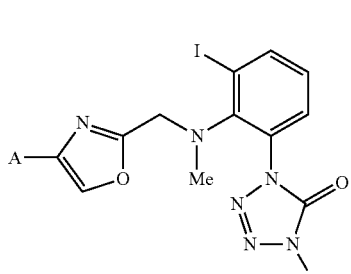 D0229
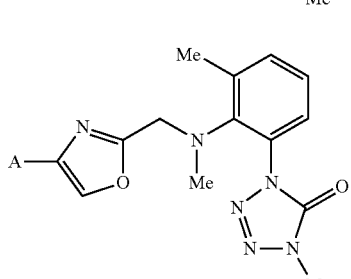 D0230
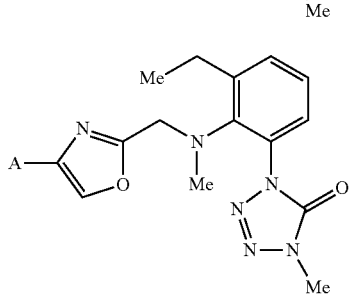 D0231
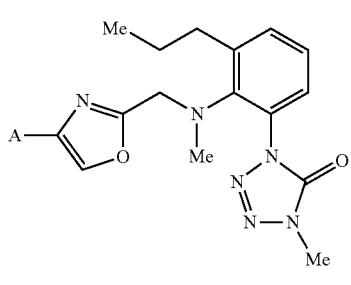 D0232
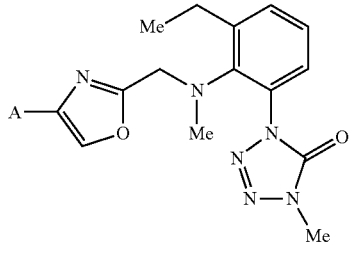 D0233

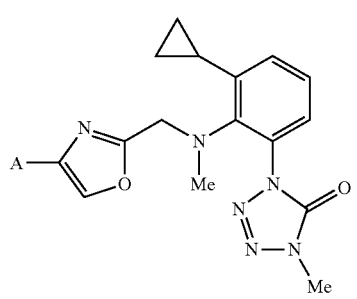
D0234
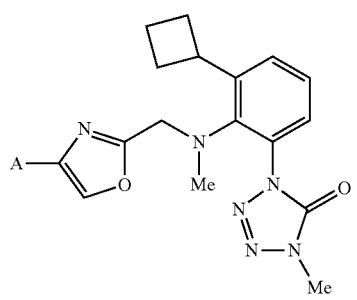
D0235
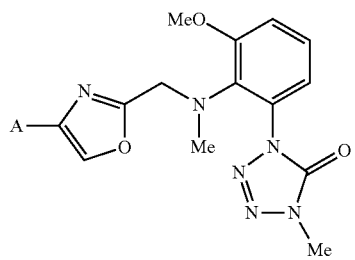
D0236
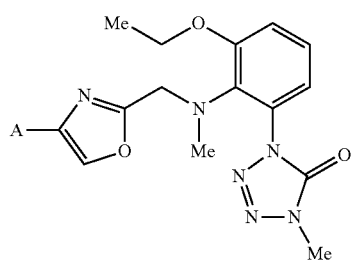
D0237
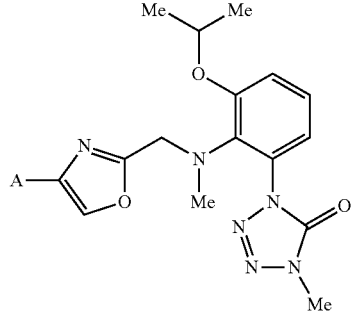
D0238
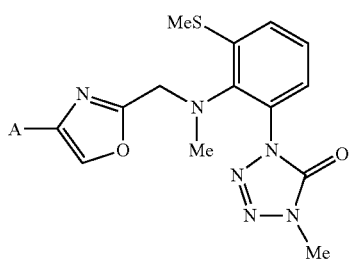
D0239
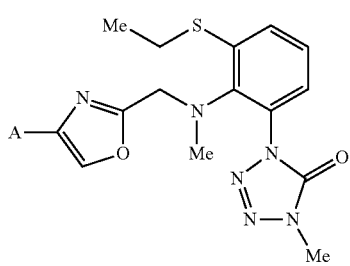
D0240
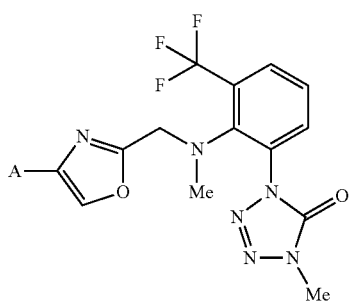
D0241
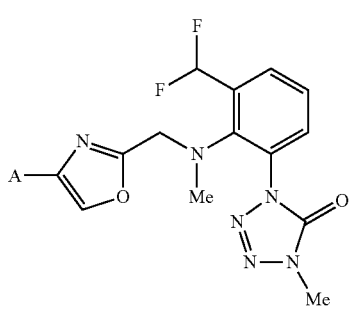
D0242
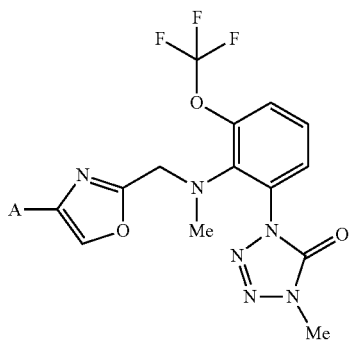
D0243

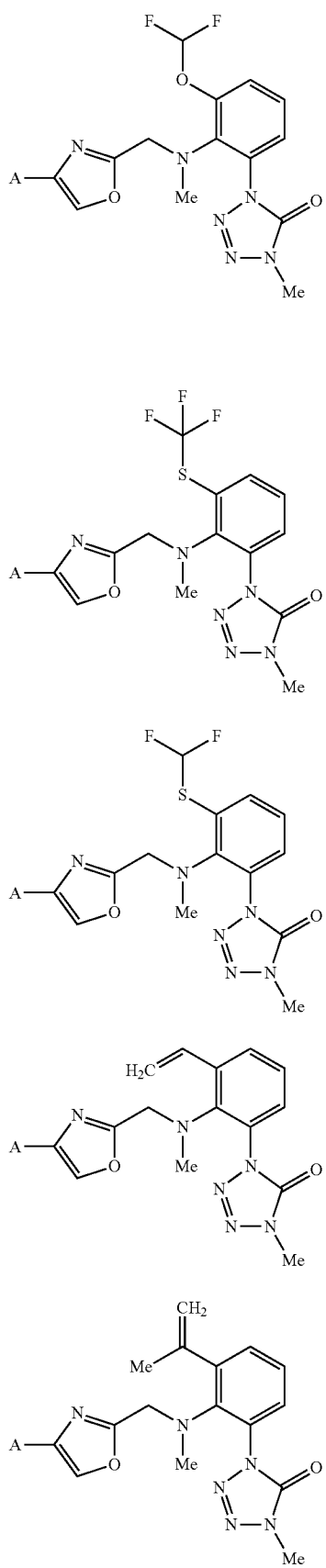
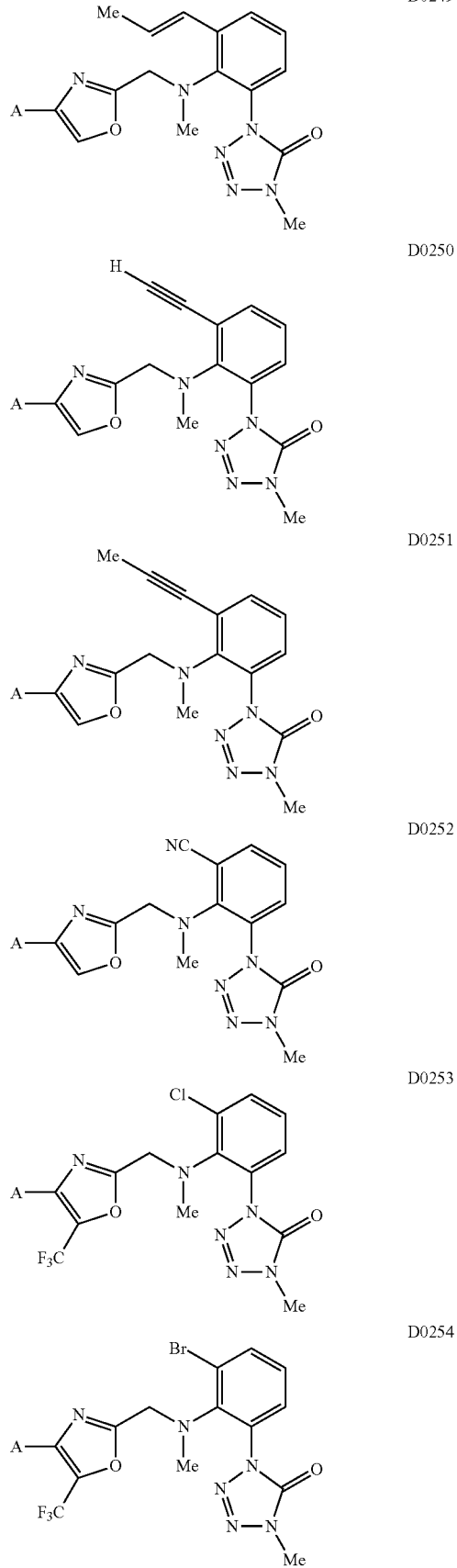

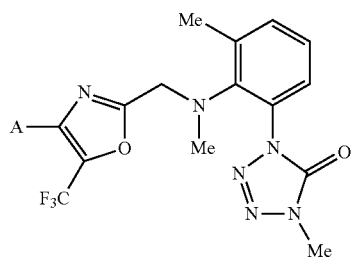
D0255
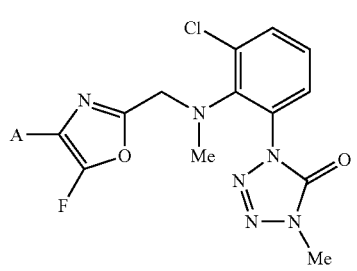
D0256
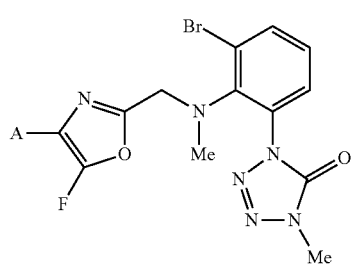
D0257
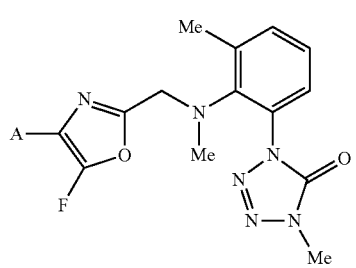
D0258
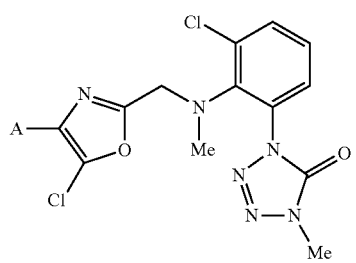
D0259
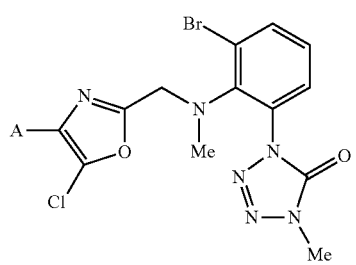
D0260
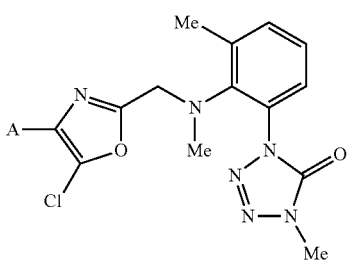
D0261
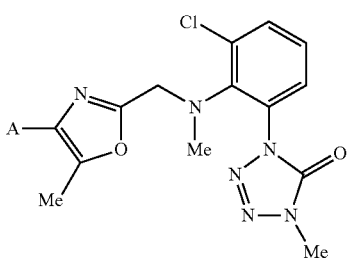
D0262
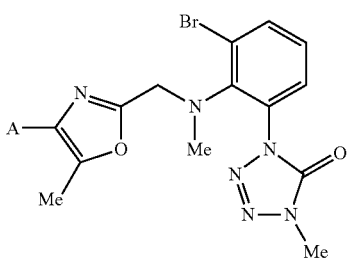
D0263
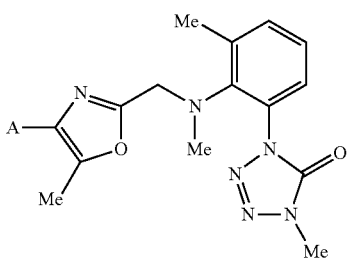
D0264
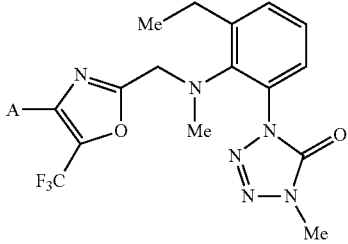
D0265
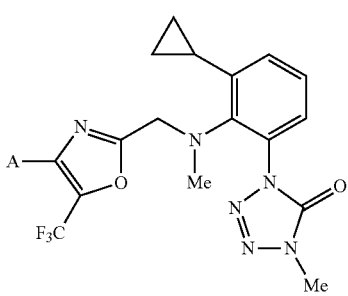
D0266

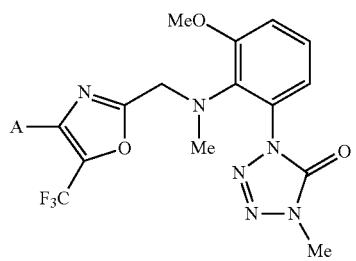
D0267
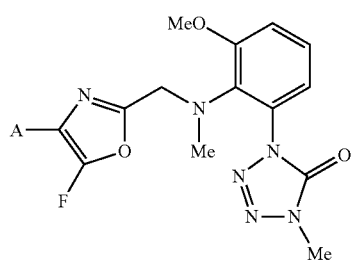
D0268
D0269
D0270
D0271
D0272
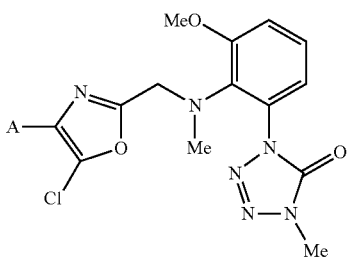
D0273
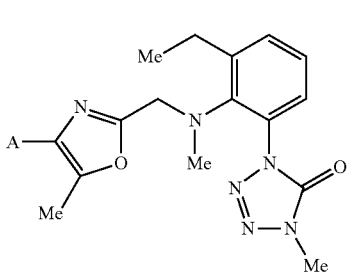
D0274
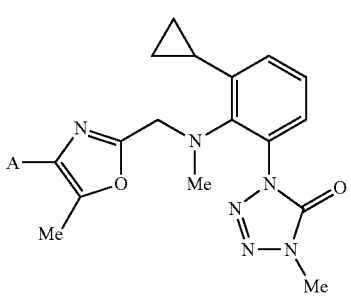
D0275
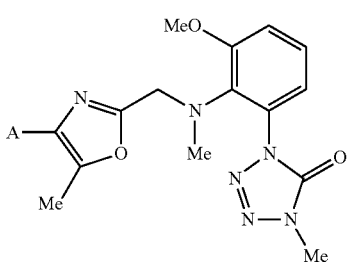
D0276
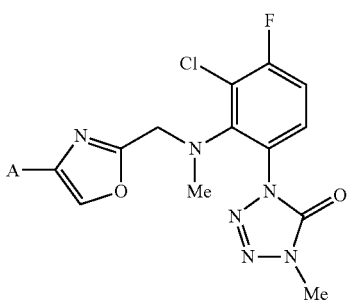
D0277

D0278
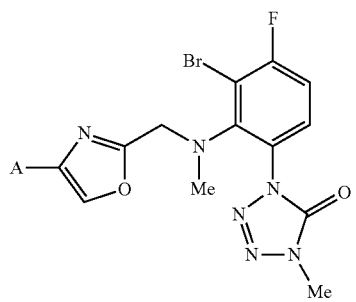
D0279
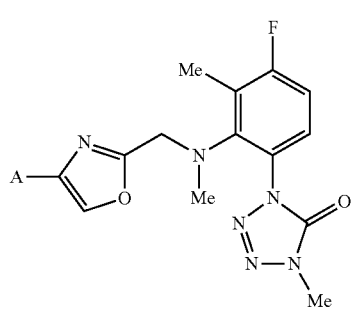
D0280
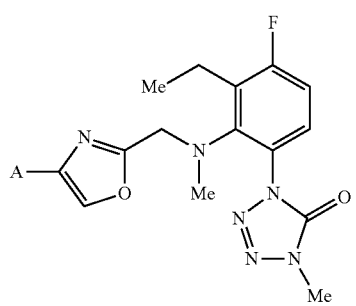
D0281
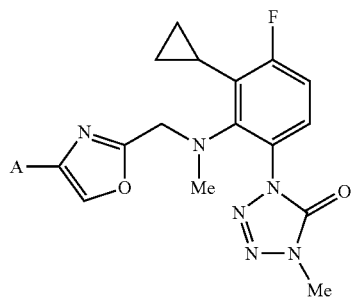
D0282
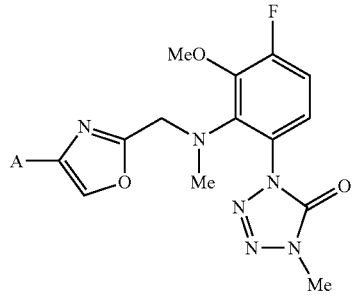
D0283
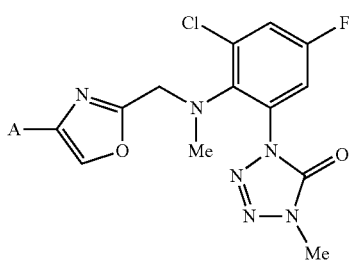
D0284
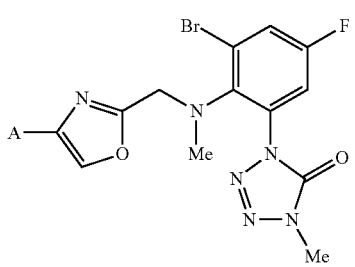
D0285
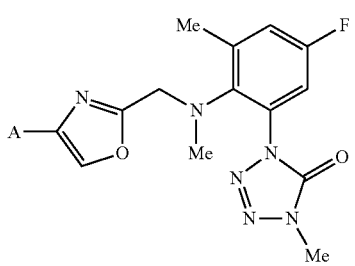
D0286
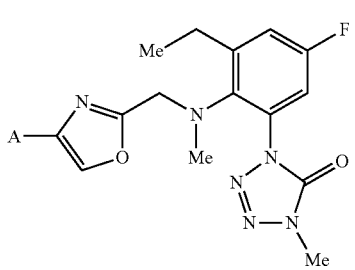
D0287
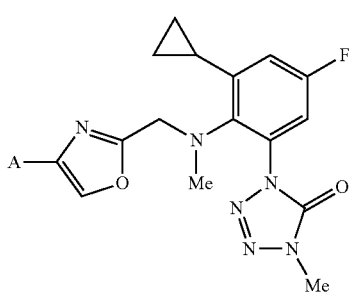
D0288
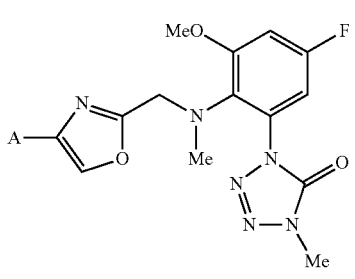

-continued
D0289
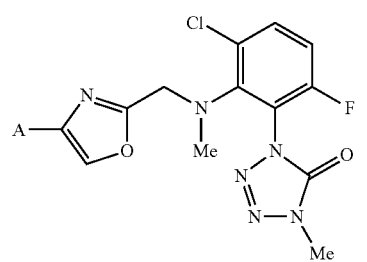
D0290
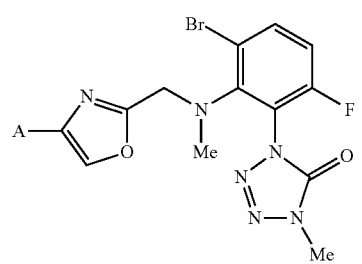
D0291
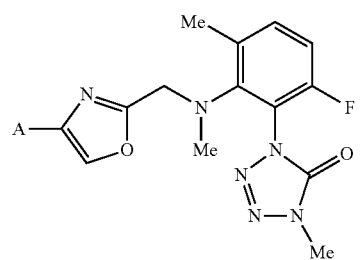
D0292
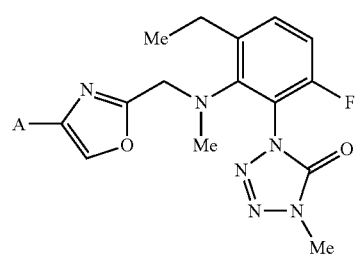
D0293
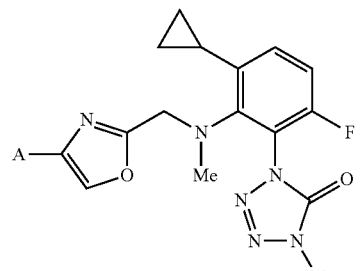
D0294
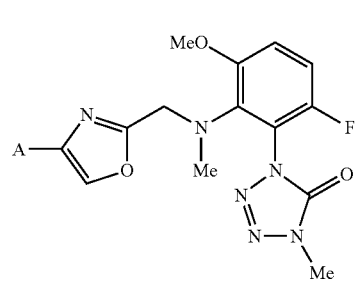
-continued
D0295
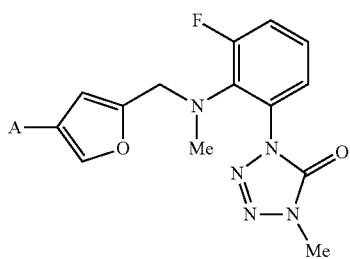
D0296
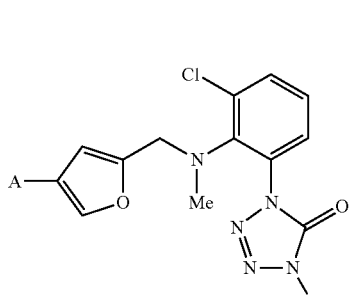
D0297
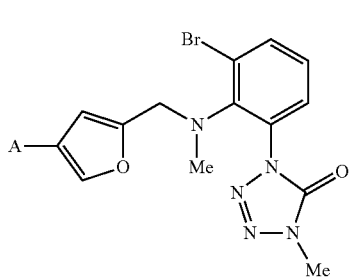
D0298
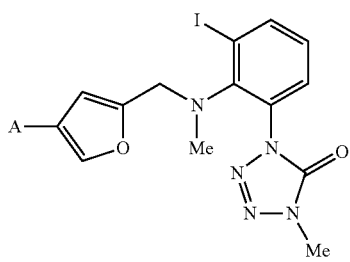
D0299
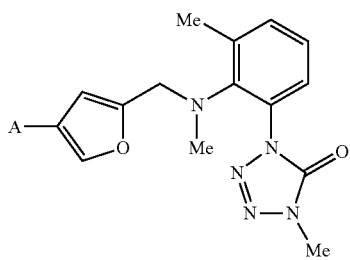
D0300
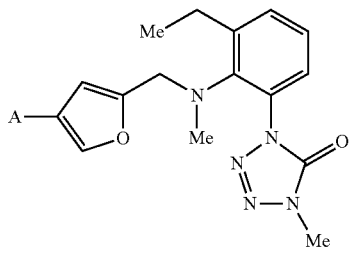

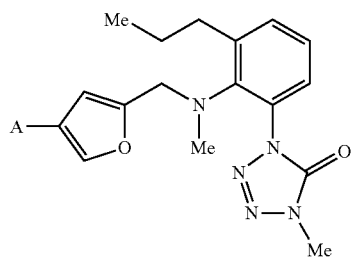
D0301
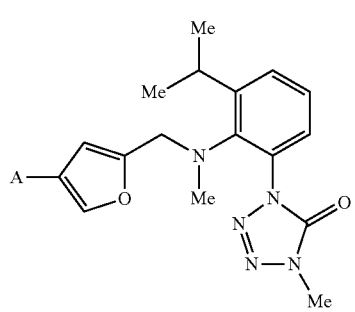
D0302
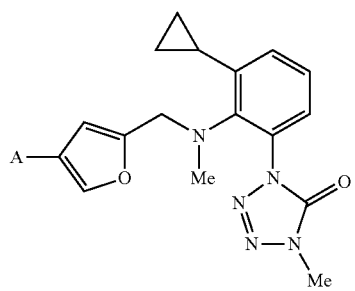
D0303
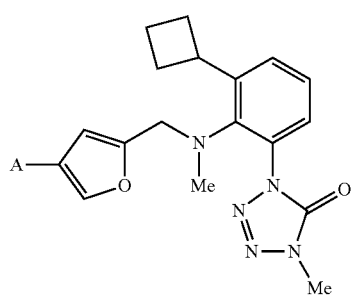
D0304
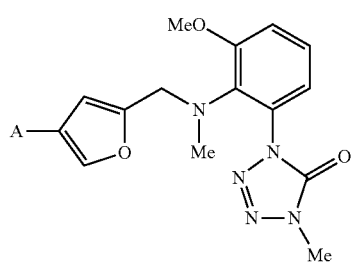
D0305
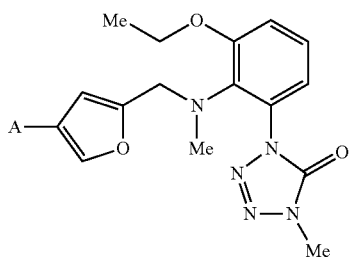
D0306
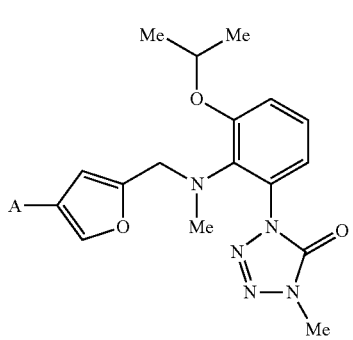
D0307
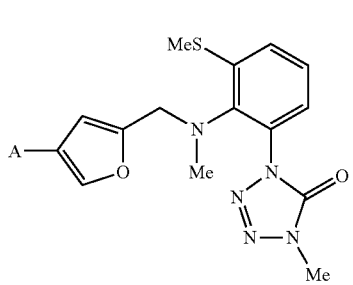
D0308
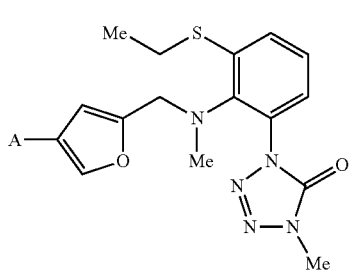
D0309
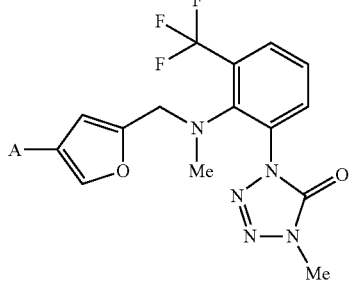
D0310

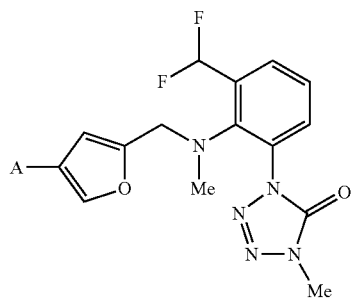 D0311
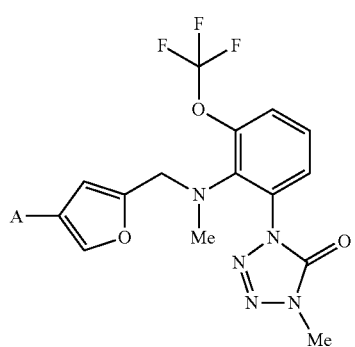 D0312
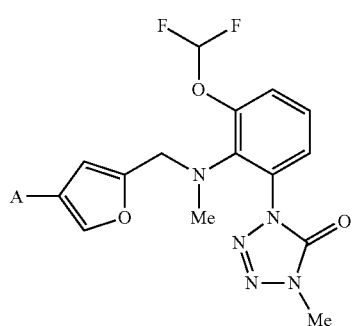 D0313
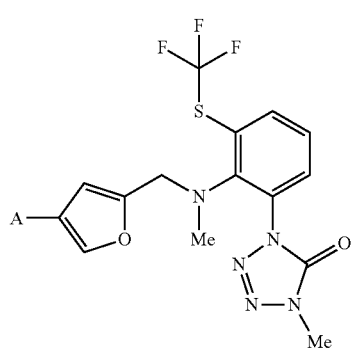 D0314
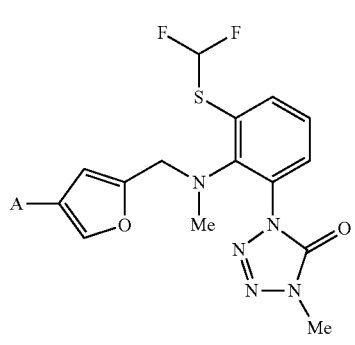 D0315
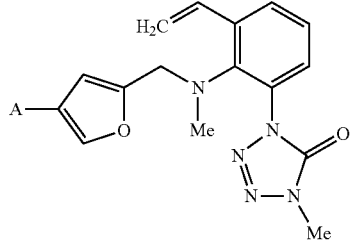 D0316
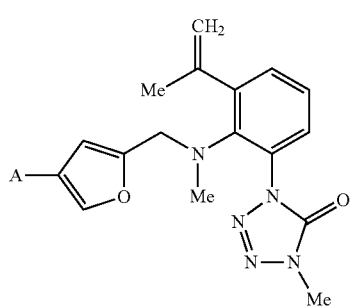 D0317
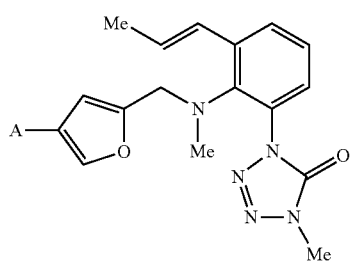 D0318
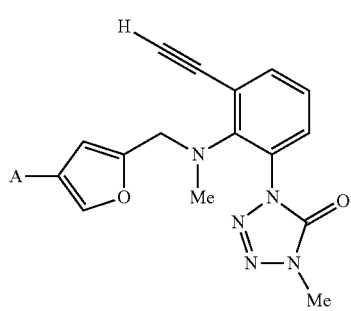 D0319
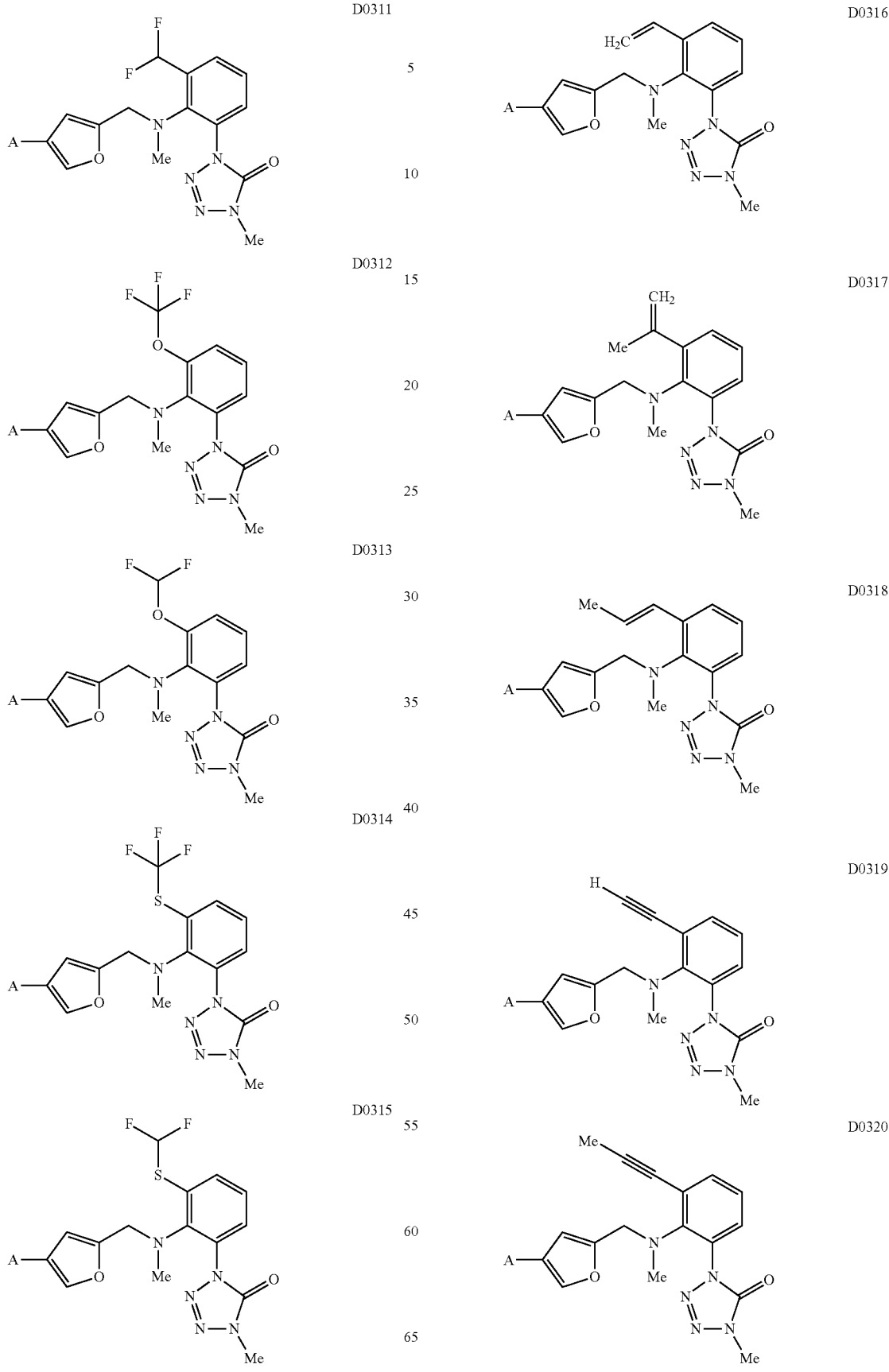 D0320

D0321 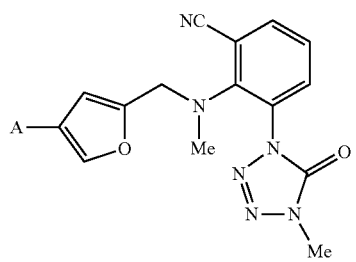
D0322 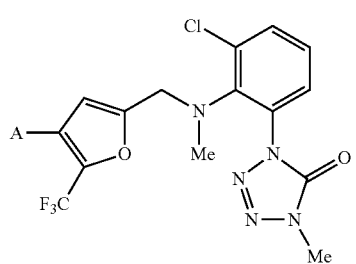
D0323 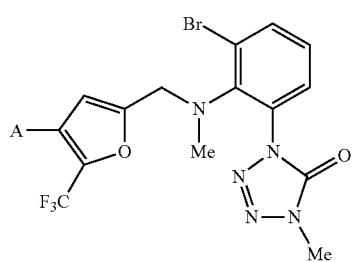
D0324 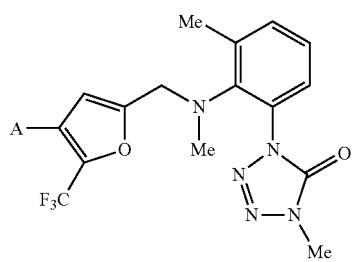
D0325 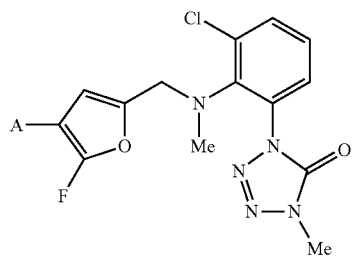
D0326 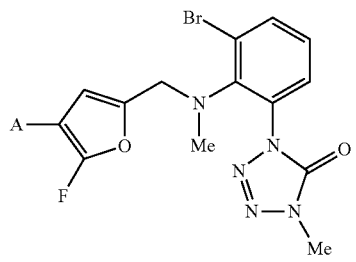
D0327 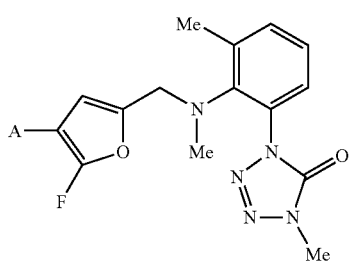
D0328 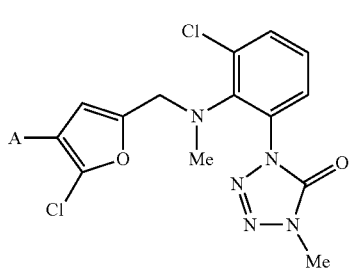
D0329 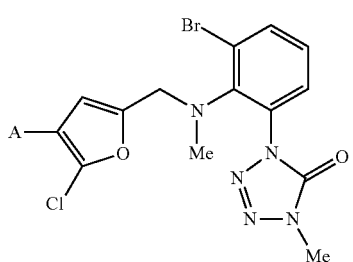
D0330 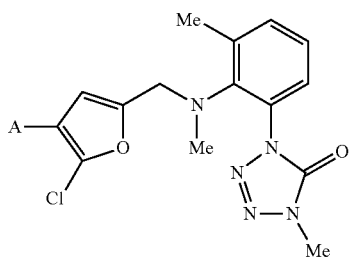
D0331 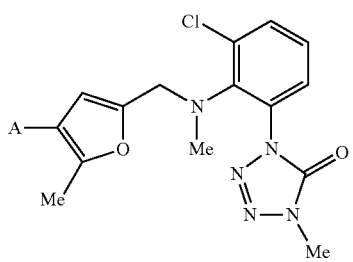
D0332 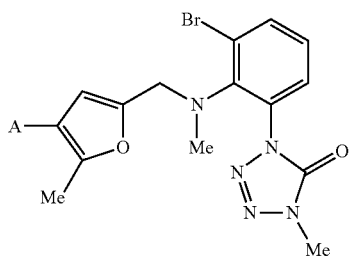

| | |
|---|---|
| 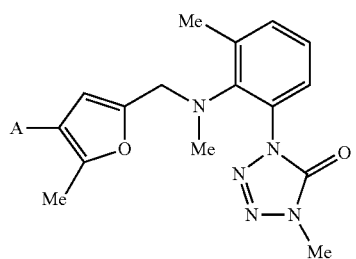 D0333 | 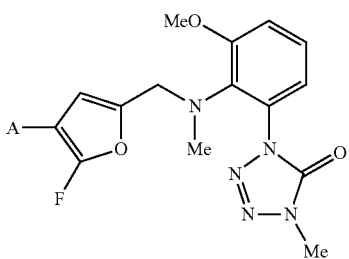 D0339 |
| 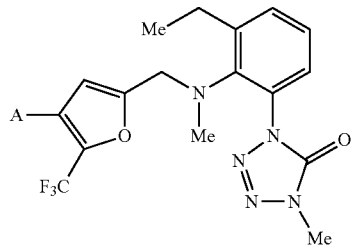 D0334 | 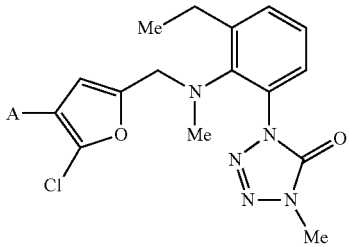 D0340 |
| 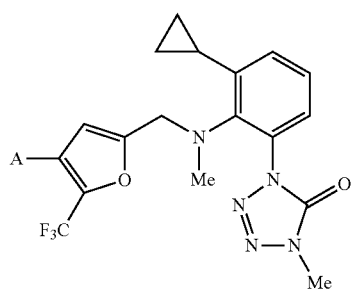 D0335 | 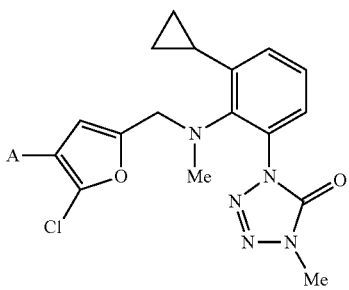 D0341 |
| 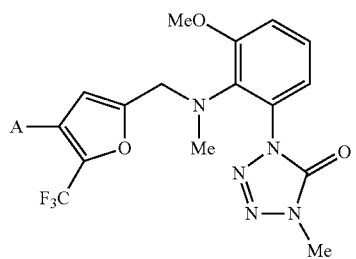 D0336 | 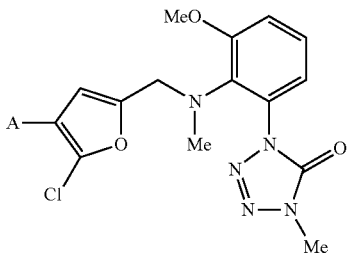 D0342 |
| 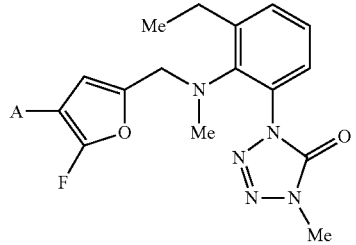 D0337 | 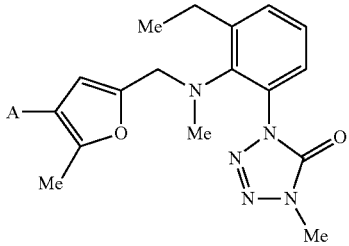 D0343 |
| 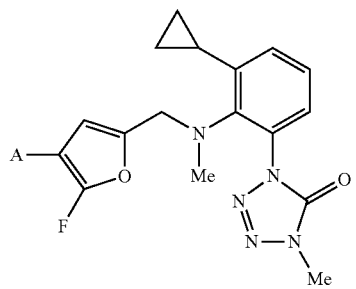 D0338 | 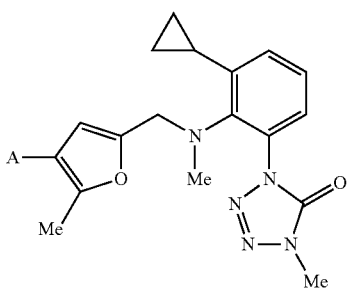 D0344 |

D0345 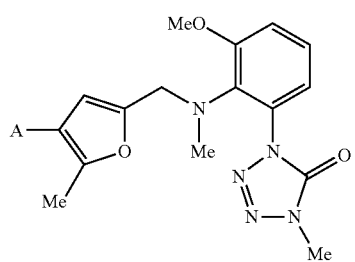
D0346 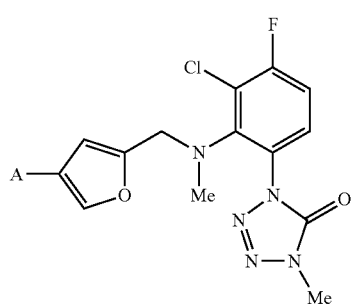
D0347 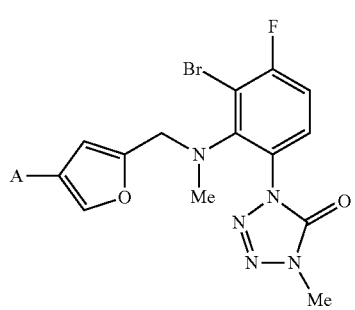
D0348 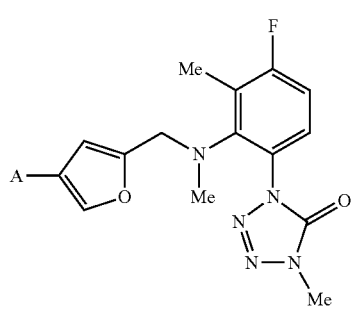
D0349 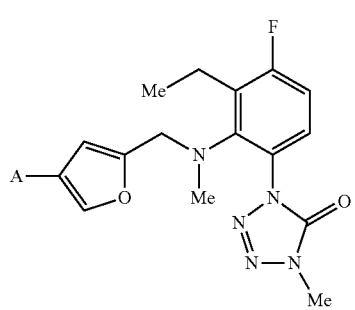
D0350 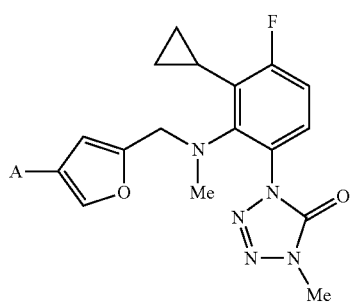
D0351 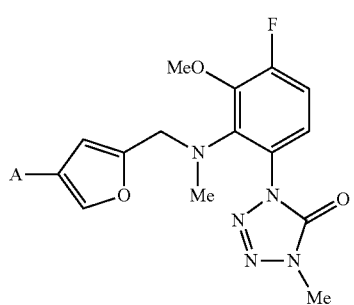
D0352 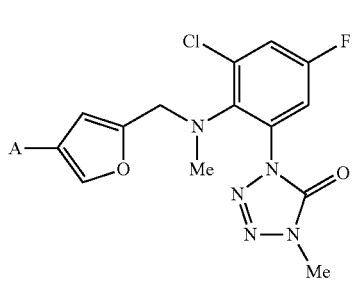
D0353 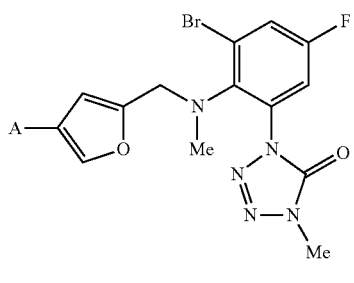
D0354

D0355 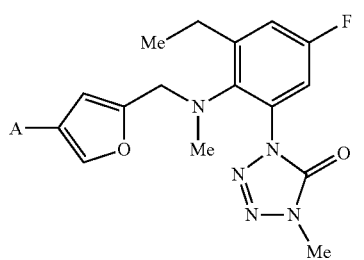
D0356 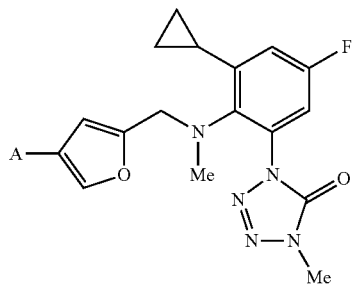
D0357 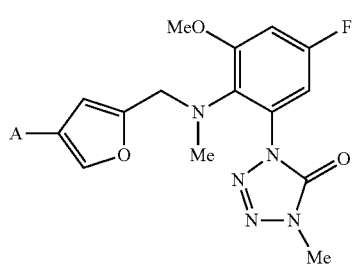
D0358 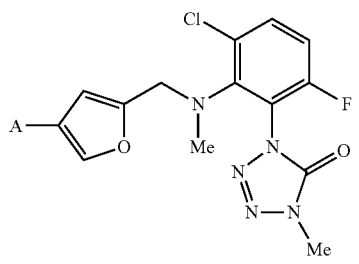
D0359 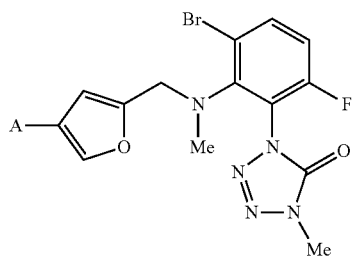
D0360 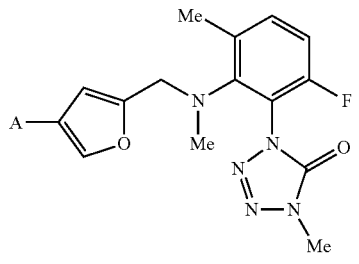
D0361 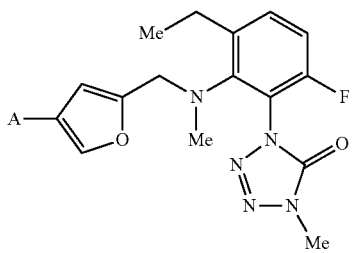
D0362 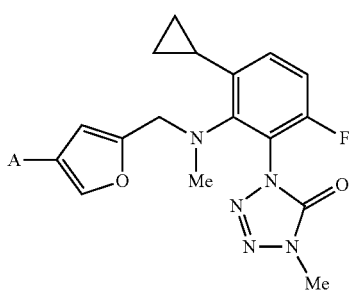
D0363 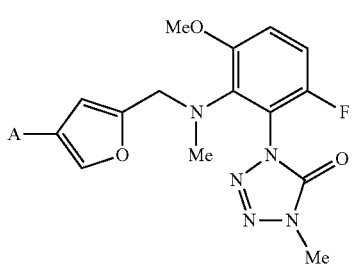
D0364 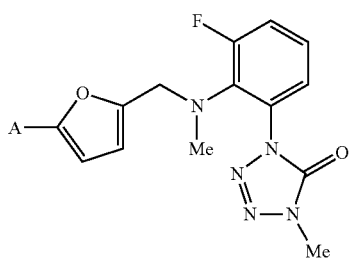
D0365 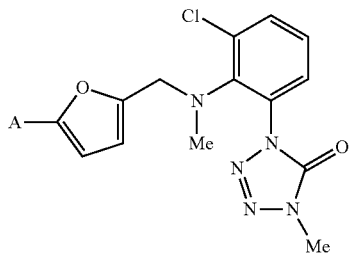
D0366 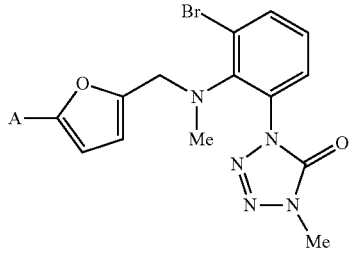

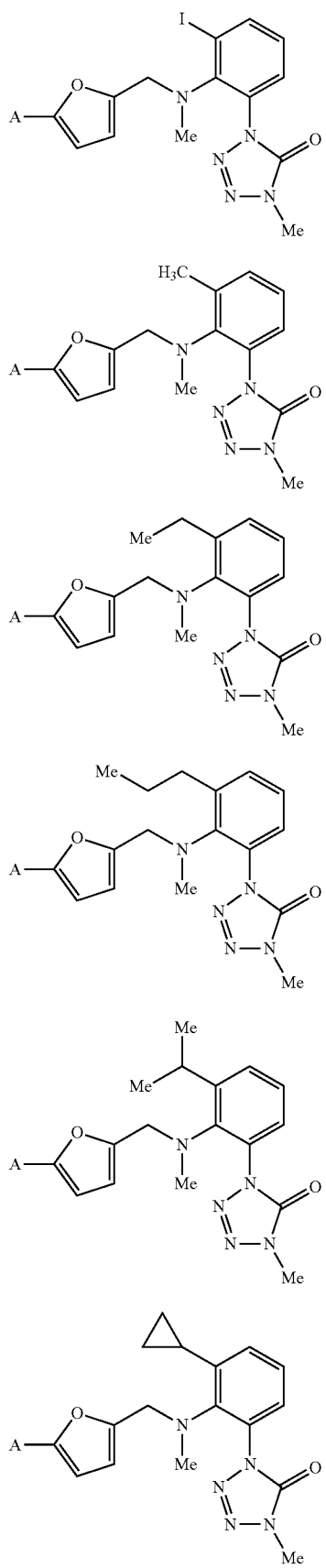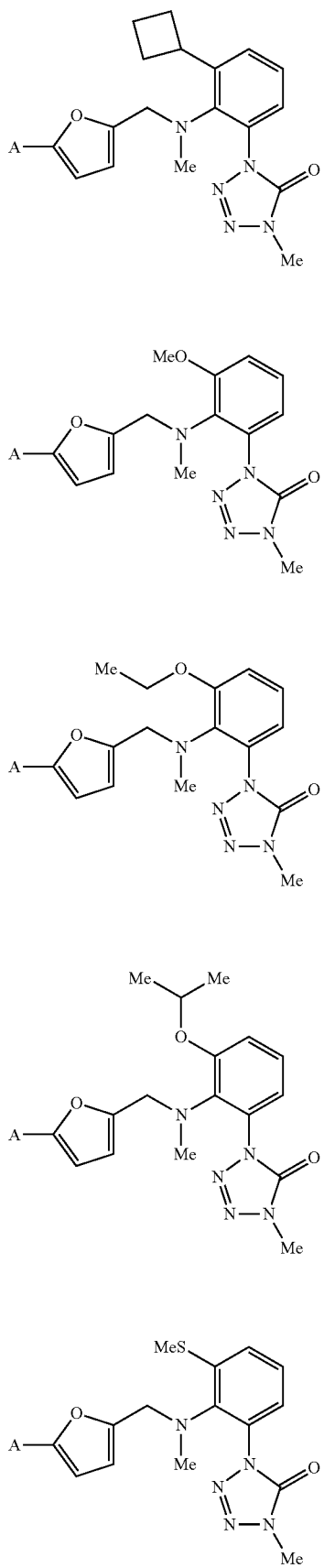

407
-continued
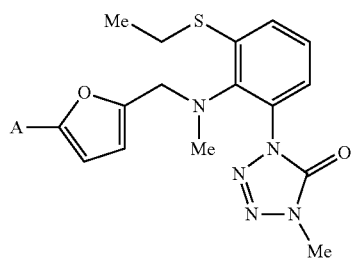
D0378
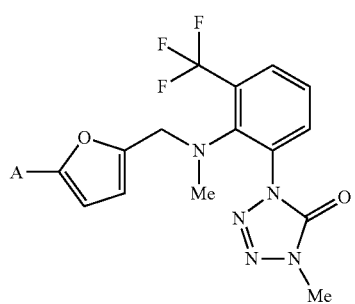
D0379
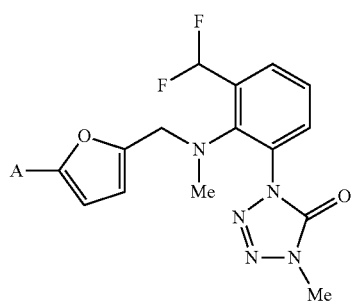
D0380
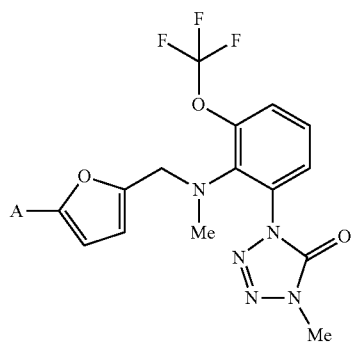
D0381
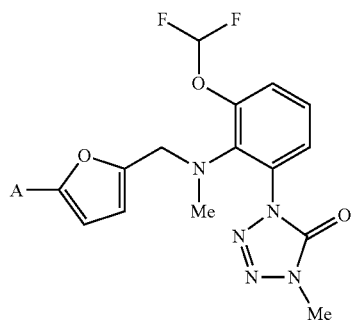
D0382
408
-continued
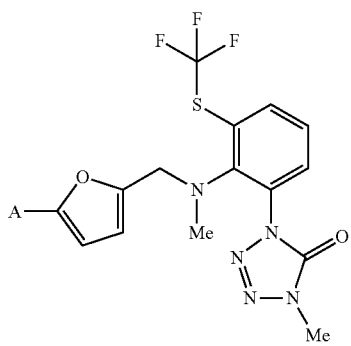
D0383
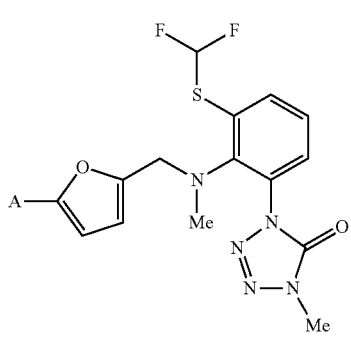
D0384
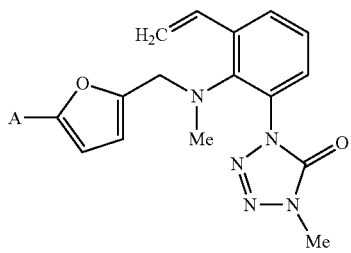
D0385
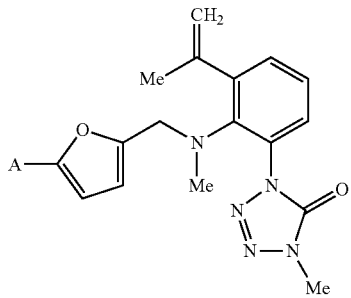
D0386
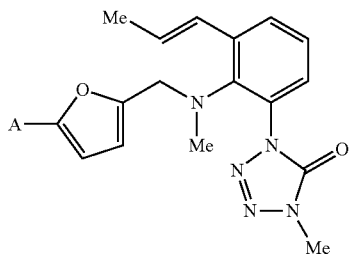
D0387

D0388 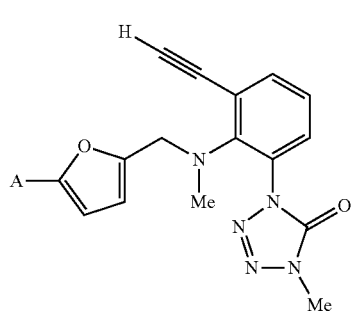
D0389 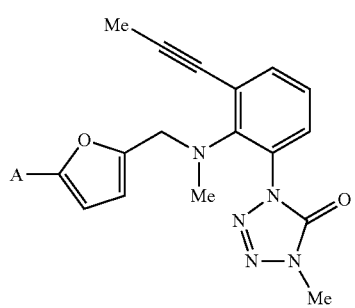
D0390 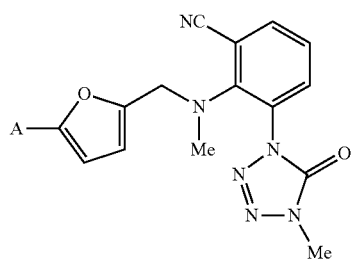
D0391 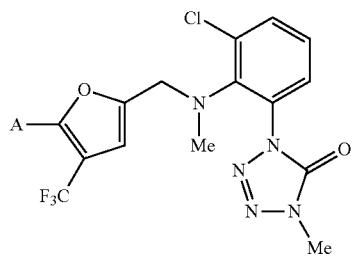
D0392 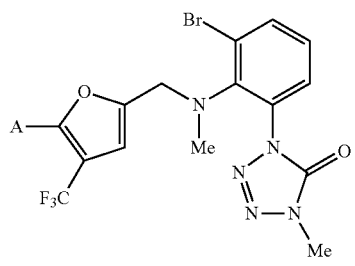
D0393 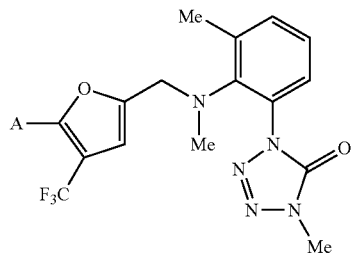
D0394 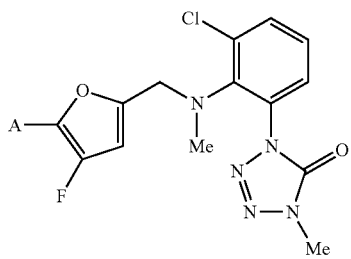
D0395 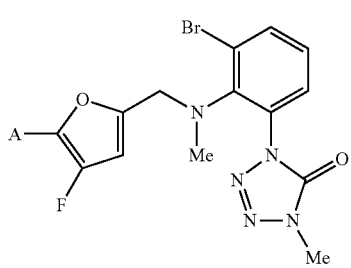
D0396 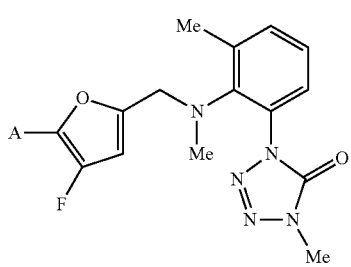
D0397 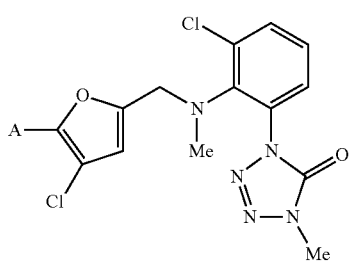
D0398 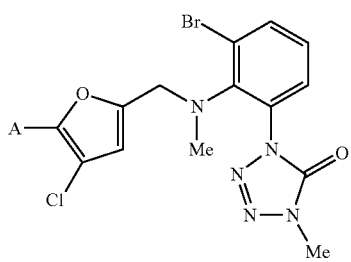
D0399 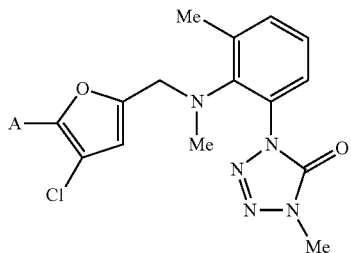

| | |
|---|---|
| D0400 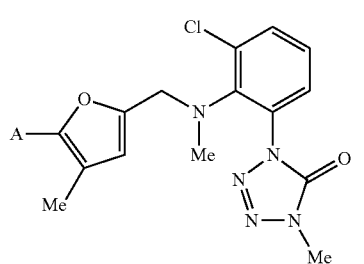 | D0406 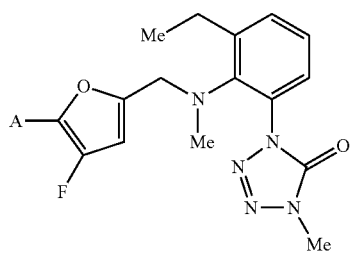 |
| D0401 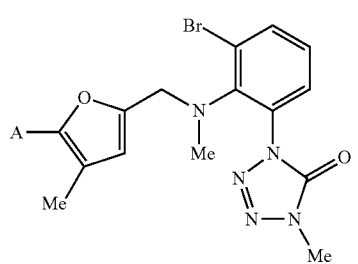 | D0407 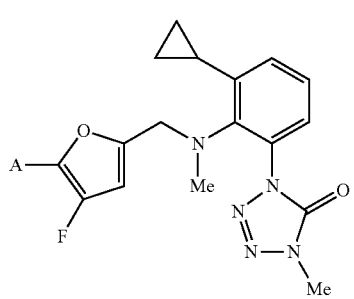 |
| D0402 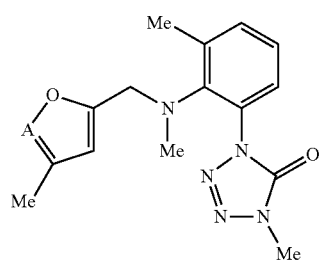 | D0408 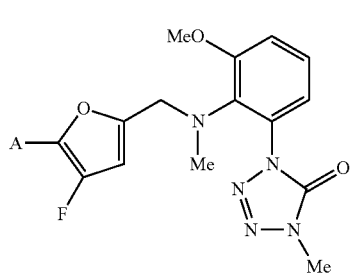 |
| D0403 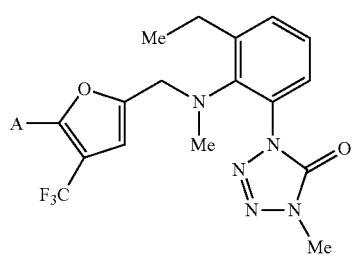 | D0409 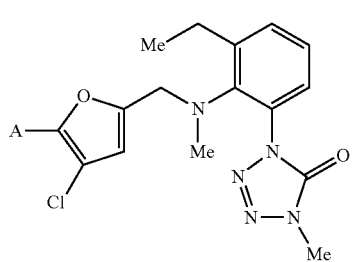 |
| D0404 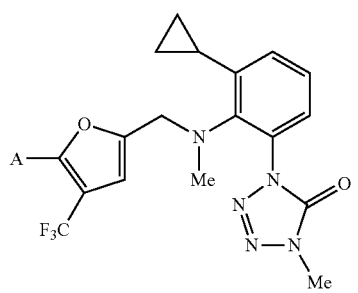 | D0410 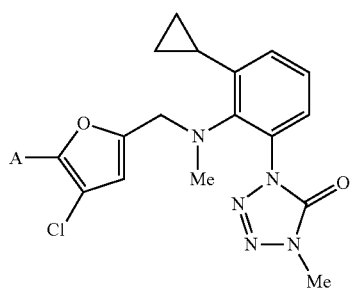 |
| D0406 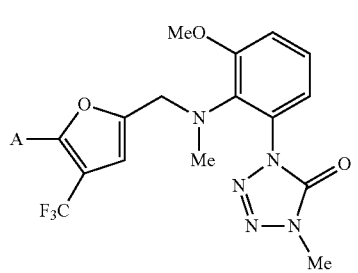 | D0411 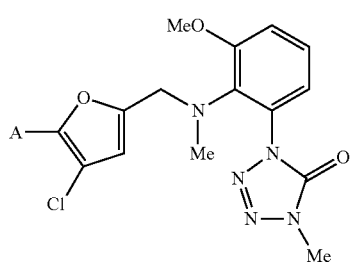 |

-continued
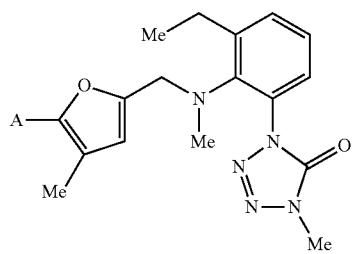
D0412
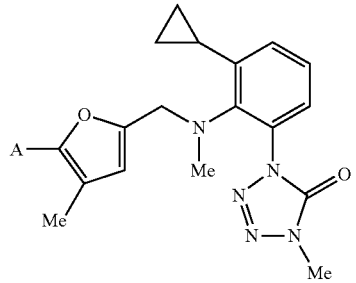
D0413
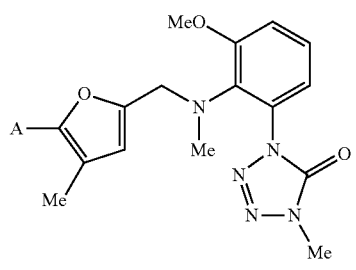
D0414
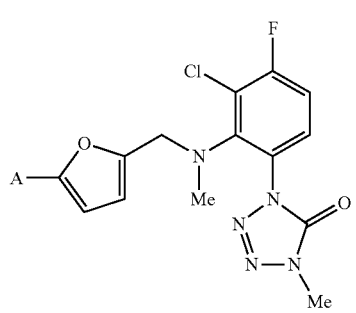
D0415
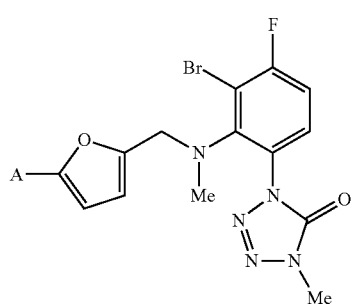
D0416
-continued
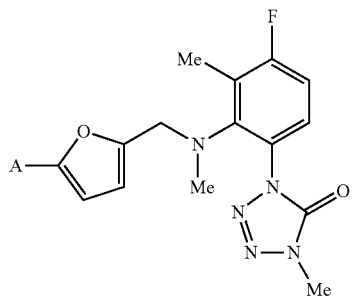
D0417
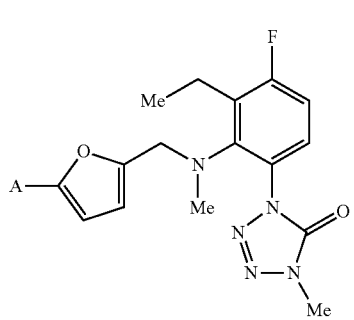
D0418
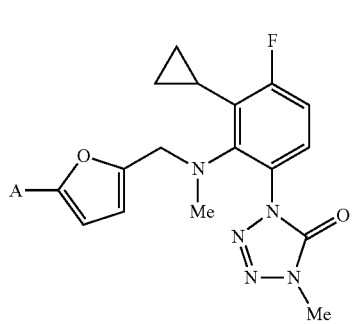
D0419
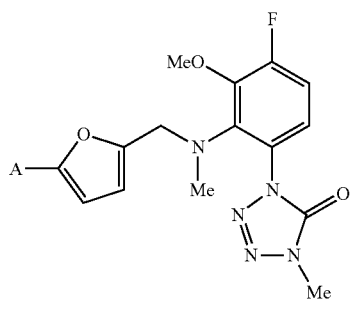
D0420
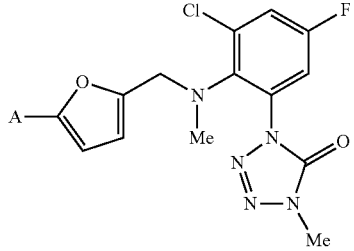
D0421

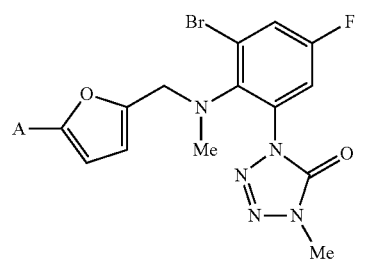
D0422
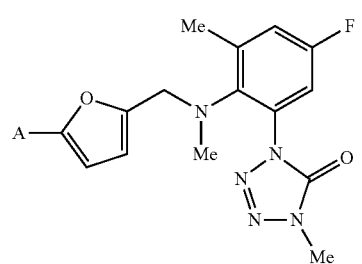
D0423
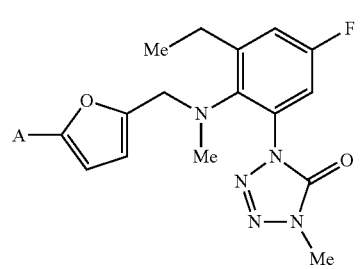
D0424
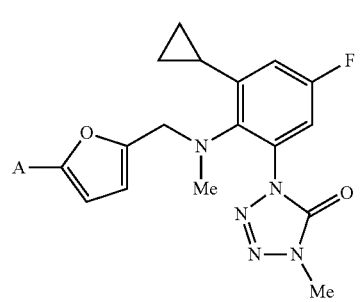
D0425
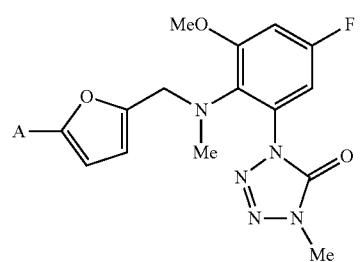
D0426
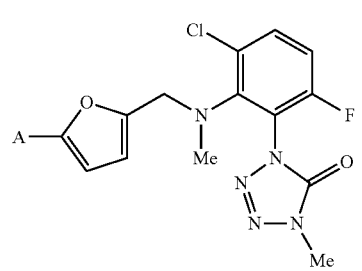
D0427
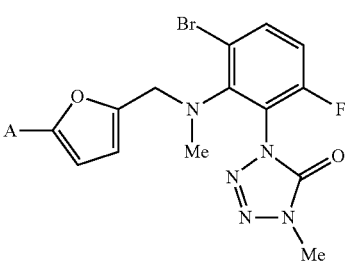
D0428
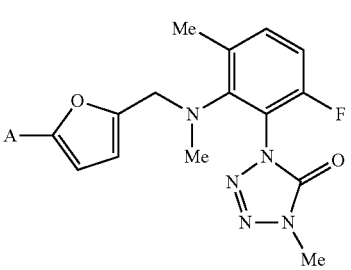
D0429
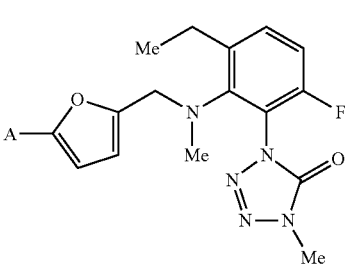
D0430
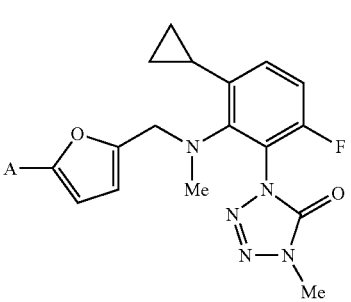
D0431
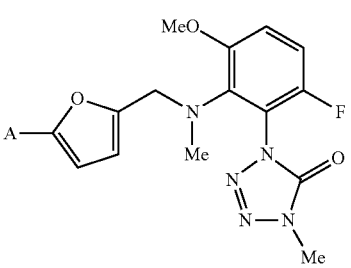
D0432
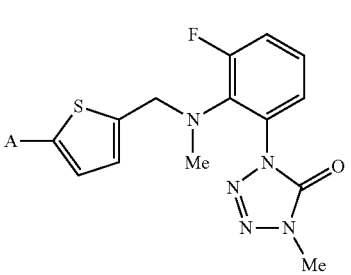
D0433

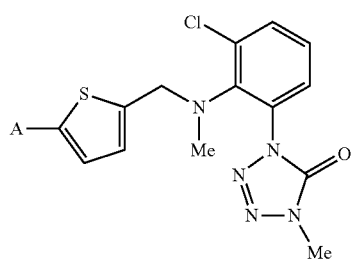 D0434
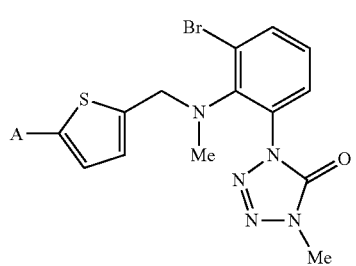 D0435
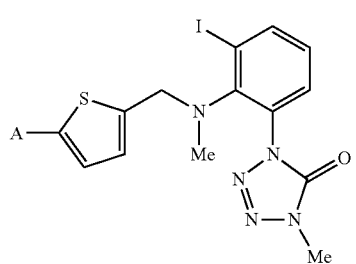 D0436
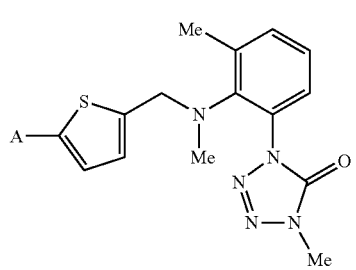 D0437
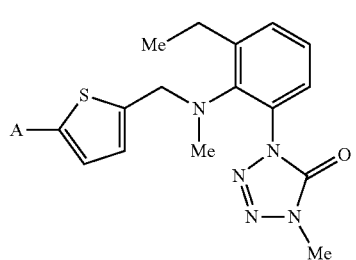 D0438
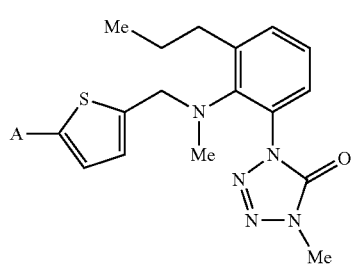 D0439
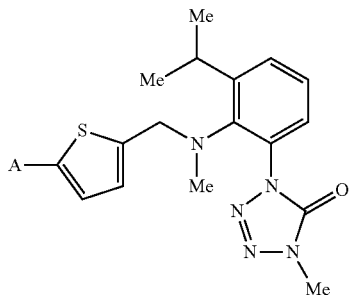 D0440
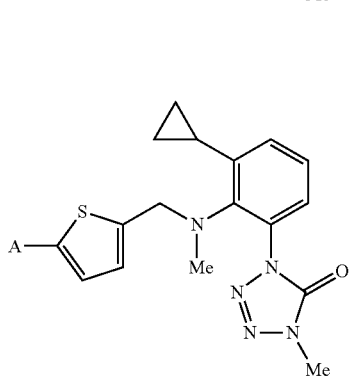 D0441
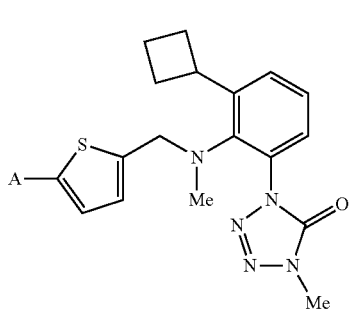 D0442
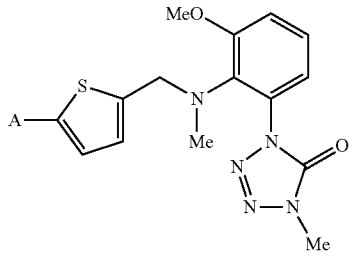 D0443
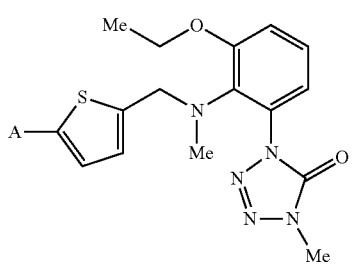 D0444

| | |
|---|---|
| 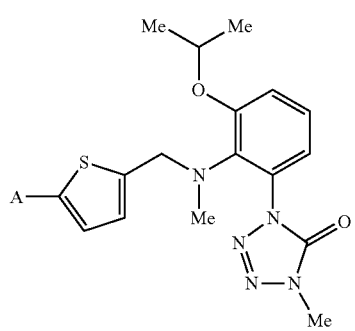 D0445 | 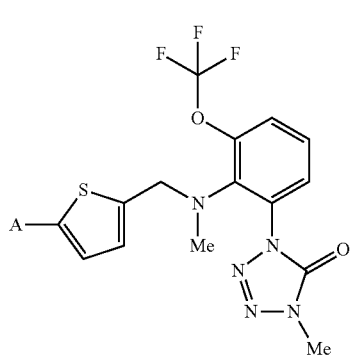 D0450 |
| 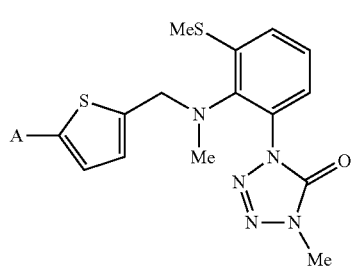 D0446 | 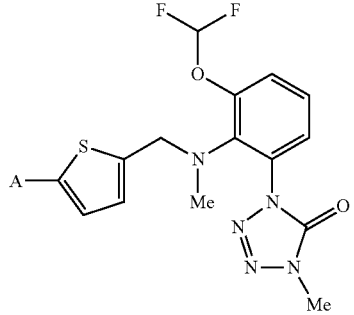 D0451 |
| 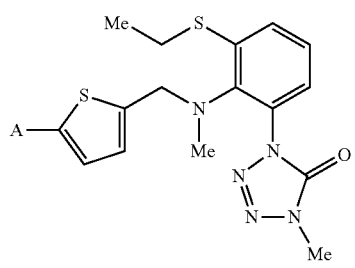 D0447 | 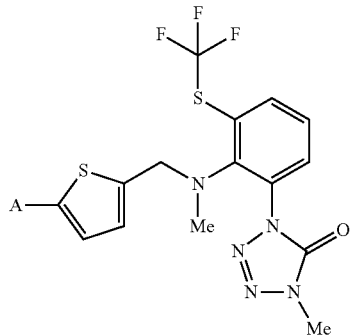 D0452 |
| 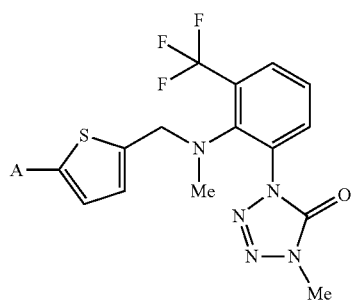 D0448 | 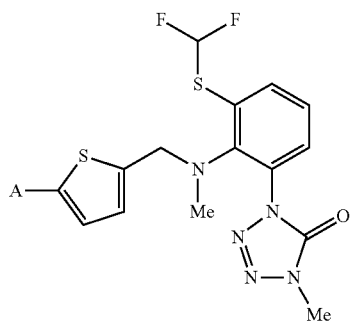 D0453 |
| 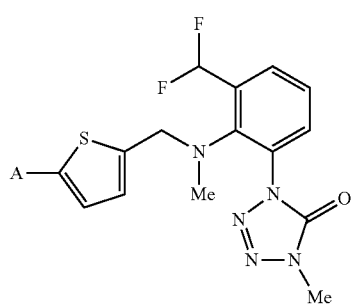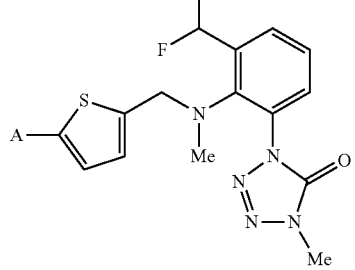 D0449 | 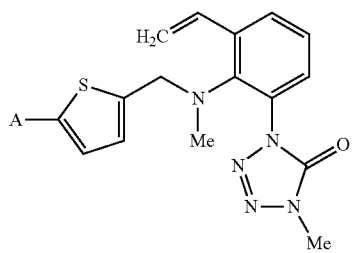 D0454 |

| | |
|---|---|
| 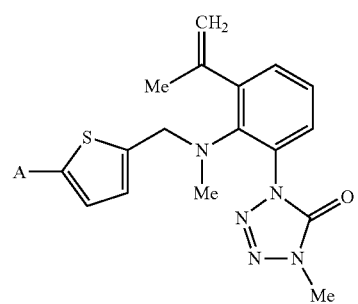 D0455 | 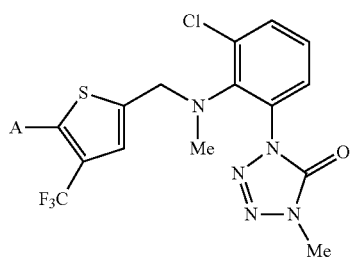 D0460 |
| 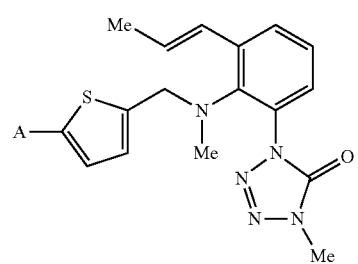 D0456 | 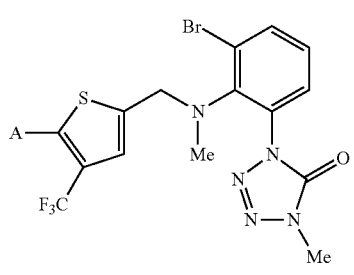 D0461 |
| 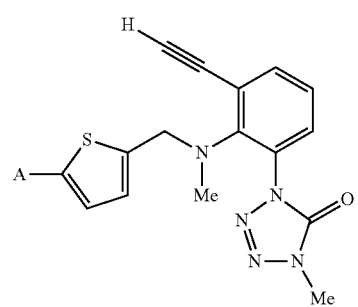 D0457 | 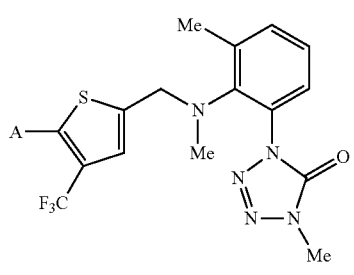 D0462 |
| 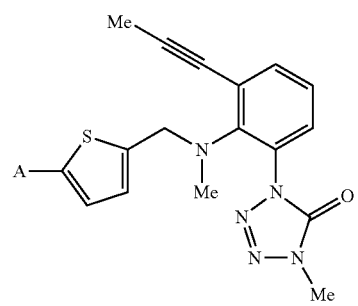 D0458 | 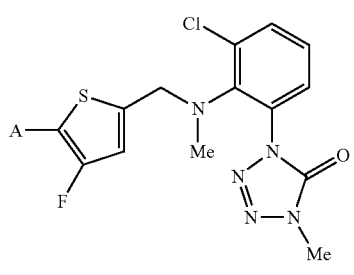 D0463 |
| 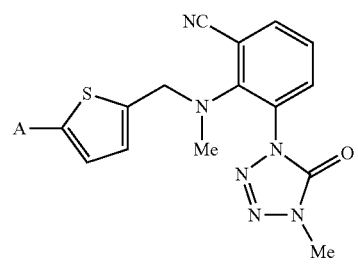 D0459 | 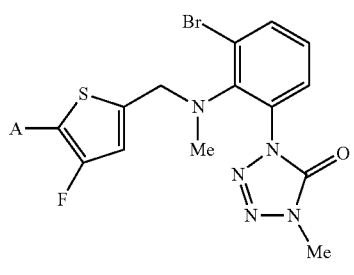 D0464 |
| | 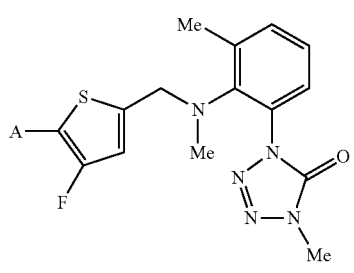 D0465 |

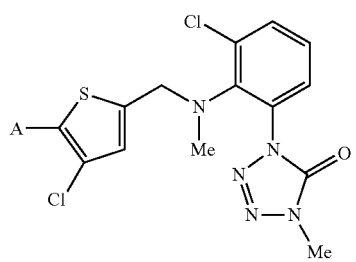
D0466
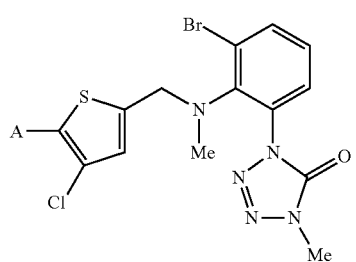
D0467
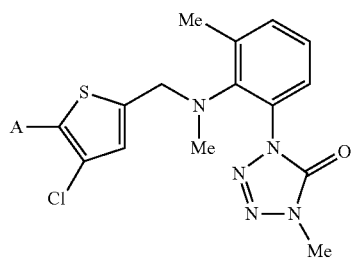
D0468
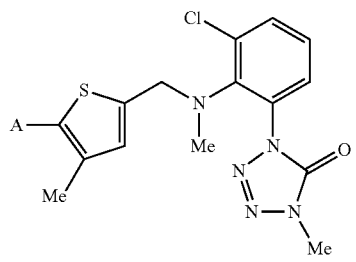
D0469
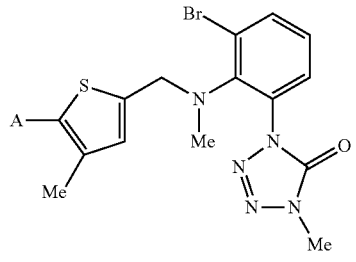
D0470
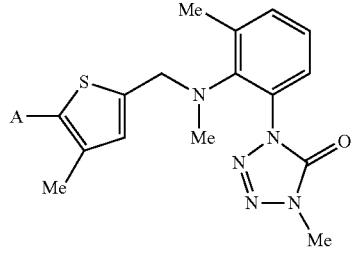
D0471
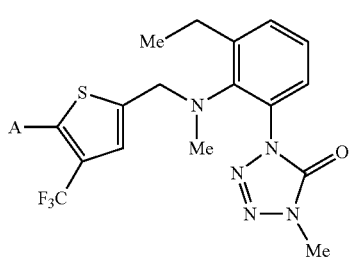
D0472
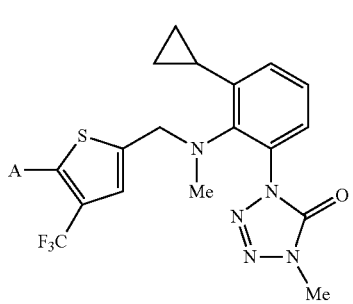
D0473
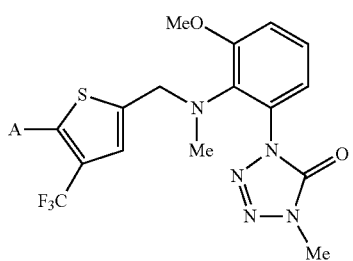
D0474
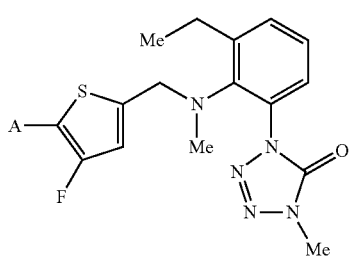
D0475
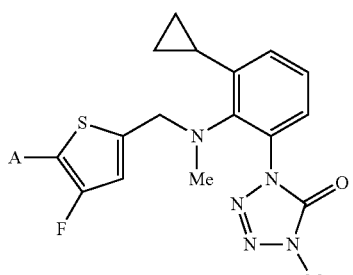
D0476
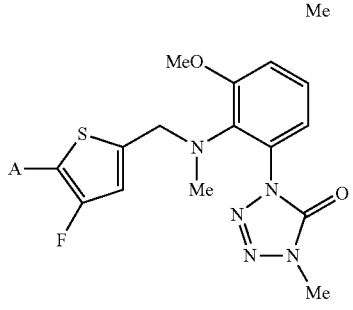
D0477

| | |
|---|---|
| D0478 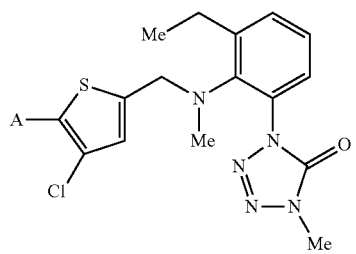 | D0484 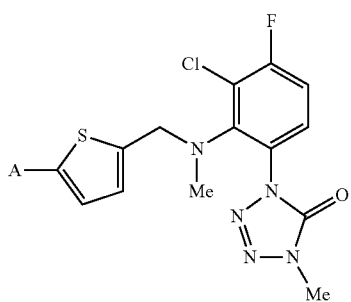 |
| D0479 | D0485 |
| D0480 | D0486 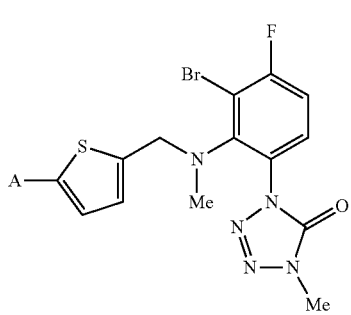 |
| D0481 | D0487 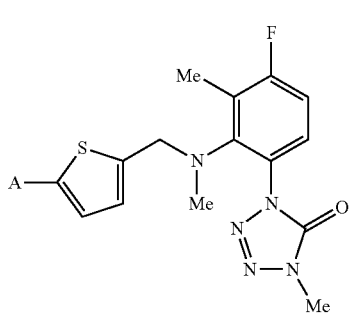 |
| D0482 | D0488 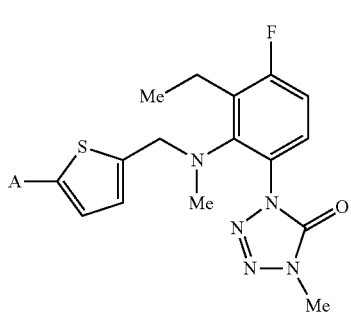 |
| D0483 | 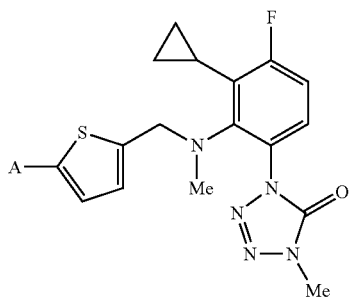 |

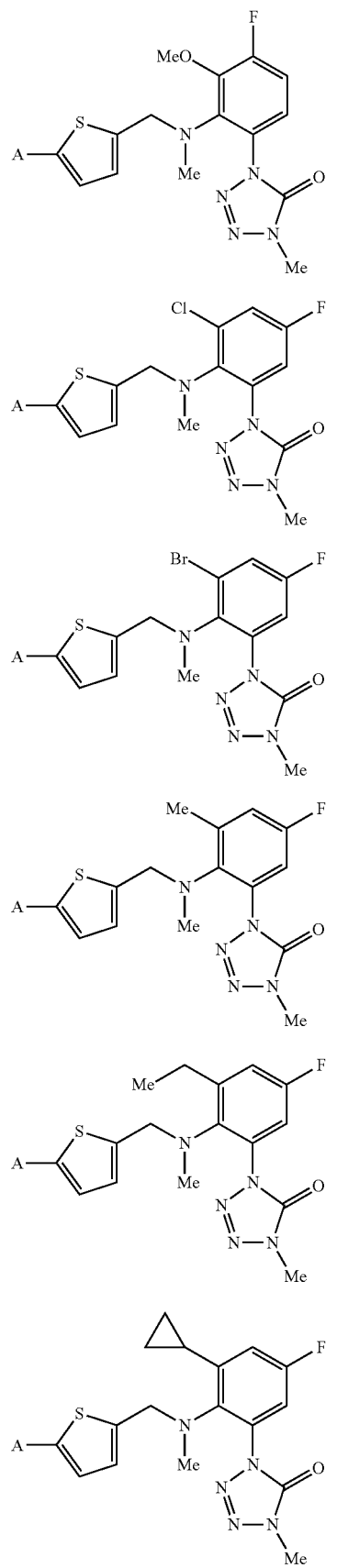
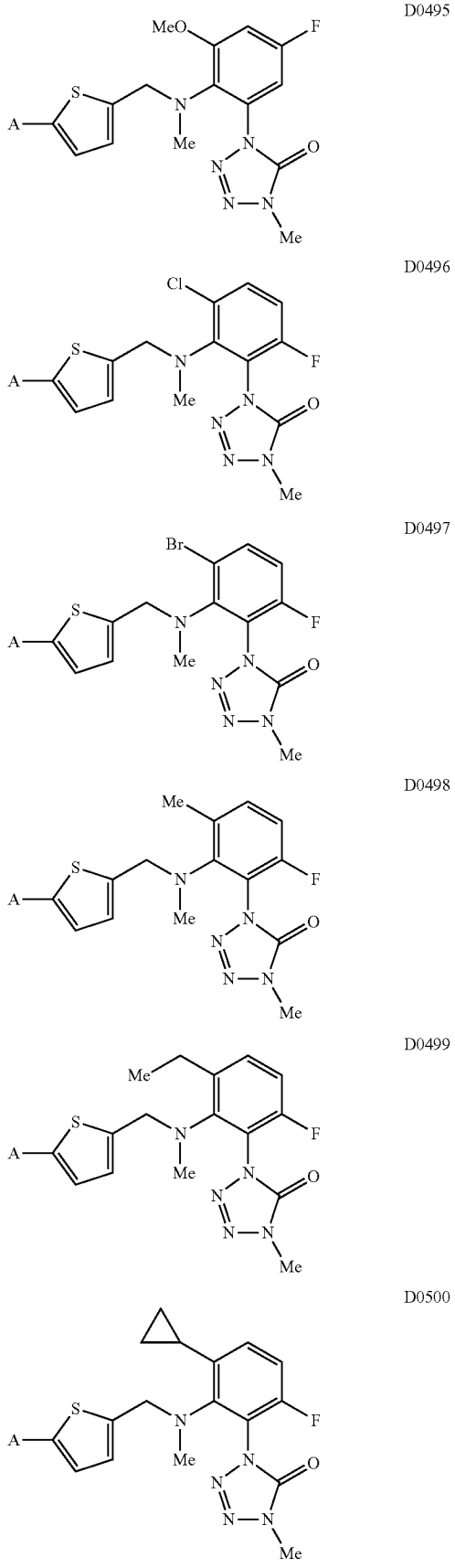

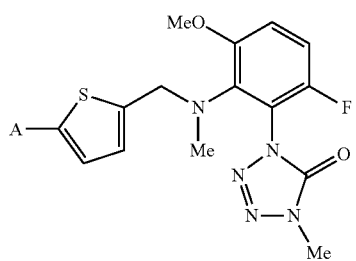 D0501
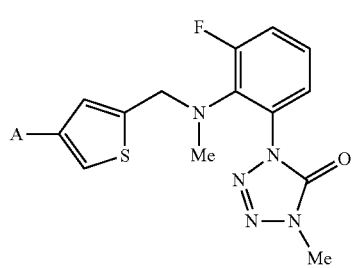 D0502
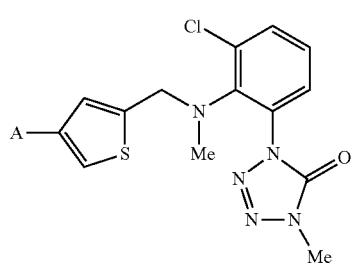 D0503
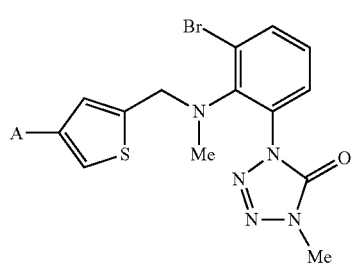 D0504
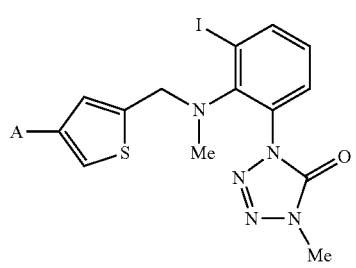 D0505
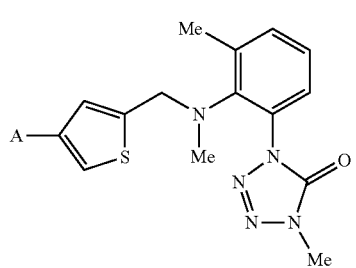 D0506
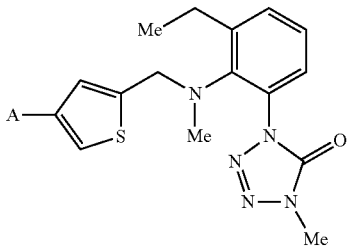 D0507
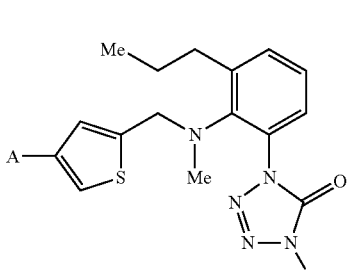 D0508
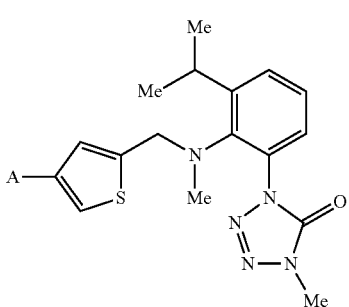 D0509
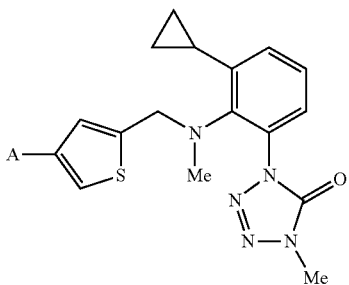 D0510
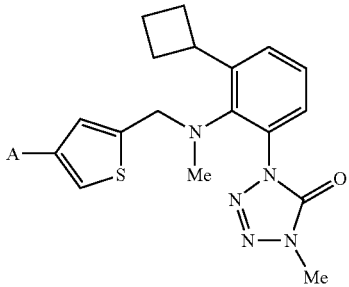 D0511

| | |
|---|---|
| D0512 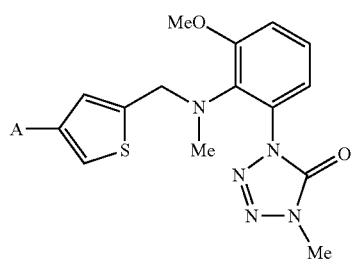 | D0517 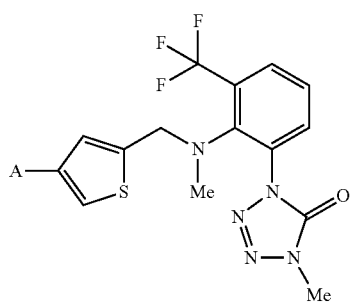 |
| D0513 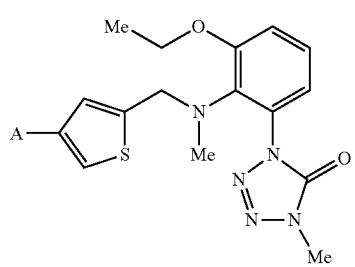 | D0518 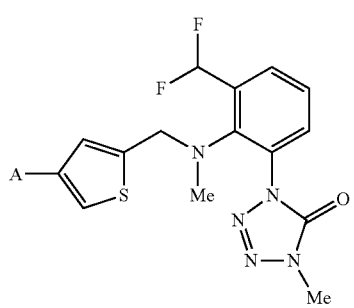 |
| D0514 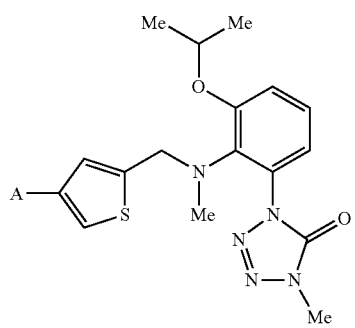 | D0519 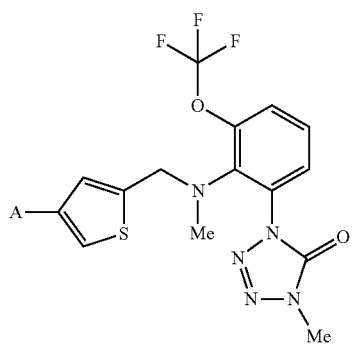 |
| D0515 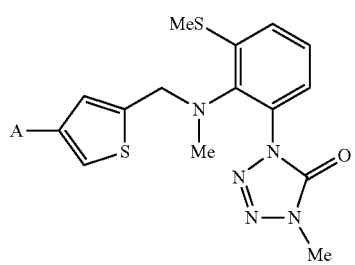 | D0520 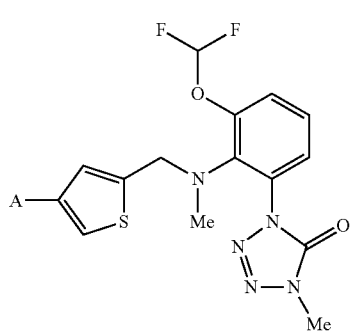 |
| D0516 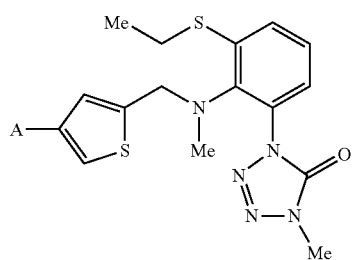 | D0521 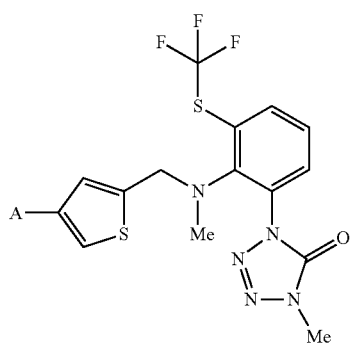 |

| | |
|---|---|
| D0522 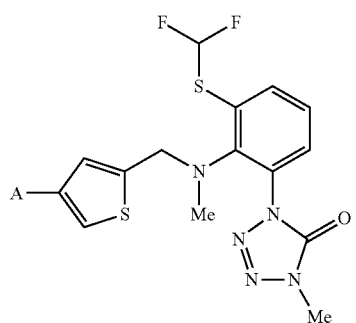 | D0527 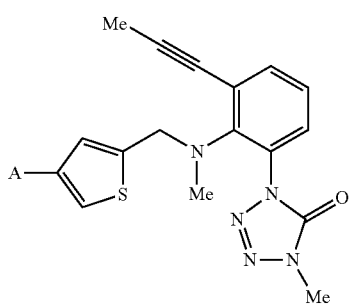 |
| D0523 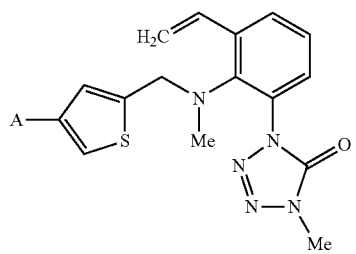 | D0528 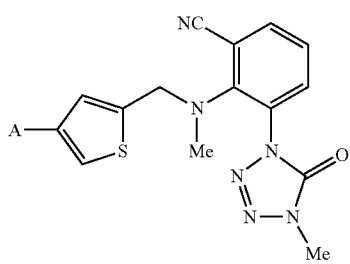 |
| D0524 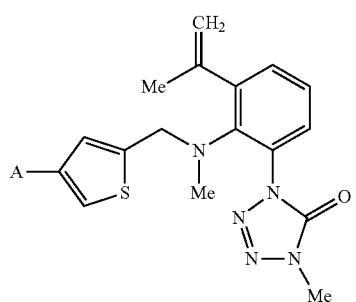 | D0529 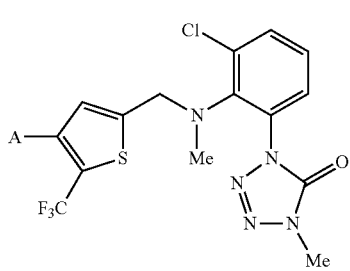 |
| D0525 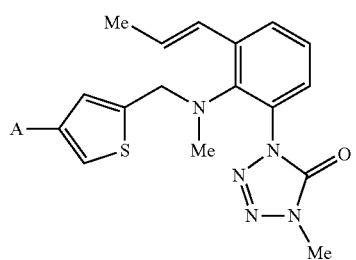 | D0530 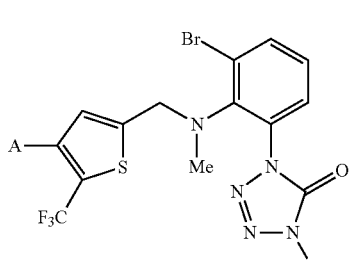 |
| D0526 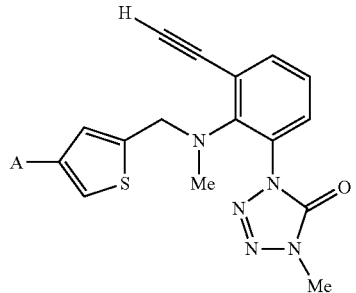 | D0531 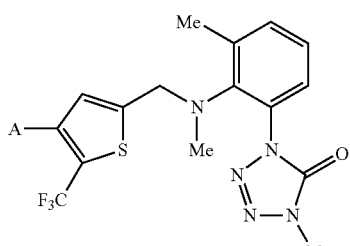 |
| | D0532 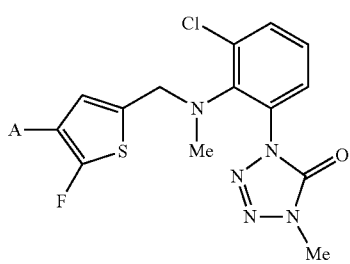 |

-continued
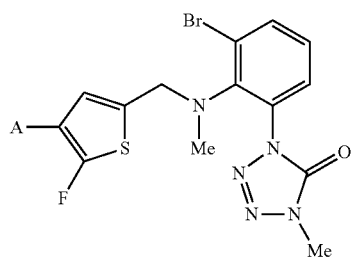 D0533
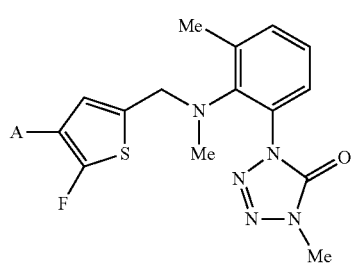 D0534
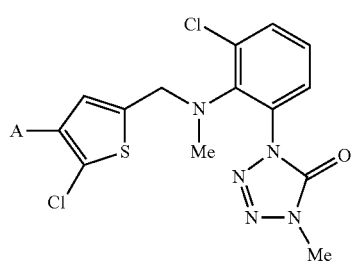 D0535
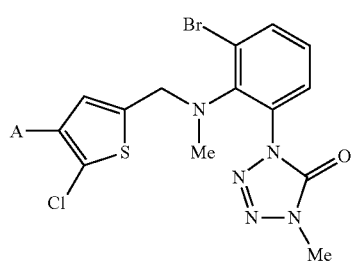 D0536
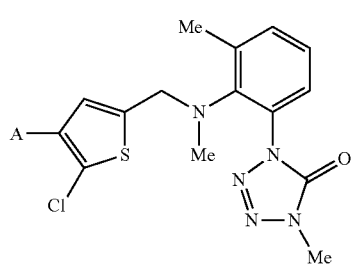 D0537
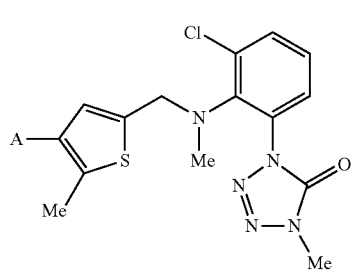 D0538
-continued
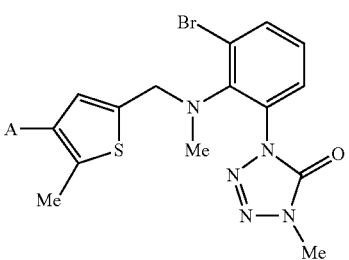 D0539
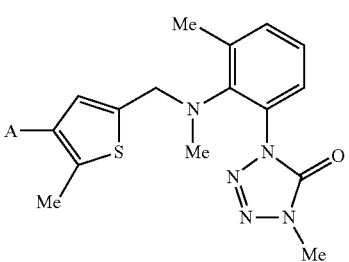 D0540
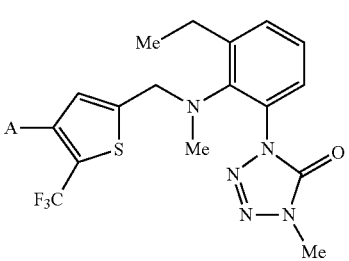 D0541
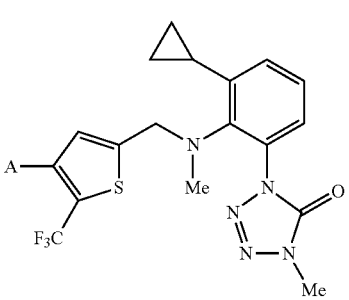 D0542
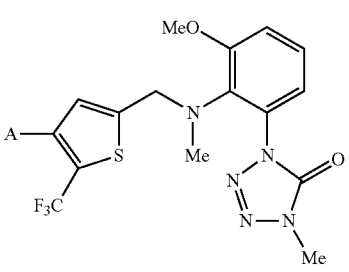 D0543
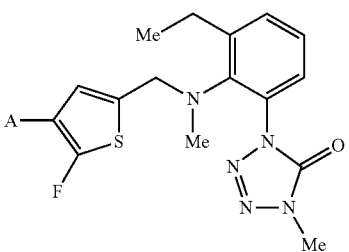 D0544

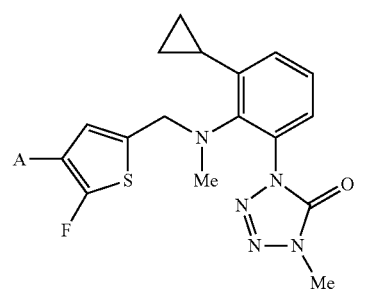
D0545
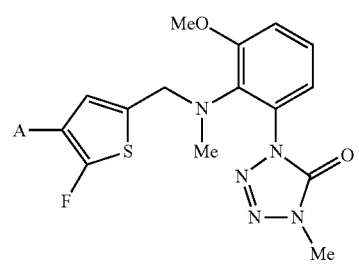
D0546
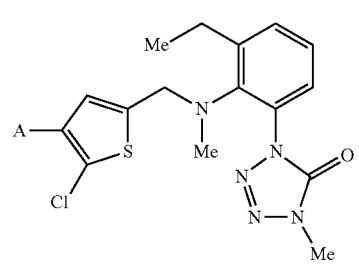
D0547
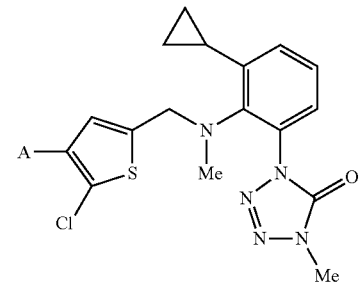
D048
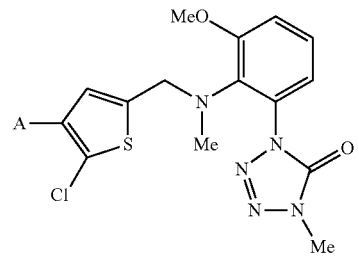
D0549
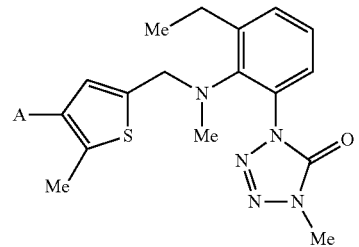
D0550
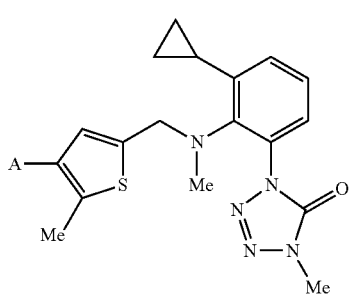
D0551
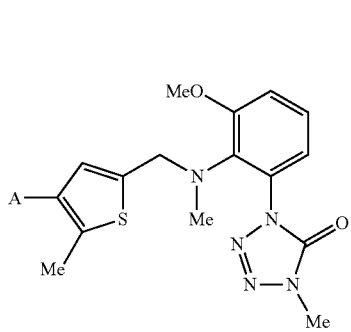
D0552
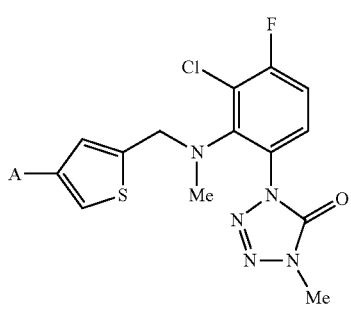
D0553
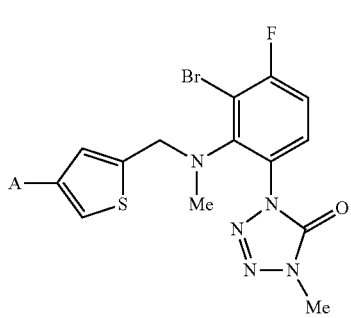
D0554
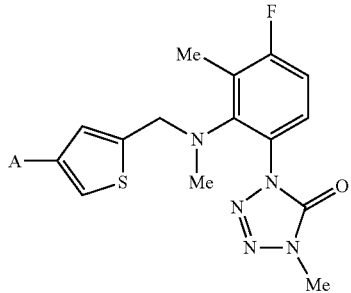
D0555

-continued
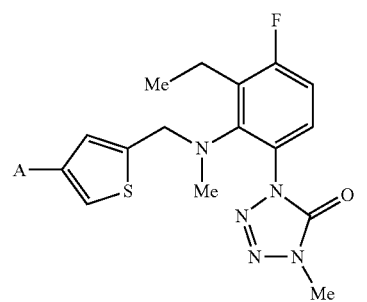
D0556
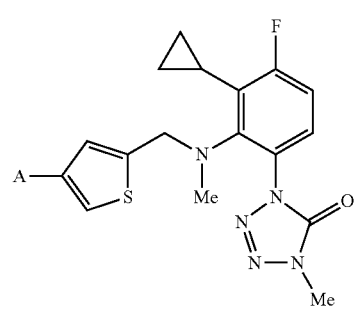
D0557
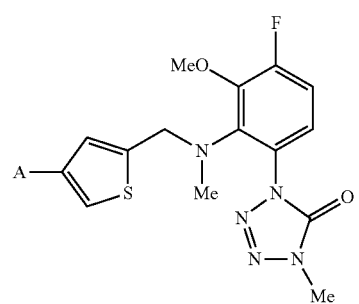
D0558
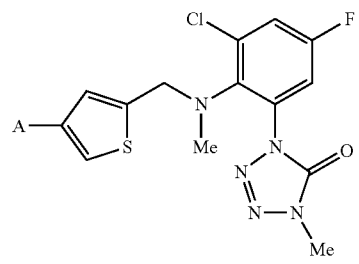
D0559
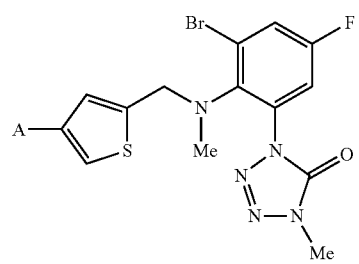
D0560
-continued
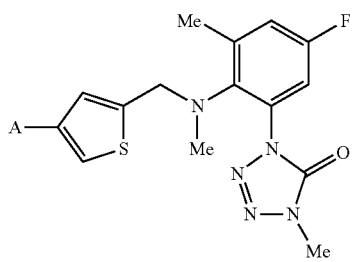
D0561
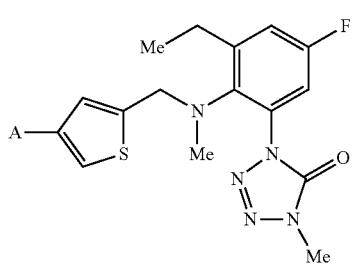
D0562
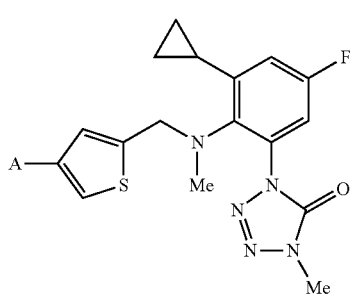
D0563
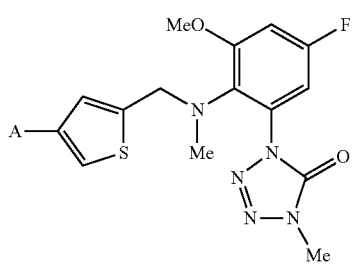
D0564
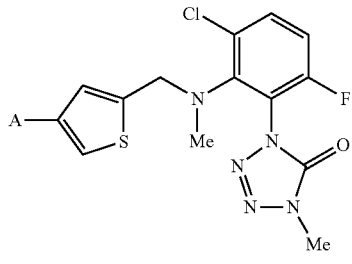
D0565
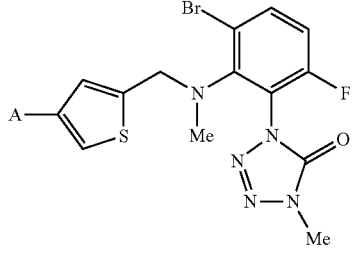
D0566

D0567 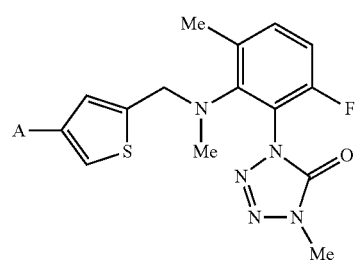
D0568 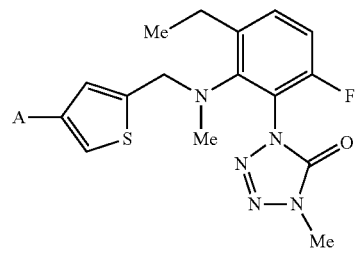
D0569 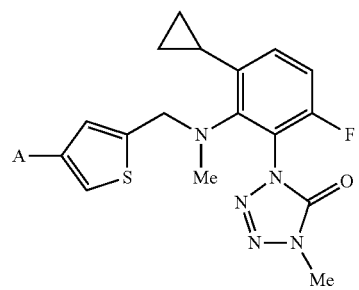
D0570 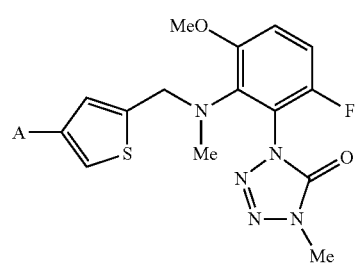
D0571 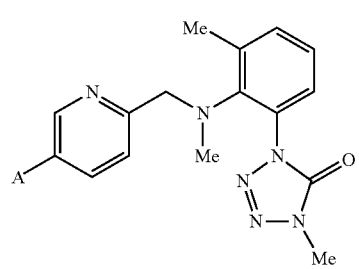
D0572 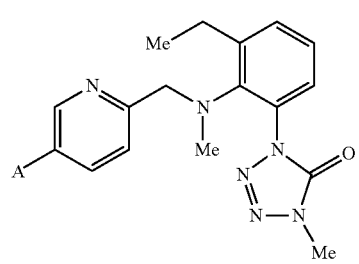
D0573 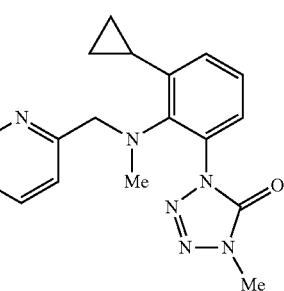
D0574 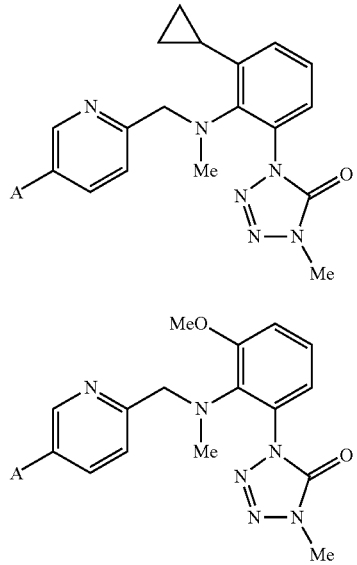
D0575 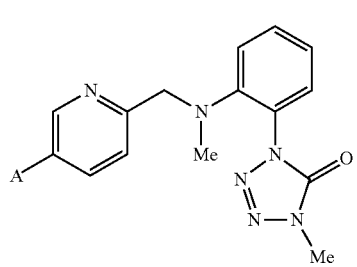
D0576 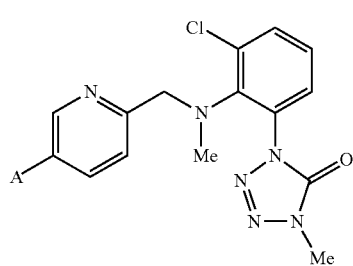
D0577 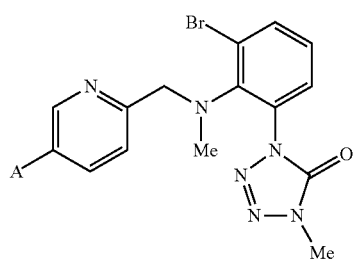
D0578 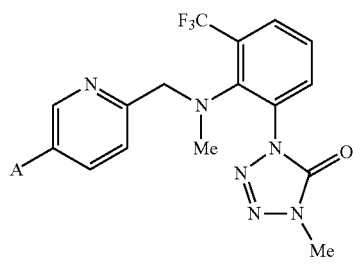

| | |
|---|---|
| D0579 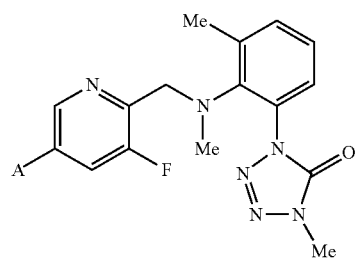 | D0585 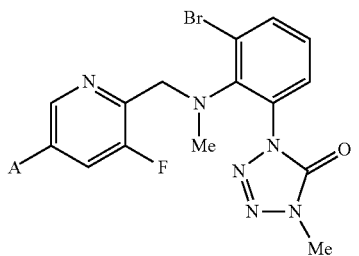 |
| D0580 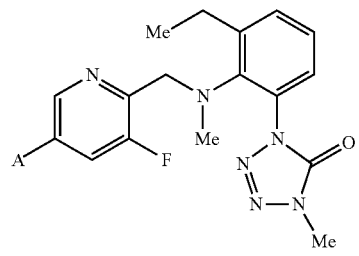 | D0586 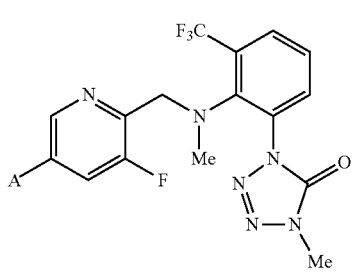 |
| D0581 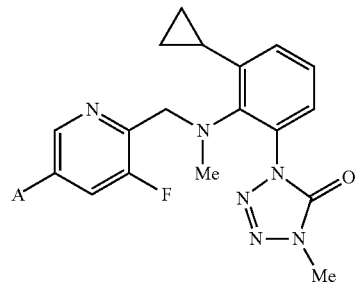 | D0587 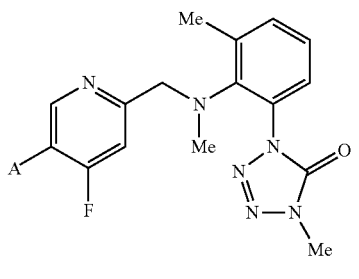 |
| D0582 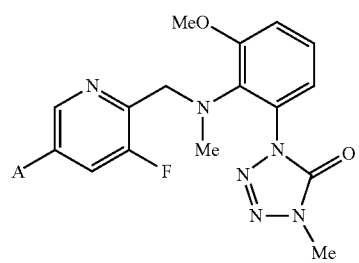 | D0588 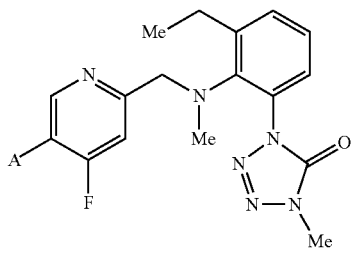 |
| D0583 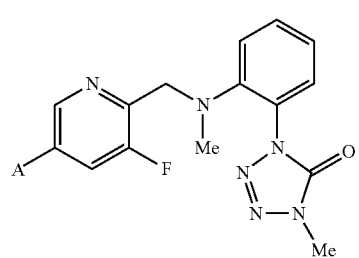 | D0589 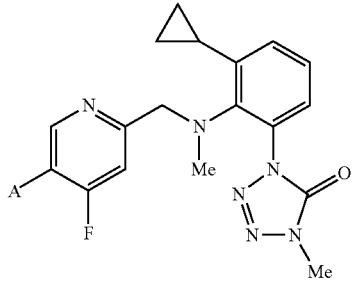 |
| D0584 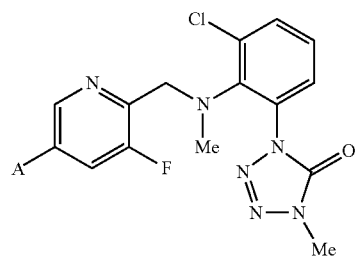 | D0590 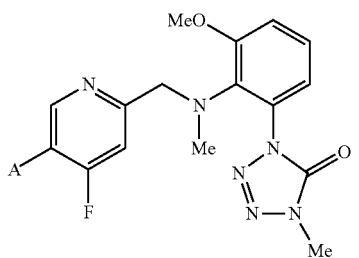 |

-continued

D0603 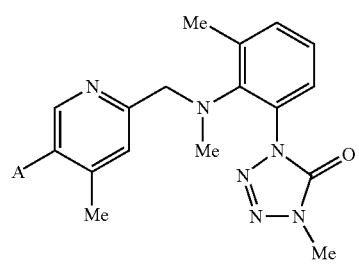
D0604 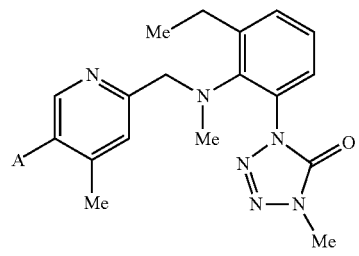
D0605 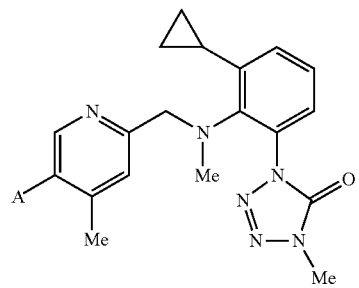
D0606 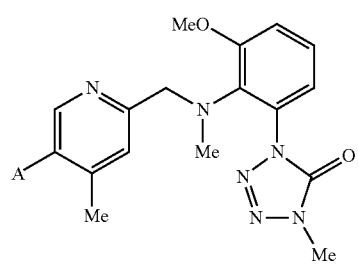
D0607 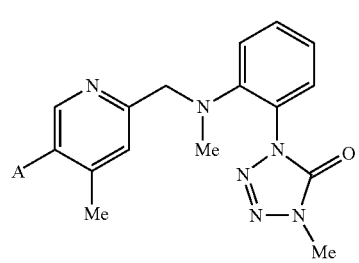
D0608 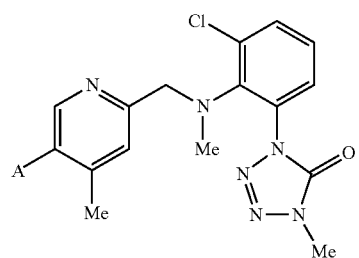
D0609 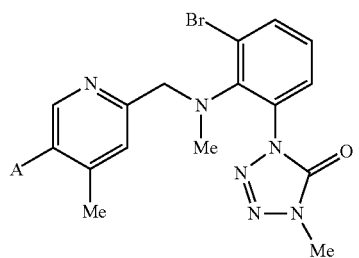
D0610 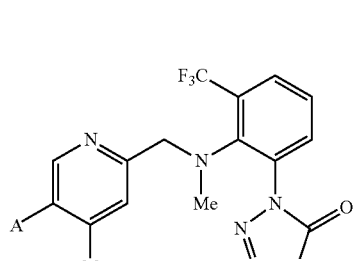
D0611 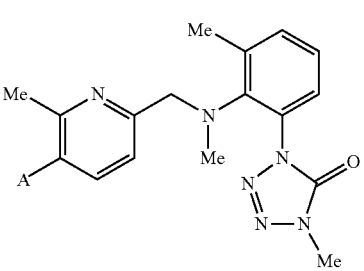
D0612 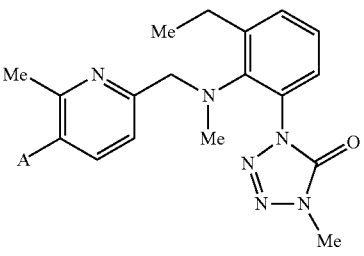
D0613 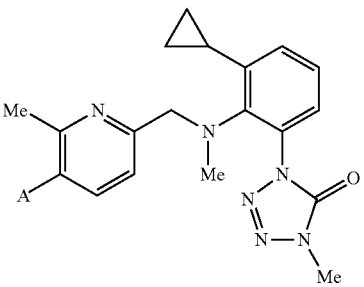

449
-continued
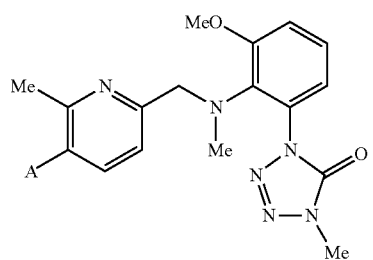
D0614
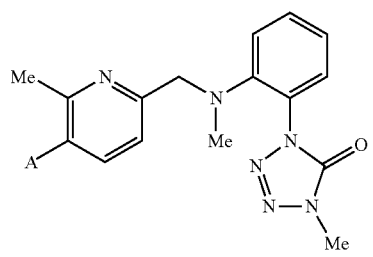
D0615
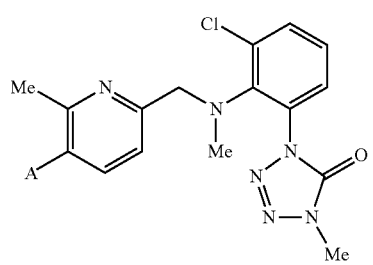
D0616
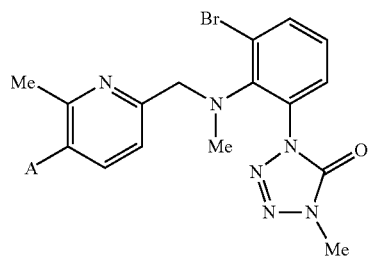
D0617
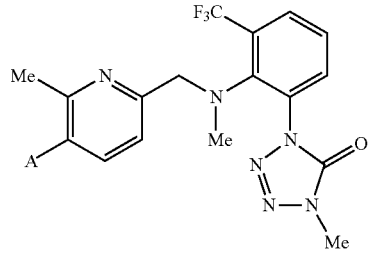
D0618
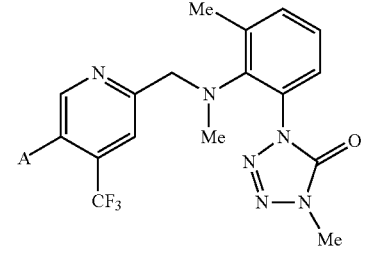
D0619
450
-continued
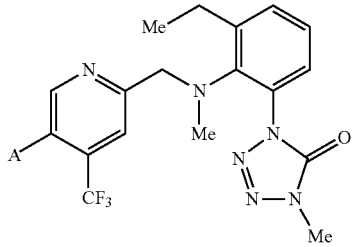
D0620
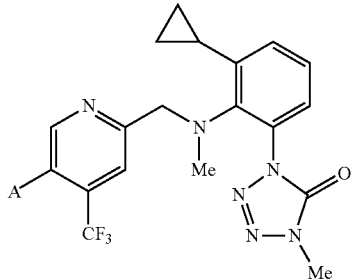
D0621
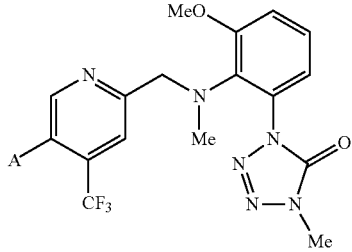
D0622
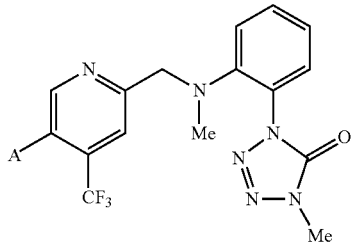
D0623
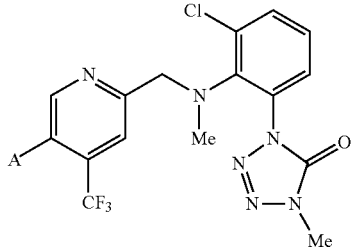
D0624
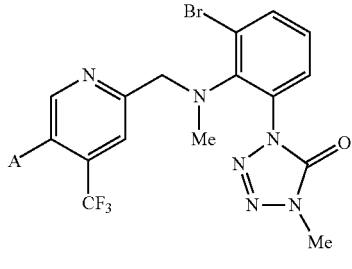
D0625

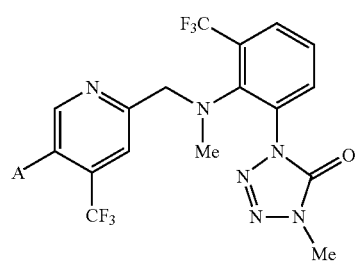
D0626
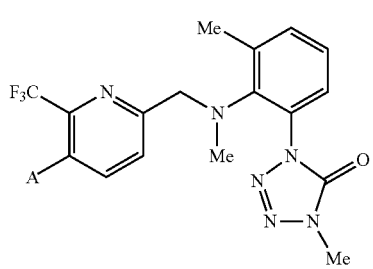
D0627
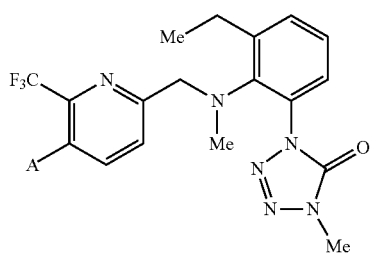
D0628
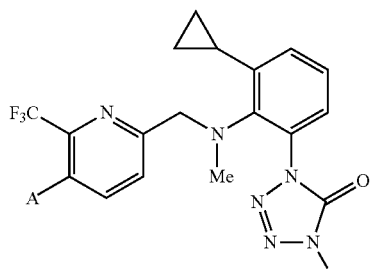
D0629
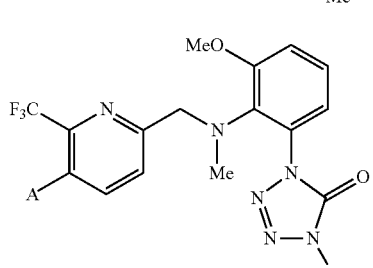
D0630
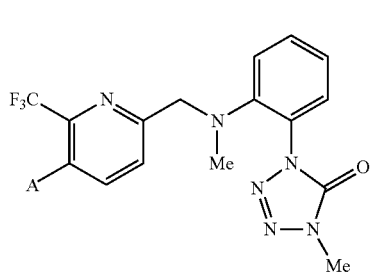
D0631
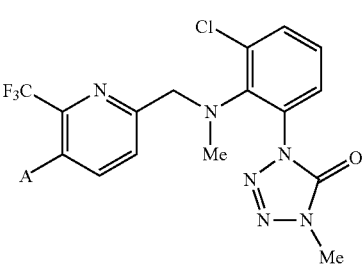
D0632
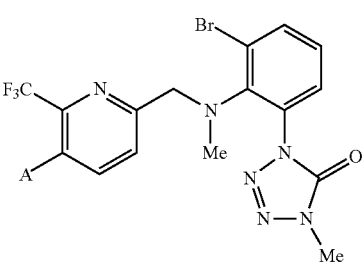
D0633
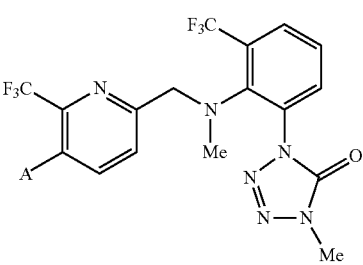
D0634
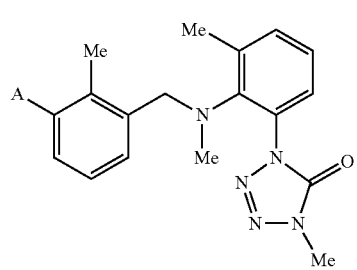
D0635
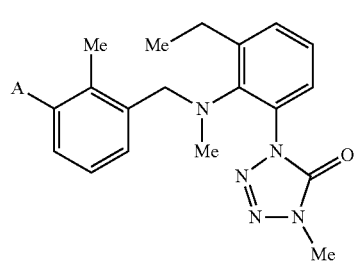
D0636
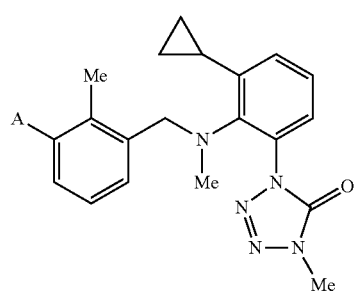
D0637

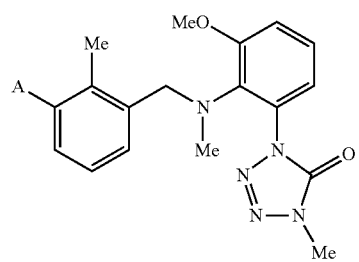
D0638
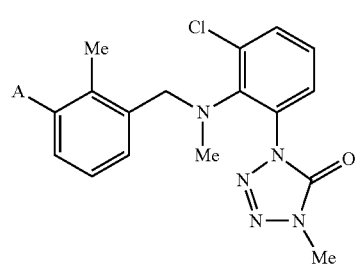
D0639
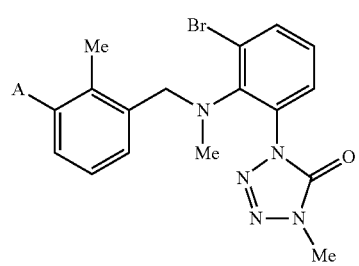
D0640
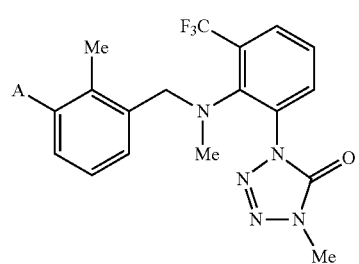
D0641
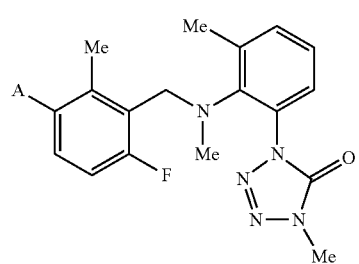
D0642
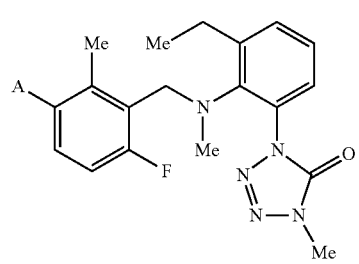
D0643
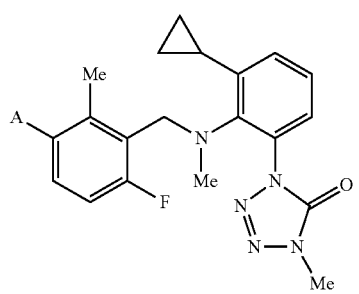
D0644
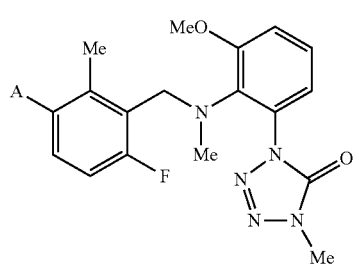
D0645
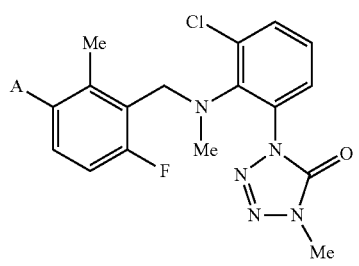
D0646
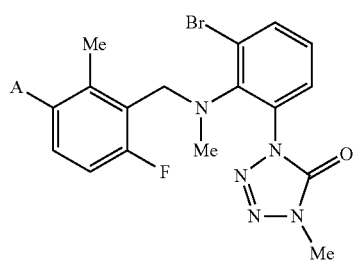
D0647
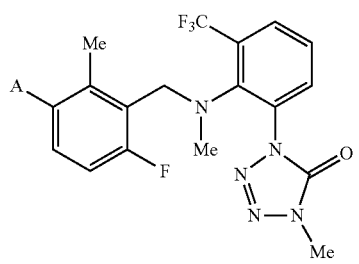
D0648
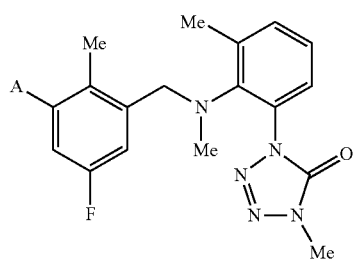
D0649

| | |
|---|---|
| D0650 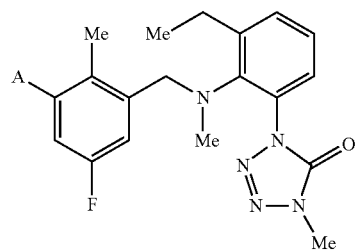 | D0656 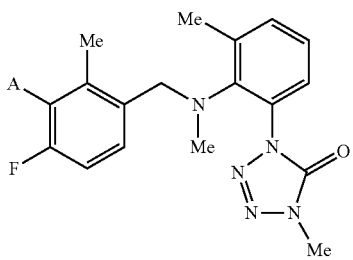 |
| D0651 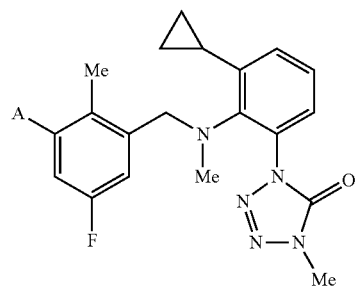 | D0657 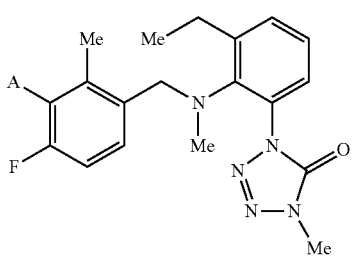 |
| D0652 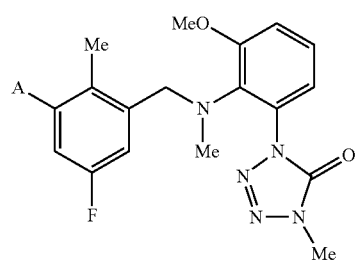 | D0658 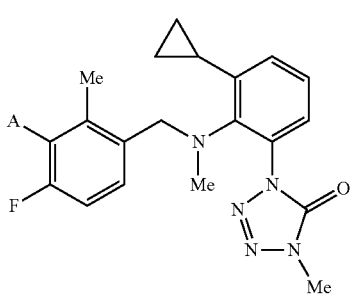 |
| D0653 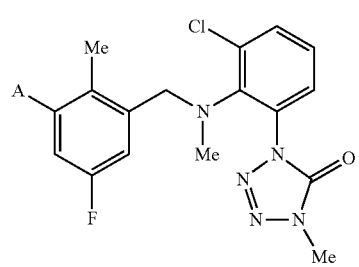 | D0659 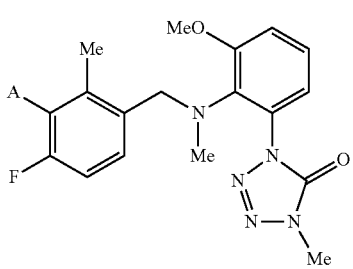 |
| D0654 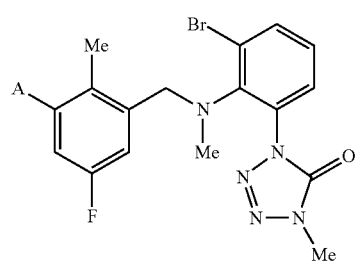 | D0660 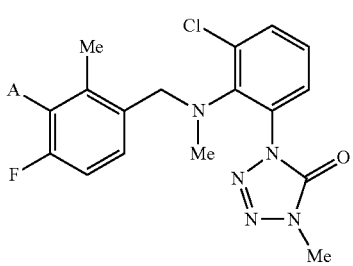 |
| D0655 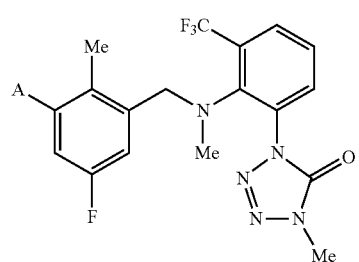 | D0661 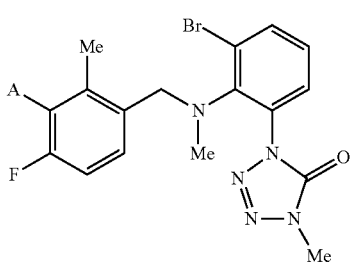 |

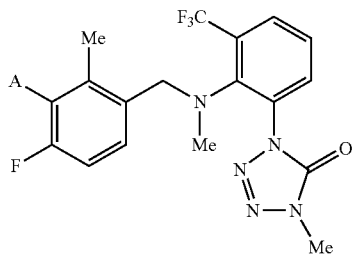
D0662
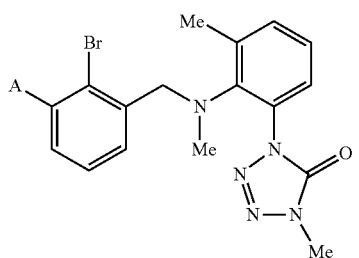
D0663
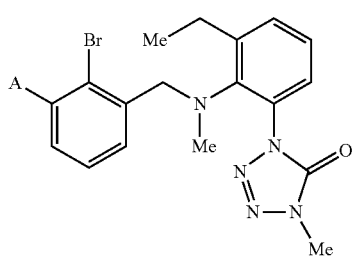
D0664
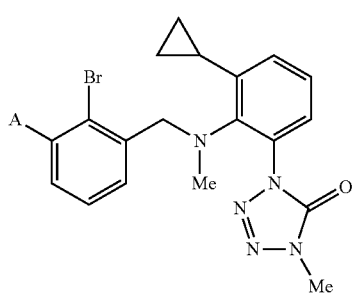
D0665
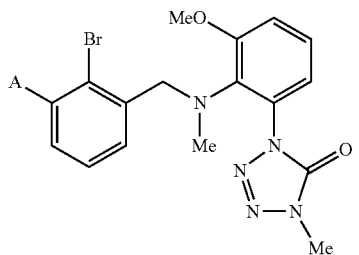
D0666
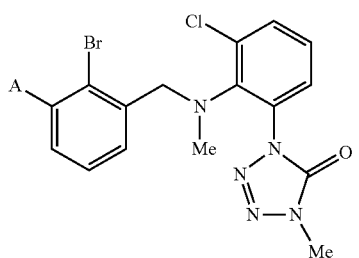
D0667
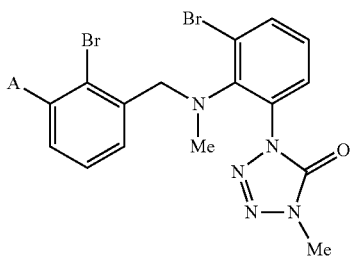
D0668
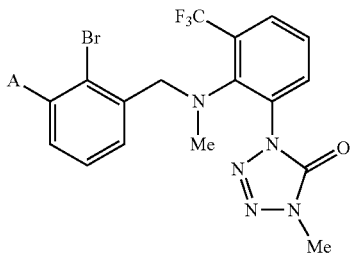
D0669
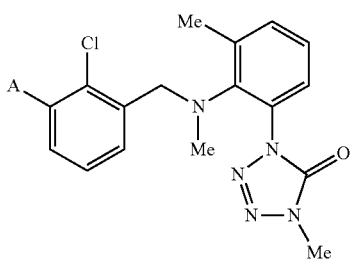
D0670
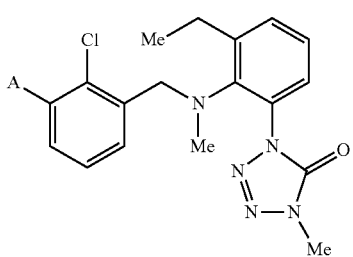
D0671
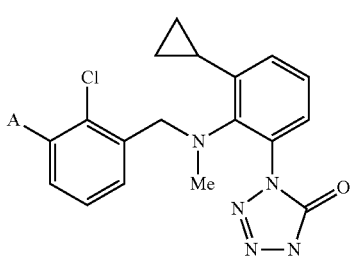
D0672
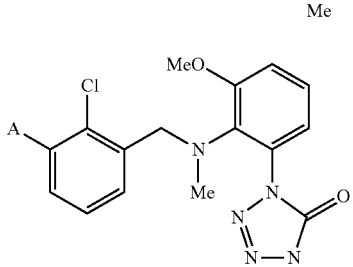
D0673

-continued
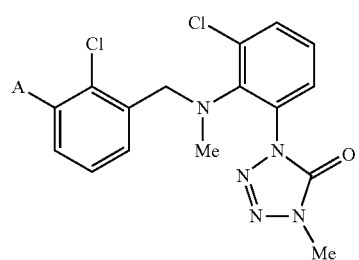
D0674
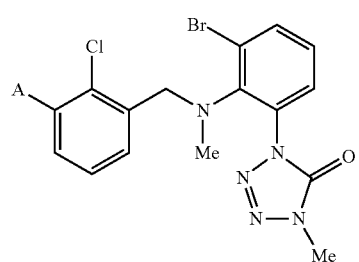
D0675
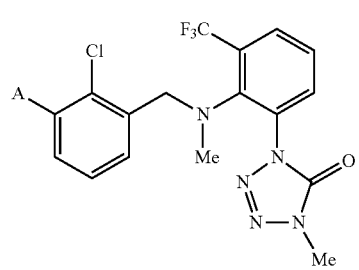
D0676
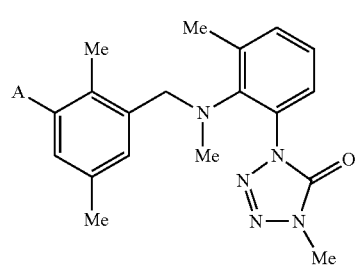
D0677
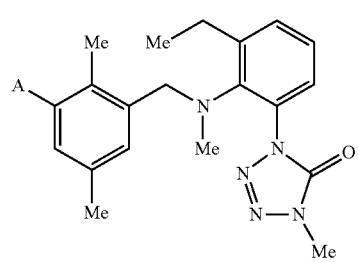
D0678
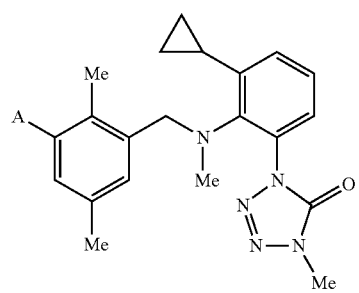
D0679
-continued
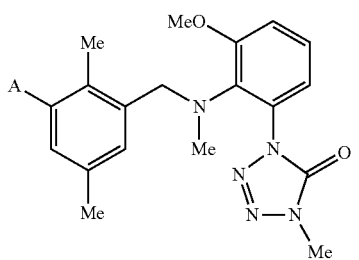
D0680
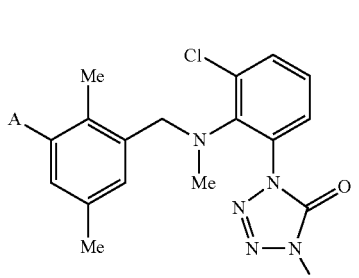
D0681
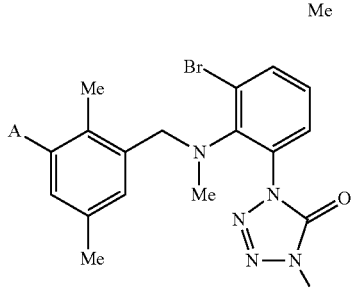
D0682
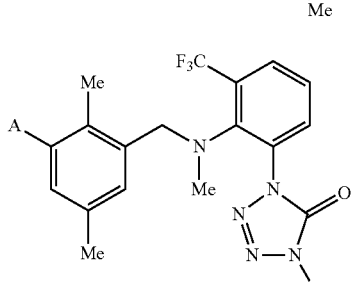
D0683
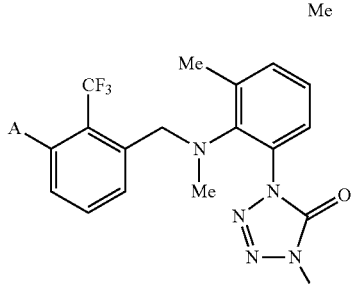
D0684
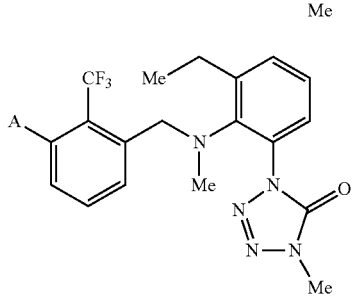
D0685

D0686 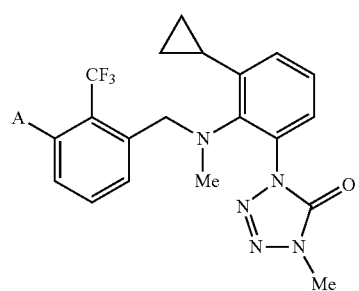
D0687 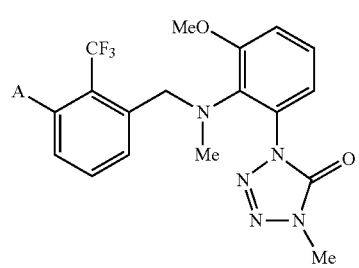
D0688 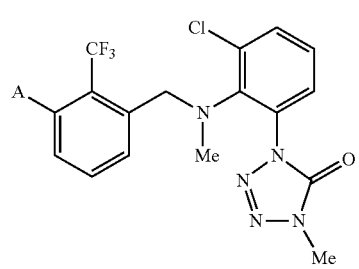
D0689 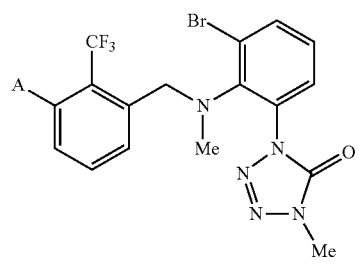
D0690 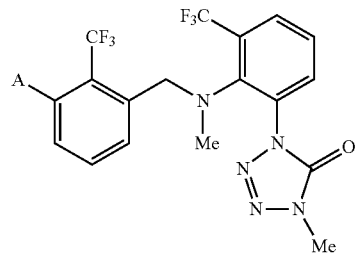
D0691 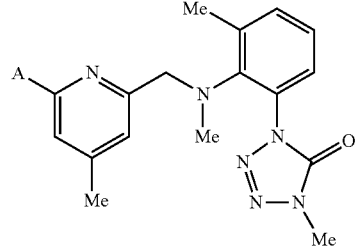
D0692 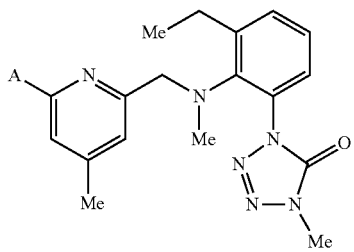
D0693 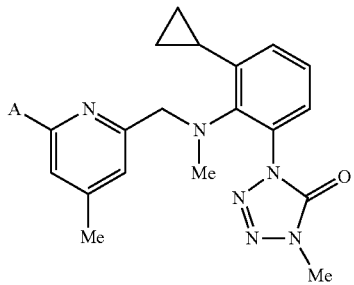
D0694 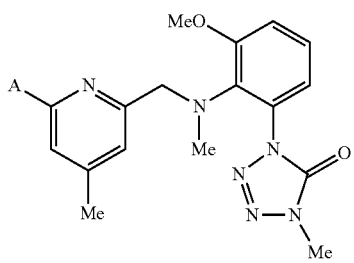
D0695 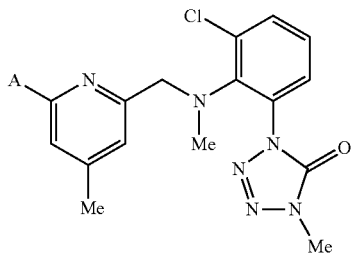
D0696 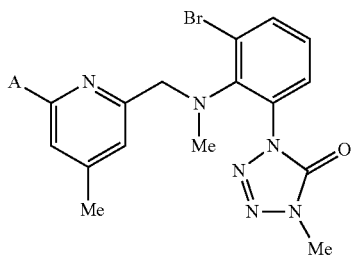
D0697 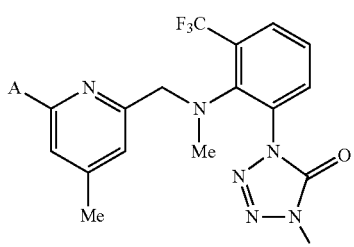

-continued
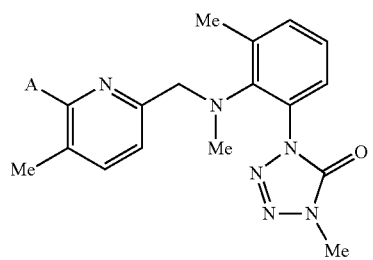 D0698
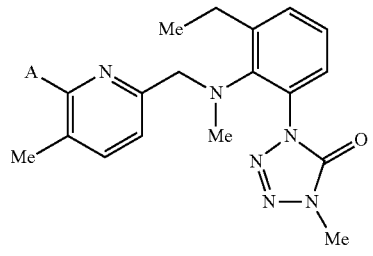 D0699
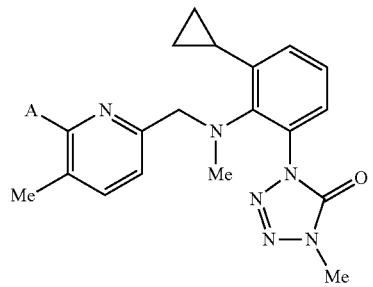 D0700
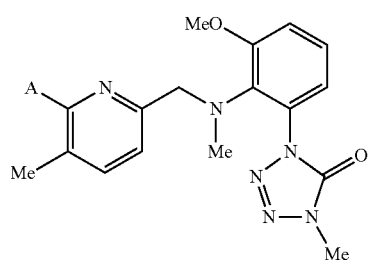 D0701
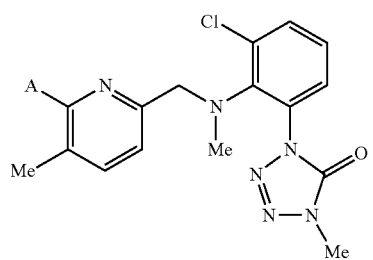 D0702
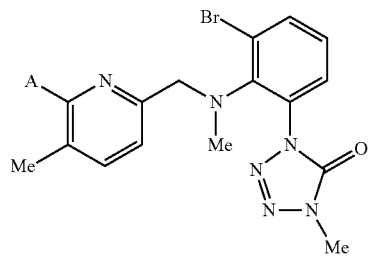 D0703
-continued
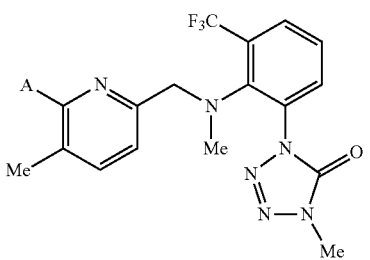 D0704
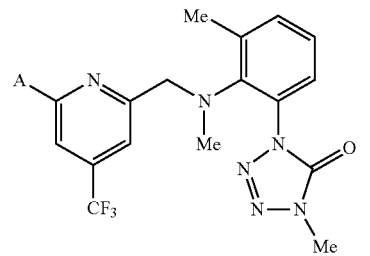 D0705
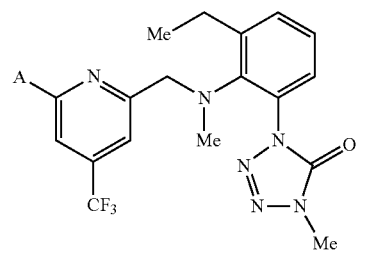 D0706
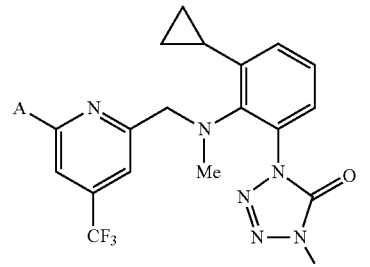 D0707
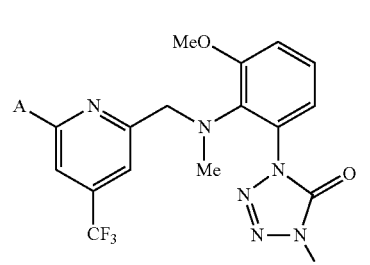 D0708
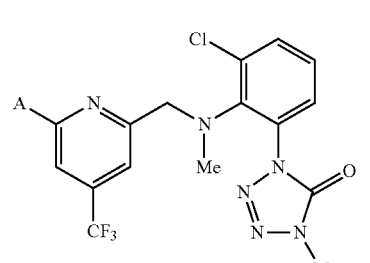 D0709

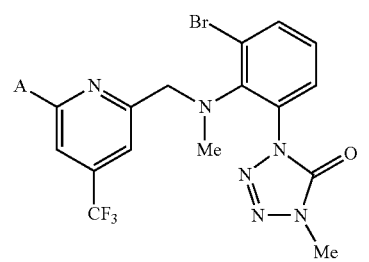
D0710
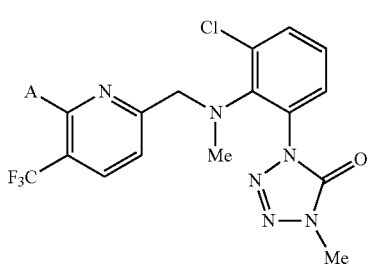
D0716
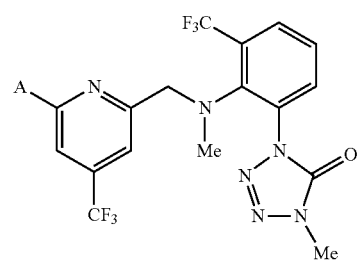
D0711
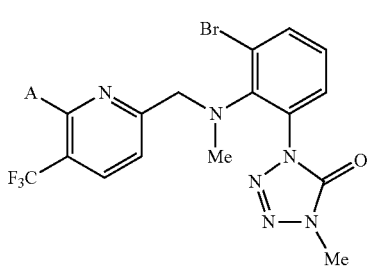
D0717
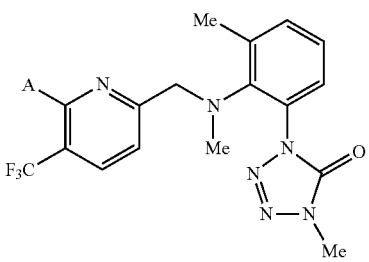
D0712
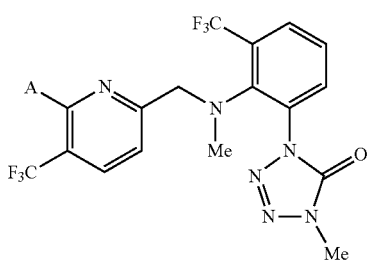
D0718
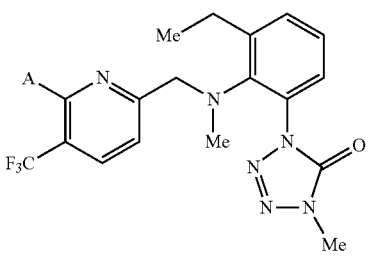
D0713
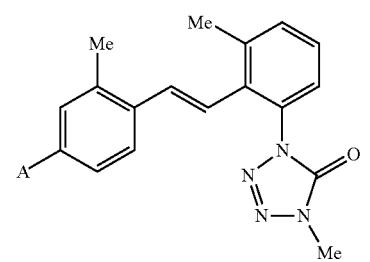
E0001
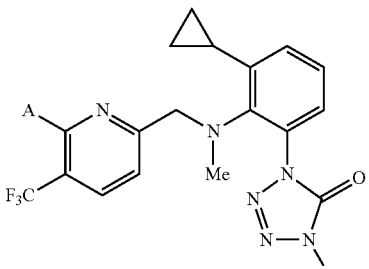
D0714
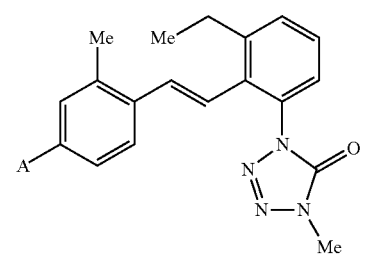
E0002
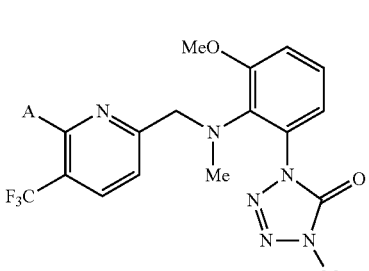
D0715
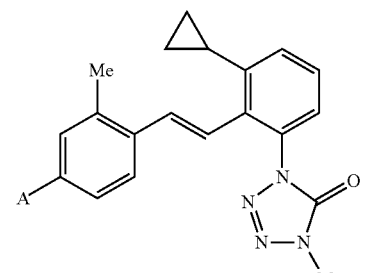
E0003

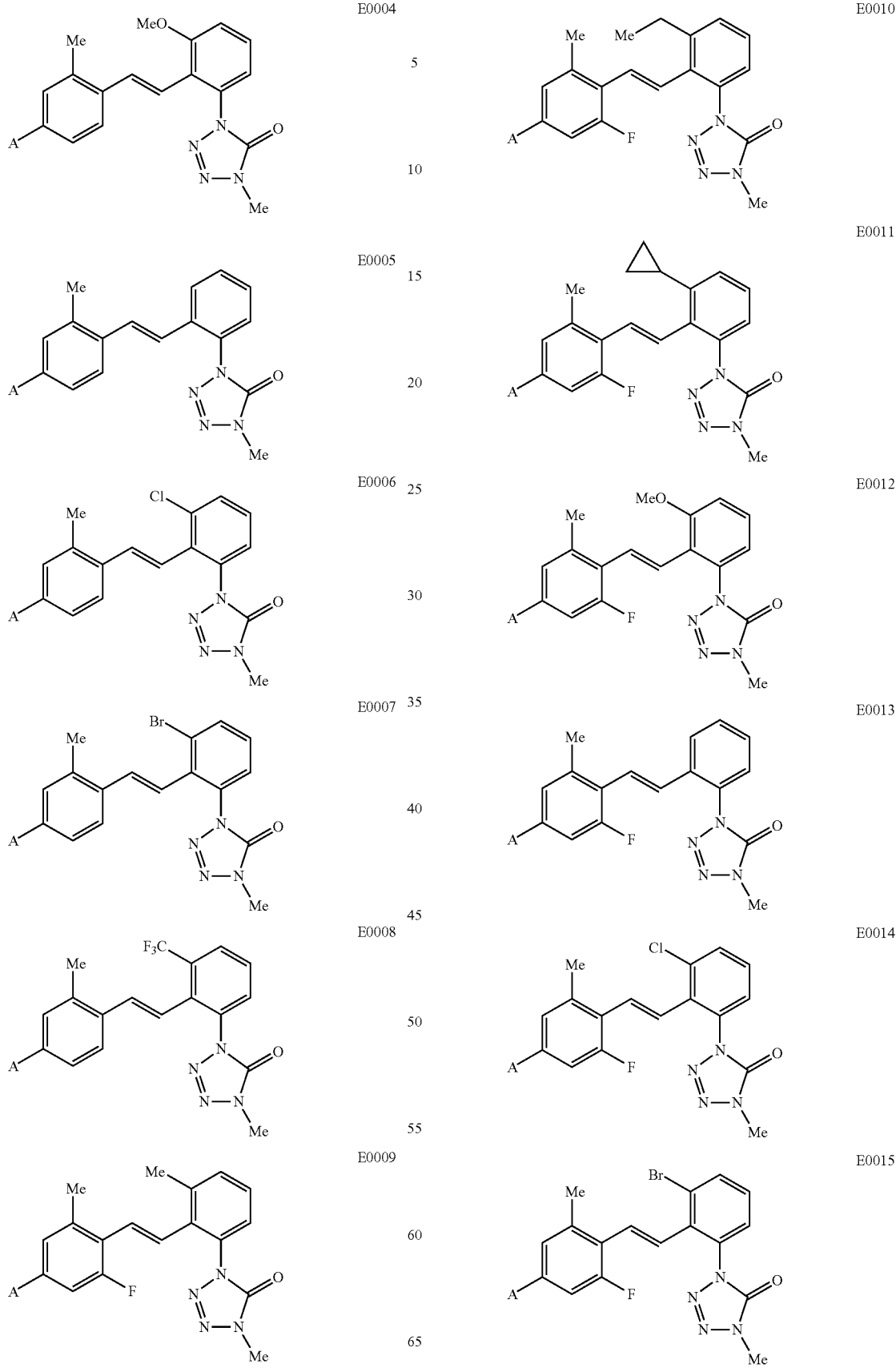

| | |
|---|---|
| E0016 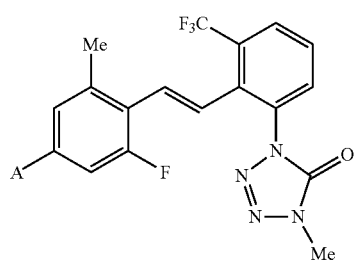 | E0022 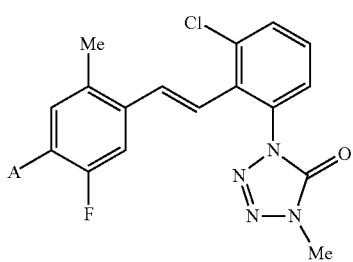 |
| E0017 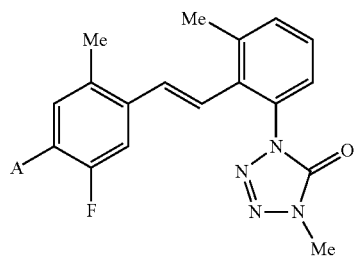 | E0023 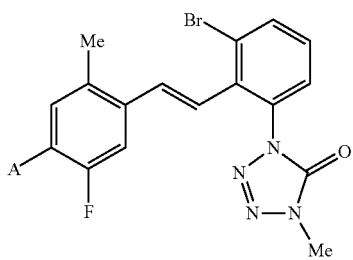 |
| E0018 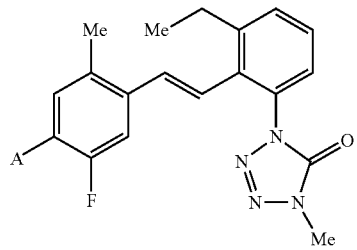 | E0024 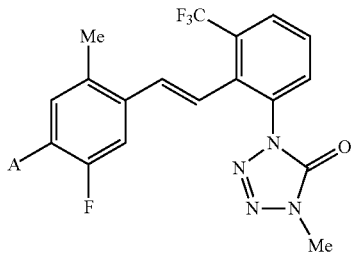 |
| E0019 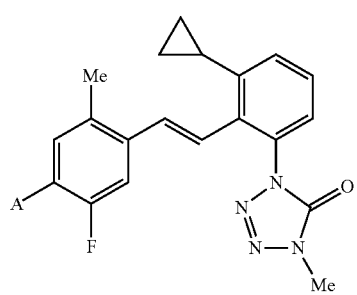 | E0025 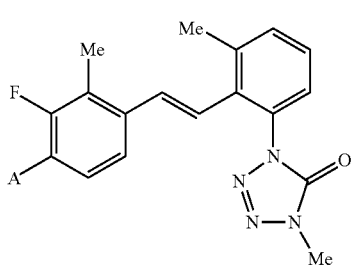 |
| E0020 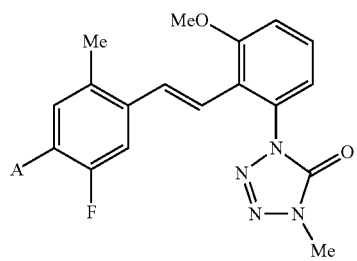 | E0026 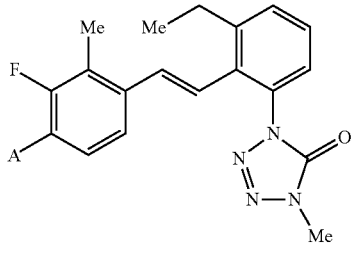 |
| E0021 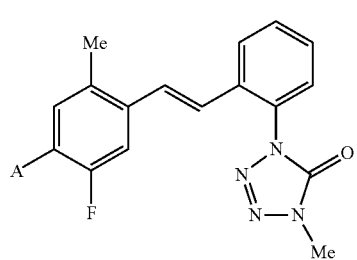 | E0027 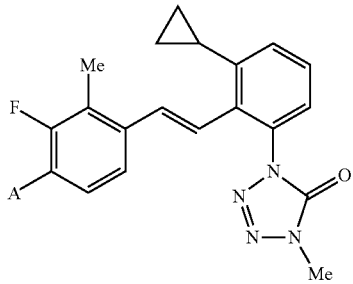 |

E0028 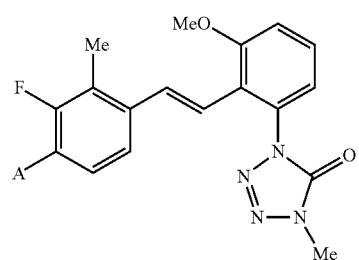
E0029 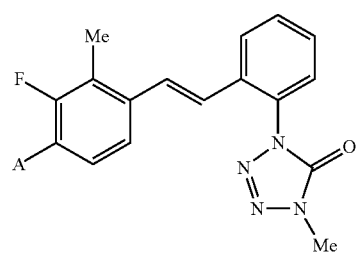
E0030 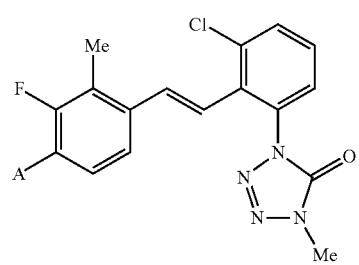
E0031 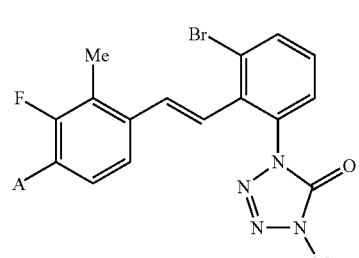
E0032 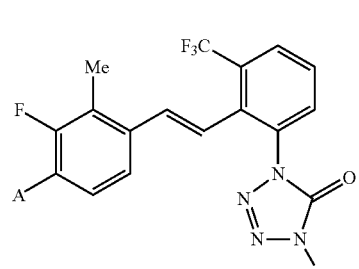
E0033 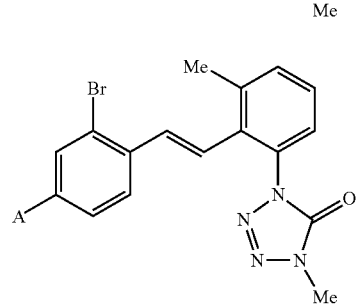
E0034 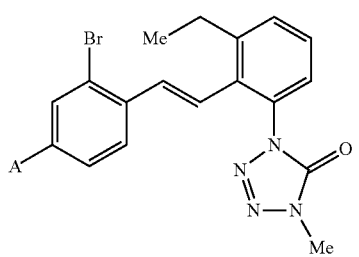
E0035 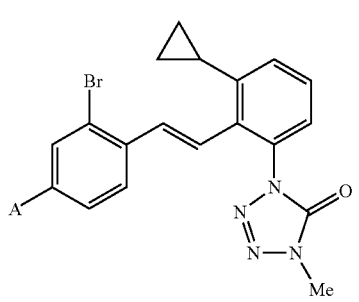
E0036 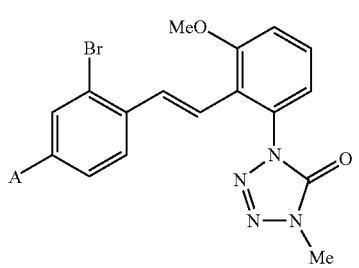
E0037 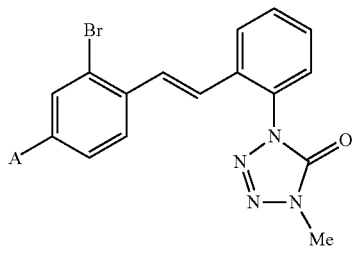
E0038 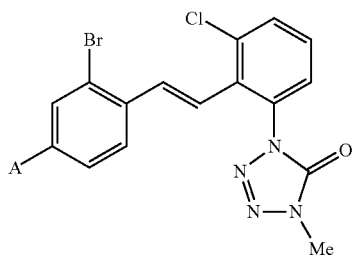
E0039 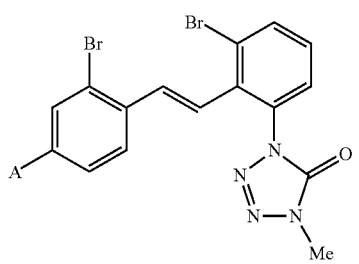

-continued
E0040 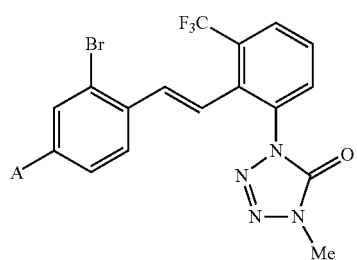
E0041 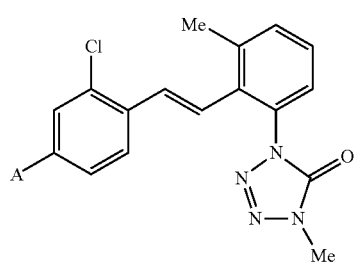
E0042 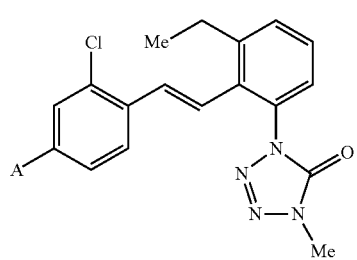
E0043 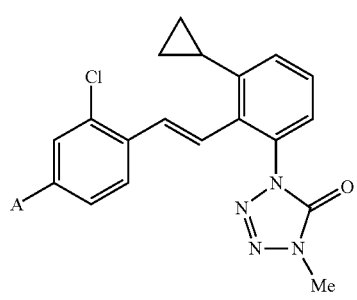
E0044 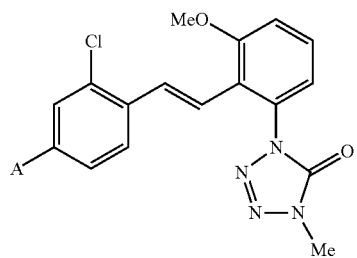
E0045 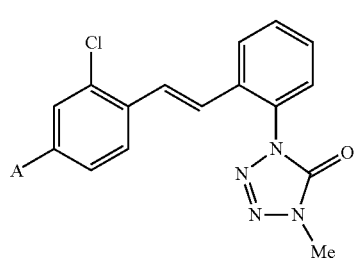
E0046 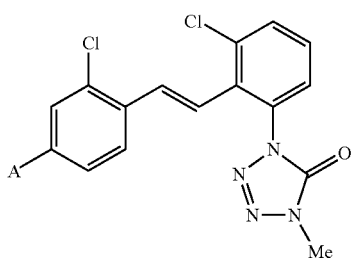
E0047 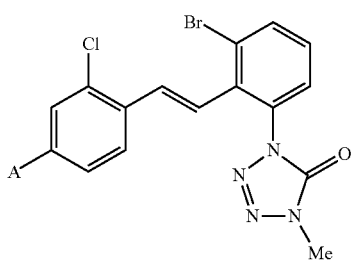
E0048 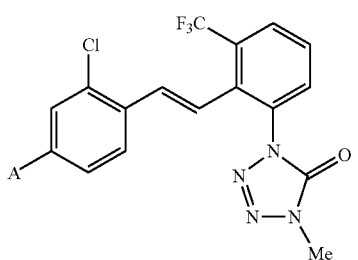
E0049 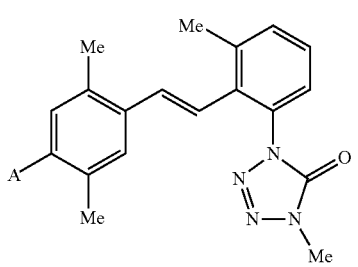
E0050 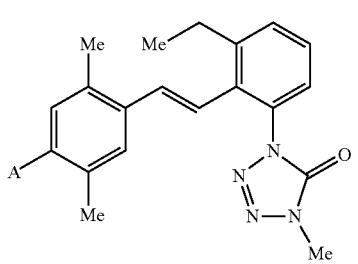
E0051 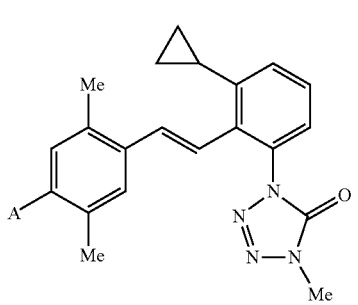

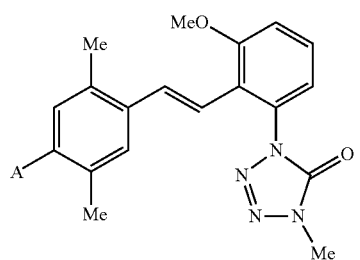
E0052
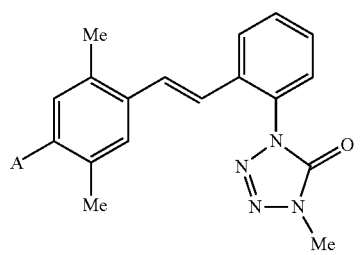
E0053
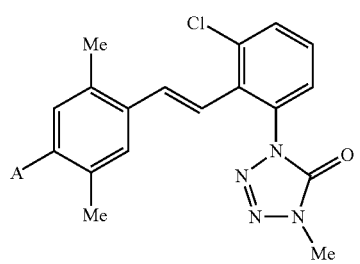
E0054
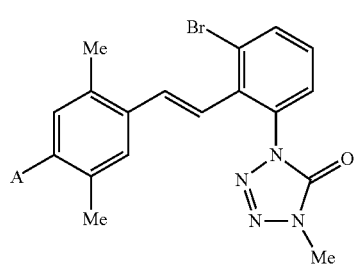
E0055
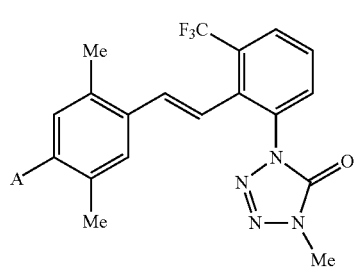
E0056
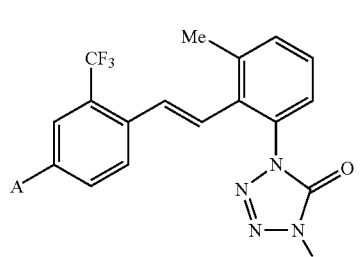
E0057
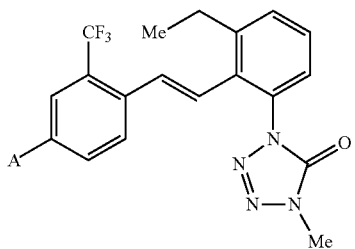
E0058
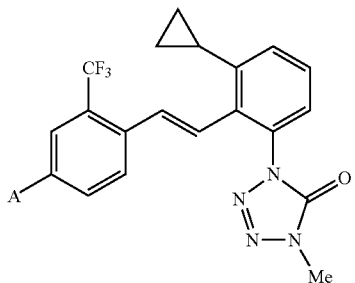
E0059
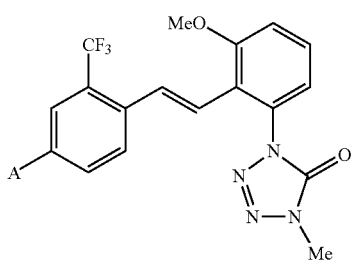
E0060
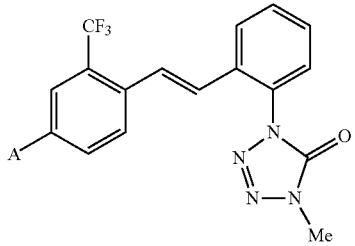
E0061
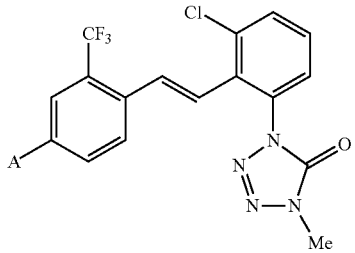
E0062
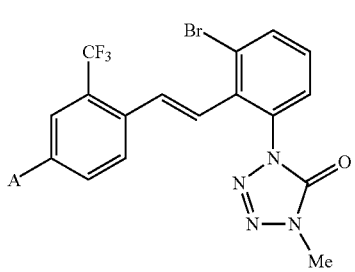
E0063

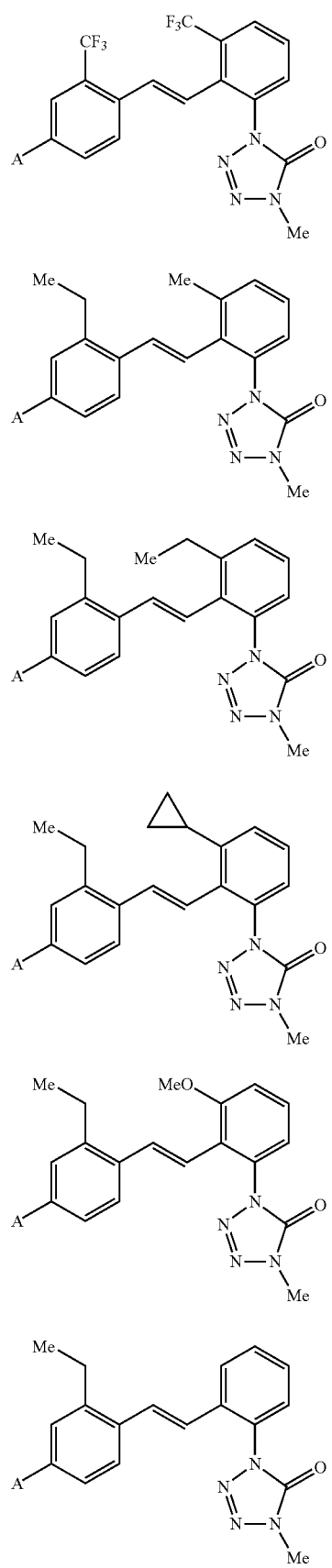
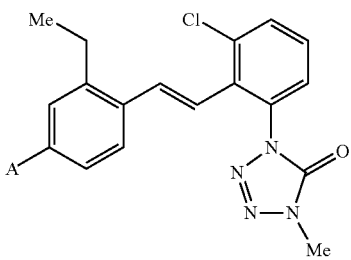
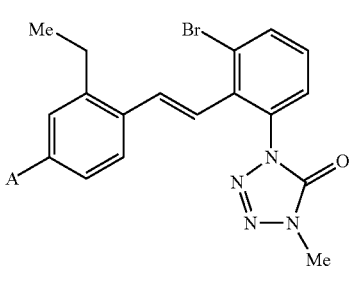
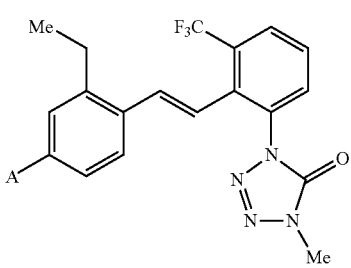
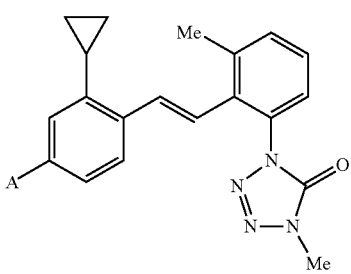
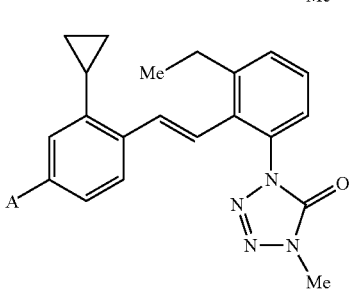
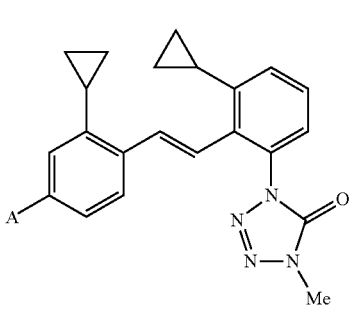

-continued
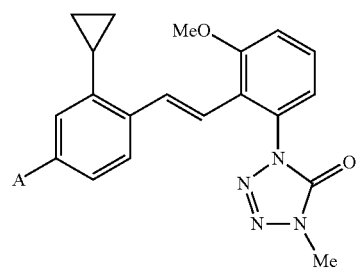 E0076
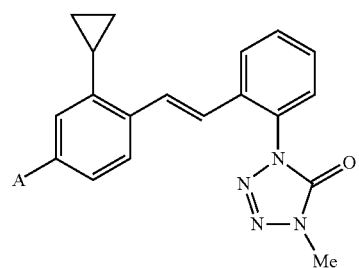 E0077
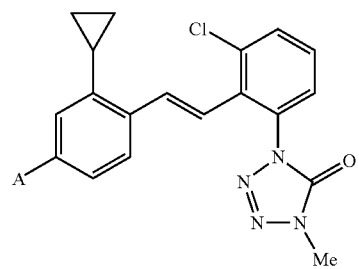 E0078
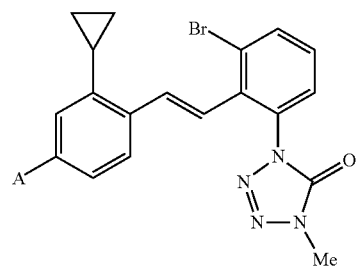 E0079
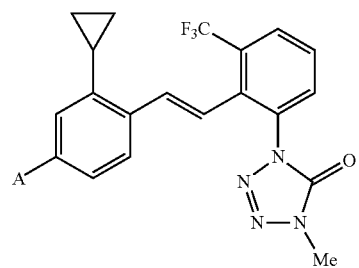 E0080
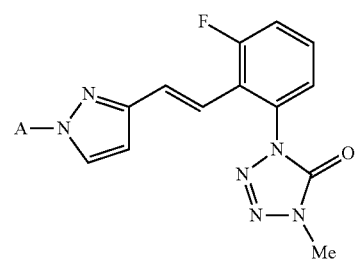 E0081
-continued
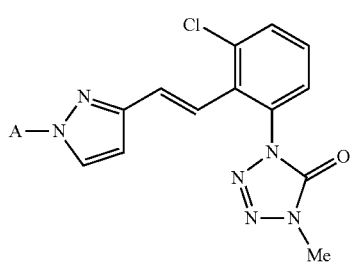 E0082
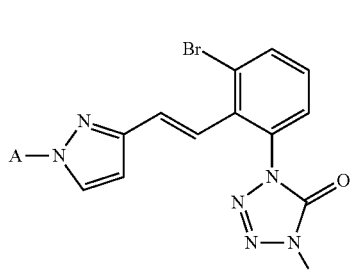 E0083
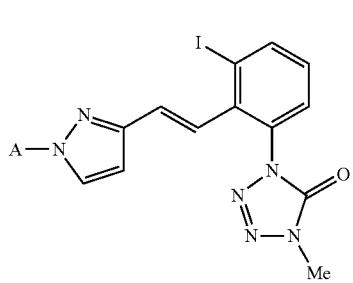 E0084
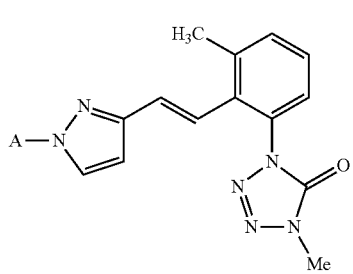 E0085
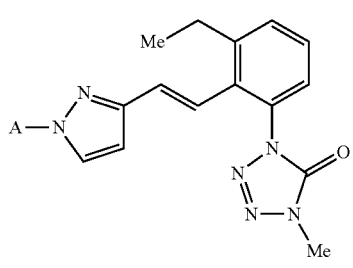 E0086
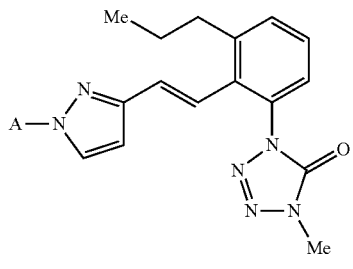 E0087

| | |
|---|---|
| E0088 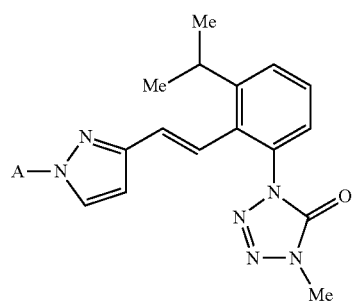 | E0093 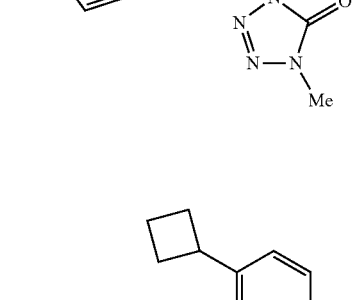 |
| E0089 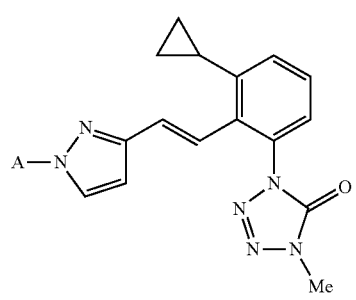 | E0094 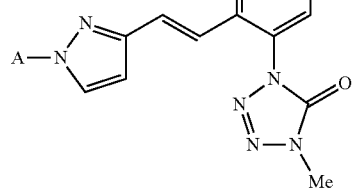 |
| E0090 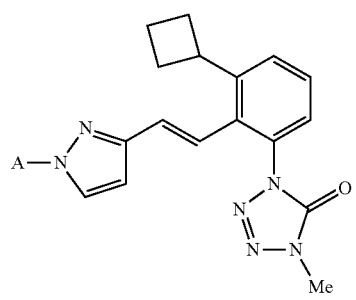 | E0095 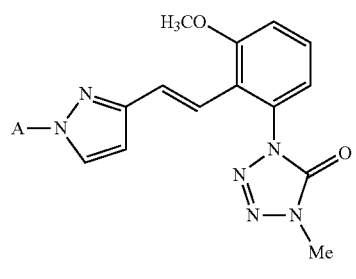 |
| E0091 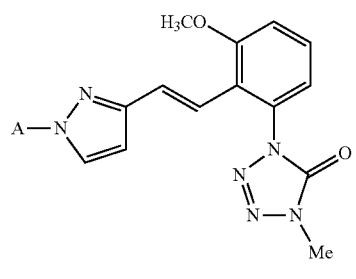 | E0096 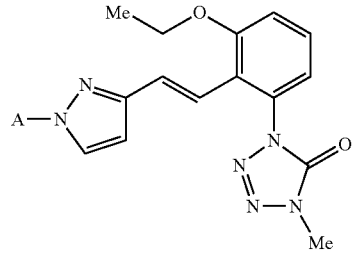 |
| E0092 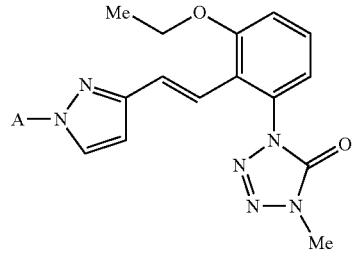 | E0097 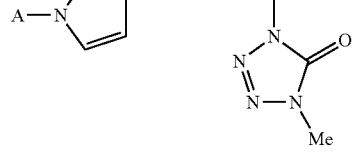 |

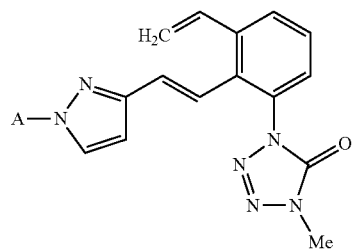
E0098
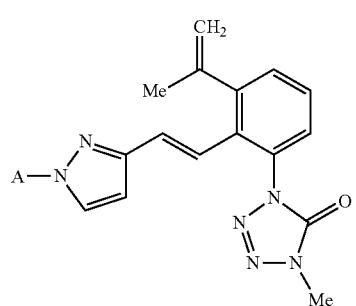
E0099
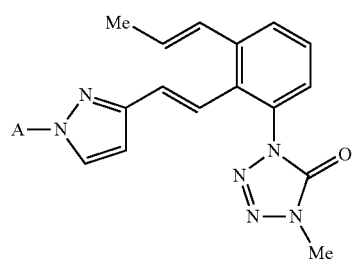
E0100
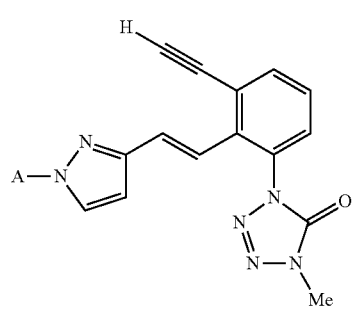
E0101
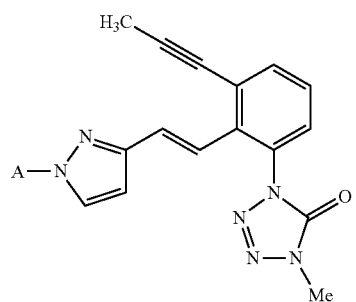
E0102
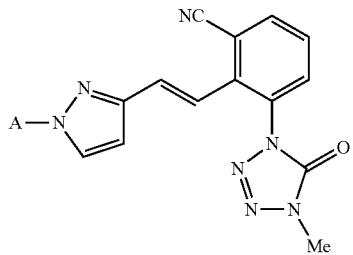
E0103
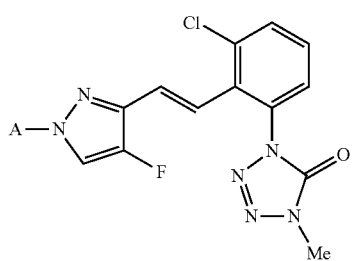
E0104
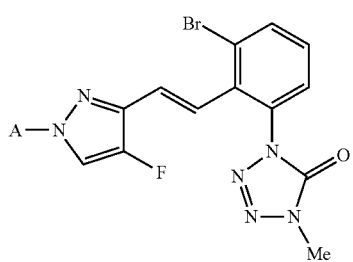
E0105
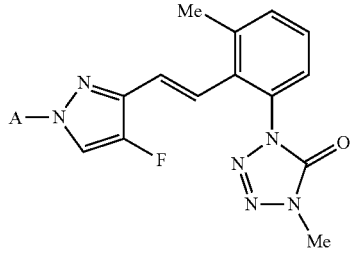
E0106
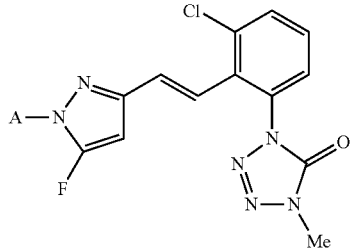
E0107
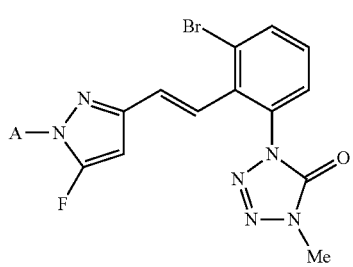
E0108

| | |
|---|---|
| E0109 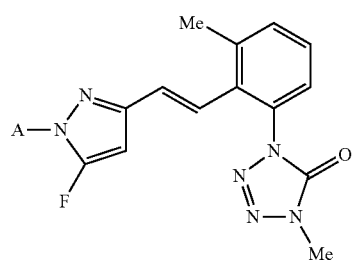 | E0115 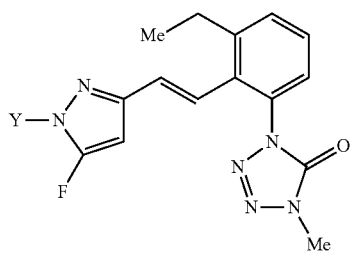 |
| E0110 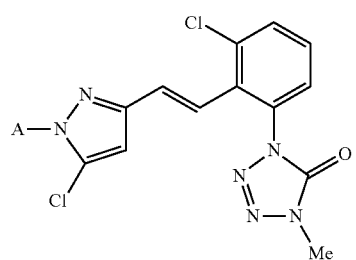 | E0116 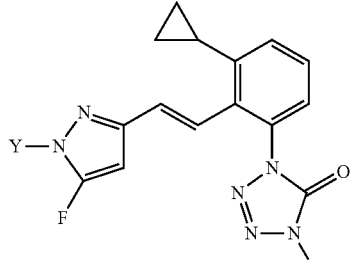 |
| E0111 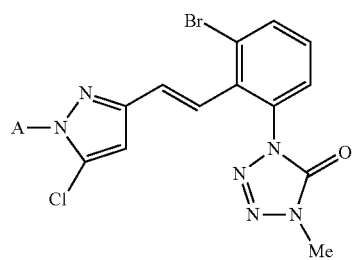 | E0117 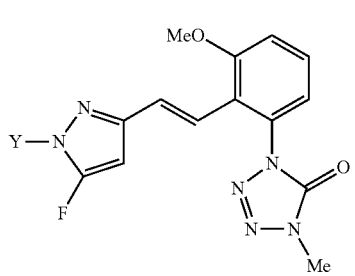 |
| E0112 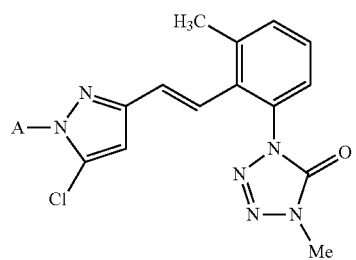 | E0118 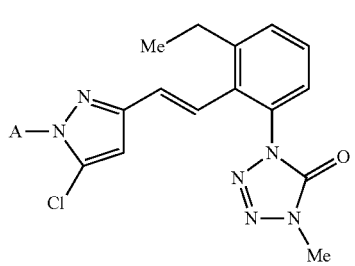 |
| E0113 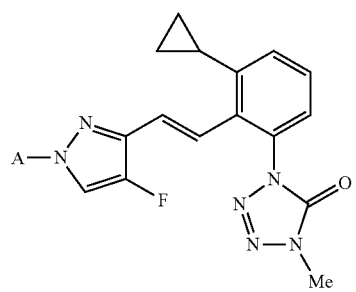 | E0119 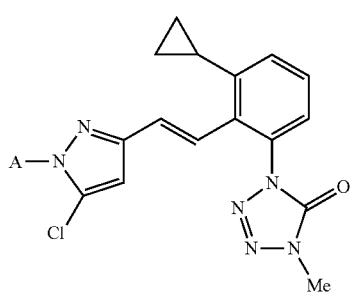 |
| E0114 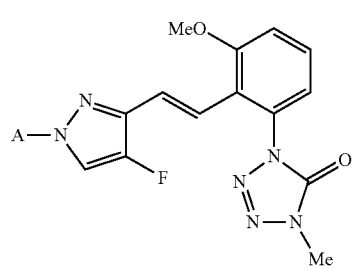 | E0120 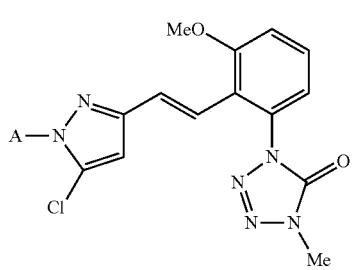 |

487
-continued
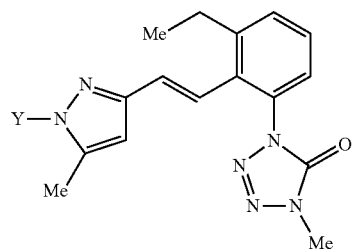 E0121
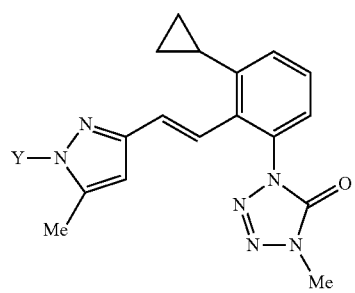 E0122
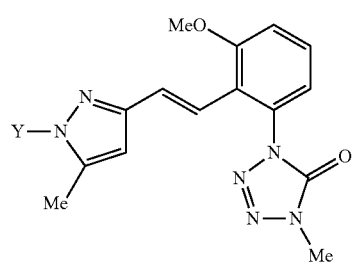 E0123
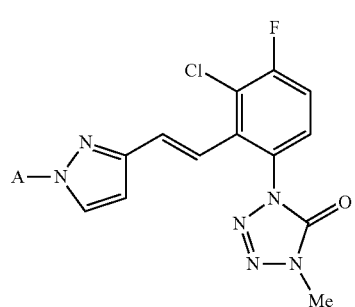 E0124
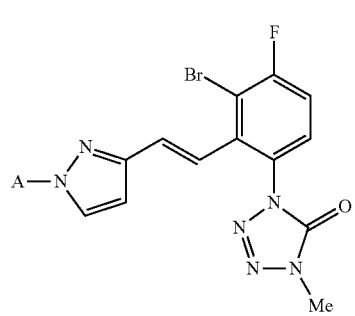 E0125
488
-continued
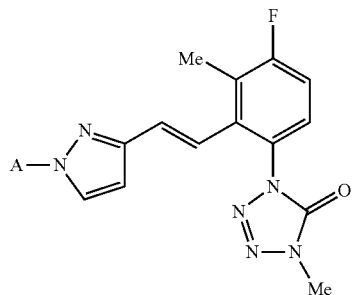 E0126
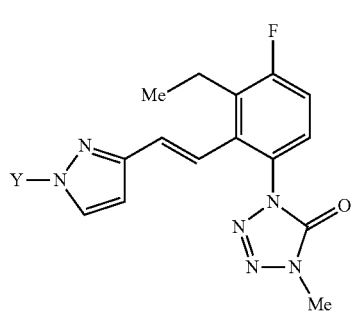 E0127
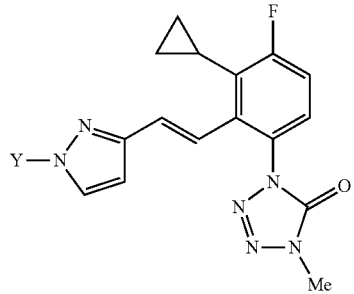 E0128
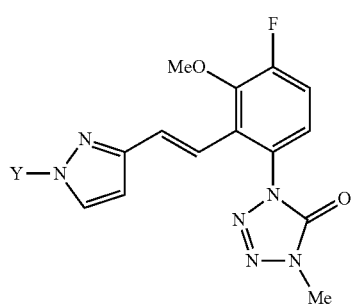 E0129
E0130

| | |
|---|---|
| E0131 | E0137 |
| E0132 | E0138 |
| E0133 | E0139 |
| E0134 | E0140 |
| E0135 | E0141 |
| E0136 | E0142 |

| E0143 | 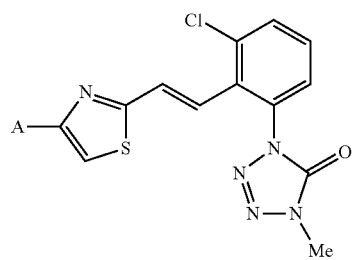 | E0149 | 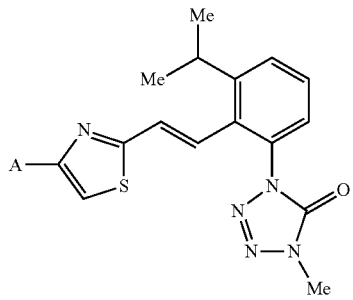 |
| E0144 | 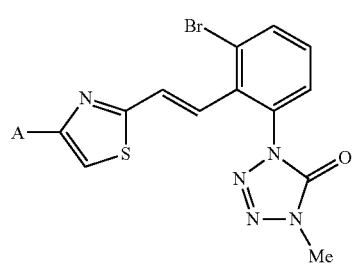 | E0150 | 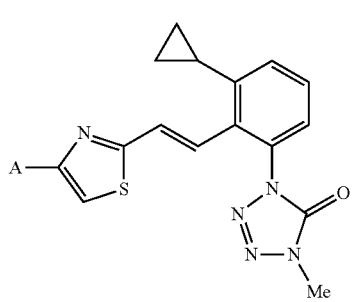 |
| E0145 | 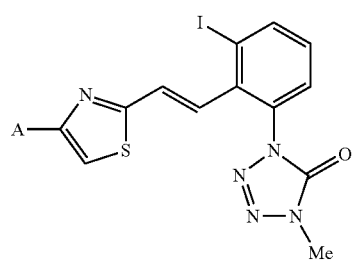 | E0151 | 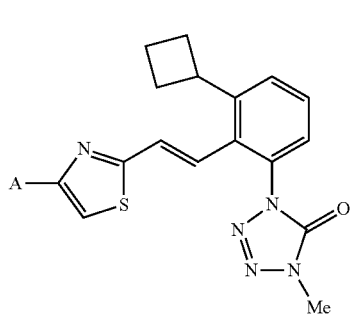 |
| E0146 | 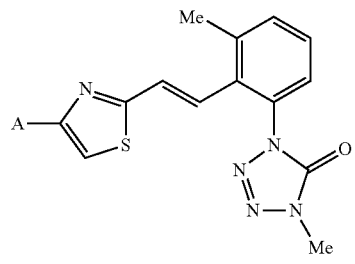 | E0152 | 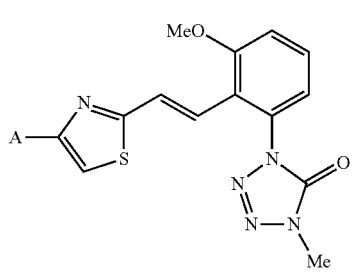 |
| E0147 | 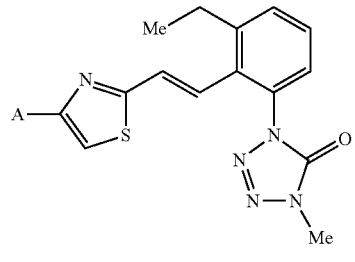 | E0153 | 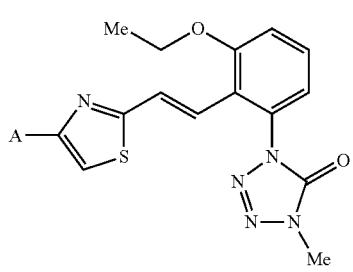 |
| E0148 | 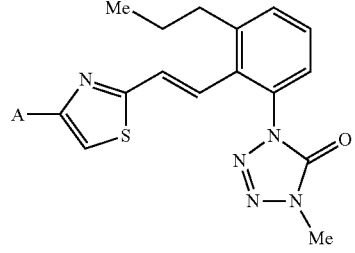 | | |

| | |
|---|---|
| E0154 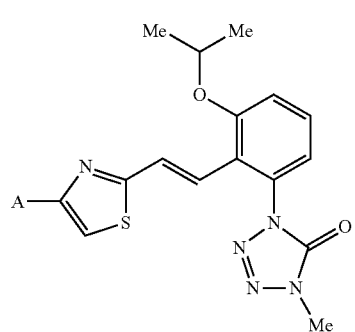 | E0159 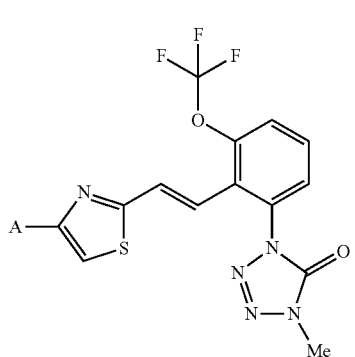 |
| E0155 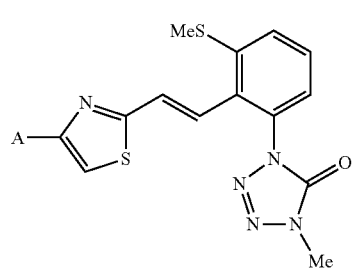 | E0160 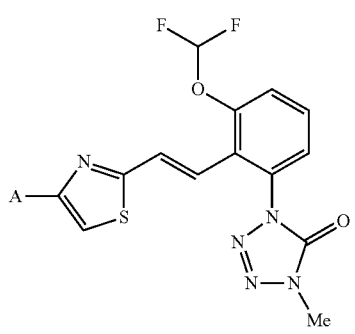 |
| E0156 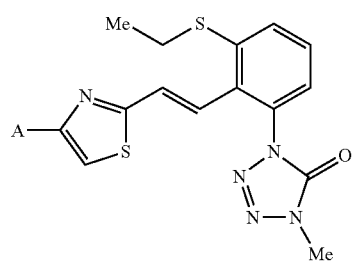 | E0161 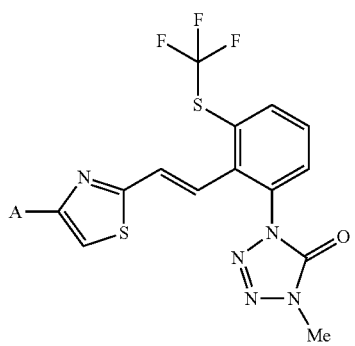 |
| E0157 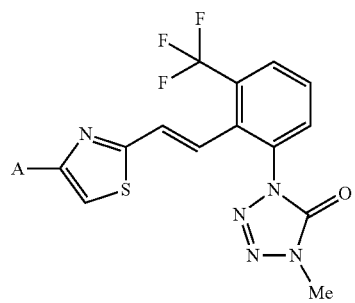 | E0162 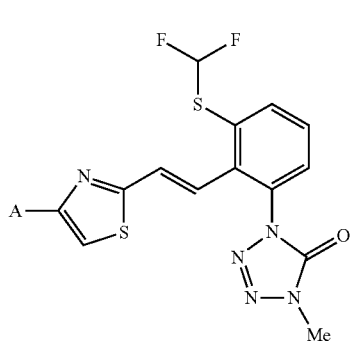 |
| E0158 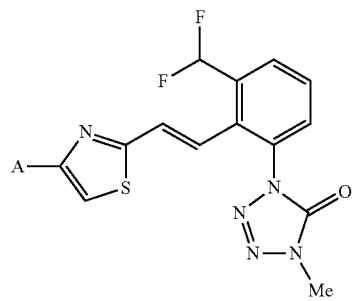 | E0163 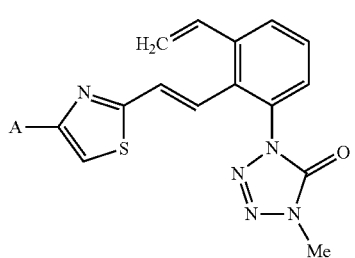 |

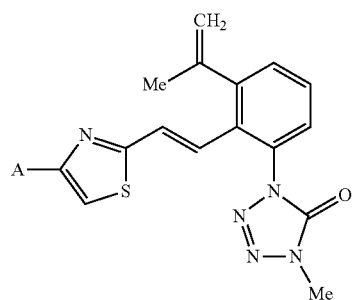 E0164
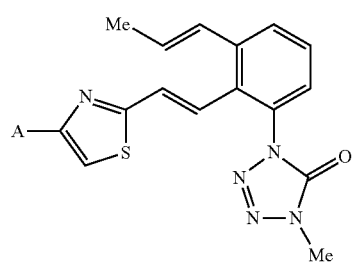 E0165
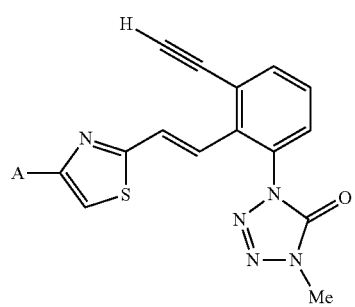 E0166
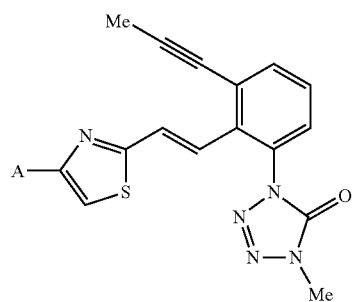 E0167
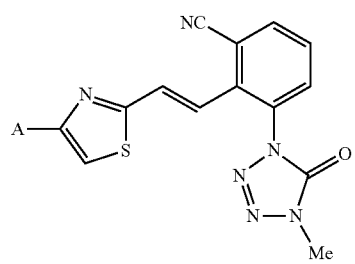 E0168
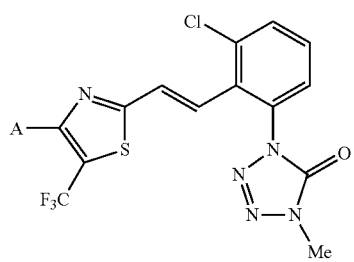 E0169
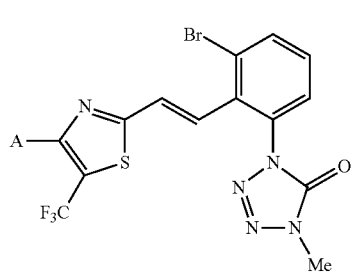 E0170
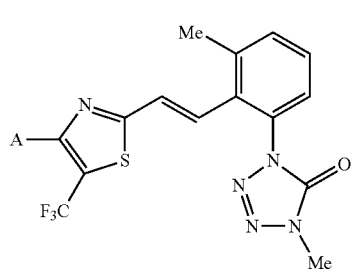 E0171
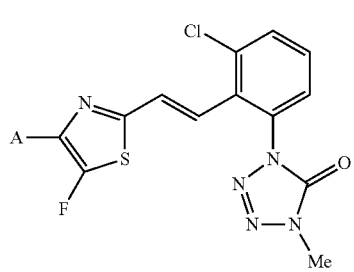 E0172
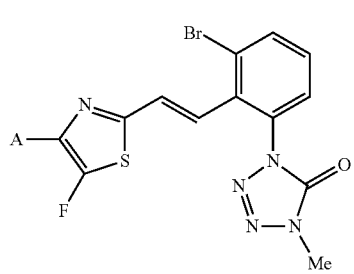 E0173
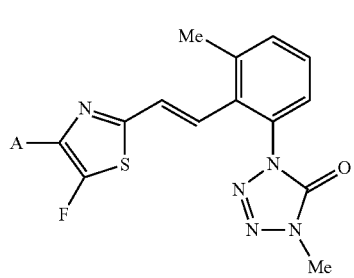 E0174

E0175 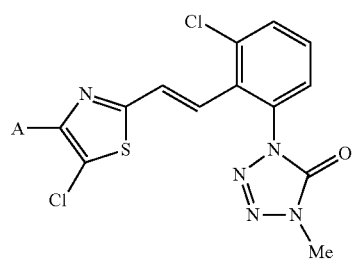
E0176 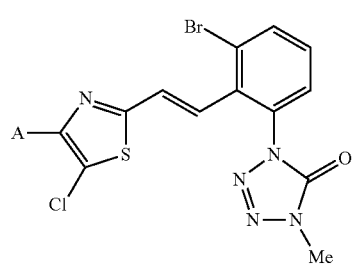
E0177 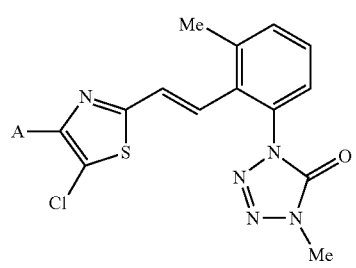
E0178 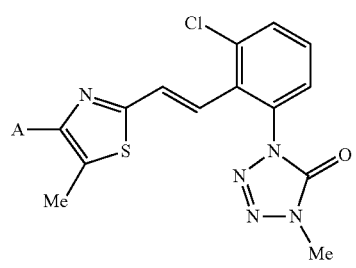
E0179 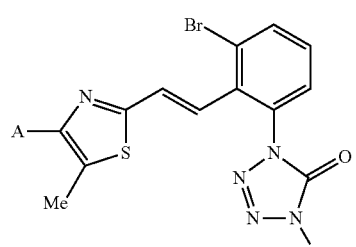
E0180 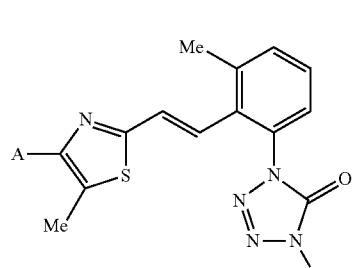
E0181 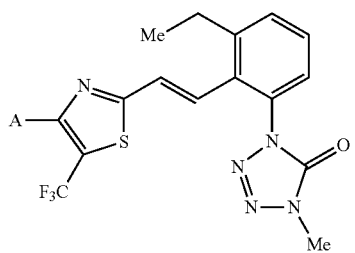
E0182 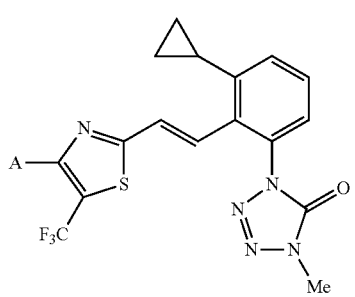
E0183 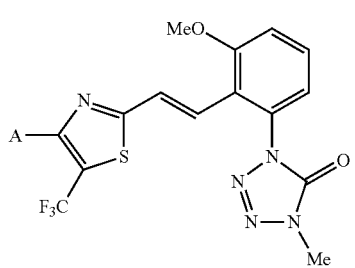
E0184 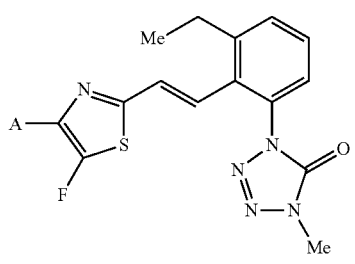
E0185 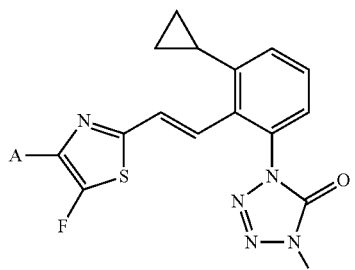
E0186 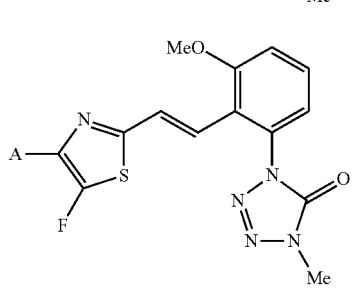

| | |
|---|---|
| E0187 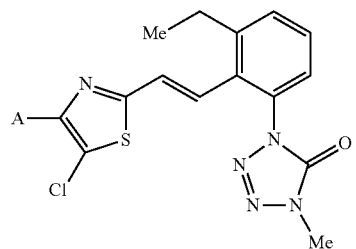 | E0193 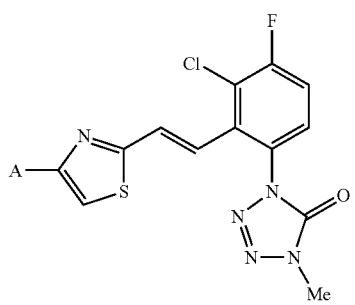 |
| E0188 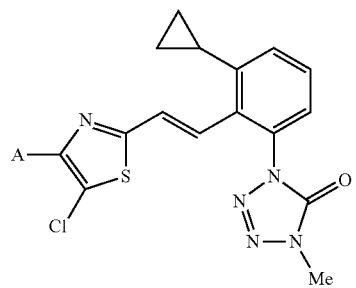 | E0194 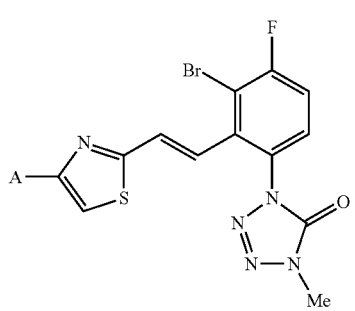 |
| E0189 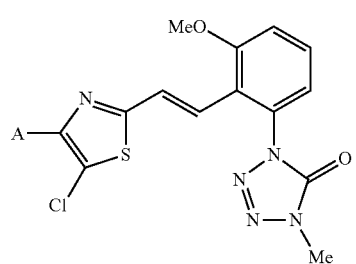 | E0195 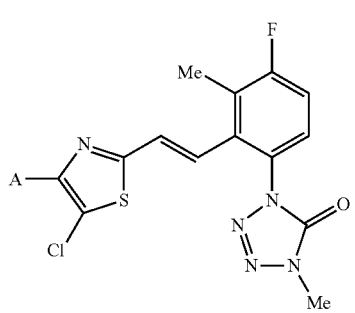 |
| E0190 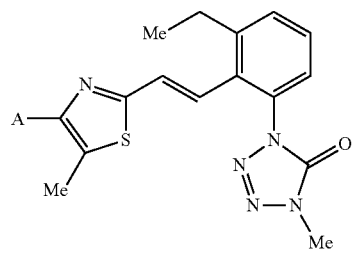 | E0196 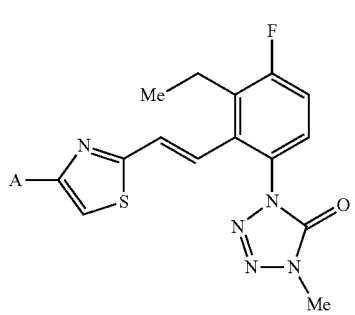 |
| E0191 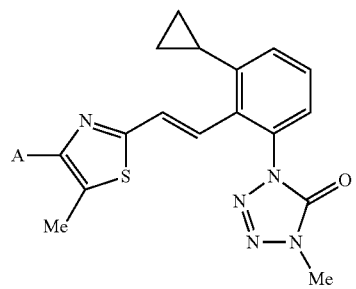 | E0197 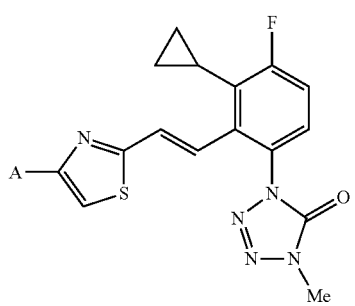 |
| E0192 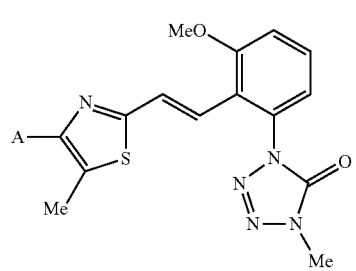 | |

-continued
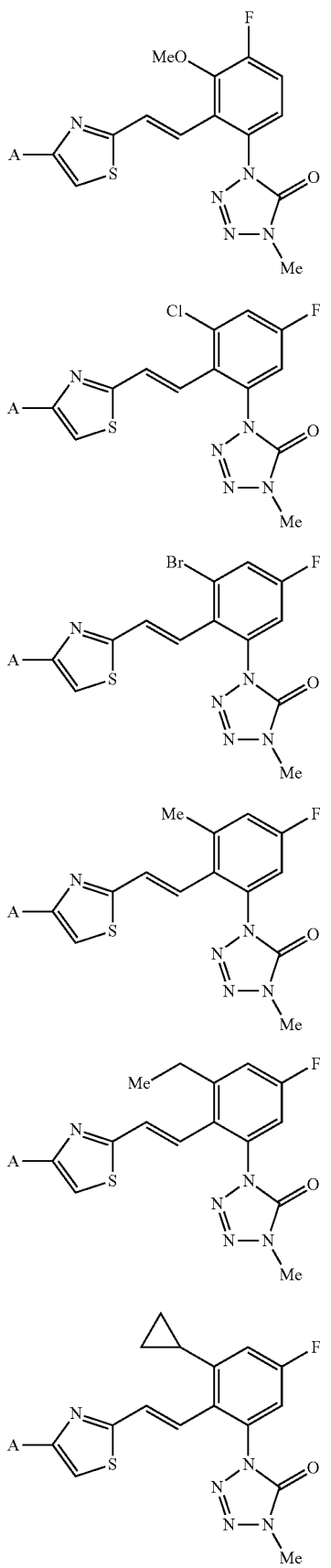
E0198
E0199
E0200
E0201
E0202
E0203
-continued
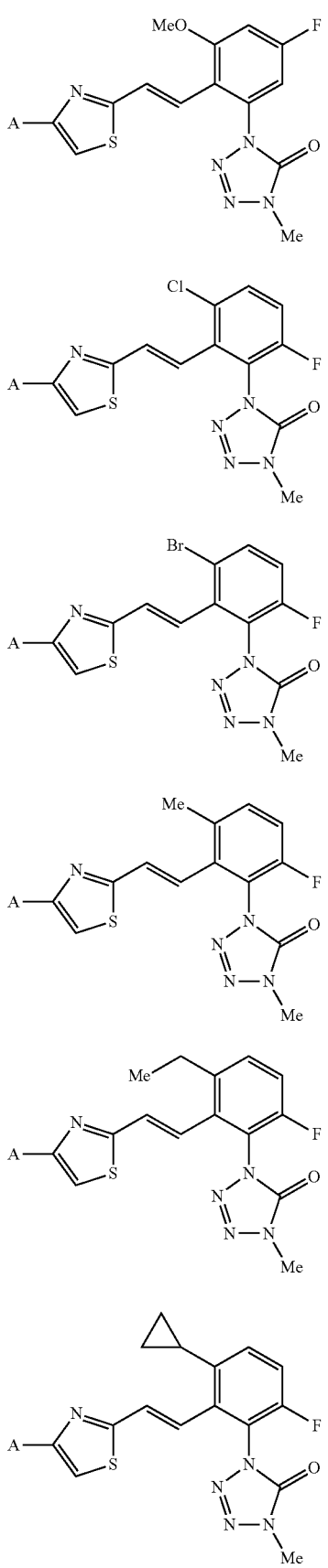
E0204
E0205
E0206
E0207
E0208
E0209

-continued
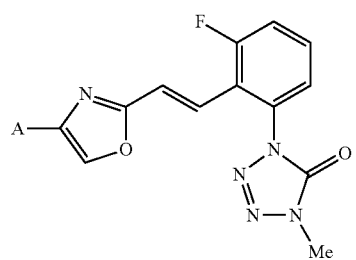
E1206
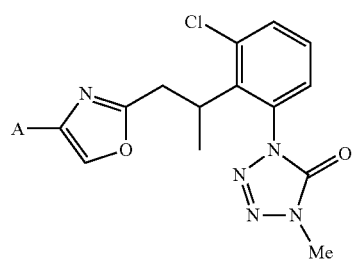
E1207
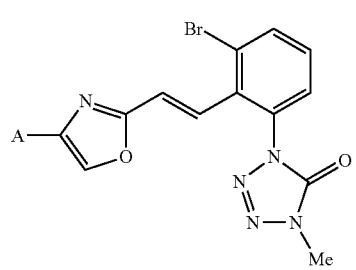
E1208
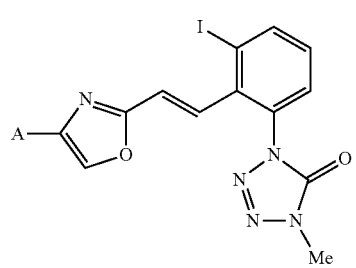
E1209
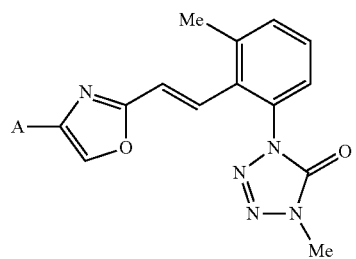
E0210
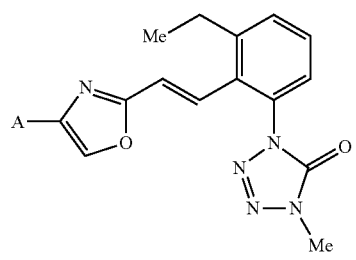
E0211
-continued
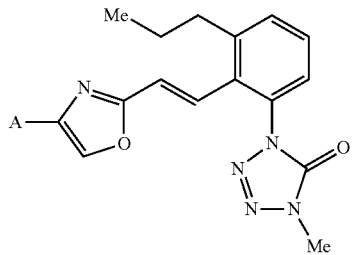
E0212
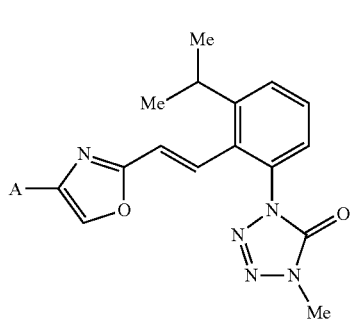
E0213
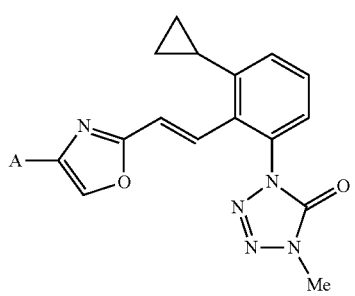
E0218
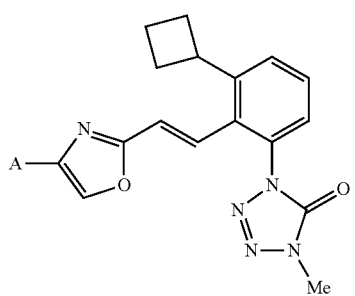
E0219
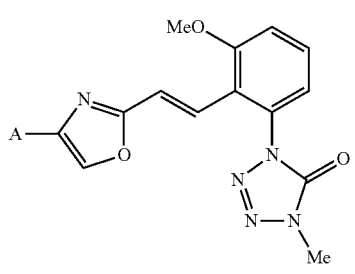
E0220

| | |
|---|---|
| E0221 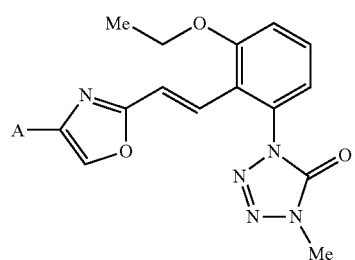 | E0226 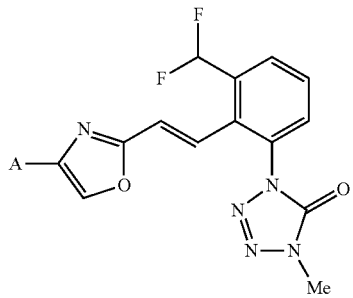 |
| E0222 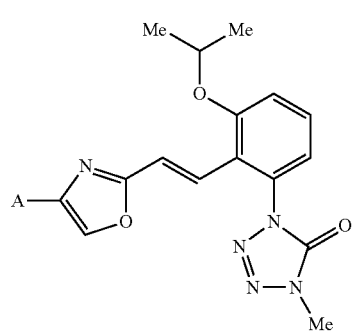 | E0227 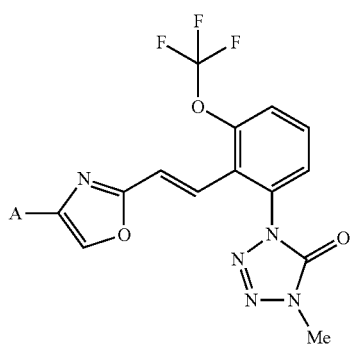 |
| E0223 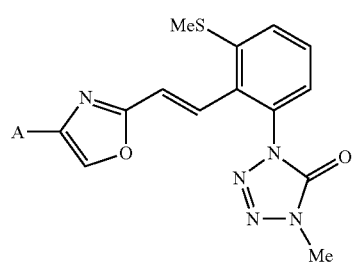 | E0228 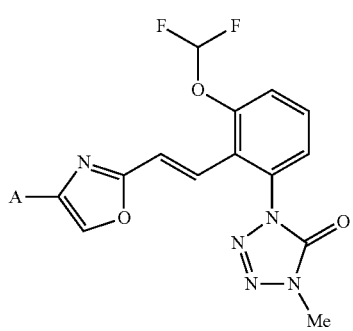 |
| E0224 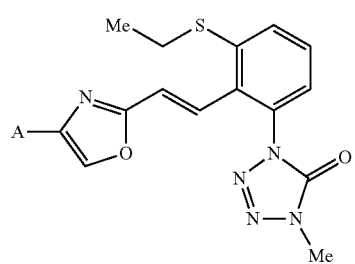 | E0229 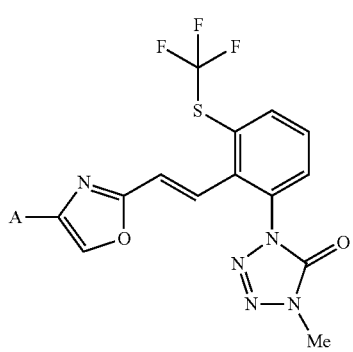 |
| E0225 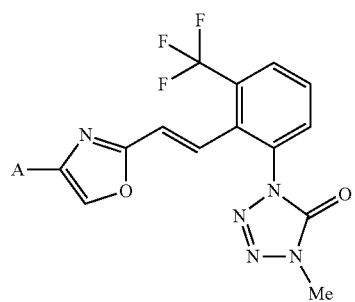 | E0230 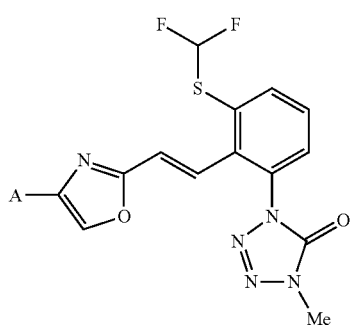 |

| | |
|---|---|
| 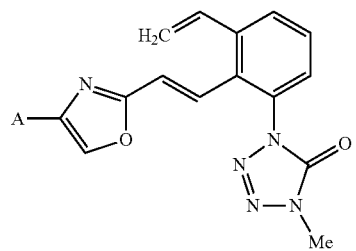 E0231 | 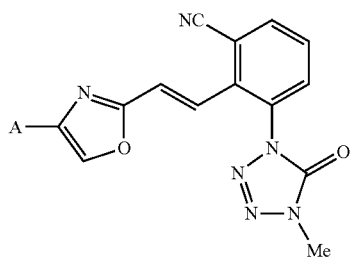 E0236 |
| 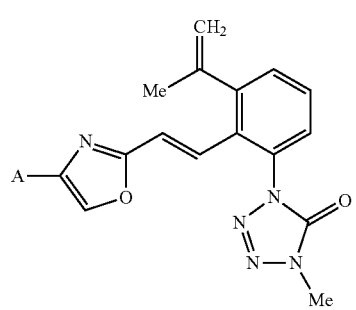 E0232 | 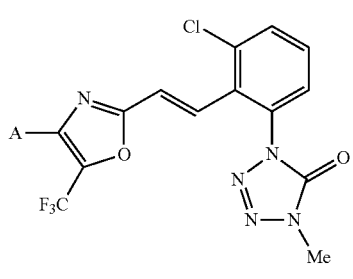 E0237 |
| 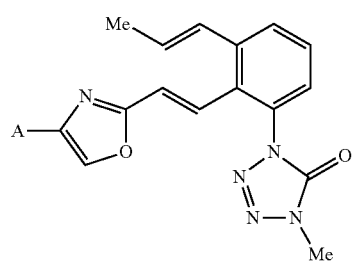 E0233 | 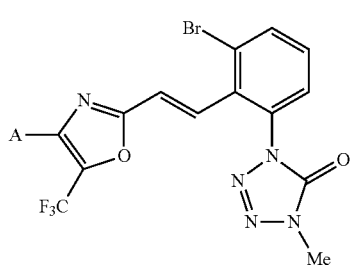 E0238 |
| 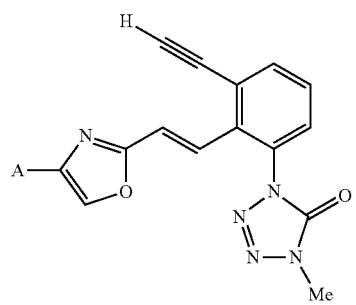 E0234 | 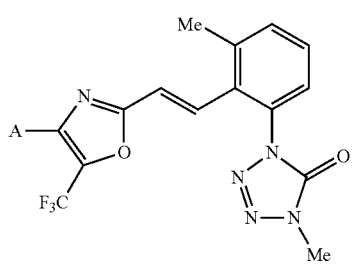 E0239 |
| | 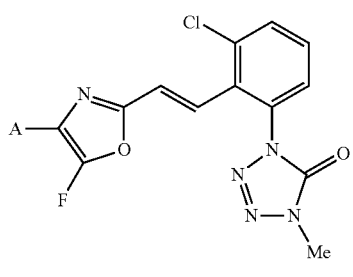 E0240 |
| 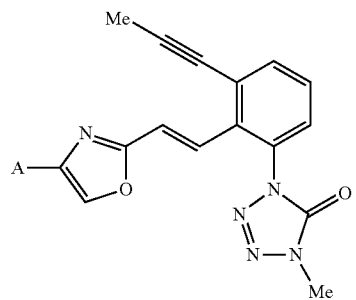 E0235 | 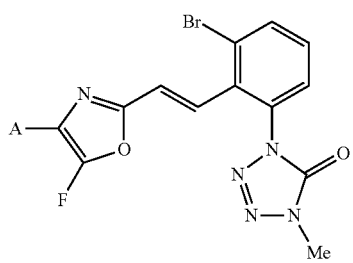 E0241 |

| | |
|---|---|
| E0242 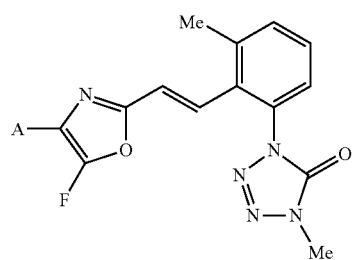 | E0248 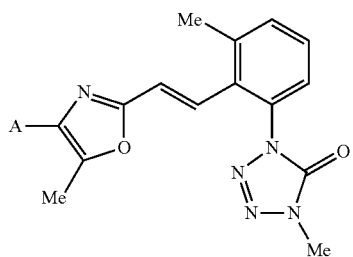 |
| E0243 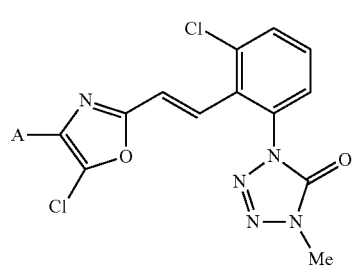 | E0249 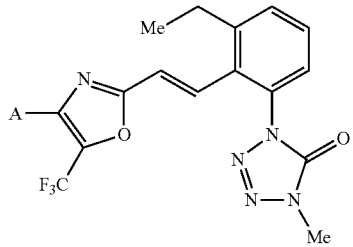 |
| E0244 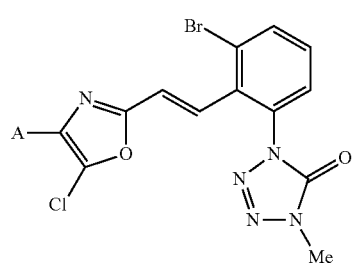 | E0250 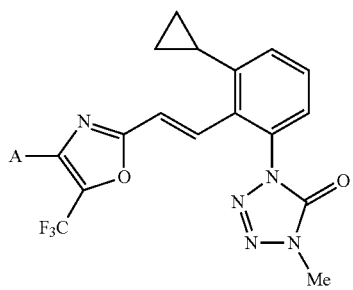 |
| E0245 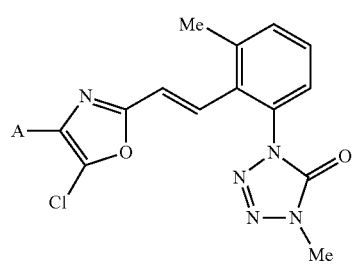 | E0251 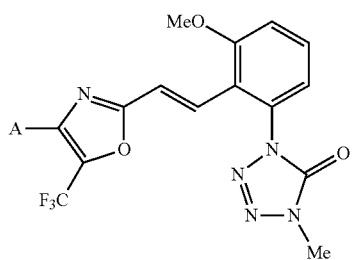 |
| E0246 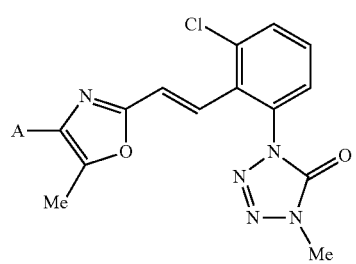 | E0252 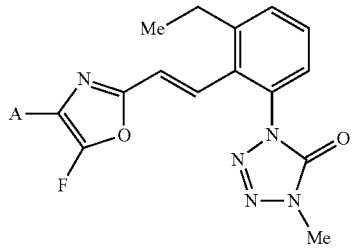 |
| E0247 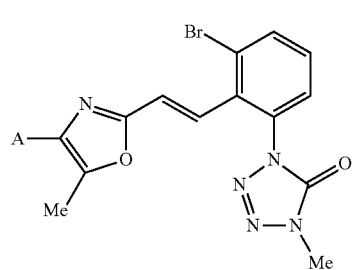 | E0253 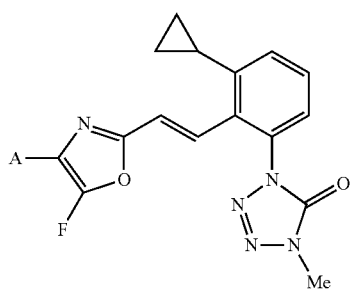 |

511 -continued
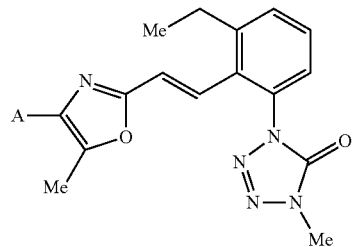
E0254
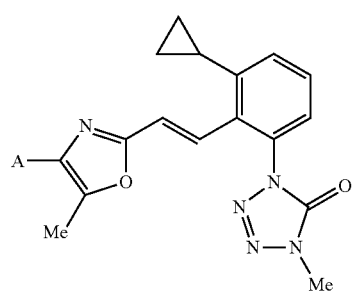
E0255
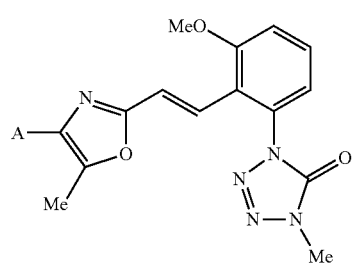
E0256
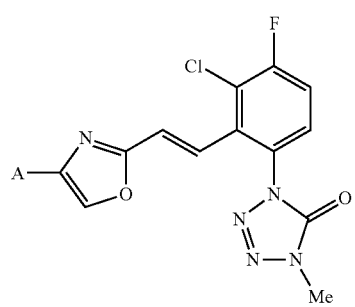
E0257
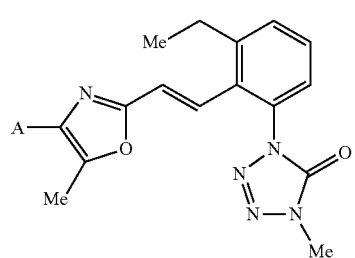
E0258
512 -continued
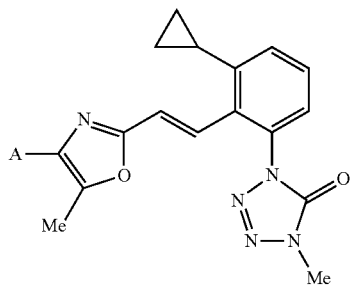
E0259
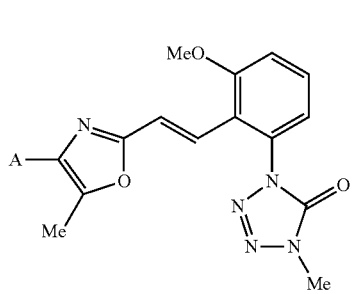
E0260
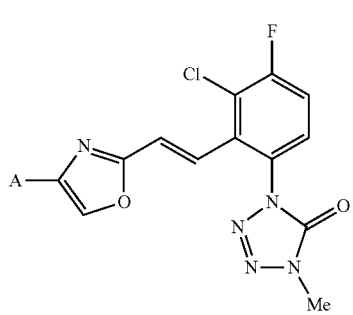
E0261
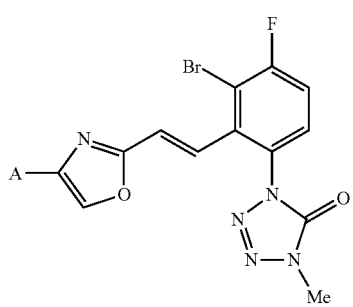
E0262
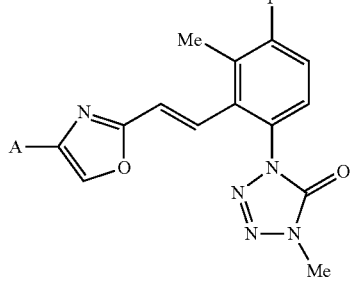
E0263

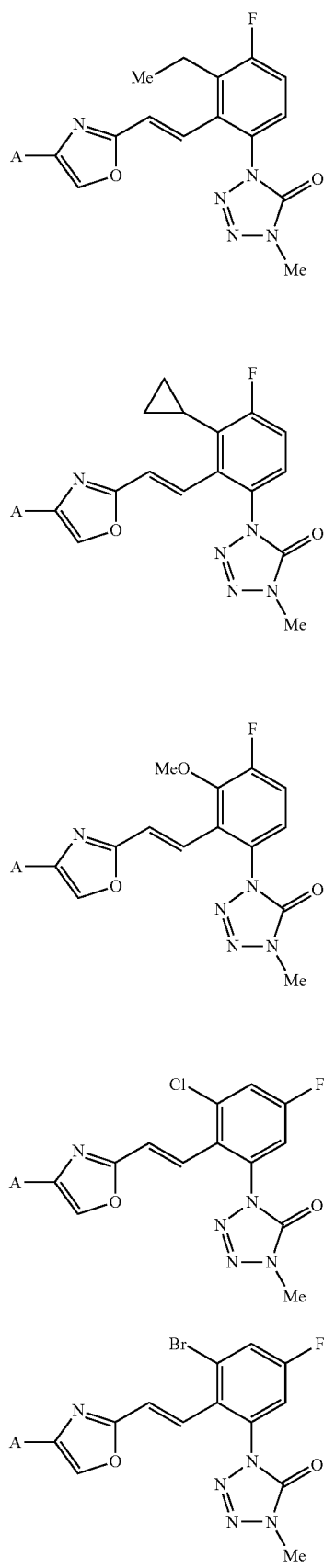
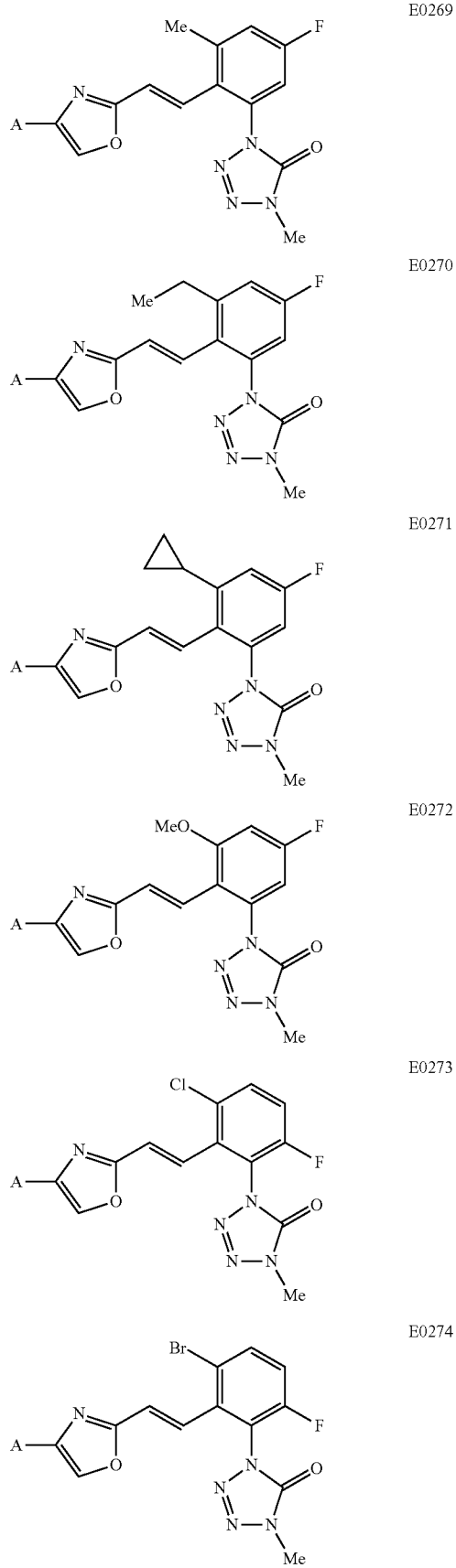

-continued
E0275
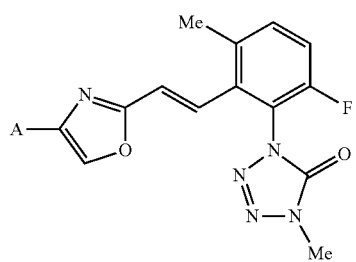
E0276
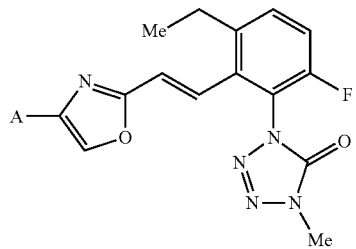
E0277
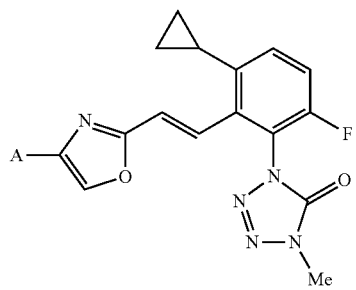
E0278
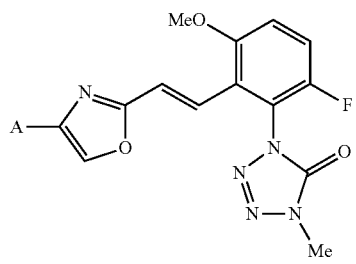
E0279
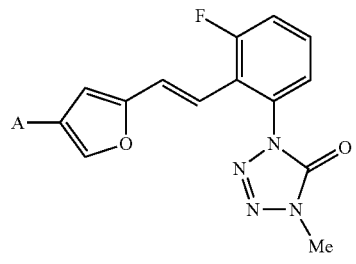
E0280
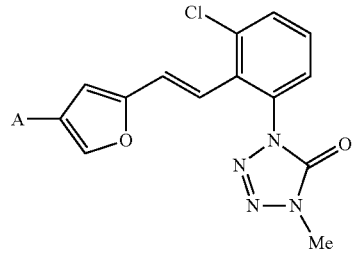
-continued
E0281
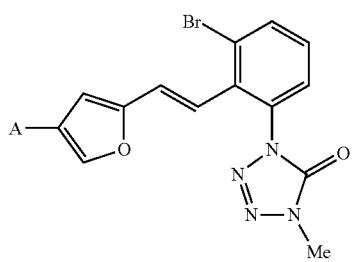
E0282
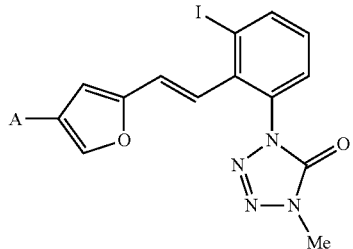
E0283
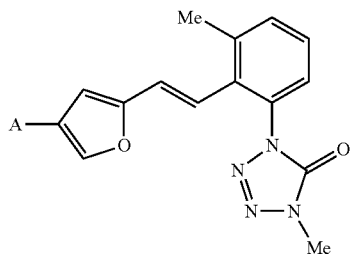
E0284
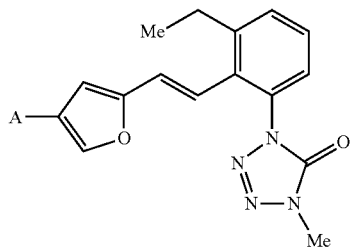
E0285
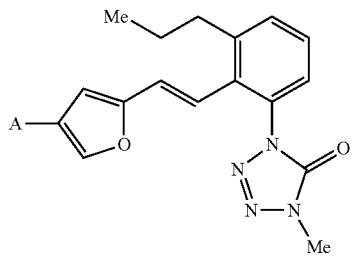
E0286
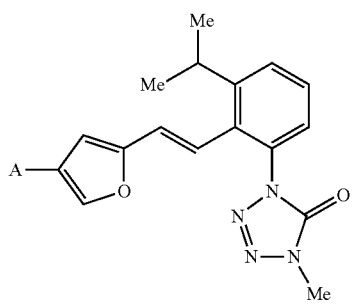

517
-continued
E0287
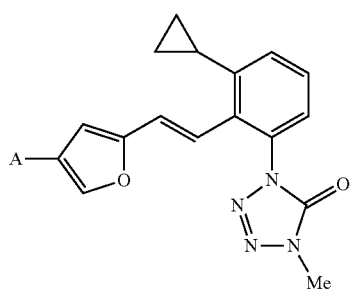
E0288
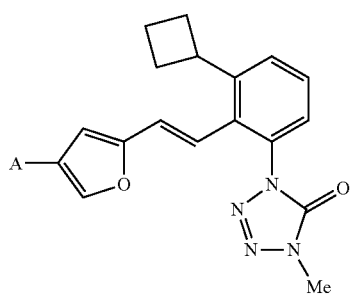
E0289
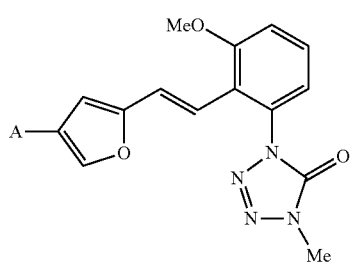
E0290
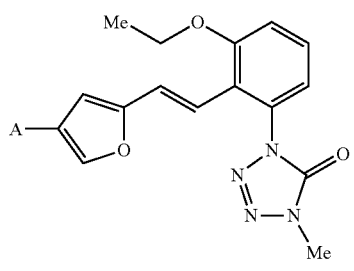
E0291
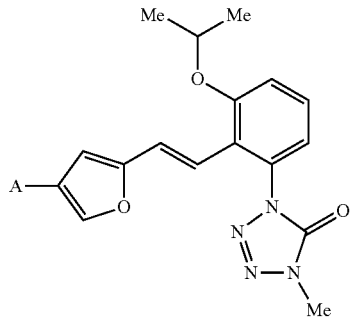
518
-continued
E0292
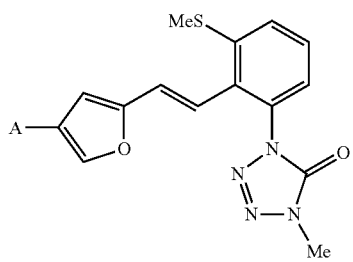
E0293
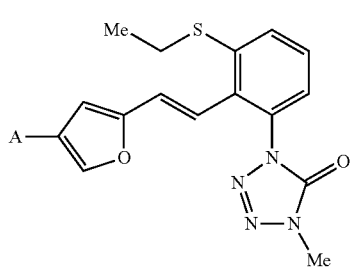
E0294
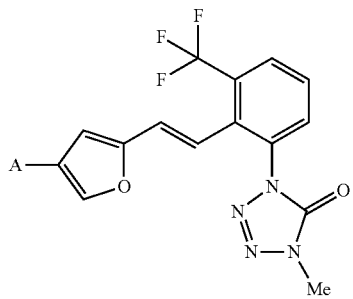
E0295
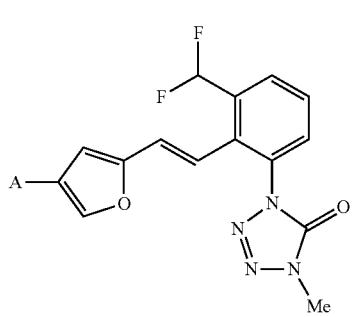
E0296

-continued
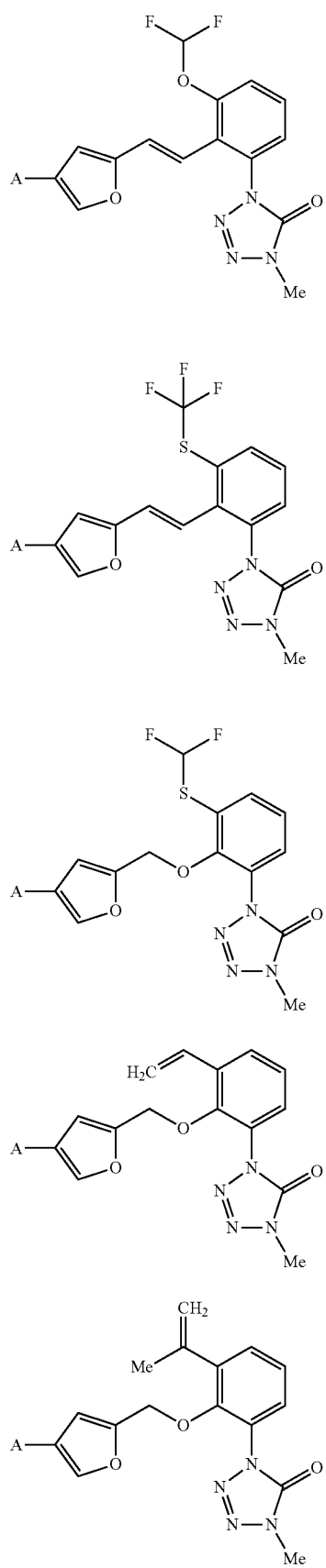
E0297
E0298
E0299
E0300
E0301
-continued
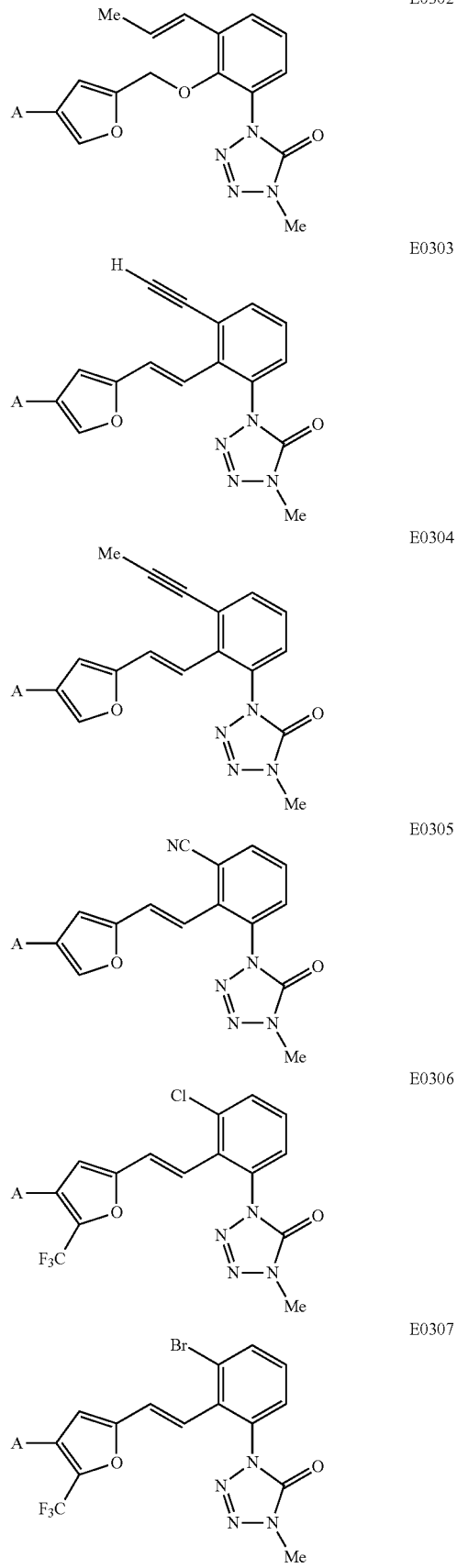
E0302
E0303
E0304
E0305
E0306
E0307

-continued
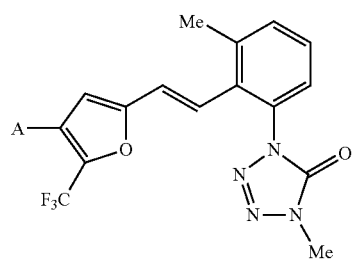
E0308
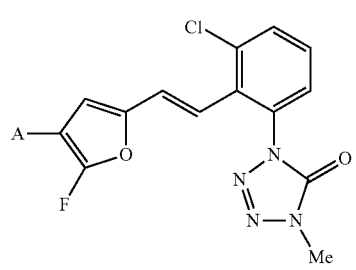
E0309
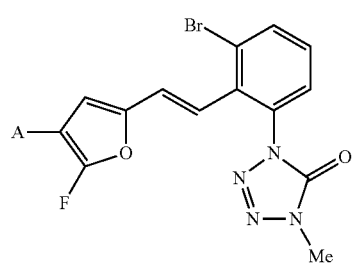
E0310
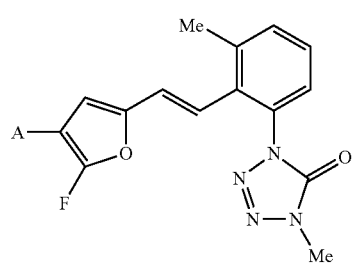
E0311
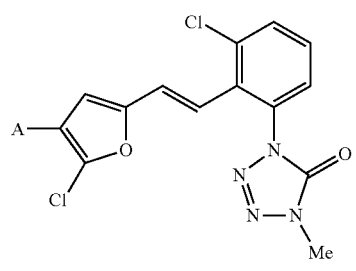
E0312
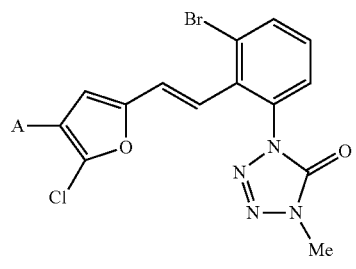
E0313
-continued
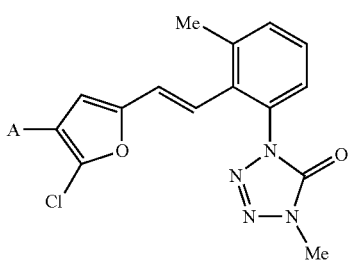
E0314
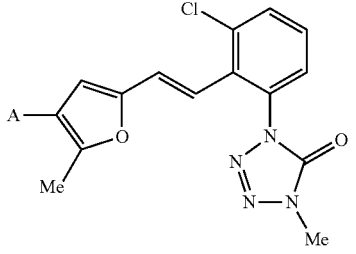
E0315
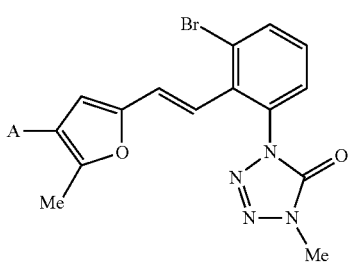
E0316
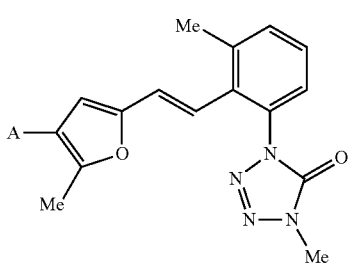
E0317
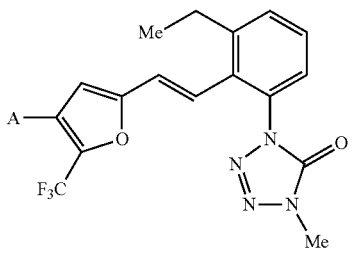
E0318
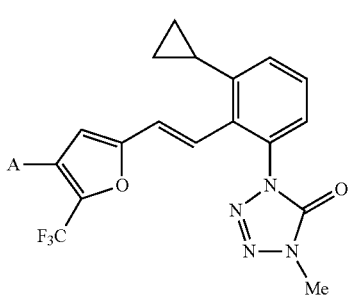
E0319

-continued
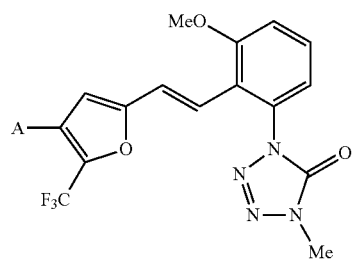 E0320
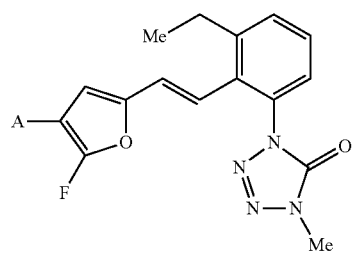 E0321
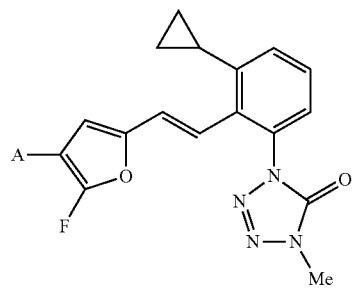 E0322
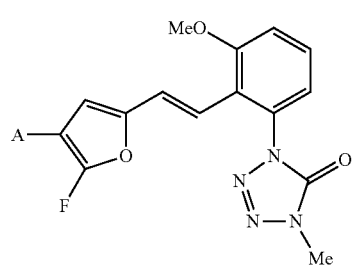 E0323
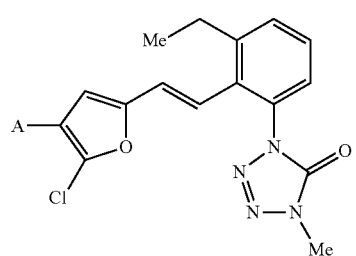 E0324
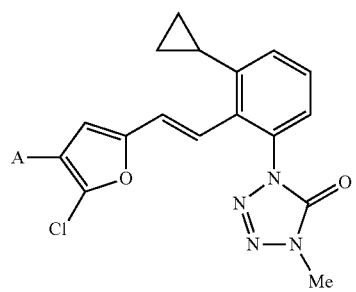 E0325
-continued
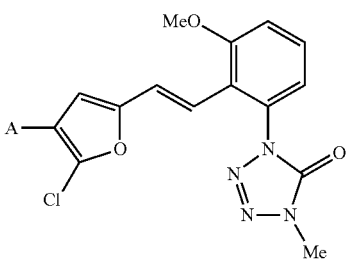 E0326
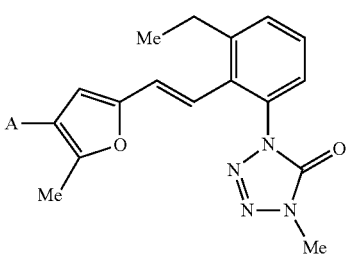 E0327
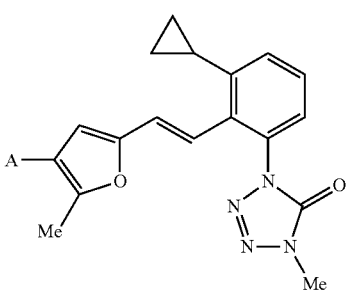 E0328
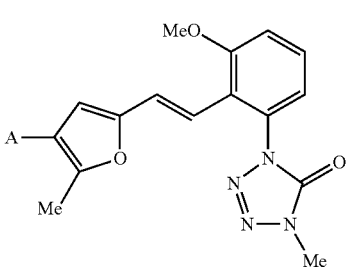 E0329
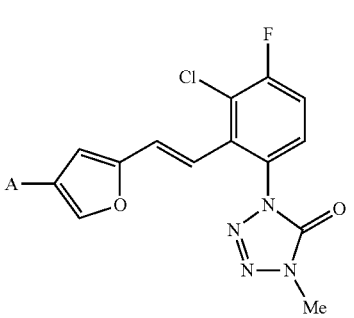 E0330

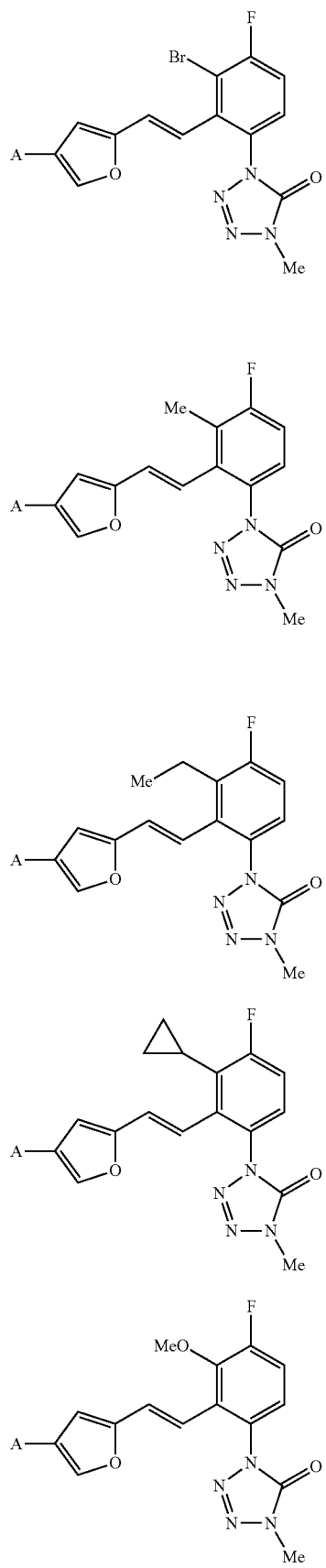

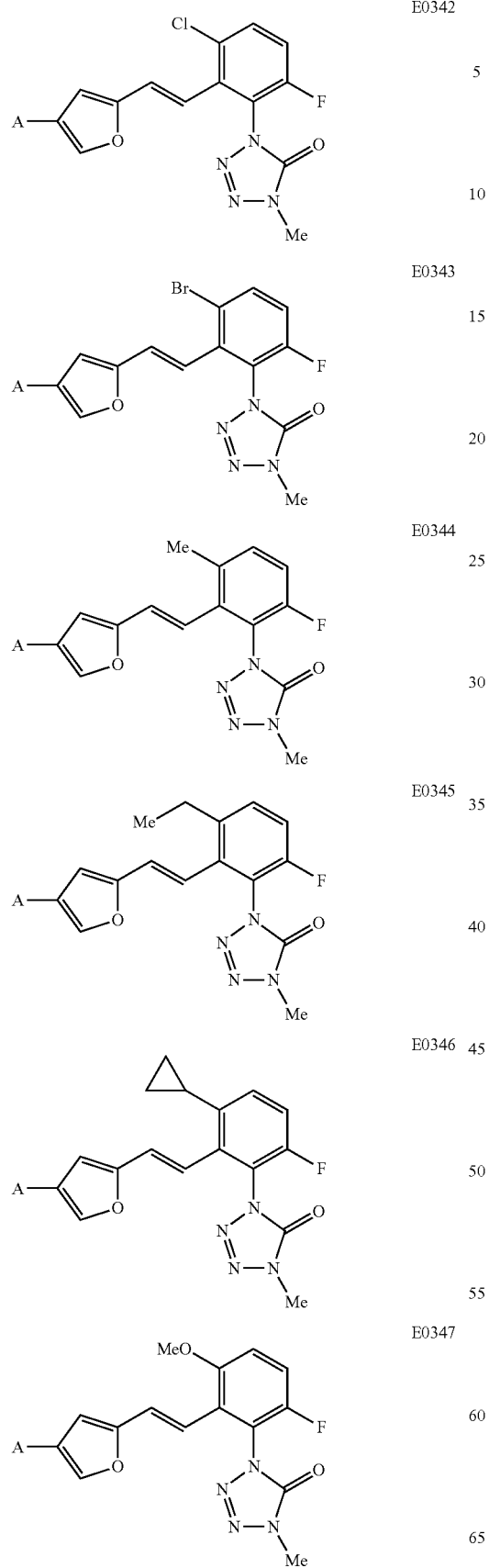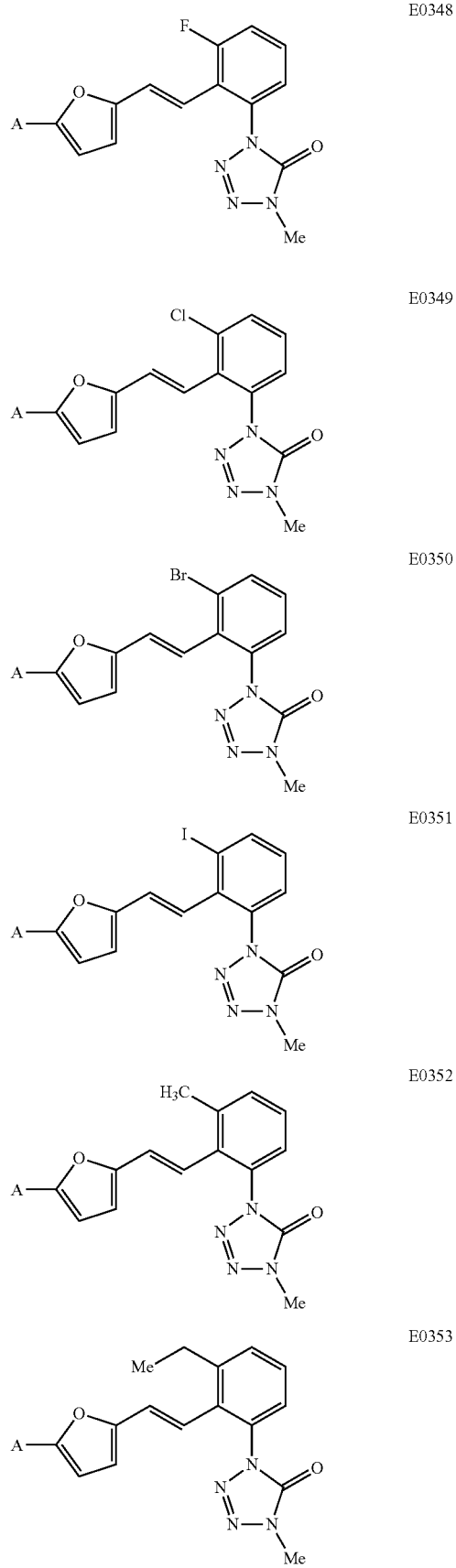

| 529 -continued | | 530 -continued | |
|---|---|---|---|
| 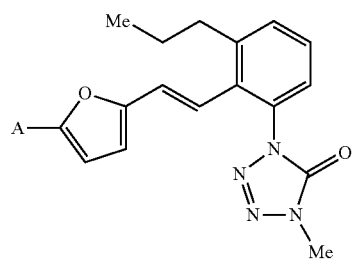 | E0354 | 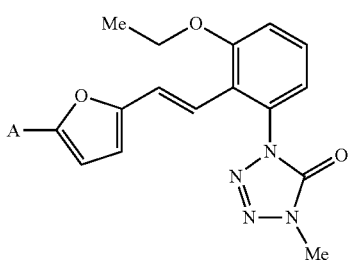 | E0359 |
| 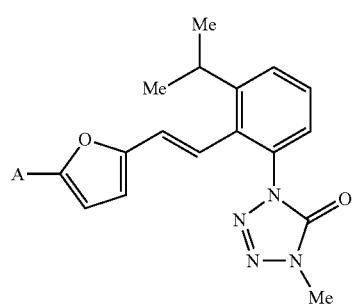 | E0355 | 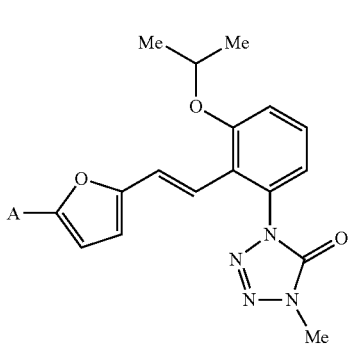 | E0360 |
| 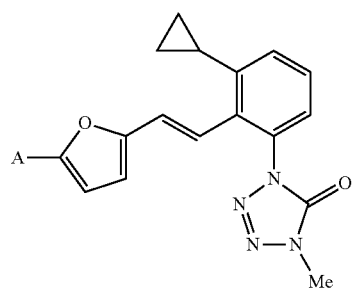 | E0356 | 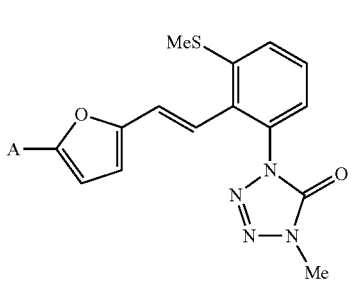 | E0361 |
| 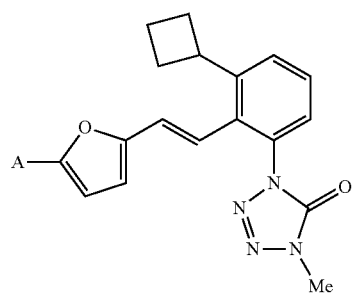 | E0357 | 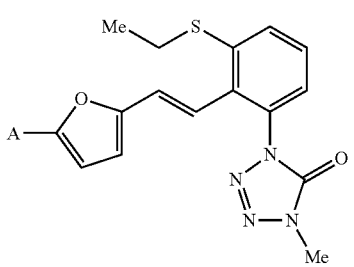 | E0362 |
| 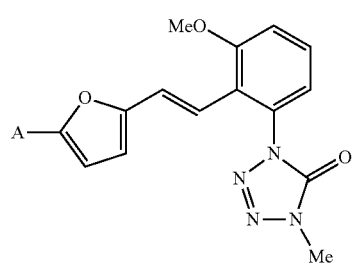 | E0358 | 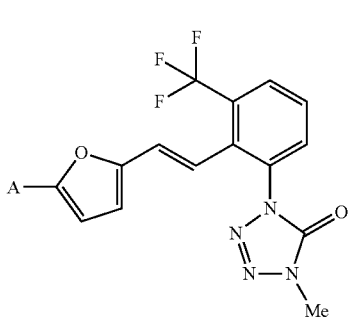 | E0363 |

531
-continued
E0364
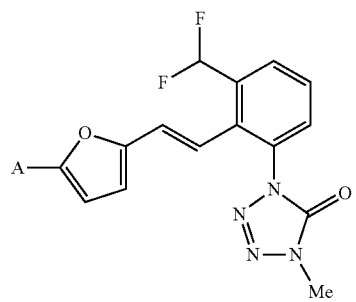
E0365
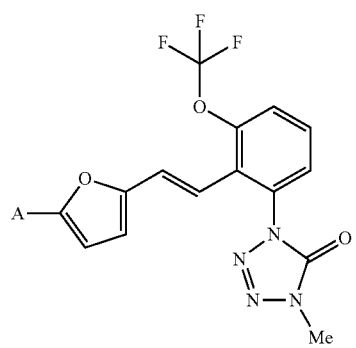
E0366
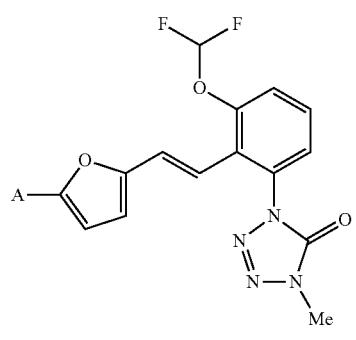
E0367
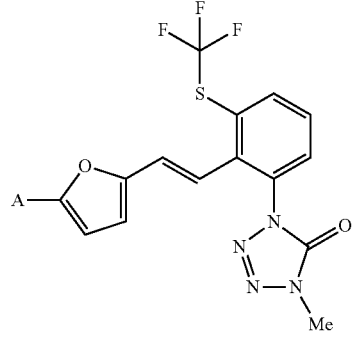
E0368
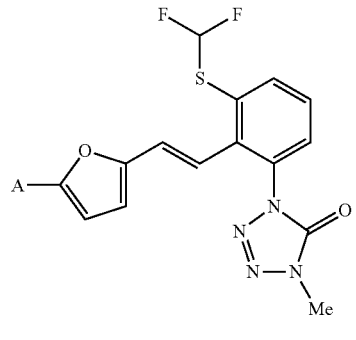
532
-continued
E0369
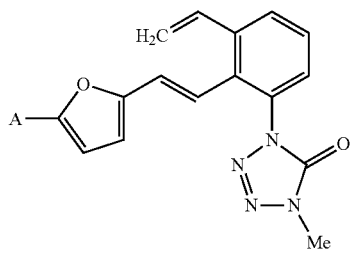
E0370
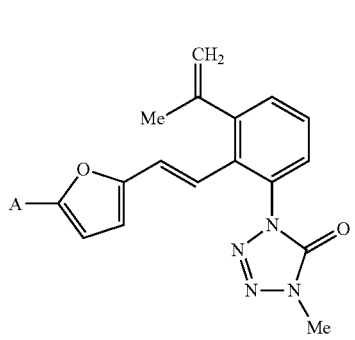
E0371
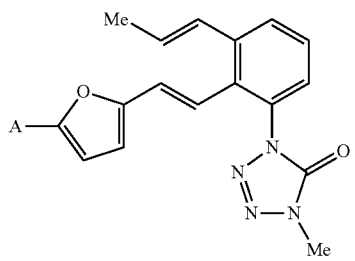
E0372
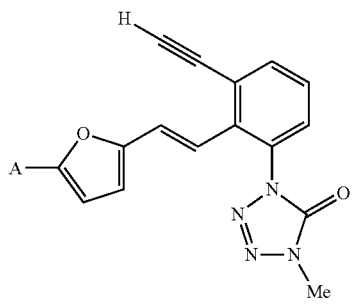
E0373
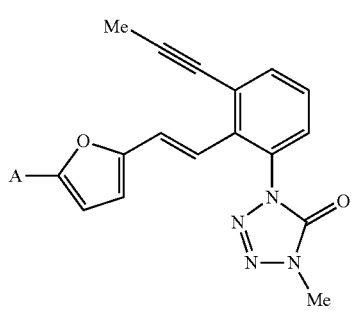

| | |
|---|---|
| E0374 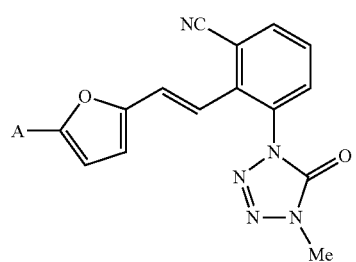 | E0380 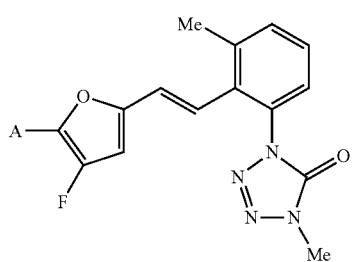 |
| E0375 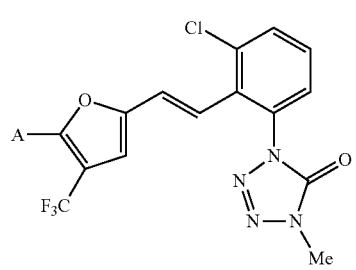 | E0381 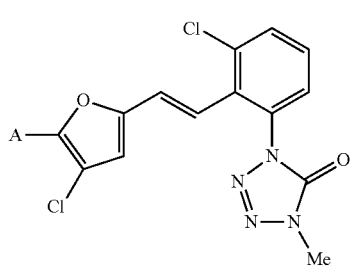 |
| E0376 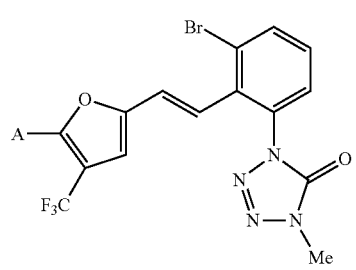 | E0382 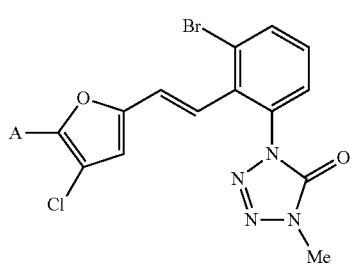 |
| E0377 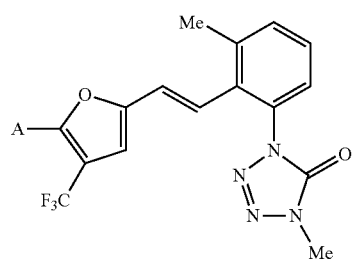 | E0383 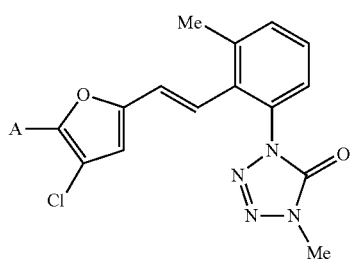 |
| E0378 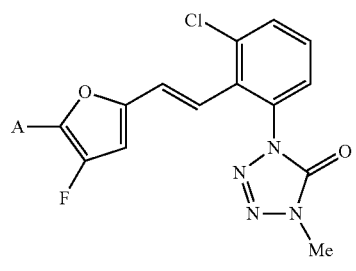 | E0384 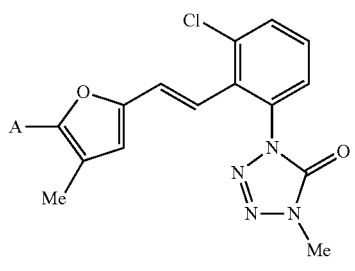 |
| E0379 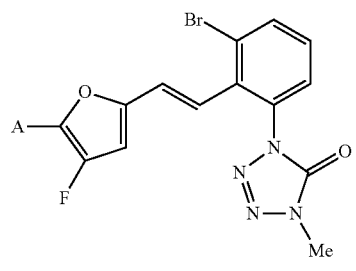 | E0385 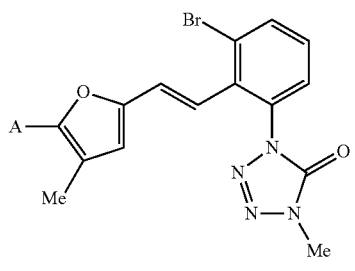 |

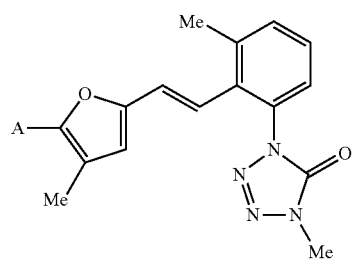 E0386
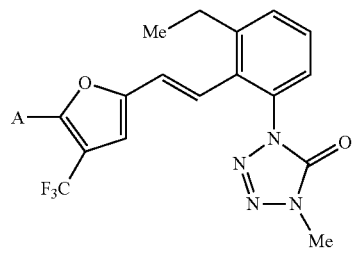 E0387
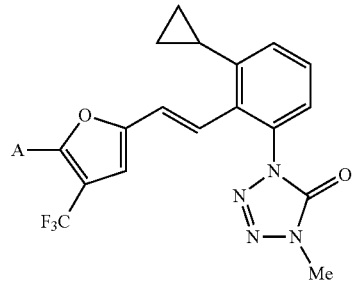 E0388
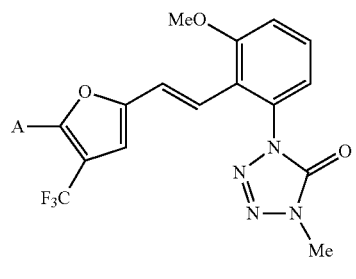 E0389
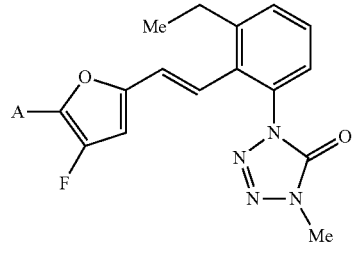 E0390
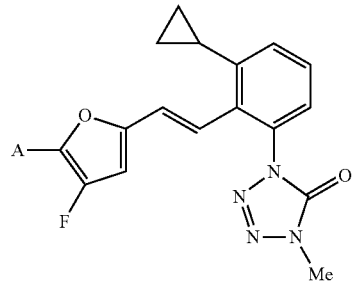 E0391
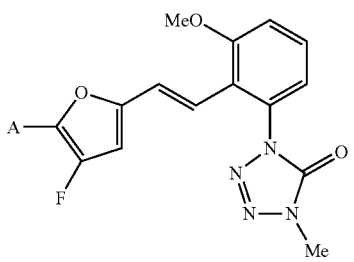 E0392
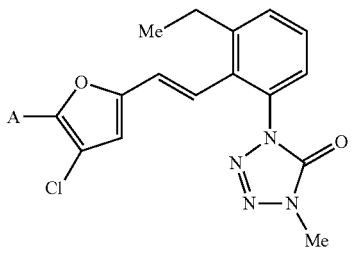 E0393
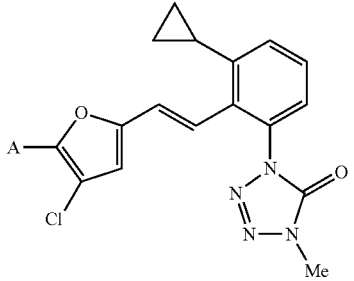 E0394
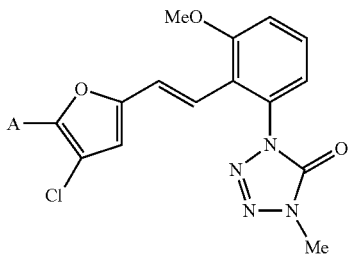 E0395
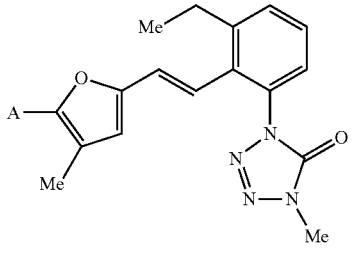 E0396
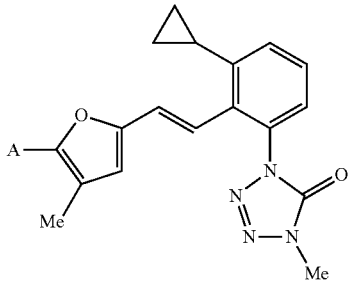 E0397

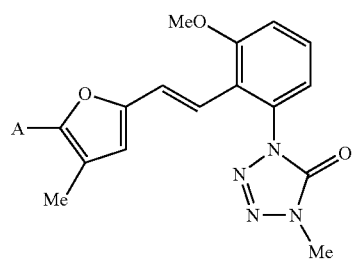
E0398
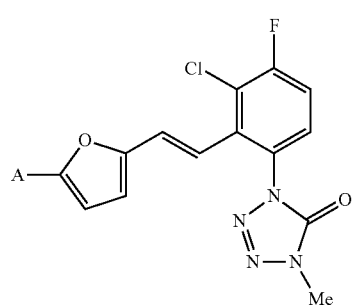
E0399
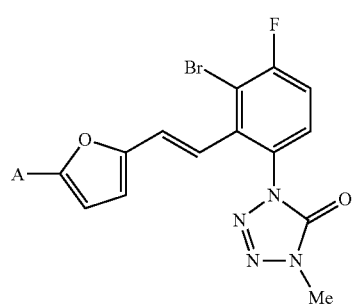
E0400
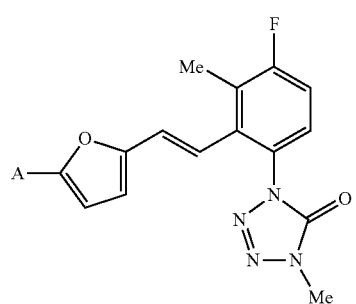
E0401
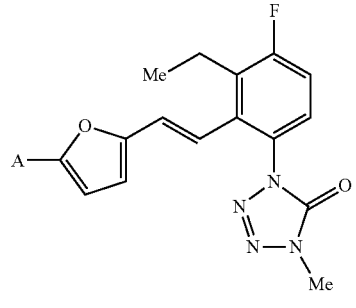
E0402
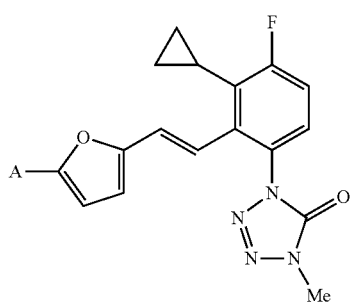
E0403
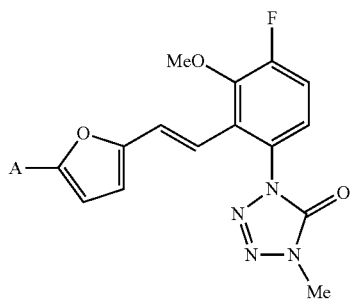
E0404
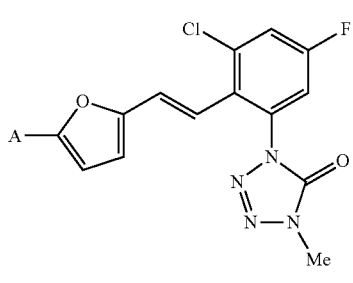
E0405
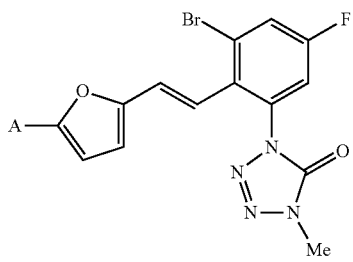
E0406
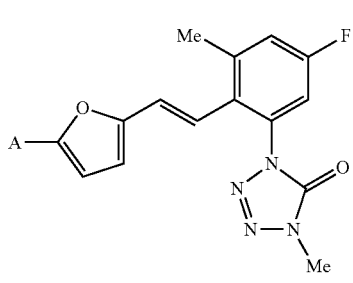
E0407
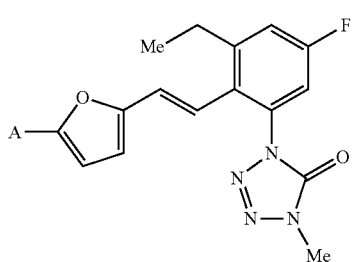
E0408

E0409 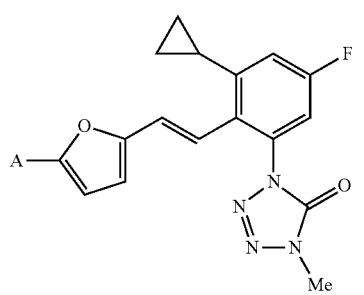
E0410 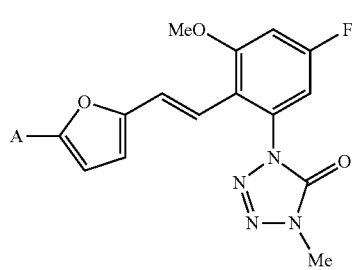
E0411 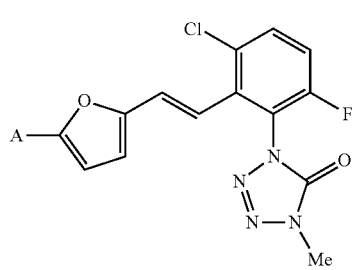
E0412 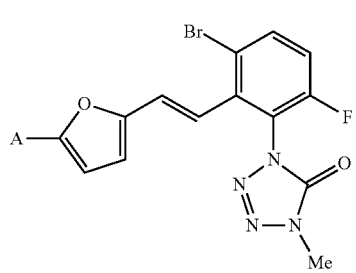
E0413 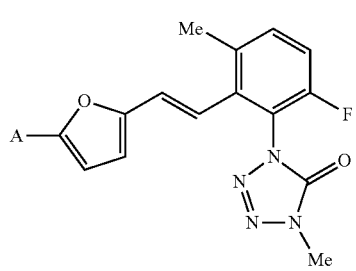
E0414 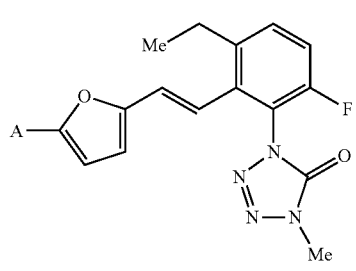
E0415 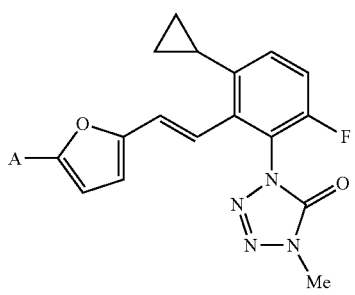
E0416 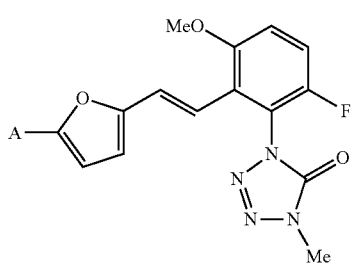
E0417 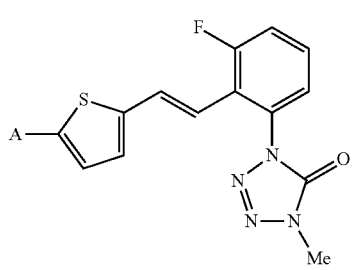
E0418 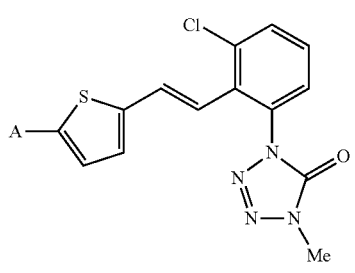
E0419 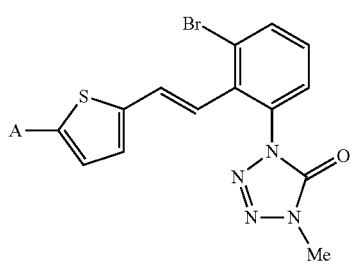
E0420 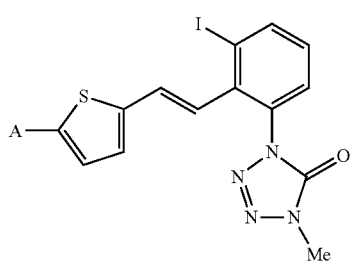

E0421 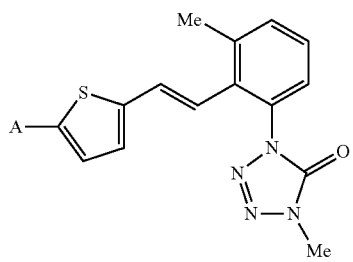
E0422 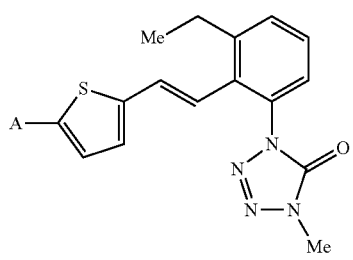
E0423 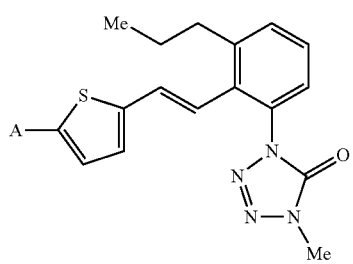
E0424 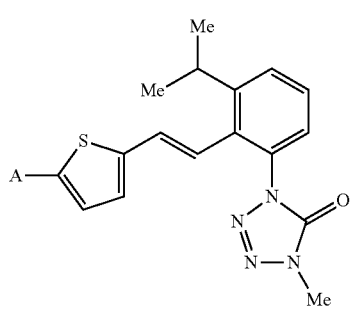
E0425 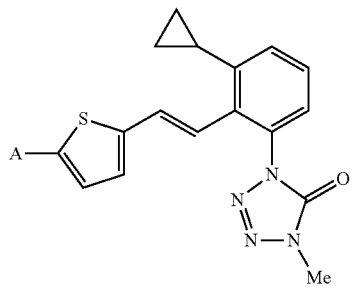
E0426 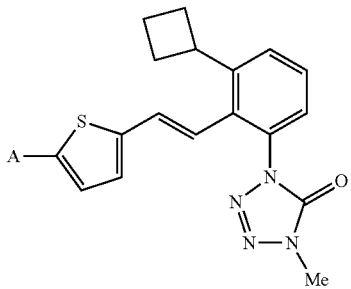
E0427 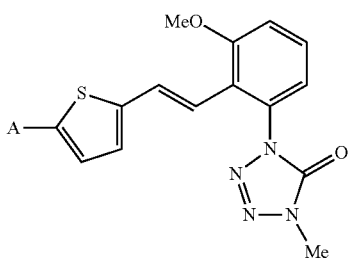
E0428 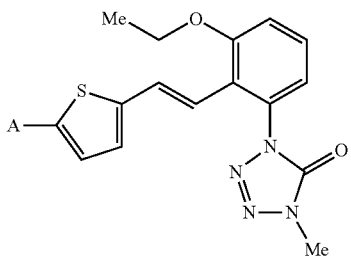
E0429 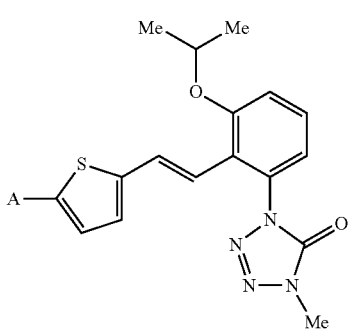
E0430 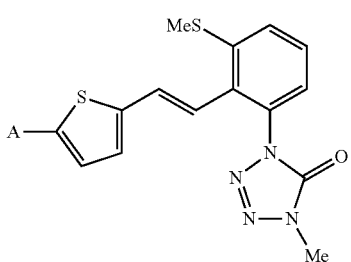

| | |
|---|---|
| 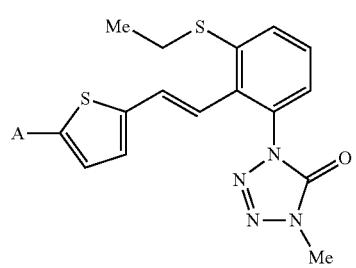 E0431 | 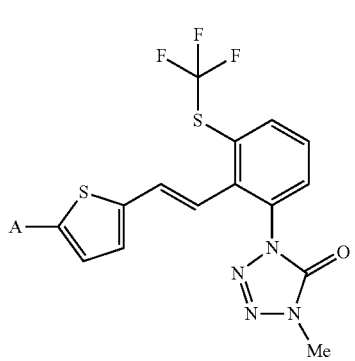 E0436 |
| 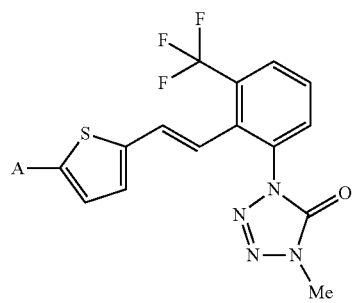 E0432 | 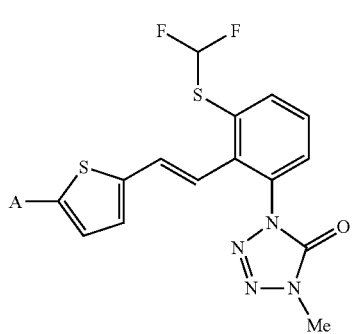 E0437 |
| 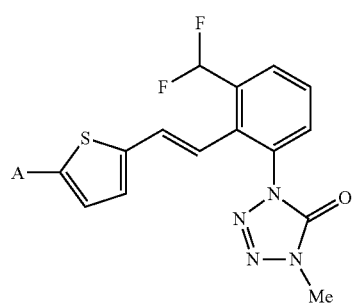 E0433 | 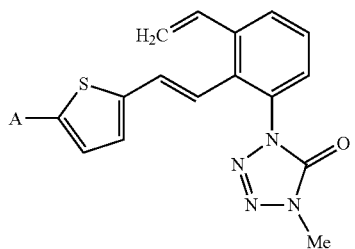 E0438 |
| 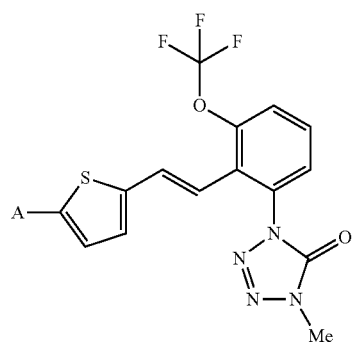 E0434 | 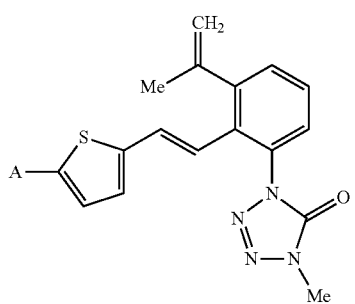 E0439 |
| 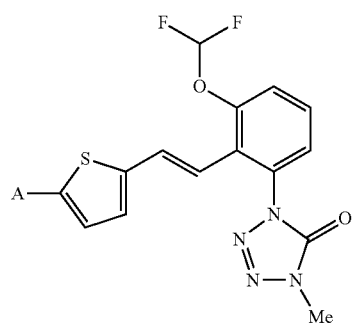 E0435 | 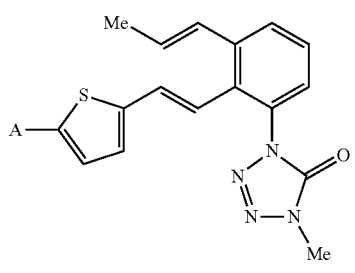 E0440 |

E0441 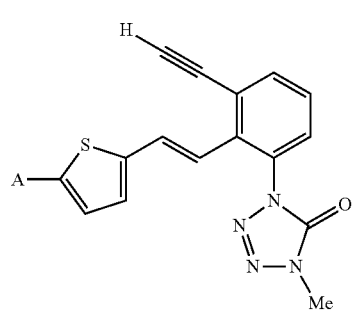
E0442 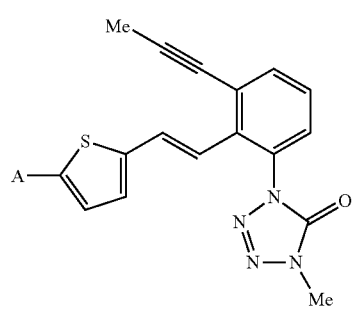
E0443 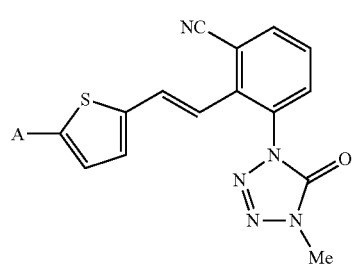
E0444 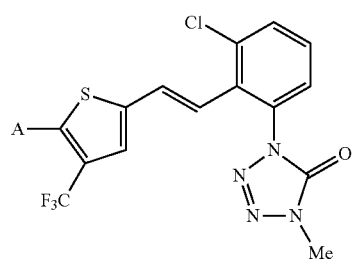
E0445 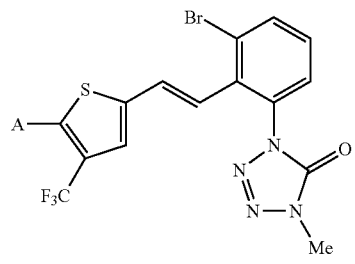
E0446 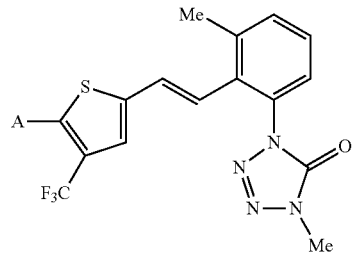
E0447 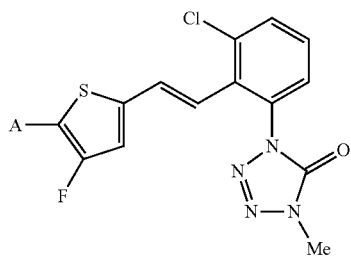
E0448 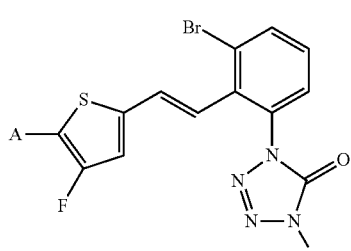
E0449 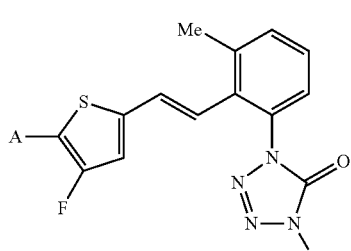
E0450 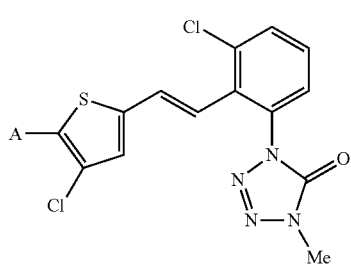
E0451 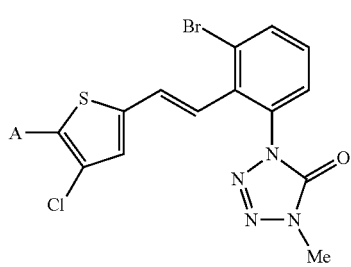
E0452 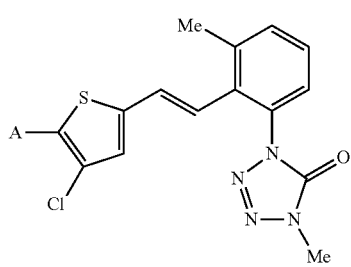

-continued
E0453
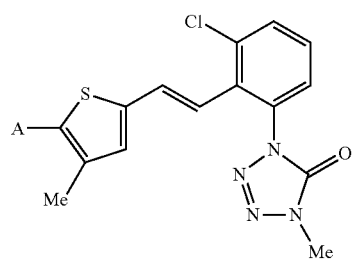
E0454
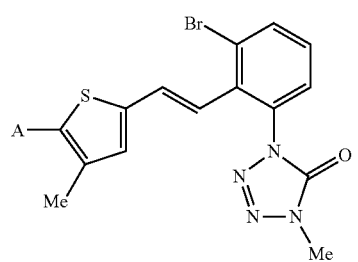
E0455
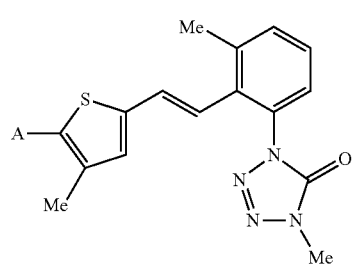
E0456
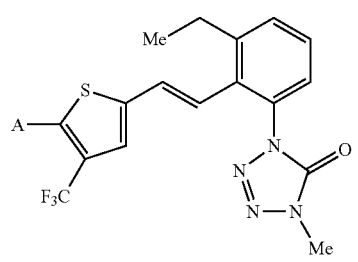
E0457
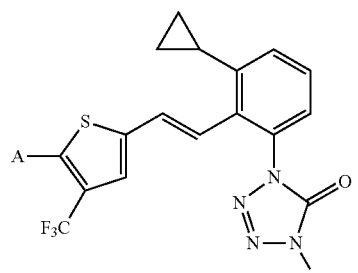
E0458
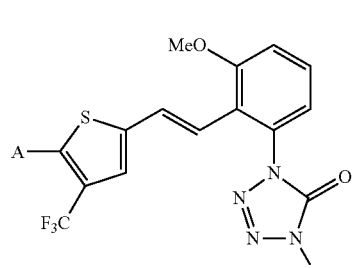
-continued
E0459
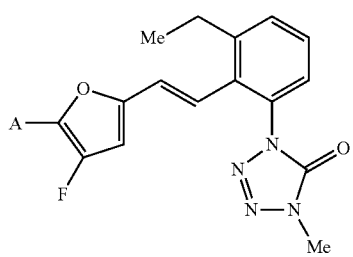
E0460
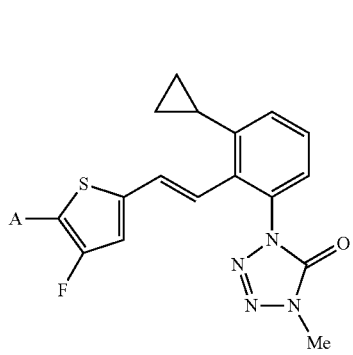
E0461
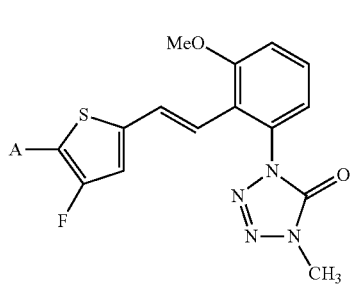
E0462
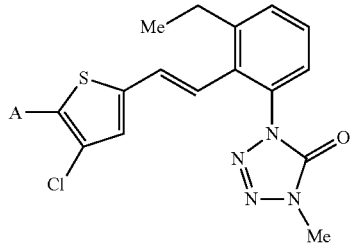
E0463
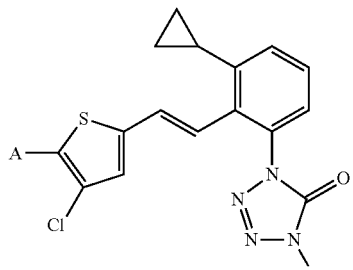

549
-continued
E0464
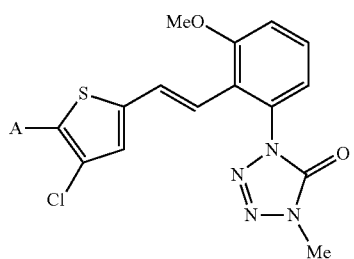
E0465
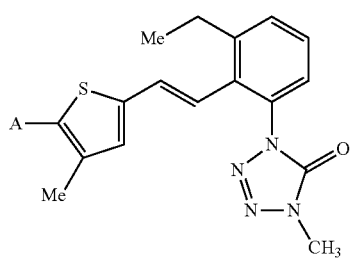
E0466
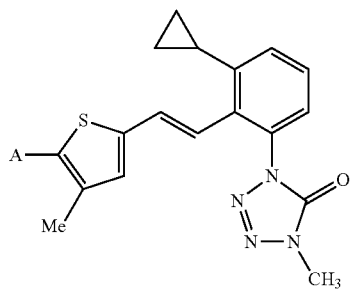
E0467
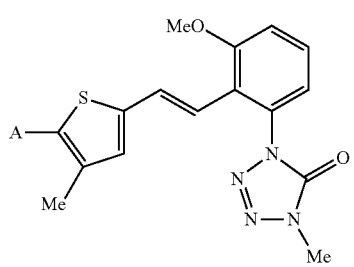
E0468
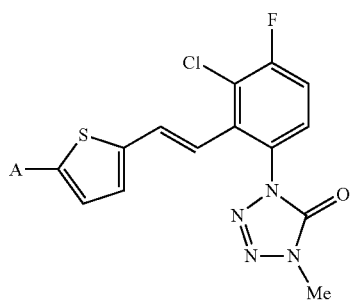
550
-continued
E0469
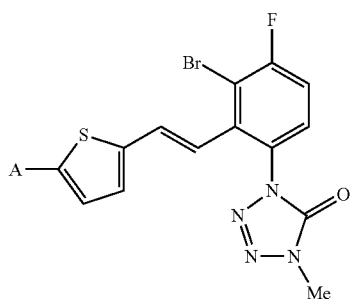
E0470
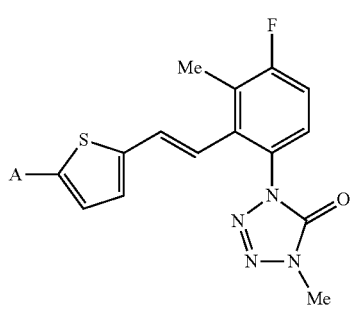
E0471
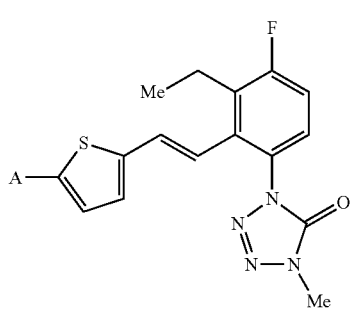
E0472
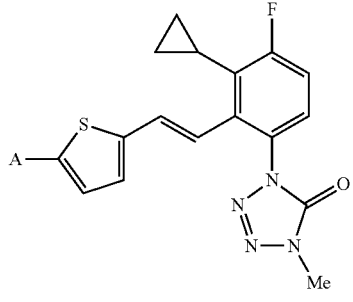
E0473
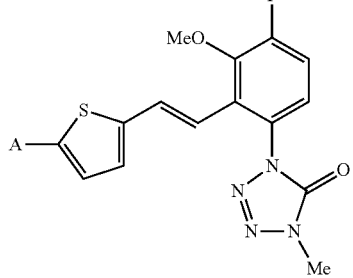

-continued
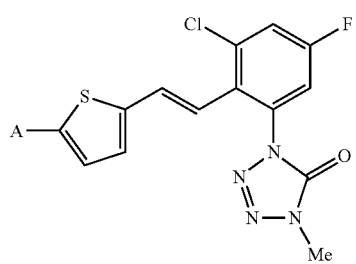 E0474
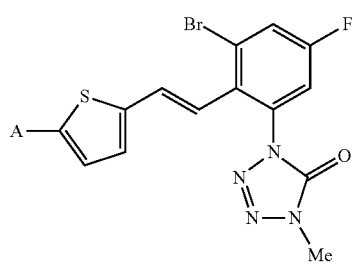 E0475
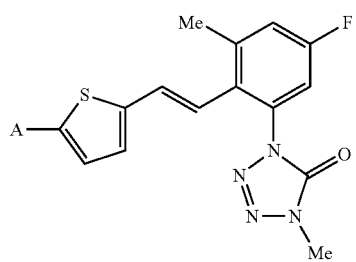 E0476
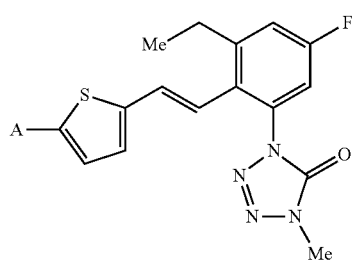 E0477
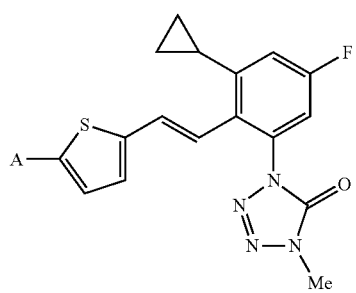 E0478
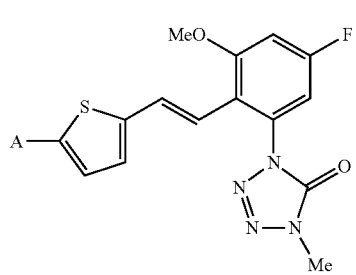 E0479
-continued
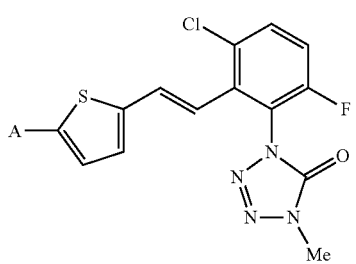 E0480
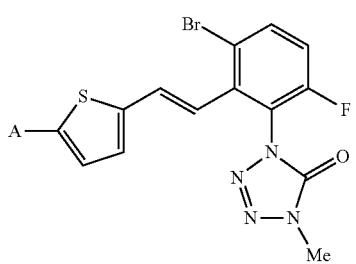 E0481
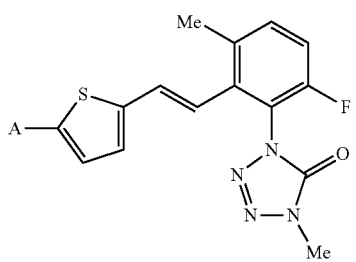 E0482
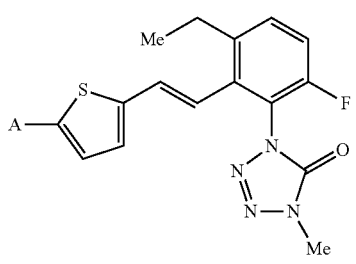 E0483
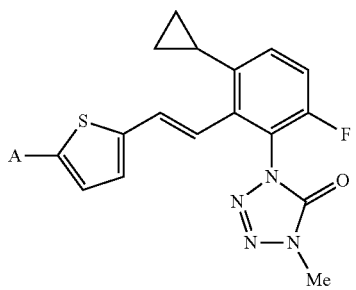 E0484
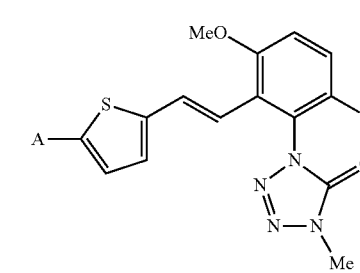 E0485

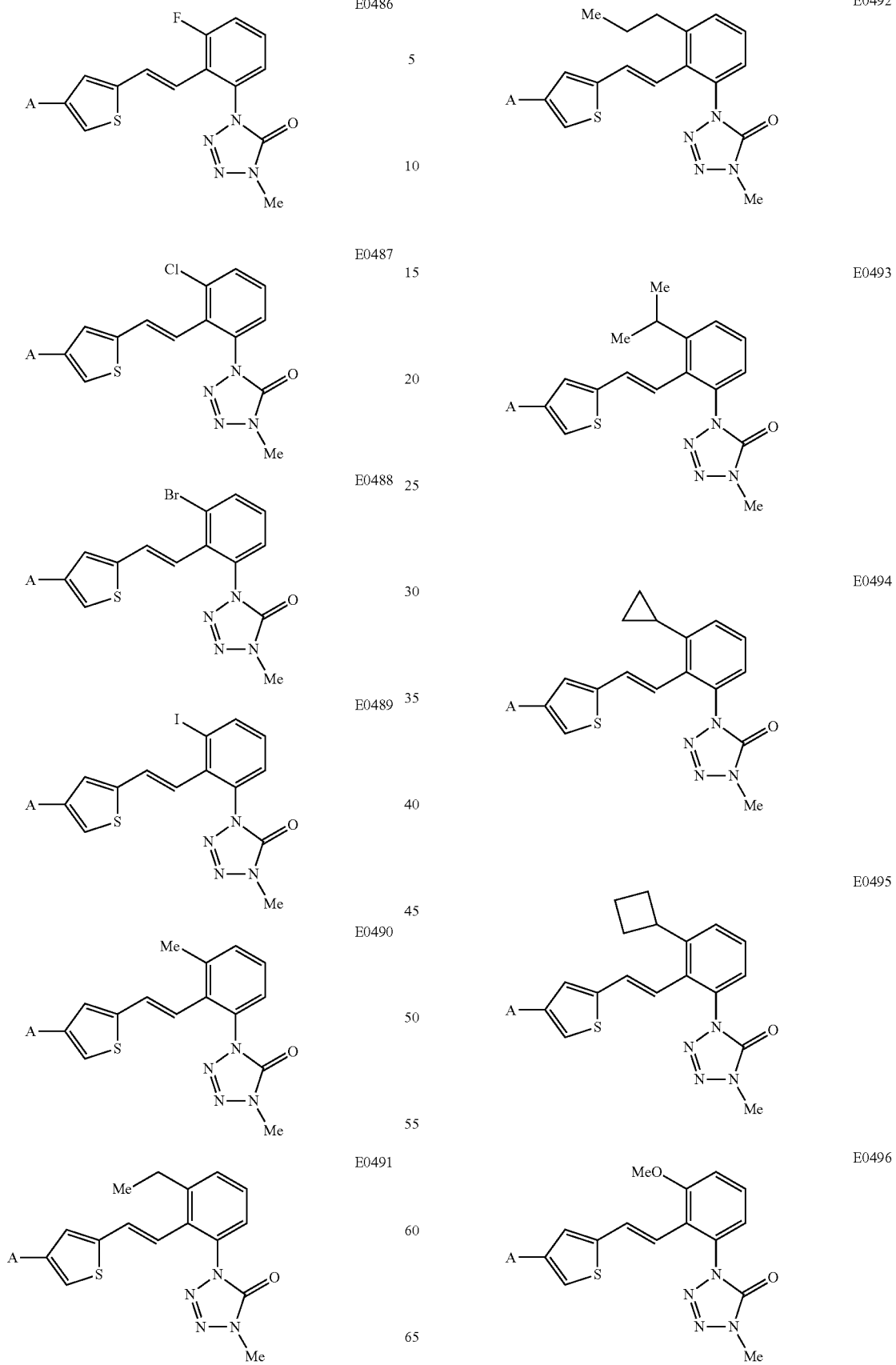

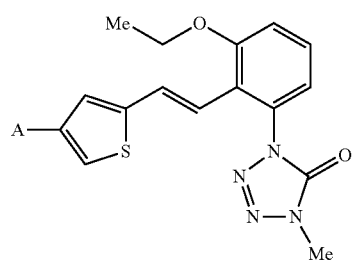
E0497
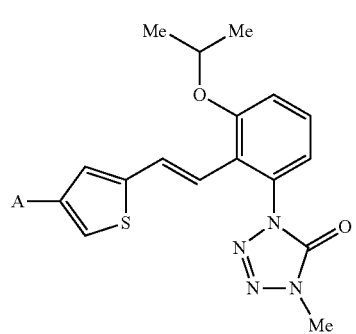
E0498
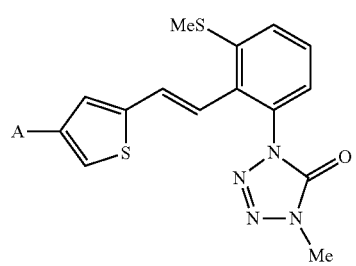
E0499
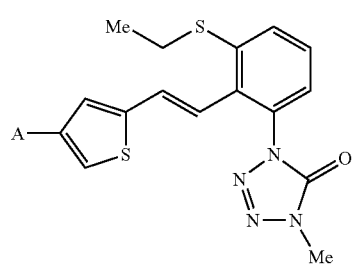
E0500
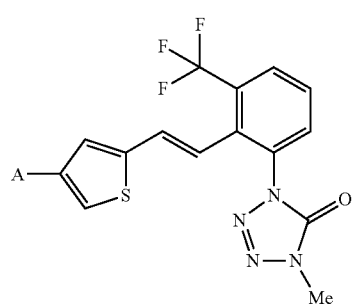
E0501
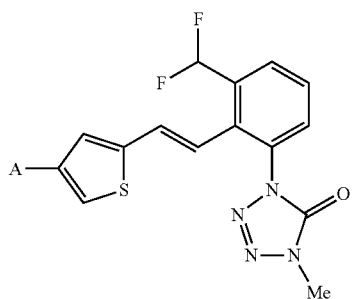
E0502
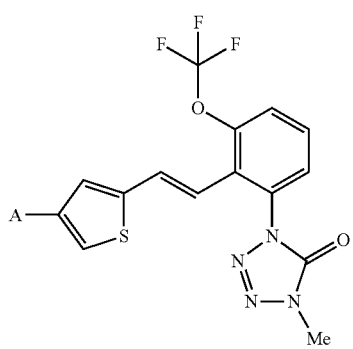
E0503
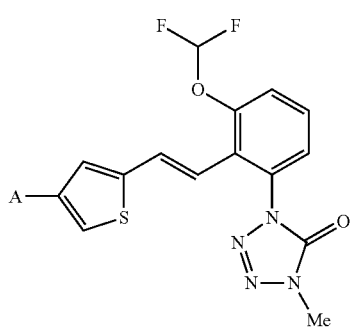
E0504
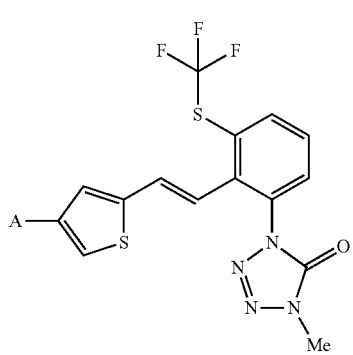
E0505
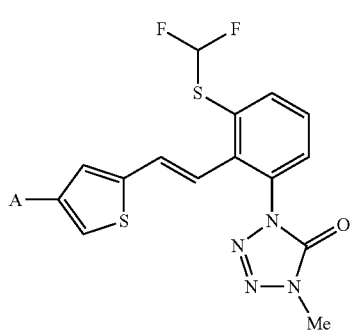
E0506

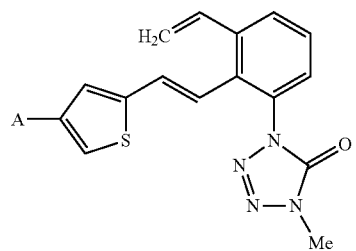
E0507
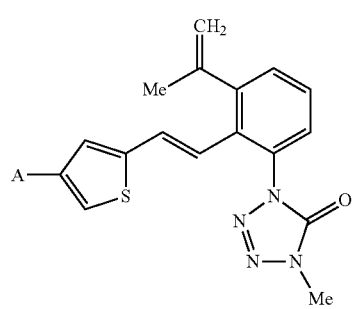
E0508
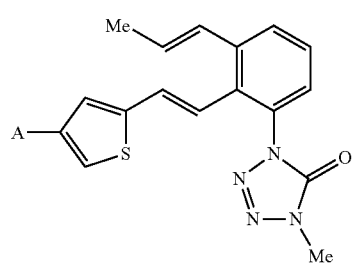
E0509
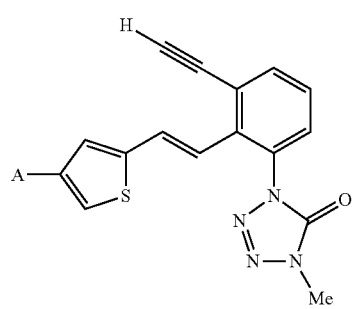
E0510
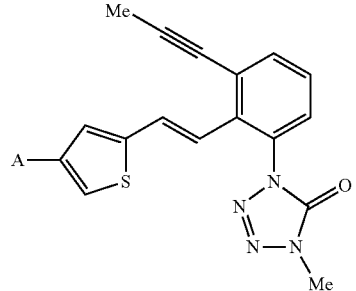
E0511
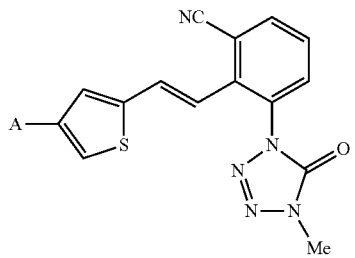
E0512
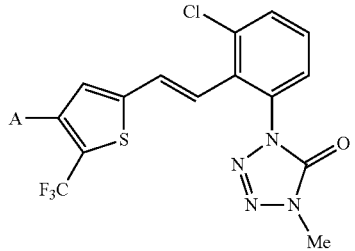
E0513
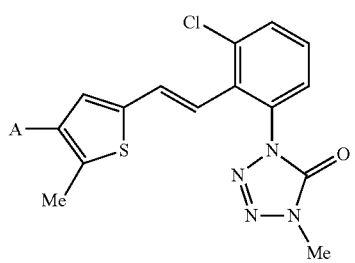
E0514
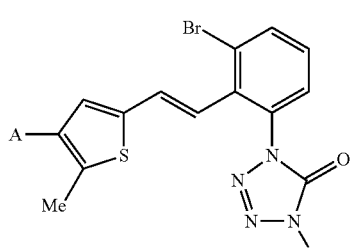
E0515
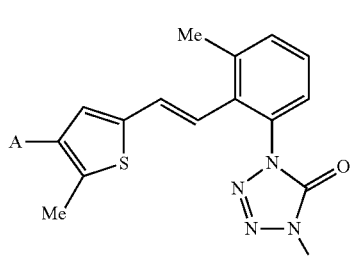
E0516
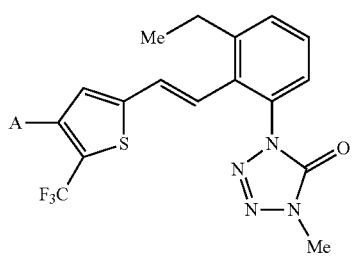
E0517

E0518 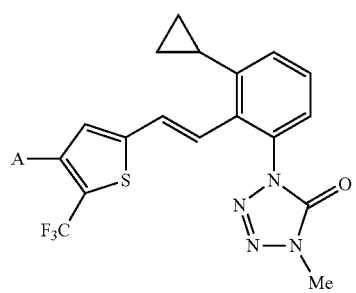
E0519 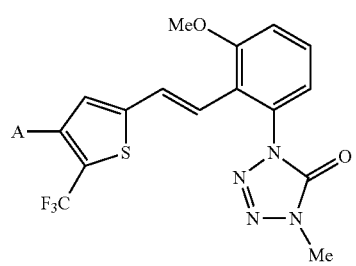
E0520 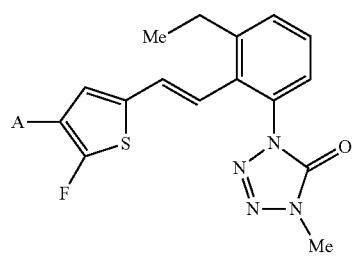
E0521 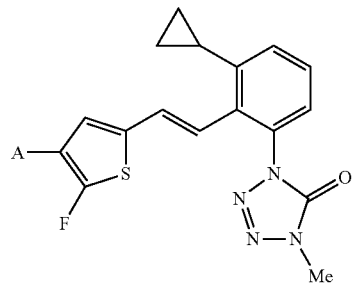
E0522 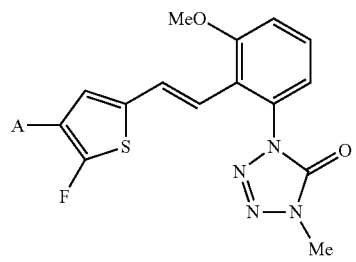
E0523 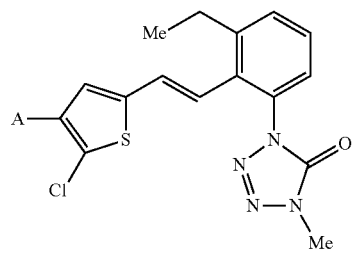
E0524 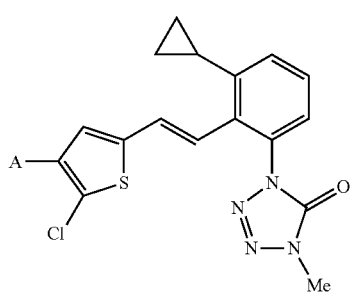
E0525 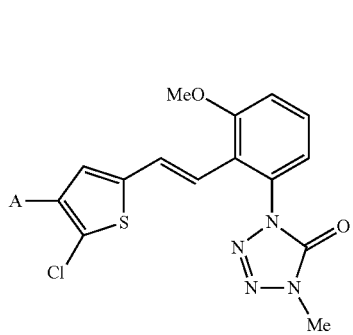
E0526 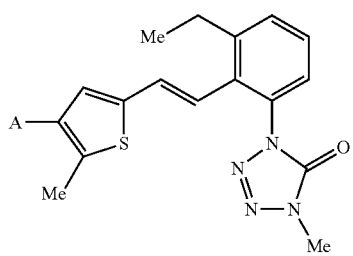
E0527 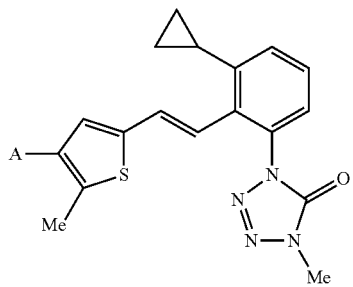
E0528 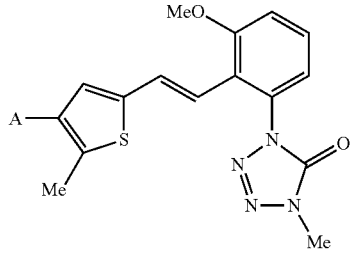

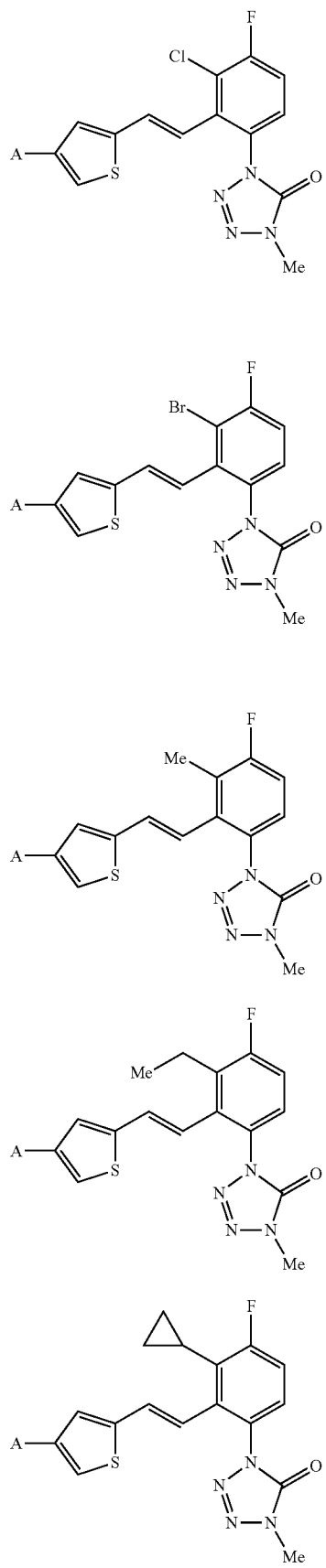
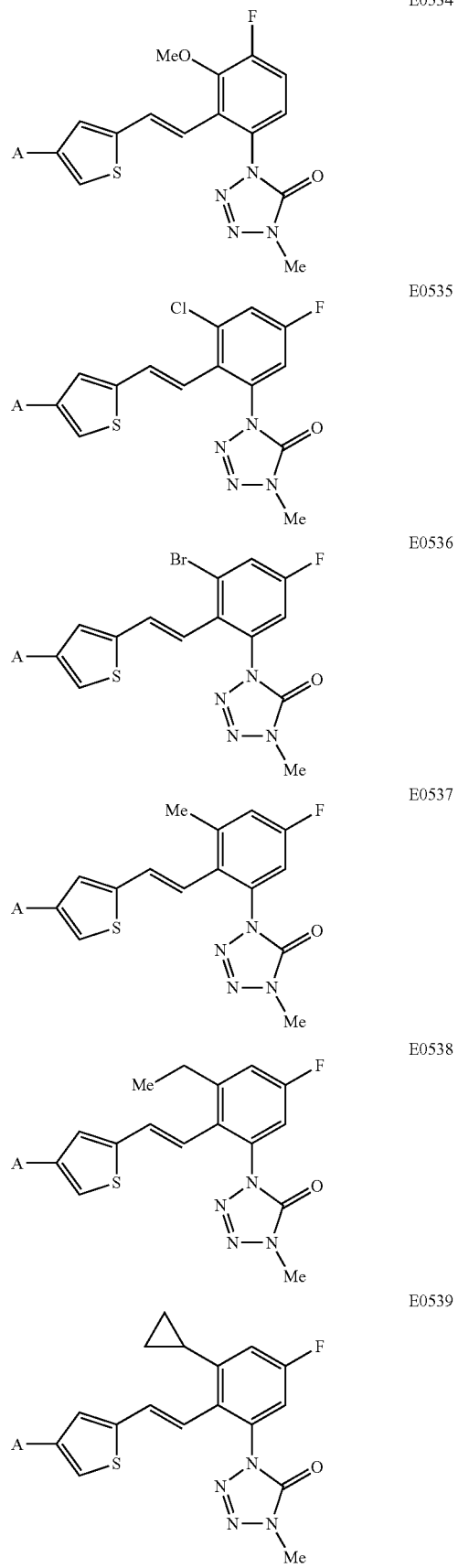

| | |
|---|---|
| 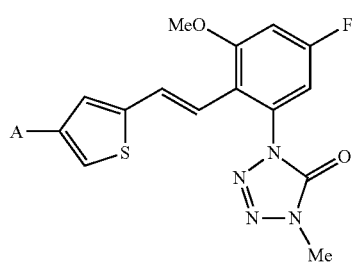 E0540 | 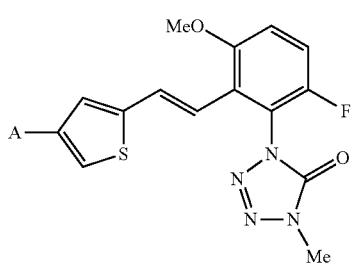 E0546 |
| 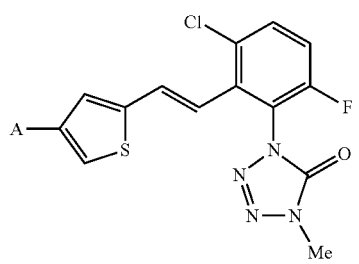 E0541 | 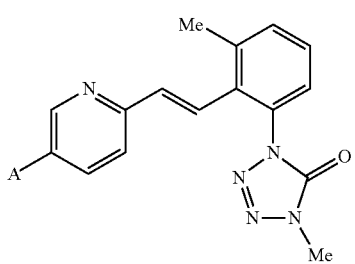 E0547 |
| 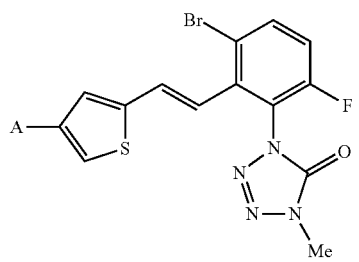 E0542 | 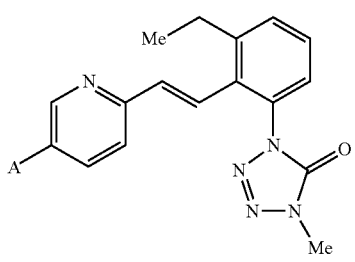 E0548 |
| 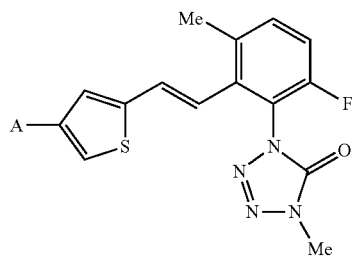 E0543 | 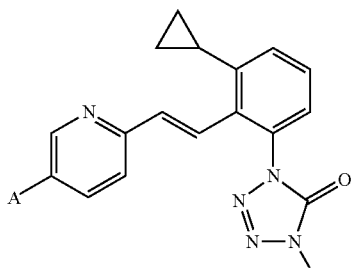 E0549 |
| 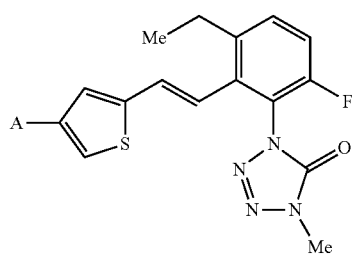 E0544 | 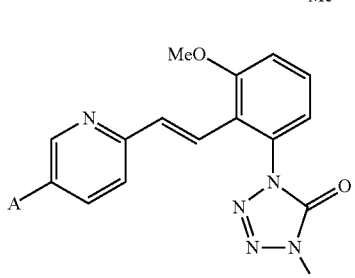 E0550 |
| 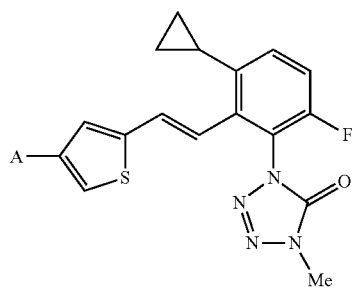 E0545 | 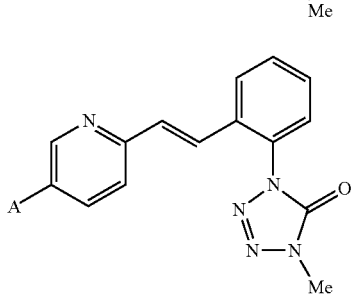 E0551 |

| | |
|---|---|
| E0552 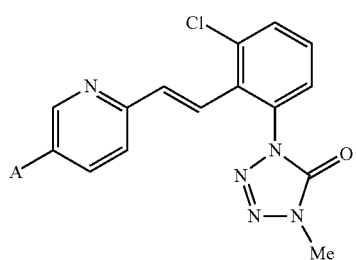 | E0558 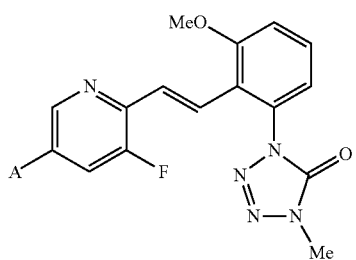 |
| E0553 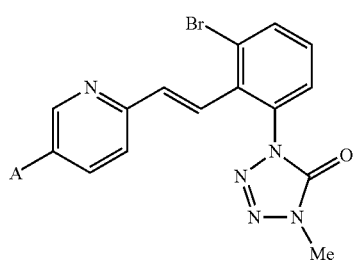 | E0559 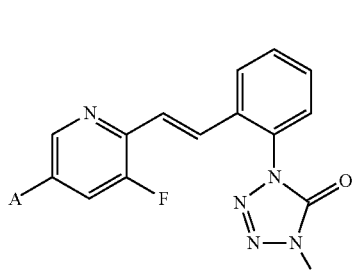 |
| E0554 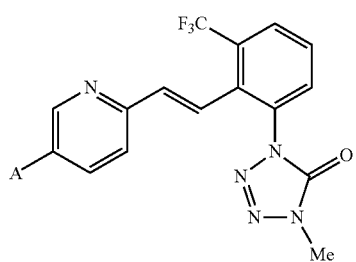 | E0560 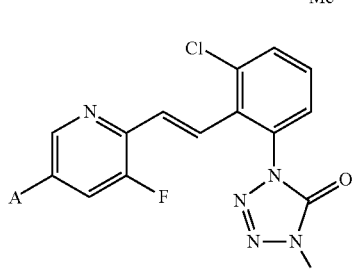 |
| E0555 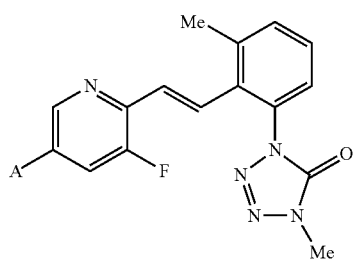 | E0561 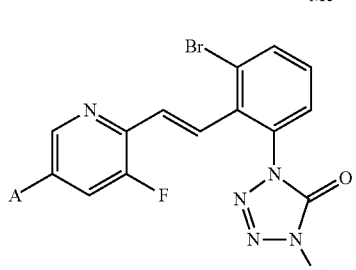 |
| E0556 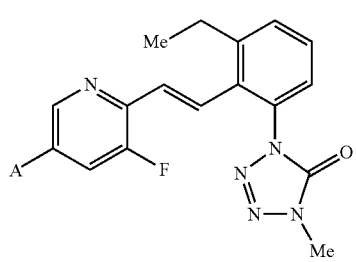 | E0562 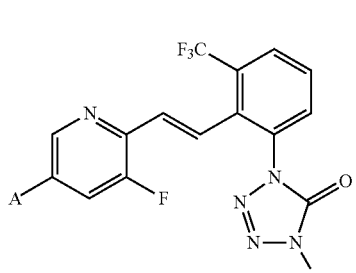 |
| E0557 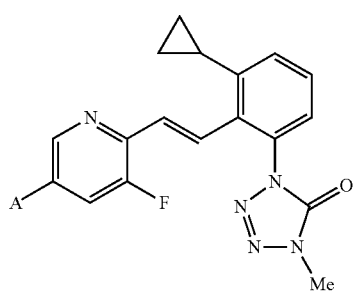 | E0563 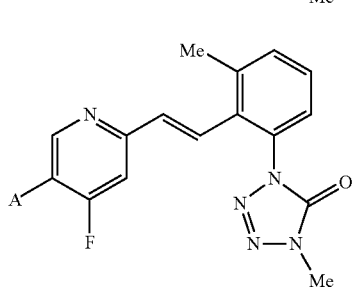 |

| | |
|---|---|
| E0564 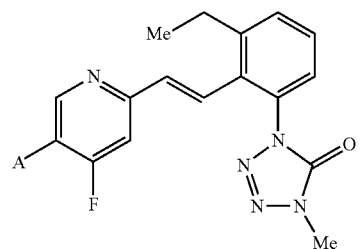 | E0570 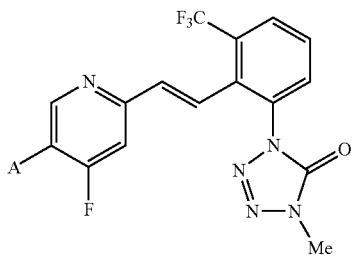 |
| E0565 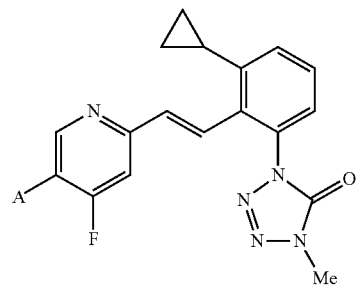 | E0571 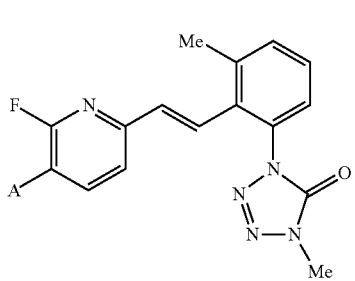 |
| E0566 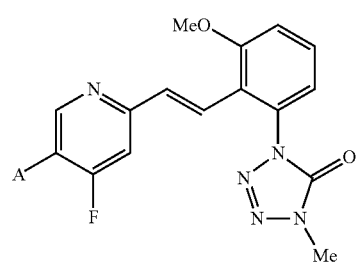 | E0572 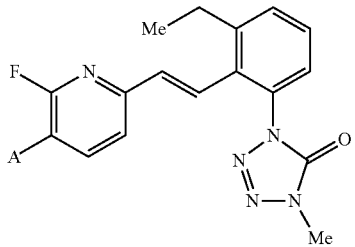 |
| E0567 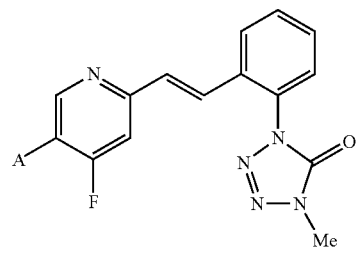 | E0573 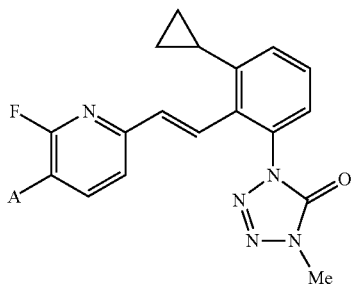 |
| E0568 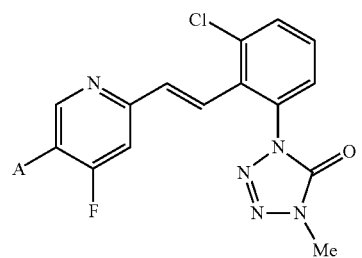 | E0574 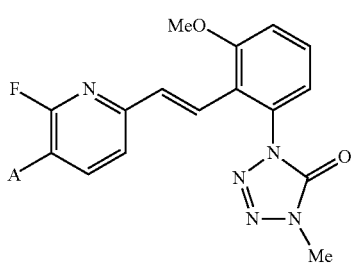 |
| E0569 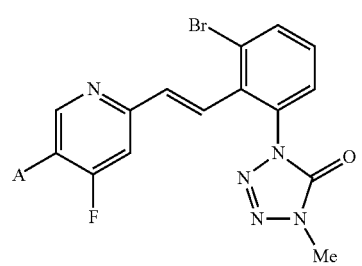 | E0575 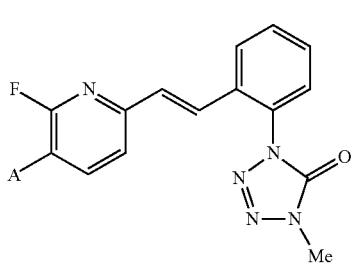 |

-continued
E0576
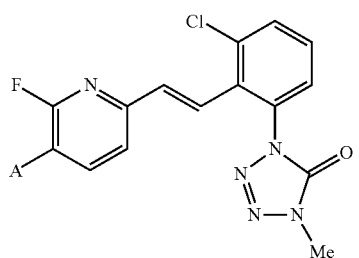
E0577
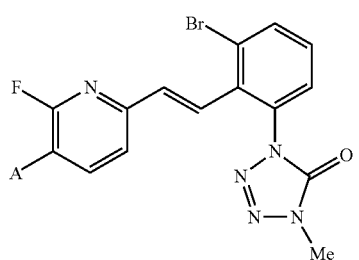
E0578
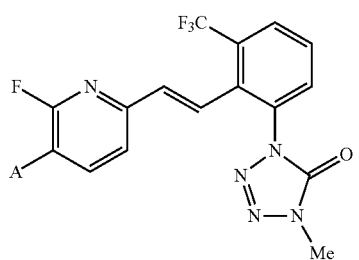
E0579
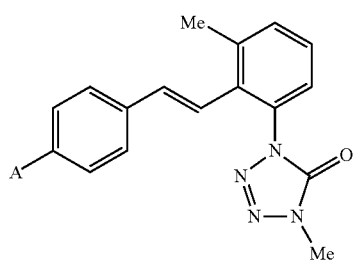
E0580
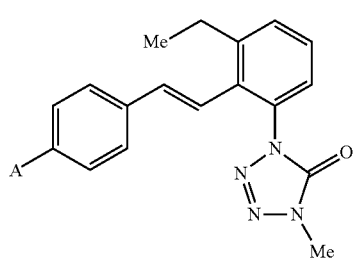
E0581
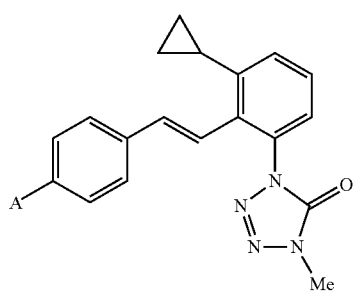
-continued
E0582
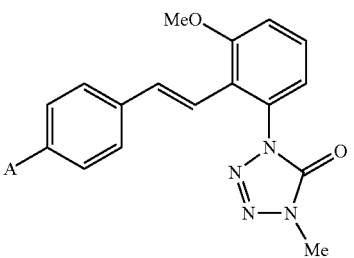
E0583
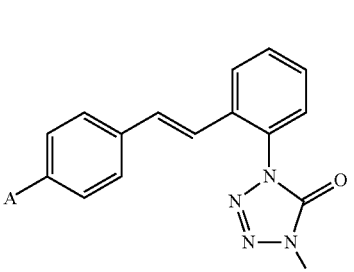
E0584
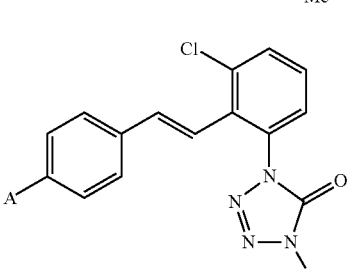
E0585
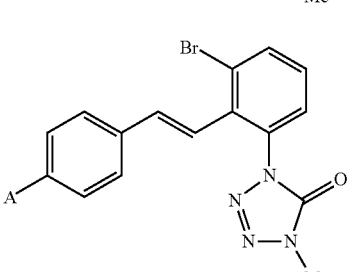
E0586
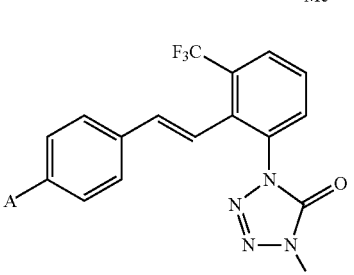
E0587
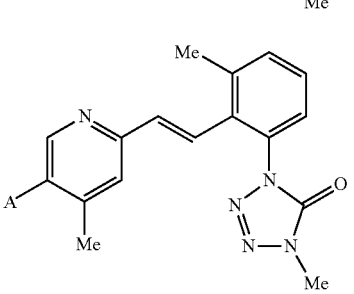

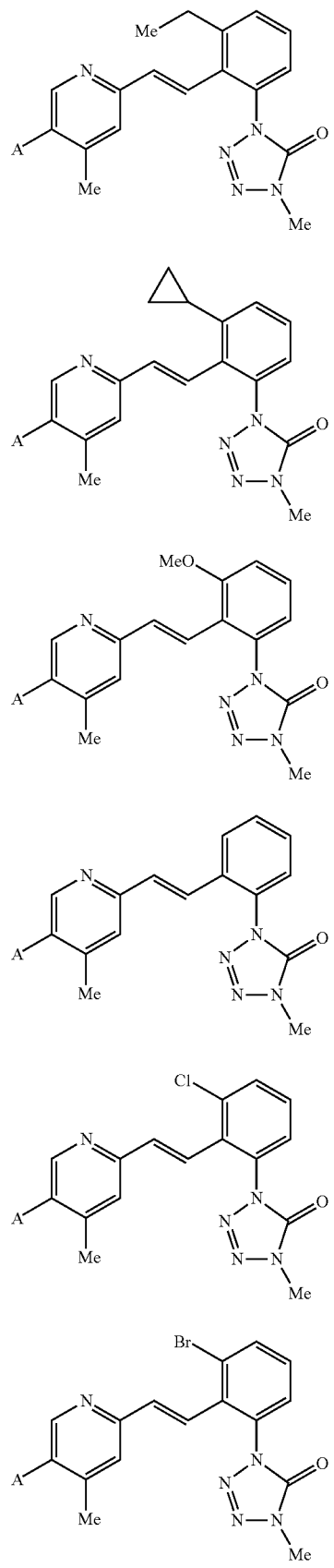
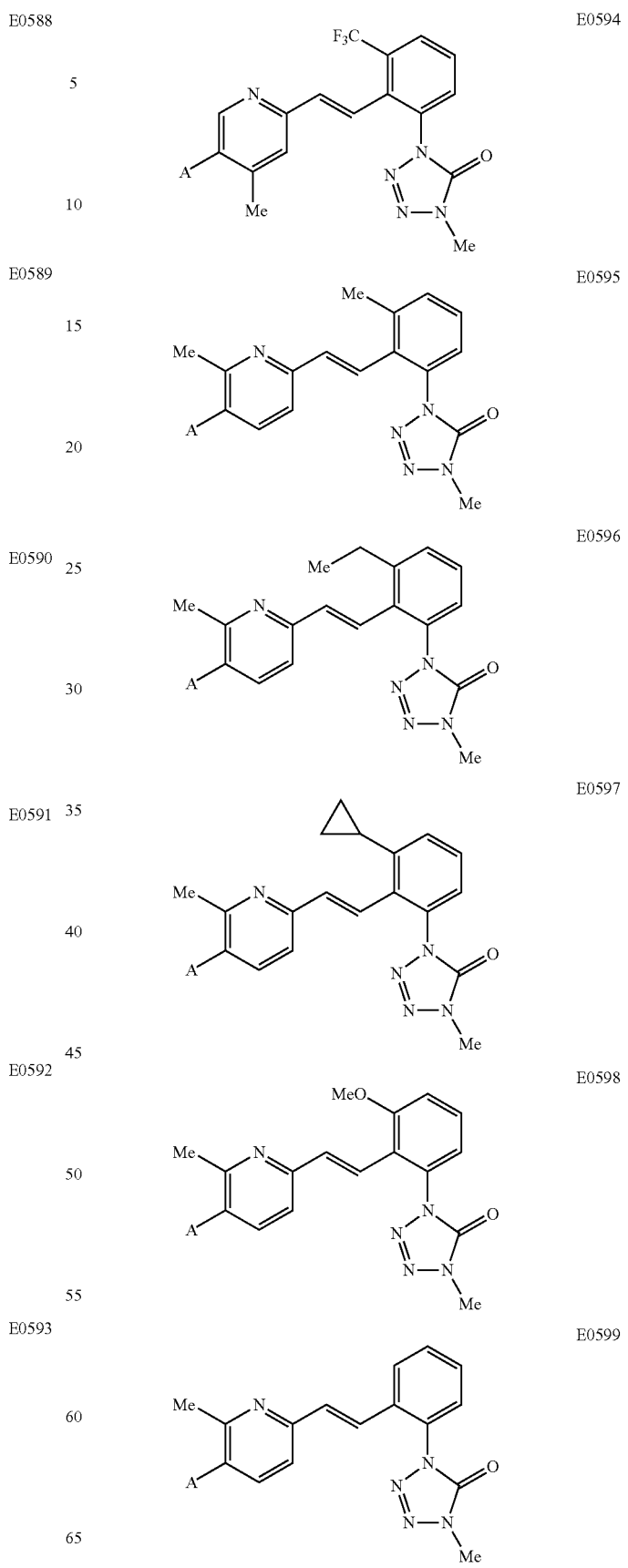

573
-continued
E0600
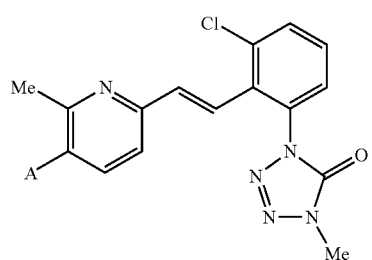
E0601
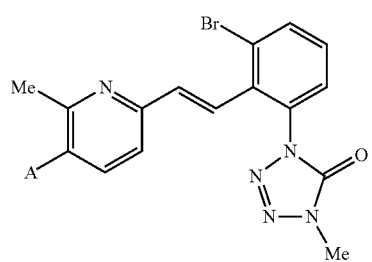
E0602
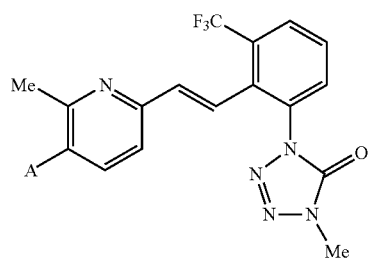
E0603
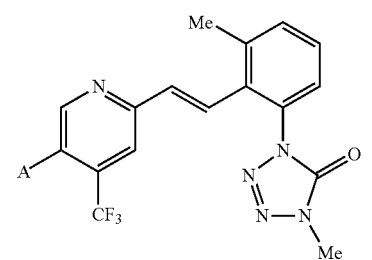
E0604
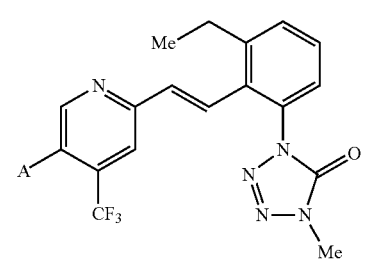
E0605
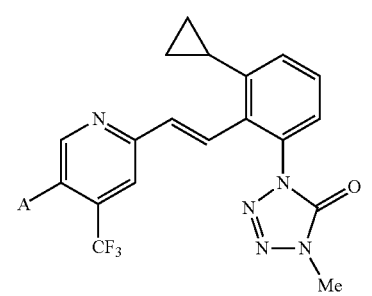
574
-continued
E0606
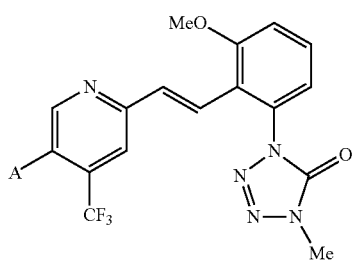
E0607
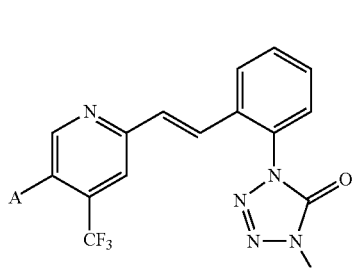
E0608
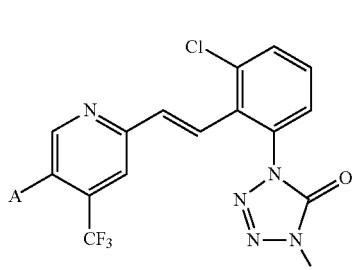
E0609
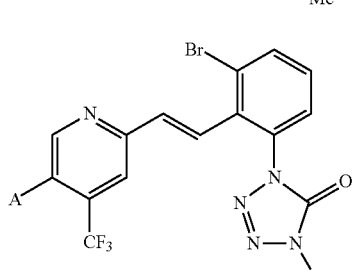
E0610
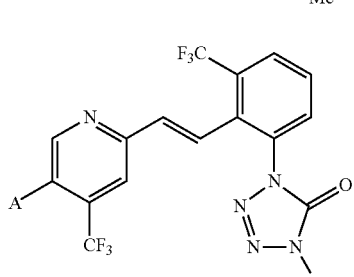
E0611
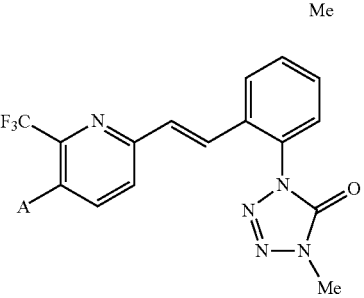

E0612 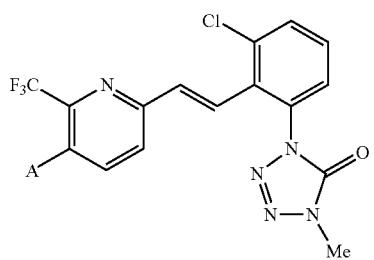
E0613 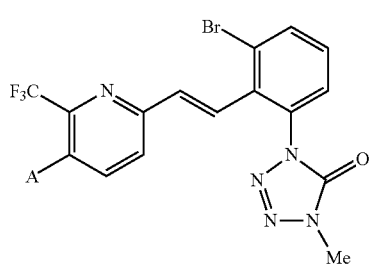
E0614 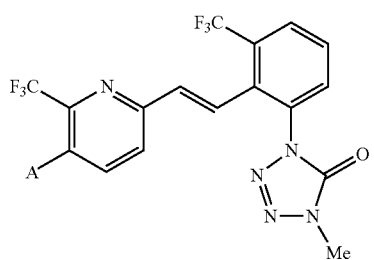
E0615 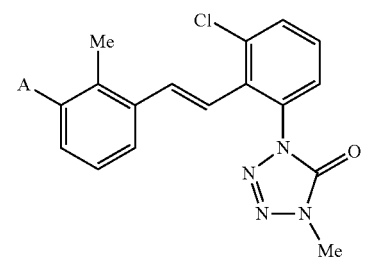
E0616 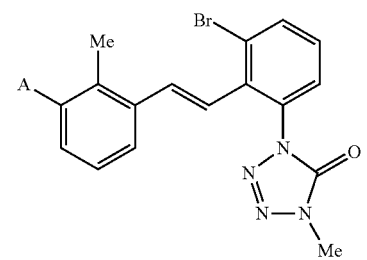
E0617 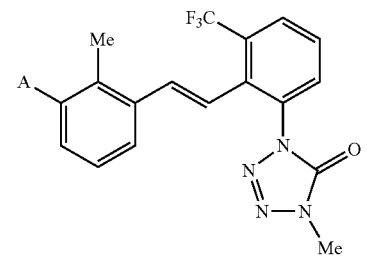
E0618 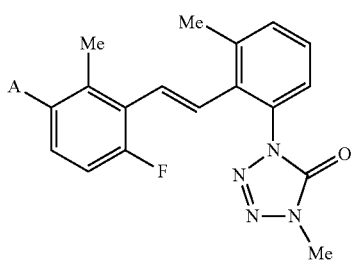
E0619 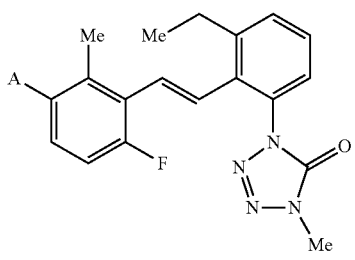
E0620 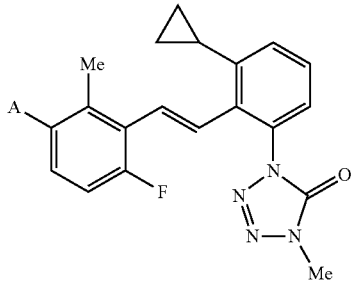
E0621 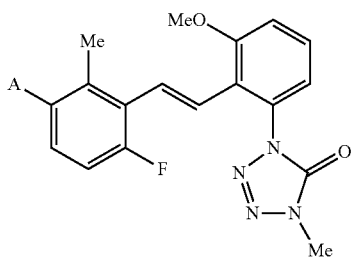
E0622 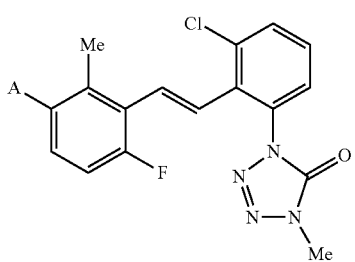
E0623 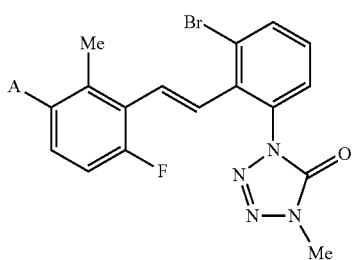

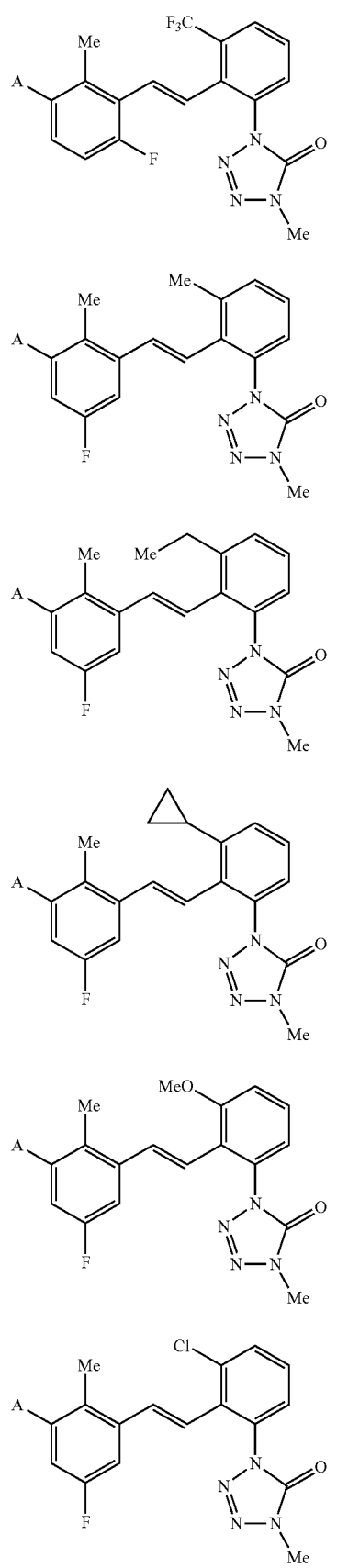
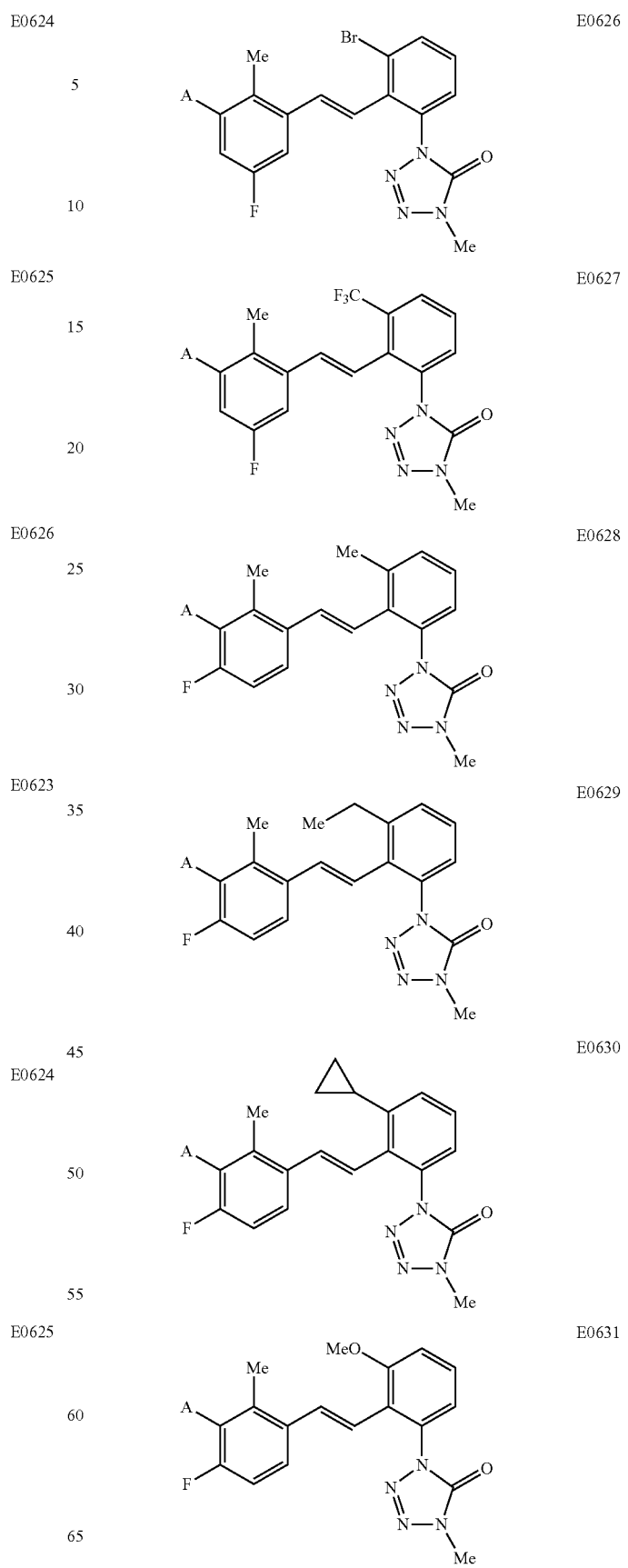

| | |
|---|---|
| E0632 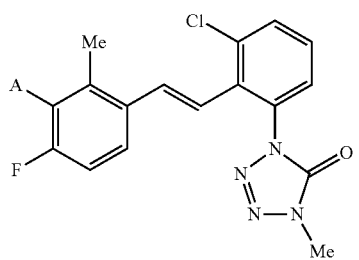 | E0638 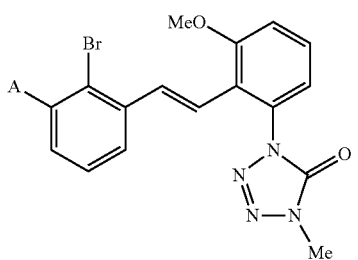 |
| E0633 | E0639 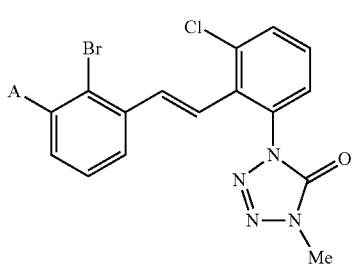 |
| E0634 | E0640 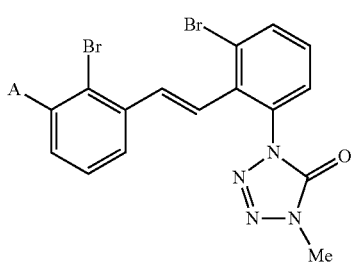 |
| E0635 | E0641 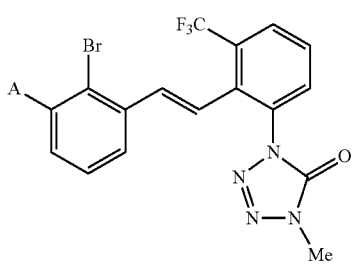 |
| E0636 | E0642 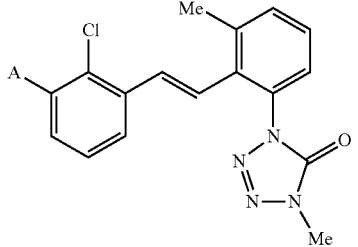 |
| E0637 | E0643 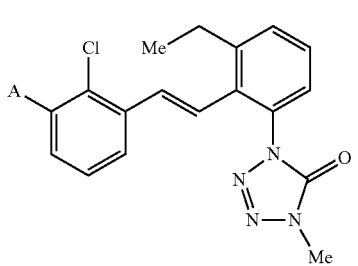 |

E0644 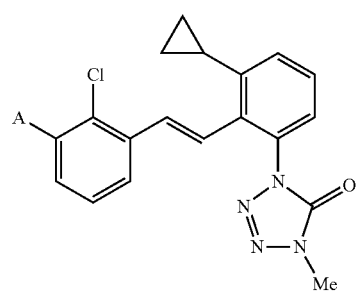
E0645 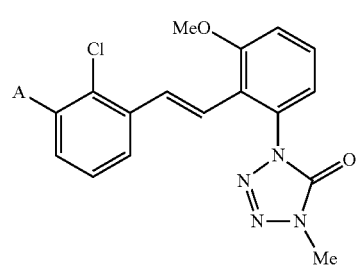
E0646 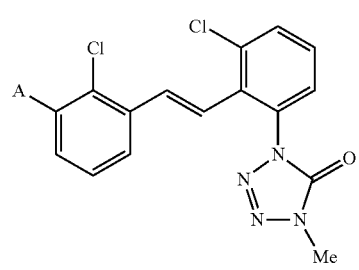
E0647 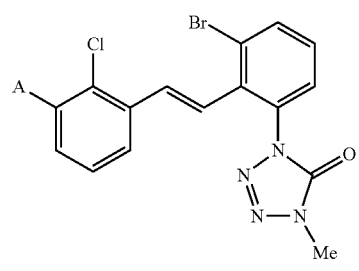
E0648 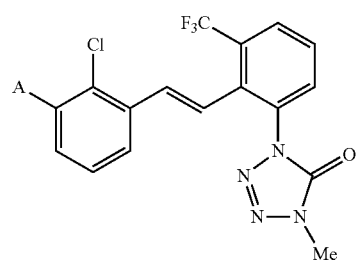
E0649 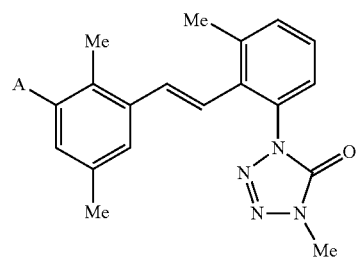
E0650 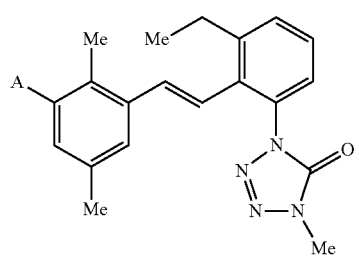
E0651 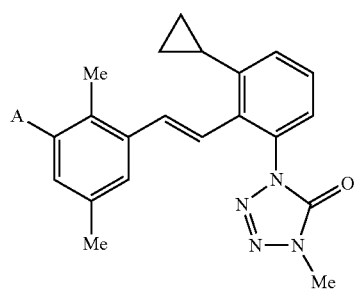
E0652 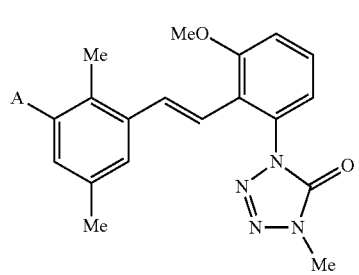
E0653 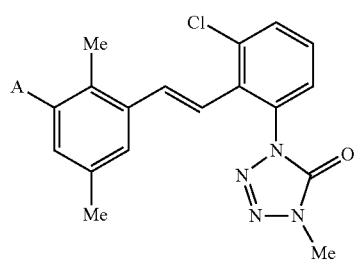
E0654 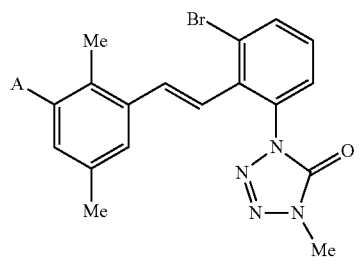
E0655 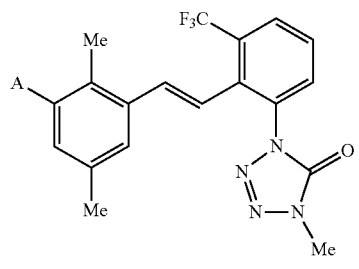

| | |
|---|---|
| E0656 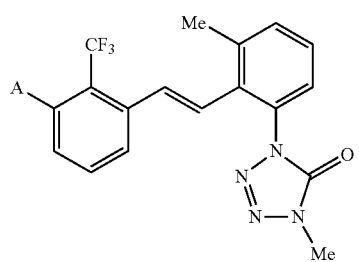 | E0662 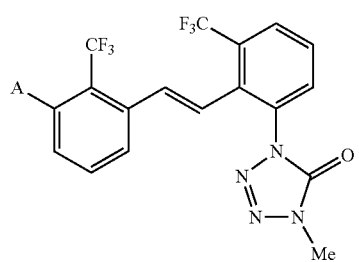 |
| E0657 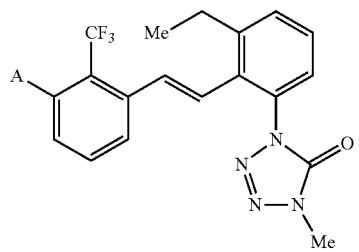 | E0663 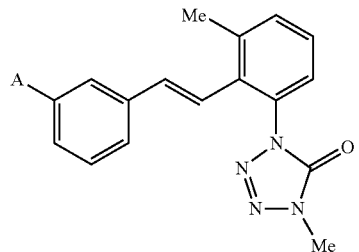 |
| E0658 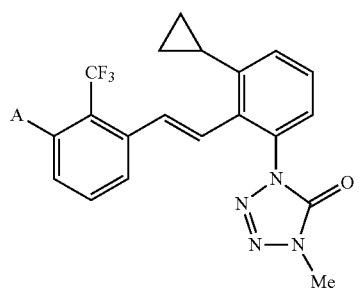 | E0664 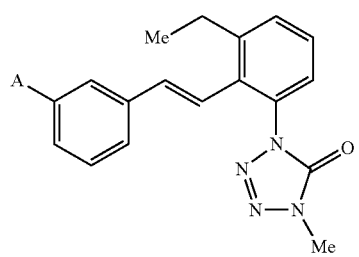 |
| E0659 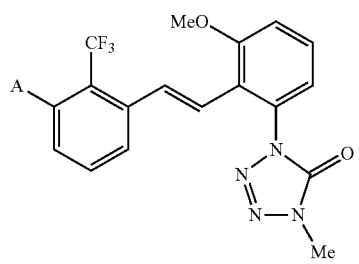 | E0665 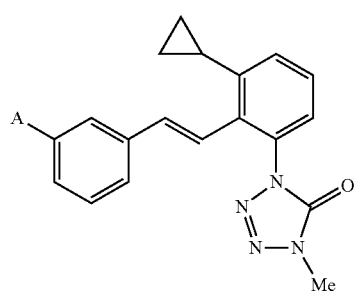 |
| E0660 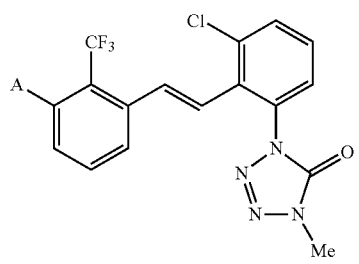 | E0666 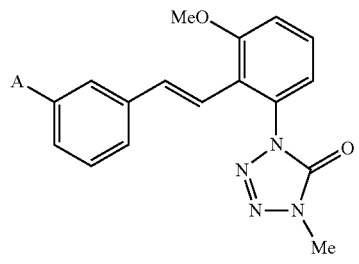 |
| E0661 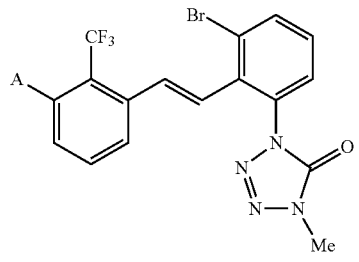 | E0667 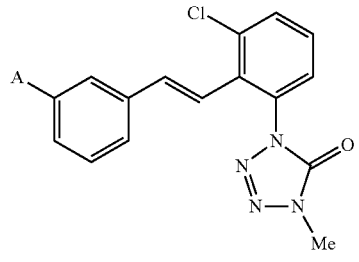 |

| | |
|---|---|
| E0668 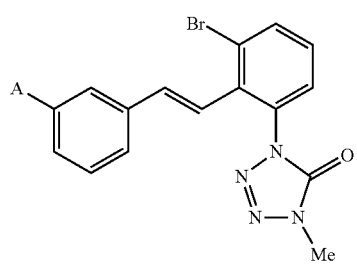 | E0675 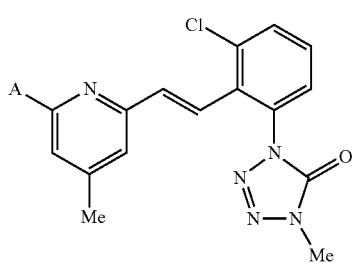 |
| E0669 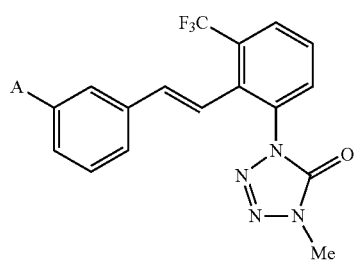 | E0676 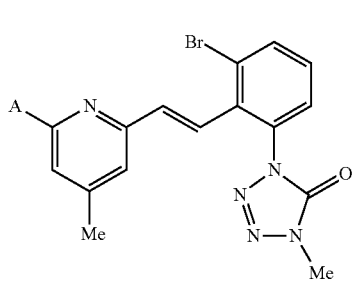 |
| E0671 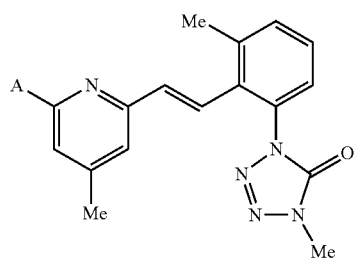 | E0677 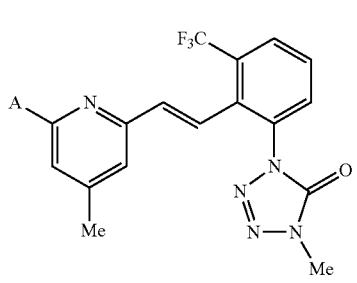 |
| E0672 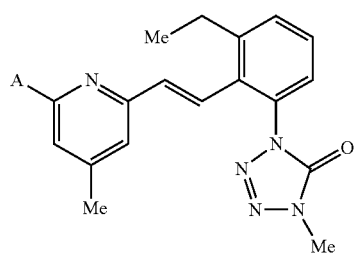 | E0678 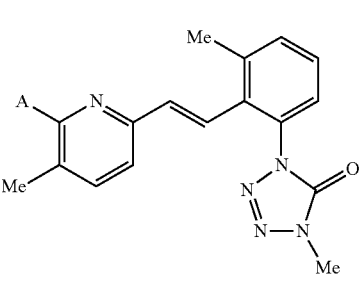 |
| E0673 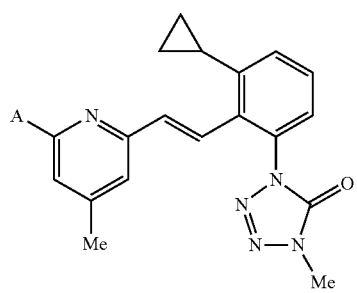 | E0679 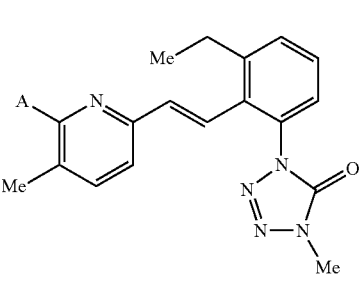 |
| E0674 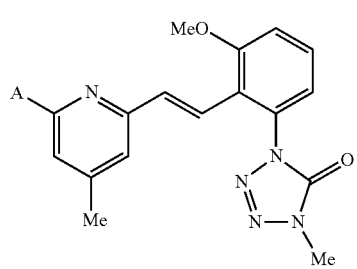 | E0680 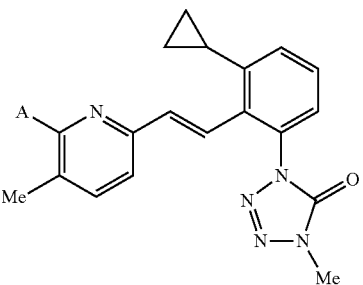 |

| | |
|---|---|
| 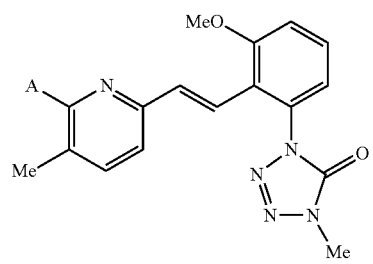 E0681 | 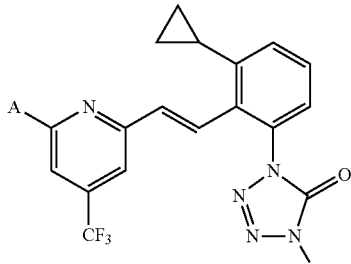 E0687 |
| 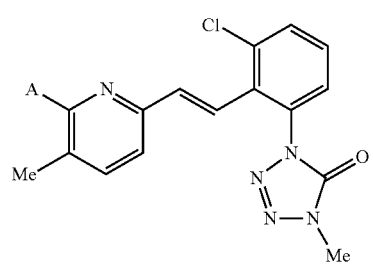 E0682 | 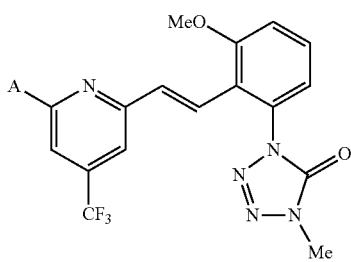 E0688 |
| 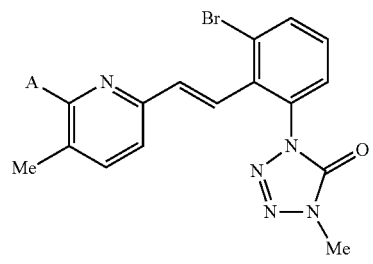 E0683 | 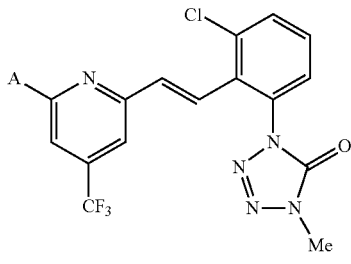 E0689 |
| 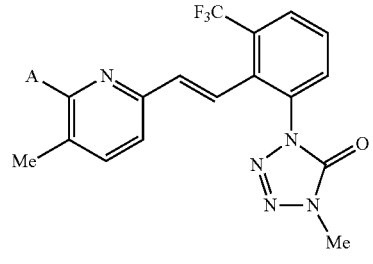 E0684 | 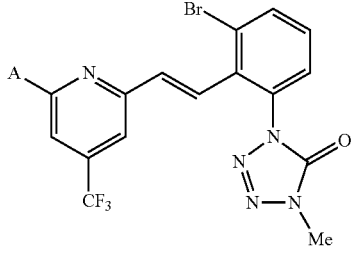 E0690 |
| 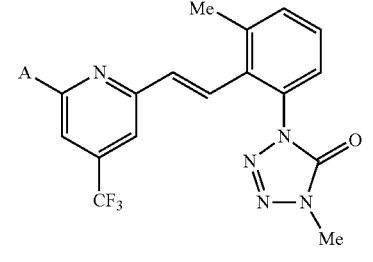 E0685 | 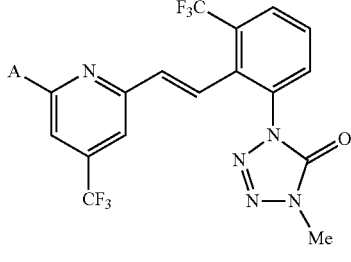 E0691 |
| 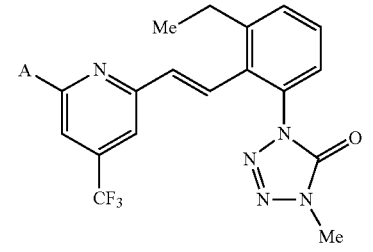 E0686 | 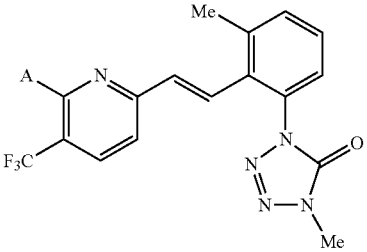 E0692 |

-continued

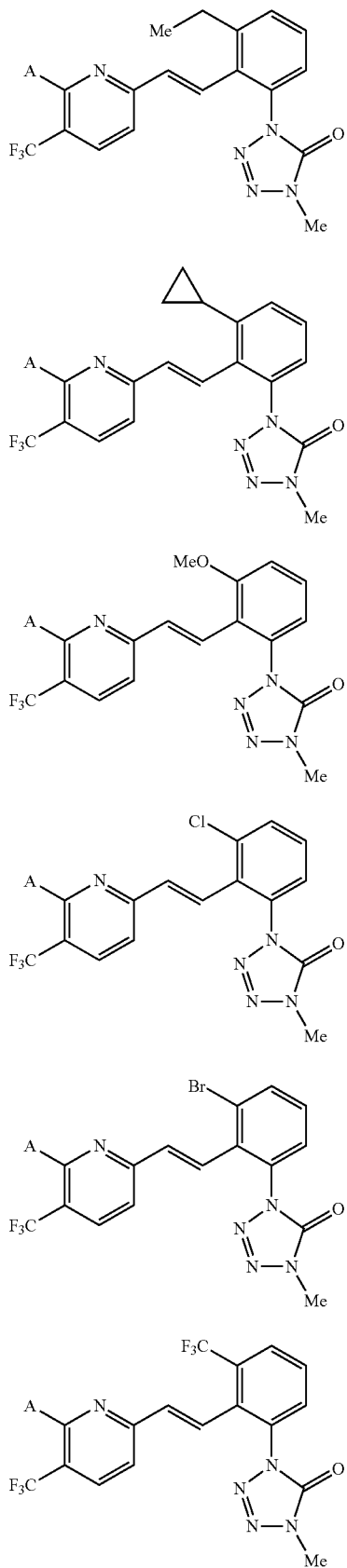

For example, PA1-1 represents a compound represented by formula (PA1) in which A is a substituent 1, and is represented by the following formula.

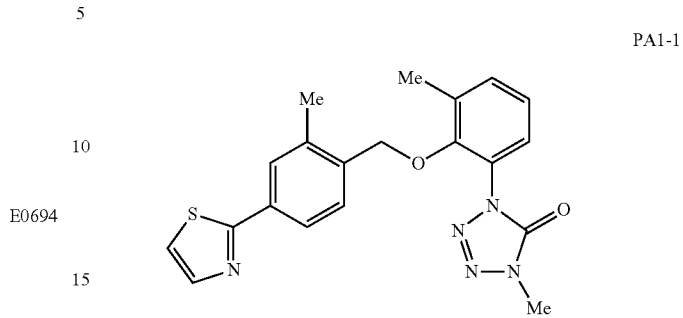

PA1-1

Substituent numbers 1 to 5122 are shown below, in which 2-Thia represents a thiazol-2-yl group, 4-Thia represents a thiazol-4-yl group, 5-Thia represents a thiazol-5-yl group, 2-Ox represents an oxazol-2-yl group, 3-Ox represents an oxazol-3-yl group, 4-Ox represents an oxazol-4-yl group, 2-Thio represents a thiophen-2-yl group, 3-Thio represents a thiophen-3-yl group, 2-Fu represents a furan-2-yl group, 3-Fu represents a furan-3-yl group, 1-Tri represents a 1,2,3-triazol-1-yl group, 2-Tri represents a 1,2,3-triazol-2-yl group, 1-Ph represents a benzen-1-yl group, 2-Py represents a pyridin-2-yl group, 3-Py represents a pyridin-3-yl group, F represents fluoro, F2 represents difluoro, Cl represents chloro, Br represents bromo, I represents iodo, CN represents cyano, SMe represents methylthio, SEt represents ethylthio, Me represents methyl, Et represents ethyl, iPr represents isopropyl, Pr represents propyl, CF3 represents trifluoromethyl, OCF3 represents trifluoromethoxy, CHF2 represents difluoromethyl, OCHF2 represents difluoromethoxy, OMe represents methoxy, OEt represents ethoxy, and cPr represents cyclopropyl.

[substituent number; A]
[1;2-Thia], [2;4-F-2-Thia], [3;4-Cl-2-Thia], [4;4-Br-2-Thia], [5;4-I-2-Thia], [6;4-Me-2-Thia], [7;4-Et-2-Thia], [8;4-Pr-2-Thia], [9;4-iPr-2-Thia], [10;4-CF3-2-Thia], [11;4-CHF2-2-Thia], [12;4-OMe-2-Thia], [13;4-OEt-2-Thia], [14;4-OCF3-2-Thia], [15;4-OCHF2-2-Thia], [16;4-CN-2-Thia], [17;4-SMe-2-Thia], [18;4-SEt-2-Thia], [19;4-cPr-2-Thia], [20;5-F-2-Thia], [21;5-Cl-2-Thia], [22;5-Br-2-Thia], [23;5-I-2-Thia], [24;5-Me-2-Thia], [25;5-Et-2-Thia], [26;5-Pr-2-Thia], [27;5-iPr-2-Thia], [28;5-CF3-2-Thia], [29;5-CHF2-2-Thia], [30;5-OMe-2-Thia], [31;5-OEt-2-Thia], [32;5-OCF3-2-Thia], [33;5-OCHF2-2-Thia], [34;5-CN-2-Thia], [35;5-SMe-2-Thia], [36;5-SEt-2-Thia], [37;5-cPr-2-Thia], [38;4-F-5-F-2-Thia], [39;4-F-5-Cl-2-Thia], [40;4-F-5-Br-2-Thia], [41;4-F-5-I-2-Thia], [42;4-F-5-Me-2-Thia], [43;4-F-5-Et-2-Thia], [44;4-F-5-Pr-2-Thia], [45;4-F-5-iPr-2-Thia], [46;4-F-5-CF3-2-Thia], [47;4-F-5-CHF2-2-Thia], [48;4-F-5-OMe-2-Thia], [49;4-F-5-OEt-2-Thia], [50;4-F-5-OCF3-2-Thia], [51;4-F-5-OCHF2-2-Thia], [52;4-F-5-CN-2-Thia], [53;4-F-5-SMe-2-Thia], [54;4-F-5-SEt-2-Thia], [55;4-F-5-cPr-2-Thia], [56;4-Cl-5-F-2-Thia], [57;4-Cl-5-Cl-2-Thia], [58;4-Cl-5-Br-2-Thia], [59;4-Cl-5-I-2-Thia], [60;4-Cl-5-Me-2-Thia], [61;4-Cl-5-Et-2-Thia], [62;4-Cl-5-Pr-2-Thia], [63;4-Cl-5-iPr-2-Thia], [64;4-Cl-5-CF3-2-Thia], [65;4-Cl-5-CHF2-2-Thia], [66;4-Cl-5-OMe-2-Thia], [67;4-Cl-5-OEt-2-Thia], [68;4-Cl-5-OCF3-2-Thia], [69;4-Cl-5-OCHF2-2-Thia], [70;4-Cl-5-CN-2-Thia], [71;4-Cl-5-SMe-2-Thia], [72;4-Cl-5-SEt-2-Thia], [73;4-Cl-5-cPr-2-Thia], [74;4-Me-5-F-2-Thia], [75;4-Me-5-Cl-2-Thia], [76;4-Me-5-Br-2-

Thia], [77;4-Me-5-I-2-Thia], [78;4-Me-5-Me-2-Thia], [79;4-Me-5-Et-2-Thia], [80;4-Me-5-Pr-2-Thia], [81;4-Me-5-iPr-2-Thia], [82;4-Me-5-CF3-2-Thia], [83;4-Me-5-CHF2-2-Thia], [84;4-Me-5-OMe-2-Thia], [85;4-Me-5-OEt-2-Thia], [86;4-Me-5-OCF3-2-Thia], [87;4-Me-5-OCHF2-2-Thia], [88;4-Me-5-CN-2-Thia], [89;4-Me-5-SMe-2-Thia], [90;4-Me-5-SEt-2-Thia], [91;4-Me-5-cPr-2-Thia], [92;4-Et-5-F-2-Thia], [93;4-Et-5-Cl-2-Thia], [94;4-Et-5-Br-2-Thia], [95;4-Et-5-I-2-Thia], [96;4-Et-5-Me-2-Thia], [97;4-Et-5-Et-2-Thia], [98;4-Et-5-Pr-2-Thia], [99;4-Et-5-iPr-2-Thia], [100;4-Et-5-CF3-2-Thia],

[101;4-Et-5-CHF2-2-Thia], [102;4-Et-5-OMe-2-Thia], [103;4-Et-5-OEt-2-Thia], [104;4-Et-5-OCF3-2-Thia], [105;4-Et-5-OCHF2-2-Thia], [106;4-Et-5-CN-2-Thia], [107;4-Et-5-SMe-2-Thia], [108;4-Et-5-SEt-2-Thia], [109;4-Et-5-cPr-2-Thia], [110;4-CF3-5-F-2-Thia], [111;4-CF3-5-Cl-2-Thia], [112;4-CF3-5-Br-2-Thia], [113;4-CF3-5-I-2-Thia], [114;4-CF3-5-Me-2-Thia], [115;4-CF3-5-Et-2-Thia], [116;4-CF3-5-Pr-2-Thia], [117;4-CF3-5-iPr-2-Thia], [118;4-CF3-5-CF3-2-Thia], [119;4-CF3-5-CHF2-2-Thia], [120;4-CF3-5-OMe-2-Thia], [121;4-CF3-5-OEt-2-Thia], [122;4-CF3-5-OCF3-2-Thia], [123;4-CF3-5-OCHF2-2-Thia], [124;4-CF3-5-CN-2-Thia], [125;4-CF3-5-SMe-2-Thia], [126;4-CF3-5-SEt-2-Thia], [127;4-CF3-5-cPr-2-Thia], [128;4-OMe-5-F-2-Thia], [129;4-OMe-5-Cl-2-Thia], [130;4-OMe-5-Br-2-Thia], [131;4-OMe-5-I-2-Thia], [132;4-OMe-5-Me-2-Thia], [133;4-OMe-5-Et-2-Thia], [134;4-OMe-5-Pr-2-Thia], [135;4-OMe-5-iPr-2-Thia], [136;4-OMe-5-CF3-2-Thia], [137;4-OMe-5-CHF2-2-Thia], [138;4-OMe-5-OMe-2-Thia], [139;4-OMe-5-OEt-2-Thia], [140;4-OMe-5-OCF3-2-Thia], [141;4-OMe-5-OCHF2-2-Thia], [142;4-OMe-5-CN-2-Thia], [143;4-OMe-5-SMe-2-Thia], [144;4-OMe-5-SEt-2-Thia], [145;4-OMe-5-cPr-2-Thia], [146;4-OEt-5-F-2-Thia], [147;4-OEt-5-Cl-2-Thia], [148;4-OEt-5-Br-2-Thia], [149;4-OEt-5-I-2-Thia], [150;4-OEt-5-Me-2-Thia], [151;4-OEt-5-Et-2-Thia], [152;4-OEt-5-Pr-2-Thia], [153;4-OEt-5-iPr-2-Thia], [154;4-OEt-5-CF3-2-Thia], [155;4-OEt-5-CHF2-2-Thia], [156;4-OEt-5-OMe-2-Thia], [157;4-OEt-5-OEt-2-Thia], [158;4-OEt-5-OCF3-2-Thia], [159;4-OEt-5-OCHF2-2-Thia], [160;4-OEt-5-CN-2-Thia], [161;4-OEt-5-SMe-2-Thia], [162;4-OEt-5-SEt-2-Thia], [163;4-OEt-5-cPr-2-Thia], [164;4-SMe-5-F-2-Thia], [165;4-SMe-5-Cl-2-Thia], [166;4-SMe-5-Br-2-Thia], [167;4-SMe-5-I-2-Thia], [168;4-SMe-5-Me-2-Thia], [169;4-SMe-5-Et-2-Thia], [170;4-SMe-5-Pr-2-Thia], [171;4-SMe-5-iPr-2-Thia], [172;4-SMe-5-CF3-2-Thia], [173;4-SMe-5-CHF2-2-Thia], [174;4-SMe-5-OMe-2-Thia], [175;4-SMe-5-OEt-2-Thia], [176;4-SMe-5-OCF3-2-Thia], [177;4-SMe-5-OCHF2-2-Thia], [178;4-SMe-5-CN-2-Thia], [179;4-SMe-5-SMe-2-Thia], [180;4-SMe-5-SEt-2-Thia], [181;4-SMe-5-cPr-2-Thia], [182;-4-Thia], [183;2-F-4-Thia], [184;2-Cl-4-Thia], [185;2-Br-4-Thia], [186;2-I-4-Thia], [187;2-Me-4-Thia], [188;2-Et-4-Thia], [189;2-Pr-4-Thia], [190;2-iPr-4-Thia], [191;2-CF3-4-Thia], [192;2-CHF2-4-Thia], [193;2-OMe-4-Thia], [194;2-OEt-4-Thia], [195;2-OCF3-4-Thia], [196;2-OCHF2-4-Thia], [197;2-CN-4-Thia], [198;2-SMe-4-Thia], [199;2-SEt-4-Thia], [200;2-cPr-4-Thia],

[201;5-F-4-Thia], [202;5-Cl-4-Thia], [203;5-Br-4-Thia], [204;5-I-4-Thia], [205;5-Me-4-Thia], [206;5-Et-4-Thia], [207;5-Pr-4-Thia], [208;5-iPr-4-Thia], [209;5-CF3-4-Thia], [210;5-CHF2-4-Thia], [211;5-OMe-4-Thia], [212;5-OEt-4-Thia], [213;5-OCF3-4-Thia], [214;5-OCHF2-4-Thia], [215;5-CN-4-Thia], [216;5-SMe-4-Thia], [217;5-SEt-4-Thia], [218;5-cPr-4-Thia], [219;2-F-5-F-4-Thia], [220;2-F-5-Cl-4-Thia], [221;2-F-5-Br-4-Thia], [222;2-F-5-I-4-Thia], [223;2-F-5-Me-4-Thia], [224;2-F-5-Et-4-Thia], [225;2-F-5-Pr-4-Thia], [226;2-F-5-iPr-4-Thia], [227;2-F-5-CF3-4-Thia], [228;2-F-5-CHF2-4-Thia], [229;2-F-5-OMe-4-Thia], [230;2-F-5-OEt-4-Thia], [231;2-F-5-OCF3-4-Thia], [232;2-F-5-OCHF2-4-Thia], [233;2-F-5-CN-4-Thia], [234;2-F-5-SMe-4-Thia], [235;2-F-5-SEt-4-Thia], [236;2-F-5-cPr-4-Thia], [237;2-Cl-5-F-4-Thia], [238;2-Cl-5-Cl-4-Thia], [239;2-Cl-5-Br-4-Thia], [240;2-Cl-5-I-4-Thia], [241;2-Cl-5-Me-4-Thia], [242;2-Cl-5-Et-4-Thia], [243;2-Cl-5-Pr-4-Thia], [244;2-Cl-5-iPr-4-Thia], [245;2-Cl-5-CF3-4-Thia], [246;2-Cl-5-CHF2-4-Thia], [247;2-Cl-5-OMe-4-Thia], [248;2-Cl-5-OEt-4-Thia], [249;2-Cl-5-OCF3-4-Thia], [250;2-Cl-5-OCHF2-4-Thia], [251;2-Cl-5-CN-4-Thia], [252;2-Cl-5-SMe-4-Thia], [253;2-Cl-5-SEt-4-Thia], [254;2-Cl-5-cPr-4-Thia], [255;2-Me-5-F-4-Thia], [256;2-Me-5-Cl-4-Thia], [257;2-Me-5-Br-4-Thia], [258;2-Me-5-I-4-Thia], [259;2-Me-5-Me-4-Thia], [260;2-Me-5-Et-4-Thia], [261;2-Me-5-Pr-4-Thia], [262;2-Me-5-iPr-4-Thia], [263;2-Me-5-CF3-4-Thia], [264;2-Me-5-CHF2-4-Thia], [265;2-Me-5-OMe-4-Thia], [266;2-Me-5-OEt-4-Thia], [267;2-Me-5-OCF3-4-Thia], [268;2-Me-5-OCHF2-4-Thia], [269;2-Me-5-CN-4-Thia], [270;2-Me-5-SMe-4-Thia], [271;2-Me-5-SEt-4-Thia], [272;2-Me-5-cPr-4-Thia], [273;2-Et-5-F-4-Thia], [274;2-Et-5-Cl-4-Thia], [275;2-Et-5-Br-4-Thia], [276;2-Et-5-I-4-Thia], [277;2-Et-5-Me-4-Thia], [278;2-Et-5-Et-4-Thia], [279;2-Et-5-Pr-4-Thia], [280;2-Et-5-iPr-4-Thia], [281;2-Et-5-CF3-4-Thia], [282;2-Et-5-CHF2-4-Thia], [283;2-Et-5-OMe-4-Thia], [284;2-Et-5-OEt-4-Thia], [285;2-Et-5-OCF3-4-Thia], [286;2-Et-5-OCHF2-4-Thia], [287;2-Et-5-CN-4-Thia], [288;2-Et-5-SMe-4-Thia], [289;2-Et-5-SEt-4-Thia], [290;2-Et-5-cPr-4-Thia], [291;2-CF3-5-F-4-Thia], [292;2-CF3-5-Cl-4-Thia], [293;2-CF3-5-Br-4-Thia], [294;2-CF3-5-I-4-Thia], [295;2-CF3-5-Me-4-Thia], [296;2-CF3-5-Et-4-Thia], [297;2-CF3-5-Pr-4-Thia], [298;2-CF3-5-iPr-4-Thia], [299;2-CF3-5-CF3-4-Thia], [300;2-CF3-5-CHF2-4-Thia],

[301;2-CF3-5-OMe-4-Thia], [302;2-CF3-5-OEt-4-Thia], [303;2-CF3-5-OCF3-4-Thia], [304;2-CF3-5-OCHF2-4-Thia], [305;2-CF3-5-CN-4-Thia], [306;2-CF3-5-SMe-4-Thia], [307;2-CF3-5-SEt-4-Thia], [308;2-CF3-5-cPr-4-Thia], [309;2-OMe-5-F-4-Thia], [310;2-OMe-5-Cl-4-Thia], [311;2-OMe-5-Br-4-Thia], [312;2-OMe-5-I-4-Thia], [313;2-OMe-5-Me-4-Thia], [314;2-OMe-5-Et-4-Thia], [315;2-OMe-5-Pr-4-Thia], [316;2-OMe-5-iPr-4-Thia], [317;2-OMe-5-CF3-4-Thia], [318;2-OMe-5-CHF2-4-Thia], [319;2-OMe-5-OMe-4-Thia], [320;2-OMe-5-OEt-4-Thia], [321;2-OMe-5-OCF3-4-Thia], [322;2-OMe-5-OCHF2-4-Thia], [323;2-OMe-5-CN-4-Thia], [324;2-OMe-5-SMe-4-Thia], [325;2-OMe-5-SEt-4-Thia], [326;2-OMe-5-cPr-4-Thia], [327;2-OEt-5-F-4-Thia], [328;2-OEt-5-Cl-4-Thia], [329;2-OEt-5-Br-4-Thia], [330;2-OEt-5-I-4-Thia], [331;2-OEt-5-Me-4-Thia], [332;2-OEt-5-Et-4-Thia], [333;2-OEt-5-Pr-4-Thia], [334;2-OEt-5-iPr-4-Thia], [335;2-OEt-5-CF3-4-Thia], [336;2-OEt-5-CHF2-4-Thia], [337;2-OEt-5-OMe-4-Thia], [338;2-OEt-5-OEt-4-Thia], [339;2-OEt-5-OCF3-4-Thia], [340;2-OEt-5-OCHF2-4-Thia], [341;2-OEt-5-CN-4-Thia], [342;2-OEt-5-SMe-4-Thia], [343;2-OEt-5-SEt-4-Thia], [344;2-OEt-5-cPr-4-Thia], [345;2-SMe-5-F-4-Thia], [346;2-SMe-5-Cl-4-Thia], [347;2-SMe-5-Br-4-Thia], [348;2-SMe-5-I-4-Thia], [349;2-SMe-5-Me-4-Thia], [350;2-SMe-5-Et-4-Thia], [351;2-SMe-5-Pr-4-Thia], [352;2-SMe-5-iPr-4-Thia], [353;2-SMe-5-CF3-4-Thia], [354;2-SMe-5-CHF2-4-Thia], [355;2-SMe-5-OMe-4-Thia], [356;2-SMe-5-OEt-4-Thia], [357;2-SMe-5-OCF3-4-Thia], [358;2-SMe-5-OCHF2-4-Thia], [359;2-SMe-5-CN-4-Thia], [360;2-SMe-5-SMe-4-Thia], [361;2-SMe-5-SEt-4-Thia], [362;2-SMe-5-cPr-4-Thia], [363;-5-Thia], [364;2-F-5-Thia], [365;2-Cl-5-Thia], [366;2-Br-5-Thia], [367;2-I-5-Thia], [368;2-Me-5-Thia], [369;2-Et-5-Thia], [370;2-Pr-5-Thia], [371;2- iPr-5-Thia], [372;2-CF3-5-Thia], [373;2-CHF2-5-Thia], [374;2-OMe-5-Thia], [375;2-OEt-5-Thia], [376;2-OCF3-5-Thia], [377;2-OCHF2-5-Thia], [378;2-CN-5-Thia], [379;2-SMe-5-Thia], [380;2-SEt-5-Thia], [381;2-cPr-5-Thia], [382;4-F-5-Thia], [383;4-Cl-5-Thia], [384;4-Br-5-Thia], [385;4-I-5-Thia], [386;4-Me-5-Thia], [387;4-Et-5-Thia], [388;4-Pr-5-Thia], [389;4-iPr-5-Thia], [390;4-CF3-5-Thia], [391;4-CHF2-5-Thia], [392;4-OMe-5-Thia], [393;4-OEt-5-Thia], [394;4-OCF3-5-Thia], [395;4-OCHF2-5-Thia], [396;4-CN-5-Thia], [397;4-SMe-5-Thia], [398;4-SEt-5-Thia], [399;4-cPr-5-Thia], [400;2-F-4-F-5-Thia],

[401;2-F-4-Cl-5-Thia], [402;2-F-4-Br-5-Thia], [403;2-F-4-I-5-Thia], [404;2-F-4-Me-5-Thia], [405;2-F-4-Et-5-Thia], [406;2-F-4-Pr-5-Thia], [407;2-F-4-iPr-5-Thia], [408;2-F-4-CF3-5-Thia], [409;2-F-4-CHF2-5-Thia], [410;2-F-4-OMe-5-Thia], [411;2-F-4-OEt-5-Thia], [412;2-F-4-OCF3-5-Thia], [413;2-F-4-OCHF2-5-Thia], [414;2-F-4-CN-5-Thia], [415;2-F-4-SMe-5-Thia], [416;2-F-4-SEt-5-Thia], [417;2-F-4-cPr-5-Thia], [418;2-Cl-4-F-5-Thia], [419;2-Cl-4-Cl-5-Thia], [420;2-Cl-4-Br-5-Thia], [421;2-Cl-4-I-5-Thia], [422;2-Cl-4-Me-5-Thia], [423;2-Cl-4-Et-5-Thia], [424;2-Cl-4-Pr-5-Thia], [425;2-Cl-4-iPr-5-Thia], [426;2-Cl-4-CF3-5-Thia], [427;2-Cl-4-CHF2-5-Thia], [428;2-Cl-4-OMe-5-Thia], [429;2-Cl-4-OEt-5-Thia], [430;2-Cl-4-OCF3-5-Thia], [431;2-Cl-4-OCHF2-5-Thia], [432;2-Cl-4-CN-5-Thia], [433;2-Cl-4-SMe-5-Thia], [434;2-Cl-4-SEt-5-Thia], [435;2-Cl-4-cPr-5-Thia], [436;2-Me-4-F-5-Thia], [437;2-Me-4-Cl-5-Thia], [438;2-Me-4-Br-5-Thia], [439;2-Me-4-I-5-Thia], [440;2-Me-4-Me-5-Thia], [441;2-Me-4-Et-5-Thia], [442;2-Me-4-Pr-5-Thia], [443;2-Me-4-iPr-5-Thia], [444;2-Me-4-CF3-5-Thia], [445;2-Me-4-CHF2-5-Thia], [446;2-Me-4-OMe-5-Thia], [447;2-Me-4-OEt-5-Thia], [448;2-Me-4-OCF3-5-Thia], [449;2-Me-4-OCHF2-5-Thia], [450;2-Me-4-CN-5-Thia], [451;2-Me-4-SMe-5-Thia], [452;2-Me-4-SEt-5-Thia], [453;2-Me-4-cPr-5-Thia], [454;2-Et-4-F-5-Thia], [455;2-Et-4-Cl-5-Thia], [456;2-Et-4-Br-5-Thia], [457;2-Et-4-I-5-Thia], [458;2-Et-4-Me-5-Thia], [459;2-Et-4-Et-5-Thia], [460;2-Et-4-Pr-5-Thia], [461;2-Et-4-iPr-5-Thia], [462;2-Et-4-CF3-5-Thia], [463;2-Et-4-CHF2-5-Thia], [464;2-Et-4-OMe-5-Thia], [465;2-Et-4-OEt-5-Thia], [466;2-Et-4-OCF3-5-Thia], [467;2-Et-4-OCHF2-5-Thia], [468;2-Et-4-CN-5-Thia], [469;2-Et-4-SMe-5-Thia], [470;2-Et-4-SEt-5-Thia], [471;2-Et-4-cPr-5-Thia], [472;2-CF3-4-F-5-Thia], [473;2-CF3-4-Cl-5-Thia], [474;2-CF3-4-Br-5-Thia], [475;2-CF3-4-I-5-Thia], [476;2-CF3-4-Me-5-Thia], [477;2-CF3-4-Et-5-Thia], [478;2-CF3-4-Pr-5-Thia], [479;2-CF3-4-iPr-5-Thia], [480;2-CF3-4-CF3-5-Thia], [481;2-CF3-4-CHF2-5-Thia], [482;2-CF3-4-OMe-5-Thia], [483;2-CF3-4-OEt-5-Thia], [484;2-CF3-4-OCF3-5-Thia], [485;2-CF3-4-OCHF2-5-Thia], [486;2-CF3-4-CN-5-Thia], [487;2-CF3-4-SMe-5-Thia], [488;2-CF3-4-SEt-5-Thia], [489;2-CF3-4-cPr-5-Thia], [490;2-OMe-4-F-5-Thia], [491;2-OMe-4-Cl-5-Thia], [492;2-OMe-4-Br-5-Thia], [493;2-OMe-4-I-5-Thia], [494;2-OMe-4-Me-5-Thia], [495;2-OMe-4-Et-5-Thia], [496;2-OMe-4-Pr-5-Thia], [497;2-OMe-4-iPr-5-Thia], [498;2-OMe-4-CF3-5-Thia], [499;2-OMe-4-CHF2-5-Thia], [500;2-OMe-4-OMe-5-Thia],

[501;2-OMe-4-OEt-5-Thia], [502;2-OMe-4-OCF3-5-Thia], [503;2-OMe-4-OCHF2-5-Thia], [504;2-OMe-4-CN-5-Thia], [505;2-OMe-4-SMe-5-Thia], [506;2-OMe-4-SEt-5-Thia], [507;2-OMe-4-cPr-5-Thia], [508;2-OEt-4-F-5-Thia], [509;2-OEt-4-Cl-5-Thia], [510;2-OEt-4-Br-5-Thia], [511;2-OEt-4-I-5-Thia], [512;2-OEt-4-Me-5-Thia], [513;2-OEt-4-Et-5-Thia], [514;2-OEt-4-Pr-5-Thia], [515;2-OEt-4-iPr-5-Thia], [516;2-OEt-4-CF3-5-Thia], [517;2-OEt-4-CHF2-5-Thia], [518;2-OEt-4-OMe-5-Thia], [519;2-OEt-4-OEt-5-Thia], [520;2-OEt-4-OCF3-5-Thia], [521;2-OEt-4-OCHF2-5-Thia], [522;2-OEt-4-CN-5-Thia], [523;2-OEt-4-SMe-5-Thia], [524;2-OEt-4-SEt-5-Thia], [525;2-OEt-4-cPr-5-Thia], [526;2-SMe-4-F-5-Thia], [527;2-SMe-4-Cl-5-Thia], [528;2-SMe-4-Br-5-Thia], [529;2-SMe-4-I-5-Thia], [530;2-SMe-4-Me-5-Thia], [531;2-SMe-4-Et-5-Thia], [532;2-SMe-4-Pr-5-Thia], [533;2-SMe-4-iPr-5-Thia], [534;2-SMe-4-CF3-5-Thia], [535;2-SMe-4-CHF2-5-Thia], [536;2-SMe-4-OMe-5-Thia], [537;2-SMe-4-OEt-5-Thia], [538;2-SMe-4-OCF3-5-Thia], [539;2-SMe-4-OCHF2-5-Thia], [540;2-SMe-4-CN-5-Thia], [541;2-SMe-4-SMe-5-Thia], [542;2-SMe-4-SEt-5-Thia], [543;2-SMe-4-cPr-5-Thia], [544;2-Ox], [545;4-F-2-Ox], [546;4-Cl-2-Ox], [547;4-Br-2-Ox], [548;4-I-2-Ox], [549;4-Me-2-Ox], [550;4-Et-2-Ox], [551;4-Pr-2-Ox], [552;4-iPr-2-Ox], [553;4-CF3-2-Ox], [554;4-CHF2-2-Ox], [555;4-OMe-2-Ox], [556;4-OEt-2-Ox], [557;4-OCF3-2-Ox], [558;4-OCHF2-2-Ox], [559;4-CN-2-Ox], [560;4-SMe-2-Ox], [561;4-SEt-2-Ox], [562;4-cPr-2-Ox], [563;5-F-2-Ox], [564;5-Cl-2-Ox], [565;5-Br-2-Ox], [566;5-I-2-Ox], [567;5-Me-2-Ox], [568;5-Et-2-Ox], [569;5-Pr-2-Ox], [570;5-iPr-2-Ox], [571;5-CF3-2-Ox], [572;5-CHF2-2-Ox], [573;5-OMe-2-Ox], [574;5-OEt-2-Ox], [575;5-OCF3-2-Ox], [576;5-OCHF2-2-Ox], [577;5-CN-2-Ox], [578;5-SMe-2-Ox], [579;5-SEt-2-Ox], [580;5-cPr-2-Ox], [581;4-F-5-F-2-Ox], [582;4-F-5-Cl-2-Ox], [583;4-F-5-Br-2-Ox], [584;4-F-5-I-2-Ox], [585;4-F-5-Me-2-Ox], [586;4-F-5-Et-2-Ox], [587;4-F-5-Pr-2-Ox], [588;4-F-5-iPr-2-Ox], [589;4-F-5-CF3-2-Ox], [590;4-F-5-CHF2-2-Ox], [591;4-F-5-OMe-2-Ox], [592;4-F-5-OEt-2-Ox], [593;4-F-5-OCF3-2-Ox], [594;4-F-5-OCHF2-2-Ox], [595;4-F-5-CN-2-Ox], [596;4-F-5-SMe-2-Ox], [597;4-F-5-SEt-2-Ox], [598;4-F-5-cPr-2-Ox], [599;4-Cl-5-F-2-Ox], [600;4-Cl-5-Cl-2-Ox],

[601;4-Cl-5-Br-2-Ox], [602;4-Cl-5-I-2-Ox], [603;4-Cl-5-Me-2-Ox], [604;4-Cl-5-Et-2-Ox], [605;4-Cl-5-Pr-2-Ox], [606;4-Cl-5-iPr-2-Ox], [607;4-Cl-5-CF3-2-Ox], [608;4-Cl-5-CHF2-2-Ox], [609;4-Cl-5-OMe-2-Ox], [610;4-Cl-5-OEt-2-Ox], [611;4-Cl-5-OCF3-2-Ox], [612;4-Cl-5-OCHF2-2-Ox], [613;4-Cl-5-CN-2-Ox], [614;4-Cl-5-SMe-2-Ox], [615;4-Cl-5-SEt-2-Ox], [616;4-Cl-5-cPr-2-Ox], [617;4-Me-5-F-2-Ox], [618;4-Me-5-Cl-2-Ox], [619;4-Me-5-Br-2-Ox], [620;4-Me-5-I-2-Ox], [621;4-Me-5-Me-2-Ox], [622;4-Me-5-Et-2-Ox], [623;4-Me-5-Pr-2-Ox], [624;4-Me-5-iPr-2-Ox], [625;4-Me-5-CF3-2-Ox], [626;4-Me-5-CHF2-2-Ox], [627;4-Me-5-OMe-2-Ox], [628;4-Me-5-OEt-2-Ox], [629;4-Me-5-OCF3-2-Ox], [630;4-Me-5-OCHF2-2-Ox], [631;4-Me-5-CN-2-Ox], [632;4-Me-5-SMe-2-Ox], [633;4-Me-5-SEt-2-Ox], [634;4-Me-5-cPr-2-Ox], [635;4-Et-5-F-2-Ox], [636;4-Et-5-Cl-2-Ox], [637;4-Et-5-Br-2-Ox], [638;4-Et-5-I-2-Ox], [639;4-Et-5-Me-2-Ox], [640;4-Et-5-Et-2-Ox], [641;4-Et-5-Pr-2-Ox], [642;4-Et-5-iPr-2-Ox], [643;4-Et-5-CF3-2-Ox], [644;4-Et-5-CHF2-2-Ox], [645;4-Et-5-OMe-2-Ox], [646;4-Et-5-OEt-2-Ox], [647;4-Et-5-OCF3-2-Ox], [648;4-Et-5-OCHF2-2-Ox], [649;4-Et-5-CN-2-Ox], [650;4-Et-5-SMe-2-Ox], [651;4-Et-5-SEt-2-Ox], [652;4-Et-5-cPr-2-Ox], [653;4-CF3-5-F-2-Ox], [654;4-CF3-5-Cl-2-Ox], [655;4-CF3-5-Br-2-Ox], [656;4-CF3-5-I-2-Ox], [657;4-CF3-5-Me-2-Ox], [658;4-CF3-5-Et-2-Ox], [659;4-CF3-5-Pr-2-Ox], [660;4-CF3-5-iPr-2-Ox], [661;4-CF3-5-CF3-2-Ox], [662;4-CF3-5-CHF2-2-Ox], [663;4-CF3-5-OMe-2-Ox], [664;4-CF3-5-OEt-2-Ox], [665;4-CF3-5-OCF3-2-Ox], [666;4-CF3-5-OCHF2-2-Ox], [667;4-CF3-5-CN-2-Ox], [668;4-CF3-5-SMe-2-Ox], [669;4-CF3-5-SEt-2-Ox], [670;4-CF3-5-cPr-2-Ox], [671;4-OMe-5-F-2-Ox], [672;4-OMe-5-Cl-2-Ox], [673;4-OMe-5-Br-2-Ox], [674;4-OMe-5-I-2-Ox], [675;4-OMe-5-Me-2-Ox], [676;4-OMe-5-Et-2-Ox], [677;4-OMe-5-Pr-2-Ox], [678;4-OMe-5-iPr-2-Ox], [679;4-OMe-5-CF3-2-Ox], [680;4-OMe-5-CHF2-2-Ox], [681;4-OMe-5-OMe-2-Ox], [682;4-OMe-5-OEt-2-Ox], [683;4-OMe-5-OCF3-2-

Ox], [684;4-OMe-5-OCHF2-2-Ox], [685;4-OMe-5-CN-2-Ox], [686;4-OMe-5-SMe-2-Ox], [687;4-OMe-5-SEt-2-Ox], [688;4-OMe-5-cPr-2-Ox], [689;4-OEt-5-F-2-Ox], [690;4-OEt-5-Cl-2-Ox], [691;4-OEt-5-Br-2-Ox], [692;4-OEt-5-I-2-Ox], [693;4-OEt-5-Me-2-Ox], [694;4-OEt-5-Et-2-Ox], [695;4-OEt-5-Pr-2-Ox], [696;4-OEt-5-iPr-2-Ox], [697;4-OEt-5-CF3-2-Ox], [698;4-OEt-5-CHF2-2-Ox], [699;4-OEt-5-OMe-2-Ox], [700;4-OEt-5-OEt-2-Ox],
[701;4-OEt-5-OCF3-2-Ox], [702;4-OEt-5-OCHF2-2-Ox], [703;4-OEt-5-CN-2-Ox], [704;4-OEt-5-SMe-2-Ox], [705;4-OEt-5-SEt-2-Ox], [706;4-OEt-5-cPr-2-Ox], [707;4-SMe-5-F-2-Ox], [708;4-SMe-5-Cl-2-Ox], [709;4-SMe-5-Br-2-Ox], [710;4-SMe-5-I-2-Ox], [711;4-SMe-5-Me-2-Ox], [712;4-SMe-5-Et-2-Ox], [713;4-SMe-5-Pr-2-Ox], [714;4-SMe-5-iPr-2-Ox], [715;4-SMe-5-CF3-2-Ox], [716;4-SMe-5-CHF2-2-Ox], [717;4-SMe-5-OMe-2-Ox], [718;4-SMe-5-OEt-2-Ox], [719;4-SMe-5-OCF3-2-Ox], [720;4-SMe-5-OCHF2-2-Ox], [721;4-SMe-5-CN-2-Ox], [722;4-SMe-5-SMe-2-Ox], [723;4-SMe-5-SEt-2-Ox], [724;4-SMe-5-cPr-2-Ox], [725;-Ox], [726;2-F-4-Ox], [727;2-Cl-4-Ox], [728;2-Br-4-Ox], [729;2-I-4-Ox], [730;2-Me-4-Ox], [731;2-Et-4-Ox], [732;2-Pr-4-Ox], [733;2-iPr-4-Ox], [734;2-CF3-4-Ox], [735;2-CHF2-4-Ox], [736;2-OMe-4-Ox], [737;2-OEt-4-Ox], [738;2-OCF3-4-Ox], [739;2-OCHF2-4-Ox], [740;2-CN-4-Ox], [741;2-SMe-4-Ox], [742;2-SEt-4-Ox], [743;2-cPr-4-Ox], [744;5-F-4-Ox], [745;5-Cl-4-Ox], [746;5-Br-4-Ox], [747;5-I-4-Ox], [748;5-Me-4-Ox], [749;5-Et-4-Ox], [750;5-Pr-4-Ox], [751;5-iPr-4-Ox], [752;5-CF3-4-Ox], [753;5-CHF2-4-Ox], [754;5-OMe-4-Ox], [755;5-OEt-4-Ox], [756;5-OCF3-4-Ox], [757;5-OCHF2-4-Ox], [758;5-CN-4-Ox], [759;5-SMe-4-Ox], [760;5-SEt-4-Ox], [761;5-cPr-4-Ox], [762;2-F-5-F-4-Ox], [763;2-F-5-Cl-4-Ox], [764;2-F-5-Br-4-Ox], [765;2-F-5-I-4-Ox], [766;2-F-5-Me-4-Ox], [767;2-F-5-Et-4-Ox], [768;2-F-5-Pr-4-Ox], [769;2-F-5-iPr-4-Ox], [770;2-F-5-CF3-4-Ox], [771;2-F-5-CHF2-4-Ox], [772;2-F-5-OMe-4-Ox], [773;2-F-5-OEt-4-Ox], [774;2-F-5-OCF3-4-Ox], [775;2-F-5-OCHF2-4-Ox], [776;2-F-5-CN-4-Ox], [777;2-F-5-SMe-4-Ox], [778;2-F-5-SEt-4-Ox], [779;2-F-5-cPr-4-Ox], [780;2-Cl-5-F-4-Ox], [781;2-Cl-5-Cl-4-Ox], [782;2-Cl-5-Br-4-Ox], [783;2-Cl-5-I-4-Ox], [784;2-Cl-5-Me-4-Ox], [785;2-Cl-5-Et-4-Ox], [786;2-Cl-5-Pr-4-Ox], [787;2-Cl-5-iPr-4-Ox], [788;2-Cl-5-CF3-4-Ox], [789;2-Cl-5-CHF2-4-Ox], [790;2-Cl-5-OMe-4-Ox], [791;2-Cl-5-OEt-4-Ox], [792;2-Cl-5-OCF3-4-Ox], [793;2-Cl-5-OCHF2-4-Ox], [794;2-Cl-5-CN-4-Ox], [795;2-Cl-5-SMe-4-Ox], [796;2-Cl-5-SEt-4-Ox], [797;2-Cl-5-cPr-4-Ox], [798;2-Me-5-F-4-Ox], [799;2-Me-5-Cl-4-Ox], [800;2-Me-5-Br-4-Ox],
[801;2-Me-5-I-4-Ox], [802;2-Me-5-Me-4-Ox], [803;2-Me-5-Et-4-Ox], [804;2-Me-5-Pr-4-Ox], [805;2-Me-5-iPr-4-Ox], [806;2-Me-5-CF3-4-Ox], [807;2-Me-5-CHF2-4-Ox], [808;2-Me-5-OMe-4-Ox], [809;2-Me-5-OEt-4-Ox], [810;2-Me-5-OCF3-4-Ox], [811;2-Me-5-OCHF2-4-Ox], [812;2-Me-5-CN-4-Ox], [813;2-Me-5-SMe-4-Ox], [814;2-Me-5-SEt-4-Ox], [815;2-Me-5-cPr-4-Ox], [816;2-Et-5-F-4-Ox], [817;2-Et-5-Cl-4-Ox], [818;2-Et-5-Br-4-Ox], [819;2-Et-5-I-4-Ox], [820;2-Et-5-Me-4-Ox], [821;2-Et-5-Et-4-Ox], [822;2-Et-5-Pr-4-Ox], [823;2-Et-5-iPr-4-Ox], [824;2-Et-5-CF3-4-Ox], [825;2-Et-5-CHF2-4-Ox], [826;2-Et-5-OMe-4-Ox], [827;2-Et-5-OEt-4-Ox], [828;2-Et-5-OCF3-4-Ox], [829;2-Et-5-OCHF2-4-Ox], [830;2-Et-5-CN-4-Ox], [831;2-Et-5-SMe-4-Ox], [832;2-Et-5-SEt-4-Ox], [833;2-Et-5-cPr-4-Ox], [834;2-CF3-5-F-4-Ox], [835;2-CF3-5-Cl-4-Ox], [836;2-CF3-5-Br-4-Ox], [837;2-CF3-5-I-4-Ox], [838;2-CF3-5-Me-4-Ox], [839;2-CF3-5-Et-4-Ox], [840;2-CF3-5-Pr-4-Ox], [841;2-CF3-5-iPr-4-Ox], [842;2-CF3-5-CF3-4-Ox], [843;2-CF3-5-CHF2-4-Ox], [844;2-CF3-5-OMe-4-Ox], [845;2-CF3-5-OEt-4-Ox], [846;2-CF3-5-OCF3-4-Ox], [847;2-CF3-5-OCHF2-4-Ox], [848;2-CF3-5-CN-4-Ox], [849;2-CF3-5-SMe-4-Ox], [850;2-CF3-5-SEt-4-Ox], [851;2-CF3-5-cPr-4-Ox], [852;2-OMe-5-F-4-Ox], [853;2-OMe-5-Cl-4-Ox], [854;2-OMe-5-Br-4-Ox], [855;2-OMe-5-I-4-Ox], [856;2-OMe-5-Me-4-Ox], [857;2-OMe-5-Et-4-Ox], [858;2-OMe-5-Pr-4-Ox], [859;2-OMe-5-iPr-4-Ox], [860;2-OMe-5-CF3-4-Ox], [861;2-OMe-5-CHF2-4-Ox], [862;2-OMe-5-OMe-4-Ox], [863;2-OMe-5-OEt-4-Ox], [864;2-OMe-5-OCF3-4-Ox], [865;2-OMe-5-OCHF2-4-Ox], [866;2-OMe-5-CN-4-Ox], [867;2-OMe-5-SMe-4-Ox], [868;2-OMe-5-SEt-4-Ox], [869;2-OMe-5-cPr-4-Ox], [870;2-OEt-5-F-4-Ox], [871;2-OEt-5-Cl-4-Ox], [872;2-OEt-5-Br-4-Ox], [873;2-OEt-5-I-4-Ox], [874;2-OEt-5-Me-4-Ox], [875;2-OEt-5-Et-4-Ox], [876;2-OEt-5-Pr-4-Ox], [877;2-OEt-5-iPr-4-Ox], [878;2-OEt-5-CF3-4-Ox], [879;2-OEt-5-CHF2-4-Ox], [880;2-OEt-5-OMe-4-Ox], [881;2-OEt-5-OEt-4-Ox], [882;2-OEt-5-OCF3-4-Ox], [883;2-OEt-5-OCHF2-4-Ox], [884;2-OEt-5-CN-4-Ox], [885;2-OEt-5-SMe-4-Ox], [886;2-OEt-5-SEt-4-Ox], [887;2-OEt-5-cPr-4-Ox], [888;2-SMe-5-F-4-Ox], [889;2-SMe-5-Cl-4-Ox], [890;2-SMe-5-Br-4-Ox], [891;2-SMe-5-I-4-Ox], [892;2-SMe-5-Me-4-Ox], [893;2-SMe-5-Et-4-Ox], [894;2-SMe-5-Pr-4-Ox], [895;2-SMe-5-iPr-4-Ox], [896;2-SMe-5-CF3-4-Ox], [897;2-SMe-5-CHF2-4-Ox], [898;2-SMe-5-OMe-4-Ox], [899;2-SMe-5-OEt-4-Ox], [900;2-SMe-5-OCF3-4-Ox],
[901;2-SMe-5-OCHF2-4-Ox], [902;2-SMe-5-CN-4-Ox], [903;2-SMe-5-SMe-4-Ox], [904;2-SMe-5-SEt-4-Ox], [905;2-SMe-5-cPr-4-Ox], [906;-5-Ox], [907;2-F-5-Ox], [908;2-Cl-5-Ox], [909;2-Br-5-Ox], [910;2-I-5-Ox], [911;2-Me-5-Ox], [912;2-Et-5-Ox], [913;2-Pr-5-Ox], [914;2-iPr-5-Ox], [915;2-CF3-5-Ox], [916;2-CHF2-5-Ox], [917;2-OMe-5-Ox], [918;2-OEt-5-Ox], [919;2-OCF3-5-Ox], [920;2-OCHF2-5-Ox], [921;2-CN-5-Ox], [922;2-SMe-5-Ox], [923;2-SEt-5-Ox], [924;2-cPr-5-Ox], [925;4-F-5-Ox], [926;4-Cl-5-Ox], [927;4-Br-5-Ox], [928;4-I-5-Ox], [929;4-Me-5-Ox], [930;4-Et-5-Ox], [931;4-Pr-5-Ox], [932;4-iPr-5-Ox], [933;4-CF3-5-Ox], [934;4-CHF2-5-Ox], [935;4-OMe-5-Ox], [936;4-OEt-5-Ox], [937;4-OCF3-5-Ox], [938;4-OCHF2-5-Ox], [939;4-CN-5-Ox], [940;4-SMe-5-Ox], [941;4-SEt-5-Ox], [942;4-cPr-5-Ox], [943;2-F-4-F-5-Ox], [944;2-F-4-Cl-5-Ox], [945;2-F-4-Br-5-Ox], [946;2-F-4-I-5-Ox], [947;2-F-4-Me-5-Ox], [948;2-F-4-Et-5-Ox], [949;2-F-4-Pr-5-Ox], [950;2-F-4-iPr-5-Ox], [951;2-F-4-CF3-5-Ox], [952;2-F-4-CHF2-5-Ox], [953;2-F-4-OMe-5-Ox], [954;2-F-4-OEt-5-Ox], [955;2-F-4-OCF3-5-Ox], [956;2-F-4-OCHF2-5-Ox], [957;2-F-4-CN-5-Ox], [958;2-F-4-SMe-5-Ox], [959;2-F-4-SEt-5-Ox], [960;2-F-4-cPr-5-Ox], [961;2-Cl-4-F-5-Ox], [962;2-Cl-4-Cl-5-Ox], [963;2-Cl-4-Br-5-Ox], [964;2-Cl-4-I-5-Ox], [965;2-Cl-4-Me-5-Ox], [966;2-Cl-4-Et-5-Ox], [967;2-Cl-4-Pr-5-Ox], [968;2-Cl-4-iPr-5-Ox], [969;2-Cl-4-CF3-5-Ox], [970;2-Cl-4-CHF2-5-Ox], [971;2-Cl-4-OMe-5-Ox], [972;2-Cl-4-OEt-5-Ox], [973;2-Cl-4-OCF3-5-Ox], [974;2-Cl-4-OCHF2-5-Ox], [975;2-Cl-4-CN-5-Ox], [976;2-Cl-4-SMe-5-Ox], [977;2-Cl-4-SEt-5-Ox], [978;2-Cl-4-cPr-5-Ox], [979;2-Me-4-F-5-Ox], [980;2-Me-4-Cl-5-Ox], [981;2-Me-4-Br-5-Ox], [982;2-Me-4-I-5-Ox], [983;2-Me-4-Me-5-Ox], [984;2-Me-4-Et-5-Ox], [985;2-Me-4-Pr-5-Ox], [986;2-Me-4-iPr-5-Ox], [987;2-Me-4-CF3-5-Ox], [988;2-Me-4-CHF2-5-Ox], [989;2-Me-4-OMe-5-Ox], [990;2-Me-4-OEt-5-Ox], [991;2-Me-4-OCF3-5-Ox], [992;2-Me-4-OCHF2-5-Ox], [993;2-Me-4-CN-5-Ox], [994;2-Me-4-SMe-5-Ox], [995;2-Me-4-SEt-5-Ox], [996;2-Me-4-cPr-5-Ox], [997;2-Et-4-F-5-Ox], [998;2-Et-4-Cl-5-Ox], [999;2-Et-4-Br-5-Ox], [1000;2-Et-4-I-5-Ox],
[1001;2-Et-4-Me-5-Ox], [1002;2-Et-4-Et-5-Ox], [1003;2-Et-4-Pr-5-Ox], [1004;2-Et-4-iPr-5-Ox], [1005;2-Et-4-CF3-5-Ox], [1006;2-Et-4-CHF2-5-Ox], [1007;2-Et-4-OMe-5-

Ox], [1008;2-Et-4-OEt-5-Ox], [1009;2-Et-4-OCF3-5-Ox], [1010;2-Et-4-OCHF2-5-Ox], [1011;2-Et-4-CN-5-Ox], [1012;2-Et-4-SMe-5-Ox], [1013;2-Et-4-SEt-5-Ox], [1014;2-Et-4-cPr-5-Ox], [1015;2-CF3-4-F-5-Ox], [1016;2-CF3-4-Cl-5-Ox], [1017;2-CF3-4-Br-5-Ox], [1018;2-CF3-4-I-5-Ox], [1019;2-CF3-4-Me-5-Ox], [1020;2-CF3-4-Et-5-Ox], [1021;2-CF3-4-Pr-5-Ox], [1022;2-CF3-4-iPr-5-Ox], [1023;2-CF3-4-CF3-5-Ox], [1024;2-CF3-4-CHF2-5-Ox], [1025;2-CF3-4-OMe-5-Ox], [1026;2-CF3-4-OEt-5-Ox], [1027;2-CF3-4-OCF3-5-Ox], [1028;2-CF3-4-OCHF2-5-Ox], [1029;2-CF3-4-CN-5-Ox], [1030;2-CF3-4-SMe-5-Ox], [1031;2-CF3-4-SEt-5-Ox], [1032;2-CF3-4-cPr-5-Ox], [1033;2-OMe-4-F-5-Ox], [1034;2-OMe-4-Cl-5-Ox], [1035;2-OMe-4-Br-5-Ox], [1036;2-OMe-4-I-5-Ox], [1037;2-OMe-4-Me-5-Ox], [1038;2-OMe-4-Et-5-Ox], [1039;2-OMe-4-Pr-5-Ox], [1040;2-OMe-4-iPr-5-Ox], [1041;2-OMe-4-CF3-5-Ox], [1042;2-OMe-4-CHF2-5-Ox], [1043;2-OMe-4-OMe-5-Ox], [1044;2-OMe-4-OEt-5-Ox], [1045;2-OMe-4-OCF3-5-Ox], [1046;2-OMe-4-OCHF2-5-Ox], [1047;2-OMe-4-CN-5-Ox], [1048;2-OMe-4-SMe-5-Ox], [1049;2-OMe-4-SEt-5-Ox], [1050;2-OMe-4-cPr-5-Ox], [1051;2-OEt-4-F-5-Ox], [1052;2-OEt-4-Cl-5-Ox], [1053;2-OEt-4-Br-5-Ox], [1054;2-OEt-4-I-5-Ox], [1055;2-OEt-4-Me-5-Ox], [1056;2-OEt-4-Et-5-Ox], [1057;2-OEt-4-Pr-5-Ox], [1058;2-OEt-4-iPr-5-Ox], [1059;2-OEt-4-CF3-5-Ox], [1060;2-OEt-4-CHF2-5-Ox], [1061;2-OEt-4-OMe-5-Ox], [1062;2-OEt-4-OEt-5-Ox], [1063;2-OEt-4-OCF3-5-Ox], [1064;2-OEt-4-OCHF2-5-Ox], [1065;2-OEt-4-CN-5-Ox], [1066;2-OEt-4-SMe-5-Ox], [1067;2-OEt-4-SEt-5-Ox], [1068;2-OEt-4-cPr-5-Ox], [1069;2-SMe-4-F-5-Ox], [1070;2-SMe-4-Cl-5-Ox], [1071;2-SMe-4-Br-5-Ox], [1072;2-SMe-4-I-5-Ox], [1073;2-SMe-4-Me-5-Ox], [1074;2-SMe-4-Et-5-Ox], [1075;2-SMe-4-Pr-5-Ox], [1076;2-SMe-4-iPr-5-Ox], [1077;2-SMe-4-CF3-5-Ox], [1078;2-SMe-4-CHF2-5-Ox], [1079;2-SMe-4-OMe-5-Ox], [1080;2-SMe-4-OEt-5-Ox], [1081;2-SMe-4-OCF3-5-Ox], [1082;2-SMe-4-OCHF2-5-Ox], [1083;2-SMe-4-CN-5-Ox], [1084;2-SMe-4-SMe-5-Ox], [1085;2-SMe-4-SEt-5-Ox], [1086;2-SMe-4-cPr-5-Ox], [1197;2-Fu], [1198;4-F-2-Fu], [1199;4-Cl-2-Fu], [1200;4-Br-2-Fu], [1201;4-I-2-Fu], [1202;4-Me-2-Fu], [1203;4-Et-2-Fu], [1204;4-Pr-2-Fu], [1205;4-iPr-2-Fu], [1206;4-CF3-2-Fu], [1207;4-CHF2-2-Fu], [1208;4-OMe-2-Fu], [1209;4-OEt-2-Fu], [1210;4-OCF3-2-Fu], [1211;4-OCHF2-2-Fu], [1212;4-CN-2-Fu], [1213;4-SMe-2-Fu], [1214;4-SEt-2-Fu], [1215;4-cPr-2-Fu], [1216;5-F-2-Fu], [1217;5-Cl-2-Fu], [1218;5-Br-2-Fu], [1219;5-I-2-Fu], [1220;5-Me-2-Fu], [1221;5-Et-2-Fu], [1222;5-Pr-2-Fu], [1223;5-iPr-2-Fu], [1224;5-CF3-2-Fu], [1225;5-CHF2-2-Fu], [1226;5-OMe-2-Fu], [1227;5-OEt-2-Fu], [1228;5-OCF3-2-Fu], [1229;5-OCHF2-2-Fu], [1230;5-CN-2-Fu], [1231;5-SMe-2-Fu], [1232;5-SEt-2-Fu], [1233;5-cPr-2-Fu], [1234;4-F-5-F-2-Fu], [1235;4-F-5-Cl-2-Fu], [1236;4-F-5-Br-2-Fu], [1237;4-F-5-I-2-Fu], [1238;4-F-5-Me-2-Fu], [1239;4-F-5-Et-2-Fu], [1240;4-F-5-Pr-2-Fu], [1241;4-F-5-iPr-2-Fu], [1242;4-F-5-CF3-2-Fu], [1243;4-F-5-CHF2-2-Fu], [1244;4-F-5-OMe-2-Fu], [1245;4-F-5-OEt-2-Fu], [1246;4-F-5-OCF3-2-Fu], [1247;4-F-5-OCHF2-2-Fu], [1248;4-F-5-CN-2-Fu], [1249;4-F-5-SMe-2-Fu], [1250;4-F-5-SEt-2-Fu], [1251;4-F-5-cPr-2-Fu], [1252;4-Cl-5-F-2-Fu], [1253;4-Cl-5-Cl-2-Fu], [1254;4-Cl-5-Br-2-Fu], [1255;4-Cl-5-I-2-Fu], [1256;4-Cl-5-Me-2-Fu], [1257;4-Cl-5-Et-2-Fu], [1258;4-Cl-5-Pr-2-Fu], [1259;4-Cl-5-iPr-2-Fu], [1260;4-Cl-5-CF3-2-Fu], [1261;4-Cl-5-CHF2-2-Fu], [1262;4-Cl-5-OMe-2-Fu], [1263;4-Cl-5-OEt-2-Fu], [1264;4-Cl-5-OCF3-2-Fu], [1265;4-Cl-5-OCHF2-2-Fu], [1266;4-Cl-5-CN-2-Fu], [1267;4-Cl-5-SMe-2-Fu], [1268;4-Cl-5-SEt-2-Fu], [1269;4-Cl-5-cPr-2-Fu], [1270;4-Me-5-F-2-Fu], [1271;4-Me-5-Cl-2-Fu], [1272;4-Me-5-Br-2-Fu], [1273;4-Me-5-I-2-Fu], [1274;4-Me-5-Me-2-Fu], [1275;4-Me-5-Et-2-Fu], [1276;4-Me-5-Pr-2-Fu], [1277;4-Me-5-iPr-2-Fu], [1278;4-Me-5-CF3-2-Fu], [1279;4-Me-5-CHF2-2-Fu], [1280;4-Me-5-OMe-2-Fu], [1281;4-Me-5-OEt-2-Fu], [1282;4-Me-5-OCF3-2-Fu], [1283;4-Me-5-OCHF2-2-Fu], [1284;4-Me-5-CN-2-Fu], [1285;4-Me-5-SMe-2-Fu], [1286;4-Me-5-SEt-2-Fu], [1287;4-Me-5-cPr-2-Fu], [1288;4-Et-5-F-2-Fu], [1289;4-Et-5-Cl-2-Fu], [1290;4-Et-5-Br-2-Fu], [1291;4-Et-5-I-2-Fu], [1292;4-Et-5-Me-2-Fu], [1293;4-Et-5-Et-2-Fu], [1294;4-Et-5-Pr-2-Fu], [1295;4-Et-5-iPr-2-Fu], [1296;4-Et-5-CF3-2-Fu], [1297;4-Et-5-CHF2-2-Fu], [1298;4-Et-5-OMe-2-Fu], [1299;4-Et-5-OEt-2-Fu], [1300;4-Et-5-OCF3-2-Fu], [1301;4-Et-5-OCHF2-2-Fu], [1302;4-Et-5-CN-2-Fu], [1303;4-Et-5-SMe-2-Fu], [1304;4-Et-5-SEt-2-Fu], [1305;4-Et-5-cPr-2-Fu], [1306;4-CF3-5-F-2-Fu], [1307;4-CF3-5-Cl-2-Fu], [1308;4-CF3-5-Br-2-Fu], [1309;4-CF3-5-I-2-Fu], [1310;4-CF3-5-Me-2-Fu], [1311;4-CF3-5-Et-2-Fu], [1312;4-CF3-5-Pr-2-Fu], [1313;4-CF3-5-iPr-2-Fu], [1314;4-CF3-5-CF3-2-Fu], [1315;4-CF3-5-CHF2-2-Fu], [1316;4-CF3-5-OMe-2-Fu], [1317;4-CF3-5-OEt-2-Fu], [1318;4-CF3-5-OCF3-2-Fu], [1319;4-CF3-5-OCHF2-2-Fu], [1320;4-CF3-5-CN-2-Fu], [1321;4-CF3-5-SMe-2-Fu], [1322;4-CF3-5-SEt-2-Fu], [1323;4-CF3-5-cPr-2-Fu], [1324;4-OMe-5-F-2-Fu], [1325;4-OMe-5-Cl-2-Fu], [1326;4-OMe-5-Br-2-Fu], [1327;4-OMe-5-I-2-Fu], [1328;4-OMe-5-Me-2-Fu], [1329;4-OMe-5-Et-2-Fu], [1330;4-OMe-5-Pr-2-Fu], [1331;4-OMe-5-iPr-2-Fu], [1332;4-OMe-5-CF3-2-Fu], [1333;4-OMe-5-CHF2-2-Fu], [1334;4-OMe-5-OMe-2-Fu], [1335;4-OMe-5-OEt-2-Fu], [1336;4-OMe-5-OCF3-2-Fu], [1337;4-OMe-5-OCHF2-2-Fu], [1338;4-OMe-5-CN-2-Fu], [1339;4-OMe-5-SMe-2-Fu], [1340;4-OMe-5-SEt-2-Fu], [1341;4-OMe-5-cPr-2-Fu], [1342;4-OEt-5-F-2-Fu], [1343;4-OEt-5-Cl-2-Fu], [1344;4-OEt-5-Br-2-Fu], [1345;4-OEt-5-I-2-Fu], [1346;4-OEt-5-Me-2-Fu], [1347;4-OEt-5-Et-2-Fu], [1348;4-OEt-5-Pr-2-Fu], [1349;4-OEt-5-iPr-2-Fu], [1350;4-OEt-5-CF3-2-Fu], [1351;4-OEt-5-CHF2-2-Fu], [1352;4-OEt-5-OMe-2-Fu], [1353;4-OEt-5-OEt-2-Fu], [1354;4-OEt-5-OCF3-2-Fu], [1355;4-OEt-5-OCHF2-2-Fu], [1356;4-OEt-5-CN-2-Fu], [1357;4-OEt-5-SMe-2-Fu], [1358;4-OEt-5-SEt-2-Fu], [1359;4-OEt-5-cPr-2-Fu], [1360;4-SMe-5-F-2-Fu], [1361;4-SMe-5-Cl-2-Fu], [1362;4-SMe-5-Br-2-Fu], [1363;4-SMe-5-I-2-Fu], [1364;4-SMe-5-Me-2-Fu], [1365;4-SMe-5-Et-2-Fu], [1366;4-SMe-5-Pr-2-Fu], [1367;4-SMe-5-iPr-2-Fu], [1368;4-SMe-5-CF3-2-Fu], [1369;4-SMe-5-CHF2-2-Fu], [1370;4-SMe-5-OMe-2-Fu], [1371;4-SMe-5-OEt-2-Fu], [1372;4-SMe-5-OCF3-2-Fu], [1373;4-SMe-5-OCHF2-2-Fu], [1374;4-SMe-5-CN-2-Fu], [1375;4-SMe-5-SMe-2-Fu], [1376;4-SMe-5-SEt-2-Fu], [1377;4-SMe-5-cPr-2-Fu], [1378;3-F-2-Fu], [1379;3-Cl-2-Fu], [1380;3-Br-2-Fu], [1381;3-I-2-Fu], [1382;3-Me-2-Fu], [1383;3-Et-2-Fu], [1384;3-Pr-2-Fu], [1385;3-iPr-2-Fu], [1386;3-CF3-2-Fu], [1387;3-CHF2-2-Fu], [1388;3-OMe-2-Fu], [1389;3-OEt-2-Fu], [1390;3-OCF3-2-Fu], [1391;3-OCHF2-2-Fu], [1392;3-F-4-F-2-Fu], [1393;3-F-4-Cl-2-Fu], [1394;3-F-4-Br-2-Fu], [1395;3-F-4-I-2-Fu], [1396;3-F-4-Me-2-Fu], [1397;3-F-4-Et-2-Fu], [1398;3-F-4-Pr-2-Fu], [1399;3-F-4-iPr-2-Fu], [1400;3-F-4-CF3-2-Fu], [1401;3-F-4-CHF2-2-Fu], [1402;3-F-4-OMe-2-Fu], [1403;3-F-4-OEt-2-Fu], [1404;3-F-4-OCF3-2-Fu], [1405;3-F-4-OCHF2-2-Fu], [1406;3-F-4-CN-2-Fu], [1407;3-F-4-SMe-2-Fu], [1408;3-F-4-SEt-2-Fu], [1409;3-F-4-cPr-2-Fu], [1410;3-Cl-4-F-2-Fu], [1411;3-Cl-4-Cl-2-Fu], [1412;3-Cl-4-Br-2-Fu], [1413;3-Cl-4-I-2-Fu], [1414;3-Cl-4-Me-2-Fu], [1415;3-Cl-4-Et-2-Fu], [1416;3-Cl-4-Pr-2-Fu], [1417;3-Cl-4-iPr-2-Fu], [1418;3-Cl-4-CF3-2-Fu], [1419;3-Cl-4-CHF2-2-Fu], [1420;3-Cl-4-OMe-2-Fu], [1421;3-Cl-4-OEt-2-Fu], [1422;3-Cl-4-OCF3-2-Fu], [1423;3-Cl-4-OCHF2-2-Fu], [1424;3-

Cl-4-CN-2-Fu], [1425;3-Cl-4-SMe-2-Fu], [1426;3-Cl-4-SEt-2-Fu], [1427;3-Cl-4-cPr-2-Fu], [1428;3-Me-4-F-2-Fu], [1429;3-Me-4-Cl-2-Fu], [1430;3-Me-4-Br-2-Fu], [1431;3-Me-4-I-2-Fu], [1432;3-Me-4-Me-2-Fu], [1433;3-Me-4-Et-2-Fu], [1434;3-Me-4-Pr-2-Fu], [1435;3-Me-4-iPr-2-Fu], [1436;3-Me-4-CF3-2-Fu], [1437;3-Me-4-CHF2-2-Fu], [1438;3-Me-4-OMe-2-Fu], [1439;3-Me-4-OEt-2-Fu], [1440;3-Me-4-OCF3-2-Fu], [1441;3-Me-4-OCHF2-2-Fu], [1442;3-Me-4-CN-2-Fu], [1443;3-Me-4-SMe-2-Fu], [1444;3-Me-4-SEt-2-Fu], [1445;3-Me-4-cPr-2-Fu], [1446;3-Et-4-F-2-Fu], [1447;3-Et-4-Cl-2-Fu], [1448;3-Et-4-Br-2-Fu], [1449;3-Et-4-I-2-Fu], [1450;3-Et-4-Me-2-Fu], [1451;3-Et-4-Et-2-Fu], [1452;3-Et-4-Pr-2-Fu], [1453;3-Et-4-iPr-2-Fu], [1454;3-Et-4-CF3-2-Fu], [1455;3-Et-4-CHF2-2-Fu], [1456;3-Et-4-OMe-2-Fu], [1457;3-Et-4-OEt-2-Fu], [1458;3-Et-4-OCF3-2-Fu], [1459;3-Et-4-OCHF2-2-Fu], [1460;3-Et-4-CN-2-Fu], [1461;3-Et-4-SMe-2-Fu], [1462;3-Et-4-SEt-2-Fu], [1463;3-Et-4-cPr-2-Fu], [1464;3-CF3-4-F-2-Fu], [1465;3-CF3-4-Cl-2-Fu], [1466;3-CF3-4-Br-2-Fu], [1467;3-CF3-4-I-2-Fu], [1468;3-CF3-4-Me-2-Fu], [1469;3-CF3-4-Et-2-Fu], [1470;3-CF3-4-Pr-2-Fu], [1471;3-CF3-4-iPr-2-Fu], [1472;3-CF3-4-CF3-2-Fu], [1473;3-CF3-4-CHF2-2-Fu], [1474;3-CF3-4-OMe-2-Fu], [1475;3-CF3-4-OEt-2-Fu], [1476;3-CF3-4-OCF3-2-Fu], [1477;3-CF3-4-OCHF2-2-Fu], [1478;3-CF3-4-CN-2-Fu], [1479;3-CF3-4-SMe-2-Fu], [1480;3-CF3-4-SEt-2-Fu], [1481;3-CF3-4-cPr-2-Fu], [1482;3-OMe-4-F-2-Fu], [1483;3-OMe-4-Cl-2-Fu], [1484;3-OMe-4-Br-2-Fu], [1485;3-OMe-4-I-2-Fu], [1486;3-OMe-4-Me-2-Fu], [1487;3-OMe-4-Et-2-Fu], [1488;3-OMe-4-Pr-2-Fu], [1489;3-OMe-4-iPr-2-Fu], [1490;3-OMe-4-CF3-2-Fu], [1491;3-OMe-4-CHF2-2-Fu], [1492;3-OMe-4-OMe-2-Fu], [1493;3-OMe-4-OEt-2-Fu], [1494;3-OMe-4-OCF3-2-Fu], [1495;3-OMe-4-OCHF2-2-Fu], [1496;3-OMe-4-CN-2-Fu], [1497;3-OMe-4-SMe-2-Fu], [1498;3-OMe-4-SEt-2-Fu], [1499;3-OMe-4-cPr-2-Fu], [1500;3-OEt-4-F-2-Fu], [1501;3-OEt-4-Cl-2-Fu], [1502;3-OEt-4-Br-2-Fu], [1503;3-OEt-4-I-2-Fu], [1504;3-OEt-4-Me-2-Fu], [1505;3-OEt-4-Et-2-Fu], [1506;3-OEt-4-Pr-2-Fu], [1507;3-OEt-4-iPr-2-Fu], [1508;3-OEt-4-CF3-2-Fu], [1509;3-OEt-4-CHF2-2-Fu], [1510;3-OEt-4-OMe-2-Fu], [1511;3-OEt-4-OEt-2-Fu], [1512;3-OEt-4-OCF3-2-Fu], [1513;3-OEt-4-OCHF2-2-Fu], [1514;3-OEt-4-CN-2-Fu], [1515;3-OEt-4-SMe-2-Fu], [1516;3-OEt-4-SEt-2-Fu], [1517;3-OEt-4-cPr-2-Fu], [1518;3-SMe-4-F-2-Fu], [1519;3-SMe-4-Cl-2-Fu], [1520;3-SMe-4-Br-2-Fu], [1521;3-SMe-4-I-2-Fu], [1522;3-SMe-4-Me-2-Fu], [1523;3-SMe-4-Et-2-Fu], [1524;3-SMe-4-Pr-2-Fu], [1525;3-SMe-4-iPr-2-Fu], [1526;3-SMe-4-CF3-2-Fu], [1527;3-SMe-4-CHF2-2-Fu], [1528;3-SMe-4-OMe-2-Fu], [1529;3-SMe-4-OEt-2-Fu], [1530;3-SMe-4-OCF3-2-Fu], [1531;3-SMe-4-OCHF2-2-Fu], [1532;3-SMe-4-CN-2-Fu], [1533;3-SMe-4-SMe-2-Fu], [1534;3-SMe-4-SEt-2-Fu], [1535;3-SMe-4-cPr-2-Fu], [1536;3-F-5-F-2-Fu], [1537;3-F-5-Cl-2-Fu], [1538;3-F-5-Br-2-Fu], [1539;3-F-5-I-2-Fu], [1540;3-F-5-Me-2-Fu], [1541;3-F-5-Et-2-Fu], [1542;3-F-5-Pr-2-Fu], [1543;3-F-5-iPr-2-Fu], [1544;3-F-5-CF3-2-Fu], [1545;3-F-5-CHF2-2-Fu], [1546;3-F-5-OMe-2-Fu], [1547;3-F-5-OEt-2-Fu], [1548;3-F-5-OCF3-2-Fu], [1549;3-F-5-OCHF2-2-Fu], [1550;3-F-5-CN-2-Fu], [1551;3-F-5-SMe-2-Fu], [1552;3-F-5-SEt-2-Fu], [1553;3-F-5-cPr-2-Fu], [1554;3-Cl-5-F-2-Fu], [1555;3-Cl-5-Cl-2-Fu], [1556;3-Cl-5-Br-2-Fu], [1557;3-Cl-5-I-2-Fu], [1558;3-Cl-5-Me-2-Fu], [1559;3-Cl-5-Et-2-Fu], [1560;3-Cl-5-Pr-2-Fu], [1561;3-Cl-5-iPr-2-Fu], [1562;3-Cl-5-CF3-2-Fu], [1563;3-Cl-5-CHF2-2-Fu], [1564;3-Cl-5-OMe-2-Fu], [1565;3-Cl-5-OEt-2-Fu], [1566;3-Cl-5-OCF3-2-Fu], [1567;3-Cl-5-OCHF2-2-Fu], [1568;3-Cl-5-CN-2-Fu], [1569;3-Cl-5-SMe-2-Fu], [1570;3-Cl-5-SEt-2-Fu], [1571;3-Cl-5-cPr-2-Fu], [1572;3-Me-5-F-2-Fu], [1573;3-Me-5-Cl-2-Fu], [1574;3-Me-5-Br-2-Fu], [1575;3-Me-5-I-2-Fu], [1576;3-Me-5-Me-2-Fu], [1577;3-Me-5-Et-2-Fu], [1578;3-Me-5-Pr-2-Fu], [1579;3-Me-5-iPr-2-Fu], [1580;3-Me-5-CF3-2-Fu], [1581;3-Me-5-CHF2-2-Fu], [1582;3-Me-5-OMe-2-Fu], [1583;3-Me-5-OEt-2-Fu], [1584;3-Me-5-OCF3-2-Fu], [1585;3-Me-5-OCHF2-2-Fu], [1586;3-Me-5-CN-2-Fu], [1587;3-Me-5-SMe-2-Fu], [1588;3-Me-5-SEt-2-Fu], [1589;3-Me-5-cPr-2-Fu], [1590;3-Et-5-F-2-Fu], [1591;3-Et-5-Cl-2-Fu], [1592;3-Et-5-Br-2-Fu], [1593;3-Et-5-I-2-Fu], [1594;3-Et-5-Me-2-Fu], [1595;3-Et-5-Et-2-Fu], [1596;3-Et-5-Pr-2-Fu], [1597;3-Et-5-iPr-2-Fu], [1598;3-Et-5-CF3-2-Fu], [1599;3-Et-5-CHF2-2-Fu], [1600;3-Et-5-OMe-2-Fu],
[1601;3-Et-5-OEt-2-Fu], [1602;3-Et-5-OCF3-2-Fu], [1603;3-Et-5-OCHF2-2-Fu], [1604;3-Et-5-CN-2-Fu], [1605;3-Et-5-SMe-2-Fu], [1606;3-Et-5-SEt-2-Fu], [1607;3-Et-5-cPr-2-Fu], [1608;3-CF3-5-F-2-Fu], [1609;3-CF3-5-Cl-2-Fu], [1610;3-CF3-5-Br-2-Fu], [1611;3-CF3-5-I-2-Fu], [1612;3-CF3-5-Me-2-Fu], [1613;3-CF3-5-Et-2-Fu], [1614;3-CF3-5-Pr-2-Fu], [1615;3-CF3-5-iPr-2-Fu], [1616;3-CF3-5-CF3-2-Fu], [1617;3-CF3-5-CHF2-2-Fu], [1618;3-CF3-5-OMe-2-Fu], [1619;3-CF3-5-OEt-2-Fu], [1620;3-CF3-5-OCF3-2-Fu], [1621;3-CF3-5-OCHF2-2-Fu], [1622;3-CF3-5-CN-2-Fu], [1623;3-CF3-5-SMe-2-Fu], [1624;3-CF3-5-SEt-2-Fu], [1625;3-CF3-5-cPr-2-Fu], [1626;3-OMe-5-F-2-Fu], [1627;3-OMe-5-Cl-2-Fu], [1628;3-OMe-5-Br-2-Fu], [1629;3-OMe-5-I-2-Fu], [1630;3-OMe-5-Me-2-Fu], [1631;3-OMe-5-Et-2-Fu], [1632;3-OMe-5-Pr-2-Fu], [1633;3-OMe-5-iPr-2-Fu], [1634;3-OMe-5-CF3-2-Fu], [1635;3-OMe-5-CHF2-2-Fu], [1636;3-OMe-5-OMe-2-Fu], [1637;3-OMe-5-OEt-2-Fu], [1638;3-OMe-5-OCF3-2-Fu], [1639;3-OMe-5-OCHF2-2-Fu], [1640;3-OMe-5-CN-2-Fu], [1641;3-OMe-5-SMe-2-Fu], [1642;3-OMe-5-SEt-2-Fu], [1643;3-OMe-5-cPr-2-Fu], [1644;3-OEt-5-F-2-Fu], [1645;3-OEt-5-Cl-2-Fu], [1646;3-OEt-5-Br-2-Fu], [1647;3-OEt-5-I-2-Fu], [1648;3-OEt-5-Me-2-Fu], [1649;3-OEt-5-Et-2-Fu], [1650;3-OEt-5-Pr-2-Fu], [1651;3-OEt-5-iPr-2-Fu], [1652;3-OEt-5-CF3-2-Fu], [1653;3-OEt-5-CHF2-2-Fu], [1654;3-OEt-5-OMe-2-Fu], [1655;3-OEt-5-OEt-2-Fu], [1656;3-OEt-5-OCF3-2-Fu], [1657;3-OEt-5-OCHF2-2-Fu], [1658;3-OEt-5-CN-2-Fu], [1659;3-OEt-5-SMe-2-Fu], [1660;3-OEt-5-SEt-2-Fu], [1661;3-OEt-5-cPr-2-Fu], [1662;3-SMe-5-F-2-Fu], [1663;3-SMe-5-Cl-2-Fu], [1664;3-SMe-5-Br-2-Fu], [1665;3-SMe-5-I-2-Fu], [1666;3-SMe-5-Me-2-Fu], [1667;3-SMe-5-Et-2-Fu], [1668;3-SMe-5-Pr-2-Fu], [1669;3-SMe-5-iPr-2-Fu], [1670;3-SMe-5-CF3-2-Fu], [1671;3-SMe-5-CHF2-2-Fu], [1672;3-SMe-5-OMe-2-Fu], [1673;3-SMe-5-OEt-2-Fu], [1674;3-SMe-5-OCF3-2-Fu], [1675;3-SMe-5-OCHF2-2-Fu], [1676;3-SMe-5-CN-2-Fu], [1677;3-SMe-5-SMe-2-Fu], [1678;3-SMe-5-SEt-2-Fu], [1679;3-SMe-5-cPr-2-Fu], [1680;3-Me-4-Me-5-F-2-Fu], [1681;3-Me-4-Me-5-Cl-2-Fu], [1682;3-Me-4-Me-5-Br-2-Fu], [1683;3-Me-4-Me-5-I-2-Fu], [1684;3-Me-4-Me-5-Me-2-Fu], [1685;3-Me-4-Me-5-Et-2-Fu], [1686;3-Me-4-Me-5-Pr-2-Fu], [1687;3-Me-4-Me-5-iPr-2-Fu], [1688;3-Me-4-Me-5-CF3-2-Fu], [1689;3-Me-4-Me-5-CHF2-2-Fu], [1690;3-Me-4-Me-5-OMe-2-Fu], [1691;3-Me-4-Me-5-OEt-2-Fu], [1692;3-Me-4-Me-5-OCF3-2-Fu], [1693;3-Me-4-Me-5-OCHF2-2-Fu], [1694;3-Me-4-Me-5-CN-2-Fu], [1695;3-Me-4-Me-5-SMe-2-Fu], [1696;3-Me-4-Me-5-SEt-2-Fu], [1697;3-Me-4-Me-5-cPr-2-Fu], [1698;3-Me-4-F-5-Me-2-Fu], [1699;3-Me-4-Cl-5-Me-2-Fu], [1700;3-Me-4-Br-5-Me-2-Fu],
[1701;3-Me-4-I-5-Me-2-Fu], [1702;3-Me-4-Et-5-Me-2-Fu], [1703;3-Me-4-Pr-5-Me-2-Fu], [1704;3-Me-4-iPr-5-Me-2-Fu], [1705;3-Me-4-CF3-5-Me-2-Fu], [1706;3-Me-4-CHF2-5-Me-2-Fu], [1707;3-Me-4-OMe-5-Me-2-Fu], [1708;3-Me-4-OEt-5-Me-2-Fu], [1709;3-Me-4-OCF3-5-Me-2-Fu],

[1710;3-Me-4-OCHF2-5-Me-2-Fu], [1711;3-Me-4-CN-5-Me-2-Fu], [1712;3-Me-4-SMe-5-Me-2-Fu], [1713;3-Me-4-SEt-5-Me-2-Fu], [1714;3-Me-4-cPr-5-Me-2-Fu], [1715;-2-Thio], [1716;3-F-2-Thio], [1717;4-Cl-2-Thio], [1718;4-Br-2-Thio], [1719;4-I-2-Thio], [1720;4-Me-2-Thio], [1721;4-Et-2-Thio], [1722;4-Pr-2-Thio], [1723;4-iPr-2-Thio], [1724;4-CF3-2-Thio], [1725;4-CHF2-2-Thio], [1726;4-OMe-2-Thio], [1727;4-OEt-2-Thio], [1728;4-OCF3-2-Thio], [1729;4-OCHF2-2-Thio], [1730;4-CN-2-Thio], [1731;4-SMe-2-Thio], [1732;4-SEt-2-Thio], [1733;4-cPr-2-Thio], [1734;5-F-2-Thio], [1735;5-Cl-2-Thio], [1736;5-Br-2-Thio], [1737;5-I-2-Thio], [1738;5-Me-2-Thio], [1739;5-Et-2-Thio], [1740;5-Pr-2-Thio], [1741;5-iPr-2-Thio], [1742;5-CF3-2-Thio], [1743;5-CHF2-2-Thio], [1744;5-OMe-2-Thio], [1745;5-OEt-2-Thio], [1746;5-OCF3-2-Thio], [1747;5-OCHF2-2-Thio], [1748;5-CN-2-Thio], [1749;5-SMe-2-Thio], [1750;5-SEt-2-Thio], [1751;5-cPr-2-Thio], [1752;4-F-5-F-2-Thio], [1753;4-F-5-Cl-2-Thio], [1754;4-F-5-Br-2-Thio], [1755;4-F-5-I-2-Thio], [1756;4-F-5-Me-2-Thio], [1757;4-F-5-Et-2-Thio], [1758;4-F-5-Pr-2-Thio], [1759;4-F-5-iPr-2-Thio], [1760;4-F-5-CF3-2-Thio], [1761;4-F-5-CHF2-2-Thio], [1762;4-F-5-OMe-2-Thio], [1763;4-F-5-OEt-2-Thio], [1764;4-F-5-OCF3-2-Thio], [1765;4-F-5-OCHF2-2-Thio], [1766;4-F-5-CN-2-Thio], [1767;4-F-5-SMe-2-Thio], [1768;4-F-5-SEt-2-Thio], [1769;4-F-5-cPr-2-Thio], [1770;4-Cl-5-F-2-Thio], [1771;4-Cl-5-Cl-2-Thio], [1772;4-Cl-5-Br-2-Thio], [1773;4-Cl-5-I-2-Thio], [1774;4-Cl-5-Me-2-Thio], [1775;4-Cl-5-Et-2-Thio], [1776;4-Cl-5-Pr-2-Thio], [1777;4-Cl-5-iPr-2-Thio], [1778;4-Cl-5-CF3-2-Thio], [1779;4-Cl-5-CHF2-2-Thio], [1780;4-Cl-5-OMe-2-Thio], [1781;4-Cl-5-OEt-2-Thio], [1782;4-Cl-5-OCF3-2-Thio], [1783;4-Cl-5-OCHF2-2-Thio], [1784;4-Cl-5-CN-2-Thio], [1785;4-Cl-5-SMe-2-Thio], [1786;4-Cl-5-SEt-2-Thio], [1787;4-Cl-5-cPr-2-Thio], [1788;4-Me-5-F-2-Thio], [1789;4-Me-5-Cl-2-Thio], [1790;4-Me-5-Br-2-Thio], [1791;4-Me-5-I-2-Thio], [1792;4-Me-5-Me-2-Thio], [1793;4-Me-5-Et-2-Thio], [1794;4-Me-5-Pr-2-Thio], [1795;4-Me-5-iPr-2-Thio], [1796;4-Me-5-CF3-2-Thio], [1797;4-Me-5-CHF2-2-Thio], [1798;4-Me-5-OMe-2-Thio], [1799;4-Me-5-OEt-2-Thio], [1800;4-Me-5-OCF3-2-Thio], [1801;4-Me-5-OCHF2-2-Thio], [1802;4-Me-5-CN-2-Thio], [1803;4-Me-5-SMe-2-Thio], [1804;4-Me-5-SEt-2-Thio], [1805;4-Me-5-cPr-2-Thio], [1806;4-Et-5-F-2-Thio], [1807;4-Et-5-Cl-2-Thio], [1808;4-Et-5-Br-2-Thio], [1809;4-Et-5-I-2-Thio], [1810;4-Et-5-Me-2-Thio], [1811;4-Et-5-Et-2-Thio], [1812;4-Et-5-Pr-2-Thio], [1813;4-Et-5-iPr-2-Thio], [1814;4-Et-5-CF3-2-Thio], [1815;4-Et-5-CHF2-2-Thio], [1816;4-Et-5-OMe-2-Thio], [1817;4-Et-5-OEt-2-Thio], [1818;4-Et-5-OCF3-2-Thio], [1819;4-Et-5-OCHF2-2-Thio], [1820;4-Et-5-CN-2-Thio], [1821;4-Et-5-SMe-2-Thio], [1822;4-Et-5-SEt-2-Thio], [1823;4-Et-5-cPr-2-Thio], [1824;4-CF3-5-F-2-Thio], [1825;4-CF3-5-Cl-2-Thio], [1826;4-CF3-5-Br-2-Thio], [1827;4-CF3-5-I-2-Thio], [1828;4-CF3-5-Me-2-Thio], [1829;4-CF3-5-Et-2-Thio], [1830;4-CF3-5-Pr-2-Thio], [1831;4-CF3-5-iPr-2-Thio], [1832;4-CF3-5-CF3-2-Thio], [1833;4-CF3-5-CHF2-2-Thio], [1834;4-CF3-5-OMe-2-Thio], [1835;4-CF3-5-OEt-2-Thio], [1836;4-CF3-5-OCF3-2-Thio], [1837;4-CF3-5-OCHF2-2-Thio], [1838;4-CF3-5-CN-2-Thio], [1839;4-CF3-5-SMe-2-Thio], [1840;4-CF3-5-SEt-2-Thio], [1841;4-CF3-5-cPr-2-Thio], [1842;4-OMe-5-F-2-Thio], [1843;4-OMe-5-Cl-2-Thio], [1844;4-OMe-5-Br-2-Thio], [1845;4-OMe-5-I-2-Thio], [1846;4-OMe-5-Me-2-Thio], [1847;4-OMe-5-Et-2-Thio], [1848;4-OMe-5-Pr-2-Thio], [1849;4-OMe-5-iPr-2-Thio], [1850;4-OMe-5-CF3-2-Thio], [1851;4-OMe-5-CHF2-2-Thio], [1852;4-OMe-5-OMe-2-Thio], [1853;4-OMe-5-OEt-2-Thio], [1854;4-OMe-5-OCF3-2-Thio], [1855;4-OMe-5-OCHF2-2-Thio], [1856;4-OMe-5-CN-2-Thio], [1857;4-OMe-5-SMe-2-Thio], [1858;4-OMe-5-SEt-2-Thio], [1859;4-OMe-5-cPr-2-Thio], [1860;4-OEt-5-F-2-Thio], [1861;4-OEt-5-Cl-2-Thio], [1862;4-OEt-5-Br-2-Thio], [1863;4-OEt-5-I-2-Thio], [1864;4-OEt-5-Me-2-Thio], [1865;4-OEt-5-Et-2-Thio], [1866;4-OEt-5-Pr-2-Thio], [1867;4-OEt-5-iPr-2-Thio], [1868;4-OEt-5-CF3-2-Thio], [1869;4-OEt-5-CHF2-2-Thio], [1870;4-OEt-5-OMe-2-Thio], [1871;4-OEt-5-OEt-2-Thio], [1872;4-OEt-5-OCF3-2-Thio], [1873;4-OEt-5-OCHF2-2-Thio], [1874;4-OEt-5-CN-2-Thio], [1875;4-OEt-5-SMe-2-Thio], [1876;4-OEt-5-SEt-2-Thio], [1877;4-OEt-5-cPr-2-Thio], [1878;4-SMe-5-F-2-Thio], [1879;4-SMe-5-Cl-2-Thio], [1880;4-SMe-5-Br-2-Thio], [1881;4-SMe-5-I-2-Thio], [1882;4-SMe-5-Me-2-Thio], [1883;4-SMe-5-Et-2-Thio], [1884;4-SMe-5-Pr-2-Thio], [1885;4-SMe-5-iPr-2-Thio], [1886;4-SMe-5-CF3-2-Thio], [1887;4-SMe-5-CHF2-2-Thio], [1888;4-SMe-5-OMe-2-Thio], [1889;4-SMe-5-OEt-2-Thio], [1890;4-SMe-5-OCF3-2-Thio], [1891;4-SMe-5-OCHF2-2-Thio], [1892;4-SMe-5-CN-2-Thio], [1893;4-SMe-5-SMe-2-Thio], [1894;4-SMe-5-SEt-2-Thio], [1895;4-SMe-5-cPr-2-Thio], [1896;3-F-2-Thio], [1897;3-Cl-2-Thio], [1898;3-Br-2-Thio], [1899;3-I-2-Thio], [1900;3-Me-2-Thio], [1901;3-Et-2-Thio], [1902;3-Pr-2-Thio], [1903;3-iPr-2-Thio], [1904;3-CF3-2-Thio], [1905;3-CHF2-2-Thio], [1906;3-OMe-2-Thio], [1907;3-OEt-2-Thio], [1908;3-OCF3-2-Thio], [1909;3-OCHF2-2-Thio], [1910;3-F-4-F-2-Thio], [1911;3-F-4-Cl-2-Thio], [1912;3-F-4-Br-2-Thio], [1913;3-F-4-I-2-Thio], [1914;3-F-4-Me-2-Thio], [1915;3-F-4-Et-2-Thio], [1916;3-F-4-Pr-2-Thio], [1917;3-F-4-iPr-2-Thio], [1918;3-F-4-CF3-2-Thio], [1919;3-F-4-CHF2-2-Thio], [1920;3-F-4-OMe-2-Thio], [1921;3-F-4-OEt-2-Thio], [1922;3-F-4-OCF3-2-Thio], [1923;3-F-4-OCHF2-2-Thio], [1924;3-F-4-CN-2-Thio], [1925;3-F-4-SMe-2-Thio], [1926;3-F-4-SEt-2-Thio], [1927;3-F-4-cPr-2-Thio], [1928;3-Cl-4-F-2-Thio], [1929;3-Cl-4-Cl-2-Thio], [1930;3-Cl-4-Br-2-Thio], [1931;3-Cl-4-I-2-Thio], [1932;3-Cl-4-Me-2-Thio], [1933;3-Cl-4-Et-2-Thio], [1934;3-Cl-4-Pr-2-Thio], [1935;3-Cl-4-iPr-2-Thio], [1936;3-Cl-4-CF3-2-Thio], [1937;3-Cl-4-CHF2-2-Thio], [1938;3-Cl-4-OMe-2-Thio], [1939;3-Cl-4-OEt-2-Thio], [1940;3-Cl-4-OCF3-2-Thio], [1941;3-Cl-4-OCHF2-2-Thio], [1942;3-Cl-4-CN-2-Thio], [1943;3-Cl-4-SMe-2-Thio], [1944;3-Cl-4-SEt-2-Thio], [1945;3-Cl-4-cPr-2-Thio], [1946;3-Me-4-F-2-Thio], [1947;3-Me-4-Cl-2-Thio], [1948;3-Me-4-Br-2-Thio], [1949;3-Me-4-I-2-Thio], [1950;3-Me-4-Me-2-Thio], [1951;3-Me-4-Et-2-Thio], [1952;3-Me-4-Pr-2-Thio], [1953;3-Me-4-iPr-2-Thio], [1954;3-Me-4-CF3-2-Thio], [1955;3-Me-4-CHF2-2-Thio], [1956;3-Me-4-OMe-2-Thio], [1957;3-Me-4-OEt-2-Thio], [1958;3-Me-4-OCF3-2-Thio], [1959;3-Me-4-OCHF2-2-Thio], [1960;3-Me-4-CN-2-Thio], [1961;3-Me-4-SMe-2-Thio], [1962;3-Me-4-SEt-2-Thio], [1963;3-Me-4-cPr-2-Thio], [1964;3-Et-4-F-2-Thio], [1965;3-Et-4-Cl-2-Thio], [1966;3-Et-4-Br-2-Thio], [1967;3-Et-4-I-2-Thio], [1968;3-Et-4-Me-2-Thio], [1969;3-Et-4-Et-2-Thio], [1970;3-Et-4-Pr-2-Thio], [1971;3-Et-4-iPr-2-Thio], [1972;3-Et-4-CF3-2-Thio], [1973;3-Et-4-CHF2-2-Thio], [1974;3-Et-4-OMe-2-Thio], [1975;3-Et-4-OEt-2-Thio], [1976;3-Et-4-OCF3-2-Thio], [1977;3-Et-4-OCHF2-2-Thio], [1978;3-Et-4-CN-2-Thio], [1979;3-Et-4-SMe-2-Thio], [1980;3-Et-4-SEt-2-Thio], [1981;3-Et-4-cPr-2-Thio], [1982;3-CF3-4-F-2-Thio], [1983;3-CF3-4-Cl-2-Thio], [1984;3-CF3-4-Br-2-Thio], [1985;3-CF3-4-I-2-Thio], [1986;3-CF3-4-Me-2-Thio], [1987;3-CF3-4-Et-2-Thio], [1988;3-CF3-4-Pr-2-Thio], [1989;3-CF3-4-iPr-2-Thio], [1990;3-CF3-4-CF3-2-Thio], [1991;3-CF3-4-CHF2-2-Thio], [1992;3-CF3-4-

OMe-2-Thio], [1993;3-CF3-4-OEt-2-Thio], [1994;3-CF3-4-OCF3-2-Thio], [1995;3-CF3-4-OCHF2-2-Thio], [1996;3-CF3-4-CN-2-Thio], [1997;3-CF3-4-SMe-2-Thio], [1998;3-CF3-4-SEt-2-Thio], [1999;3-CF3-4-cPr-2-Thio], [2000;3-OMe-4-F-2-Thio], [2001;3-OMe-4-Cl-2-Thio], [2002;3-OMe-4-Br-2-Thio], [2003;3-OMe-4-I-2-Thio], [2004;3-OMe-4-Me-2-Thio], [2005;3-OMe-4-Et-2-Thio], [2006;3-OMe-4-Pr-2-Thio], [2007;3-OMe-4-iPr-2-Thio], [2008;3-OMe-4-CF3-2-Thio], [2009;3-OMe-4-CHF2-2-Thio], [2010;3-OMe-4-OMe-2-Thio], [2011;3-OMe-4-OEt-2-Thio], [2012;3-OMe-4-OCF3-2-Thio], [2013;3-OMe-4-OCHF2-2-Thio], [2014;3-OMe-4-CN-2-Thio], [2015;3-OMe-4-SMe-2-Thio], [2016;3-OMe-4-SEt-2-Thio], [2017;3-OMe-4-cPr-2-Thio], [2018;3-OEt-4-F-2-Thio], [2019;3-OEt-4-Cl-2-Thio], [2020;3-OEt-4-Br-2-Thio], [2021;3-OEt-4-I-2-Thio], [2022;3-OEt-4-Me-2-Thio], [2023;3-OEt-4-Et-2-Thio], [2024;3-OEt-4-Pr-2-Thio], [2025;3-OEt-4-iPr-2-Thio], [2026;3-OEt-4-CF3-2-Thio], [2027;3-OEt-4-CHF2-2-Thio], [2028;3-OEt-4-OMe-2-Thio], [2029;3-OEt-4-OEt-2-Thio], [2030;3-OEt-4-OCF3-2-Thio], [2031;3-OEt-4-OCHF2-2-Thio], [2032;3-OEt-4-CN-2-Thio], [2033;3-OEt-4-SMe-2-Thio], [2034;3-OEt-4-SEt-2-Thio], [2035;3-OEt-4-cPr-2-Thio], [2036;3-SMe-4-F-2-Thio], [2037;3-SMe-4-Cl-2-Thio], [2038;3-SMe-4-Br-2-Thio], [2039;3-SMe-4-I-2-Thio], [2040;3-SMe-4-Me-2-Thio], [2041;3-SMe-4-Et-2-Thio], [2042;3-SMe-4-Pr-2-Thio], [2043;3-SMe-4-iPr-2-Thio], [2044;3-SMe-4-CF3-2-Thio], [2045;3-SMe-4-CHF2-2-Thio], [2046;3-SMe-4-OMe-2-Thio], [2047;3-SMe-4-OEt-2-Thio], [2048;3-SMe-4-OCF3-2-Thio], [2049;3-SMe-4-OCHF2-2-Thio], [2050;3-SMe-4-CN-2-Thio], [2051;3-SMe-4-SMe-2-Thio], [2052;3-SMe-4-SEt-2-Thio], [2053;3-SMe-4-cPr-2-Thio], [2054;3-F-5-F-2-Thio], [2055;3-F-5-Cl-2-Thio], [2056;3-F-5-Br-2-Thio], [2057;3-F-5-I-2-Thio], [2058;3-F-5-Me-2-Thio], [2059;3-F-5-Et-2-Thio], [2060;3-F-5-Pr-2-Thio], [2061;3-F-5-iPr-2-Thio], [2062;3-F-5-CF3-2-Thio], [2063;3-F-5-CHF2-2-Thio], [2064;3-F-5-OMe-2-Thio], [2065;3-F-5-OEt-2-Thio], [2066;3-F-5-OCF3-2-Thio], [2067;3-F-5-OCHF2-2-Thio], [2068;3-F-5-CN-2-Thio], [2069;3-F-5-SMe-2-Thio], [2070;3-F-5-SEt-2-Thio], [2071;3-F-5-cPr-2-Thio], [2072;3-Cl-5-F-2-Thio], [2073;3-Cl-5-Cl-2-Thio], [2074;3-Cl-5-Br-2-Thio], [2075;3-Cl-5-I-2-Thio], [2076;3-Cl-5-Me-2-Thio], [2077;3-Cl-5-Et-2-Thio], [2078;3-Cl-5-Pr-2-Thio], [2079;3-Cl-5-iPr-2-Thio], [2080;3-Cl-5-CF3-2-Thio], [2081;3-Cl-5-CHF2-2-Thio], [2082;3-Cl-5-OMe-2-Thio], [2083;3-Cl-5-OEt-2-Thio], [2084;3-Cl-5-OCF3-2-Thio], [2085;3-Cl-5-OCHF2-2-Thio], [2086;3-Cl-5-CN-2-Thio], [2087;3-Cl-5-SMe-2-Thio], [2088;3-Cl-5-SEt-2-Thio], [2089;3-Cl-5-cPr-2-Thio], [2090;3-Me-5-F-2-Thio], [2091;3-Me-5-Cl-2-Thio], [2092;3-Me-5-Br-2-Thio], [2093;3-Me-5-I-2-Thio], [2094;3-Me-5-Me-2-Thio], [2095;3-Me-5-Et-2-Thio], [2096;3-Me-5-Pr-2-Thio], [2097;3-Me-5-iPr-2-Thio], [2098;3-Me-5-CF3-2-Thio], [2099;3-Me-5-CHF2-2-Thio], [2100;3-Me-5-OMe-2-Thio],
[2101;3-Me-5-OEt-2-Thio], [2102;3-Me-5-OCF3-2-Thio], [2103;3-Me-5-OCHF2-2-Thio], [2104;3-Me-5-CN-2-Thio], [2105;3-Me-5-SMe-2-Thio], [2106;3-Me-5-SEt-2-Thio], [2107;3-Me-5-cPr-2-Thio], [2108;3-Et-5-F-2-Thio], [2109;3-Et-5-Cl-2-Thio], [2110;3-Et-5-Br-2-Thio], [2111;3-Et-5-I-2-Thio], [2112;3-Et-5-Me-2-Thio], [2113;3-Et-5-Et-2-Thio], [2114;3-Et-5-Pr-2-Thio], [2115;3-Et-5-iPr-2-Thio], [2116;3-Et-5-CF3-2-Thio], [2117;3-Et-5-CHF2-2-Thio], [2118;3-Et-5-OMe-2-Thio], [2119;3-Et-5-OEt-2-Thio], [2120;3-Et-5-OCF3-2-Thio], [2121;3-Et-5-OCHF2-2-Thio], [2122;3-Et-5-CN-2-Thio], [2123;3-Et-5-SMe-2-Thio], [2124;3-Et-5-SEt-2-Thio], [2125;3-Et-5-cPr-2-Thio], [2126;3-CF3-5-F-2-Thio], [2127;3-CF3-5-Cl-2-Thio], [2128;3-CF3-5-Br-2-Thio], [2129;3-CF3-5-I-2-Thio], [2130;3-CF3-5-Me-2-Thio], [2131;3-CF3-5-Et-2-Thio], [2132;3-CF3-5-Pr-2-Thio], [2133;3-CF3-5-iPr-2-Thio], [2134;3-CF3-5-CF3-2-Thio], [2135;3-CF3-5-CHF2-2-Thio], [2136;3-CF3-5-OMe-2-Thio], [2137;3-CF3-5-OEt-2-Thio], [2138;3-CF3-5-OCF3-2-Thio], [2139;3-CF3-5-OCHF2-2-Thio], [2140;3-CF3-5-CN-2-Thio], [2141;3-CF3-5-SMe-2-Thio], [2142;3-CF3-5-SEt-2-Thio], [2143;3-CF3-5-cPr-2-Thio], [2144;3-OMe-5-F-2-Thio], [2145;3-OMe-5-Cl-2-Thio], [2146;3-OMe-5-Br-2-Thio], [2147;3-OMe-5-I-2-Thio], [2148;3-OMe-5-Me-2-Thio], [2149;3-OMe-5-Et-2-Thio], [2150;3-OMe-5-Pr-2-Thio], [2151;3-OMe-5-iPr-2-Thio], [2152;3-OMe-5-CF3-2-Thio], [2153;3-OMe-5-CHF2-2-Thio], [2154;3-OMe-5-OMe-2-Thio], [2155;3-OMe-5-OEt-2-Thio], [2156;3-OMe-5-OCF3-2-Thio], [2157;3-OMe-5-OCHF2-2-Thio], [2158;3-OMe-5-CN-2-Thio], [2159;3-OMe-5-SMe-2-Thio], [2160;3-OMe-5-SEt-2-Thio], [2161;3-OMe-5-cPr-2-Thio], [2162;3-OEt-5-F-2-Thio], [2163;3-OEt-5-Cl-2-Thio], [2164;3-OEt-5-Br-2-Thio], [2165;3-OEt-5-I-2-Thio], [2166;3-OEt-5-Me-2-Thio], [2167;3-OEt-5-Et-2-Thio], [2168;3-OEt-5-Pr-2-Thio], [2169;3-OEt-5-iPr-2-Thio], [2170;3-OEt-5-CF3-2-Thio], [2171;3-OEt-5-CHF2-2-Thio], [2172;3-OEt-5-OMe-2-Thio], [2173;3-OEt-5-OEt-2-Thio], [2174;3-OEt-5-OCF3-2-Thio], [2175;3-OEt-5-OCHF2-2-Thio], [2176;3-OEt-5-CN-2-Thio], [2177;3-OEt-5-SMe-2-Thio], [2178;3-OEt-5-SEt-2-Thio], [2179;3-OEt-5-cPr-2-Thio], [2180;3-SMe-5-F-2-Thio], [2181;3-SMe-5-Cl-2-Thio], [2182;3-SMe-5-Br-2-Thio], [2183;3-SMe-5-I-2-Thio], [2184;3-SMe-5-Me-2-Thio], [2185;3-SMe-5-Et-2-Thio], [2186;3-SMe-5-Pr-2-Thio], [2187;3-SMe-5-iPr-2-Thio], [2188;3-SMe-5-CF3-2-Thio], [2189;3-SMe-5-CHF2-2-Thio], [2190;3-SMe-5-OMe-2-Thio], [2191;3-SMe-5-OEt-2-Thio], [2192;3-SMe-5-OCF3-2-Thio], [2193;3-SMe-5-OCHF2-2-Thio], [2194;3-SMe-5-CN-2-Thio], [2195;3-SMe-5-SMe-2-Thio], [2196;3-SMe-5-SEt-2-Thio], [2197;3-SMe-5-cPr-2-Thio], [2198;3-Me-4-Me-5-F-2-Thio], [2199;3-Me-4-Me-5-Cl-2-Thio], [2200;3-Me-4-Me-5-Br-2-Thio], [2201;3-Me-4-Me-5-I-2-Thio], [2202;3-Me-4-Me-5-Me-2-Thio], [2203;3-Me-4-Me-5-Et-2-Thio], [2204;3-Me-4-Me-5-Pr-2-Thio], [2205;3-Me-4-Me-5-iPr-2-Thio], [2206;3-Me-4-Me-5-CF3-2-Thio], [2207;3-Me-4-Me-5-CHF2-2-Thio], [2208;3-Me-4-Me-5-OMe-2-Thio], [2209;3-Me-4-Me-5-OEt-2-Thio], [2210;3-Me-4-Me-5-OCF3-2-Thio], [2211;3-Me-4-Me-5-OCHF2-2-Thio], [2212;3-Me-4-Me-5-CN-2-Thio], [2213;3-Me-4-Me-5-SMe-2-Thio], [2214;3-Me-4-Me-5-SEt-2-Thio], [2215;3-Me-4-Me-5-cPr-2-Thio], [2216;3-Me-4-F-5-Me-2-Thio], [2217;3-Me-4-Cl-5-Me-2-Thio], [2218;3-Me-4-Br-5-Me-2-Thio], [2219;3-Me-4-I-5-Me-2-Thio], [2220;3-Me-4-Et-5-Me-2-Thio], [2221;3-Me-4-Pr-5-Me-2-Thio], [2222;3-Me-4-iPr-5-Me-2-Thio], [2223;3-Me-4-CF3-5-Me-2-Thio], [2224;3-Me-4-CHF2-5-Me-2-Thio], [2225;3-Me-4-OMe-5-Me-2-Thio], [2226;3-Me-4-OEt-5-Me-2-Thio], [2227;3-Me-4-OCF3-5-Me-2-Thio], [2228;3-Me-4-OCHF2-5-Me-2-Thio], [2229;3-Me-4-CN-5-Me-2-Thio], [2230;3-Me-4-SMe-5-Me-2-Thio], [2231;3-Me-4-SEt-5-Me-2-Thio], [2232;3-Me-4-cPr-5-Me-2-Thio], [2233;-3-Fu], [2234;F-3-Fu], [2235;Cl-3-Fu], [2236;Br-3-Fu], [2237;I-3-Fu], [2238;Me-3-Fu], [2239;Et-3-Fu], [2240;Pr-3-Fu], [2241;iPr-3-Fu], [2242;CF3-3-Fu], [2243;CHF2-3-Fu], [2244;OMe-3-Fu], [2245;OEt-3-Fu], [2246;OCF3-3-Fu], [2247;OCHF2-3-Fu], [2248;CN-3-Fu], [2249;SMe-3-Fu], [2250;SEt-3-Fu], [2251;cPr-3-Fu], [2252;5-F-3-Fu], [2253;5-Cl-3-Fu], [2254;5-Br-3-Fu], [2255;5-I-3-Fu], [2256;5-Me-3-Fu], [2257;5-Et-3-Fu], [2258;5-Pr-3-Fu], [2259;5-iPr-3-Fu], [2260;5-CF3-3-Fu],

[2261;5-CHF2-3-Fu], [2262;5-OMe-3-Fu], [2263;5-OEt-3-Fu], [2264;5-OCF3-3-Fu], [2265;5-OCHF2-3-Fu], [2266;5-CN-3-Fu], [2267;5-SMe-3-Fu], [2268;5-SEt-3-Fu], [2269;5-cPr-3-Fu], [2270;2-F-5-F-3-Fu], [2271;2-F-5-Cl-3-Fu], [2272;2-F-5-Br-3-Fu], [2273;2-F-5-I-3-Fu], [2274;2-F-5-Me-3-Fu], [2275;2-F-5-Et-3-Fu], [2276;2-F-5-Pr-3-Fu], [2277;2-F-5-iPr-3-Fu], [2278;2-F-5-CF3-3-Fu], [2279;2-F-5-CHF2-3-Fu], [2280;2-F-5-OMe-3-Fu], [2281;2-F-5-OEt-3-Fu], [2282;2-F-5-OCF3-3-Fu], [2283;2-F-5-OCHF2-3-Fu], [2284;2-F-5-CN-3-Fu], [2285;2-F-5-SMe-3-Fu], [2286;2-F-5-SEt-3-Fu], [2287;2-F-5-cPr-3-Fu], [2288;2-Cl-5-F-3-Fu], [2289;2-Cl-5-Cl-3-Fu], [2290;2-Cl-5-Br-3-Fu], [2291;2-Cl-5-I-3-Fu], [2292;2-Cl-5-Me-3-Fu], [2293;2-Cl-5-Et-3-Fu], [2294;2-Cl-5-Pr-3-Fu], [2295;2-Cl-5-iPr-3-Fu], [2296;2-Cl-5-CF3-3-Fu], [2297;2-Cl-5-CHF2-3-Fu], [2298;2-Cl-5-OMe-3-Fu], [2299;2-Cl-5-OEt-3-Fu], [2300;2-Cl-5-OCF3-3-Fu],

[2301;2-Cl-5-OCHF2-3-Fu], [2302;2-Cl-5-CN-3-Fu], [2303;2-Cl-5-SMe-3-Fu], [2304;2-Cl-5-SEt-3-Fu], [2305;2-Cl-5-cPr-3-Fu], [2306;2-Me-5-F-3-Fu], [2307;2-Me-5-Cl-3-Fu], [2308;2-Me-5-Br-3-Fu], [2309;2-Me-5-I-3-Fu], [2310;2-Me-5-Me-3-Fu], [2311;2-Me-5-Et-3-Fu], [2312;2-Me-5-Pr-3-Fu], [2313;2-Me-5-iPr-3-Fu], [2314;2-Me-5-CF3-3-Fu], [2315;2-Me-5-CHF2-3-Fu], [2316;2-Me-5-OMe-3-Fu], [2317;2-Me-5-OEt-3-Fu], [2318;2-Me-5-OCF3-3-Fu], [2319;2-Me-5-OCHF2-3-Fu], [2320;2-Me-5-CN-3-Fu], [2321;2-Me-5-SMe-3-Fu], [2322;2-Me-5-SEt-3-Fu], [2323;2-Me-5-cPr-3-Fu], [2324;2-Et-5-F-3-Fu], [2325;2-Et-5-Cl-3-Fu], [2326;2-Et-5-Br-3-Fu], [2327;2-Et-5-I-3-Fu], [2328;2-Et-5-Me-3-Fu], [2329;2-Et-5-Et-3-Fu], [2330;2-Et-5-Pr-3-Fu], [2331;2-Et-5-iPr-3-Fu], [2332;2-Et-5-CF3-3-Fu], [2333;2-Et-5-CHF2-3-Fu], [2334;2-Et-5-OMe-3-Fu], [2335;2-Et-5-OEt-3-Fu], [2336;2-Et-5-OCF3-3-Fu], [2337;2-Et-5-OCHF2-3-Fu], [2338;2-Et-5-CN-3-Fu], [2339;2-Et-5-SMe-3-Fu], [2340;2-Et-5-SEt-3-Fu], [2341;2-Et-5-cPr-3-Fu], [2342;2-CF3-5-F-3-Fu], [2343;2-CF3-5-Cl-3-Fu], [2344;2-CF3-5-Br-3-Fu], [2345;2-CF3-5-I-3-Fu], [2346;2-CF3-5-Me-3-Fu], [2347;2-CF3-5-Et-3-Fu], [2348;2-CF3-5-Pr-3-Fu], [2349;2-CF3-5-iPr-3-Fu], [2350;2-CF3-5-CF3-3-Fu], [2351;2-CF3-5-CHF2-3-Fu], [2352;2-CF3-5-OMe-3-Fu], [2353;2-CF3-5-OEt-3-Fu], [2354;2-CF3-5-OCF3-3-Fu], [2355;2-CF3-5-OCHF2-3-Fu], [2356;2-CF3-5-CN-3-Fu], [2357;2-CF3-5-SMe-3-Fu], [2358;2-CF3-5-SEt-3-Fu], [2359;2-CF3-5-cPr-3-Fu], [2360;2-OMe-5-F-3-Fu], [2361;2-OMe-5-Cl-3-Fu], [2362;2-OMe-5-Br-3-Fu], [2363;2-OMe-5-I-3-Fu], [2364;2-OMe-5-Me-3-Fu], [2365;2-OMe-5-Et-3-Fu], [2366;2-OMe-5-Pr-3-Fu], [2367;2-OMe-5-iPr-3-Fu], [2368;2-OMe-5-CF3-3-Fu], [2369;2-OMe-5-CHF2-3-Fu], [2370;2-OMe-5-OMe-3-Fu], [2371;2-OMe-5-OEt-3-Fu], [2372;2-OMe-5-OCF3-3-Fu], [2373;2-OMe-5-OCHF2-3-Fu], [2374;2-OMe-5-CN-3-Fu], [2375;2-OMe-5-SMe-3-Fu], [2376;2-OMe-5-SEt-3-Fu], [2377;2-OMe-5-cPr-3-Fu], [2378;2-OEt-5-F-3-Fu], [2379;2-OEt-5-Cl-3-Fu], [2380;2-OEt-5-Br-3-Fu], [2381;2-OEt-5-I-3-Fu], [2382;2-OEt-5-Me-3-Fu], [2383;2-OEt-5-Et-3-Fu], [2384;2-OEt-5-Pr-3-Fu], [2385;2-OEt-5-iPr-3-Fu], [2386;2-OEt-5-CF3-3-Fu], [2387;2-OEt-5-CHF2-3-Fu], [2388;2-OEt-5-OMe-3-Fu], [2389;2-OEt-5-OEt-3-Fu], [2390;2-OEt-5-OCF3-3-Fu], [2391; 2-OEt-5-OCHF2-3-Fu], [2392;2-OEt-5-CN-3-Fu], [2393;2-OEt-5-SMe-3-Fu], [2394;2-OEt-5-SEt-3-Fu], [2395;2-OEt-5-cPr-3-Fu], [2396;2-SMe-5-F-3-Fu], [2397;2-SMe-5-Cl-3-Fu], [2398;2-SMe-5-Br-3-Fu], [2399;2-SMe-5-I-3-Fu], [2400;2-SMe-5-Me-3-Fu], [2401;2-SMe-5-Et-3-Fu], [2402;2-SMe-5-Pr-3-Fu], [2403;2-SMe-5-iPr-3-Fu], [2404;2-SMe-5-CF3-3-Fu], [2405;2-SMe-5-CHF2-3-Fu], [2406;2-SMe-5-OMe-3-Fu], [2407;2-SMe-5-OEt-3-Fu], [2408;2-SMe-5-OCF3-3-Fu], [2409;2-SMe-5-OCHF2-3-Fu], [2410;2-SMe-5-CN-3-Fu], [2411;2-SMe-5-SMe-3-Fu], [2412;2-SMe-5-SEt-3-Fu], [2413;2-SMe-5-cPr-3-Fu], [2414;4-F-3-Fu], [2415;4-Cl-3-Fu], [2416;4-Br-3-Fu], [2417;4-I-3-Fu], [2418;4-Me-3-Fu], [2419;4-Et-3-Fu], [2420;4-Pr-3-Fu], [2421;4-iPr-3-Fu], [2422;4-CF3-3-Fu], [2423;4-CHF2-3-Fu], [2424;4-OMe-3-Fu], [2425;4-OEt-3-Fu], [2426;4-OCF3-3-Fu], [2427;4-OCHF2-3-Fu], [2428;2-F-4-F-3-Fu], [2429;2-Cl-4-F-3-Fu], [2430;2-Br-4-F-3-Fu], [2431;2-I-4-F-3-Fu], [2432;2-Me-4-F-3-Fu], [2433;2-Et-4-F-3-Fu], [2434;2-Pr-4-F-3-Fu], [2435;2-iPr-4-F-3-Fu], [2436;2-CF3-4-F-3-Fu], [2437;2-CHF2-4-F-3-Fu], [2438;2-OMe-4-F-3-Fu], [2439;2-OEt-4-F-3-Fu], [2440;2-OCF3-4-F-3-Fu], [2441;2-OCHF2-4-F-3-Fu], [2442;2-CN-4-F-3-Fu], [2443;2-SMe-4-F-3-Fu], [2444;2-SEt-4-F-3-Fu], [2445;2-cPr-4-F-3-Fu], [2446;2-F-4-Cl-3-Fu], [2447;2-Cl-4-Cl-3-Fu], [2448;2-Br-4-Cl-3-Fu], [2449;2-I-4-Cl-3-Fu], [2450;2-Me-4-Cl-3-Fu], [2451;2-Et-4-Cl-3-Fu], [2452;2-Pr-4-Cl-3-Fu], [2453;2-iPr-4-Cl-3-Fu], [2454;2-CF3-4-Cl-3-Fu], [2455;2-CHF2-4-Cl-3-Fu], [2456;2-OMe-4-Cl-3-Fu], [2457;2-OEt-4-Cl-3-Fu], [2458;2-OCF3-4-Cl-3-Fu], [2459;2-OCHF2-4-Cl-3-Fu], [2460;2-CN-4-Cl-3-Fu], [2461;2-SMe-4-Cl-3-Fu], [2462;2-SEt-4-Cl-3-Fu], [2463;2-cPr-4-Cl-3-Fu], [2464;2-F-4-Me-3-Fu], [2465;2-Cl-4-Me-3-Fu], [2466;2-Br-4-Me-3-Fu], [2467;2-I-4-Me-3-Fu], [2468;2-Me-4-Me-3-Fu], [2469;2-Et-4-Me-3-Fu], [2470;2-Pr-4-Me-3-Fu], [2471;2-iPr-4-Me-3-Fu], [2472;2-CF3-4-Me-3-Fu], [2473;2-CHF2-4-Me-3-Fu], [2474;2-OMe-4-Me-3-Fu], [2475;2-OEt-4-Me-3-Fu], [2476;2-OCF3-4-Me-3-Fu], [2477;2-OCHF2-4-Me-3-Fu], [2478;2-CN-4-Me-3-Fu], [2479;2-SMe-4-Me-3-Fu], [2480;2-SEt-4-Me-3-Fu], [2481;2-cPr-4-Me-3-Fu], [2482;2-F-4-Et-3-Fu], [2483;2-Cl-4-Et-3-Fu], [2484;2-Br-4-Et-3-Fu], [2485;2-I-4-Et-3-Fu], [2486;2-Me-4-Et-3-Fu], [2487;2-Et-4-Et-3-Fu], [2488;2-Pr-4-Et-3-Fu], [2489;2-iPr-4-Et-3-Fu], [2490;2-CF3-4-Et-3-Fu], [2491;2-CHF2-4-Et-3-Fu], [2492;2-OMe-4-Et-3-Fu], [2493;2-OEt-4-Et-3-Fu], [2494;2-OCF3-4-Et-3-Fu], [2495;2-OCHF2-4-Et-3-Fu], [2496;2-CN-4-Et-3-Fu], [2497;2-SMe-4-Et-3-Fu], [2498;2-SEt-4-Et-3-Fu], [2499;2-cPr-4-Et-3-Fu], [2500;2-F-4-CF3-3-Fu], [2501;2-Cl-4-CF3-3-Fu], [2502;2-Br-4-CF3-3-Fu], [2503;2-I-4-CF3-3-Fu], [2504;2-Me-4-CF3-3-Fu], [2505;2-Et-4-CF3-3-Fu], [2506;2-Pr-4-CF3-3-Fu], [2507;2-iPr-4-CF3-3-Fu], [2508;2-CF3-4-CF3-3-Fu], [2509;2-CHF2-4-CF3-3-Fu], [2510;2-OMe-4-CF3-3-Fu], [2511;2-OEt-4-CF3-3-Fu], [2512;2-OCF3-4-CF3-3-Fu], [2513;2-OCHF2-4-CF3-3-Fu], [2514;2-CN-4-CF3-3-Fu], [2515;2-SMe-4-CF3-3-Fu], [2516;2-SEt-4-CF3-3-Fu], [2517;2-cPr-4-CF3-3-Fu], [2518;2-F-4-OMe-3-Fu], [2519;2-Cl-4-OMe-3-Fu], [2520;2-Br-4-OMe-3-Fu], [2521;2-I-4-OMe-3-Fu], [2522;2-Me-4-OMe-3-Fu], [2523;2-Et-4-OMe-3-Fu], [2524;2-Pr-4-OMe-3-Fu], [2525;2-iPr-4-OMe-3-Fu], [2526;2-CF3-4-OMe-3-Fu], [2527;2-CHF2-4-OMe-3-Fu], [2528;2-OMe-4-OMe-3-Fu], [2529;2-OEt-4-OMe-3-Fu], [2530;2-OCF3-4-OMe-3-Fu], [2531;2-OCHF2-4-OMe-3-Fu], [2532;2-CN-4-OMe-3-Fu], [2533;2-SMe-4-OMe-3-Fu], [2534;2-SEt-4-OMe-3-Fu], [2535;2-cPr-4-OMe-3-Fu], [2536;2-F-4-OEt-3-Fu], [2537;2-Cl-4-OEt-3-Fu], [2538;2-Br-4-OEt-3-Fu], [2539;2-I-4-OEt-3-Fu], [2540;2-Me-4-OEt-3-Fu], [2541;2-Et-4-OEt-3-Fu], [2542;2-Pr-4-OEt-3-Fu], [2543;2-iPr-4-OEt-3-Fu], [2544;2-CF3-4-OEt-3-Fu], [2545;2-CHF2-4-OEt-3-Fu], [2546;2-OMe-4-OEt-3-Fu], [2547;2-OEt-4-OEt-3-Fu], [2548;2-OCF3-4-OEt-3-Fu], [2549;2-OCHF2-4-OEt-3-Fu], [2550;2-CN-4-OEt-3-Fu], [2551;2-SMe-4-OEt-3-Fu], [2552;2-SEt-4-OEt-3-Fu], [2553;2-cPr-4-OEt-3-Fu], [2554;2-F-4-SMe-3-Fu], [2555;2-Cl-4-SMe-3-Fu], [2556;2-Br-4-SMe-3-Fu], [2557;2-I-4-SMe-3-Fu], [2558;2-Me-4-SMe-3-Fu], [2559;2-Et-4-SMe-3-Fu], [2560;2-Pr-4-SMe-3-Fu],

[2561;2-iPr-4-SMe-3-Fu], [2562;2-CF3-4-SMe-3-Fu], [2563;2-CHF2-4-SMe-3-Fu], [2564;2-OMe-4-SMe-3-Fu], [2565;2-OEt-4-SMe-3-Fu], [2566;2-OCF3-4-SMe-3-Fu], [2567;2-OCHF2-4-SMe-3-Fu], [2568;2-CN-4-SMe-3-Fu], [2569;2-SMe-4-SMe-3-Fu], [2570;2-SEt-4-SMe-3-Fu], [2571;2-cPr-4-SMe-3-Fu], [2572;4-F-5-F-3-Fu], [2573;4-F-5-Cl-3-Fu], [2574;4-F-5-Br-3-Fu], [2575;4-F-5-I-3-Fu], [2576;4-F-5-Me-3-Fu], [2577;4-F-5-Et-3-Fu], [2578;4-F-5-Pr-3-Fu], [2579;4-F-5-iPr-3-Fu], [2580;4-F-5-CF3-3-Fu], [2581;4-F-5-CHF2-3-Fu], [2582;4-F-5-OMe-3-Fu], [2583;4-F-5-OEt-3-Fu], [2584;4-F-5-OCF3-3-Fu], [2585;4-F-5-OCHF2-3-Fu], [2586;4-F-5-CN-3-Fu], [2587;4-F-5-SMe-3-Fu], [2588;4-F-5-SEt-3-Fu], [2589;4-F-5-cPr-3-Fu], [2590;4-Cl-5-F-3-Fu], [2591;4-Cl-5-Cl-3-Fu], [2592;4-Cl-5-Br-3-Fu], [2593;4-Cl-5-I-3-Fu], [2594;4-Cl-5-Me-3-Fu], [2595;4-Cl-5-Et-3-Fu], [2596;4-Cl-5-Pr-3-Fu], [2597;4-Cl-5-iPr-3-Fu], [2598;4-Cl-5-CF3-3-Fu], [2599;4-Cl-5-CHF2-3-Fu], [2600;4-Cl-5-OMe-3-Fu],

[2601;4-Cl-5-OEt-3-Fu], [2602;4-Cl-5-OCF3-3-Fu], [2603;4-Cl-5-OCHF2-3-Fu], [2604;4-Cl-5-CN-3-Fu], [2605;4-Cl-5-SMe-3-Fu], [2606;4-Cl-5-SEt-3-Fu], [2607;4-Cl-5-cPr-3-Fu], [2608;4-Me-5-F-3-Fu], [2609;4-Me-5-Cl-3-Fu], [2610;4-Me-5-Br-3-Fu], [2611;4-Me-5-I-3-Fu], [2612;4-Me-5-Me-3-Fu], [2613;4-Me-5-Et-3-Fu], [2614;4-Me-5-Pr-3-Fu], [2615;4-Me-5-iPr-3-Fu], [2616;4-Me-5-CF3-3-Fu], [2617;4-Me-5-CHF2-3-Fu], [2618;4-Me-5-OMe-3-Fu], [2619;4-Me-5-OEt-3-Fu], [2620;4-Me-5-OCF3-3-Fu], [2621;4-Me-5-OCHF2-3-Fu], [2622;4-Me-5-CN-3-Fu], [2623;4-Me-5-SMe-3-Fu], [2624;4-Me-5-SEt-3-Fu], [2625;4-Me-5-cPr-3-Fu], [2626;4-Et-5-F-3-Fu], [2627;4-Et-5-Cl-3-Fu], [2628;4-Et-5-Br-3-Fu], [2629;4-Et-5-I-3-Fu], [2630;4-Et-5-Me-3-Fu], [2631;4-Et-5-Et-3-Fu], [2632;4-Et-5-Pr-3-Fu], [2633;4-Et-5-iPr-3-Fu], [2634;4-Et-5-CF3-3-Fu], [2635;4-Et-5-CHF2-3-Fu], [2636;4-Et-5-OMe-3-Fu], [2637;4-Et-5-OEt-3-Fu], [2638;4-Et-5-OCF3-3-Fu], [2639;4-Et-5-OCHF2-3-Fu], [2640;4-Et-5-CN-3-Fu], [2641;4-Et-5-SMe-3-Fu], [2642;4-Et-5-SEt-3-Fu], [2643;4-Et-5-cPr-3-Fu], [2644;4-CF3-5-F-3-Fu], [2645;4-CF3-5-Cl-3-Fu], [2646;4-CF3-5-Br-3-Fu], [2647;4-CF3-5-I-3-Fu], [2648;4-CF3-5-Me-3-Fu], [2649;4-CF3-5-Et-3-Fu], [2650;4-CF3-5-Pr-3-Fu], [2651;4-CF3-5-iPr-3-Fu], [2652;4-CF3-5-CF3-3-Fu], [2653;4-CF3-5-CHF2-3-Fu], [2654;4-CF3-5-OMe-3-Fu], [2655;4-CF3-5-OEt-3-Fu], [2656;4-CF3-5-OCF3-3-Fu], [2657;4-CF3-5-OCHF2-3-Fu], [2658;4-CF3-5-CN-3-Fu], [2659;4-CF3-5-SMe-3-Fu], [2660;4-CF3-5-SEt-3-Fu], [2661;4-CF3-5-cPr-3-Fu], [2662;4-OMe-5-F-3-Fu], [2663;4-OMe-5-Cl-3-Fu], [2664;4-OMe-5-Br-3-Fu], [2665;4-OMe-5-I-3-Fu], [2666;4-OMe-5-Me-3-Fu], [2667;4-OMe-5-Et-3-Fu], [2668;4-OMe-5-Pr-3-Fu], [2669;4-OMe-5-iPr-3-Fu], [2670;4-OMe-5-CF3-3-Fu], [2671;4-OMe-5-CHF2-3-Fu], [2672;4-OMe-5-OMe-3-Fu], [2673;4-OMe-5-OEt-3-Fu], [2674;4-OMe-5-OCF3-3-Fu], [2675;4-OMe-5-OCHF2-3-Fu], [2676;4-OMe-5-CN-3-Fu], [2677;4-OMe-5-SMe-3-Fu], [2678;4-OMe-5-SEt-3-Fu], [2679;4-OMe-5-cPr-3-Fu], [2680;4-OEt-5-F-3-Fu], [2681;4-OEt-5-Cl-3-Fu], [2682;4-OEt-5-Br-3-Fu], [2683;4-OEt-5-I-3-Fu], [2684;4-OEt-5-Me-3-Fu], [2685;4-OEt-5-Et-3-Fu], [2686;4-OEt-5-Pr-3-Fu], [2687;4-OEt-5-iPr-3-Fu], [2688;4-OEt-5-CF3-3-Fu], [2689;4-OEt-5-CHF2-3-Fu], [2690;4-OEt-5-OMe-3-Fu], [2691;4-OEt-5-OEt-3-Fu], [2692;4-OEt-5-OCF3-3-Fu], [2693;4-OEt-5-OCHF2-3-Fu], [2694;4-OEt-5-CN-3-Fu], [2695;4-OEt-5-SMe-3-Fu], [2696;4-OEt-5-SEt-3-Fu], [2697;4-OEt-5-cPr-3-Fu], [2698;4-SMe-5-F-3-Fu], [2699;4-SMe-5-Cl-3-Fu], [2700;4-SMe-5-Br-3-Fu], [2701;4-SMe-5-I-3-Fu], [2702;4-SMe-5-Me-3-Fu], [2703;4-SMe-5-Et-3-Fu], [2704;4-SMe-5-Pr-3-Fu], [2705;4-SMe-5-iPr-3-Fu], [2706;4-SMe-5-CF3-3-Fu], [2707;4-SMe-5-CHF2-3-Fu], [2708;4-SMe-5-OMe-3-Fu], [2709;4-SMe-5-OEt-3-Fu], [2710;4-SMe-5-OCF3-3-Fu], [2711;4-SMe-5-OCHF2-3-Fu], [2712;4-SMe-5-CN-3-Fu], [2713;4-SMe-5-SMe-3-Fu], [2714;4-SMe-5-SEt-3-Fu], [2715;4-SMe-5-cPr-3-Fu], [2716;2-Me-4-Me-5-F-3-Fu], [2717;2-Me-4-Me-5-Cl-3-Fu], [2718;2-Me-4-Me-5-Br-3-Fu], [2719;2-Me-4-Me-5-I-3-Fu], [2720;2-Me-4-Me-5-Me-3-Fu], [2721;2-Me-4-Me-5-Et-3-Fu], [2722;2-Me-4-Me-5-Pr-3-Fu], [2723;2-Me-4-Me-5-iPr-3-Fu], [2724;2-Me-4-Me-5-CF3-3-Fu], [2725;2-Me-4-Me-5-CHF2-3-Fu], [2726;2-Me-4-Me-5-OMe-3-Fu], [2727;2-Me-4-Me-5-OEt-3-Fu], [2728;2-Me-4-Me-5-OCF3-3-Fu], [2729;2-Me-4-Me-5-OCHF2-3-Fu], [2730;2-Me-4-Me-5-CN-3-Fu], [2731;2-Me-4-Me-5-SMe-3-Fu], [2732;2-Me-4-Me-5-SEt-3-Fu], [2733;2-Me-4-Me-5-cPr-3-Fu], [2734;2-F-4-Me-5-Me-3-Fu], [2735;2-Cl-4-Me-5-Me-3-Fu], [2736;2-Br-4-Me-5-Me-3-Fu], [2737;2-I-4-Me-5-Me-3-Fu], [2738;2-Et-4-Me-5-Me-3-Fu], [2739;2-Pr-4-Me-5-Me-3-Fu], [2740;2-iPr-4-Me-5-Me-3-Fu], [2741;2-CF3-4-Me-5-Me-3-Fu], [2742;2-CHF2-4-Me-5-Me-3-Fu], [2743;2-OMe-4-Me-5-Me-3-Fu], [2744;2-OEt-4-Me-5-Me-3-Fu], [2745;2-OCF3-4-Me-5-Me-3-Fu], [2746;2-OCHF2-4-Me-5-Me-3-Fu], [2747;2-CN-4-Me-5-Me-3-Fu], [2748;2-SMe-4-Me-5-Me-3-Fu], [2749;2-SEt-4-Me-5-Me-3-Fu], [2750;2-cPr-4-Me-5-Me-3-Fu], [2751;-3-Thio], [2752;2-F-3-Thio], [2753;2-Cl-3-Thio], [2754;2-Br-3-Thio], [2755;2-I-3-Thio], [2756;2-Me-3-Thio], [2757;2-Et-3-Thio], [2758;2-Pr-3-Thio], [2759;2-iPr-3-Thio], [2760;2-CF3-3-Thio], [2761;2-CHF2-3-Thio], [2762;2-OMe-3-Thio], [2763;2-OEt-3-Thio], [2764;2-OCF3-3-Thio], [2765;2-OCHF2-3-Thio], [2766;2-CN-3-Thio], [2767;2-SMe-3-Thio], [2768;2-SEt-3-Thio], [2769;2-cPr-3-Thio], [2770;5-F-3-Thio], [2771;5-Cl-3-Thio], [2772;5-Br-3-Thio], [2773;5-I-3-Thio], [2774;5-Me-3-Thio], [2775;5-Et-3-Thio], [2776;5-Pr-3-Thio], [2777;5-iPr-3-Thio], [2778;5-CF3-3-Thio], [2779;5-CHF2-3-Thio], [2780;5-OMe-3-Thio], [2781;5-OEt-3-Thio], [2782;5-OCF3-3-Thio], [2783;5-OCHF2-3-Thio], [2784;5-CN-3-Thio], [2785;5-SMe-3-Thio], [2786;5-SEt-3-Thio], [2787;5-cPr-3-Thio], [2788;2-F-5-F-3-Thio], [2789;2-F-5-Cl-3-Thio], [2790;2-F-5-Br-3-Thio], [2791;2-F-5-I-3-Thio], [2792;2-F-5-Me-3-Thio], [2793;2-F-5-Et-3-Thio], [2794;2-F-5-Pr-3-Thio], [2795;2-F-5-iPr-3-Thio], [2796;2-F-5-CF3-3-Thio], [2797;2-F-5-CHF2-3-Thio], [2798;2-F-5-OMe-3-Thio], [2799;2-F-5-OEt-3-Thio], [2800;2-F-5-OCF3-3-Thio],

[2801;2-F-5-OCHF2-3-Thio], [2802;2-F-5-CN-3-Thio], [2803;2-F-5-SMe-3-Thio], [2804;2-F-5-SEt-3-Thio], [2805;2-F-5-cPr-3-Thio], [2806;2-Cl-5-F-3-Thio], [2807;2-Cl-5-Cl-3-Thio], [2808;2-Cl-5-Br-3-Thio], [2809;2-Cl-5-I-3-Thio], [2810;2-Cl-5-Me-3-Thio], [2811;2-Cl-5-Et-3-Thio], [2812;2-Cl-5-Pr-3-Thio], [2813;2-Cl-5-iPr-3-Thio], [2814;2-Cl-5-CF3-3-Thio], [2815;2-Cl-5-CHF2-3-Thio], [2816;2-Cl-5-OMe-3-Thio], [2817;2-Cl-5-OEt-3-Thio], [2818;2-Cl-5-OCF3-3-Thio], [2819;2-Cl-5-OCHF2-3-Thio], [2820;2-Cl-5-CN-3-Thio], [2821;2-Cl-5-SMe-3-Thio], [2822;2-Cl-5-SEt-3-Thio], [2823;2-Cl-5-cPr-3-Thio], [2824;2-Me-5-F-3-Thio], [2825;2-Me-5-Cl-3-Thio], [2826;2-Me-5-Br-3-Thio], [2827;2-Me-5-I-3-Thio], [2828;2-Me-5-Me-3-Thio], [2829;2-Me-5-Et-3-Thio], [2830;2-Me-5-Pr-3-Thio], [2831;2-Me-5-iPr-3-Thio], [2832;2-Me-5-CF3-3-Thio], [2833;2-Me-5-CHF2-3-Thio], [2834;2-Me-5-OMe-3-Thio], [2835;2-Me-5-OEt-3-Thio], [2836;2-Me-5-OCF3-3-Thio], [2837;2-Me-5-OCHF2-3-Thio], [2838;2-Me-5-CN-3-Thio], [2839;2-Me-5-SMe-3-Thio], [2840;2-Me-5-SEt-3-Thio], [2841;2-Me-5-cPr-3-Thio], [2842;2-Et-5-F-3-Thio], [2843;2-Et-5-Cl-3-Thio], [2844;2-Et-5-Br-3-Thio], [2845;2-Et-5-I-3-Thio], [2846;2-Et-5-Me-3-Thio], [2847;2-Et-5-Et-3-Thio], [2848;2-Et-5-Pr-3-Thio], [2849;2-Et-5-iPr-3-Thio],

[2850;2-Et-5-CF3-3-Thio], [2851;2-Et-5-CHF2-3-Thio], [2852;2-Et-5-OMe-3-Thio], [2853;2-Et-5-OEt-3-Thio], [2854;2-Et-5-OCF3-3-Thio], [2855;2-Et-5-OCHF2-3-Thio], [2856;2-Et-5-CN-3-Thio], [2857;2-Et-5-SMe-3-Thio], [2858;2-Et-5-SEt-3-Thio], [2859;2-Et-5-cPr-3-Thio], [2860;2-CF3-5-F-3-Thio], [2861;2-CF3-5-Cl-3-Thio], [2862;2-CF3-5-Br-3-Thio], [2863;2-CF3-5-I-3-Thio], [2864;2-CF3-5-Me-3-Thio], [2865;2-CF3-5-Et-3-Thio], [2866;2-CF3-5-Pr-3-Thio], [2867;2-CF3-5-iPr-3-Thio], [2868;2-CF3-5-CF3-3-Thio], [2869;2-CF3-5-CHF2-3-Thio], [2870;2-CF3-5-OMe-3-Thio], [2871;2-CF3-5-OEt-3-Thio], [2872;2-CF3-5-OCF3-3-Thio], [2873;2-CF3-5-OCHF2-3-Thio], [2874;2-CF3-5-CN-3-Thio], [2875;2-CF3-5-SMe-3-Thio], [2876;2-CF3-5-SEt-3-Thio], [2877;2-CF3-5-cPr-3-Thio], [2878;2-OMe-5-F-3-Thio], [2879;2-OMe-5-Cl-3-Thio], [2880;2-OMe-5-Br-3-Thio], [2881;2-OMe-5-I-3-Thio], [2882;2-OMe-5-Me-3-Thio], [2883;2-OMe-5-Et-3-Thio], [2884;2-OMe-5-Pr-3-Thio], [2885;2-OMe-5-iPr-3-Thio], [2886;2-OMe-5-CF3-3-Thio], [2887;2-OMe-5-CHF2-3-Thio], [2888;2-OMe-5-OMe-3-Thio], [2889;2-OMe-5-OEt-3-Thio], [2890;2-OMe-5-OCF3-3-Thio], [2891;2-OMe-5-OCHF2-3-Thio], [2892;2-OMe-5-CN-3-Thio], [2893;2-OMe-5-SMe-3-Thio], [2894;2-OMe-5-SEt-3-Thio], [2895;2-OMe-5-cPr-3-Thio], [2896;2-OEt-5-F-3-Thio], [2897;2-OEt-5-Cl-3-Thio], [2898;2-OEt-5-Br-3-Thio], [2899;2-OEt-5-I-3-Thio], [2900;2-OEt-5-Me-3-Thio],
[2901;2-OEt-5-Et-3-Thio], [2902;2-OEt-5-Pr-3-Thio], [2903;2-OEt-5-iPr-3-Thio], [2904;2-OEt-5-CF3-3-Thio], [2905;2-OEt-5-CHF2-3-Thio], [2906;2-OEt-5-OMe-3-Thio], [2907;2-OEt-5-OEt-3-Thio], [2908;2-OEt-5-OCF3-3-Thio], [2909;2-OEt-5-OCHF2-3-Thio], [2910;2-OEt-5-CN-3-Thio], [2911;2-OEt-5-SMe-3-Thio], [2912;2-OEt-5-SEt-3-Thio], [2913;2-OEt-5-cPr-3-Thio], [2914;2-SMe-5-F-3-Thio], [2915;2-SMe-5-Cl-3-Thio], [2916;2-SMe-5-Br-3-Thio], [2917;2-SMe-5-I-3-Thio], [2918;2-SMe-5-Me-3-Thio], [2919;2-SMe-5-Et-3-Thio], [2920;2-SMe-5-Pr-3-Thio], [2921;2-SMe-5-iPr-3-Thio], [2922;2-SMe-5-CF3-3-Thio], [2923;2-SMe-5-CHF2-3-Thio], [2924;2-SMe-5-OMe-3-Thio], [2925;2-SMe-5-OEt-3-Thio], [2926;2-SMe-5-OCF3-3-Thio], [2927;2-SMe-5-OCHF2-3-Thio], [2928;2-SMe-5-CN-3-Thio], [2929;2-SMe-5-SMe-3-Thio], [2930;2-SMe-5-SEt-3-Thio], [2931;2-SMe-5-cPr-3-Thio], [2932;4-F-3-Thio], [2933;4-Cl-3-Thio], [2934;4-Br-3-Thio], [2935;4-I-3-Thio], [2936;4-Me-3-Thio], [2937;4-Et-3-Thio], [2938;4-Pr-3-Thio], [2939;4-iPr-3-Thio], [2940;4-CF3-3-Thio], [2941;4-CHF2-3-Thio], [2942;4-OMe-3-Thio], [2943;4-OEt-3-Thio], [2944;4-OCF3-3-Thio], [2945;4-OCHF2-3-Thio], [2946;2-F-4-F-3-Thio], [2947;2-Cl-4-F-3-Thio], [2948;2-Br-4-F-3-Thio], [2949;2-I-4-F-3-Thio], [2950;2-Me-4-F-3-Thio], [2951;2-Et-4-F-3-Thio], [2952;2-Pr-4-F-3-Thio], [2953;2-iPr-4-F-3-Thio], [2954;2-CF3-4-F-3-Thio], [2955;2-CHF2-4-F-3-Thio], [2956;2-OMe-4-F-3-Thio], [2957;2-OEt-4-F-3-Thio], [2958;2-OCF3-4-F-3-Thio], [2959;2-OCHF2-4-F-3-Thio], [2960;2-CN-4-F-3-Thio], [2961;2-SMe-4-F-3-Thio], [2962;2-SEt-4-F-3-Thio], [2963;2-cPr-4-F-3-Thio], [2964;2-F-4-Cl-3-Thio], [2965;2-Cl-4-Cl-3-Thio], [2966;2-Br-4-Cl-3-Thio], [2967;2-I-4-Cl-3-Thio], [2968;2-Me-4-Cl-3-Thio], [2969;2-Et-4-Cl-3-Thio], [2970;2-Pr-4-Cl-3-Thio], [2971;2-iPr-4-Cl-3-Thio], [2972;2-CF3-4-Cl-3-Thio], [2973;2-CHF2-4-Cl-3-Thio], [2974;2-OMe-4-Cl-3-Thio], [2975;2-OEt-4-Cl-3-Thio], [2976;2-OCF3-4-Cl-3-Thio], [2977;2-OCHF2-4-Cl-3-Thio], [2978;2-CN-4-Cl-3-Thio], [2979;2-SMe-4-Cl-3-Thio], [2980;2-SEt-4-Cl-3-Thio], [2981;2-cPr-4-Cl-3-Thio], [2982;2-F-4-Me-3-Thio], [2983;2-Cl-4-Me-3-Thio], [2984;2-Br-4-Me-3-Thio], [2985;2-I-4-Me-3-Thio], [2986;2-Me-4-Me-3-Thio], [2987;2-Et-4-Me-3-Thio], [2988;2-Pr-4-Me-3-Thio], [2989;2-iPr-4-Me-3-Thio], [2990;2-CF3-4-Me-3-Thio], [2991;2-CHF2-4-Me-3-Thio], [2992;2-OMe-4-Me-3-Thio], [2993;2-OEt-4-Me-3-Thio], [2994;2-OCF3-4-Me-3-Thio], [2995;2-OCHF2-4-Me-3-Thio], [2996;2-CN-4-Me-3-Thio], [2997;2-SMe-4-Me-3-Thio], [2998;2-SEt-4-Me-3-Thio], [2999;2-cPr-4-Me-3-Thio], [3000;2-F-4-Et-3-Thio],
[3001;2-Cl-4-Et-3-Thio], [3002;2-Br-4-Et-3-Thio], [3003;2-I-4-Et-3-Thio], [3004;2-Me-4-Et-3-Thio], [3005;2-Et-4-Et-3-Thio], [3006;2-Pr-4-Et-3-Thio], [3007;2-iPr-4-Et-3-Thio], [3008;2-CF3-4-Et-3-Thio], [3009;2-CHF2-4-Et-3-Thio], [3010;2-OMe-4-Et-3-Thio], [3011;2-OEt-4-Et-3-Thio], [3012;2-OCF3-4-Et-3-Thio], [3013;2-OCHF2-4-Et-3-Thio], [3014;2-CN-4-Et-3-Thio], [3015;2-SMe-4-Et-3-Thio], [3016;2-SEt-4-Et-3-Thio], [3017;2-cPr-4-Et-3-Thio], [3018;2-F-4-CF3-3-Thio], [3019;2-Cl-4-CF3-3-Thio], [3020;2-Br-4-CF3-3-Thio], [3021;2-I-4-CF3-3-Thio], [3022;2-Me-4-CF3-3-Thio], [3023;2-Et-4-CF3-3-Thio], [3024;2-Pr-4-CF3-3-Thio], [3025;2-iPr-4-CF3-3-Thio], [3026;2-CF3-4-CF3-3-Thio], [3027;2-CHF2-4-CF3-3-Thio], [3028;2-OMe-4-CF3-3-Thio], [3029;2-OEt-4-CF3-3-Thio], [3030;2-OCF3-4-CF3-3-Thio], [3031;2-OCHF2-4-CF3-3-Thio], [3032;2-CN-4-CF3-3-Thio], [3033;2-SMe-4-CF3-3-Thio], [3034;2-SEt-4-CF3-3-Thio], [3035;2-cPr-4-CF3-3-Thio], [3036;2-F-4-OMe-3-Thio], [3037;2-Cl-4-OMe-3-Thio], [3038;2-Br-4-OMe-3-Thio], [3039;2-I-4-OMe-3-Thio], [3040;2-Me-4-OMe-3-Thio], [3041;2-Et-4-OMe-3-Thio], [3042;2-Pr-4-OMe-3-Thio], [3043;2-iPr-4-OMe-3-Thio], [3044;2-CF3-4-OMe-3-Thio], [3045;2-CHF2-4-OMe-3-Thio], [3046;2-OMe-4-OMe-3-Thio], [3047;2-OEt-4-OMe-3-Thio], [3048;2-OCF3-4-OMe-3-Thio], [3049;2-OCHF2-4-OMe-3-Thio], [3050;2-CN-4-OMe-3-Thio], [3051;2-SMe-4-OMe-3-Thio], [3052;2-SEt-4-OMe-3-Thio], [3053;2-cPr-4-OMe-3-Thio], [3054;2-F-4-OEt-3-Thio], [3055;2-Cl-4-OEt-3-Thio], [3056;2-Br-4-OEt-3-Thio], [3057;2-I-4-OEt-3-Thio], [3058;2-Me-4-OEt-3-Thio], [3059;2-Et-4-OEt-3-Thio], [3060;2-Pr-4-OEt-3-Thio], [3061;2-iPr-4-OEt-3-Thio], [3062;2-CF3-4-OEt-3-Thio], [3063;2-CHF2-4-OEt-3-Thio], [3064;2-OMe-4-OEt-3-Thio], [3065;2-OEt-4-OEt-3-Thio], [3066;2-OCF3-4-OEt-3-Thio], [3067;2-OCHF2-4-OEt-3-Thio], [3068;2-CN-4-OEt-3-Thio], [3069;2-SMe-4-OEt-3-Thio], [3070;2-SEt-4-OEt-3-Thio], [3071;2-cPr-4-OEt-3-Thio], [3072;2-F-4-SMe-3-Thio], [3073;2-Cl-4-SMe-3-Thio], [3074;2-Br-4-SMe-3-Thio], [3075;2-I-4-SMe-3-Thio], [3076;2-Me-4-SMe-3-Thio], [3077;2-Et-4-SMe-3-Thio], [3078;2-Pr-4-SMe-3-Thio], [3079;2-iPr-4-SMe-3-Thio], [3080;2-CF3-4-SMe-3-Thio], [3081;2-CHF2-4-SMe-3-Thio], [3082;2-OMe-4-SMe-3-Thio], [3083;2-OEt-4-SMe-3-Thio], [3084;2-OCF3-4-SMe-3-Thio], [3085;2-OCHF2-4-SMe-3-Thio], [3086;2-CN-4-SMe-3-Thio], [3087;2-SMe-4-SMe-3-Thio], [3088;2-SEt-4-SMe-3-Thio], [3089;2-cPr-4-SMe-3-Thio], [3090;4-F-5-F-3-Thio], [3091;4-F-5-Cl-3-Thio], [3092;4-F-5-Br-3-Thio], [3093;4-F-5-I-3-Thio], [3094;4-F-5-Me-3-Thio], [3095;4-F-5-Et-3-Thio], [3096;4-F-5-Pr-3-Thio], [3097;4-F-5-iPr-3-Thio], [3098;4-F-5-CF3-3-Thio], [3099;4-F-5-CHF2-3-Thio], [3100;4-F-5-OMe-3-Thio],
[3101;4-F-5-OEt-3-Thio], [3102;4-F-5-OCF3-3-Thio], [3103;4-F-5-OCHF2-3-Thio], [3104;4-F-5-CN-3-Thio], [3105;4-F-5-SMe-3-Thio], [3106;4-F-5-SEt-3-Thio], [3107;4-F-5-cPr-3-Thio], [3108;4-Cl-5-F-3-Thio], [3109;4-Cl-5-Cl-3-Thio], [3110;4-Cl-5-Br-3-Thio], [3111;4-Cl-5-I-3-Thio], [3112;4-Cl-5-Me-3-Thio], [3113;4-Cl-5-Et-3-Thio], [3114;4-Cl-5-Pr-3-Thio], [3115;4-Cl-5-iPr-3-Thio], [3116;4-Cl-5-CF3-3-Thio], [3117;4-Cl-5-CHF2-3-Thio], [3118;4-Cl-5-OMe-3-Thio], [3119;4-Cl-5-OEt-3-Thio], [3120;4-Cl- 5-OCF3-3-Thio], [3121;4-Cl-5-OCHF2-3-Thio], [3122;4-Cl-5-CN-3-Thio], [3123;4-Cl-5-SMe-3-Thio], [3124;4-Cl-5-SEt-3-Thio], [3125;4-Cl-5-cPr-3-Thio], [3126;4-Me-5-F-3-Thio], [3127;4-Me-5-Cl-3-Thio], [3128;4-Me-5-Br-3-Thio], [3129;4-Me-5-I-3-Thio], [3130;4-Me-5-Me-3-Thio], [3131;4-Me-5-Et-3-Thio], [3132;4-Me-5-Pr-3-Thio], [3133;4-Me-5-iPr-3-Thio], [3134;4-Me-5-CF3-3-Thio], [3135;4-Me-5-CHF2-3-Thio], [3136;4-Me-5-OMe-3-Thio], [3137;4-Me-5-OEt-3-Thio], [3138;4-Me-5-OCF3-3-Thio], [3139;4-Me-5-OCHF2-3-Thio], [3140;4-Me-5-CN-3-Thio], [3141;4-Me-5-SMe-3-Thio], [3142;4-Me-5-SEt-3-Thio], [3143;4-Me-5-cPr-3-Thio], [3144;4-Et-5-F-3-Thio], [3145;4-Et-5-Cl-3-Thio], [3146;4-Et-5-Br-3-Thio], [3147;4-Et-5-I-3-Thio], [3148;4-Et-5-Me-3-Thio], [3149;4-Et-5-Et-3-Thio], [3150;4-Et-5-Pr-3-Thio], [3151;4-Et-5-iPr-3-Thio], [3152;4-Et-5-CF3-3-Thio], [3153;4-Et-5-CHF2-3-Thio], [3154;4-Et-5-OMe-3-Thio], [3155;4-Et-5-OEt-3-Thio], [3156;4-Et-5-OCF3-3-Thio], [3157;4-Et-5-OCHF2-3-Thio], [3158;4-Et-5-CN-3-Thio], [3159;4-Et-5-SMe-3-Thio], [3160;4-Et-5-SEt-3-Thio], [3161;4-Et-5-cPr-3-Thio], [3162;4-CF3-5-F-3-Thio], [3163;4-CF3-5-Cl-3-Thio], [3164;4-CF3-5-Br-3-Thio], [3165;4-CF3-5-I-3-Thio], [3166;4-CF3-5-Me-3-Thio], [3167;4-CF3-5-Et-3-Thio], [3168;4-CF3-5-Pr-3-Thio], [3169;4-CF3-5-iPr-3-Thio], [3170;4-CF3-5-CF3-3-Thio], [3171;4-CF3-5-CHF2-3-Thio], [3172;4-CF3-5-OMe-3-Thio], [3173;4-CF3-5-OEt-3-Thio], [3174;4-CF3-5-OCF3-3-Thio], [3175;4-CF3-5-OCHF2-3-Thio], [3176;4-CF3-5-CN-3-Thio], [3177;4-CF3-5-SMe-3-Thio], [3178;4-CF3-5-SEt-3-Thio], [3179;4-CF3-5-cPr-3-Thio], [3180;4-OMe-5-F-3-Thio], [3181;4-OMe-5-Cl-3-Thio], [3182;4-OMe-5-Br-3-Thio], [3183;4-OMe-5-I-3-Thio], [3184;4-OMe-5-Me-3-Thio], [3185;4-OMe-5-Et-3-Thio], [3186;4-OMe-5-Pr-3-Thio], [3187;4-OMe-5-iPr-3-Thio], [3188;4-OMe-5-CF3-3-Thio], [3189;4-OMe-5-CHF2-3-Thio], [3190;4-OMe-5-OMe-3-Thio], [3191;4-OMe-5-OEt-3-Thio], [3192;4-OMe-5-OCF3-3-Thio], [3193;4-OMe-5-OCHF2-3-Thio], [3194;4-OMe-5-CN-3-Thio], [3195;4-OMe-5-SMe-3-Thio], [3196;4-OMe-5-SEt-3-Thio], [3197;4-OMe-5-cPr-3-Thio], [3198;4-OEt-5-F-3-Thio], [3199;4-OEt-5-Cl-3-Thio], [3200;4-OEt-5-Br-3-Thio],

[3201;4-OEt-5-I-3-Thio], [3202;4-OEt-5-Me-3-Thio], [3203;4-OEt-5-Et-3-Thio], [3204;4-OEt-5-Pr-3-Thio], [3205;4-OEt-5-iPr-3-Thio], [3206;4-OEt-5-CF3-3-Thio], [3207;4-OEt-5-CHF2-3-Thio], [3208;4-OEt-5-OMe-3-Thio], [3209;4-OEt-5-OEt-3-Thio], [3210;4-OEt-5-OCF3-3-Thio], [3211;4-OEt-5-OCHF2-3-Thio], [3212;4-OEt-5-CN-3-Thio], [3213;4-OEt-5-SMe-3-Thio], [3214;4-OEt-5-SEt-3-Thio], [3215;4-OEt-5-cPr-3-Thio], [3216;4-SMe-5-F-3-Thio], [3217;4-SMe-5-Cl-3-Thio], [3218;4-SMe-5-Br-3-Thio], [3219;4-SMe-5-I-3-Thio], [3220;4-SMe-5-Me-3-Thio], [3221;4-SMe-5-Et-3-Thio], [3222;4-SMe-5-Pr-3-Thio], [3223;4-SMe-5-iPr-3-Thio], [3224;4-SMe-5-CF3-3-Thio], [3225;4-SMe-5-CHF2-3-Thio], [3226;4-SMe-5-OMe-3-Thio], [3227;4-SMe-5-OEt-3-Thio], [3228;4-SMe-5-OCF3-3-Thio], [3229;4-SMe-5-OCHF2-3-Thio], [3230;4-SMe-5-CN-3-Thio], [3231;4-SMe-5-SMe-3-Thio], [3232;4-SMe-5-SEt-3-Thio], [3233;4-SMe-5-cPr-3-Thio], [3234;2-Me-4-Me-5-F-3-Thio], [3235;2-Me-4-Me-5-Cl-3-Thio], [3236;2-Me-4-Me-5-Br-3-Thio], [3237;2-Me-4-Me-5-I-3-Thio], [3238;2-Me-4-Me-5-Me-3-Thio], [3239;2-Me-4-Me-5-Et-3-Thio], [3240;2-Me-4-Me-5-Pr-3-Thio], [3241;2-Me-4-Me-5-iPr-3-Thio], [3242;2-Me-4-Me-5-CF3-3-Thio], [3243;2-Me-4-Me-5-CHF2-3-Thio], [3244;2-Me-4-Me-5-OMe-3-Thio], [3245;2-Me-4-Me-5-OEt-3-Thio], [3246;2-Me-4-Me-5-OCF3-3-Thio], [3247;2-Me-4-Me-5-OCHF2-3-Thio], [3248;2-Me-4-Me-5-CN-3-Thio], [3249;2-Me-4-Me-5-SMe-3-Thio], [3250;2-Me-4-Me-5-SEt-3-Thio], [3251;2-Me-4-Me-5-cPr-3-Thio], [3252;2-F-4-Me-5-Me-3-Thio], [3253;2-Cl-4-Me-5-Me-3-Thio], [3254;2-Br-4-Me-5-Me-3-Thio], [3255;2-I-4-Me-5-Me-3-Thio], [3256;2-Et-4-Me-5-Me-3-Thio], [3257;2-Pr-4-Me-5-Me-3-Thio], [3258;2-iPr-4-Me-5-Me-3-Thio], [3259;2-CF3-4-Me-5-Me-3-Thio], [3260;2-CHF2-4-Me-5-Me-3-Thio], [3261;2-OMe-4-Me-5-Me-3-Thio], [3262;2-OEt-4-Me-5-Me-3-Thio], [3263;2-OCF3-4-Me-5-Me-3-Thio], [3264;2-OCHF2-4-Me-5-Me-3-Thio], [3265;2-CN-4-Me-5-Me-3-Thio], [3266;2-SMe-4-Me-5-Me-3-Thio], [3267;2-SEt-4-Me-5-Me-3-Thio], [3268;2-cPr-4-Me-5-Me-3-Thio], [3383;-2-Tri], [3384;4-F-2-Tri], [3385;4-Cl-2-Tri], [3386;4-Br-2-Tri], [3387;4-Me-2-Tri], [3388;4-Et-2-Tri], [3389;4-OMe-2-Tri], [3390;4-SMe-2-Tri], [3391;4-CF3-2-Tri], [3392;4-F-5-F-2-Tri], [3393;4-F-5-Cl-2-Tri], [3394;4-F-5-Br-2-Tri], [3395;4-F-5-Me-2-Tri], [3396;4-F-5-Et-2-Tri], [3397;4-F-5-OMe-2-Tri], [3398;4-F-5-SMe-2-Tri], [3399;4-F-5-CF3-2-Tri], [3400;4-Me-5-F-2-Tri],
[3401;4-Me-5-Cl-2-Tri], [3402;4-Me-5-Br-2-Tri], [3403;4-Me-5-Me-2-Tri], [3404;4-Me-5-Et-2-Tri], [3405;4-Me-5-OMe-2-Tri], [3406;4-Me-5-SMe-2-Tri], [3407;4-Me-5-CF3-2-Tri], [3408;4-OMe-5-F-2-Tri], [3409;4-OMe-5-Cl-2-Tri], [3410;4-OMe-5-Br-2-Tri], [3411;4-OMe-5-Me-2-Tri], [3412;4-OMe-5-Et-2-Tri], [3413;4-OMe-5-OMe-2-Tri], [3414;4-OMe-5-SMe-2-Tri], [3415;4-OMe-5-CF3-2-Tri], [3416;1-Tri], [3417;4-F-1-Tri], [3418;4-Cl-1-Tri], [3419;4-Br-1-Tri], [3420;4-Me-1-Tri], [3421;4-Et-1-Tri], [3422;4-OMe-1-Tri], [3423;4-SMe-1-Tri], [3424;4-CF3-1-Tri], [3425;5-F-1-Tri], [3426;5-Cl-1-Tri], [3427;5-Br-1-Tri], [3428;5-Me-1-Tri], [3429;5-Et-1-Tri], [3430;5-OMe-1-Tri], [3431;5-SMe-1-Tri], [3432;5-CF3-1-Tri], [3433;4-F-5-F-1-Tri], [3434;4-F-5-Cl-1-Tri], [3435;4-F-5-Br-1-Tri], [3436;4-F-5-Me-1-Tri], [3437;4-F-5-Et-1-Tri], [3438;4-F-5-OMe-1-Tri], [3439;4-F-5-SMe-1-Tri], [3440;4-F-5-CF3-1-Tri], [3441;4-Me-5-F-1-Tri], [3442;4-Me-5-Cl-1-Tri], [3443;4-Me-5-Br-1-Tri], [3444;4-Me-5-Me-1-Tri], [3445;4-Me-5-Et-1-Tri], [3446;4-Me-5-OMe-1-Tri], [3447;4-Me-5-SMe-1-Tri], [3448;4-Me-5-CF3-1-Tri], [3449;4-OMe-5-F-1-Tri], [3450;4-OMe-5-Cl-1-Tri], [3451;4-OMe-5-Br-1-Tri], [3452;4-OMe-5-Me-1-Tri], [3453;4-OMe-5-Et-1-Tri], [3454;4-OMe-5-OMe-1-Tri], [3455;4-OMe-5-SMe-1-Tri], [3456;4-OMe-5-CF3-1-Tri], [3854;2-oxazolin-4-ly], [3855;2-Me-2-oxazolin-4-ly], [3856;4-Me-2-oxazolin-4-ly], [3857;5-Me-2-oxazolin-4-ly], [3858;2-Me-4-Me-2-oxazolin-4-ly], [3859;2-Me-5-Me-2-oxazolin-4-ly], [3860;4-Me-5-Me-2-oxazolin-4-ly], [3861;5-Me-5-Me-2-oxazolin-4-ly], [3862;2-Me-4-Me-5-Me-2-oxazolin-5-ly], [3863;2-oxazolin-5-ly], [3864;2-Me-2-oxazolin-5-ly], [3865;5-Me-2-oxazolin-5-ly], [3866;4-Me-2-oxazolin-5-ly], [3867;2-Me-5-Me-2-oxazolin-5-ly], [3868;2-Me-4-Me-2-oxazolin-5-ly], [3869;5-Me-4-Me-2-oxazolin-5-ly], [3870;4-Me-4-Me-2-oxazolin-5-ly], [3871;2-Me-5-Me-4-Me-2-oxazolin-5-ly], [3872;3-oxazolin-2-ly], [3873;2-Me-3-oxazolin-2-ly], [3874;4-Me-3-oxazolin-2-ly], [3875;5-Me-3-oxazolin-2-ly], [3876;2-Me-4-Me-3-oxazolin-2-ly], [3877;2-Me-5-Me-3-oxazolin-2-ly], [3878;4-Me-5-Me-3-oxazolin-2-ly], [3879;5-Me-5-Me-3-oxazolin-2-ly], [3880;2-Me-4-Me-5-Me-3-oxazolin-2-ly], [3881;3-oxazolin-4-ly], [3882;2-Me-3-oxazolin-4-ly], [3883;5-Me-3-oxazolin-4-ly], [3884;2-Me-2-Me-3-oxazolin-4-ly], [3885;5-Me-5-Me-3-oxazolin-4-ly], [3886;2-Me-5-Me-3-oxazolin-4-ly], [3887;3-oxazolin-5-ly], [3888;2-Me-3-oxazolin-5-ly], [3889;4-Me-3-oxazolin-5-ly], [3890;5-Me-3-oxazolin-5-ly], [3891;2-Me-2-Me-3-oxazolin-5-ly], [3892;2-Me-4-Me-3-oxazolin-5-ly], [3893;2-Me-5-Me-3-oxazolin-5-ly], [3894;4-Me-5-Me-3-oxazolin-5-ly], [3895;2-Me-4-Me-5-Me-3-oxazolin- 5-ly], [3896;N-Me-4-oxazolin-2-ly], [3897;2-Me-N-Me-4-oxazolin-2-ly], [3898;4-Me-N-Me-4-oxazolin-2-ly], [3899;5-Me-N-Me-4-oxazolin-2-ly], [3900;2-Me-5-Me-N-Me-4-oxazolin-2-ly], [3901;4-Me-5-Me-N-Me-4-oxazolin-2-ly], [3902;2-Me-4-Me-5-Me-N-Me-4-oxazolin-2-ly], [3903;2-Me-4-Me-N-Me-4-oxazolin-2-ly], [3904;N-Me-4-oxazolin-4-ly], [3905;2-Me-N-Me-4-oxazolin-4-ly], [3906;5-Me-N-Me-4-oxazolin-4-ly], [3907;2-Me-5-Me-N-Me-4-oxazolin-4-ly], [3908;2-Me-2-Me-5-Me-N-Me-4-oxazolin-4-ly], [3909;N-Me-4-oxazolin-5-ly], [3910;2-Me-N-Me-4-oxazolin-5-ly], [3911;5-Me-N-Me-4-oxazolin-5-ly], [3912;2-Me-5-Me-N-Me-4-oxazolin-5-ly], [3913;2-Me-2-Me-5-Me-N-Me-4-oxazolin-5-ly], [3914;oxazolidin-2-on-4-ly], [3915;4-Me-oxazolidin-2-on-4-ly], [3916;5-Me-oxazolidin-2-on-4-ly], [3917;4-Me-5-Me-oxazolidin-2-on-4-ly], [3918;5-Me-5-Me-oxazolidin-2-on-4-ly], [3919;-oxazolidin-2-on-5-ly], [3920;4-Me-oxazolidin-2-on-5-ly], [3921;5-Me-oxazolidin-2-on-5-ly], [3922;4-Me-5-Me-oxazolidin-2-on-5-ly], [3923;4-Me-4-Me-oxazolidin-2-on-5-ly], [3924;N-Me-oxazolidin-4-on-2-ly], [3925;2-Me-N-Me-oxazolidin-4-on-2-ly], [3926;5-Me-N-Me-oxazolidin-4-on-2-ly], [3927;2-Me-5-Me-N-Me-oxazolidin-4-on-2-ly], [3928;2-Me-5-Me-5-Me-N-Me-oxazolidin-4-on-2-ly], [3929;N-Me-oxazolidin-4-on-5-ly], [3930;2-Me-N-Me-oxazolidin-4-on-5-ly], [3931;5-Me-N-Me-oxazolidin-4-on-5-ly], [3932;2-Me-5-Me-N-Me-oxazolidin-4-on-5-ly], [3933;2-Me-2-Me-5-Me-N-Me-oxazolidin-4-on-5-ly], [3934;N-Me-oxazolidin-5-on-2-ly], [3935;2-Me-N-Me-oxazolidin-5-on-2-ly], [3936;4-Me-N-Me-oxazolidin-5-on-2-ly], [3937;2-Me-4-Me-N-Me-oxazolidin-5-on-2-ly], [3938;2-Me-4-Me-4-Me-N-Me-oxazolidin-5-on-2-ly], [3939;N-Me-oxazolidin-5-on-4-ly], [3940;2-Me-N-Me-oxazolidin-5-on-4-ly], [3941;4-Me-N-Me-oxazolidin-5-on-4-ly], [3942;2-Me-4-Me-N-Me-oxazolidin-5-on-4-ly], [3943;2-Me-2-Me-4-Me-N-Me-oxazolidin-5-on-4-ly], [3944;2-thiazolin-4-ly], [3945;2-Me-2-thiazolin-4-ly], [3946;4-Me-2-thiazolin-4-ly], [3947;5-Me-2-thiazolin-4-ly], [3948;2-Me-4-Me-2-thiazolin-4-ly], [3949;2-Me-5-Me-2-thiazolin-4-ly], [3950;4-Me-5-Me-2-thiazolin-4-ly], [3951;5-Me-5-Me-2-thiazolin-4-ly], [3952;2-Me-4-Me-5-Me-2-thiazolin-5-ly], [3953;2-thiazolin-5-ly], [3954;2-Me-2-thiazolin-5-ly], [3955;5-Me-2-thiazolin-5-ly], [3956;4-Me-2-thiazolin-5-ly], [3957;2-Me-5-Me-2-thiazolin-5-ly], [3958;2-Me-4-Me-2-thiazolin-5-ly], [3959;5-Me-4-Me-2-thiazolin-5-ly], [3960;4-Me-4-Me-2-thiazolin-5-ly], [3961;2-Me-5-Me-4-Me-2-thiazolin-5-ly], [3962;3-thiazolin-2-ly], [3963;2-Me-3-thiazolin-2-ly], [3964;4-Me-3-thiazolin-2-ly], [3965;5-Me-3-thiazolin-2-ly], [3966;2-Me-4-Me-3-thiazolin-2-ly], [3967;2-Me-5-Me-3-thiazolin-2-ly], [3968;4-Me-5-Me-3-thiazolin-2-ly], [3969;5-Me-5-Me-3-thiazolin-2-ly], [3970;2-Me-4-Me-5-Me-3-thiazolin-2-ly], [3971;3-thiazolin-4-ly], [3972;2-Me-3-thiazolin-4-ly], [3973;5-Me-3-thiazolin-4-ly], [3974;2-Me-2-Me-3-thiazolin-4-ly], [3975;5-Me-5-Me-3-thiazolin-4-ly], [3976;2-Me-5-Me-3-thiazolin-4-ly], [3977;3-thiazolin-5-ly], [3978;2-Me-3-thiazolin-5-ly], [3979;4-Me-3-thiazolin-5-ly], [3980;5-Me-3-thiazolin-5-ly], [3981;2-Me-2-Me-3-thiazolin-5-ly], [3982;2-Me-4-Me-3-thiazolin-5-ly], [3983;2-Me-5-Me-3-thiazolin-5-ly], [3984;4-Me-5-Me-3-thiazolin-5-ly], [3985;2-Me-4-Me-5-Me-3-thiazolin-5-ly], [3986;N-Me-4-thiazolin-2-ly], [3987;2-Me-N-Me-4-thiazolin-2-ly], [3988;4-Me-N-Me-4-thiazolin-2-ly], [3989;5-Me-N-Me-4-thiazolin-2-ly], [3990;2-Me-5-Me-N-Me-4-thiazolin-2-ly], [3991;4-Me-5-Me-N-Me-4-thiazolin-2-ly], [3992;2-Py], [3993;3-Me-2-Py], [3994;4-Me-2-Py], [3995;5-Me-2-Py], [3996;6-Me-2-Py], [3997;3-Me-4-Me-2-Py], [3998;3-Me-5-Me-2-Py], [3999;3-Me-6-Me-2-Py], [4000;4-Me-5-Me-2-Py], [4001;4-Me-6-Me-2-Py], [4002;5-Me-6-Me-2-Py], [4003;3-Me-4-Me-5-Me-2-Py], [4004;3-Me-4-Me-6-Me-2-Py], [4005;3-Me-5-Me-6-Me-2-Py], [4006;4-Me-5-Me-6-Me-2-Py], [4007;3-F-4-Me-2-Py], [4008;5-F-4-Me-2-Py], [4009;6-F-4-Me-2-Py], [4010;3-F-5-Me-2-Py], [4011;4-F-5-Me-2-Py], [4012;6-F-5-Me-2-Py], [4013;3-F-6-Me-2-Py], [4014;4-F-6-Me-2-Py], [4015;5-F-6-Me-2-Py], [4016;3-F-4-F-6-Me-2-Py], [4017;3-F-5-F-6-Me-2-Py], [4018;4-F-5-F-6-Me-2-Py], [4019;3-Cl-4-Me-2-Py], [4020;5-Cl-4-Me-2-Py], [4021;6-Cl-4-Me-2-Py], [4022;3-Cl-5-Me-2-Py], [4023;4-Cl-5-Me-2-Py], [4024;6-Cl-5-Me-2-Py], [4025;3-Cl-6-Me-2-Py], [4026;4-Cl-6-Me-2-Py], [4027;5-Cl-6-Me-2-Py], [4028;3-Cl-4-Cl-6-Me-2-Py], [4029;3-Cl-5-Cl-6-Me-2-Py], [4030;4-Cl-5-Cl-6-Me-2-Py], [4031;3-Br-6-Me-2-Py], [4032;4-Br-6-Me-2-Py], [4033;5-Br-6-Me-2-Py], [4034;3-CN-6-Me-2-Py], [4035;4-CN-6-Me-2-Py], [4036;5-CN-6-Me-2-Py], [4037;3-OMe-6-Me-2-Py], [4038;4-OMe-6-Me-2-Py], [4039;5-OMe-6-Me-2-Py], [4040;3-Et-6-Me-2-Py], [4041;4-Et-6-Me-2-Py], [4042;5-Et-6-Me-2-Py], [4043;3-Br-5-Me-2-Py], [4044;4-Br-5-Me-2-Py], [4045;6-Br-5-Me-2-Py], [4046;3-CN-5-Me-2-Py], [4047;4-CN-5-Me-2-Py], [4048;6-CN-5-Me-2-Py], [4049;3-OMe-5-Me-2-Py], [4050;4-OMe-5-Me-2-Py], [4051;6-OMe-5-Me-2-Py], [4052;3-Br-4-Me-2-Py], [4053;5-Br-4-Me-2-Py], [4054;6-Br-4-Me-2-Py], [4055;3-CN-4-Me-2-Py], [4056;5-CN-4-Me-2-Py], [4057;6-CN-4-Me-2-Py], [4058;3-OMe-4-Me-2-Py], [4059;5-OMe-4-Me-2-Py], [4060;6-OMe-4-Me-2-Py], [4061;3-Et-4-Me-2-Py], [4062;5-Et-4-Me-2-Py], [4063;6-Et-4-Me-2-Py], [4064;3-Et-2-Py], [4065;4-Et-2-Py], [4066;5-Et-2-Py], [4067;6-Et-2-Py], [4068;3-Et-4-Et-2-Py], [4069;3-Et-5-Et-2-Py], [4070;3-Et-6-Et-2-Py], [4071;4-Et-5-Et-2-Py], [4072;4-Et-6-Et-2-Py], [4073;5-Et-6-Et-2-Py], [4074;3-F-4-Et-2-Py], [4075;5-F-4-Et-2-Py], [4076;6-F-4-Et-2-Py], [4077;3-F-5-Et-2-Py], [4078;4-F-5-Et-2-Py], [4079;6-F-5-Et-2-Py], [4080;3-F-6-Et-2-Py], [4081;4-F-6-Et-2-Py], [4082;5-F-6-Et-2-Py], [4083;3-F-4-F-6-Et-2-Py], [4084;3-F-5-F-6-Et-2-Py], [4085;4-F-5-F-6-Et-2-Py], [4086;3-Cl-4-Et-2-Py], [4087;5-Cl-4-Et-2-Py], [4088;6-Cl-4-Et-2-Py], [4089;3-Cl-5-Et-2-Py], [4090;4-Cl-5-Et-2-Py], [4091;6-Cl-5-Et-2-Py], [4092;3-Cl-6-Et-2-Py], [4093;4-Cl-6-Et-2-Py], [4094;5-Cl-6-Et-2-Py], [4095;3-Cl-4-Cl-6-Et-2-Py], [4096;3-Cl-5-Cl-6-Et-2-Py], [4097;4-Cl-5-Cl-6-Et-2-Py], [4098;3-Br-5-Et-2-Py], [4099;4-Br-5-Et-2-Py], [4100;6-Br-5-Et-2-Py], [4101;3-CN-5-Et-2-Py], [4102;4-CN-5-Et-2-Py], [4103;6-CN-5-Et-2-Py], [4104;3-OMe-5-Et-2-Py], [4105;4-OMe-5-Et-2-Py], [4106;6-OMe-5-Et-2-Py], [4107;3-Et-5-Et-2-Py], [4108;4-Et-5-Et-2-Py], [4109;6-Et-5-Et-2-Py], [4110;3-Br-6-Et-2-Py], [4111;4-Br-6-Et-2-Py], [4112;5-Br-6-Et-2-Py], [4113;3-CN-6-Et-2-Py], [4114;4-CN-6-Et-2-Py], [4115;5-CN-6-Et-2-Py], [4116;3-OMe-6-Et-2-Py], [4117;4-OMe-6-Et-2-Py], [4118;5-OMe-6-Et-2-Py], [4119;3-Pr-2-Py], [4120;4-Pr-2-Py], [4121;5-Pr-2-Py], [4122;6-Pr-2-Py], [4123;3-iPr-2-Py], [4124;4-iPr-2-Py], [4125;5-iPr-2-Py], [4126;6-iPr-2-Py], [4127;3-cPr-2-Py], [4128;4-cPr-2-Py], [4129;5-cPr-2-Py], [4130;6-cPr-2-Py], [4131;3-F-4-cPr-2-Py], [4132;5-F-4-cPr-2-Py], [4133;6-F-4-cPr-2-Py], [4134;3-F-5-cPr-2-Py], [4135;4-F-5-cPr-2-Py], [4136;6-F-5-cPr-2-Py], [4137;3-F-6-cPr-2-Py], [4138;4-F-6-cPr-2-Py], [4139;5-F-6-cPr-2-Py], [4140;3,4-F2-6-cPr-2-Py], [4141;3,5-F2-6-cPr-2-Py], [4142;4,5-F2-6-cPr-2-Py], [4143;3-Cl-4-cPr-2-Py], [4144;5-Cl-4-cPr-2-Py], [4145;6-Cl-4-cPr-2-Py], [4146;3-Cl-5-cPr-2-Py], [4147;4-Cl-5-cPr-2-Py], [4148;6-Cl-5-cPr-2-Py], [4149;3-Cl-6-cPr-2-Py], [4150;4-Cl-6-cPr-2-Py], [4151;5-Cl-6-cPr-2-Py], [4152;3-Cl-4-Cl-6-cPr-2-Py], [4153;3-Cl-5-Cl-6-cPr-2-Py], [4154;4-Cl-5-Cl-6-cPr-2-Py], [4155;3-F-2-Py], [4156;4-F-2-Py], [4157;5-F-2-Py],

[4158;6-F-2-Py], [4159;3-F-4-F-2-Py], [4160;3-F-5-F-2-Py], [4161; 3-F-6-F-2-Py], [4162; 4-F-5-F-2-Py], [4163;4-F-6-F-2-Py], [4164; 5-F-6-F-2-Py], [4165; 3-F-4-F-5-F-2-Py], [4166; 3-F-4-F-6-F-2-Py], [4167;3-F-5-F-6-F-2-Py], [4168;4-F-5-F-6-F-2-Py], [4169;3-Cl-2-Py], [4170;4-Cl-2-Py], [4171;5-Cl-2-Py], [4172;6-Cl-2-Py], [4173;3-F-4-Cl-2-Py], [4174;5-F-4-Cl-2-Py], [4175;6-F-4-Cl-2-Py], [4176;3-F-5-Cl-2-Py], [4177;4-F-5-Cl-2-Py], [4178;6-F-5-Cl-2-Py], [4179;3-F-6-Cl-2-Py], [4180;4-F-6-Cl-2-Py], [4181;5-F-6-Cl-2-Py], [4182;3-F-4-F-6-Cl-2-Py], [4183;3-F-5-F-6-Cl-2-Py], [4184;4-F-5-F-6-Cl-2-Py], [4185;3-Cl-4-Cl-2-Py], [4186;3-Cl-5-Cl-2-Py], [4187;3-Cl-6-Cl-2-Py], [4188;4-Cl-5-Cl-2-Py], [4189;4-Cl-6-Cl-2-Py], [4190;5-Cl-6-Cl-2-Py], [4191;3-Cl-4-Cl-5-Cl-2-Py], [4192;3-Cl-4-Cl-6-Cl-2-Py], [4193;3-Cl-5-Cl-6-Cl-2-Py], [4194;4-Cl-5-Cl-6-Cl-2-Py], [4195;3-Br-2-Py], [4196;4-Br-2-Py], [4197;5-Br-2-Py], [4198;6-Br-2-Py], [4199;3-CN-2-Py], [4200;4-CN-2-Py], [4201;5-CN-2-Py], [4202;6-CN-2-Py], [4203;3-F-4-CN-2-Py], [4204;5-F-4-CN-2-Py], [4205;6-F-4-CN-2-Py], [4206; 3-F-5-CN-2-Py], [4207;4-F-5-CN-2-Py], [4208;6-F-5-CN-2-Py], [4209;3-F-6-CN-2-Py], [4210;4-F-6-CN-2-Py], [4211;5-F-6-CN-2-Py], [4212;3-F-4-F-6-CN-2-Py], [4213; 3-F-5-F-6-CN-2-Py], [4214;4-F-5-F-6-CN-2-Py], [4215;3-Cl-4-CN-2-Py], [4216;5-Cl-4-CN-2-Py], [4217;6-Cl-4-CN-2-Py], [4218;3-Cl-5-CN-2-Py], [4219;4-Cl-5-CN-2-Py], [4220;6-Cl-5-CN-2-Py], [4221;3-Cl-6-CN-2-Py], [4222;4-Cl-6-CN-2-Py], [4223;5-Cl-6-CN-2-Py], [4224;3-Cl-4-Cl-6-CN-2-Py], [4225;3-Cl-5-Cl-6-CN-2-Py], [4226;4-Cl-5-Cl-6-CN-2-Py], [4227;3-OMe-2-Py], [4228;4-OMe-2-Py], [4229;5-OMe-2-Py], [4230;6-OMe-2-Py], [4231;3-OMe-4-OMe-2-Py], [4232;3-OMe-5-OMe-2-Py], [4233;3-OMe-6-OMe-2-Py], [4234;4-OMe-5-OMe-2-Py], [4235;4-OMe-6-OMe-2-Py], [4236;5-OMe-6-OMe-2-Py], [4237;3-F-4-OMe-2-Py], [4238;5-F-4-OMe-2-Py], [4239;6-F-4-OMe-2-Py], [4240;3-F-5-OMe-2-Py], [4241;4-F-5-OMe-2-Py], [4242;6-F-5-OMe-2-Py], [4243;3-F-6-OMe-2-Py], [4244;4-F-6-OMe-2-Py], [4245;5-F-6-OMe-2-Py], [4246;3,4-F2-6-OMe-2-Py], [4247;3,5-F2-6-OMe-2-Py], [4248;4,5-F2-6-OMe-2-Py], [4249;3-Cl-4-OMe-2-Py], [4250;5-Cl-4-OMe-2-Py], [4251;6-Cl-4-OMe-2-Py], [4252;3-Cl-5-OMe-2-Py], [4253;4-Cl-5-OMe-2-Py], [4254;6-Cl-5-OMe-2-Py], [4255; 3-Cl-6-OMe-2-Py], [4256;4-Cl-6-OMe-2-Py], [4257;5-Cl-6-OMe-2-Py], [4258;3-Cl-4-Cl-6-OMe-2-Py], [4259;3-Cl-5-Cl-6-OMe-2-Py], [4260;4-Cl-5-Cl-6-OMe-2-Py], [4261; 3-OEt-2-Py], [4262;4-OEt-2-Py], [4263;5-OEt-2-Py], [4264;6-OEt-2-Py], [4265;3-CF3-2-Py], [4266;4-CF3-2-Py], [4267;5-CF3-2-Py], [4268;6-CF3-2-Py], [4269;3-F-4-CF3-2-Py], [4270;5-F-4-CF3-2-Py], [4271;6-F-4-CF3-2-Py], [4272;3-F-5-CF3-2-Py], [4273;4-F-5-CF3-2-Py], [4274;6-F-5-CF3-2-Py], [4275;3-F-6-CF3-2-Py], [4276;4-F-6-CF3-2-Py], [4277;5-F-6-CF3-2-Py], [4278;3-F-4-F-6-CF3-2-Py], [4279;3-F-5-F-6-CF3-2-Py], [4280;4-F-5-F-6-CF3-2-Py], [4281;3-Cl-4-CF3-2-Py], [4282;5-Cl-4-CF3-2-Py], [4283;6-Cl-4-CF3-2-Py], [4284;3-Cl-5-CF3-2-Py], [4285;4-Cl-5-CF3-2-Py], [4286;6-Cl-5-CF3-2-Py], [4287; 3-Cl-6-CF3-2-Py], [4288;4-Cl-6-CF3-2-Py], [4289;5-Cl-6-CF3-2-Py], [4290;3-Cl-4-Cl-6-CF3-2-Py], [4291; 3-Cl-5-Cl-6-CF3-2-Py], [4292;4-Cl-5-Cl-6-CF3-2-Py], [4293;3-amino-2-Py], [4294;4-amino-2-Py], [4295;5-amino-2-Py], [4296;6-amino-2-Py], [4297;3-N,N-dimethylamino-2-Py], [4298;4-N,N-dimethylamino-2-Py], [4299;5-N,N-dimethylamino-2-Py], [4300;6-N,N-dimethylamino-2-Py], [4301;3-SMe-2-Py], [4302;4-SMe-2-Py], [4303;5-SMe-2-Py], [4304;6-SMe-2-Py], [4305;-3-Py], [4306;2-Me-3-Py], [4307;4-Me-3-Py], [4308;5-Me-3-Py], [4309;6-Me-3-Py], [4310;2-Me-4-Me-3-Py], [4311;2-Me-5-Me-3-Py], [4312;2-Me-6-Me-3-Py], [4313;4-Me-5-Me-3-Py], [4314;4-Me-6-Me-3-Py], [4315;5-Me-6-Me-3-Py], [4316;2-Me-4-Me-5-Me-3-Py], [4317;2-Me-4-Me-6-Me-3-Py], [4318;2-Me-5-Me-6-Me-3-Py], [4319;4-Me-5-Me-6-Me-3-Py], [4320;2-F-4-Me-3-Py], [4321;5-F-4-Me-3-Py], [4322;6-F-4-Me-3-Py], [4323;2-F-5-Me-3-Py], [4324;4-F-5-Me-3-Py], [4325;6-F-5-Me-3-Py], [4326;2-F-6-Me-3-Py], [4327;4-F-6-Me-3-Py], [4328;5-F-6-Me-3-Py], [4329;2-F-4-F-6-Me-3-Py], [4330; 2-F-5-F-6-Me-3-Py], [4331;4-F-5-F-6-Me-3-Py], [4332;2-Cl-4-Me-3-Py], [4333;5-Cl-4-Me-3-Py], [4334;6-Cl-4-Me-3-Py], [4335;2-Cl-5-Me-3-Py], [4336;4-Cl-5-Me-3-Py], [4337;6-Cl-5-Me-3-Py], [4338;2-Cl-6-Me-3-Py], [4339;4-Cl-6-Me-3-Py], [4340;5-Cl-6-Me-3-Py], [4341;2-Cl-4-Cl-6-Me-3-Py], [4342;2-Cl-5-Cl-6-Me-3-Py], [4343;4-Cl-5-Cl-6-Me-3-Py], [4344;2-Br-6-Me-3-Py], [4345;4-Br-6-Me-3-Py], [4346;5-Br-6-Me-3-Py], [4347;2-CN-6-Me-3-Py], [4348;4-CN-6-Me-3-Py], [4349;5-CN-6-Me-3-Py], [4350;2-OMe-6-Me-3-Py], [4351;4-OMe-6-Me-3-Py], [4352;5-OMe-6-Me-3-Py], [4353;2-Et-6-Me-3-Py], [4354;4-Et-6-Me-3-Py], [4355;5-Et-6-Me-3-Py], [4356;3-Br-5-Me-2-Py], [4357;4-Br-5-Me-2-Py], [4358;6-Br-5-Me-2-Py], [4359;3-CN-5-Me-2-Py], [4360;4-CN-5-Me-2-Py], [4361;6-CN-5-Me-2-Py], [4362;3-OMe-5-Me-2-Py], [4363;4-OMe-5-Me-2-Py], [4364;6-OMe-5-Me-2-Py], [4365;3-Br-4-Me-2-Py], [4366; 5-Br-4-Me-2-Py], [4367;6-Br-4-Me-2-Py], [4368;3-CN-4-Me-2-Py], [4369;5-CN-4-Me-2-Py], [4370;6-CN-4-Me-2-Py], [4371;3-OMe-4-Me-2-Py], [4372;5-OMe-4-Me-2-Py], [4373;6-OMe-4-Me-2-Py], [4374;3-Et-4-Me-2-Py], [4375; 5-Et-4-Me-2-Py], [4376;6-Et-4-Me-2-Py], [4377;2-Et-3-Py], [4378;4-Et-3-Py], [4379;5-Et-3-Py], [4380;6-Et-3-Py], [4381;2-Et-4-Et-3-Py], [4382;2-Et-5-Et-3-Py], [4383;2-Et-6-Et-3-Py], [4384;4-Et-5-Et-3-Py], [4385;4-Et-6-Et-3-Py], [4386;5-Et-6-Et-3-Py], [4387;2-F-4-Et-3-Py], [4388;5-F-4-Et-3-Py], [4389;6-F-4-Et-3-Py], [4390;2-F-5-Et-3-Py], [4391;4-F-5-Et-3-Py], [4392;6-F-5-Et-3-Py], [4393;2-F-6-Et-3-Py], [4394;4-F-6-Et-3-Py], [4395;5-F-6-Et-3-Py], [4396;2-F-4-F-6-Et-3-Py], [4397;2-F-5-F-6-Et-3-Py], [4398;4-F-5-F-6-Et-3-Py], [4399;2-Cl-4-Et-3-Py], [4400;5-Cl-4-Et-3-Py],
[4401;6-Cl-4-Et-3-Py], [4402;2-Cl-5-Et-3-Py], [4403;4-Cl-5-Et-3-Py], [4404;6-Cl-5-Et-3-Py], [4405;2-Cl-6-Et-3-Py], [4406;4-Cl-6-Et-3-Py], [4407;5-Cl-6-Et-3-Py], [4408; 2-Cl-4-Cl-6-Et-3-Py], [4409;2-Cl-5-Cl-6-Et-3-Py], [4410;4-Cl-5-Cl-6-Et-3-Py], [4411;2-Br-5-Et-3-Py], [4412;4-Br-5-Et-3-Py], [4413;6-Br-5-Et-3-Py], [4414;2-CN-5-Et-3-Py], [4415; 4-CN-5-Et-3-Py], [4416;6-CN-5-Et-3-Py], [4417;2-OMe-5-Et-3-Py], [4418;4-OMe-5-Et-3-Py], [4419;6-OMe-5-Et-3-Py], [4420;2-Et-5-Et-3-Py], [4421;4-Et-5-Et-3-Py], [4422; 6-Et-5-Et-3-Py], [4423;2-Br-6-Et-3-Py], [4424;4-Br-6-Et-3-Py], [4425;5-Br-6-Et-3-Py], [4426;2-CN-6-Et-3-Py], [4427; 4-CN-6-Et-3-Py], [4428;5-CN-6-Et-3-Py], [4429;2-OMe-6-Et-3-Py], [4430;4-OMe-6-Et-3-Py], [4431;5-OMe-6-Et-3-Py], [4432;2-Pr-3-Py], [4433;4-Pr-3-Py], [4434;5-Pr-3-Py], [4435;6-Pr-3-Py], [4436;2-iPr-3-Py], [4437;4-iPr-3-Py], [4438;5-iPr-3-Py], [4439;6-iPr-3-Py], [4440;2-cPr-3-Py], [4441;4-cPr-3-Py], [4442;5-cPr-3-Py], [4443;6-cPr-3-Py], [4444;2-F-4-cPr-3-Py], [4445;5-F-4-cPr-3-Py], [4446;6-F-4-cPr-3-Py], [4447;2-F-5-cPr-3-Py], [4448;4-F-5-cPr-3-Py], [4449;6-F-5-cPr-3-Py], [4450;2-F-6-cPr-3-Py], [4451;4-F-6-cPr-3-Py], [4452;5-F-6-cPr-3-Py], [4453;2,4-F2-6-cPr-3-Py], [4454;2,5-F2-6-cPr-3-Py], [4455;4,5-F2-6-cPr-3-Py], [4456;2-Cl-4-cPr-3-Py], [4457;5-Cl-4-cPr-3-Py], [4458;6-Cl-4-cPr-3-Py], [4459;2-Cl-5-cPr-3-Py], [4460;4-Cl-5-cPr-3-Py], [4461;6-Cl-5-cPr-3-Py], [4462;2-Cl-6-cPr-3-Py], [4463;4-Cl-6-cPr-3-Py], [4464;5-Cl-6-cPr-3-Py], [4465;2-Cl-4-Cl-6-cPr-3-Py], [4466;2-Cl-5-Cl-6-cPr-3-Py], [4467;4-Cl-5-Cl-6-cPr-3-Py], [4468;2-F-3-Py], [4469;4-F-3-Py], [4470;5-F-3-Py], [4471;6-F-3-Py], [4472;2-F-4-F-3-Py],

[4473;2-F-5-F-3-Py], [4474;2-F-6-F-3-Py], [4475; 4-F-5-F-3-Py], [4476;4-F-6-F-3-Py], [4477; 5-F-6-F-3-Py], [4478;2-F-4-F-5-F-3-Py], [4479;2-F-4-F-6-F-3-Py], [4480;2-F-5-F-6-F-3-Py], [4481;4-F-5-F-6-F-3-Py], [4482;2-Cl-3-Py], [4483;4-Cl-3-Py], [4484;5-Cl-3-Py], [4485;6-Cl-3-Py], [4486;2-F-4-Cl-3-Py], [4487;5-F-4-Cl-3-Py], [4488;6-F-4-Cl-3-Py], [4489;2-F-5-Cl-3-Py], [4490;4-F-5-Cl-3-Py], [4491;6-F-5-Cl-3-Py], [4492;2-F-6-Cl-3-Py], [4493;4-F-6-Cl-3-Py], [4494;5-F-6-Cl-3-Py], [4495;2-F-4-F-6-Cl-3-Py], [4496;2-F-5-F-6-Cl-3-Py], [4497;4-F-5-F-6-Cl-3-Py], [4498;2-Cl-4-Cl-3-Py], [4499;2-Cl-5-Cl-3-Py], [4500;2-Cl-6-Cl-3-Py],

[4501;4-Cl-5-Cl-3-Py], [4502;4-Cl-6-Cl-3-Py], [4503;5-Cl-6-Cl-3-Py], [4504;2-Cl-4-Cl-5-Cl-3-Py], [4505;2-Cl-4-Cl-6-Cl-3-Py], [4506;2-Cl-5-Cl-6-Cl-3-Py], [4507;4-Cl-5-Cl-6-Cl-3-Py], [4508;2-Br-3-Py], [4509;4-Br-3-Py], [4510;5-Br-3-Py], [4511;6-Br-3-Py], [4512;2-CN-3-Py], [4513;4-CN-3-Py], [4514;5-CN-3-Py], [4515;6-CN-3-Py], [4516;2-F-4-CN-3-Py], [4517;5-F-4-CN-3-Py], [4518;6-F-4-CN-3-Py], [4519;2-F-5-CN-3-Py], [4520;4-F-5-CN-3-Py], [4521;6-F-5-CN-3-Py], [4522;2-F-6-CN-3-Py], [4523;4-F-6-CN-3-Py], [4524;5-F-6-CN-3-Py], [4525;2-F-4-F-6-CN-3-Py], [4526;2-F-5-F-6-CN-3-Py], [4527;4-F-5-F-6-CN-3-Py], [4528;2-Cl-4-CN-3-Py], [4529;5-Cl-4-CN-3-Py], [4530;6-Cl-4-CN-3-Py], [4531;2-Cl-5-CN-3-Py], [4532;4-Cl-5-CN-3-Py], [4533;6-Cl-5-CN-3-Py], [4534;2-Cl-6-CN-3-Py], [4535;4-Cl-6-CN-3-Py], [4536;5-Cl-6-CN-3-Py], [4537;2-Cl-4-Cl-6-CN-3-Py], [4538;2-Cl-5-Cl-6-CN-3-Py], [4539;4-Cl-5-Cl-6-CN-3-Py], [4540;2-OMe-3-Py], [4541;4-OMe-3-Py], [4542;5-OMe-3-Py], [4543;6-OMe-3-Py], [4544;2-OMe-4-OMe-3-Py], [4545;2-OMe-5-OMe-3-Py], [4546;2-OMe-6-OMe-3-Py], [4547;4-OMe-5-OMe-3-Py], [4548;4-OMe-6-OMe-3-Py], [4549;5-OMe-6-OMe-3-Py], [4550;2-F-4-OMe-3-Py], [4551;5-F-4-OMe-3-Py], [4552;6-F-4-OMe-3-Py], [4553;2-F-5-OMe-3-Py], [4554;4-F-5-OMe-3-Py], [4555;6-F-5-OMe-3-Py], [4556;2-F-6-OMe-3-Py], [4557;4-F-6-OMe-3-Py], [4558;5-F-6-OMe-3-Py], [4559;2-F-4-F-6-OMe-3-Py], [4560;2-F-5-F-6-OMe-3-Py], [4561;4-F-5-F-6-OMe-3-Py], [4562;2-Cl-4-OMe-3-Py], [4563;5-Cl-4-OMe-3-Py], [4564;6-Cl-4-OMe-3-Py], [4565;2-Cl-5-OMe-3-Py], [4566;4-Cl-5-OMe-3-Py], [4567;6-Cl-5-OMe-3-Py], [4568;2-Cl-6-OMe-3-Py], [4569;4-Cl-6-OMe-3-Py], [4570;5-Cl-6-OMe-3-Py], [4571;2-Cl-4-Cl-6-OMe-3-Py], [4572;2-Cl-5-Cl-6-OMe-3-Py], [4573;4-Cl-5-Cl-6-OMe-3-Py], [4574;2-OEt-3-Py], [4575;4-OEt-3-Py], [4576;5-OEt-3-Py], [4577;6-OEt-3-Py], [4578;2-CF3-3-Py], [4579;4-CF3-3-Py], [4580;5-CF3-3-Py], [4581;6-CF3-3-Py], [4582;2-F-4-CF3-3-Py], [4583;5-F-4-CF3-3-Py], [4584;6-F-4-CF3-3-Py], [4585;2-F-5-CF3-3-Py], [4586;4-F-5-CF3-3-Py], [4587;6-F-5-CF3-3-Py], [4588;2-F-6-CF3-3-Py], [4589;4-F-6-CF3-3-Py], [4590;5-F-6-CF3-3-Py], [4591;2-F-4-F-6-CF3-3-Py], [4592;2-F-5-F-6-CF3-3-Py], [4593;4-F-5-F-6-CF3-3-Py], [4594;2-Cl-4-CF3-3-Py], [4595;5-Cl-4-CF3-3-Py], [4596;6-Cl-4-CF3-3-Py], [4597;2-Cl-5-CF3-3-Py], [4598;4-Cl-5-CF3-3-Py], [4599;6-Cl-5-CF3-3-Py], [4600;2-Cl-6-CF3-3-Py],

[4601;4-Cl-6-CF3-3-Py], [4602;5-Cl-6-CF3-3-Py], [4603;2-Cl-4-Cl-6-CF3-3-Py], [4604;2-Cl-5-Cl-6-CF3-3-Py], [4605;4-Cl-5-Cl-6-CF3-3-Py], [4606;2-amino-3-Py], [4607;4-amino-3-Py], [4608;5-amino-3-Py], [4609;6-amino-3-Py], [4610;2-N,N-dimethylamino-3-Py], [4611;4-N,N-dimethylamino-3-Py], [4612;5-N,N-dimethylamino-3-Py], [4613;6-N,N-dimethylamino-3-Py], [4614;2-SMe-3-Py], [4615;4-SMe-3-Py], [4616;5-SMe-3-Py], [4617;6-SMe-3-Py], [4618;-2-Pyrimidine], [4619;4-Me-2-Pyrimidine], [4620;5-Me-2-Pyrimidine], [4621;4-Me-5-Me-2-Pyrimidine], [4622;4-Me-6-Me-2-Pyrimidine], [4623;4-Me-5-Me-6-Me-2-Pyrimidine], [4624;5-F-4-Me-2-Pyrimidine], [4625;6-F-4-Me-2-Pyrimidine], [4626;5-F-6-F-4-Me-2-Pyrimidine], [4627;4-F-5-Me-2-Pyrimidine], [4628;4-F-6-F-5-Me-2-Pyrimidine], [4629;6-F-4-Me-5-Me-2-Pyrimidine], [4630;5-F-4-Me-6-Me-2-Pyrimidine], [4631;5-Cl-4-Me-2-Pyrimidine], [4632;6-Cl-4-Me-2-Pyrimidine], [4633;5-Cl-6-Cl-4-Me-2-Pyrimidine], [4634;4-Cl-5-Me-2-Pyrimidine], [4635;4-Cl-6-Cl-5-Me-2-Pyrimidine], [4636;6-Cl-4-Me-5-Me-2-Pyrimidine], [4637;5-Cl-4-Me-6-Me-2-Pyrimidine], [4638;5-Br-4-Me-2-Pyrimidine], [4639;6-Br-4-Me-2-Pyrimidine], [4640;5-Br-6-Br-4-Me-2-Pyrimidine], [4641;4-Br-5-Me-2-Pyrimidine], [4642;4-Br-6-Br-5-Me-2-Pyrimidine], [4643;6-Br-4-Me-5-Me-2-Pyrimidine], [4644;5-Br-4-Me-6-Me-2-Pyrimidine], [4645;4-F-2-Pyrimidine], [4646;5-F-2-Pyrimidine], [4647;4-F-5-F-2-Pyrimidine], [4648;4-F-6-F-2-Pyrimidine], [4649;4-F-5-F-6-F-2-Pyrimidine], [4650;5-Cl-4-F-2-Pyrimidine], [4651;6-Cl-4-F-2-Pyrimidine], [4652;5-Cl-6-Cl-4-F-2-Pyrimidine], [4653;4-Cl-5-F-2-Pyrimidine], [4654;4-Cl-6-Cl-5-F-2-Pyrimidine], [4655;6-Cl-4-F-5-F-2-Pyrimidine], [4656;5-Cl-4-F-6-F-2-Pyrimidine], [4657;4-Et-2-Pyrimidine], [4658;5-Et-2-Pyrimidine], [4659;4-Et-5-Et-2-Pyrimidine], [4660;4-Et-6-Et-2-Pyrimidine], [4661;4-Et-5-Et-6-Me-2-Pyrimidine], [4662;5-Cl-4-Et-2-Pyrimidine], [4663;6-Cl-4-Et-2-Pyrimidine], [4664;5-Cl-6-Cl-4-Et-2-Pyrimidine], [4665;4-Cl-5-Et-2-Pyrimidine], [4666;4-Cl-6-Cl-5-Et-2-Pyrimidine], [4667;5-F-4-Et-2-Pyrimidine], [4668;6-F-4-Et-2-Pyrimidine], [4669;5-F-6-F-4-Et-2-Pyrimidine], [4670;4-F-5-Et-2-Pyrimidine], [4671;4-F-6-F-5-Et-2-Pyrimidine], [4672;4-OMe-2-Pyrimidine], [4673;5-OMe-2-Pyrimidine], [4674;4-OMe-5-OMe-2-Pyrimidine], [4675;4-OMe-6-OMe-2-Pyrimidine], [4676;5-Cl-4-OMe-2-Pyrimidine], [4677;6-Cl-4-OMe-2-Pyrimidine], [4678;5-Cl-6-Cl-4-OMe-2-Pyrimidine], [4679;4-Cl-5-OMe-2-Pyrimidine], [4680;4-Cl-6-Cl-5-OMe-2-Pyrimidine], [4681;5-F-4-OMe-2-Pyrimidine], [4682;6-F-4-OMe-2-Pyrimidine], [4683;5-F-6-F-4-OMe-2-Pyrimidine], [4684;4-F-5-OMe-2-Pyrimidine], [4685;4-F-6-F-5-OMe-2-Pyrimidine], [4686;4-Pr-2-Pyrimidine], [4687;5-Pr-2-Pyrimidine], [4688;4-SMe-2-Pyrimidine], [4689;5-SMe-2-Pyrimidine], [4690;Ph], [4691;2-Me-1-Ph], [4692;3-Me-1-Ph], [4693;4-Me-1-Ph], [4694;2-Me-3-Me-1-Ph], [4695;2-Me-4-Me-1-Ph], [4696;2-Me-5-Me-1-Ph], [4697;2-Me-6-Me-1-Ph], [4698;3-Me-4-Me-1-Ph], [4699;3-Me-5-Me-1-Ph], [4700;2-Me-3-Me-4-Me-1-Ph],

[4701;2-Me-3-Me-5-Me-1-Ph], [4702;2-Me-3-Me-6-Me-1-Ph], [4703;2-Me-4-Me-5-Me-1-Ph], [4704;2-Me-4-Me-6-Me-1-Ph], [4705;3-Me-4-Me-5-Me-1-Ph], [4706;2-Me-3-Me-4-Me-5-Me-1-Ph], [4707;2-Me-3-Me-4-Me-6-Me-1-Ph], [4708;2-Me-3-Me-5-Me-6-Me-1-Ph], [4709;2-F-4-Me-1-Ph], [4710;3-F-4-Me-1-Ph], [4711;5-F-4-Me-1-Ph], [4712;2-F-5-Me-1-Ph], [4713;3-F-5-Me-1-Ph], [4714;4-F-5-Me-1-Ph], [4715;6-F-5-Me-1-Ph], [4716;2-F-6-Me-1-Ph], [4717;3-F-6-Me-1-Ph], [4718;4-F-6-Me-1-Ph], [4719;5-F-6-Me-1-Ph], [4720;2-F-3-F-6-Me-1-Ph], [4721;2-F-4-F-6-Me-1-Ph], [4722;2-F-5-F-6-Me-1-Ph], [4723;3-F-4-F-6-Me-1-Ph], [4724;3-F-5-F-6-Me-1-Ph], [4725;4-F-5-F-6-Me-1-Ph], [4726;2-Cl-4-Me-1-Ph], [4727;3-Cl-4-Me-1-Ph], [4728;5-Cl-4-Me-1-Ph], [4729;6-Cl-4-Me-1-Ph], [4730;2-Cl-5-Me-1-Ph], [4731;3-Cl-5-Me-1-Ph], [4732;4-Cl-5-Me-1-Ph], [4733;6-Cl-5-Me-1-Ph], [4734;2-Cl-6-Me-1-Ph], [4735;3-Cl-6-Me-1-Ph], [4736;4-Cl-6-Me-1-Ph], [4737;5-Cl-6-Me-1-Ph], [4738;2-Cl-3-Cl-6-Me-1-Ph], [4739;2-Cl-4-Cl-6-Me-1-Ph], [4740;2-Cl-5-Cl-6-Me-1-Ph], [4741;2-Cl-6-Cl-6-Me-1-Ph], [4742;3-Cl-4-Cl-6-Me-1-Ph], [4743;3-Cl-5-Cl-6-Me-1-Ph], [4744;4-Cl-5-Cl-6-Me-1-Ph], [4745;2-Br-6-Me-1-Ph], [4746;3-Br-6-Me-1-Ph], [4747;4-Br-6-Me-1-

Ph], [4748;5-Br-6-Me-1-Ph], [4749;2-CN-6-Me-1-Ph], [4750;3-CN-6-Me-1-Ph], [4751;4-CN-6-Me-1-Ph], [4752;5-CN-6-Me-1-Ph], [4753;2-OMe-6-Me-1-Ph], [4754;3-OMe-6-Me-1-Ph], [4755;4-OMe-6-Me-1-Ph], [4756;5-OMe-6-Me-1-Ph], [4757;2-Et-6-Me-1-Ph], [4758;3-Et-6-Me-1-Ph], [4759;4-Et-6-Me-1-Ph], [4760;5-Et-6-Me-1-Ph], [4761;2-Br-5-Me-1-Ph], [4762;3-Br-5-Me-1-Ph], [4763;4-Br-5-Me-1-Ph], [4764;6-Br-5-Me-1-Ph], [4765;2-CN-5-Me-1-Ph], [4766;3-CN-5-Me-1-Ph], [4767;4-CN-5-Me-1-Ph], [4768;6-CN-5-Me-1-Ph], [4769;2-OMe-5-Me-1-Ph], [4770;3-OMe-5-Me-1-Ph], [4771;4-OMe-5-Me-1-Ph], [4772;6-OMe-5-Me-1-Ph], [4773;2-Br-4-Me-1-Ph], [4774;3-Br-4-Me-1-Ph], [4775;5-Br-4-Me-1-Ph], [4776;6-Br-4-Me-1-Ph], [4777;2-CN-4-Me-1-Ph], [4778;3-CN-4-Me-1-Ph], [4779;5-CN-4-Me-1-Ph], [4780;6-CN-4-Me-1-Ph], [4781;2-OMe-4-Me-1-Ph], [4782;3-OMe-4-Me-1-Ph], [4783;5-OMe-4-Me-1-Ph], [4784;6-OMe-4-Me-1-Ph], [4785;2-Et-4-Me-1-Ph], [4786;3-Et-4-Me-1-Ph], [4787;5-Et-4-Me-1-Ph], [4788;6-Et-4-Me-1-Ph], [4789;2-Et-1-Ph], [4790;3-Et-1-Ph], [4791;4-Et-1-Ph], [4792;5-Et-1-Ph], [4793;6-Et-1-Ph], [4794;2-Et-3-Et-1-Ph], [4795;2-Et-4-Et-1-Ph], [4796;2-Et-5-Et-1-Ph], [4797;2-Et-6-Et-1-Ph], [4798;3-Et-4-Et-1-Ph], [4799;3-Et-5-Et-1-Ph], [4800;4-Et-6-Et-1-Ph],

[4801;2-F-4-Et-1-Ph], [4802;3-F-4-Et-1-Ph], [4803;5-F-4-Et-1-Ph], [4804;6-F-4-Et-1-Ph], [4805;2-F-5-Et-1-Ph], [4806;3-F-5-Et-1-Ph], [4807;4-F-5-Et-1-Ph], [4808;6-F-5-Et-1-Ph], [4809;2-F-6-Et-1-Ph], [4810;3-F-6-Et-1-Ph], [4811;4-F-6-Et-1-Ph], [4812;5-F-6-Et-1-Ph], [4813;2-F-3-F-6-Et-1-Ph], [4814;2-F-4-F-6-Et-1-Ph], [4815;2-F-5-F-6-Et-1-Ph], [4816;3-F-4-F-6-Et-1-Ph], [4817;3-F-5-F-6-Et-1-Ph], [4818;4-F-5-F-6-Et-1-Ph], [4819;2-Cl-4-Et-1-Ph], [4820;3-Cl-4-Et-1-Ph], [4821;5-Cl-4-Et-1-Ph], [4822;6-Cl-4-Et-1-Ph], [4823;2-Cl-5-Et-1-Ph], [4824;3-Cl-5-Et-1-Ph], [4825;4-Cl-5-Et-1-Ph], [4826;6-Cl-5-Et-1-Ph], [4827;2-Cl-6-Et-1-Ph], [4828;3-Cl-6-Et-1-Ph], [4829;4-Cl-6-Et-1-Ph], [4830;5-Cl-6-Et-1-Ph], [4831;2-Cl-3-Cl-6-Et-1-Ph], [4832;2-Cl-4-Cl-6-Et-1-Ph], [4833;2-Cl-5-Cl-6-Et-1-Ph], [4834;3-Cl-4-Cl-6-Et-1-Ph], [4835;3-Cl-5-Cl-6-Et-1-Ph], [4836;4-Cl-5-Cl-6-Et-1-Ph], [4837;2-Br-5-Et-1-Ph], [4838;3-Br-5-Et-1-Ph], [4839;4-Br-5-Et-1-Ph], [4840;6-Br-5-Et-1-Ph], [4841;2-CN-5-Et-1-Ph], [4842;3-CN-5-Et-1-Ph], [4843;4-CN-5-Et-1-Ph], [4844;6-CN-5-Et-1-Ph], [4845;2-OMe-5-Et-1-Ph], [4846;3-OMe-5-Et-1-Ph], [4847;4-OMe-5-Et-1-Ph], [4848;6-OMe-5-Et-1-Ph], [4849;2-Et-5-Et-1-Ph], [4850;3-Et-5-Et-1-Ph], [4851;4-Et-5-Et-1-Ph], [4852;6-Et-5-Et-1-Ph], [4853;2-Br-6-Et-1-Ph], [4854;3-Br-6-Et-1-Ph], [4855;4-Br-6-Et-1-Ph], [4856;5-Br-6-Et-1-Ph], [4857;2-CN-6-Et-1-Ph], [4858;3-CN-6-Et-1-Ph], [4859;4-CN-6-Et-1-Ph], [4860;5-CN-6-Et-1-Ph], [4861;2-OMe-6-Et-1-Ph], [4862;3-OMe-6-Et-1-Ph], [4863;4-OMe-6-Et-1-Ph], [4864;5-OMe-6-Et-1-Ph], [4865;2-Pr-1-Ph], [4866;3-Pr-1-Ph], [4867;4-Pr-1-Ph], [4868;5-Pr-1-Ph], [4869;6-Pr-1-Ph], [4870;2-iPr-1-Ph], [4871;3-iPr-1-Ph], [4872;4-iPr-1-Ph], [4873;5-iPr-1-Ph], [4874;6-iPr-1-Ph], [4875;2-cPr-1-Ph], [4876;3-cPr-1-Ph], [4877;4-cPr-1-Ph], [4878;5-cPr-1-Ph], [4879;6-cPr-1-Ph], [4880;2-F-4-cPr-1-Ph], [4881;3-F-4-cPr-1-Ph], [4882;5-F-4-cPr-1-Ph], [4883;6-F-4-cPr-1-Ph], [4884;2-F-5-cPr-1-Ph], [4885;3-F-5-cPr-1-Ph], [4886;4-F-5-cPr-1-Ph], [4887;6-F-5-cPr-1-Ph], [4888;2-F-6-cPr-1-Ph], [4889;3-F-6-cPr-1-Ph], [4890;4-F-6-cPr-1-Ph], [4891;5-F-6-cPr-1-Ph], [4892;2-F-3-F-6-cPr-1-Ph], [4893;2-F-4-F-6-cPr-1-Ph], [4894;2-F-5-F-6-cPr-1-Ph], [4895;3-F-4-F-6-cPr-1-Ph], [4896;3-F-5-F-6-cPr-1-Ph], [4897;4-F-5-F-6-cPr-1-Ph], [4898;2-Cl-4-cPr-1-Ph], [4899;3-Cl-4-cPr-1-Ph], [4900;5-Cl-4-cPr-1-Ph],

[4901;6-Cl-4-cPr-1-Ph], [4902;2-Cl-5-cPr-1-Ph], [4903;3-Cl-5-cPr-1-Ph], [4904;4-Cl-5-cPr-1-Ph], [4905;6-Cl-5-cPr-1-Ph], [4906;2-Cl-6-cPr-1-Ph], [4907;3-Cl-6-cPr-1-Ph], [4908;4-Cl-6-cPr-1-Ph], [4909;5-Cl-6-cPr-1-Ph], [4910;2-Cl-3-Cl-6-cPr-1-Ph], [4911;2-Cl-4-Cl-6-cPr-1-Ph], [4912;2-Cl-5-Cl-6-cPr-1-Ph], [4913;3-Cl-4-Cl-6-cPr-1-Ph], [4914;3-Cl-5-Cl-6-cPr-1-Ph], [4915;4-Cl-5-Cl-6-cPr-1-Ph], [4916;2-F-1-Ph], [4917;3-F-1-Ph], [4918;4-F-1-Ph], [4919;5-F-1-Ph], [4920;6-F-1-Ph], [4921;2-F-3-F-1-Ph], [4922;2-F-4-F-1-Ph], [4923;2-F-5-F-1-Ph], [4924;2-F-6-F-1-Ph], [4925;3-F-4-F-1-Ph], [4926;3-F-5-F-1-Ph], [4927;4-F-5-F-1-Ph], [4928;2-F-3-F-4-F-1-Ph], [4929;2-F-3-F-5-F-1-Ph], [4930;2-F-3-F-6-F-1-Ph], [4931;2-F-4-F-6-F-1-Ph], [4932;2-F-4-F-5-F-1-Ph], [4933;3-F-4-F-5-F-1-Ph], [4934;2-Cl-1-Ph], [4935;3-Cl-1-Ph], [4936;4-Cl-1-Ph], [4937;5-Cl-1-Ph], [4938;6-Cl-1-Ph], [4939;2-F-4-Cl-1-Ph], [4940;3-F-4-Cl-1-Ph], [4941;5-F-4-Cl-1-Ph], [4942;6-F-4-Cl-1-Ph], [4943;2-F-5-Cl-1-Ph], [4944;3-F-5-Cl-1-Ph], [4945;4-F-5-Cl-1-Ph], [4946;6-F-5-Cl-1-Ph], [4947;2-F-6-Cl-1-Ph], [4948;3-F-6-Cl-1-Ph], [4949;4-F-6-Cl-1-Ph], [4950;5-F-6-Cl-1-Ph], [4951;2-F-3-F-6-Cl-1-Ph], [4952;2-F-4-F-6-Cl-1-Ph], [4953;2-F-5-F-6-Cl-1-Ph], [4954;3-F-4-F-6-Cl-1-Ph], [4955;3-F-5-F-6-Cl-1-Ph], [4956;4-F-5-F-6-Cl-1-Ph], [4957;2-Cl-3-Cl-1-Ph], [4958;2-Cl-4-Cl-1-Ph], [4959;2-Cl-5-Cl-1-Ph], [4960;2-Cl-6-Cl-1-Ph], [4961;3-Cl-4-Cl-1-Ph], [4962;3-Cl-5-Cl-1-Ph], [4963;4-Cl-5-Cl-1-Ph], [4964;2-Cl-3-Cl-4-Cl-1-Ph], [4965;2-Cl-3-Cl-5-Cl-1-Ph], [4966;2-Cl-3-Cl-6-Cl-1-Ph], [4967;2-Cl-4-Cl-5-Cl-1-Ph], [4968;2-Cl-4-Cl-6-Cl-1-Ph], [4969;3-Cl-4-Cl-5-Cl-1-Ph], [4970;2-Br-1-Ph], [4971;3-Br-1-Ph], [4972;4-Br-1-Ph], [4973;5-Br-1-Ph], [4974;6-Br-1-Ph], [4975;2-CN-1-Ph], [4976;3-CN-1-Ph], [4977;4-CN-1-Ph], [4978;5-CN-1-Ph], [4979;6-CN-1-Ph], [4980;2-F-4-CN-1-Ph], [4981;3-F-4-CN-1-Ph], [4982;5-F-4-CN-1-Ph], [4983;6-F-4-CN-1-Ph], [4984;2-F-5-CN-1-Ph], [4985;3-F-5-CN-1-Ph], [4986;4-F-5-CN-1-Ph], [4987;6-F-5-CN-1-Ph], [4988;2-F-6-CN-1-Ph], [4989;3-F-6-CN-1-Ph], [4990;4-F-6-CN-1-Ph], [4991;5-F-6-CN-1-Ph], [4992;2-F-3-F-6-CN-1-Ph], [4993;2-F-4-F-6-CN-1-Ph], [4994;2-F-5-F-6-CN-1-Ph], [4995;3-F-4-F-6-CN-1-Ph], [4996;3-F-5-F-6-CN-1-Ph], [4997;4-F-5-F-6-CN-1-Ph], [4998;2-Cl-4-CN-1-Ph], [4999;3-Cl-4-CN-1-Ph], [5000;5-Cl-4-CN-1-Ph],

[5001;6-Cl-4-CN-1-Ph], [5002;2-Cl-5-CN-1-Ph], [5003;3-Cl-5-CN-1-Ph], [5004;4-Cl-5-CN-1-Ph], [5005;6-Cl-5-CN-1-Ph], [5006;2-Cl-6-CN-1-Ph], [5007;3-Cl-6-CN-1-Ph], [5008;4-Cl-6-CN-1-Ph], [5009;5-Cl-6-CN-1-Ph], [5010;2-Cl-3-Cl-6-CN-1-Ph], [5011;2-Cl-4-Cl-6-CN-1-Ph], [5012;2-Cl-5-Cl-6-CN-1-Ph], [5013;3-Cl-4-Cl-6-CN-1-Ph], [5014;3-Cl-5-Cl-6-CN-1-Ph], [5015;4-Cl-5-Cl-6-CN-1-Ph], [5016;2-OMe-1-Ph], [5017;3-OMe-1-Ph], [5018;4-OMe-1-Ph], [5019;5-OMe-1-Ph], [5020;6-OMe-1-Ph], [5021;2-OMe-3-OMe-1-Ph], [5022;2-OMe-4-OMe-1-Ph], [5023;2-OMe-5-OMe-1-Ph], [5024;2-OMe-6-OMe-1-Ph], [5025;3-OMe-4-OMe-1-Ph], [5026;3-OMe-5-OMe-1-Ph], [5027;4-OMe-5-OMe-1-Ph], [5028;2-F-4-OMe-1-Ph], [5029;3-F-4-OMe-1-Ph], [5030;5-F-4-OMe-1-Ph], [5031;6-F-4-OMe-1-Ph], [5032;2-F-5-OMe-1-Ph], [5033;3-F-5-OMe-1-Ph], [5034;4-F-5-OMe-1-Ph], [5035;6-F-5-OMe-1-Ph], [5036;2-F-6-OMe-1-Ph], [5037;3-F-6-OMe-1-Ph], [5038;4-F-6-OMe-1-Ph], [5039;5-F-6-OMe-1-Ph], [5040;2-F-3-F-6-OMe-1-Ph], [5041;2-F-4-F-6-OMe-1-Ph], [5042;2-F-5-F-6-OMe-1-Ph], [5043;3-F-4-F-6-OMe-1-Ph], [5044;3-F-5-F-6-OMe-1-Ph], [5045;4-F-5-F-6-OMe-1-Ph], [5046;2-Cl-4-OMe-1-Ph], [5047;3-Cl-4-OMe-1-Ph], [5048;2-Cl-5-OMe-1-Ph], [5049;3-Cl-5-OMe-1-Ph], [5050;4-Cl-5-OMe-1-Ph], [5051;6-Cl-5-OMe-1-Ph], [5052;2-Cl-6-OMe-1-Ph], [5053;3-Cl-6-OMe-1-Ph], [5054;4-Cl-6-OMe-1-Ph], [5055;5-Cl-

6-OMe-1-Ph], [5056;2-Cl-3-Cl-6-OMe-1-Ph], [5057;2-Cl-4-Cl-6-OMe-1-Ph], [5058;2-Cl-5-Cl-6-OMe-1-Ph], [5059;3-Cl-4-Cl-6-OMe-1-Ph], [5060;3-Cl-5-Cl-6-OMe-1-Ph], [5061;4-Cl-5-Cl-6-OMe-1-Ph], [5062;2-OEt-1-Ph], [5063;3-OEt-1-Ph], [5064;4-OEt-1-Ph], [5065;5-OEt-1-Ph], [5066;6-OEt-1-Ph], [5067;2-CF3-1-Ph], [5068;3-CF3-1-Ph], [5069;4-CF3-1-Ph], [5070;5-CF3-1-Ph], [5071;6-CF3-1-Ph], [5072;2-F-4-CF3-1-Ph], [5073;3-F-4-CF3-1-Ph], [5074;5-F-4-CF3-1-Ph], [5075;6-F-4-CF3-1-Ph], [5076;2-F-5-CF3-1-Ph], [5077;3-F-5-CF3-1-Ph], [5078;4-F-5-CF3-1-Ph], [5079;6-F-5-CF3-1-Ph], [5080;2-F-6-CF3-1-Ph], [5081;3-F-6-CF3-1-Ph], [5082;4-F-6-CF3-1-Ph], [5083;5-F-6-CF3-1-Ph], [5084;2-F-3-F-6-CF3-1-Ph], [5085;2-F-4-F-6-CF3-1-Ph], [5086;2-F-5-F-6-CF3-1-Ph], [5087;3-F-4-F-6-CF3-1-Ph], [5088;3-F-5-F-6-CF3-1-Ph], [5089;4-F-5-F-6-CF3-1-Ph], [5090;2-Cl-4-CF3-1-Ph], [5091;3-Cl-4-CF3-1-Ph], [5092;5-Cl-4-CF3-1-Ph], [5093;6-Cl-4-CF3-1-Ph], [5094;2-Cl-5-CF3-1-Ph], [5095;3-Cl-5-CF3-1-Ph], [5096;4-Cl-5-CF3-1-Ph], [5097;6-Cl-5-CF3-1-Ph], [5098;2-Cl-6-CF3-1-Ph], [5099;3-Cl-6-CF3-1-Ph], [5100;4-Cl-6-CF3-1-Ph], [5101;5-Cl-6-CF3-1-Ph], [5102;2-Cl-3-Cl-6-CF3-1-Ph], [5103;2,4-Cl-6-CF3-1-Ph], [5104;2,5-Cl-6-CF3-1-Ph], [5105;3,4-Cl-6-CF3-1-Ph], [5106;3,5-Cl-6-CF3-1-Ph], [5107;4-Cl-5-Cl-6-CF3-1-Ph], [5108;2-amino-1-Ph], [5109;3-amino-1-Ph], [5110;4-amino-1-Ph], [5111;5-amino-1-Ph], [5112;6-amino-1-Ph], [5113;2-N,N-dimethylamino-1-Ph], [5114;3-N,N-dimethylamino-1-Ph], [5115;4-N,N-dimethylamino-1-Ph], [5116;5-N,N-dimethylamino-1-Ph], [5117;6-N,N-dimethylamino-1-Ph], [5118;2-SMe-1-Ph], [5119;3-SMe-1-Ph], [5120;4-SMe-1-Ph], [5121;5-SMe-1-Ph], [5122;6-SMe-1-Ph]

Formulation Examples will be shown below. Parts are by weight.

Formulation Example 1

Fifty parts (50 parts) of any one of the present compounds 1 to 59, 3 parts of calcium ligninsulfonate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds 1 to 59 and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds 1 to 59, 88 parts of kaolin clay, and 10 parts of talc are thoroughly ground and mixed to obtain each formulation.

Formulation Example 4

Five parts (5 parts) of any one of the present compounds 1 to 50, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of any one of the present compounds 1 to 59, 1 part of synthetic hydrated silicon oxide, 2 parts of calcium ligninsulfonate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of any one of the present compounds 1 to 59, 35 parts of white carbon containing 50 parts of a polyoxyethylene alkyl ether sulfate ammonium salt, and 55 parts of water were finely ground by a wet grinding method to obtain each formulation.

The following Test Examples will show that the present compounds are useful for controlling plant diseases.

The control effect was evaluated by visually observing the area of lesion on each of test plants at the time of investigation, and comparing the area of lesion on a plant treated with the present compound with that on an untreated plant.

Test Example 1

Each of plastic pots was filled with soil and barley (cultivar: MIKAMO GOLDEN) was sowed and grown in a greenhouse for 7 days. Then, each water dilution prepared by adjusting so as to contain a predetermined concentration (200 ppm) of any one compound of the present compounds 1, 2, 4, 5, 6, 7, 8, 9, 10, 11, 12, 13, 14, 15, 16, 17, 18, 19, 20, 21, 22, 23, 24, 26, 27, 28, 29, 30, 31, 32, 33, 33, 34, 35, 36, 37, 38, 39, 40, 41, 42, 43, 44, 45, 46, 47, 48, 49, 50, 52, 54, 56, and 57 was sprayed over stems and leaves of the barley so that it sufficiently adhered to the surface of the leaves of the barley. After spraying, the plant was air-dried. After 2 days, an aqueous suspension containing spores of barley scald fungus (*Rhynchosporium secalis*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion was investigated.

As a result, it has been found that the area of lesion on the plant treated with of the present compound 1, 2, 4, 5, 6, 7, 8, 9, 10, 11, 12, 13, 14, 15, 16, 17, 18, 19, 20, 21, 22, 23, 24, 26, 27, 28, 29, 30, 31, 32, 33, 33, 34, 35, 36, 37, 38, 39, 40, 41, 42, 43, 44, 45, 46, 47, 48, 49, 50, 52, 54, 56, or 57 was 30% or less of that on an untreated plant.

Test Example 2

Each of plastic pots was filled with soil and rice (cultivar: NIHONBARE) was sowed and grown in a greenhouse for 20 days. Then, each water dilution prepared by adjusting so as to contain a predetermined concentration (200 ppm) of any one compound of the present compounds 11, 13, 14, 15, 16, 17, 18, 19, 20, 21, 22, 23, 26, 27, 28, 29, 30, 44, 46, 48, and 57 was sprayed over stems and leaves so that it sufficiently adhered to the surface of the leaves of the rice. After spraying, the plant was air-dried and placed for 6 days at 24° C. in the daytime and 20° C. at night under high humidity condition, while being in contact with the rice seedling (cultivar: NIHONBARE) infected by the rice blast fungus (*Magnaporthe grisea*), and then the area of lesion was investigated.

As a result, the lesion areas on the plant treated with the present compound 11, 13, 14, 15, 16, 17, 18, 19, 20, 21, 22, 23, 26, 27, 28, 29, 30, 44, 46, 48, or 57 were 30% or less with respect to the lesion area on the non-treated plant.

Test Example 3

Each of plastic pots was filled with soil and wheat (cultivar: SHIROGANE) was sowed and grown in a greenhouse for 9 days. Then, each water dilution prepared by adjusting so as to contain a predetermined concentration (200 ppm) of any one compound of the present compounds 4, 11, 13, 14, 15, 16, 18, 19, 20, 22, 23, 27, 28, 29, 30, 44, 56, and 57 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion was investigated.

As a result, it has been found that the area of lesion on the plant treated with the present compound 4, 11, 13, 14, 15, 16, 18, 19, 20, 22, 23, 27, 28, 29, 30, 44, 56, or 57 was 30% or less of that on an untreated plant.

Test Example 4

Each of plastic pots was filled with soil and barley (cultivar: MIKAMO GOLDEN) was sowed and grown in a greenhouse for 7 days. Then, each water dilution prepared by adjusting so as to contain a predetermined concentration (200 ppm) of any one compound of the present compounds 2, 4, 5, 6, 7, 10, 11, 12, 13, 14, 15, 16, 17, 18, 19, 20, 21, 22, 23, 24, 26, 27, 28, 29, 30, 31, 32, 33, 33, 34, 35, 36, 37, 38, 39, 40, 41, 42, 43, 44, 45, 46, 47, 48, 49, 50, 56, and 57 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion was investigated.

As a result, it has been found that the area of lesion on the plant treated with of the present compound 2, 4, 5, 6, 7, 10, 11, 12, 13, 14, 15, 16, 17, 18, 19, 20, 21, 22, 23, 24, 26, 27, 28, 29, 30, 31, 32, 33, 33, 34, 35, 36, 37, 38, 39, 40, 41, 42, 43, 44, 45, 46, 47, 48, 49, 50, 56, or 57 was 30% or less of that on an untreated plant.

Test Example 5

Each of plastic pots was filled with soil and kidney bean (cultivar: NAGAUZURA SAIYTOU) was sowed and grown in a greenhouse for 8 days. Then, each water dilution prepared by adjusting so as to contain a predetermined concentration (200 ppm) of any one compound of the present compounds 2, 4, 8, 10, 13, 14, 15, 16, 17, 18, 19, 20, 21, 22, 23, 26, 29, 44, 48, 49, and 57 was sprayed over stems and leaves of the kidney bean so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion was investigated.

As a result, the area of lesion on the plant treated with the present compound 2, 4, 8, 10, 13, 14, 15, 16, 17, 18, 19, 20, 21, 22, 23, 26, 29, 44, 48, 49, or 57 was 30% or less of that on an untreated plant.

Test Example 6

Each of plastic pots was filled with soil and wheat (cultivar: APOGEE) was sowed and grown in a greenhouse for 10 days. Then, each water dilution prepared by adjusting so as to contain a predetermined concentration (200 ppm) of any one compound of the present compounds 4, 5, 6, 7, 8, 10, 11, 12, 13, 14, 15, 17, 18, 19, 20, 21, 22, 23, 24, 26, 27, 28, 29, 30, 31, 32, 33, 33, 34, 35, 36, 37, 38, 39, 40, 41, 42, 43, 44, 45, 46, 47, 48, 49, 50, 54, 56, 57, 58, and 59 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion was investigated.

As a result, the area of lesion on the plant treated with the present compound 4, 5, 7, 8, 10, 11, 12, 13, 14, 15, 17, 18, 19, 20, 21, 22, 23, 24, 26, 27, 28, 29, 30, 31, 32, 33, 33, 34, 35, 36, 37, 38, 39, 40, 41, 42, 43, 44, 45, 46, 47, 48, 49, 50, 54, 56, 57, 58, or 59 was 30% or less of that on an untreated plant.

Test Example 7

Each of plastic pots was filled with soil and cucumber (cultivar: SAGAMI HANJIRO) was sowed and grown in a greenhouse for 12 days. Then, each water dilution prepared by adjusting so as to contain a predetermined concentration (200 ppm) of any one compound of the present compounds 1, 4, 6, 7, 8, 10, 11, 13, 28, 29, 41, and 46 was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion was investigated.

As a result, the area of lesion on the plant treated with the present compound 1, 4, 6, 7, 8, 10, 11, 13, 28, 29, 41, or 46 was 30% or less of that on an untreated plant.

Test Example 8

Each of plastic pots was filled with soil and soybean (cultivar: KUROSENGOKU) was sowed and grown in a greenhouse for 13 days. Then, each water dilution prepared by adjusting so as to contain a predetermined concentration (200 ppm) of any one compound of the present compounds 13, 18, 19, 20, 28, and 30 was sprayed over stems and leaves of the soybean so that it sufficiently adhered to the surface of the leaves of the soybean. After spraying, the plant was air-dried. After 2 days, an aqueous suspension containing spores of soybean rust fungus (*Phakopsora pachyrhizi*) was sprayed to inoculate the spores. After completion of the inoculation, the plant was left to stand for 3 days in a greenhouse at 23° C. in the daytime and 20° C. at night under high humidity condition and cultivated in a greenhouse for 14 days, and then the area of lesion was investigated.

As a result, it has been found that the area of lesion on the plant treated with the present compound 13, 18, 19, 20, 28, or 30 was 30% or less of that on an untreated plant.

Test Example 9

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of any one compound of the present compounds 4, 6, 7, 8, 10, 11, 13, 14, 15, 17, 30, and 56 was sprayed over stems and leaves of the cucumber so that it sufficiently adhered to the surface of the leaves of the cucumber. After spraying, the plant was air-dried. After 1 day, an aqueous suspension containing spores of cucumber target spot (*Corynespora cassiicola*) was sprayed to inoculate the spores. After the inoculation, the plant was cultivated in a greenhouse at 24° C. in the daytime and 20° C. at night for 7 days, and then the area of lesion was investigated.

As a result, the area of lesion on the plant treated with the present compound 4, 6, 7, 8, 10, 11, 13, 14, 15, 17, 30, or 56 was 30% or less of that on an untreated plant.

Test Example 10

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of any one compound of the present compounds 6, 8, 9, 10, 11, 13, 14, 15, 17, 18, 19, 20, 21, 23, 26, 27, 28, 29, 30, and 57 was sprayed over stems and leaves of the cucumber so that it sufficiently adhered to the surface of the leaves of the cucumber. After spraying, the plant was air-dried and then, after 1 day, an aqueous suspension containing spores of cucumber anthracnose fungus (*Colletotrichum lagenarium*) was sprayed to inoculate the spores. After the inoculation, the plant was left to stand at 23° C. for one day under high humidity condition, and then cultivated in a greenhouse at 24° C. in the daytime and 20° C. at night for 6 days, and then the area of lesion was investigated.

As a result, the area of lesion on the plant treated with the present compound 6, 8, 9, 10, 11, 13, 14, 15, 17, 18, 19, 20, 21, 23, 26, 27, 28, 29, 30, or 57 was 30% or less of that on an untreated plant.

Test Example 11

As a test chemical solution used in the present test example, a water dilution (test chemical solution) was prepared so as to contain a predetermined concentration (500 ppm) of any one compound of the present compounds 1, 15, 17, and 55.

The test chemical solution was sprayed over cabbage in three-leaf stage sowed and grown in a polyethylene at a rate of 20 mL per cup. After drying the chemical solution, the stem and leaf portions were cut and disposed in a 50 mL cup. Five (5) heads of second-instar larvae of diamondback moth (*Plutella xylostella*) were released and then a lid was put on the cup. After storage at 25° C. for 5 days, the number of the dead insects was counted and mortality was calculated by the following equation.

Mortality (%)=(number of dead insects/number of tested insects)×100

As a result, the present compounds 1, 15, 17, and 55 showed 80% or more of mortality in the area treated with the test chemical solution.

Comparative Test Example

Each of plastic pots was filled with soil and cucumber (cultivar: SAGAMI HANJIRO) was sowed and grown in a greenhouse for 12 days. Then, each water dilution prepared by adjusting so as to contain a predetermined concentration (500 ppm) of 1-[2-(phenylmethoxy)phenyl]-4-methyl-1,4-dihydrotetrazol-5-one was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion was investigated.

As a result, the area of lesion on the plant treated with 1-[2-(phenylmethoxy)phenyl]-4-methyl-1,4-dihydrotetrazol-5-one was 70% or more of that on an untreated plant.

The present compound has control activity against pests and is useful as an active ingredient of a pest control agent.

The invention claimed is:
1. A tetrazolinone compound represented by formula (1):

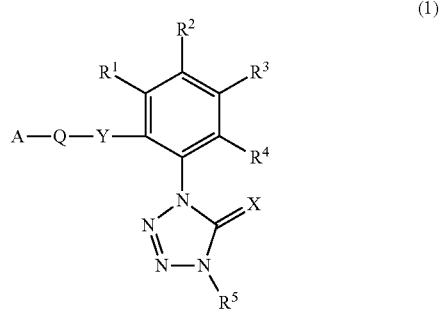

wherein
R$^1$ represents a C1-C6 alkyl group, a C3-C6 cycloalkyl group, a halogen atom, a C1-C6 haloalkyl group, a C2-C6 alkenyl group, a C1-C6 alkoxy group, a C1-C6 alkylthio group, a C2-C6 alkynyl group, a nitro group, a cyano group, an aminocarbonyl group optionally having a C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a C2-C6 alkoxycarbonyl group, a hydroxy group, a sulfanyl group, an amino group optionally having a C1-C6 alkyl group, a pentafluorosulfanyl group, a C3-C9 trialkylsilyl group, a C5-C14 trialkylsilylethynyl group, a C1-C6 alkylsulfonyl group, a C1-C6 haloalkylsulfonyl group, a C1-C6 alkylsulfinyl group, a C1-C6 haloalkylsulfinyl group, a C2-C6 alkoxyalkyl group, or a C2-C6 alkylthioalkyl group;

$R^2$, $R^3$, and $R^4$ each independently represents a hydrogen atom, a halogen atom, a C1-C3 alkyl group, a C1-C3 haloalkyl group, a C2-C3 alkenyl group, a C2-C3 haloalkenyl group, or a C1-C3 alkoxy group;

$R^5$ represents a C1-C3 alkyl group optionally having one or more halogen atoms;

Y represents #—C($R^{A\,1}$ $R^{A\,2}$)—Z—, #—C($R^{A\,1}$ $R^{A\,2}$)C($R^{A\,3}$ $R^{A\,4}$)—Z—, #—C($R^{A\,1}$ $R^{A\,2}$)—Z—C($R^{A\,3}$ $R^{A\,4}$)—, #—Z—C($R^{A\,1}$ $R^{A\,2}$)C($R^{A\,3}$ $R^{A\,4}$)—, #—C($R^{A\,1}$ $R^{A\,2}$)C($R^{A\,3}$ $R^{A\,4}$)C($R^{A\,5}$ $R^{A\,6}$)—Z—, #—C($R^{A\,1}$ $R^{A\,2}$)C($R^{A\,3}$ $R^{A\,4}$)—Z—C($R^{A\,5}$ $R^{A\,6}$)—, #—C($R^{A\,1}$ $R^{A\,2}$)—Z—C($R^{A\,3}$ $R^{A\,4}$)C($R^{A\,5}$ $R^{A\,6}$), #—Z—C($R^{A\,1}$ $R^{A\,2}$)C($R^{A\,3}$ $R^{A\,4}$)C($R^{A\,5}$ $R^{A\,6}$)—, #—C($R^{A\,1}$)=C($R^{A\,2}$)C($R^{A\,3}$ $R^{A\,4}$)—Z—, #—Z—C($R^{A\,1}$ $R^{A\,2}$)C($R^{A\,3}$)=C($R^{A\,4}$)—, #—C≡C—C($R^{A\,1}$ $R^{A\,2}$)—Z—, #—Z—C($R^{A\,1}$ $R^{A\,2}$)—C≡C—, #—Z—C($R^{A\,1}$ $R^{A\,2}$)C($R^{A\,3}$ $R^{A\,4}$)—, #—C($R^{A\,1}$)=C($R^{A\,2}$)—, #—C($R^{A\,1}$)=C($R^{A\,2}$)C($R^{A\,3}$ $R^{A\,4}$)—, #—C($R^{A\,1}$)=C($R^{A\,2}$)C($R^{A\,3}$ $R^{A\,4}$)C($R^{A\,5}$ $R^{A\,6}$)—, #—C($R^{A\,1}$ $R^{A\,2}$)C($R^{A\,3}$)=C($R^{A\,4}$)C($R^{A\,5}$ $R^{A\,6}$), #—C($R^{A\,1}$ $R^{A\,2}$)C($R^{A\,3}$ $R^{A\,4}$)C($R^{A\,5}$)=C($R^{A\,6}$)—, #—C($R^{A\,1}$)=C($R^{A\,2}$)C($R^{A\,3}$)=C($R^{A\,4}$)—, —C≡C—, #—C≡C—C($R^{A\,1}$ $R^{A\,2}$)—, #—C≡C—C($R^{A\,1}$ $R^{A\,2}$)C($R^{A\,3}$ $R^{A\,4}$)—, #—C($R^{A\,1}$ $R^{A\,2}$)C($R^{A\,3}$ $R^{A\,4}$)—C≡C—, or #—C($R^{A\,1}$ $R^{A\,2}$)—C≡C—C($R^{A\,3}$ $R^{A\,4}$)—, wherein the symbol # represents a binding site for Q, $R^{A\,1}$, $R^{A\,2}$, $R^{A\,3}$, $R^{A\,4}$, $R^{A\,5}$, and $R^{A\,6}$ each independently represents a hydrogen atom, a halogen atom, or a C1-C3 alkyl group, Z represents an oxygen atom, a sulfur atom, or $NR^C$, and $R^C$ represents a C1-C6 alkyl group, a C1-C6 haloalkyl group, a C3-C6 cycloalkyl group, or a C3-C6 halocycloalkyl group;

Q represents a divalent C3-C10 carbocyclic group or a divalent heterocyclic group, wherein the divalent heterocyclic group is a single or fused ring having, as a ring-constituent atom, one or more atoms selected from the group consisting of a nitrogen atom, an oxygen atom, and a sulfur atom, and when two or more of the atoms are present, those atoms may be the same or different to each other, and the heterocyclic group represents a ring in which a 5-membered ring is fused with a 5-membered ring, a 5-membered ring is fused with a 6-membered ring, and a 6-membered ring is fused with a 6-membered ring when the heterocyclic group is a fused ring;

X represents an oxygen atom or a sulfur atom;

A represents a C6-C10 aryl group, a C6-C10 aryloxy group, a C6-C10 arylthio group, a C6-C10 arylsulfonyl group, a C6-C10 arylamino group, a hydrogen atom, a heterocyclic group, or $R^B$—O—N=C($R^B$)—, wherein the heterocyclic group has, as a ring-constituent atom, one or more atoms selected from the group consisting of a nitrogen atom, an oxygen atom, and a sulfur atom, and when two or more of the atoms are present, those atoms may be the same or different to each other, and $R^B$ represents a C1-C6 alkyl group, a C1-C6 haloalkyl group, a C3-C6 cycloalkyl group, or a C3-C6 halocycloalkyl group, wherein the divalent C3-C10 carbocyclic group and the divalent heterocyclic group of Q, and the C6-C10 aryl group, the C6-C10 aryloxy group, the C6-C10 arylthio group, the C6-C10 arylamino group, and the heterocyclic group of A optionally have one or more atoms or groups selected from Group $P^1$:

Group $P^1$: Group consisting of a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a carboxy group, a formyl group, a C2-C6 alkoxycarbonyl group, a nitro group, a cyano group, a hydroxy group, a C1-C6 alkylsulfonyl group, a C1-C6 haloalkylsulfonyl group, a C1-C6 alkylsulfinyl group, a C1-C6 haloalkylsulfinyl group, an amino group optionally having a C1-C6 alkyl group, an aminosulfonyl group optionally having a C1-C6 alkyl group, and an aminocarbonyl group optionally having a C1-C6 alkyl group.

2. The tetrazolinone compound according to claim 1, wherein, in formula (1), $R^1$ is a methyl group;

$R^2$, $R^3$, and $R^4$ are hydrogen atoms;

$R^5$ is a methyl group;

Y is #—CH($R^{A7}$)—O—, #—CH($R^{A7}$)—O—CH$_2$—, #—CH($R^{A7}$)CH$_2$—O—CH$_2$—, or —CH=CH—, wherein the symbol # represents a binding site for Q, and $R^{A7}$ represents a hydrogen atom or a methyl group;

Q is a divalent benzene ring, a thiazole ring, or a pyrazole ring group, wherein the divalent benzene ring, the thiazole ring, or the pyrazole ring group of Q optionally has one or more atoms or groups selected from Group $P^2$;

X is an oxygen atom; and

A is a phenyl group, a phenoxy group, a hydrogen atom, a 2-pyridyl group, or a 2-pyrimidinyl group, wherein the phenyl group, the phenoxy group, the hydrogen atom, the 2-pyridyl group, or the 2-pyrimidinyl group optionally has one or more atoms or groups selected from Group $P^2$:

Group $P^2$: Group consisting of a halogen atom, a methyl group, a trifluoromethyl group, and a methoxy group.

3. The tetrazolinone compound according to claim 2, wherein, in formula (1), $R^1$ is a methyl group;

$R^2$, $R^3$, and $R^4$ are hydrogen atoms;

$R^5$ is a methyl group;

Y is #—CH($R^{A7}$)—O—, wherein the symbol # represents a binding site for Q and $R^{A7}$ represents a hydrogen atom or a methyl group;

Q is a divalent benzene ring, a thiazole ring, or a pyrazole ring group, wherein the divalent benzene ring, the thiazole ring, or the pyrazole ring group of Q optionally has one or more atoms or groups selected from Group $P^2$;

X is an oxygen atom; and

A is a phenyl group, a hydrogen atom, or a 2-pyridyl group, wherein the phenyl group or the 2-pyridyl group optionally has one or more atoms or groups selected from Group $P^2$:

Group $P^2$: Group consisting of a halogen atom, a methyl group, a trifluoromethyl group, and a methoxy group.

4. A pest control agent comprising the tetrazolinone compound according to claim 1.

5. A method for controlling pests, which comprises treating plants or soil with an effective amount of the tetrazolinone compound according to claim 1.

* * * * *